US006737508B1

(12) United States Patent
Pelletier et al.

(10) Patent No.: US 6,737,508 B1
(45) Date of Patent: May 18, 2004

(54) **DNA SEQUENCES FROM *STAPHYLOCOCUS AUREUS* BACTERIOPHAGES 3A, 77, AND 96 THAT ENCODE ANTI-MICROBIAL POLYPEPTIDES**

(76) Inventors: Jerry Pelletier, 8 Lakeview, Baie-D'Urfe, Quebec (CA), H9X 3B1; Philippe Gros, 107 Montrose, St. Lambert, Quebec (CA), J4R 1X4; Michael DuBow, 4901 Coolbrook Avenue, Montreal, Quebec (CA), H3X 2K8

( * ) Notice: Subject to any disclaimer, the term of this patent is extended or adjusted under 35 U.S.C. 154(b) by 0 days.

(21) Appl. No.: 09/676,519

(22) Filed: Sep. 28, 2000

Related U.S. Application Data

(63) Continuation-in-part of application No. 09/407,804, filed on Sep. 28, 1999.
(60) Provisional application No. 60/110,992, filed on Dec. 3, 1998.

(51) Int. Cl.[7] .......................... C07K 7/00; A61K 38/04; A61K 38/16

(52) U.S. Cl. ....................... 530/326; 530/324; 530/350; 435/5; 435/883

(58) Field of Search ................................ 530/350, 324, 530/326; 435/5, 883

(56) References Cited

U.S. PATENT DOCUMENTS

| | | | |
|---|---|---|---|
| 3,691,016 | A | 9/1972 | Patel |
| 3,969,287 | A | 7/1976 | Jaworek et al. |
| 4,195,128 | A | 3/1980 | Hildebrand et al. |
| 4,229,537 | A | 10/1980 | Hodgins et al. |
| 4,247,642 | A | 1/1981 | Hirohara |
| 4,330,440 | A | 5/1982 | Ayers et al. |

FOREIGN PATENT DOCUMENTS

| | | | |
|---|---|---|---|
| EP | 0 072 925 | A2 | 3/1983 |
| EP | 0 748 871 | A1 | 12/1996 |
| EP | 786519 | A2 * | 1/1997 |
| EP | 0 786 519 | A2 | 7/1997 |
| WO | WO 89/00199 | | 1/1989 |
| WO | WO 95/27043 | | 10/1995 |

OTHER PUBLICATIONS

Adelman et al., "In Vitro Deletional Mutagenesis For Bacterial Production Of The 20,000–Dalton Form Of Human Pituitary Growth Hormone", DNA, 2(3):183–93, 1983.

Altshul et al., "Gapped BLAST and PSI–BLAST: a new generation of protein database search programs", Nucleic Acids Research, 1997, vol. 25, No. 17, pp. 3389–3402.

Cohen, "Epidemiology of Drug Resistance: Implications for a Post–Antimicrobial Era", ML Science, vol. 257, Aug. 21, 1992, pp. 1050–1055.

Diaz et al., "Construction of a broad–host–range pneumococcal promoter–probe plasmid", Gene, 90:163–167, 1990.

Durfee et al., "The retinoblastoma protein associates with the protein phosphatase type 1 catalytic subunit", Genes & Development, 7:555–569, 1993.

Eichenbaum et al., "Use of Lactococcal nisA Promoter To Regulate Gene Expression in Gram–Positive Bacteria: Comparison of Induction Level and Promoter Strength", Applied and Environmental Microbiology, 64:2763–2769, 1998.

Endo et al., "A new protein containing an SH2 domain that inhibits JAK kinases", Nature, 387:921–924, 1997.

Field et al., "Purifications Of A RAS–Responsive Adenylyl Cyclase Complex From Saccharomyces Cerevisiae By Use Of An Epitope Addition Method", Mol. Cell. Biol., 8:2159–2165, 1988.

Fink, "Where are the Limits of Life?", Book Reviews, 322:469–470, 1998.

Garvey et al., "The complete sequence of *Bacillus* phage Ø29 gene 16: a protein required for the genome encapsidation reaction", Gene, 40:311–316, 1985.

Gutierrez et al., "Signals in the Ø29 DNA–Terminal Protein Template for the Initiation of Phage Ø29 DNA Replication", Virology, 155:474–483, 1986.

Jorgensen et al., "Antimicrobial Resistance among Respiratory Isolates of *Haemophilus influenza, Moraxella catarrhalis*, and *Streptococcus pneumoniae* in the United States", Antimicrobial Agents and Chemotherapy, 34:2075–2080, 1990.

Kaneko et al., "Complete nucleotide sequence and molecular characterization of the temperate staphylococcal bacteriophage ΦPVL carrying Pantom–Valentine leukocidin genes", Genes 215:57–67, 1998.

Karimova et al., "A Bacterial two–hybrid system based on a reconstituted signal transduction pathway", Proc. Natl. Acad. Sci., 95:5752–5756, 1998.

Katagari et al., "Multiple Possible Sites of BRCA2 Interacting With DNA Repair Protein RAD5 1", Genes, Chromosomes & CaNCER, 21:217–222, 1998.

Kreiswirth et al., "The Toxic Shock Syndrome Exotoxin Structural Gene Is Not Detectably Transmitted By A Prophage", Nature, Oct. 20–26;305(5936):709–12, 1983.

Kodaira et al., "The dnaX gene Encodes the DNA Polymerase III Holoenzyme τSubmit, the dnaZ Gene Product", Mol Gene Genet, 192:80–86, 1983.

Lee et al., "*Escherichia coli* DnaX Product, the τsubunit of DNA polymerase III, is a multifunctional protein with single–stranded DNA–dependent ATPase activity", Proc. Natl. Acad. Sci., 84:2713–2717, 1987.

Loessner et al., "The Two–Component Lysis System Of *Staphylococcus Aureus* Bacteriophage Twort: A Large TTG–Start Holin And An Associated Amidase Endolysin", FEMS Microbiol Lett., May 15;162(2):265–74, 1998.

(List continued on next page.)

*Primary Examiner*—Robert A. Wax

(57) ABSTRACT

The disclosure concerns particular bacteriophage open reading frames, and portions and products of those open reading frames which have antimicrobial activity. Methods of using such products are also described.

11 Claims, 18 Drawing Sheets-

OTHER PUBLICATIONS

Maki et al., "DNA Polymerase III Holoenzyme of *Escherichica coli*", The Journal of Biological Chemistry, 263:6547–6554, 1988.

Mancini et al., "Complementation of the fol2 Deletion in *Sccharmoyces cerevisiae* by Human and *Escherichia coli* Genes Encoding GTP Cyclohydrolase ", Biochemical and Biophysical Research Communications, 255:521–527, 1999.

Martin et al., "Analysis of the Complete Nucleotide Sequence and Functional Organization of the Genome of *Streptococcus pneumoniae* Bacteriophage Cp–1", Journal of Virology, 70:3678–3687, 1996.

McDonnell et al., "Diplophage": A Bacteriophage of *Diplococcus pneumoniae* , Virology, 63:577–582, 1975.

Nardese et al., "Disruption of the GTP–Cyclohidrolase I Gene In *Saccharomyces cerevisiae* ", Biochemical and Biophysical Research Communications, 218:273–279, 1996.

Neu, "The Crisis in Antibiotic Resistance", Science, 257:1064–1073, 1992.

Oskouian et al., "Repression And Catabolite Repression Of The Lactose Operon Of *Staphylococcus Aureus* ", J. Bacteriol, Jul., 172(7):3804–12, 1990.

Pickett et al., "Encapsidation of Heterologous RNAs by Bacteriophage MS2 Coat Protein", Nucleic Acids Research, 21:4621–4626, 1993.

Qin et al., "A Strategy for Rapid, High–Confidence Protein Identification", Anal. Chem., 69:3995–4001, 1997.

Qiu et al., "Dimerization by Translation Initiation Factor 2 Kinase GCN2 Is Mediated by Interactions in the C–Terminal Ribosome–Binding Region and the Protein Kinase Domain", Molecular and Cellular Biology, 18:2697–2711, 1998.

Reisinger et al., "Lambda Kil–Mediated Lysis Requirse the Phage Context", Virology, 193:1033–1036, 1993.

Rost et al., "Bridging The Protein Sequence–Structure Gap By Structure Predictions", Annu. Rev.Biophys, Biomol. Struct., 25:113–36, 1996.

* cited by examiner

Functional assay on semi-solid support medium

Functional assay in liquid medium

Fig. 4A

3A ORFs tested for functional analysis

| UID | POS |
|---|---|
| 3AORF003 | 32266..34218 |
| 3AORF004 | 17529..19439 |
| 3AORF005 | 412..2103 |
| 3AORF006 | 15640..17223 |
| 3AORF007 | 19439..20905 |
| 3AORF009 | 40795..42162 |
| 3AORF010 | 2117..3346 |
| 3AORF011 | 4115..5278 |
| 3AORF012 | 30448..31614 |
| 3AORF013 | 13581..14807 |
| 3AORF014 | 14807..15631 |
| 3AORF015 | 3330..4103 |
| 3AORF016 | 26342..25656 |
| 3AORF017 | 6798..7439 |
| 3AORF018 | 24609..25223 |
| 3AORF019 | 31640..32197 |
| 3AORF021 | 24089..24604 |
| 3AORF022 | 12998..12492 |
| 3AORF023 | 7531..7986 |
| 3AORF025 | 42175..42612 |
| 3AORF026 | 35330..35740 |
| 3AORF027 | 34416..34817 |
| 3AORF028 | 5966..6367 |
| 3AORF029 | 6368..6763 |
| 3AORF030 | 20905..21294 |
| 3AORF031 | 28294..27914 |

| | |
|---|---|
| 3AORF032 | 28940..28575 |
| 3AORF033 | 30089..30451 |
| 3AORF034 | 8044..8394 |
| 3AORF036 | 5637..5969 |
| 3AORF037 | 117..422 |
| 3AORF038 | 29751..30074 |
| 3AORF040 | 42769..43083 |
| 3AORF041 | 21497..21796 |
| 3AORF044 | 17223..17513 |
| 3AORF045 | 40524..40814 |
| 3AORF046 | 5347..5625 |
| 3AORF053 | 26131..26361 |
| 3AORF054 | 28361..28606 |
| 3AORF055 | 36819..37064 |
| 3AORF059 | 37484..37684 |
| 3AORF063 | 27660..27448 |
| 3AORF067 | 28995..29210 |
| 3AORF070 | 26540..26752 |
| 3AORF076 | 40329..40129 |
| 3AORF077 | 27730..27927 |
| 3AORF079 | 34231..34416 |
| 3AORF088 | 27258..27407 |
| 3AORF089 | 21287..21451 |
| 3AORF097 | 5465..5602 |
| 3AORF130 | 25345..25220 |
| 3AORF137 | 41951..42055 |

Fig. 4B

77 ORFs tested for functional analysis

| UID | POSITION |
|---|---|
| 77ORF001 | 8481..13010 |
| 77ORF002 | 14507..18292 |
| 77ORF003 | 443..2104 |
| 77ORF004 | 13007..14491 |
| 77ORF005 | 19572..21026 |
| 77ORF006 | 3976..5196 |
| 77ORF007 | 23076..21871 |
| 77ORF008 | 2120..3307 |
| 77ORF009 | 32803..31946 |
| 77ORF010 | 26092..26889 |
| 77ORF011 | 25208..24441 |
| 77ORF012 | 29788..30576 |
| 77ORF013 | 33620..34399 |
| 77ORF014 | 27760..28512 |
| 77ORF015 | 3291..4028 |
| 77ORF016 | 32867..33610 |
| 77ORF017 | 23982..23269 |
| 77ORF018 | 31169..31840 |
| 77ORF019 | 39851..40501 |
| 77ORF020 | 6926..7570 |
| 77ORF021 | 37762..38304 |
| 77ORF022 | 30605..31156 |
| 77ORF023 | 26903..27346 |
| 77ORF024 | 11140..10700 |
| 77ORF025 | 10147..9707 |
| 77ORF026 | 40729..41145 |
| 77ORF027 | 6518..6925 |
| 77ORF028 | 34795..35199 |
| 77ORF029 | 6117..6521 |
| 77ORF030 | 36478..36879 |
| 77ORF031 | 39151..39546 |
| 77ORF032 | 34266..33892 |
| 77ORF033 | 5758..6120 |
| 77ORF034 | 7886..8236 |
| 77ORF035 | 19258..19560 |
| 77ORF036 | 36876..37223 |
| 77ORF037 | 102..446 |
| 77ORF038 | 35219..34908 |
| 77ORF039 | 37220..37528 |
| 77ORF040 | 41377..41676 |
| 77ORF041 | 35454..35753 |
| 77ORF042 | 5490..5774 |
| 77ORF043 | 29304..29564 |
| 77ORF044 | 18481..18768 |
| 77ORF045 | 5216..5500 |
| 77ORF046 | 25663..25935 |
| 77ORF047 | 11425..11159 |
| 77ORF048 | 28776..29039 |
| 77ORF049 | 36013..36255 |
| 77ORF050 | 35753..36007 |

| | |
|---|---|
| 77ORF051 | 38931..39167 |
| 77ORF052 | 2013..1762 |
| 77ORF053 | 37521..37757 |
| 77ORF054 | 22818..23060 |
| 77ORF055 | 17788..17546 |
| 77ORF058 | 18892..19122 |
| 77ORF059 | 34564..34785 |
| 77ORF064 | 29574..29795 |
| 77ORF065 | 28528..28746 |
| 77ORF066 | 27703..27494 |
| 77ORF069 | 38341..38547 |
| 77ORF070 | 36269..36475 |
| 77ORF071 | 40498..40701 |
| 77ORF072 | 38735..38938 |
| 77ORF073 | 30945..31148 |
| 77ORF074 | 38544..38738 |
| 77ORF075 | 13870..13673 |
| 77ORF077 | 25357..25605 |
| 77ORF079 | 29089..29280 |
| 77ORF080 | 35204..35389 |
| 77ORF085 | 24242..24060 |
| 77ORF092 | 39876..39706 |
| 77ORF094 | 32226..32393 |
| 77ORF096 | 13773..13606 |
| 77ORF098 | 7092..7256 |
| 77ORF102 | 29051..29212 |
| 77ORF104 | 34393..34551 |
| 77ORF108 | 39692..39844 |
| 77ORF109 | 18282..18434 |
| 77ORF112 | 39543..39692 |
| 77ORF117 | 27361..27501 |
| 77ORF118 | 38390..38530 |
| 77ORF120 | 36199..36059 |
| 77ORF124 | 33699..33833 |
| 77ORF128 | 14355..14221 |
| 77ORF130 | 15675..15806 |
| 77ORF133 | 8414..8542 |
| 77ORF140 | 13113..13235 |
| 77ORF147 | 7148..7029 |
| 77ORF149 | 30787..30668 |
| 77ORF151 | 31837..31953 |
| 77ORF155 | 30278..30391 |
| 77ORF157 | 4157..4044 |
| 77ORF167 | 20692..20799 |
| 77ORF175 | 35821..35717 |
| 77ORF176 | 6940..6836 |
| 77ORF178 | 35390..35491 |
| 77ORF179 | 8419..8318 |
| 77ORF182 | 29268..29564 |

Fig. 4C

96 ORFs tested for functional analysis

| UID | POS |
|---|---|
| 96ORF007 | 18617..20041 |
| 96ORF008 | 8910..10151 |
| 96ORF009 | 17397..18620 |
| 96ORF011 | 1118..69 |
| 96ORF013 | 21875..22789 |
| 96ORF015 | 7802..8557 |
| 96ORF017 | 28950..28231 |
| 96ORF019 | 21274..21858 |
| 96ORF020 | 24486..25043 |
| 96ORF023 | 14431..14964 |
| 96ORF024 | 15540..15034 |
| 96ORF027 | 16943..17404 |
| 96ORF029 | 23598..24047 |
| 96ORF030 | 13134..13565 |
| 96ORF031 | 24060..24485 |
| 96ORF034 | 27882..27478 |
| 96ORF035 | 12554..12946 |
| 96ORF039 | 25251..25616 |
| 96ORF040 | 11463..11822 |
| 96ORF041 | 22950..23300 |
| 96ORF042 | 8557..8913 |
| 96ORF043 | 29692..30048 |
| 96ORF044 | 23303..23647 |

| | |
|---|---|
| 96ORF046 | 21026..20832 |
| 96ORF048 | 4952..5212 |
| 96ORF052 | 36274..36573 |
| 96ORF055 | 13973..14254 |
| 96ORF059 | 42741..42947 |
| 96ORF061 | 11194..11451 |
| 96ORF066 | 20965..21171 |
| 96ORF074 | 35153..35374 |
| 96ORF078 | 10148..10363 |
| 96ORF079 | 15164..15373 |
| 96ORF080 | 12082..12282 |
| 96ORF081 | 23857..24057 |
| 96ORF089 | 42962..43162 |
| 96ORF093 | 13799..13972 |
| 96ORF094 | 12943..13134 |
| 96ORF097 | 15001..15189 |
| 96ORF100 | 11008..11193 |
| 96ORF102 | 29513..29695 |
| 96ORF114 | 14255..14416 |
| 96ORF132 | 22798..22944 |
| 96ORF186 | 42270..42169 |
| 96ORF217 | 15050..15151 |

| | | Semi-solid support media | | |
|---|---|---|---|---|
| ORF ID | *Staphylococcus aureus* transformants | Without induction | | With induction (5uM sodium arsenite) |
| 3AORF33 | Clone 1 |  | |  |
| | Clone 2 |  | |  |
| | Clone 3 |  | |  |
| | | | | |
| 3AORF41 | Clone 1 |  | |  |
| | Clone 2 |  | |  |
| | Clone 3 |  | |  |
| | | | | |
| 3AORF79 | Clone 1 |  | |  |
| | Clone 2 |  | |  |
| | Clone 3 |  | |  |
| | | | | |
| 3AORF93 | Clone 1 |  | |  |
| | Clone 2 |  | |  |
| | Clone 3 |  | |  |
| | | | | |

| | | Semi-solid support media | | |
|---|---|---|---|---|
| ORF ID | *Staphylococcus aureus* transformants | Without induction | | With induction (5uM sodium arsenite) |
| 77ORF1 | Clone 1 |  | |  |
| | Clone 2 |  | |  |
| | Clone 3 |  | |  |
| | | | | |
| 96ORF48 | Clone 1 |  | |  |
| | Clone 2 |  | |  |
| | Clone 3 |  | |  |
| | | | | |
| 96ORF100 | Clone 1 |  | |  |
| | Clone 2 |  | |  |
| | Clone 3 |  | |  |
| | | | | |
| control 44AHJD ORF114 | Clone 1 |  | |  |
| | | | | |

DNA SEQUENCES FROM *STAPHYLOCOCUS AUREUS* BACTERIOPHAGES 3A, 77, AND 96 THAT ENCODE ANTI-MICROBIAL POLYPEPTIDES

RELATED APPLICATIONS

This application is a continuation in part of U.S. application Ser. No. 09/407,804 filed Sep. 28, 1999, entitled DNA SEQUENCES FROM *STAPHYLOCCUS AUREUS* BACTERIOPHAGE 77 THAT ENCODE ANTI-MICROBIAL POLYPEPTIDES, which claims the benefit of U.S. Provisional Application No. 60/110,992 filed Dec. 3, 1998 entitled DEVELOPMENT OF NOVEL ANTIMICROBIAL AGENTS BASED ON BACTERIOPHAGE GENOMICS, both of which are hereby incorporated by reference in its entirety, including drawings.

BACKGROUND OF THE INVENTION

This invention relates to the identification of antimicrobial agents and of microbial targets of such agents, and in particular to the isolation of bacteriophage DNA sequences, and their translated protein products, showing anti-microbial activity. The DNA sequences can be expressed in expression vectors. These expression constructs and the proteins produced therefrom can be used for a variety of purposes including therapeutic methods and identification of microbial targets.

The following description is provided to assist the understanding of the reader. None of the information provided or references cited is admitted to be prior art to the present invention.

The frequency and spectrum of antibiotic-resistant infections have, in recent years, increased in both the hospital and community. Certain infections have become essentially untreatable and are growing to epidemic proportions in the developing world as well as in institutional settings in the developed world. The staggering spread of antibiotic resistance in pathogenic bacteria has been attributed to microbial genetic characteristics, widespread use of antibiotic drugs and changes in society that enhance the transmission of drug-resistant organisms (for a review, see Cohen, 1992). This spread of drug resistant microbes is leading to ever-increasing morbidity, mortality and health-care costs.

There are over 160 antibiotics currently available for treatment of microbial infections, all based on a few basic chemical structures and targeting a small number of metabolic pathways: bacterial cell wall synthesis, protein synthesis, and DNA replication. Despite all these antibiotics, a person could succumb to an infection as a result of a resistant bacterial infection. Resistance now reaches all classes of antibiotics currently in use, including: β-lactams, fluoroquinolones, aminoglycosides, macrolide peptides, chloramphenicol, tetracyclines, rifampicin, folate inhibitors, glycopeptides, and mupirocin. There is thus a need for new antibiotics, and this need will not subside given the ability bacteria have to overcome each new agent synthesized. It is also likely that targeting new pathways will play an important role in discovery of these new antibiotics. In fact, a number of crucial cellular pathways, such as secretion, cell division, and many metabolic functions, remain untargeted today.

Most major pharmaceutical companies have on-going drug discovery programs for novel anti-microbials. These are based on screens for small molecule inhibitors (e.g., natural products, bacterial culture media, libraries of small molecules, combinatorial chemistry) of crucial metabolic pathways of the micro-organism of interest. The screening process is largely for cytotoxic compounds and in most cases is not based on a known mechanism of action of the compounds. Classical drug screening programs are being exhausted and many of these pharmaceutical companies are looking towards rational drug design programs. Several small to mid-size biotechnology companies, as well as large pharmaceutical companies, have developed systematic high-throughput sequencing programs to decipher the genetic code of specific micro-organisms of interest. The goal is to identify, through sequencing, unique biochemical pathways or intermediates that are unique to the microorganism. Knowledge of the function of these bacterial genes, may form the rationale for a drug discovery program based on the mechanism of action of the identified enzymes/proteins. However, one of the most critical steps in this approach is the ascertainment that the identified proteins and biochemical pathways are 1) non-redundant and essential for bacterial survival, and 2) constitute suitable and accessible targets for drug discovery. These two issues are not easily addressed since to date, 18 prokaryotic genomes have been sequenced and 200 sequenced genomes are expected by the year 2000. For a majority of the sequenced genomes, less than 50% of the open reading frames (ORFs) have been linked to a known function. Even with the genome of *Escherichia coli* (*E. coli*), the most extensively studied bacterium, less than two-thirds of the annotated protein coding genes showed significant similarity to genes with ascribed functions (Rusterholtz and Pohlschroder, 1999). Thus considerable work must be undertaken to identify appropriate bacterial targets for drug screening.

SUMMARY OF THE INVENTION

The present invention is based on the identification of, and demonstration that, specific DNA sequences of a bacteriophage, when introduced into a host bacterium can kill, or inhibit growth, of the host. Thus, these DNA sequences are anti-microbial agents. Information based on these DNA sequences can be utilized to develop peptide mimetics that can also function as anti-microbials. The identification of the host bacterial proteins, targeted by the anti-microbial bacteriophage DNA sequences, can provide novel targets for drug design and compound screening.

In this regard, the terms "inhibit", "inhibition", "inhibitory", and "inhibitor" all refer to a function of reducing a biological activity or function. Such reduction in activity or function can, for example, be in connection with a cellular component (e.g., an enzyme), or in connection with a cellular process (e.g., synthesis of a particular protein), or in connection with an overall process of a cell (e.g., cell growth). In reference to cell growth, the inhibitory effects may be bactericidal (killing of bacterial cells) or bacteriostatic (i.e., stopping or at least slowing bacterial cell growth). The latter slows or prevents cell growth such that fewer cells of the strain are produced relative to uninhibited cells over a given time period. From a molecular standpoint, such inhibition may equate with a reduction in the level of, or elimination of, the transcription and/or translation of a specific bacterial target(s), or reduction or elimination of activity of a particular target biomolecule.

In a first aspect the invention provides methods for identifying a target for antibacterial agents by identifying the bacterial target(s) of at least one inhibitory gene product, e.g., protein from ORFs 33, 41, 79 of bacteriophage 3A, ORF 1 of bacteriophage 77 and ORFs 48, 78, 100 of bacteriophage 96 or a homologous product. Such identification allows the development of antibacterial agents active on such targets. Preferred embodiments for identifying such targets involve the identification of binding of target and phage ORF products to one another. The target molecule may be a bacterial protein or other bacterial biomolecule, e.g., a nucleotprotein, a nucleic acid, a lipid or lipid-containing molecule, a nucleoside or nucleoside derivative, a polysaccharide or polysaccharide-containing molecule, or a peptidoglycan. The phage ORF products may be subportions of a larger ORF product that also binds the host target. Exemplary approaches are described below in the Detailed Description.

Additionally, the invention provides methods for identifying targets for antibacterial agents by identifying homologs of a *Staphylococcus aureus* target of a bacteriophage 3A ORF product, for example, ORFs 33, 41 or 79, bacteriophage 77 ORF product, such as for example, ORF 1 or bacteriophage 96 ORF products, such as for example, ORFs 48, 78, or 100 product. Such homologs may be utilized in the various aspects and embodiments described herein.

The term "fragment" refers to a portion of a larger molecule or assembly. For proteins, the term "fragment" refers to a molecule which includes at least 5 contiguous amino acids from the reference polypeptide or protein, preferably at least 6, 8, 10, 12, 15, 20, 30, 50 or more contiguous amino acids. In connection with oligo- or polynucleotides, the term "fragment" refers to a molecule which includes at least 15 contiguous nucleotides from a reference polynucleotide, preferably at least 18, 21, 24, 30, 36, 45, 60, 90, 150, or more contiguous nucleotides. Also in preferred embodiments, the fragment has a length in a range with the minimum as described above and a maximum which is no more than 90% of the length (or contains that percent of the contiguous amino acids or nucleotides) of the larger molecule (e.g., of the specified ORF), in other embodiments, the upper limit is no more than 60, 70, or 80% of the length of the larger molecule.

Stating that an agent or compound is "active on" a particular cellular target, such as the product of a particular gene, means that the target is an important part of a cellular pathway which includes that target and that the agent acts on that pathway. Thus, in some cases the agent may act on a component upstream or downstream of the stated target, including a regulator of that pathway or a component of that pathway. In general, an antibacterial agent is active on an essential cellular function, often on a product of an essential gene.

By "essential", in connection with a gene or gene product, is meant that the host cannot survive without, or is significantly growth compromised, in the absence or depletion of functional product. An "essential gene" is thus one that encodes a product that is beneficial, or preferably necessary, for cellular growth in vitro in a medium appropriate for growth of a strain having a wild-type allele corresponding to the particular gene in question. Therefore, if an essential gene is inactivated or inhibited, that cell will grow significantly more slowly or even not at all. Preferably growth of a strain in which such a gene has been inactivated will be less than 20%, more preferably less than 10%, most preferably less than 5% of the growth rate of the wild-type, or not at all, in the growth medium. Preferably, in the absence of activity provided by a product of the gene, the cell will not grow at all or will be non-viable, at least under culture conditions similar to normal in vivo growth conditions. For example, absence of the biological activity of certain enzymes involved in bacterial cell wall synthesis can result in the lysis of cells under normal osmotic conditions, even though protoplasts can be maintained under controlled osmotic conditions. Preferably, but not necessarily, if such a gene is inhibited, e.g., with an antibacterial agent or a phage product, the growth rate of the inhibited bacteria will be less than 50%, more preferably less than 30%, still more preferably less than 20%, and most preferably less than 10% of the growth rate of the uninhibited bacteria. As recognized by those skilled in the art, the degree of growth inhibition will generally depend on the concentration of the inhibitory agent. In the context of the invention, essential genes are generally the preferred targets of antimicrobial agents. Essential genes can encode target molecules directly or can encode a product involved in the production, modification, or maintenance of a target molecule.

A "target" refers to a biomolecule that can be acted on by an exogenous agent, thereby modulating, preferably inhibiting, growth or viability of a cell. In most cases such a target will be a nucleic acid sequence or molecule, or a polypeptide or protein. However, other types of biomolecules can also be targets, e.g., membrane lipids and cell wall structural components.

The term "bacterium" refers to a single bacterial strain, and includes a single cell, and a plurality or population of cells of that strain unless clearly indicated to the contrary. In reference to bacteria or bacteriophage, the term "strain" refers to bacteria or phage having a particular genetic content. The genetic content includes genomic content as well as recombinant vectors. Thus, for example, two otherwise identical bacterial cells would represent different strains if each contained a vector, e.g., a plasmid, with different phage ORF inserts.

In the context of the phage nucleic acid sequences, e.g., gene sequences, of this invention, the terms "homolog" and "homologous" denote nucleotide sequences from different bacteria or phage strains or species or from other types of organisms that have significantly related nucleotide sequences, and consequently significantly related encoded gene products, preferably having related function. Homologous gene sequences or coding sequences have at least 70% sequence identity (as defined by the maximal base match in a computer-generated alignment of two or more nucleic acid sequences) over at least one sequence window of 48 nucleotides (or at least 99, 150, 200, or even the entire ORF or other sequence of interest), more preferably at least 80 or 85%, still more preferably at least 90%, and most preferably at least 95%. The polypeptide products of homologous genes have at least 35% amino acid sequence identity over at least one sequence window of 18 amino acid residues (or 24, 30, 33, 50, 100, or an entire polypeptide), more preferably at least 40%, still more preferably at least 50% or 60%, and most preferably at least 70%, 80%, or 90%. Preferably, the homologous gene product is also a functional homolog, meaning that the homolog will functionally complement one or more biological activities of the product being compared. For nucleotide or amino acid sequence comparisons where a homology is defined by a % sequence identity, the percentage is determined using BLAST programs (with default parameters (Altschul et al., 1997, "Gapped BLAST and PSI-BLAST: a new generation of protein database search programs, Nucleic Acid Res. 25:3389–3402). Any of a variety of algorithms known in the art which provide comparable results can also be used, preferably using default parameters. Performance characteristics for three different algorithms in homology searching is described in Salamov et al., 1999, "Combining sensitive database searches with multiple intermediates to detect distant homologues." *Protein Eng.* 12:95–100. Another exemplary program package is the GCG™ package from the University of Wisconsin.

Homologs may also or in addition be characterized by the ability of two complementary nucleic acid strands to hybridize to each other under appropriately stringent conditions. Hybridizations are typically and preferably conducted with probe-length nucleic acid molecules, preferably 20–100 nucleotides in length. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g.,. Maniatis, T. et al. (1989) *Molecular Cloning: A Laboratory Manual*, Cold Spring Harbor University Press, Cold Spring, N.Y.; Ausubel, F. M. et al. (1994) *Current Protocols in Molecular Biology*. John Wiley & Sons, Secaucus, N.J. Homologs and homologous gene sequences may thus be identified using any nucleic acid sequence of interest, including the phage ORFs and bacterial target genes of the present invention.

A typical hybridization, for example, utilizes, besides the labeled probe of interest, a salt solution such as 6×SSC (NaCl and Sodium Citrate base) to stabilize nucleic acid strand interaction, a mild detergent such as 0.5% SDS, together with other typical additives such as Denhardt's solution and salmon sperm DNA. The solution is added to the immobilized sequence to be probed and incubated at suitable temperatures to preferably permit specific binding while minimizing non-specific binding. The temperature of the incubations and ensuing washes is critical to the success and clarity of the hybridization. Stringent conditions employ relatively higher temperatures, lower salt concentrations, and/or more detergent than do non-stringent conditions. Hybridization temperatures also depend on the length, complementarity level, and nature (i.e., "GC content") of the sequences to be tested. Typical stringent hybridizations and washes are conducted at temperatures of at least 40° C., while lower stringency hybridizations and washes are typically conducted at 37° C. down to room temperature (~25° C.). One of ordinary skill in the art is aware that these conditions may vary according to the parameters indicated above, and that certain additives such as formamide and dextran sulphate may also be added to affect the conditions.

By "stringent hybridization conditions" is meant hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

Homologous nucleotide sequences will distinguishably hybridize with a reference sequence with up to three mismatches in ten (i.e., at least 70% base match in two sequences of equal length). Preferably, the allowable mismatch level is up to two mismatches in 10, or up to one mismatch in ten, more preferably up to one mismatch in twenty. (Those ratios can, of course, be applied to larger sequences.)

Preferred embodiments involve identification of binding between ORF product and bacterial cellular component that include methods for distinguishing bound molecules, for example, affinity chromatography, immunoprecipitation, crosslinking, and/or genetic screen methods that permit protein:protein interactions to be monitored. One of skill in the art is familiar with these techniques and common materials utilized (see, e.g., Coligan, J. et al. (eds.) (1995) *Current Protocols in Protein Science*, John Wiley & Sons, Secaucus, N.J.).

Genetic screening for the identification of protein:protein interactions typically involves the co-introduction of both a chimeric bait nucleic acid sequence (here, the phage ORF to be tested) and a chimeric target nucleic acid sequence that, when co-expressed and having affinity for one another in a host cell, stimulate reporter gene expression to indicate the relationship. A "positive" can thus suggest a potential inhibitory effect in bacteria. This is discussed in further detail in the Detailed Description section below. In this way, new bacterial targets can be identified that are inhibited by specific phage ORF products or derivatives, fragments, mimetics, or other molecules.

Other embodiments involve the identification and/or utilization of a target which is mutated at the site of phage 3A, 77 or 96 protein interaction but still functional in the cell by virtue of their host's relatively unresponsive nature in the presence of expression of ORFs previously identified as inhibitory to the non-mutant or wild-type strain. Such mutants have the effect of protecting the host from an inhibition that would otherwise occur by, for example, competing for binding with the phage ORF product and indirectly allow identification of the precise responsible target. The identified target can then be used for, for example, follow-up studies and anti-microbial development. In certain embodiments, rescue and/or protection from inhibition occurs under conditions in which a bacterial target or mutant target is highly expressed. This is performed, for example, through coupling of the sequence with regulatory element promoters, as known in the art, which regulate expression at levels higher than wild-type at, for example, a level sufficiently higher than the inhibitor can be competitively bound to the highly expressed target such that the bacterium is detectably less inhibited.

Identification of the bacterial target can involve identification of a phage-specific site of action. This can involve a newly identified target, or a target where the phage site of action differs from the site of action of a previously known antibacterial agent or inhibitor. For example, phage T7 genes 0.7 and 2.0 target the host RNA polymerase, which is also the cellular target for the antibacterial agent, rifampin. To the extent that a phage product is found to act at a different site than previously described inhibitors, aspects of the present invention can utilize those new, phage-specific sites for identification and use of new agents. The site of action can be identified by techniques known to those skilled in the art, for example, by mutational analysis, binding competition analysis, and/or other appropriate techniques.

Once a bacterial host target or mutant target sequence has been identified, it too can be conveniently sequenced, sequence analyzed (e.g., by computer), and the underlying gene(s), and corresponding translated product(s) further characterized. Preferred embodiments include such analysis and identification. Preferably such a target has not previously been identified as an appropriate target for antibacterial action.

Also in preferred embodiments in which the bacterial target is a polypeptide or nucleic acid molecule, the identification of a bacterial target of a phage ORF product or fragment includes identification of a cellular and/or biochemical function of the bacterial target. As understood by those skilled in the art, this can, for example, include identification of function by identification of homologous polypeptides or nucleic acid molecules having known function, or identification of the presence of known motifs or sequences corresponding to known function. Such identifications can be readily performed using sequence comparison computer software, such as the BLAST programs and similar other programs and sequence and motif databases.

In embodiments involving expression of a phage ORF in a bacterial strain, in preferred embodiments that expression is inducible. By "inducible" is meant that expression is absent or occurs at a low level until the occurrence of an appropriate environmental stimulus provides otherwise. For the present invention such induction is preferably controlled by an artificial environmental change, such as by contacting a bacterial strain population with an inducing compound (i.e., an inducer). However, induction could also occur, for example, in response to build-up of a compound produced by the bacteria in the bacterial culture, e.g., in the medium. As uncontrolled or constitutive expression of inhibitory ORFs can severely compromise bacteria to the point of eradication, such expression is therefore undesirable in many cases because it would prevent effective evaluation of the strain and inhibitor being studied. For example, such uncontrolled expression could prevent any growth of the strain following insertion of a recombinant ORF, thus preventing determination of effective transfection or transformation. A controlled or inducible expression is therefore advantageous and is generally provided through the provision of suitable regulatory elements, e.g., promoter/operator sequences that can be conveniently transcriptionally linked to a coding sequence to be evaluated. In most cases, the vector will also contain sequences suitable for efficient replication of the vector in the same or different host cells and/or sequences allowing selection of cells containing the vector, i.e., "selectable markers." Further, preferred vectors include convenient primer sequences flanking the cloning region from which PCR and/or sequencing may be performed. In preferred embodiments where the purification of phage product is desired, preferably the bacterium or other cell type does not produce a target for the inhibitory product, or is otherwise resistant to the inhibitory product.

In preferred embodiments, the target of the phage ORF product or fragment is identified from a bacterial animal pathogen, preferably a mammalian pathogen, more preferably a human pathogen, and is preferably a gene or gene product of such a pathogen. Also in preferred embodiments, the target is a gene or gene product, where the sequence of the target is homologous to a gene or gene product from such a pathogen as identified above.

As used herein, the term "mammal" has its usual biological meaning, and particularly includes bovines, swine, dogs, cats, and humans.

Other aspects of the invention provide isolated, purified, or enriched specific phage nucleic acid and amino acid sequences, subsequences, and homologs thereof from or corresponding to ORFs 33, 41 and 79 from bacteriophage 3A, ORF 1 from bacteriophage 77 or ORFs 48, 78 and 100 from bacteriophage 96 (*Staphylococcus aureus* host bacterium). Such nucleotide sequences are at least 15 nucleotides in length, preferably at least 18, 21, 24, or 27 nucleotides in length, more preferably at least 30, 50, or 90 nucleotides in length. In certain embodiments, longer nucleic acids are preferred, for example those of at least 120, 150, 200, 300, 600, 900 or more nucleotides. Such sequences can, for example, be amplification oligonucleotides (e.g., PCR primers), oligonucleotide probes, sequences encoding a portion or all of a phage-encoded protein, or a fragment or all of a phage-encoded protein. In preferred embodiments, the nucleic acid sequence or amino acid sequence contains a sequence which has a lower length as specified above, and an upper-length limit which is no more than 50, 60, 70, 80, or 90% of the length of the full-length ORF or ORF product. The upper-length limit can also be expressed in terms of the number of base pairs of the ORF (coding region).

As it is recognized that alternate codons will encode the same amino acid for most amino acids due to the degeneracy of the genetic code, the sequences of this aspect includes nucleic acid sequences utilizing such alternate codon usage for one or more codons of a coding sequence. For example, all four nucleic acid sequences GCT, GCC, GCA, and GCG encode the amino acid, alanine. Therefore, if for an amino acid there exists an average of three codons, a polypeptide of 100 amino acids in length will, on average, be encoded by $3^{100}$, or $5\times10^{47}$, nucleic acid sequences. Thus, a nucleic acid sequence can be modified (e.g., a nucleic acid sequence from a phage as specified above) to form a second nucleic acid sequence encoding the same polypeptide as encoded by the first nucleic acid sequence using routine procedures and without undue experimentation. Thus, all possible nucleic acid sequences that encode the amino acid sequences encoded by the phage 3A ORFs 33, 41, and 79, the phage 77 ORF 1 and the phage 96 ORF 48, 78 and 100 as if all were written out in full, taking into account the codon usage, especially that preferred in the host bacterium.

The alternate codon descriptions are available in common textbooks, for example, Stryer, BIOCHEMISTRY $3^{rd}$ ed., and Lehninger, BIOCHEMISTRY $3^{rd}$ ed. Codon preference tables for various types of organisms are available in the literature. Because of the number of sequence variations involving alternate codon usage, for the sake of brevity, individual sequences are not separately listed herein. Instead the alternate sequences are described by reference to the natural sequence with replacement of one or more (up to all) of the degenerate codons with alternate codons from the alternate codon table (Table 2), preferably with selection according to preferred codon usage for the normal host organism or a host organism in which a sequence is intended to be expressed. Those skilled in the art also understand how to alter the alternate codons to be used for expression in organisms where certain codons code differently than shown in the "universal" codon table.

For amino acid sequences, sequences contain at least 5 peptide-linked amino acid residues, and preferably at least 6, 7, 10, 15, 20, 30, or 40, amino acids having identical amino acid sequence as the same number of contiguous amino acid residues in a phage 3A ORF 33, 41, or 79, or phage 77 ORF 1, or phage 96 ORF 48, 78, or 100 product. In some cases longer sequences may be preferred, for example, those of at least 50, 70, or 100 amino acids in length. In preferred embodiments, the sequence has bacteria-inhibiting function when expressed or otherwise present in a bacterial cell which is a host for the bacteriophage from which the sequence was derived.

By "isolated" in reference to a nucleic acid is meant that a naturally occurring sequence has been removed from its normal cellular (e.g., chromosomal) environment or is synthesized in a non-natural environment (e.g., artificially synthesized). Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

The term "enriched" means that the specific DNA or RNA sequence constitutes a significantly higher fraction (2–5 fold) of the total DNA or RNA present in the cells or solution of interest than in normal or diseased cells or in cells from which the sequence was originally taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased.

The term "significant" is used to indicate that the level of increase is useful to the person making such an increase and an increase relative to other nucleic acids of about at least 2-fold, more preferably at least 5- to 10-fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation). Instead, it represents an indication that the sequence is relatively more pure than in the natural environment (compared to the natural level, this level should be at least 2–5 fold greater, e.g., in terms of mg/mL). Individual clones isolated from a genomic or cDNA library may be purified to electrophoretic homogeneity. The claimed DNA molecules obtained from these clones could be obtained directly from total DNA or from total RNA. cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated. A genomic library can be used in the same way and yields the same approximate levels of purification.

The terms "isolated", "enriched", and "purified" with respect to the nucleic acids, above, may similarly be used to denote the relative purity and abundance of polypeptides (multimers of amino acids joined one to another by $\alpha$-carboxyl:$\alpha$-amino group (peptide) bonds). These, too, may be stored in, grown in, screened in, and selected from libraries using biochemical techniques familiar in the art. Such polypeptides may be natural, synthetic or chimeric and may be extracted using any of a variety of methods, such as antibody immunoprecipitation, other "tagging" techniques, conventional chromatography and/or electrophoretic methods. Some of the above utilize the corresponding nucleic acid sequence.

As indicated above, aspects and embodiments of the invention are not limited to entire genes and proteins. The invention also provides and utilizes fragments and portions thereof, preferably those which are "active" in the inhibitory sense described above. Such peptides or oligopeptides and oligo or polynucleotides have preferred lengths as specified above for nucleic acid and amino acid sequences from phage; corresponding recombinant constructs can be made to express the encoded same. Also included are homologous sequences and fragments thereof.

The nucleotide and amino acid sequences identified herein are believed to be correct, however, certain sequences may contain a small percentage of errors, e.g., 1–5%. In the event that any of the sequences have errors, the corrected sequences can be readily provided by one skilled in the art using routine methods. For example, the nucleotide sequences can be confirmed or corrected by obtaining and culturing the relevant phage, and purifying phage genomic nucleic acids. A region or regions of interest can be amplified, e.g., by PCR from the appropriate genomic template, using primers based on the described sequence. The amplified regions can then be sequenced using any of the available methods (e.g., a dideoxy termination method, for example, using commercially available products). This can be done redundantly to provide the corrected sequence or to confirm that the described sequence is correct. Alternatively, a particular sequence or sequences can be identified and isolated as an insert or inserts in a phage genomic library and isolated, amplified, and sequenced by standard methods. Confirmation or correction of a nucleotide sequence for a phage gene provides an amino acid sequence of the encoded product by merely reading off the amino acid sequence according to the normal codon relationships and/or expressed in a standard expression system and the polypeptide product sequenced by standard techniques. The sequences described herein thus provide unique identification of the corresponding genes and other sequences, allowing those sequences to be used in the various aspects of the present invention. Confirmation of a phage ORF encoded amino acid sequence can also be confirmed by constructing a recombinant vector from which the ORF can be expressed in an appropriate host (e.g., *E. coli*), purified, and sequenced by conventional protein sequencing methods.

In other aspects the invention provides recombinant vectors and cells harboring phage 3A ORF 33, 41, or 79, or phage 77 ORF 1, or phage 96 ORF 48, 78, or 100 or portions thereof, or bacterial target sequences described herein, preferably where the phage or bacterial sequence is inserted in a recombinant vector. As understood by those skilled in the art, vectors may assume different forms, including, for example, plasmids, cosmids, and virus-based vectors. See, e.g., Maniatis, T. et al. (1989) *Molecular Cloning: A Laboratory Manual*, Cold Spring Harbor University Press, Cold Spring, N.Y.; See also, Ausubel, F. M. et al. (eds.) (1994) *Current Protocols in Molecular Biology*. John Wiley & Sons, Secaucus, N.J.

In preferred embodiments, the vectors will be expression vectors, preferably shuttle vectors that permit cloning, replication, and expression within bacteria. An "expression vector" is one having regulatory nucleotide sequences containing transcriptional and translational regulatory information that controls expression of the nucleotide sequence in a host cell. Preferably the vector is constructed to allow amplification from vector sequences flanking an insert locus. In certain embodiments, the expression vectors may additionally or alternatively support expression, and/or replication in animal, plant and/or yeast cells due to the presence of suitable regulatory sequences, e.g., promoters, enhancers, 3' stabilizing sequences, primer sequences, etc. In preferred embodiments, the promoters are inducible and specific for the system in which expression is desired, e.g., bacteria, animal, plant, or yeast. The vectors may optionally encode a "tag" sequence or sequences to facilitate protein purification or protein detection. Convenient restriction enzyme cloning sites and suitable selective marker(s) are also optionally included. Such selective markers can be, for example, antibiotic resistance markers or markers which supply an essential nutritive growth factor to an otherwise deficient mutant host, e.g., tryptophan, histidine, or leucine in the Yeast Two-Hybrid systems described below.

The term "recombinant vector" relates to a single- or double-stranded circular nucleic acid molecule that can be transfected into cells and replicated within or independently of a cell genome. A circular double-stranded nucleic acid molecule can be cut and thereby linearized upon treatment with appropriate restriction enzymes. An assortment of nucleic acid vectors, restriction enzymes, and the knowledge of the nucleotide sequences cut by restriction enzymes are readily available to those skilled in the art. A nucleic acid molecule encoding a desired product can be inserted into a vector by cutting the vector with restriction enzymes and ligating the two pieces together. Preferably the vector is an expression vector, e.g., a shuttle expression vector as described above.

By "recombinant cell" is meant a cell possessing introduced or engineered nucleic acid sequences, e.g., as described above. The sequence may be in the form of or part of a vector or may be integrated into the host cell genome. Preferably the cell is a bacterial cell.

In preferred embodiments, the inserted nucleic acid sequence corresponding to at least a portion of a phage 3A ORF 33, 41, and 79, phage 77 ORF 1 and phage 96 ORF48, 78, and 100 gene product has a length as specified for the isolated purified or enriched nucleic acid sequences in an aspect above.

In another aspect, the invention also provides methods for identifying and/or screening compounds "active on" at least one bacterial target of a bacteriophage inhibitor protein or RNA. Preferred embodiments involve contacting bacterial target proteins with a test compound, and determining whether the compound binds to or reduces the level of activity of the bacterial target, e.g., a bacterial protein. Preferably this is done in vivo under approximately physiological conditions. The compounds that can be used may be large or small, synthetic or natural, organic or inorganic, proteinaceous or non-proteinaceous. In preferred embodiments, the compound is a peptidomimetic, as described herein, a bacteriophage inhibitor protein or fragment or derivative thereof, preferably an "activeportion", or a small molecule. In particular embodiments, the methods include the identification of bacterial targets as described above or otherwise described herein. Preferably the fragment of a bacteriophage inhibitor protein includes less than 80% of an intact bacteriophage inhibitor protein. Preferably, the at least one target includes a plurality of different targets of bacteriophage inhibitor proteins, preferably a plurality of different targets. The plurality of targets can be in or from a plurality of different bacteria, but preferably is from a single bacterial species.

In embodiments involving binding assays, preferably binding is to a fragment or portion of a bacterial target protein, where the fragment includes less than 90%, 80%, 70%, 60%, 50%, 40%, or 30% of an intact bacterial target protein. Preferably, the at least one bacterial target includes a plurality of different targets of bacteriophage inhibitor proteins, preferably a plurality of different targets. The plurality of targets can be in or from a plurality of different bacteria, but preferably is from a single bacterial species.

A "method of screening" refers to a method for evaluating a relevant activity or property of a large plurality of compounds, rather than just one or a few compounds. For example, a method of screening can be used to conveniently test at least 100, more preferably at least 1000, still more preferably at least 10,000, and most preferably at least 100,000 different compounds, or even more.

In the context of this invention, the term "small molecule" refers to compounds having molecular mass of less than 3000 Daltons, preferably less than 2000 or 1500, still more preferably less than 1000, and most preferably less than 600 Daltons. Preferably but not necessarily, a small molecule is not an oligopeptide.

In a related aspect or in preferred embodiments, the invention provides a method of screening for potential antibacterial agents by determining whether any of a plurality of compounds, preferably a plurality of small molecules, is active on at least one target of a bacteriophage inhibitor protein or RNA. Preferred embodiments include those described for the above aspect, including embodiments which involve determining whether one or more test compounds bind to or reduce the level of activity of a bacterial target, and embodiments which utilize a plurality of different targets as described above.

The identification of bacteria-inhibiting phage ORFs and their encoded products also provides a method for identifying an active portion of such an encoded product. This also provides a method for identifying a potential antibacterial agent by identifying such an active portion of a phage ORF or ORF product. In preferred embodiments, the identification of an active portion involves one or more of mutational analysis, deletion analysis, or analysis of fragments of such products. The method can also include determination of a 3-dimensional structure of an active portion, such as by analysis of crystal diffraction patterns. In further embodiments, the method involves constructing or synthesizing a peptidomimetic compound, where the structure of the peptidomimetic compound corresponds to the structure of the active portion.

In this context, "corresponds" means that the peptidomimetic compound structure has sufficient similarities to the structure of the active portion that the peptidomimetic will interact with the same molecule as the phage protein and preferably will elicit at least one cellular response in common which relates to the inhibition of the cell by the phage protein.

The methods for identifying or screening for compounds or agents active on a bacterial target of a phage-encoded inhibitor can also involve identification of a phage-specific site of action on the target.

An "active portion" as used herein denotes an epitope, a catalytic or regulatory domain, or a fragment of a bacteriophage inhibitor protein that is responsible for, or a significant factor in, bacterial target inhibition. The active portion preferably may be removed from its contiguous sequences and, in isolation, still effect inhibition.

By "mimetic" is meant a compound structurally and functionally related to a reference compound that can be natural, synthetic, or chimeric. In terms of the present invention, a "peptidomimetic," for example, is a compound that mimics the activity-related aspects of the 3-dimensional structure of a peptide or polypeptide in a non-peptide compound, for example mimics the structure of a peptide or active portion of a phage- or bacterial ORF-encoded polypeptide.

A related aspect provides a method for inhibiting a bacterial cell by contacting the bacterial cell with a compound active on a bacterial target of a bacteriophage inhibitor protein or RNA encoded by bacteriophage 3A ORF 33, 41, or 79, bacteriophage 77 ORF 1, or bacteriophage 96 ORF 48, 78, or 100, where the target was uncharacterized. In preferred embodiments, the compound is such a protein, or a fragment or derivative thereof; a structural mimetic, e.g., a peptidomimetic, of such a protein or fragment; a small molecule; the contacting is performed in vitro, the contacting is performed in vivo in an infected or at risk organism, e.g., an animal such as a mammal or bird, for example, a human, or other mammal described herein, or in a plant.

In the context of this invention, the term "bacteriophage inhibitor protein" refers to a protein encoded by a bacteriophage nucleic acid sequence which inhibits bacterial function in a host bacterium. Thus, it is a bacteria-inhibiting phage product.

In the context of this invention, the phrase "contacting the bacterial cell with a compound active on a bacterial target of a bacteriophage inhibitor protein" or equivalent phrases refer to contacting with an isolated, purified, or enriched compound or a composition including such a compound, but specifically does not rely on contacting the bacterial cell with an intact naturally occurring phage which encodes the compound. Preferably no intact phage are involved in the contacting.

Related aspects provide methods for prophylactic or therapeutic treatment of a bacterial infection by administering to an infected, challenged or at risk organism a therapeutically or prophylactically effective amount of a compound active on a target of a bacteriophage 3A ORF 33, 41, or 79, bacteriophage 77 ORF 1, or bacteriophage 96 ORF 48, 78, or 100 product, e.g., as described for the previous aspect. Preferably the bacterium involved in the infection or risk of infection produces the identified target of the bacteriophage inhibitor protein or alternatively produces a homologous target compound. In preferred embodiments, the host organism is a plant or animal, preferably a mammal or bird, and more preferably, a human or other mammal described herein. Preferred embodiments include, without limitation, those as described for the preceding aspect.

Compounds useful for the methods of inhibiting, methods of treating, and pharmaceutical compositions can include novel compounds, but can also include compounds which had previously been identified for a purpose other than inhibition of bacteria. Such compounds can be utilized as described and can be included in pharmaceutical compositions.

By "treatment" or "treating" is meant administering a compound or pharmaceutical composition for prophylactic and/or therapeutic purposes. The term "prophylactic treatment" refers to treating a patient or animal that is not yet infected but is susceptible to or otherwise at risk of a bacterial infection. The term "therapeutic treatment" refers to administering treatment to a patient already suffering from infection.

The term "bacterial infection" refers to the invasion of the host organism, animal or plant, by pathogenic bacteria. This includes the excessive growth of bacteria which are normally present in or on the body of the organism, but more generally, a bacterial infection can be any situation in which the presence of a bacterial population(s) is damaging to a host organism. Thus, for example, an organism suffers from a bacterial infection when excessive numbers of a bacterial population are present in or on the organism's body, or when the effects of the presence of a bacterial population(s) is damaging to the cells, tissue, or organs of the organism.

The terms "administer", "administering", and "administration" refer to a method of giving a dosage of a compound or composition, e.g., an antibacterial pharmaceutical composition, to an organism. Where the organism is a mammal, the method is, e.g., topical, oral, intravenous, transdermal, intraperitoneal, intramuscular, or intrathecal. The preferred method of administration can vary depending on various factors, e.g., the components of the pharmaceutical composition, the site of the potential or actual bacterial infection, the bacterium involved, and the infection severity.

The term "mammal" has its usual biological meaning, referring to any organism of the Class Mammalia of higher vertebrates that nourish their young with milk secreted by mammary glands, e.g., mouse, rat, and, in particular, human, bovine, sheep, swine, dog, and cat.

In the context of treating a bacterial infection a "therapeutically effective amount" or "pharmaceutically effective amount" indicates an amount of an antibacterial agent, e.g., as disclosed for this invention, which has a therapeutic effect. This generally refers to the inhibition, to some extent, of the normal cellular functioning of bacterial cells that renders or contributes to bacterial infection.

The dose of antibacterial agent that is useful as a treatment is a "therapeutically effective amount." Thus, as used herein, a therapeutically effective amount means an amount of an antibacterial agent that produces the desired therapeutic effect as judged by clinical trial results and/or animal models. This amount can be routinely determined by one skilled in the art and will vary depending on several factors, such as the particular bacterial strain involved and the particular antibacterial agent used.

In connection with claims to methods of inhibiting bacteria and therapeutic or prophylactic treatments, "a compound active on a target of a bacteriophage inhibitor protein" or terms of equivalent meaning differ from administration of or contact with an intact phage naturally encoding the full-length inhibitor compound. While an intact phage may conceivably be incorporated in the present methods, the method at least includes the use of an active compound as specified different from a full length inhibitor protein naturally encoded by a bacteriophage and/or a delivery or contacting method different from administration of or contact with an intact phage naturally encoding the full-length protein. Similarly, pharmaceutical compositions described herein at least include an active compound or composition different from a phage naturally coding the full-length inhibitor protein, or such a full-length protein is provided in the composition in a form different from being encoded by an intact phage. Preferably the methods and compositions do not include an intact phage.

In accordance with the above aspects, the invention also provides antibacterial agents and compounds active on a bacterial target of bacteriophage 3A ORF 33, 41, or 79, bacteriophage 77 ORF 1, or bacteriophage 96 ORF 48, 78, or 100, where the target was uncharacterized as indicated above. As previously indicated, such active compounds include both novel compounds and compounds which had previously been identified for a purpose other than inhibition of bacteria. Such previously identified biologically active compounds can be used in embodiments of the above methods of inhibiting and treating. In preferred embodiments, the targets, bacteriophage, and active compound are as described herein for methods of inhibiting and methods of treating. Preferably the agent or compound is formulated in a pharmaceutical composition which includes a pharmaceutically acceptable carrier, excipient, or diluent. In addition, the invention provides agents, compounds, and pharmaceutical compositions where an active compound is active on an uncharacterized phage-specific site on the target.

In preferred embodiments, the target is as described for embodiments of aspects above.

Likewise, the invention provides a method of making an antibacterial agent. The method involves identifying a target of a bacteriophage 3A ORF 33, 41, or 79, bacteriophage 77 ORF 1, or bacteriophage 96 ORF 48, 78, or 100 product, screening a plurality of compounds to identify a compound active on the target, and synthesizing the compound in an amount sufficient to provide a therapeutic effect when administered to an organism infected by a bacterium naturally producing the target.

In preferred embodiments, the identification of the target and identification of active compounds include steps or methods and/or components as described above (or otherwise herein) for such identification. Likewise, the active compound can be as described above, including fragments and derivatives of phage inhibitor proteins, peptidomimetics, and small molecules. As recognized by those skilled in the art, peptides can be synthesized by expression systems and purified, or can be synthesized artificially by methods well known in the art.

In the context of nucleic acid or amino acid sequences of this invention, the term "corresponding" and "correspond" indicates that the sequence is at least 95% identical, preferably at least 97% identical, and more preferably at least 99% identical to a sequence from the specified phage genome or bacterial genome, a ribonucleotide equivalent, a degenerate equivalent (utilizing one or more degenerate codons), or a homologous sequence, where the homolog provides functionally equivalent biological function.

In embodiments where the bacterial target of a bacteriophage inhibitor ORF product, e.g., an inhibitory protein or polypeptide, the target is preferably encoded by a *S. aureus* nucleic acid coding sequence from a host bacterium for bacteriophages 3A, 77, or 96. Target sequences are described herein by reference to sequence source sites. The sequence encoding the target preferably corresponds to a *S. aureus* nucleic acid sequence available from numerous sources including *S. aureus* sequences deposited in GenBank, *S. aureus* sequences found in European Patent Application No. 97100110.7 to Human Genome Sciences, Inc. filed Jan. 7, 1997, *S. aureus* sequences available from TIGR at http://www.tigr.org/tdb/mdb/mdb.html, and *S. aureus* sequences available from the Oklahoma University *S. aureus* sequencing project at the following URL: http://www.genome.ou.edu/staph_new.html.

The amino acid sequence of a polypeptide target is readily provided by translating the corresponding coding region. For the sake of brevity, the sequences are not reproduced herein. Also, in preferred embodiments, a target sequence corresponds to a *S. aureus* coding sequences corresponding to a sequence listed in Table 7. The listings in Table 7 describe *S. aureus* sequences currently deposited in GenBank. Again, for the sake of brevity, the sequences are described by reference to the GenBank entries instead of being written out in full herein. In cases where an entry for a coding region is not complete, the complete sequence can be readily obtained by routine methods, by isolating a clone in a phages 3A, 77, and 96 host *S. aureus* genomic library, and sequencing the clone insert to provide the relevant coding region. The boundaries of the coding region can be identified by conventional sequence analysis and/or by expression in a bacterium in which the endogenous copy of the coding region has been inactivated and using subcloning to identify the functional start and stop codons for the coding region.

In an additional aspect, the present invention provides a nucleic acid segment which encodes a protein and corresponds to a segment of the nucleic acid sequence of an ORF (open reading frame) from *Staphylococcus aureus* bacteriophages 3A, 77 or 96 as provided in Table 1. Preferably, the protein is a functional protein. One of ordinary skill in the art would recognize that bacteriophage possess genes which encode proteins which may be either beneficial or detrimental to a bacterial cell. Such proteins act to replicate DNA, translate RNA, manipulate DNA or RNA, and enable the phage to integrate into the bacterial genome. Proteins from bacteriophage can function as, for example, a polymerase, kinase, phosphatase, helicase, nuclease, topoisomerase, endonuclease, reverse transcriptase, endoribonuclease, dehydrogenase, gyrase, integrase, carboxypeptidase, proteinase, amidase, transcriptional regulators and the like, and/or the protein may be a functional protein such as a chaperon, capsid protein, head and tail proteins, a DNA or RNA binding protein, or a membrane protein, all of which are provided as non-limiting examples. Proteins with functions such as these are useful as tools for the scientific community.

Thus, the present invention provides a group of novel proteins from bacteriophage which can be used as tools for biotechnical applications such as, for example, DNA and/or RNA sequencing, polymerase chain reaction and/or reverse transcriptase PCR, cloning experiments, cleavage of DNA and/or RNA, reporter assays and the like. Preferably, the protein is encoded by an open reading frame in the nucleic acid sequences of bacteriophages 3A, 77 or 96. Within the scope of the present invention are fragments of proteins and/or truncated portions of proteins which have been either engineered through automated protein synthesis, or prepared from nucleic acid segments which correspond to segments of the nucleic acid sequences of bacteriophages 3A, 77 or 96, and which are then inserted into cells via plasmid vectors which can be induced to express the protein. It is understood by one of skill in the art that mutational analysis of proteins has been known to help provide proteins which are more stable and which have higher and/or more specific activities. Such mutations are also within the scope of the present invention, hence, the present invention provides a mutated protein and/or the mutated nucleic acid segment from bacteriophages 3A, 77 or 96 which encodes the protein.

In another aspect, the invention provides antibodies which bind proteins encoded by a nucleic acid segment which corresponds to the nucleic acid sequence of an ORF (open reading frame) from *Staphylococcus aureus* bacteriophages 3A, 77 or 96 as provided in Table 1. Bacteriophages are bacterial viruses which contain nucleic acid sequences which encode proteins that can correspond to proteins of other bacteriophages and other viruses. Antibodies targeted for proteins encoded by nucleic acid segments of phages 3A, 77 or 96 can serve to bind targets encoded by nucleic acid segments from other viruses which correspond to the sequences provided in Table 1. Furthermore, antibodies to proteins encoded by nucleic acid segments of phages 3A, 77 or 96 can also bind to proteins from other viruses that share similar functions but may not share corresponding sequences. It is understood in the art that proteins with similar activities/functions from a variety of sources generally share motifs, regions, or domains which correspond. Thus, antibodies to motifs, regions, or domains of functional proteins from phages 3A, 77 or 96 should be useful in detecting corresponding proteins in other bacteriophages and viruses. Such antibodies can also be used to detect the presence of a virus sharing a similar protein. Preferably the virus to be detected is pathogenic to a mammal, such as a dog, cat, bovine, sheep, swine, or a human.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Additional features and embodiments of the present invention will be apparent from the following Detailed Description and from the claims, all within the scope of the present invention.

BRIEF DESCRIPTION OF THE DRAWINGS

FIG. 3 shows a schematic representation of the functional assays used to characterize the bactericidal and bacteriostatic potential of predicted ORFs (>33 amino acids) encoded by bacteriophages 3A, 77, 96.

DETAILED DESCRIPTION OF THE PREFERRED EMBODIMENTS

Figure 1A:
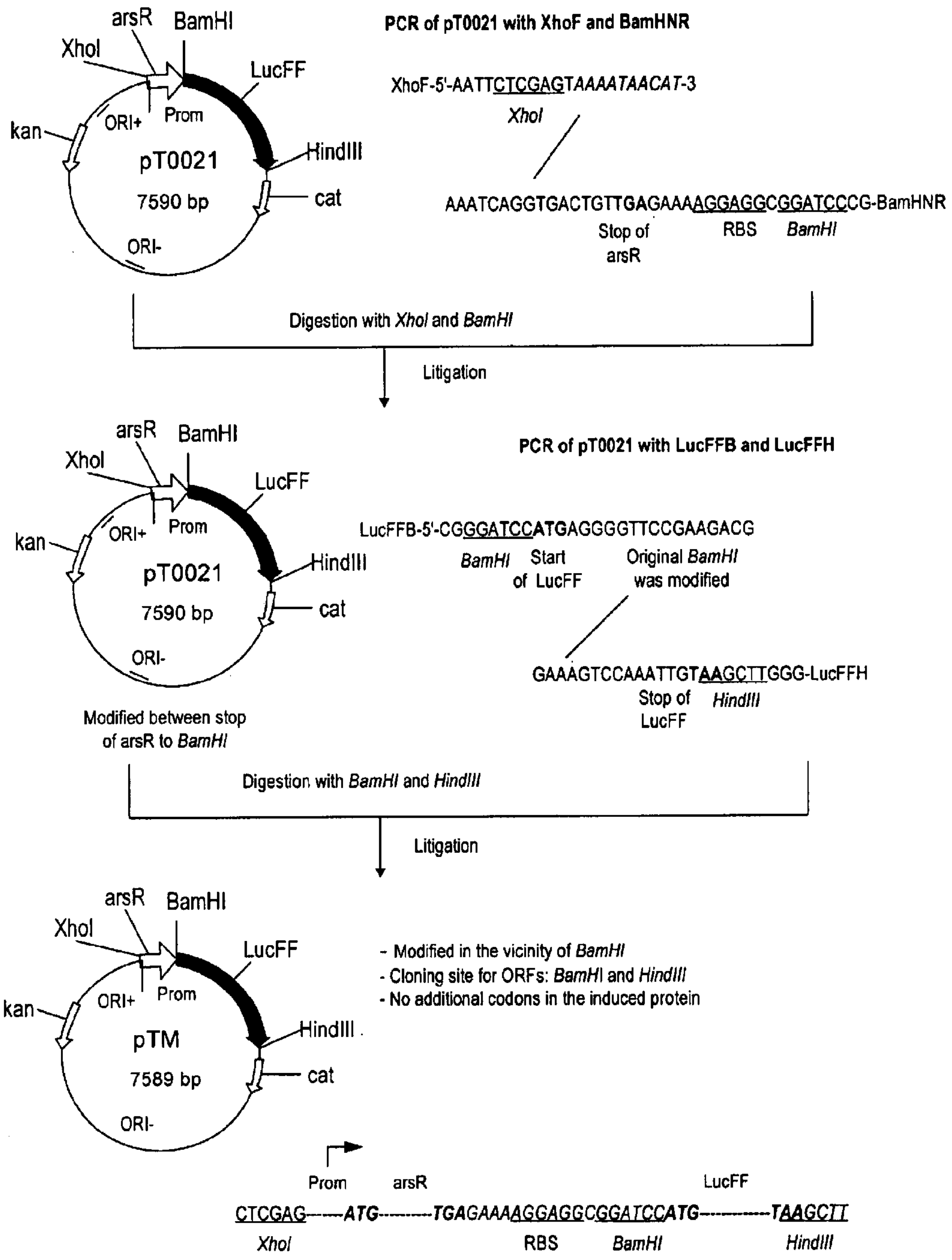
FIG. 1 are flow schematics showing the manipulations necessary to convert pT0021, an arsenite inducible vector containing the luciferase gene, into a) pTM, b) pTMSM or c) pTHA three ars inducible vectors. Vector pTM contains Bam HI and Hind III cloning sites. Vector pTMSM contains BamHI, SalI and MluI cloning sites. Vector pTHA contains BamHI and SalI cloning sites and a downstream HA epitope tag. This figure also shows in d), the characteristic of the lactose-inducible vector pTMSLac containing Bam HI and SalI cloning sites.

Preliminarily the tables will be briefly described.

Table 1 shows the complete nucleotide sequence of the genomes of *Staphylococcus aureus* bacteriophages 3A, 77 and 96.

Table 2 is a table from Alberts et al., MOLECULAR BIOLOGY OF THE CELL $3^{rd}$ ed., showing the redundancy of the "universal" genetic code.

Table 3 shows the nucleotide and predicted amino acid sequences of ORF 33, 41, and 79 from bacteriophage 3A, ORF1 from bacteriophage 77, and ORF 48, 78, and 100 from bacteriophage 96.

Table 4 shows the sequence similarities identified to date between ORFs predicted to be encoded by *Staphylococcus aureus* bacteriophages 3A, 77 and 96 and sequences present in the Genbank and Swissprot sequence databases. More specifically, these results indicate that: I) ORF 1 from phage 77 has significant homology to various genes in the NCBI non-redundant nucleotide database—such as the gene encoding for ORF 16 of the bacteriophage phi PVL, and II) ORF 48 from phage 96 has significant homology to one gene in the NCBI non-redundant nucleotide database—the gene encoding ORF 39 of the bacteriophage phi PVL.

Table 5 shows sequence alignment of phage 96 inhibitory ORFs with other identified inhibitory phage ORFs. The results of this search indicate that the inhibitory 96 ORF 100 has significant homology to the the inhibitory 3A ORF 79 and 96 ORF 48 has a significant homology to the previously identified phage 77 inhibitory ORFs 43 and 182.

Table 6 shows the physiochemical parameters of phage 3A ORF 33, 41, 79, phage 77 ORF 1 and phage 96 ORF 48, 78, 100. These include the primary amino acid sequence of the predicted protein, the average molecular weight, amino acid composition, theoretical pI and hydrophobicity properties.

Table 7 shows *S. aureus* coding sequences corresponding sequences currently deposited in GenBank.

The present invention is based on the identification of naturally-occurring DNA sequence elements encoding RNA or proteins with anti-microbial activity. Bacteriophages or phages, are viruses that infect and kill bacteria. They are natural enemies of bacteria and, over the course of evolution have perfected enzymes and proteins (products of DNA sequences) which enable them to infect a host bacteria, replicate their genetic material, usurp host metabolism, and ultimately kill their host. The scientific literature documents well the fact that many known bacteria have a large number of such bacteriophages that can infect and kill them (for example, see the ATCC bacteriophage collection at http://www.atcc.org) (Ackermann and DuBow, 1987). Although we know that many bacteriophages encode proteins which can significantly alter their host's metabolism, determination of the killing potential of a given bacteriophage gene product can only be assessed by expressing the gene product in the target bacterial strain.

As indicated in the Summary above, the present invention is concerned with the use of bacteriophage 3A, 77, and 96 coding sequences and the encoded polypeptides or RNA transcripts to identify bacterial targets for potential new antibacterial agents. Thus, the invention concerns the selection of relevant bacteria. Particularly relevant bacteria are those which are pathogens of a complex organism such as an animal, e.g., mammals, reptiles, and birds, and plants. However, the invention can be applied to any bacterium (whether pathogenic or not) for which bacteriophage are available or which are found to have cellular components closely homologous to components targeted by phage 3A ORF 33, 41, 79, phage 77 ORF 1, and phage 96 ORF 48, 78, 100.

Identification of ORFs 33, 41 and 78 from phage 3A, ORF 1 from phage 77 and ORF 48, 78, 100 from phage 96 and products from the phage which inhibit the host bacterium both provides an inhibitor compound and allows identification of the bacterial target affected by the phage-encoded inhibitor. Such a target is thus identified as a potential target for development of other antibacterial agents or inhibitors and the use of those targets to inhibit those bacteria. As indicated above, even if such a target is not initially identified in a particular bacterium, such a target can still be identified if a homologous target is identified in another bacterium. Usually, but not necessarily, such another bacterium would be a genetically closely related bacterium. Indeed, in some cases, an inhibitor encoded by phage 3A ORF 33, 41, or 79, phage 77 ORF1 or phage 96 ORF 48, 78, or 100 can also inhibit such a homologous bacterial cellular component.

The demonstration that bacteriophage have adapted to inhibiting a host bacterium by acting on a particular cellular component or target provides a strong indication that that component is an appropriate target for developing and using antibacterial agents, e.g., in therapeutic treatments. Thus, the present invention provides additional guidance over mere identification of bacterial essential genes, as the present invention also provides an indication of accessibility of the target to an inhibitor, and an indication that the target is sufficiently stable over time (e.g., not subject to high rates of mutation) as phage acting on that target were able to develop and persist. Thus, the present invention identifies a particular subset of essential cellular components which are particularly likely to be appropriate targets for development of antibacterial agents.

The invention also, therefore, concerns the development or identification of inhibitors of bacteria, in addition to the phage-encoded inhibitory proteins (or RNA transcripts), which are active on the targets of bacteriophage-encoded inhibitors. As described herein, such inhibitors can be of a variety of different types, but are preferably small molecules.

The following description provides preferred methods for implementing the various aspects of the invention. However, as those skilled in the art will readily recognize, other approaches can be used to obtain and process relevant information. Thus, the invention is not limited to the specifically described methods. In addition, the following description provides a set of steps in a particular order. That series of steps describes the overall development involved in the present invention. However, it is clear that individual steps or portions of steps may be usefully practiced separately, and, further, that certain steps may be performed in a different order or even bypassed if appropriate information is already available or is provided by other sources or methods.

Identification of Inhibitory ORF

The methodology previously described in U.S. application Ser. No. 09/407,804 filed Sep. 28, 1999, and PCT International Application No. PCT/IB99/02040, was used to identify and characterize DNA sequences from *Staphylococcus aureus* bacteriophages 3A, 77 and 96 that can act as anti-microbials.

A nucleic acid segment isolated from *Staphylococcus aureus* bacteriophages 3A, 77 or 96 encodes a protein, whose gene is referred to as ORF (open reading frame) 33, 41, 79, 1, 48, 78, or 100 Thus, the present invention provides a nucleic acid sequence isolated from *Staphylococcus aureus* (*Staph A* or *S. aureus*) bacteriophages 3A, 77, or 96 comprising at least a portion of the gene encoding phage 3A ORF 33, 41, or 79, phage 77 ORF 1, or phage 96 ORF 48, 78, or 100 with anti-microbial activity. The nucleic acid sequence can be isolated using a method similar to those described herein, or using another method. In addition, such a nucleic acid sequence can be chemically synthesized. Having the anti-microbial nucleic acid sequence of the present invention, parts thereof or oligonucleotides derived therefrom, other anti-microbial sequences from other bacteriophage sources using methods described herein or other methods can be isolated, including screening methods based on nucleic acid sequence hybridization.

The present invention provides the use of the *Staph A* bacteriophages 3A, 77, or 96 anti-microbial DNA segment encoding phage 3A ORF 33, 41, or 79, phage 77 ORF 1, or phage 96 ORF 48, 78, or 100, as a pharmacological agent, either wholly or in part, as well as the use of peptidomimetics, developed from amino acid or nucleotide sequence knowledge of *Staph A* phage 3A ORF 33, 41, or 79, phage 77 ORF 1, or phage 96 ORF 48, 78, or 100. This can be achieved where the structure of the peptidomimetic compound corresponds to the structure of the active portion of phage 3A ORF 33, 41, or 79, phage 77 ORF 1, or phage 96 ORF 48, 78, or 100. In this analysis, the peptide backbone is transformed into a carbon-based hydrophobic structure that can retain cytostatic or cytocidal activity for the bacterium. This is done by standard medicinal chemistry methods, measuring growth inhibition of the various molecules in liquid cultures or on solid medium. These mimetics also represent lead compounds for the development of novel antibiotics.

In this context, "corresponds" means that the peptidomimetic compound structure has sufficient similarities to the structure of the active portion of phage 3A ORF 33, 41, or 79, phage 77 ORF 1, or phage 96 ORF 48, 78, or 100 that the peptidomimetic will interact with the same molecule as the product of phage 3A ORF 33, 41, or 79, phage 77 ORF 1, or phage 96 ORF 48, 78, or 100 and preferably will elicit at least one cellular response in common which relates to the inhibition of the cell by the phage protein.

The invention also provides bacteriophage anti-microbial DNA segments from other phages based on nucleic acids and sequences hybridizing to the presently identified inhibitory ORF under high stringency conditions or sequences which are homologous as described above. The bacteriophage anti-microbial DNA segment from phage 3A ORF 33, 41, or 79, phage 77 ORF 1, or phage 96 ORF 48, 78, or 100 can be used to identify a related segment from another related or unrelated phage based on conditions of hybridization or sequence comparison.

Identification of Bacterial Targets

The present invention provides the use of Staphylococcus phage 3A ORF 33, 41, or 79, phage 77 ORF 1, or phage 96 ORF 48, 78, or 100 anti-microbial activity to identify essential host bacterium interacting proteins or other targets that could, in turn, be used for drug design and/or screening of test compounds. Thus, the invention provides a method of screening for antibacterial agents by determining whether test compounds interact with (e.g., bind to) the bacterial target. The invention also provides a method of making an antibacterial agent based on production and purification of the protein or RNA product of phage 3A ORF 33, 41, or 79, phage 77 ORF 1, or phage 96 ORF 48, 78, or 100. The method involves identifying a bacterial target of the product of phage 3A ORF 33, 41, or 79, phage 77 ORF 1, or phage 96 ORF 48, 78, or 100, screening a plurality of compounds to identify a compound active on the target, and synthesizing the compound in an amount sufficient to provide a therapeutic effect when administered to an organism infected by a bacterium naturally producing the target. The rationale is that the product of phage 3A ORF 33, 41, or 79, phage 77 ORF 1, or phage 96 ORF 48, 78, or 100 can physically interact and/or modify certain microbial host components to block their function.

A variety of methods are known to those skilled in the art for identifying interacting molecules and for identifying target cellular components. Several approaches and techniques are described below which can be used to identify the host bacterial pathway and protein that interact or are inhibited by phage 3A ORF 33, 41, or 79, phage 77 ORF 1, or phage 96 ORF 48, 78, or 100.

The first approach is a genetic screen for protein:protein interaction, e.g., either some form of two hybrid screen or some form of suppressor screen. In one form of the two hybrid screen involving the yeast two hybrid system, the nucleic acid segment encoding phage 3A ORF 33, 41, or 79, phage 77 ORF 1, or phage 96 ORF 48, 78, or 100, or a portion thereof, is fused to the carboxyl terminus of the yeast Gal4 DNA binding domain to create a bait vector. A genomic DNA library of cloned *S. aureus* sequences which have been engineered into a plasmid where the *S. aureus* sequences are fused to the carboxyl terminus of the yeast of Gal4 activation domain II (amino acids 768–881), is also generated. These plasmids are introduced alone, or in combination, into a yeast strain, e.g., Y190, previously engineered with chromosomally integrated copies of the *E. coli* lacZ and the selectable His3 genes, both under Gal4 regulation (Durfee et al., 1993). If the two proteins expressed in yeast interact, the resulting complex will activate transcription from promoters containing Gal4 binding sites. A lacZ and His3 gene, each driven by a promoter containing Gal4 binding sites, have been integrated into the genome of the host yeast system and are used for measuring protein-protein interactions. Such a system provides a physiological environment in which to detect potential protein interactions.

This system has been extensively used to identify novel protein-protein interaction partners and to map the sites required for interaction (for example, to identify interacting partners of translation factors (Qui et al., 1998), transcription factors (Katagiri et al., 1998), proteins involved in signal transduction (Endo et al., 1997). Alternatively, a bacterial two-hybrid screen can be utilized to circumvent the need for the interacting proteins to be targeted to the nucleus, as is the case in the yeast system (Karimova et al., 1998).

The protein targets of phage 3A ORF 33, 41, or 79, phage 77 ORF 1, or phage 96 ORF 48, 78, or 100 can also be identified using bacterial genetic screens. One approach involves the overexpression of phage 3A ORF 33, 41, or 79, phage 77 ORF 1, or phage 96 ORF 48, 78, or 100 protein in mutagenized *S. aureus* followed by plating the cells and searching for colonies that can survive the anti-microbial activity of phage 3A ORF 33, 41, or 79, phage 77 ORF 1, or phage 96 ORF 48, 78, or 100. These colonies are then grown, their DNA extracted, and cloned into an expression vector that contains a replicon of a different incompatibility group from the plasmid expressing phage 3A ORF 33, 41, or 79, phage 77 ORF 1, or phage 96 ORF 48, 78, or 100. This library is then introduced into a wild-type *Staph A* bacterium in conjunction with an expression vector driving synthesis of phage 3A ORF 33, 41, or 79, phage 77 ORF 1, or phage 96 ORF 48, 78, or 100, followed by selection for surviving bacteria. Thus, *Staph A* DNA fragments from the survivors presumably contain a DNA fragment from the original mutagenized *Staph A* genome that can protect the cell from the antimicrobial activity phage 3A ORF 33, 41, or 79, phage 77 ORF 1, or phage 96 ORF 48, 78, or 100. This fragment can be sequenced and compared with that of the bacterial host to determine in which gene the mutation lies. This approach enables one to determine the targets and pathways that are affected by the killing function.

Alternatively, the bacterial targets can be determined in the absence of selecting for mutations using the approach known as "multicopy suppression". In this approach, the DNA from the wild type *Staph A* host is cloned into an expression vector that can coexist with the one containing phage 3A ORF 33, 41, or 79, phage 77 ORF 1, or phage 96 ORF 48, 78, or 100. Those plasmids that contain host DNA fragments and genes which protect the host from the anti microbial activity of phage 3A ORF 33, 41, or 79, phage 77 ORF 1, or phage 96 ORF 48, 78, or 100 can then be isolated and sequenced to identify putative targets and pathways in the host bacteria.

Another approach is based on identifying protein:protein interactions between the product of phage 3A ORF 33, 41, or 79, phage 77 ORF 1, or phage 96 ORF 48, 78, or 100 and *S. aureus* host proteins, using a biochemical approach based on affinity chromatography. This approach has been used to identify interactions between lambda phage proteins and proteins from their *E. coli* host (Sopta et al., 1995). The product of phage 3A ORF 33, 41, or 79, phage 77 ORF 1, or phage 96 ORF 48, 78, or 100 is fused to a tag (e.g. -glutathione-S-transferase) after insertion in a commercially available plasmid vector which directs high-level expression after induction of the responsive promoter driving the fusion protein. The fusion protein is expressed in *E. coli*, purified, and immobilized on a solid phase matrix. Total cell extracts from *S. aureus* are then passed through the affinity matrix containing the immobilized phage ORF fusion protein; host proteins retained on the column are then eluted under different conditions of ionic strength, pH, and detergents and identified by gel electrophoresis. They are recovered from the gel by transfer to a high affinity membrane. The proteins are individually digested to completion with a protease (e.g.-trypsin) and either molecular mass or the amino acid sequence of the tryptic fragments can be determined by mass spectrometry using MALDI-TOF technology (Qin et al., 1997). The sequence of the individual peptides from a single protein are then analyzed by a bioinformatics approach to identify the *S. aureus* protein interacting with the phage ORF. This is performed by a computer search of the *S. aureus* genome for the identified sequence. Alternatively, tryptic peptide fragments of the *S. aureus* genome can be predicted by computer software based on the nucleotide sequence of the genome, and the predicted molecular mass of peptide fragments generated in silico compared to the molecular mass of the peptides obtained from each interacting protein eluted from the affinity matrix.

In addition, an oligonucleotide cocktail can be synthesized based on the primary amino acid sequence determined for an interacting *S. aureus* protein fragment. This oligonucleotide cocktail would comprise a mixture of oligonucleotides based on the nucleotide sequences of the primary amino acid of the predicted peptide, but in which all possible codons for a particular amino acid sequence are present in a subset of the oligonucleotide pool. This cocktail can then be used as a degenerate probe set to screen, by hybridization to genomic or cDNA libraries, to isolate the corresponding gene.

Alternatively, antibodies raised to peptides which correspond to an interacting *S. aureus* protein fragment can be used to screen expression libraries (genomic or cDNA) to identify the gene encoding the interacting protein.

Vectors

The invention also provides vectors, preferably expression vectors, harboring the anti-microbial DNA nucleic acid segment of the invention in an expressible form, and cells transformed with the same. Such cells can serve a variety of purposes, such as in vitro models for the function of the anti-microbial nucleic acid segment and screening for downstream targets of the anti-microbial nucleic acid segment, as well as expression to provide relatively large quantities of the inhibitory product.

Thus, an expression vector harboring the anti-microbial nucleic acid segment or parts thereof (*Staph A* bacteriophage 3A ORF 33, 41, 79, bacteriophage 77 ORF 1, bacteriophage 96 ORF 48, 78, 100) can also be used to obtain substantially pure protein. Well-known vectors, such as the pGEX series (available from Pharmacia), can be used to obtain large amounts of the protein which can then be purified by standard biochemical methods based on charge, molecular mass, solubility, or affinity selection of the protein by using gene fusion techniques (such as GST fusion, which permits the purification of the protein of interest on a glutathione column). Other types of purification methods or fusion proteins could also be used as recognized by those skilled in the art.

Likewise, vectors containing phage 3A ORF 33, 41, or 79, phage 77 ORF 1, or phage 96 ORF 48, 78, or 100 can be used in methods for identifying targets of the encoded antibacterial ORF product, e.g., as described above, and/or for testing inhibition of homologous bacterial targets or other potential targets in bacterial species other than *Staphylococcus aureus*.

Antibodies

Antibodies, both polyclonal and monoclonal, can be prepared against the protein encoded by a bacteriophage anti-microbial DNA segment of the invention (e.g., *Staph A* phage 3A ORF 33, 41, or 79, phage 77 ORF 1, or phage 96 ORF 48, 78, or 100) by methods well known in the art. Protein for preparation of such antibodies can be prepared by purification, usually from a recombinant cell expressing the specified ORF or fragment thereof. Those skilled in the art are familiar with methods for preparing polyclonal or monoclonal antibodies (See, e.g., *Antibodies: A Laboratory Manual*, Harlow and Lane, Cold Spring Harbor Laboratory, CSHL Press, N.Y., 1988).

Such antibodies can be used for a variety of purposes including affinity purification of the protein encoded by the bacteriophage anti-microbial DNA segment, tethering of the protein encoded by the bacteriophage anti-microbial DNA segment to a solid matrix for purposes of identifying interacting host bacterium proteins, and for monitoring of expression of the protein encoded by the bacteriophage anti-microbial DNA segment.

Recombinant Cells

Bacterial cells containing an inducible vector regulating expression of the bacteriophage anti-microbial DNA segment can be used to generate an animal model system for the study of infection by the host bacterium. The functional activity of the proteins encoded by the bacteriophage anti-microbial DNA segments, whether native or mutated, can be tested in animal in vitro or in vivo models.

While such cells containing inducible expression vectors is preferred, other recombinant cells containing a recombinant phage 3A ORF 33, 41, or 79, phage 77 ORF 1, or phage 96 ORF 48, 78, or 100 sequence or portion thereof are also provided by the present invention.

Also, a recombinant cell may contain a recombinant sequence encoding at least a portion of a protein which is a target of phage 3A ORF 33, 41, or 79, phage 77 ORF 1, or phage 96 ORF 48, 78, or 100 inhibitory ORF product.

In the context of this invention, in connection with nucleic acid sequences, the term "recombinant" refers to nucleic acid sequences which have been placed in a genetic location by intervention using molecular biology techniques, and does not include the relocation of phage sequences during or as a result of phage infection of a bacterium or normal genetic exchange processes such as bacterial conjugation.

Derivatization of Identified Anti-microbials

In cases where the identified anti-microbials above are peptidic compounds, the in vivo effectiveness of such compounds may be advantageously enhanced by chemical modification using the natural polypeptide as a starting point and incorporating changes that provide advantages for use, for example, increased stability to proteolytic degradation, reduced antigenicity, improved tissue penetration, and/or improved delivery characteristics.

In addition to active modifications and derivative creations, it can also be useful to provide inactive modifications or derivatives for use as negative controls or introduction of immunologic tolerance. For example, a biologically inactive derivative which has essentially the same epitopes as the corresponding natural antimicrobial can be used to induce immunological tolerance in a patient being treated. The induction of tolerance can then allow uninterrupted treatment with the active anti-microbial to continue for a significantly longer period of time.

Modified anti-microbial polypeptides and derivatives can be produced using a number of different types of modifications to the amino acid chain. Many such methods are known to those skilled in the art. The changes can include, for example, reduction of the size of the molecule, and/or the modification of the amino acid sequence of the molecule. In addition, a variety of different chemical modifications of the naturally occurring polypeptide can be used, either with or without modifications to the amino acid sequence or size of the molecule. Such chemical modifications can, for example, include the incorporation of modified or non-natural amino acids or non-amino acid moieties during synthesis of the peptide chain, or the post-synthesis modification of incorporated chain moieties.

The oligopeptides of this invention can be synthesized chemically or through an appropriate gene expression system. Synthetic peptides can include both naturally occurring amino acids and laboratory synthesized, modified amino acids.

Also provided herein are functional derivatives of anti-microbial proteins or polypeptides. By "functional derivative" is meant a "chemical derivative," "fragment," "variant," "chimera," or "hybrid" of the polypeptide or protein, which terms are defined below. A functional derivative retains at least a portion of the function of the protein, for example, reactivity with a specific antibody, enzymatic activity or binding activity.

A "chemical derivative" of the complex contains additional chemical moieties not normally a part of the protein or peptide. Such moieties may improve the molecule's solubility, absorption, biological half-life, and the like. The moieties may alternatively decrease the toxicity of the molecule, eliminate or attenuate any undesirable side effect of the molecule, and the like. Moieties capable of mediating such effects are disclosed in *Genaro*, 1995, *Remington's Pharmaceutical Science*. Procedures for coupling such moieties to a molecule are well known in the art. Covalent modifications of the protein or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing primary amine-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl) carbodiumide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking component peptides to each other or the complex to a water-insoluble support matrix or to other macromolecular carriers. Commonly used cross-linking agents include, for example, 1,1-bis (diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[p-azidophenyl) dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., *Proteins: Structure and Molecular Properties*, W. H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, biological half-life, and the like. The moieties may alternatively eliminate or attenuate any undesirable side effect of the protein complex. Moieties capable of mediating such effects are disclosed, for example, in *Genaro*, 1995, *Remington's Pharmaceutical Science.*

The term "fragment" is used to indicate a polypeptide derived from the amino acid sequence of the protein or polypeptide having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence.

Another functional derivative intended to be within the scope of the present invention is a "variant" polypeptide which either lacks one or more amino acids or contains additional or substituted amino acids relative to the native polypeptide. The variant may be derived from a naturally occurring polypeptide by appropriately modifying the protein DNA coding sequence to add, remove, and/or to modify codons for one or more amino acids at one or more sites of the C-terminus, N-terminus, and/or within the native sequence.

A functional derivative of a protein or polypeptide with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, *DNA* 2:183; Sambrook et al., 1989) wherein nucleotides in the DNA coding sequence are modified such that a modified coding sequence is produced, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art.

Insofar as other anti-microbial inhibitor compounds identified by the invention described herein may not be peptidal in nature, other chemical techniques exist to allow their suitable modification, as well, and according the desirable principles discussed above.

Administration and Pharmnaceutical Compositions

For the therapeutic and prophylactic treatment of infection, the preferred method of preparation or administration of anti-microbial compounds will generally vary depending on the precise identity and nature of the anti-microbial being delivered. Thus, those skilled in the art will understand that administration methods known in the art will also be appropriate for the compounds of this invention. Pharmaceutical compositions are prepared, as understood by those skilled in the art, to be appropriate for therapeutic use. Thus, generally the components and composition are prepared to be sterile and free of components or contaminants which would pose an unacceptable risk to a patient. For compositions to be administered internally is is generally important that the composition be pyrogen free, for example.

The particularly desired anti-microbial can be administered to a patient either by itself, or in pharmaceutical compositions where it is mixed with suitable carriers or excipient(s). In treating an infection, a therapeutically effective amount of an agent or agents is administered. A therapeutically effective dose refers to that amount of the compound that results in amelioration of one or more symptoms of bacterial infection and/or a prolongation of patient survival or patient comfort.

Toxicity,. therapeutic and prophylactic efficacy of anti-microbials can be determined by standard pharmaceutical procedures in cell cultures and/or experimental organisms such as animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

For any compound identified and used in the method of the invention, the therapeutically effective dose can be estimated initially from cell culture assays. Such information can be used to more accurately determine useful doses in organisms such as plants and animals, preferably mammals, and most preferably humans. Levels in plasma may be measured, for example, by HPLC or other means appropriate for detection of the particular compound.

The exact formulation, route of administration and dosage can be chosen by the individual physician in view of the patient's condition (see e.g. Fingl et. al., in *The Pharmacological Basis of Therapeutics*, 1975, Ch. 1 p.1).

It should be noted that the attending physician would know how and when to terminate, interrupt, or adjust administration due to toxicity, organ dysfunction, or other systemic malady. Conversely, the attending physician would also know to adjust treatment to higher levels if the clinical response were not adequate (precluding toxicity). The magnitude of an administered dose in the management of the disorder of interest will vary with the severity of the condition to be treated and the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary or phyto medicine.

Depending on the specific infection target being treated and the method selected, such agents may be formulated and administered systemically or locally, i.e., topically. Techniques for formulation and administration may be found in *Genaro*, 1995, *Remington's Pharmaceutical Science*. Suitable routes may include, for example, oral, rectal, transdermal, vaginal, transmucosal, intestinal, parenteral, intramuscular, subcutaneous, or intramedullary injections, as well as intrathecal, intravenous, or intraperitoneal injections.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate identified anti-microbials of the present invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active anti-microbial compounds in water-soluble form. Alternatively, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The above methodologies may be employed either actively or prophylactically against an infection of interest.

To identify DNA segments of *Staph A* bacteriophages 3A, 77 and 96 capable of acting as anti-microbial agents, a strategy described in U.S. application Ser. No. 09/407,804 filed Sep. 28, 1999, and PCT International Application No. PCT/IB99/02040 was employed. In essence, the procedure involved sequence characterization of the bacteriophage, identification of protein coding regions (open reading frames or ORFs), subcloning of all ORFs into an appropriate inducible expression vector, transfer of the ORF subclones into *Staph. A*, followed by induction of ORF expression and assessment of effect on growth. We employed discovery steps as described in the Examples.

EXAMPLE I

Growth of *Staphylococcus aureus* Bacteriophages 3A, 77 and 96 and Purification of Genomic DNA The *Staphylococcus aureus* propagating strain (PS 3A, 77 and 96) (Laboratory Center for Disease Control. (CDC) Health Canada, Ottawa, Ontario) were used as host to propagate their respective phages 3A, 77 and 96, also obtained from the CDC. Two rounds of plaque purification of phages were performed on soft agar essentially as described in Sambrook et al (1989). Briefly, the PS 3A, 77 and 96 strains were grown overnight at 37° C. in Nutrient broth [NB: 0.3% Bacto beef extract, 0.5% Bacto peptone (Difco Laboratories) and 0.5% NaCl (w/v)]. The culture was then diluted 20× in NB and incubated at 37° C. until the $OD_{540}$=0.2 (early log phase) with constant agitation. In order to obtain single plaques, phages 3A, 77 or 96 were subjected to 10-fold serial dilutions using phage buffer (1 mM $MgSO_4$, 5 mM $MgCl_2$, 80 mM NaCl and 0.1% Gelatin (w/v)) and 10 μl of each dilution was used to infect 0.5 ml of the cell suspension in the presence of 400 μg/ml $CaCl_2$. After incubation of 15 min at room temperature (RT), 2 ml of melted soft agar kept at 45° C. (NB supplemented with 0.6% agar) was added to the mixture and poured onto the surface of 100 mm nutrient agar plates (0.3% Bacto Beef extract, 0.5% Bacto peptone, 0.5% NaCl and 1.5% Bacto agar (w/v)). After overnight incubation at 30° C., a single plaque was isolated, resuspended in 1 ml of phage buffer by end over end rotation for 2 hrs at 20° C., and the phage suspension was diluted and used for a second infection as described above. After overnight incubation at 30° C., a single plaque was isolated and used as a stock.

The propagation procedure for bacteriophages 3A, 77 and 96 was modified from the agar layer method of Swanstörm and Adams (1951). Briefly, the respective PS strains were grown to stationary phase overnight at 37° C. in Nutrient broth. Each culture was then diluted twenty-fold in NB and incubated at 37° C. until the $OD_{540}$=0.2. The suspension (15×$10^7$ Bacteria) was then mixed with 15×$10^5$ plaque forming units (pfu) to give a ratio of 100-bacteria/phage particle in the presence of 400 μg/ml of $CaCl_2$. After incubation for 15 min at 20° C., 7.5 ml of melted soft agar (NB plus 0.6% agar) were added to the mixture and poured onto the surface of 150 mm nutrient agar plates and incubated 16 hrs at 37° C. To collect the phage plate lysate, 20 ml of NB were added to each plate and the soft agar layer was collected by scrapping off with a clean microscope slide followed by shaking of the agar suspension for 5 min to break up the agar. The mixture was then centrifuged for 10 min at 4,000 RPM (2,830×g) in a JA-10 rotor (Beckman) and the supernatant fluid (lysate) was collected and subjected to a treatment with 10 μg /ml of DNase I and RNase A for 30 min at 37° C. To precipitate the phage particles, the phage suspension was adjusted to 10% (w/v) PEG 8000 and 0.5 M of NaCl followed by incubation at 4° C. for 16 hrs. The phage was recovered by centrifugation at 4,000 rpm (3,500×g) for 20 min at 4° C. on a GS-6R table top centrifuge (Beckman). The pellet was resuspended with 2 ml of phage buffer (1 mM $MgSO_4$, 5 mM $MgCl_2$, 80 mM NaCl and 0.1% Gelatin). The phage suspension was extracted with 1 volume of chloroform and further purified by centrifugation on a cesium chloride step gradient as described in Sambrook et al. (1989), using a TLS 55 rotor centrifuged in an Optima TLX ultracentrifuge (Beckman) for 2 h at 28,000 rpm (67,000×g) at 4° C. Banded phage was collected and ultracentrifuged again on an isopycnic cesium chloride gradient (1.45 g/ml) at 40,000 rpm (64,000×g) for 24 h at 4° C. using a TLV rotor (Beckman). The phage was harvested and dialyzed for 4 h at room temperature against 4 L of dialysis buffer consisting of 10 mM NaCl, 50 mM Tris-HCl [pH 8] and 10 mM $MgCl_2$. Phage DNA was prepared from the phage suspension by adding 20 mM EDTA, 50 ug/ml Proteinase K and 0.5% SDS and incubating for 1 h at 65° C., followed by successive extractions with 1 volume of phenol, 1 volume of phenol-chloroform and 1 volume of chloroform. The DNA was then dialyzed overnight at 4° C. against 4 L of TE (10 mM Tris-HCl [pH 8.0], 1 mM EDTA).

EXAMPLE II

DNA Sequencing of Bacteriophage 3A, 77 and 96 Genomes

Four micrograms of phage DNA was diluted in 200 μl of TE, 1 mM EDTA in a 1.5 ml eppendorf tube and sonication was performed (550 Sonic Dismembrator™, Fisher Scientific). Samples were sonicated under an amplitude of 3 μm with bursts of 5 s spaced by 15 s cooling in ice/water for 3 to 4 cycles. The sonicated DNA was then size fractionated by electrophoresis on 1% agarose gels utilizing TAE (1×TAE is: 40 mM Tris-acetate, 1 mM EDTA [pH 8.0]) as the running buffer. Fractions ranging from 1 to 2 kbp were excised from the agarose gel and purified using a commercial DNA extraction system according to the instructions of the manufacturer (Qiagen), with a final elution of 50 μl of 1 mM Tris-HCl [pH 8.5].

The ends of the sonicated DNA fragments were repaired with a combination of T4 DNA polymerase and the Klenow fragment of *E. coli* DNA polymerase 1, as follows. Reactions were performed in a reaction mixture (final volume, 100 μl) containing sonicated phage DNA, 10 mM Tris-HCl [pH 8.0], 50 mM NaCl, 10 mM $MgCl_2$, 1 mM DTT, 50 μg/ml BSA, 100 μM of each dNTP and 15 units of T4 DNA polymerase (New England Biolabs) for 20 min at 12° C. followed by addition of 12.5 units of Klenow large fragment (New England Biolabs) for 15 min at room temperature. The reaction was stopped by two phenol/chloroform extractions and the DNA was precipitated with ethanol and the final DNA pellet was resuspended in 20 μl of $H_2O$.

Blunt-ended DNA fragments were cloned by ligation directly into the Hinc II site of pKSII+ vector (Stratagene) dephosphorylated by treatment with calf intestinal alkaline phosphatase (New England Biolabs). A typical ligation reaction contained 100 ng of vector DNA, 2 to 5 μl of repaired sonicated phage DNA (50–100 ng) in a final volume of 20 μl containing 800 units of T4 DNA ligase (New England Biolabs) and was incubated overnight at 16° C. Transformation and selection of bacterial clones containing recombinant plasmids was performed in *E. coli* DH10β according to standard procedures (Sambrook et al., 1989).

Recombinant clones were picked from agar plates into 96-well plates containing 100 μl LB and 100 μg/ml ampicillin and incubated at 37° C. The presence of phage DNA insert was confirmed by PCR amplification using T3 and T7 primers flanking the Hinc II cloning site of the pKS II+ vector. PCR amplification of foreign insert was performed in a 15 μl reaction volume containing 10 mM Tris-HCl [pH 8.3], 50 mM KCl, 1.5 mM $MgCl_2$, 0.02% gelatin, 1 μM primer, 187.5 μM each dNTP, and 0.75 units Taq polymerase (BRL). The thermocycling parameters were as follows: 2 min initial denaturation at 94° C. for 2 min, followed by 20 cycles of 30 sec denaturation at 94° C., 30 sec annealing at 57° C., and 2 min extension at 72° C., followed by a single extension step at 72° C. for 10 min. Clones with insert sizes of 1 to 2 kbp were selected and plasmid DNA was prepared from the selected clones using QIAprep™ spin miniprep kit (Qiagen).

The nucleotide sequence of the extremities of each recombinant clone was determined using an ABI 377-36 automated sequencer with two types of chemistry:ABI prism Big Dye™ primer cycle sequencing (21M13 primer: #403055) (M13REV primer: #403056) or ABI prism Big Dye™ terminator cycle sequencing ready reaction kit (Applied Biosystems, #4303152). To ensure co-linearity of the sequence data and the genome, all regions of phage genome were sequenced at least once from both directions on two separate clones. In areas that this criteria was not initially met, a sequencing primer was selected and phage DNA was used directly as sequencing template employing ABI prism Big Dye™ terminator cycle sequencing ready reaction kit.

EXAMPLE III

Bioinformatic Management of Primary Nucleotide Sequence

Sequence contigs were assembled using Sequencher™ 3.1 software (GeneCodes). To close contig gaps, sequencing primers were selected near the edge of the contigs. Phage DNA was used directly as sequencing template employing ABI prism BIG DYE™ terminator cycle sequencing ready reaction kit. The complete sequences of bacteriophages 3A, 77 and 96 are shown in Table 1.

A software program was developed and used on the assembled sequence of the bacteriophages to identify all putative ORFs larger than 33 codons. Other ORF identification software can also be utilized, preferably programs which allow alternative start codons. The software scans the primary nucleotide sequence starting at nucleotide #1 for an appropriate start codon. Three possible selections can be made for defining the nature of the start codon; I) selection of ATG, II) selection of ATG or GTG, and III) selection of either ATG, GTG, TTG, CTG, ATT, ATC, and ATA. This latter initiation codon set corresponds to the one reported by the NCBI (http://www.ncbi.nlm.nih.gov/htbin-post/Taxonomy/wprintyc?mode=c) for the bacterial genetic code.

When an appropriate start codon is encountered, a counting mechanism is employed to count the number of codons (groups of three nucleotides) between this start codon and the next stop codon downstream of it. If a threshold value of 33 is reached, or exceeded, then the sequence encompassed by these two codons (start and stop codons) is defined as an ORF. This procedure is repeated, each time starting at the next nucleotide following the previous stop codon found, in order to identify all the other putative ORFs. The scan is performed on all three reading frames of both DNA strands of the phage sequence.

Sequence homology (BLAST) searches for each ORF are then carried out using an implementation of BLAST programs, although any of a variety of different sequence comparison and matching programs can be utilized as known to those skilled in the art. Downloaded public databases used for sequence analysis include:

i) non-redundant GenBank (ftp://ncbi.nlm.nih.gov/blast/db/nr.Z), ii) Swissprot (ftp://ncbi.nlm.nih.gov/blast/db/swissprot.Z);

iii) vector (ftp://ncbi.nlm.nih.gov/blast/db/vector.Z);

iv) pdbaa databases (ftp://ncbi.nlm.nih.gov/blast/db/pdbaa.Z);

v) *staphylococcus aureus* NCTC 8325 (ftp://ftp.genome.ou.edu/pub/staph/staph-1k.fa);

vi) *streptococcus pyogenes* (ftp://ftp.genome.ou.edu/pub/strep/strep-1k.fa);

vii) *streptococcus pneumoniae* (ftp://ftp.tigr.org/pub/data/s__neumoniae/gsp.contigs.112197.Z);

viii) *mycobacterium tuberculosis* CSU#9 (ftp://ftp.tigr.org/pub/data/m__tuberculosis/TB__091097.Z) and ix) *pseudomonas aeruginosa* (http://www.genome.washington.edu/pseudo/data.html).

The results of the homology searches performed on the bacteriophage 3A, 77 and 96 ORFs are shown in Table 4.

EXAMPLE IV

Figure 1B:
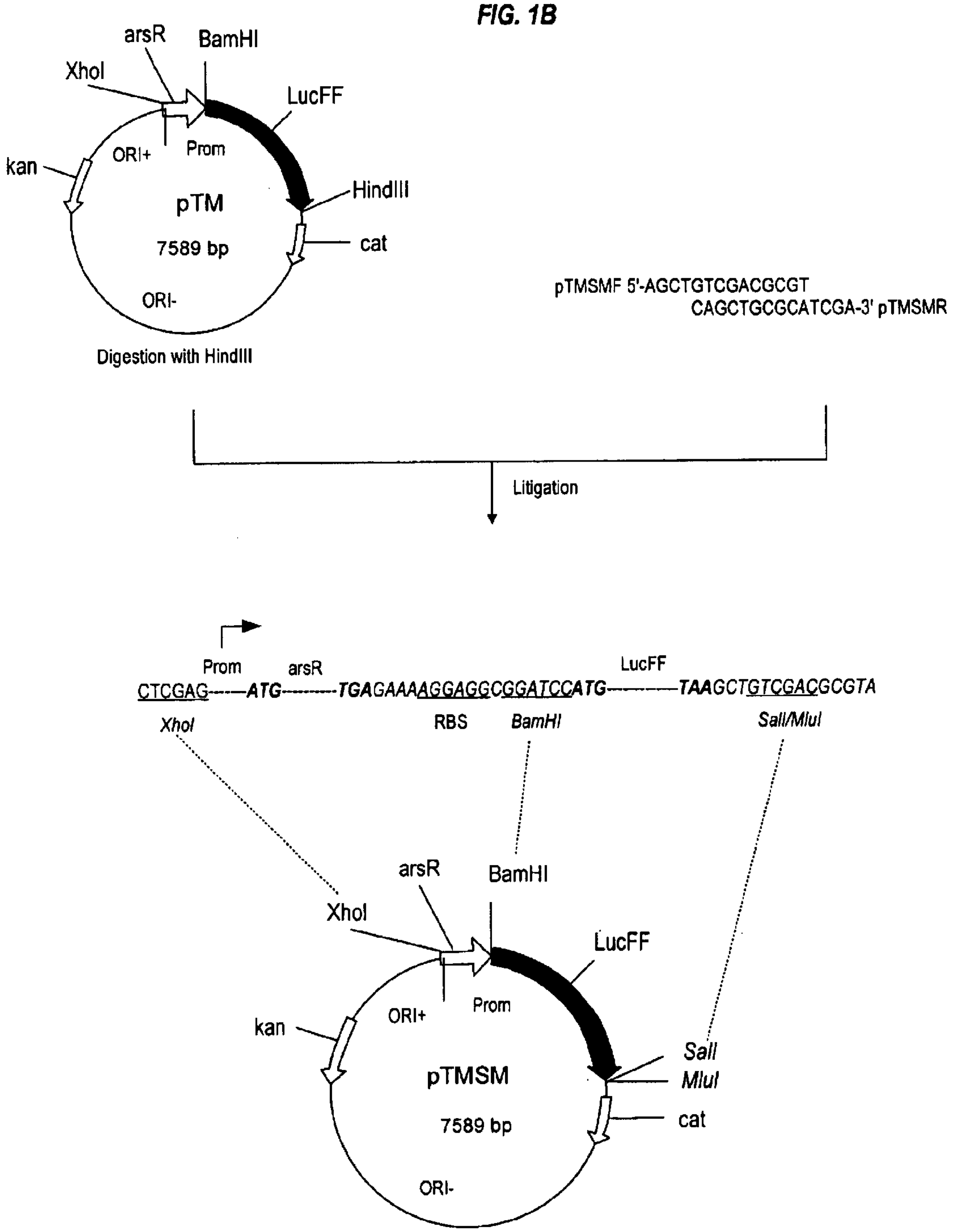

Subcloning of Bacteriophage 3A, 77 and 96 ORFs into a *Staph A* Inducible Expression System Preparation of the Shuttle Expression Vectors The shuttle vector pT0021, in which the firefly luciferase (lucFF) expression is controlled by the ars (arsenite) promoter/operator (Tauriainen et al., 1997), was modified as below to suit our specific application. Two oligonucleotides were synthesized. The sense strand sequence (with XhoI cloning site) is: 5'-AATTCTCGAGTAAAATAACAT-3' (SEQ ID NO. 1); the antisense strand sequence (with a BamHI cloning site) is: 5'-CGGGATCCG CCTCCTTTTCTCAACAGTCACCTGATTT-3' (SEQ ID NO. 2). The two oligonucleotides were used for polymerase chain reaction (PCR) amplification of pT0021 vector. The PCR product was gel purified using the Qiagen kit as described, and digested with XhoI and BamHI. The digested PCR product was again gel purified, ligated into XhoI and BamHI digested pT0021 vector, and used to transform *E. coli* bacterial strain DH10β (as described above). This manipulation results in the construction of a pT0021-intermediated vector containing a RBS sequence located immediately upstream of the BamHI cloning site. Two other oligonucleotides were synthesized. The sense strand sequence (with BamHI cloning site) is: 5'-CGGGATCCATGAGGGGTTCCGAAGACG-3' (SEQ ID NO. 3); the antisense strand sequence (with a HindIII cloning site) is: 5'-CCCAAGCTTACAATTTGGACTTTC-3' (SEQ ID NO. 4). The two oligonucleotides were used for PCR amplification of pT0021-intermediated vector. The PCR product was gel purified and digested with BamHI and HindIII. The digested PCR product was then gel purified as described, ligated into BamHI and HindIII digested pT0021-intermediated vector, and used to transform *E. coli* bacterial strain DH10β. This modified shuttle vector containing the ATG of the lucFF gene located immediately downstream of the BamHI cloning site was named pTM. A diagram outlining our modification of pT0021 to generate pTM is shown in FIG. 1A. The pTMSM vector is a modified version of the pTM vector containing the SalI and MluI cloning sites replacing the HindIII cloning site as shown in FIG. 1B. These modified shuttle vectors contain the arsenite inducible promoter/operator and the arsR gene.

Figure 1C:
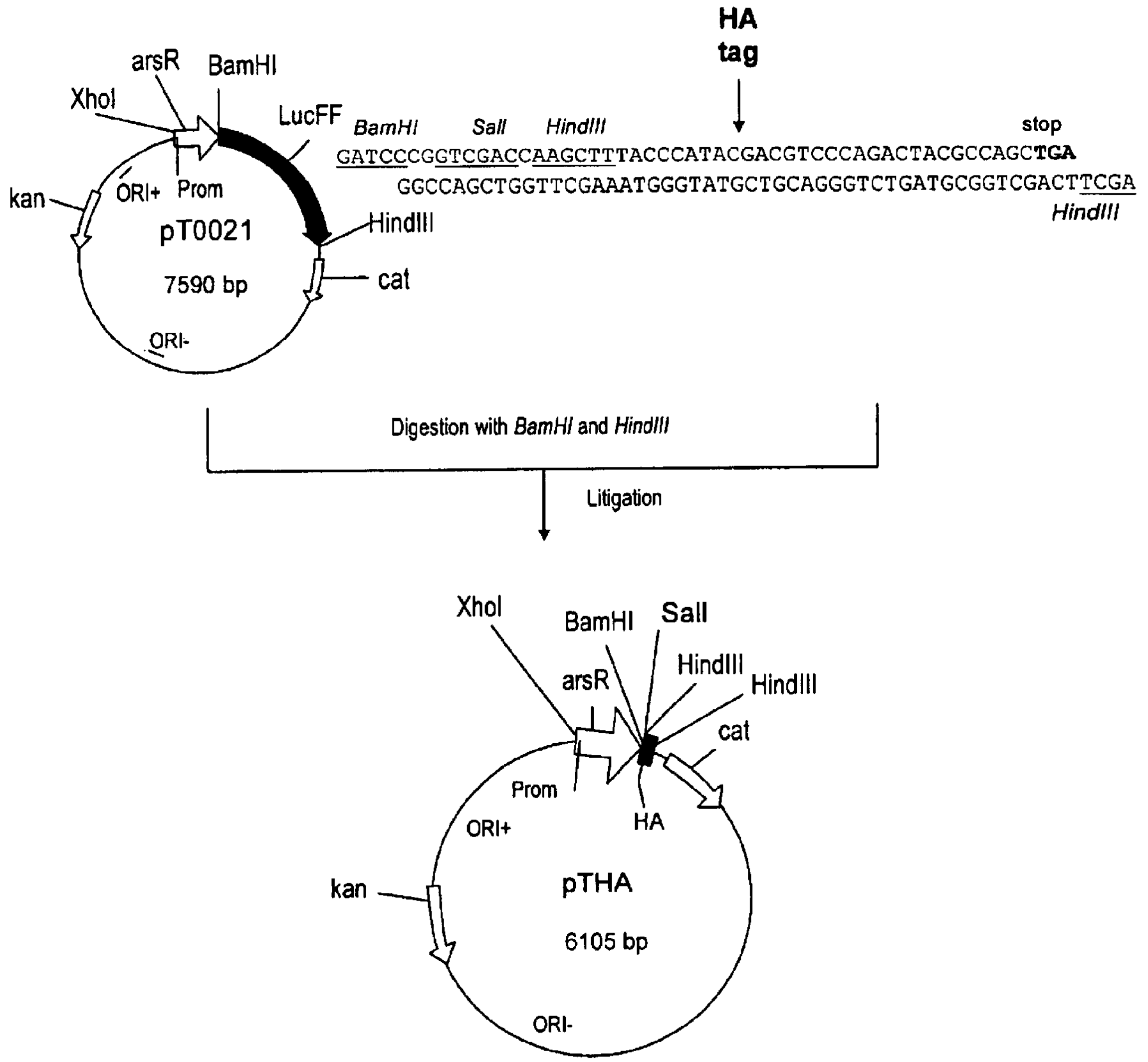
Figure 1D:
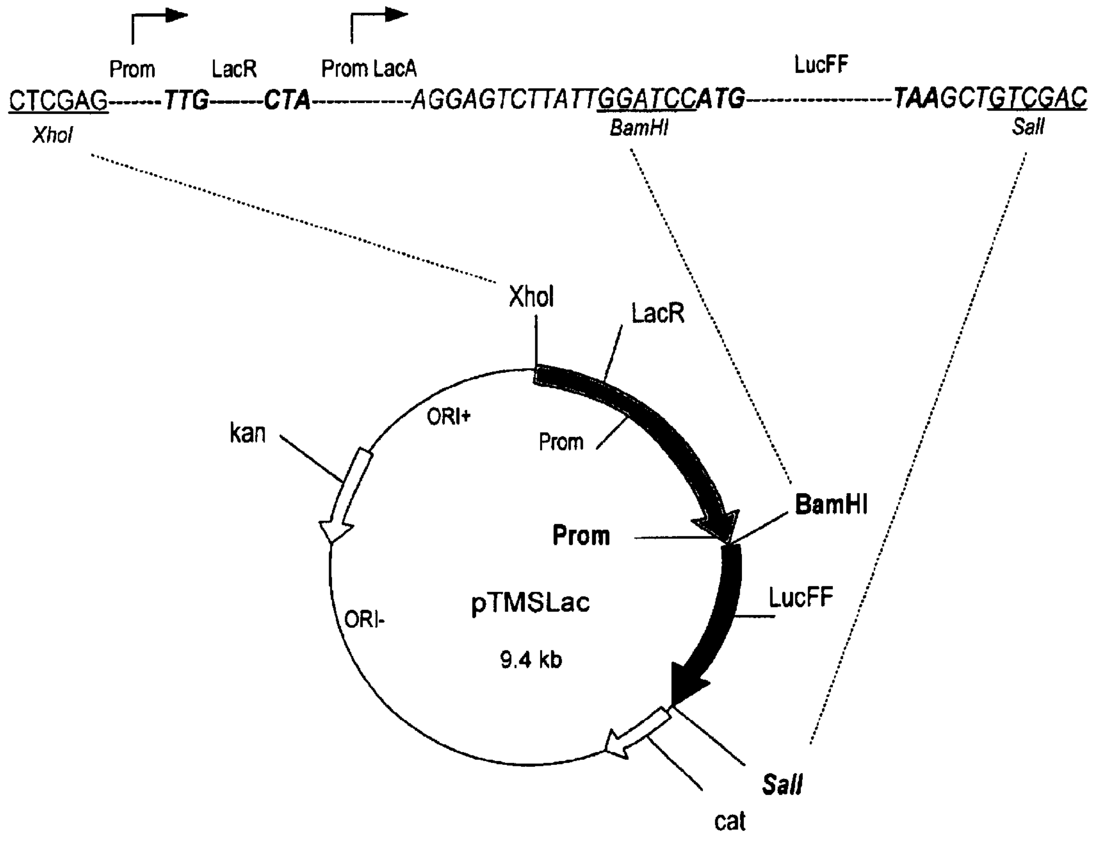
Figure 2A:
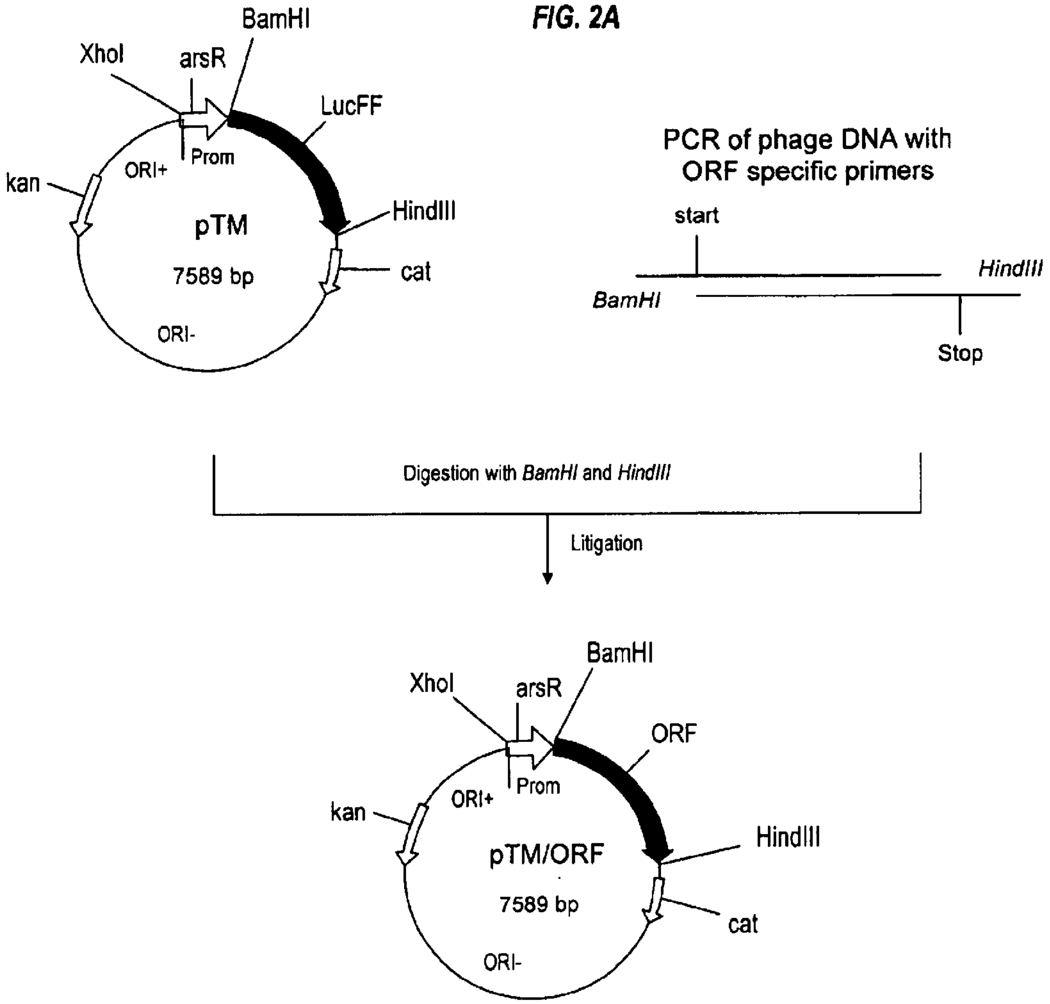
FIG. 2 is a schematic representation of the cloning steps involved to place the DNA segments of any ORFs e.g. 3A ORF 33, 41, 79, or 77 ORF 1, or 96 ORF 48, 78, 100 or other sequences into vector to assess inhibitory potential. For subcloning into a) pTM (and similarly into pTMSM and pTMSLac) individual ORFs were amplified by the PCR using oligonucleotides targetting the start and stop codons of the ORFs. Using this strategy cloning sites (here BamHI and HindIII), were positioned immediately upstream or downstream, respectively of the start and stop codons of each ORF. Following digestion with BamHI and HindIII, the PCR fragments were subcloned into the same sites of pTM (BamHI and HindIII). For subcloning into b) pTHA, individual ORFs e.g. 3A ORF 33, 41, 77 ORF 1 and 96 ORF 48, 78 were amplified by the PCR using oligonucleotides targetting the start codon and the penultimated codon of the ORFs. Using this strategy, BamHI and SalI sites were positioned immediately upstream or downstream, respectively of these two codons. Following digestion with BamHI and SalI, the PCR fragments were subcloned into the same sites of pTHA. Clones were verified by direct sequencing.
Figure 2B:
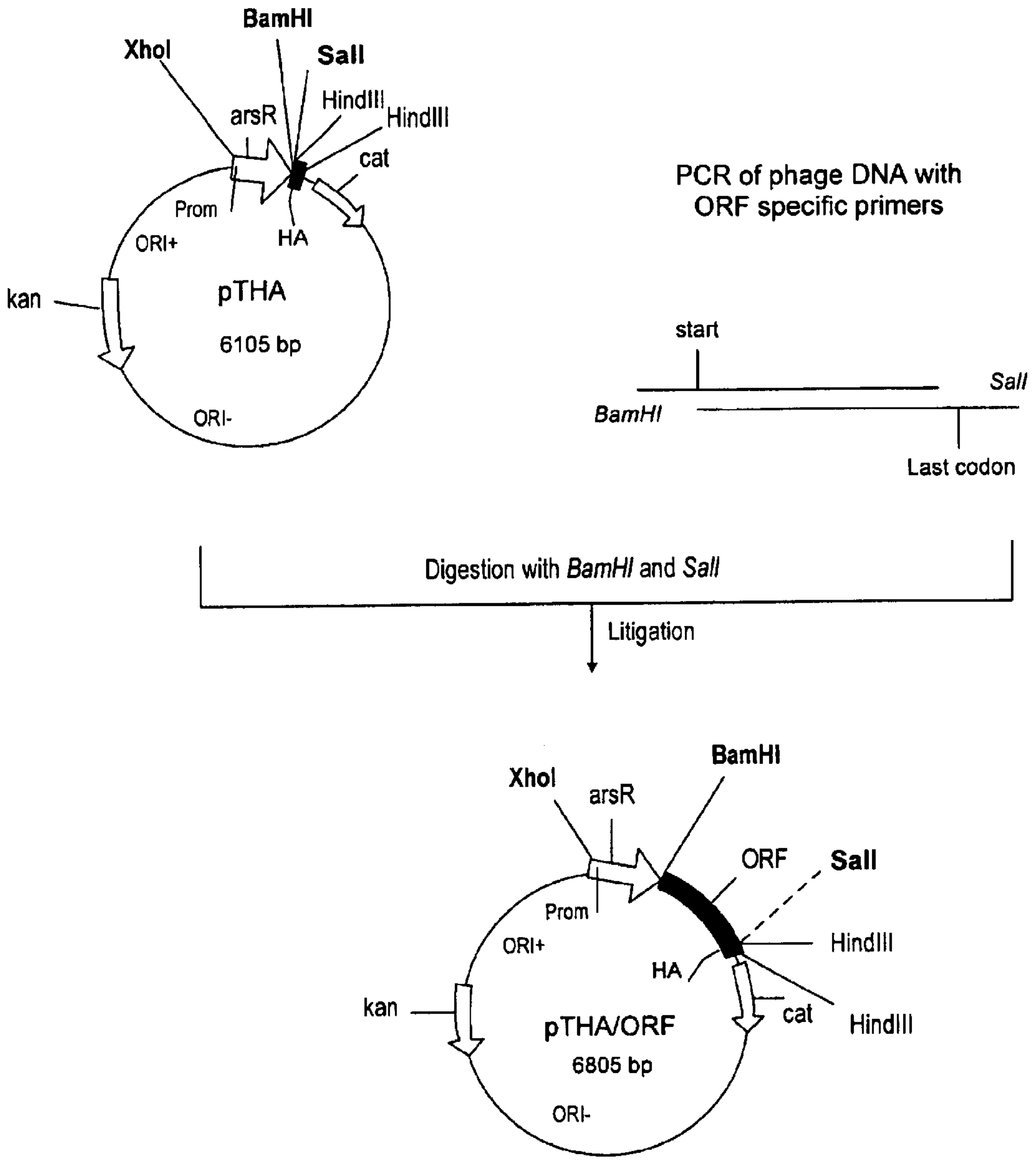

As another example of inducible promotor, the arsenite-inducible promotor and the asrR gene from the pTMSM vector were replaced by a lactose-inducible promotor and the lacR gene from *Staphylococcus aureus*. The *S. aureus* gene encoding for the repressor of the lac operon (lacR) is found immediately upstream of the promoter-proximal end of the the lacA-G genes. Two oligonucleotides corresponding to a 2.18 kb-DNA region encompassing the lacR and the lac operon promotor region were synthesized. The sense strand sequence is: 5'-ccgctcgagCTCCAAATTCCAAAACAG-3' (SEQ ID NO. 11) (with a XhoI cloning site, ctcgag); the antisense strand sequence is: 5'-cgggatccAATAAGACTCCTTTTTAC-3' (SEQ ID NO. 12) (with a BamHI cloning site, ggatcc). These two oligonucleotides were used for the PCR amplification of *Staphylococcus aureus* DNA. The PCR product was gel purified and digested with XhoI and BamHI. The digested PCR product was also gel purified, ligated into XhoI and BamHI-digested pTMSM vector, and used to transform *E. coli* bacterial strain DH10β. In the resulting vector, pTMSLac, the firefly luciferase (lucFF) expression is under the control of the *S. aureus* lac operon promoter/operator. Recombinant pTMSLac clones were picked and the sequence integrity of the 2.1 8 kb-lac operon region (lacR+ lac promotor) was verified directly by DNA sequencing. A diagram outlining the pTMSLac vector characteristics is shown in FIG. 1D.

For the analysis of the inhibitory ORFs expression in *S. aureus*, the pT0021 vectors was modified in the following fashion. Two oligonucleotides corresponding to a short antigenic peptide derived from the heamaglutinin protein of influenza virus (HA epitope tag) were synthesized (Field et al., 1988). The sense strand HA tag sequence (with BamHI, SalI and HindIII cloning sites) is: 5'-gatcccggtcgacc aagctt-TACCCATACGACGTCCCAGACTACGCCAG CTGA-3' (SEQ ID NO. 9) (where upper case letters denote the nucleotide sequence of the HA tag); the antisense strand HA tag sequence (with a HindIII cloning site) is: 5'-agctTCAG CTGGCGTAGTCTGGGACGTCGTATGGGTAaagcttgg tcgaccgg-3' (SEQ ID NO. 10) (where upper case letters denote the sequence of the HA tag). The two HA tag oligonucleotides were annealed and ligated into pT0021 vector which had been digested with BamHI and HindIII. This manipulation resulted in replacement of the lucFF gene by the HA tag. This modified shuttle vector containing the arsenite inducible promoter, the arsR gene, and HA tag was named pTHA. A diagram outlining our modification of pT0021 to generate pTHA is shown in FIG. 1C.

Cloning of ORFs With a Shine-Dalgarno Sequence.

Individual ORF, encoded by Bacteriophages 3A, 77 and 96, larger than 33 amino acids and having a Shine-Dalgarno sequence upstream of the initiation codon was selected for functional analysis. In total, 52 ORFs from phage 3A, 99 ORFs from phage 77 and 45 ORFs from phage 96 were selected and screened as detailed below. A list of these is presented in FIG. 4A. Each individual ORF, from initiation codon to stop codon was amplified from phage genomic DNA using the polymerase chain reaction (PCR). For PCR amplification of ORFs, each sense strand primer targets the initiation codon and is preceded by a BamHI restriction site (5'-cgggatcc-3') and each antisense oligonucleotide targets the stop codon of the ORF and is preceded by a HindIII restriction site (5'-cccaagctt-3') The PCR product of each ORF was purified using the Quiagen kit as described and digested with BamHI and HindIII. The digested PCR product was also purified using the Quiagen kit, ligated into BamHI and HindIII digested pTM vector and used to transform *E. coli* bacterial strain DH10β (as described above). As a result of this manipulation, the ORF is under the control of the arsenite-inducible promotor. Recombinant pTM/ORF clones were picked and their insert sizes were confirmed by PCR analysis using primers flanking the cloning site. The names and sequences of the primers that were used for the PCR amplification were: HAF: 5'-TATTATCCAAAACTTGAACA-3' (SEQ ID NO. 14); HAR: 5'-CGGTGGTATATCCAGTGATT-3' (SEQ ID NO. 15). The sequence integrity of cloned ORFs was verified directly by DNA sequencing using primers HAF and HAR. In cases where verification of ORF sequence could not be achieved by one pass with the sequencing primers, additional internal primers were selected and used for sequencing. In cases of ORF harboring internal HindIII site in their sequence, SalI instead of HindIII cloning site was used for the ORF cloning into the BamHI and SalI digested pTMSM vector. For the cloning into the lactose-inducible vector, the ORFs were excised from pTMSM vector by BamHI and SalI digestion and ligated to the same cloning sites into pTMSLac vector.

For the cloning into pTHA vector, each inhibitory ORF, from initiation codon to last codon (excluding the stop codon), was amplified from phage genomic DNA using the PCR. For PCR amplification of ORFs, each sense strand primer targets the initiation codon and is preceded by a BamHI restriction site (5'-cgggatcc-3') and each antisense oligonucleotide targets the pentultimate codon (the one before the stop codon) of the ORF and is preceded by a Sal I restriction site (5'-gcgtcgaccg-3') SEQ ID NO. 36). The PCR product of each ORF was gel purified and digested with BamHI and SalI. The digested PCR product was purified using the Qiagen kit as described, ligated into BaHI and SalI digested pTHA vector, and used to transform *E. coli* bacterial strain DH10β. As a result of this manipulation, the HA tag is set inframe with the ORF and is positioned at the carboxy terminus of each ORF (pTHA/ORF clones). Recombinant pTHA/ORF clones were picked and their insert sizes were confirmed as described above.

EXAMPLE V

Functional Assay for Bacterial Inhibitory Activity of Bacteriophage 3A, 77 and 96 ORFs Transformation of *Staphylococcus aureus* With Expression Construct *Staphylococcus aureus* strain RN4220 (Kreiswirth et al., 1983) was used as a recipient for the expression of recombinant plasmids. Electoporation was performed essentially as previously described (Schenk and Laddaga, 1992). Selection of recombinant clones was performed on Luria-Broth agar (LB-agar) plates containing 30 μg/ml of kanamycin.

For each ORF introduced in the pTM vector, 3 independent transformants were isolated and used to individually inoculate cultures in 5 ml of TSB containing 30 μg/ml kanamycin, followed by growth to saturation (16 hrs at 37° C.). An aliquot of this stationary phase culture was used to generate a frozen glycerol stock of the transformant (stored at −80° C.). With certain phage ORF, e.g. by phage 77 ORF 1 and 96 ORF 78, no *S. aureus* transformants could be obtained following cloning into pTM or pTMSM vector. In these cases, phage ORFs were cloned in alternative vectors pTHA and pTMSLac.

The presence of individual phage 3A, 77 or 96 ORF DNA inserts in the plasmid was verified by PCR amplification using 1.5 μl transformant miniprep DNA in a PCR with primers flanking the cloning site of ORF in pTM vector (HAF and HAR). The composition of the PCR reaction and the cycling parameters are identical to those employed for library screening described above.

Induction of Gene Expression From the ars- and lac-Inducible Promotors

Sodium arsenite ($NaAsO_2$) was purchased from Sigma (Sigma-Aldrich Canada LTD, Oakville) and was used as heavy metals to induce gene expression from the ars promoter/operator in solid and liquid medium assays.

The lactose (lac) genes of *Staphylococcus aureus* have been shown to be inducible with the addition of either lactose or galactose to the culture medium (Oskouian & Stewart, 1990, J. Bacteriol. 172 3804–3812). Galactose (2%w/v) was used to induce the gene expression from the lac promotor/operator in liquid assay.

At pre-determined times, sodium arsenite or galactose was added to the culture to induce transcription of the phage ORFs cloned immediately downstream from an arsenite-inducible promoter in the expression plasmids pTM, pTMSM or pTHA, or a lactose-inducible promotor in the expression plasmid pTMSLac. The anti-microbial activity of individual phage 3A, 77 and 96 ORFs was monitored by two growth inhibitory assays, one on solid agar medium, the other in liquid medium.

a-Screening on Semi-solid Support Media

Figure 3A:
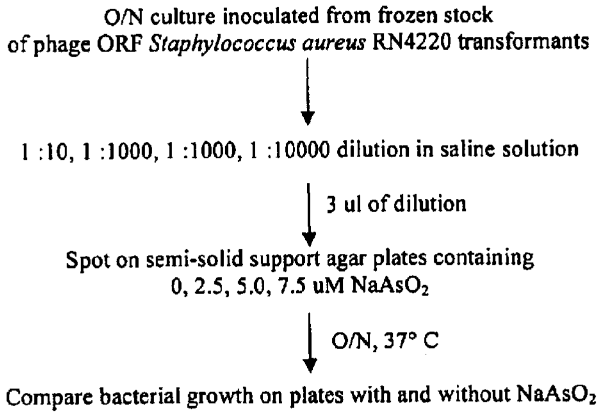
FIG. 3*a*) Functional assay on semi-solid support media.

ORFs were first screened by the functional assay on semi-solid medium as outlined in FIG. 3A. Cells containing different recombinant plasmids were grown overnight at 37° C. in LB medium supplemented with 30 μg/ml of kanamycin. The cells were then diluted and the identification of inhibitory ORFs was performed by spotting 3 ul of each dilution of *S. aureus* transformed cells containing phage 3A, 77 or 96 ORFs onto agar plates containing increasing concentrations of sodium arsenite (0; 2.5; 5; and 7.5 μM) and Kanamycin. The plates were incubated overnight at 37° C., after which a growth inhibition of the ORF transformants on plates that contain arsenite are compared to plates without arsenite. Noninduced and induced cultures of *S aureus* transformed with a non-inhibitory ORF (44AHJD bacteriophage ORF 114 cloned into pTM vector) were included as negative control. The 44AHJD ORF 114 amino acids residue composition from N-terminal to C-terminal is:M-VNVDNAPEEKGQAYTEMLQLFNKLIQWN-PAYTFDNAINLLSACQQLLLNYNSSVVQFLNDELNNETKPESILSYIAGDDPIEQWNMHKG-FYETYNVYVF (SEQ ID NO. 16).

Figure 4D:
FIG. 4 shows the results of the functional assay on semi-solid support media to identify bacteriophage 3A, 77 and 96 ORFs with anti-microbial activity.
FIG. 4*a*) shows the lists of the bacteriophage 3A, 77 and 96 ORFs that were screened in the functional assay and FIG. 4*b*) shows inhibition of bacterial growth following induction of expression of phage 3A ORF 33, 41 and 79, phage 77 ORF1 and phage 96 ORF 48 and 100 from three clones of *Staphylococcus aureus* transformants. One clone of *Staphylococcus aureus* transformed with the non-inhibitory ORF (44AHJD bacteriophage ORF 114 cloned into pTM vector) was used as control. From these experiments, it is clear that expression of these ORFs leads to the inhibition of growth of *Staphylococcus aureus.*
Figure 4D:
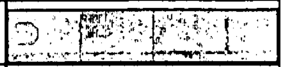
Figure 4D:
Figure 4D:
Figure 4D:
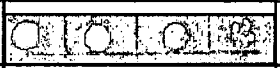
Figure 4D:
Figure 4D:
Figure 4D:
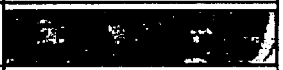
Figure 4D:
Figure 4D:
Figure 4D:
Figure 4D:
Figure 4D:
Figure 4D:
Figure 4D:
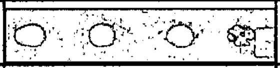
Figure 4D:
Figure 4D:
Figure 4D:
Figure 4D:
Figure 4D:
Figure 4D:
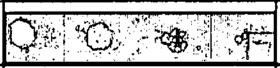
Figure 4D:
Figure 4D:
Figure 4D:
Figure 4E:
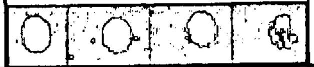
Figure 4E:
Figure 4E:
Figure 4E:
Figure 4E:
Figure 4E:
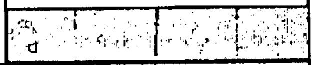
Figure 4E:
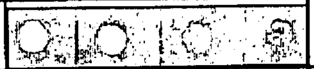
Figure 4E:
Figure 4E:
Figure 4E:
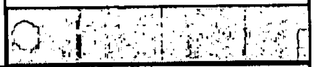
Figure 4E:
Figure 4E:
Figure 4E:
Figure 4E:
Figure 4E:
Figure 4E:
Figure 4E:
Figure 4E:
Figure 4E:
Figure 4E:
Figure 5A:
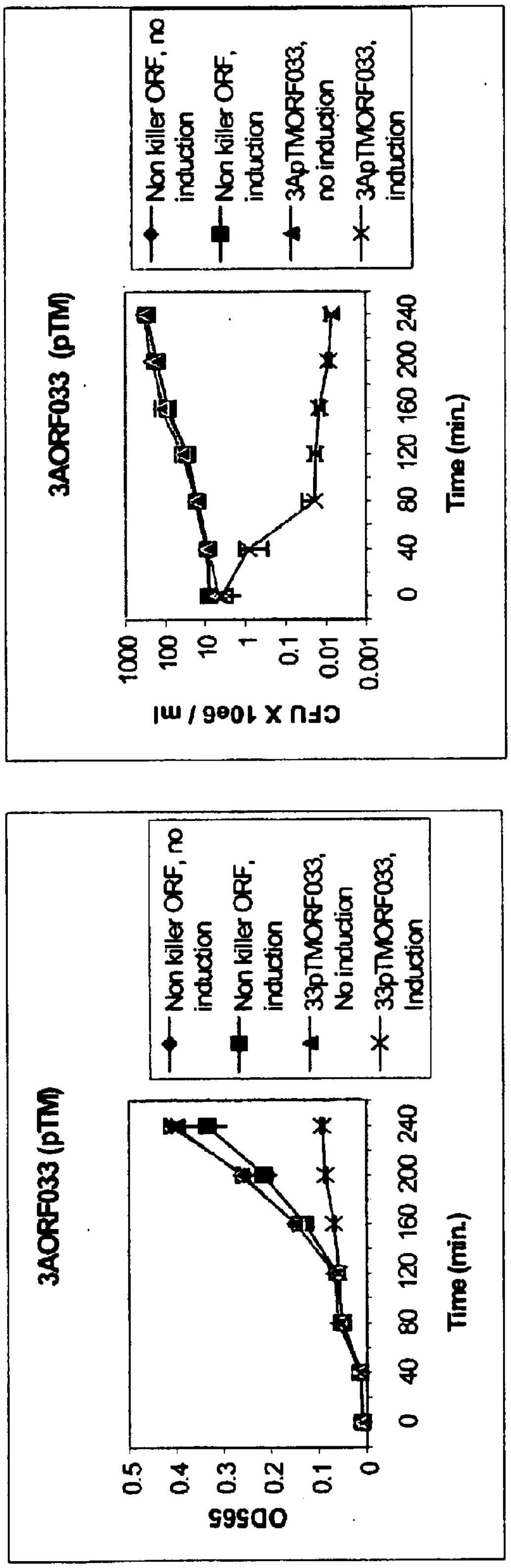
FIG. 5 are the graphs of $OD_{565}$ values and colony forming units (CFU) over time showing the results of functional assay in liquid media to assess bacteriostatic or bactericidal activity of bacteriophage 3A ORF 33, 41 and 79, bacteriophage 77 ORF 1 and bacteriophage 96 ORF 48, 78 and 100. Growth inhibition assays were performed as detailed in the Detailed Description. The $OD_{565}$ values and the number of CFU were determined from cultures of *Staphylococcus aureus* transformants harboring a given bacteriophage inhibitory ORF, in the absence or presence of the inducer. The identity of the expression vector and subcloned ORF harbored by the *Staphylococcus aureus* is given at the top of the each graph. The value of OD and the number of CFU was also determined from non-induced and induced control cultures of *Staphylococcus aureus* transformants harboring a non-inhibitory phage ORF cloned into the same vector. Each graph represents the average obtained from three *Staphylococcus aureus* transformants.
Figure 5B:
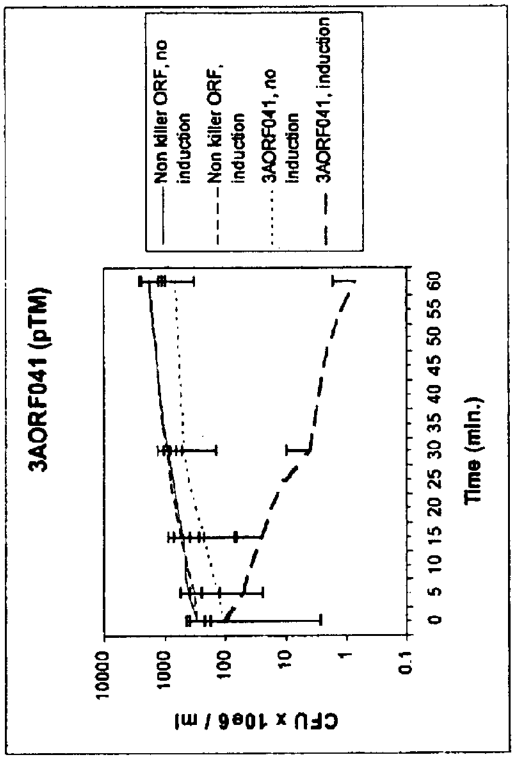
Figure 5B:
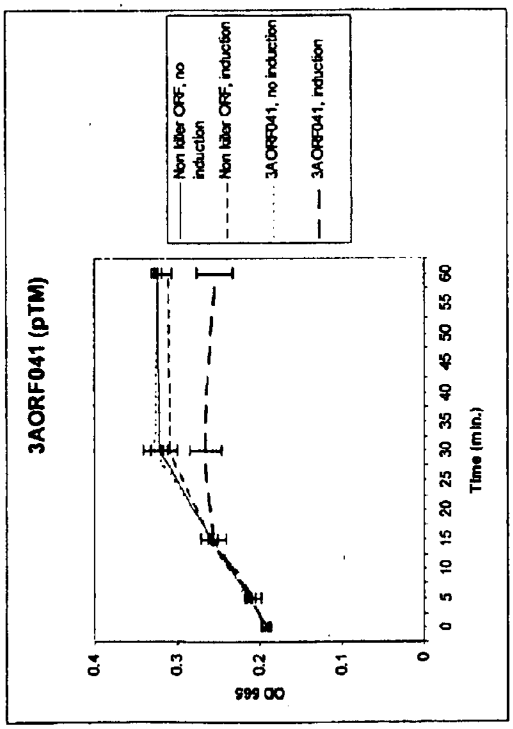
Figure 5C:
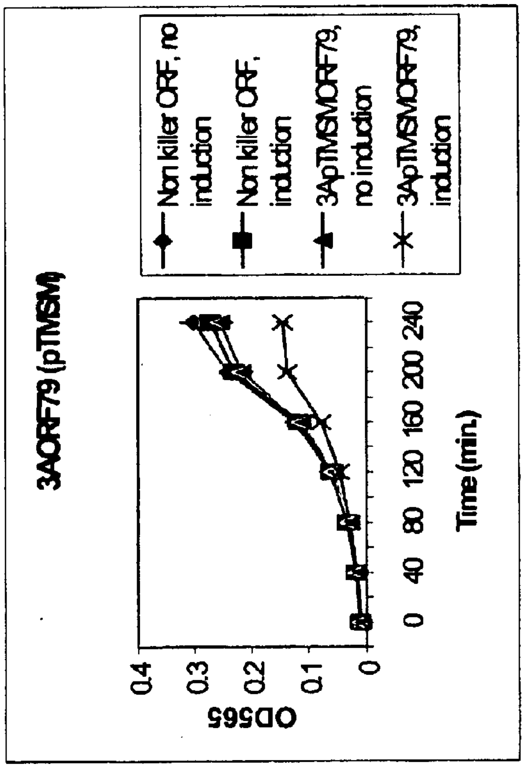
Figure 5C:
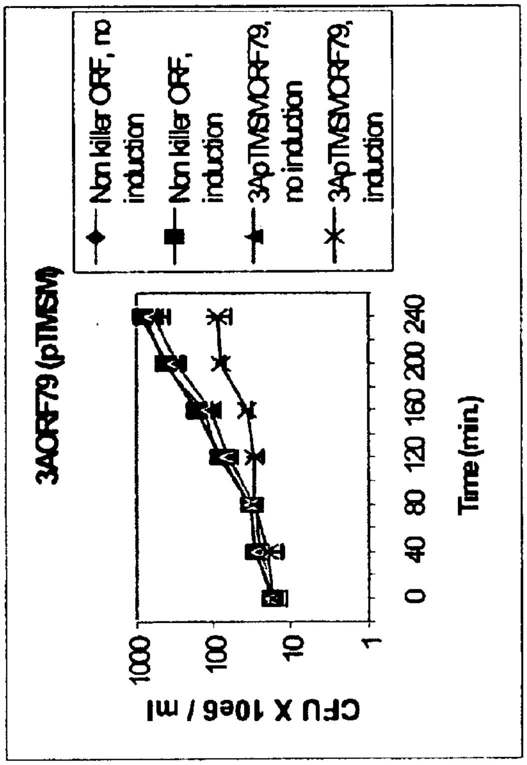
Figure 5D:
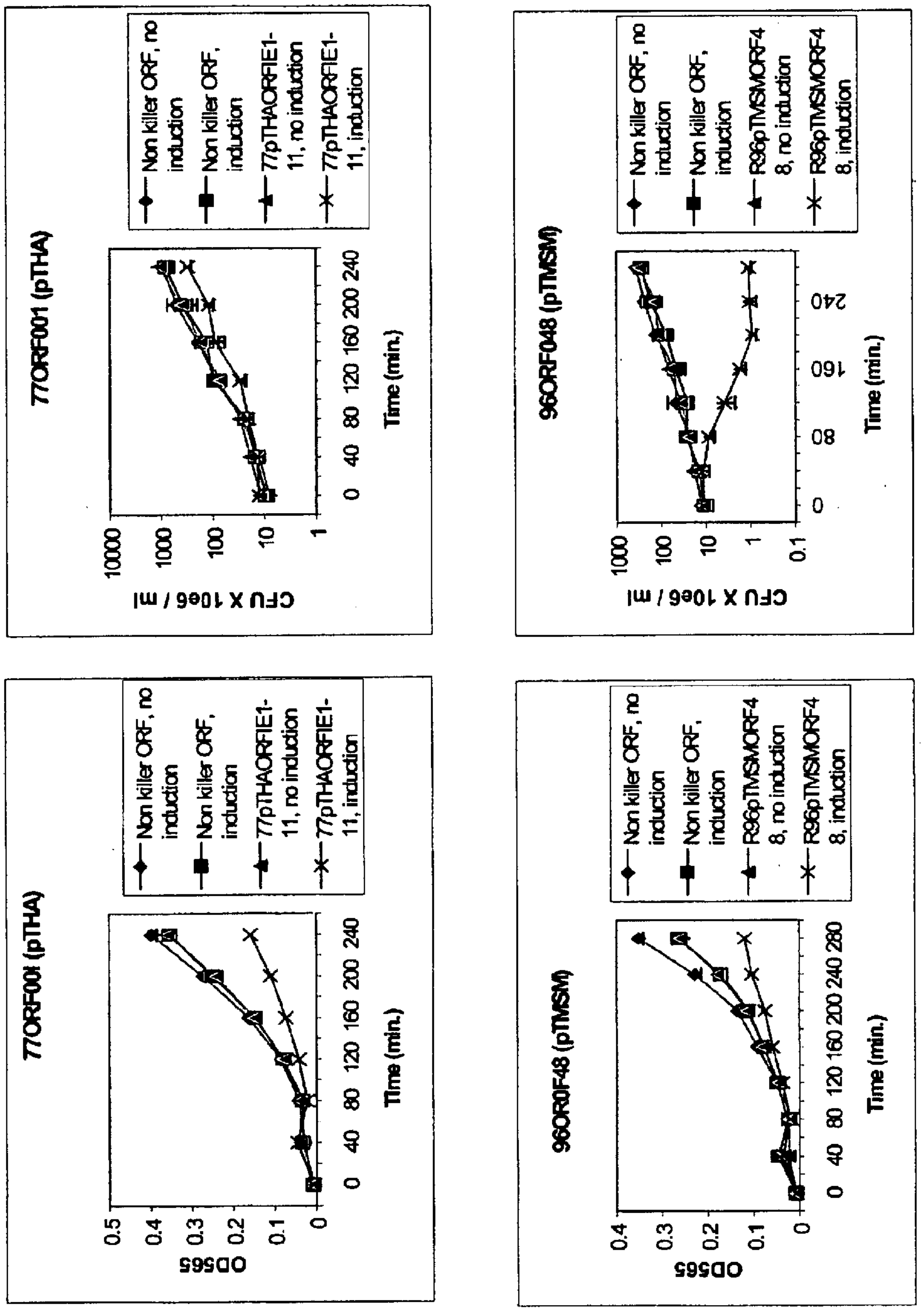
Figure 5E:
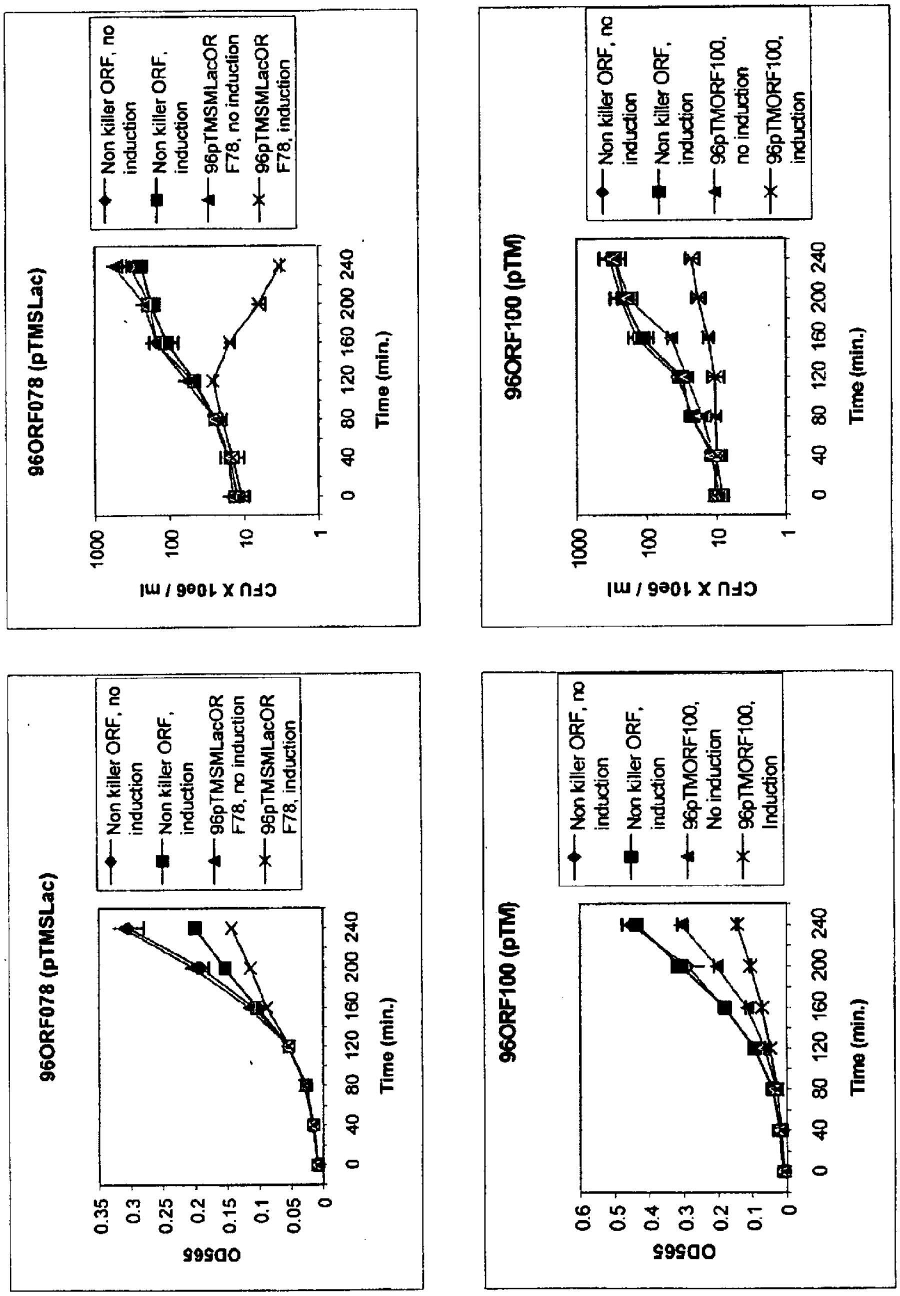

Results of the bacteriophage ORFs tested for functional assay on semi-solid media are listed in FIG. 4A. Among them, induction of expression of phage 3A ORF 33, 41 or 79, phage 77 ORF 1, or phage 96 ORF 48 or 100 results in the inhibition of growth of the *S. aureus* transformants. FIG. 4B shows the result of growth inhibition with three clones of *S. aureus* expressing these inhibitory ORFs or the control non-inhibitory 44AHJD ORF 114.

b-Quantification of Growth inhibition in Liquid Medium

Figure 3B:
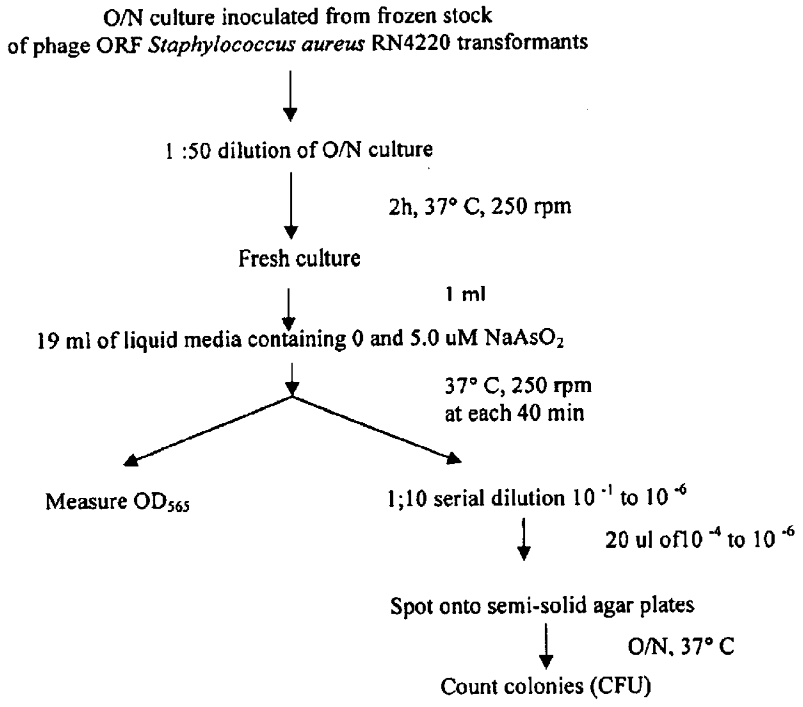
FIG. 3*b*) Functional assay in liquid culture.

As outlined in FIG. 3B, the effect of ORF induction on bacterial growth inhibition was then further quantitated by functional assay in liquid medium. Cells containing phage 3A ORF 33, 41 or 79, phage 77 ORF 1, or phage 96 ORF 48, 78 or 100 were grown for overnight at 37° C. in LB medium supplemented with the appropriate antibiotic selection. These cultures were 50-fold dilution with fresh media containing kanamycin and the growth was continued for 2 h at 37° C. The same $OD_{565}$ equivalent of cultures (approximately 1 ml) was added to 19 ml of fresh media containing kanamycin and transferred to a 125 ml-Erlenmeyer flask. The cultures were incubated for an additional 4 hrs at 37° C. in the absence or in the presence of inducer (sodium arsenite at the final concentrations of 5.0 μM or 2.0% galactose). During that period of time, the effect of expression of the phage 3A, 77 and 96 ORFs on bacterial cell growth was monitored, at each 40 min, by measuring the $OD_{565}$ and the number of colony forming units (CFU) in the cultures containing or not the inducer. The number of CFU was evaluated as followed. Cultures were serially diluted and aliquots from induced and uninduced cultures were plated out on agar plates containing an appropriate antibiotic selection but lacking inducer. Following incubation overnight at 37° C., the number of colonies was counted. Cultures of *S aureus* transformed with a non-inhibitory ORF (44AHJD bacteriophage ORF 114 cloned into pTM vector) were included as control.

As shown in FIG. 5, for each inhibitory ORFs, the number of CFU increased over time under non-induced conditions. Similar growth rates were also observed with transformants harboring non-inhibitory ORFs under both induced and non-induced conditions. Transformants of *S.aureus* harboring C) phage 3A ORF 79 or D) phage 77 ORF 1 showed a significantly lower growth rate compared to their respective control cultures grown under non-induced conditions. Induction of expression of E) phage 96 ORF 100 was cytostatic. In contrast, four phage ORFs were cytocidal for bacterial growth. The expression of B) phage 3A ORF 41 resulted in a very rapid decrease in the number of viable cells as assayed as CFU. A 2 log reduction in the number of CFU after 1 hr of growth compared to the number of CFU initially present in the same culture was observed following induction of 3A ORF 41 with sodium arsenite. At 4 hr following induction, the number of viable cells relative to uninduced cultures was reduced by either 2 logs (phage 3A ORF 33 (A)), 1 log (phage 96 ORF 48 (D)), or 0.5 log (phage 96 ORF 78 (E)).

The presence of four phage ORFs were cytocydal for the bacterial growth. The expression of B) phage 3A ORF 41 results in a very rapid decrease in the number of CFU. A 2 log reduction in the number of CFU compared to the number of CFU initially present in the same culture was observed at 1 h following induction with sodium arsenite.

At 4 h following induction with sodium arsenite, the expression of A) phage 3A ORF 33 results in a 2 log reduction in the number of CFU compared to the number of CFU initially present in the same culture. The expression of D) phage 96 ORF 48 results in a log reduction in the number of CFU compared to the number of CFU initially present in the same culture.

At 4 h following induction of the expression of E) phage 96 ORF 78 with galactose a half log reduction in the number of CFU compared to the number of CFU initially present in the same culture was observed.

EXAMPLE VI

Phage ORF Protein Expression Analysis in *S. aureus*

The level of expression of the inhibitory ORFs was measured by performing Western blot analyses. *Staphylococcus aureus* strain RN4220 was electroporated with each inhibitory ORFs cloned into pTHA vector as described above. Cells containing different recombinant plasmids were grown for overnight at 37° C. in TSB (Tryptic soy broth, DIFCO) medium in the presence of 30 μg/ml kanamycin. The overnight cultures were subjected to a 50-fold dilution with fresh media containing kanamycin and the growth was continued for 2 h at 37° C. At the end, cells were diluted with fresh TSB medium containing or not 5.0 μM of Sodium Arsenite, in the presence of kanamycin and incubated at 37° C. for an additional 3.5 h. The same $OD_{565}$ equivalent of cultures was centrifuged at 3000 g for 5 min and washed with 20 ml of TBS buffer (140 mM NaCl, 25 mM Tris-HCl, pH 7.5) containing protease inhibitors (1 mM of each phenylmethylsulfonyl fluoride (PMSF) and N-ethylmalemyde (NEM)). For lysis, cell pellets were resuspend in 25 μl with TBS buffer containing 1 mM PMSF, 1 mM NEM, 20 μg of each DNAse I and RNase A and 50 Units/ml of lysostaphin, and incubated at 37° C. for 1 h. The reaction was stopped by the addition of 25 μl of 2×SDS buffer (100 mM Tris pH 6.8, 4% SDS, 200 mM DTT, 20% Glycerol and 0.2% Bromophenol blue). Cell lysates were boiled for 10 min, centrifuged for 10 min at 13,000 g and 10–15 μl of the lysates were loaded onto a 15–18% SDS-page using Tris-Glycine-SDS as a running buffer (3.03 g of Tris HCl, 14.4 g of Glycine and 0.1% SDS per liter). After migration, proteins were transferred onto an immobilon-P membrane (PVDF, Millipore) using Tris-Glycin-Methanol as a transfer buffer (3.03 g Tris, 14.4 Glycine and 200 ml Methanol per liter) for 2 hrs at 4° C. at 100 V. PVDF membrane was pretreated in methanol for 30 s, washed 4–5 times with $H_2O$ and soaked in transfer buffer.

Figure 6:
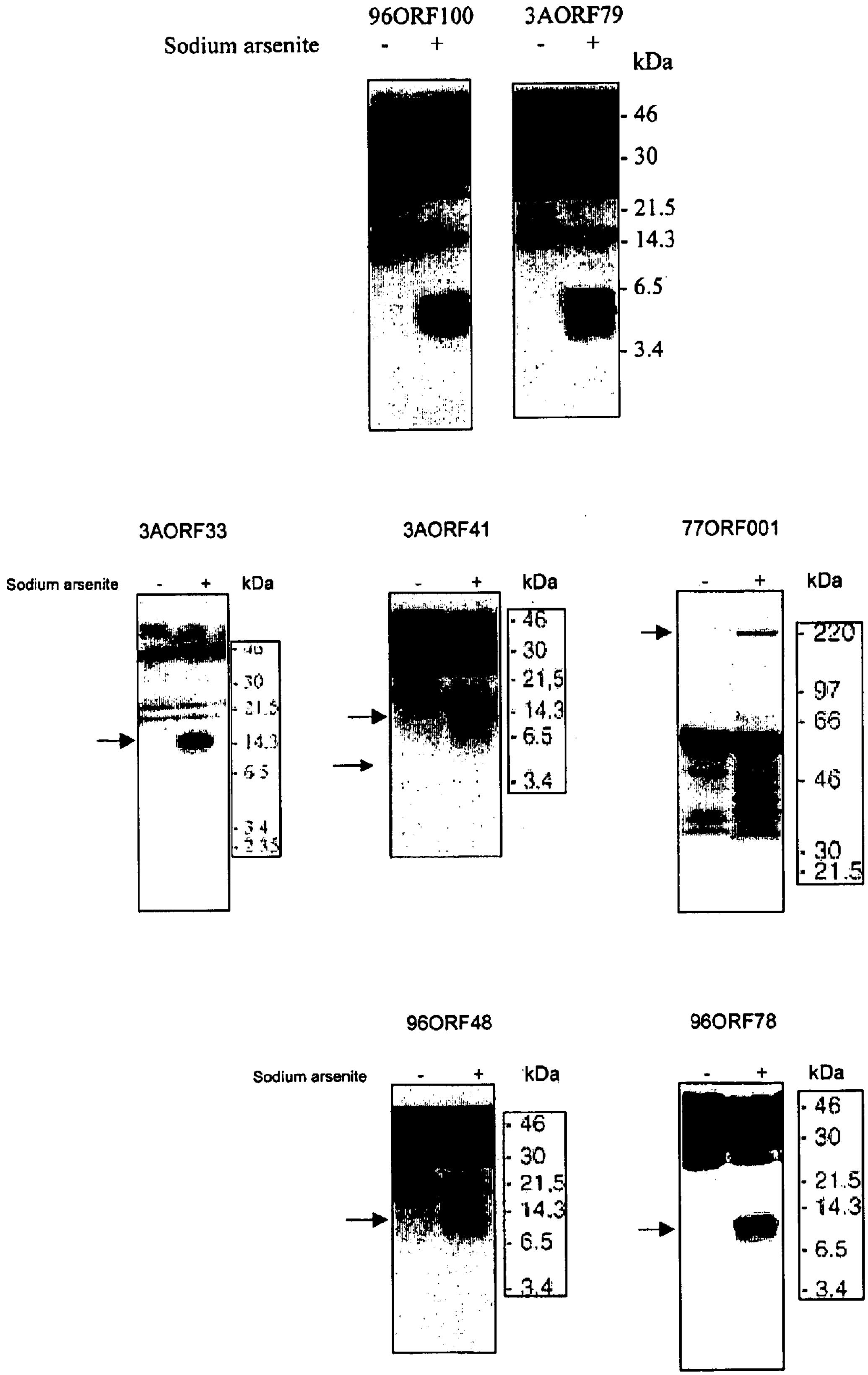
FIG. 6 shows the pattern of protein expression of the inhibitory ORF in *S. aureus* in the presence or in the absence of induction with sodium arsenite. Individual inhibitory ORF (phage 3A ORF 33, 41 and 79, phage 77 ORF 1, phage 96 ORF 48, 78 and 100) were subcloned into the pTHA vector. This vector contains BamH I, Sal I cloning sites and a downstream HA epitope tag. The HA tag is set inframe with the ORF and is positioned at the carboxy terminus of each ORF. An anti-HA tag antibody was used for the detection of the ORF expression. The identity of the subcdoned ORF harbored by the *Staphylococcus aureus* transformants is given at the top of each panel.

After the transfer, the membrane was blocked in 20 ml of TBS containing 0.05% Tween-20 (TBST), 5% skim milk and 0.5% gelatin for 1 hr at room temperature and then, a pre-blocking antibody (ChromPureRabbit IgG, Jackson immunoResearch lab. #011-000-003) was added at a dilution of 1/750 and incubated for 1 hr at room temperature or ON at 4° C. Membrane was washed 6 times for 5 min in TBST at room temperature. The primary antibody (murine mono-HA antibody, Babco # MMS-101 P) directed against the HA epitope tag and diluted 1/1000 was then added and incubated for 3 h at room temperature in the presence of 5% Skim Milk and 0.5% Gelatin. Membrane was washed 6 times for 5 min in TBST at room temperature. A secondary antibody (anti-mouse IgG, peroxidase-linked species-specific whole antibody, Amersham # NA 931) diluted 1/1500 (7.5 μl in 10 ml) was then added and incubated for 1 hr at room temperature. After 6 washes in TBST, the membrane was briefly dried and then, the substrate (Chemiluminescence reagent plus, Mandel # NEL104) was added to the membrane and incubated for I min at room temperature. The membrane was briefly dried and exposed to x-ray film (Kodak, Biomax MS/MR ) for different periods of time (30 s to 10 min). As shows in FIG. 6, the presence of sodium arsenite in the cultures induces the expression of proteins corresponding to the phage 3A ORF 33, 41 and 79, phage 77 ORF 1, and phage 96 ORF 48, 78 and 100.

References

Cohen, M. L. (1992). Science 257: 1050–1055.

Rusterholtz, K., and Pohlschroder, M. (1999). Cell 96, 469–470.

Ackermann, H.-W. and DuBow, M. S. (1987). Viruses of Prokaryotes. CRC Press. Volumes 1 and 2.

Durfee, T., Becherer, K., Chen, P.-L., Yeh, S.-H., Yang, Y., Kilburn, A. E., Lee, W.-H., and Elledge, S. J. (1993). Genes & Dev. 7: 555–569.

Sopta, M., Carthew, R. W., and Greenblatt, J. (1995) J. Biol. Chem. 260: 10353–10369.

Qin, J., Fenyo, D., Zhao, Y., Hall, W. W., Chao, D. M., Wilson, C. J., Young, R. A. and Chait, B. T. (1997). *Anal. Chem*. 69: 3995–4001.

Sambrook, J., Fritsch, E. F. and Maniatis, T (1989). Molecular cloning: A laboratory Manual. Cold Spring Harbor Laboratory, New York. Cold Spring Harbor Laboratory Press.

Swanström, M. and Adams, M. H. (1951). Agar layer method for production of high titer phage stocks. Proc. Soc. Exptl. Biol. & Med. 78: 372–375.

Tauriainen, S., Karp, M., Chang, W and Virta, M. (1997). Recombinant luminescent bacteria for measuring bioavailable arsenite and antimonite. Appl. Environ. Microbiol. 63:4456–4461.

Field, J., Nikawa, J.-I., Broek, D., MacDonald, B., Rodgers, L., Wilson, I. A., Lemer, R. A., and Wigler, M. (1988). Purification of a RAS-responsive adenylyl cyclase complex from *Saccharomyces cerevisiae* by use of an epitope addition method. Mol. Cell. Biol. 8: 2159–2165.

Kreiswirth, B N., Lofdahl, S., Belley, M J., O'Reilly, M., Shlievert, P M., Bergdoll, M S. and Novicks, R P. 1983. Nature #305: 709–712.

Schenk, S. and Laddaga, R A. 1992. FEMS Microbiology Letters #94: 133–138.

Oskouian, B. and Stewart, G S. 1990. J. Bacteriol. #172: 3804–3812.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The specific methods and compositions described herein as presently representative of preferred embodiments are exemplary and are not intended as limitations on the scope of the invention. One of ordinary skill in the art would recognize that Bacteriophages 3A, 77 and 96 ORFs described herein are provided and discussed by way of example, and other the ORFs of Bacteriophages 3A, 77 and 96, including amino acid sequences and nucleic acid sequences which encode products, are within the scope of the present invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention. For example, those skilled in the art will recognize that the invention may suitably be practiced using a variety of different expression vectors and sequencing methods within the general descriptions provided.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is not intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group. For example, if there are alternatives A, B, and C, all of the following possibilities are included: A separately, B separately, C separately, A and B, A and C, B and C, and A and B and C.

Thus, additional embodiments are within the scope of the invention and within the following claims.

TABLE 2

| 1st position | 2nd position | | | | 3rd position |
|---|---|---|---|---|---|
| (5' end) | U | C | A | G | (3' end) |
| U | Phe | Ser | Tyr | Cys | U |
| | Phe | Ser | Tyr | Cys | C |
| | Leu | Ser | Stop | Stop | A |
| | Leu | Ser | Stop | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

TABLE 3

| 3AORF033, Nucleotides and amino acids sequences (SEQ ID NO. 20) | |
|---|---|
| 30089 | atggcaatattagaaggtattttgaagaattaaaactattaaat |
| 1 | M A I L E G I F E E L K L L N |
| 30134 | aagaatttacgtgtgctaaatactgaactatcaactgtagattca |
| 16 | K N L R V L N T E L S T V D S |
| 30179 | tcaattgtacaagagaaagttaaagaagcaccaatgccaaaagat |
| 31 | S I V Q E K V K E A P M P K D |
| 30224 | gaaacagctcaactggaatcagttgaagaagttaaggaaacttct |
| 46 | E T A Q L E S V E E V K E T S |
| 30269 | gctgatttaactaaagattatgttttatcagtaggaaaagagttc |
| 61 | A D L T K D Y V L S V G K E F |
| 30314 | cttaaaaaagcagatacttctgataagaaagaatttagaaataaa |
| 76 | L K K A D T S D K K E F R N K |
| 30359 | cttaacgaacttggtgcggataagctatctactatcaaagaagag |
| 91 | L N E L G A D K L S T I K E E |
| 30404 | cattatgaaaaaattgttgattttatgaatgcgagaataaatgca |
| 106 | H Y E K I V D F M N A R I N A |
| 30449 | tga 30451 |
| 121 | * |

| 3AORF041, Nucleotides and amino acids sequences (SEQ ID NO. 22) | |
|---|---|
| 21497 | atgtttggatttaccaaacgacacgaacaagattggcgtttaacg |
| 1 | M F G F T K R H E Q D W R L T |
| 21542 | cgattagaagaaaatgataagactatgtttgaaaaattcgacaga |
| 16 | R L E E N D K T M F E K F D R |
| 21587 | atagaagacagtctgagaacgcaagaaaaaatttatgacaagtta |
| 31 | I E D S L R T Q E K I Y D K L |
| 21632 | gatagaaatttcgaagaactaaggcgtgacaaagaagaagatgaa |
| 46 | D R N F E E L R R D K E E D E |
| 21677 | aaaaataaagagaaaaatgctaaaaatattagagacatcaagatg |
| 61 | K N K E K N A K N I R D I K M |
| 21722 | tggattctaggattaatagggacgattctaagtacatttgttata |
| 76 | W I L G L I G T I L S T F V I |
| 21767 | gccttgttaaaaactatttttggcatttaa 21796 |
| 91 | A L L K T I F G I * |

| 3AORF079, Nucleotides and amino acids sequences (SEQ ID NO. 24) | |
|---|---|
| 34231 | atgcaacatcaagcttatatcaatgcttctgttgacattagaatt |
| 1 | M Q H Q A Y I N A S V D I R I |
| 34276 | cctacagaagtcgaaagtgttaattacaatcagattgataaagaa |
| 16 | P T E V E S V N Y N Q I D K E |
| 34321 | aaagaaaatttggcggactatttatttaataatccaggtgaacta |
| 31 | K E N L A D Y L F N N P G E L |
| 34366 | ttaaaatataacgttataaatattaaggttttagatttagaggtg |
| 46 | L K Y N V I N I K V L D L E V |
| 34411 | gaatga 34416 |
| 61 | E * |

| 77ORF001, Nucleotides and amino acids sequences (SEQ ID NO. 26) | |
|---|---|
| 8481 | atgggagaaagaataaaaggtttatctataggtttggatttagat |
| 1 | M G E R I K G L S I G L D L D |
| 8526 | gcagcaaatttaaatagatcatttgcagaaatcaaacgaaacttt |
| 16 | A A N L N R S F A E I K R N F |
| 8571 | aaaactttaaattctgacttaaaattaacaggcaacaacttcaaa |
| 31 | K T L N S D L K L T G N N F K |
| 8616 | tataccgaaaaatcaactgatagttacaaacaaaggattaaagaa |
| 46 | Y T E K S T D S Y K Q R I K E |
| 8661 | cttgatggaactatcacaggttataagaaaaacgttgatgattta |
| 61 | L D G T I T G Y K K N V D D L |
| 8706 | gccaagcaatatgacaaggtatctcaagaacagggcgaaaacagt |
| 76 | A K Q Y D K V S Q E Q G E N S |
| 8751 | gcagaagctcaaaagttacgacaagaatataacaaacaagcaaat |
| 91 | A E A Q K L R Q E Y N K Q A N |
| 8796 | gagctgaattatttagaaagagaattacaaaaaacatcagccgaa |
| 106 | E L N Y L E R E L Q K T S A E |
| 8841 | tttgaagagttcaaaaaagctcaagttgaagctcaaagaatggca |
| 121 | F E E F K K A Q V E A Q R M A |
| 8886 | gaaagtggctggggaaaaaccagtaaagtttttgaaagtatggga |
| 136 | E S G W G K T S K V F E S M G |
| 8931 | cctaaattaacaaaaatgggtgatggtttaaaatccattggtaaa |
| 151 | P K L T K M G D G L K S I G K |
| 8976 | ggtttgatgattggtgtaactgcacctgttttaggtattgcagca |
| 166 | G L M I G V T A P V L G I A A |
| 9021 | gcatcaggaaaagcttttgcagaagttgataaaggtttagatact |
| 181 | A S G K A F A E V D K G L D T |
| 9066 | gttactcaagcaacaggcgcaacaggcagtgaattaaaaaaattg |
| 196 | V T Q A T G A T G S E L K K L |

TABLE 3-continued

| | |
|---|---|
| 9111 | cagaactcatttaaagatgtttatggcaattttccagcagatgct |
| 211 | Q N S F K D V Y G N F P A D A |
| 9156 | gaaactgttggtggagttttaggagaagttaatacaaggttaggt |
| 226 | E T V G G V L G E V N T R L G |
| 9201 | tttacaggtaaagaacttgaaaatgccacagagtcattcttgaaa |
| 241 | F T G K E L E N A T E S F L K |
| 9246 | ttcagtcatataacaggttctgacggtgtgcaagccgtacagtta |
| 256 | F S H I T G S D G V Q A V Q L |
| 9291 | attacccgtgcaatgggcgatgcaggtatcgaagcaagtgaatat |
| 271 | I T R A M G D A G I E A S E Y |
| 9336 | caaagtgttttggatatggtagcaaaagcggcgcaagctagtggg |
| 286 | Q S V L D M V A K A A Q A S G |
| 9381 | ataagtgttgatacattagctgatagtattactaaatacggcgct |
| 301 | I S V D T L A D S I T K Y G A |
| 9426 | ccaatgagagctatgggctttgagatgaaagaatcaattgcttta |
| 316 | P M R A M G F E M K E S I A L |
| 9471 | ttctctcaatgggaaaagtcaggcgttaatactgaaatagcattc |
| 331 | F S Q W E K S G V N T E I A F |
| 9516 | agtggtttgaaaaaagctatatcaaattggggtaaagctggtaaa |
| 346 | S G L K K A I S N W G K A G K |
| 9561 | aacccaagagaagaatttaagaagacattagcagaaattgaaaag |
| 361 | N P R E E F K K T L A E I E K |
| 9606 | acgccggatatagctagcgcaacaagtttagcgattgaagcattt |
| 376 | T P D I A S A T S L A I E A F |
| 9651 | ggtgcaaaggcaggtcctgatttagcagacgctattaaaggtggt |
| 391 | G A K A G P D L A D A I K G G |
| 9696 | cgctttagttatcaagaatttttaaaaactattgaagattcccaa |
| 406 | R F S Y Q E F L K T I E D S Q |
| 9741 | ggcacagtaaaccaaacatttaaagattctgaaagtggctccgaa |
| 421 | G T V N Q T F K D S E S G S E |
| 9786 | agatttaaagtagcaatgaataaattaaaattagtaggtgctgat |
| 436 | R F K V A M N K L K L V G A D |
| 9831 | gtatgggcttctattgaaagtgcgtttgctcccgtaatggaagaa |
| 451 | V W A S I E S A F A P V M E E |
| 9876 | ttaatcaaaaagctatctatagcggttgattggttttccaattta |
| 466 | L I K K L S I A V D W F S N L |
| 9921 | agtgatggttctaaaagatcaattgttattttcagtggtattgct |
| 481 | S D G S K R S I V I F S G I A |
| 9966 | gctgcaattggtcctgtagtttttgggttaggtgcatttataagt |
| 496 | A A I G P V V F G L G A F I S |
| 10011 | acaattggcaatgcagtaactgtattagctccattgttagctagt |
| 511 | T I G N A V T V L A P L L A S |
| 10056 | attgcaaaggctggtggattgattagtttttttatcgactaaagta |
| 526 | I A K A G G L I S F L S T K V |
| 10101 | cctatattaggaactgtcttcacagctttaactggtccaattggc |
| 541 | P I L G T V F T A L T G P I G |
| 10146 | attgtattaggtgtattggctggtttagcagtcgcatttacaatt |
| 556 | I V L G V L A G L A V A F T I |
| 10191 | gcttataagaaatctgaaacatttagaaattttgttaatggtgca |
| 571 | A Y K K S E T F R N F V N G A |
| 10236 | attgaaagtgttaaacaaacatttagtaattttattcaatttatt |
| 586 | I E S V K Q T F S N F I Q F I |
| 10281 | caacctttcgttgattctgttaaaaacatctttaaacaagcgata |
| 601 | Q P F V D S V K N I F K Q A I |
| 10326 | tcagcaatagttgatttcgcaaaagatatttggagtcaaatcaat |
| 616 | S A I V D F A K D I W S Q I N |
| 10371 | ggattctttaatgaaaacggaatttccattgttcaagcacttcaa |
| 631 | G F F N E N G I S I V Q A L Q |
| 10416 | aatatatgcaactttattaaagcgacatttgaatttattttaaat |
| 646 | N I C N F I K A I F E F I L N |
| 10461 | tttgtaattaaaccaattatgttcgcgatttggcaagtgatgcaa |
| 661 | F V I K R I M F A I W Q V M Q |
| 10506 | tttatttggccggcggttaaagccttgattgtcagtacttgggag |
| 676 | F I W P A V K A L I V S T W E |
| 10551 | aacataaaaggtgtaatacaaggtgctttaaatatcatacttggc |
| 691 | N I K G V I Q G A L N I I L G |
| 10596 | ttgattaagttcttctcaagtttattcgttggtgattggcgagga |
| 706 | L I K F F S S L F V G D W R G |
| 10641 | gtttgggacgccgttgtgatgattcttaaaggagcagttcaatta |
| 721 | V W D A V V M I L K G A V Q L |
| 10686 | atttggaatttagttcaattatggtttgtaggtaaaatacttggt |
| 736 | I W N L V Q L W F V G K I L G |
| 10731 | gttgttaggtactttggcgggttgctaaaaggattgatagcagga |
| 751 | V V R Y F G G L L K G L I A G |
| 10776 | atttgggacgtaataagaagtatattcagtaaatctttatcagca |
| 766 | I W D V I R S I F S K S L S A |
| 10821 | atttggaatgcaacaaaaagtatttttggatttttatttaatagc |
| 781 | I W N A T K S I F G F L F N S |

TABLE 3-continued

| | |
|---|---|
| 10866 | gtaaaatcaattttcacaaatatgaaaaattggttatctaatact |
| 796 | V K S I F T N M K N W L S N T |
| 10911 | tggagcagtatccgtacgaatacaataggaaaagcgcagtcatta |
| 811 | W S S I R T N T I G K A Q S L |
| 10956 | tttagtggcgtcaaatcaaaatttactaatttatggaatgcgacg |
| 826 | F S G V K S K F T N L W N A T |
| 11001 | aaagaaattttagtaatttaagaaattggatgtcaaatatttgg |
| 841 | K E I F S N L R N W M S N I W |
| 11046 | aattccattaaagataatacggtaggaattgcaagccgtttatgg |
| 856 | N S I K D N T V G I A S R L W |
| 11091 | agtaaggtacgtggaattttcacaaatatgcgcgatggcttgagt |
| 871 | S K V R G I F T N M R D G L S |
| 11136 | tccattatagataagattaaaagtcatatcggcggtatggtaagc |
| 886 | S I I D K I K S H I G G M V S |
| 11181 | gctattaaaaaaggacttaataaattaatcgacggtttaaactgg |
| 901 | A I K K G L N K L I D G L N W |
| 11226 | gtcggtggtaagttgggaatggataaaatacctaagttacacact |
| 916 | V G G K L G M D K I P K L H T |
| 11271 | ggtacagagcacacacatactactacaagattagttaagaacggt |
| 931 | G T E H T H T T T R L V K N G |
| 11316 | aagattgcacgtgacacattcgctacagttggggataagggacgc |
| 946 | K I A R D T F A T V G D K G R |
| 11361 | ggaaatggtccaaatggttttagaaatgaaatgattgaattccct |
| 961 | G N G P N G F R N E M I E F P |
| 11406 | aacggtaaacgtgtaatcacacctaatacagatactaccgcttat |
| 976 | N G K R V I T P N T D T T A Y |
| 11451 | ttacctaaaggctcaaaagtatacaacggtgcacaaacttattca |
| 991 | L P K G S K V Y N G A Q T Y S |
| 11496 | atgttaaacggaacgcttccaagatttagtttaggtactatgtgg |
| 1006 | M L N G T L P R F S L G T M W |
| 11541 | aaagatattaaatctggtgcatcatcggcatttaactggacaaaa |
| 1021 | K D I K S G A S S A F N W T K |
| 11586 | gataaaataggtaaaggtaccaaatggcttggcgataaagttggc |
| 1036 | D K I G K G T K W L G D K V G |
| 11631 | gatgttttagattttatggaaaatccaggcaaacttttaaattat |
| 1051 | D V L D F M E N P G K L L N Y |
| 11676 | atacttgaagcttttggaattgatttcaattctttaactaaaggt |
| 1066 | I L E A F G I D F N S L T K G |
| 11721 | atgggaattgcaggcgacataacaaaagctgcatggtctaagatt |
| 1081 | M G I A G D I T K A A W S K I |
| 11766 | aagaaaagtgctactgattggataaaagaaaatttagaagctatg |
| 1096 | K K S A T D W I K E N L E A M |
| 11811 | ggcggtggcgatttagtcggcggaatattagaccctgacaaaatt |
| 1111 | G G G D L V G G I L D P D K I |
| 11856 | aattatcattatggacgtaccgcagcttataccgctgcaactgga |
| 1126 | N Y H Y G R T A A Y T A A T G |
| 11901 | agaccatttcatgaaggtgtcgattttccatttgtatatcaagaa |
| 1141 | R P F H E G V D F P F V Y Q E |
| 11946 | gttagaacgccgatgggtggcagacttacaagaatgccatttatg |
| 1156 | V R T P M G G R L T R M P F M |
| 11991 | tctggtggttatggtaattatgtaaaaattactagtggcgttatc |
| 1171 | S G G Y G N Y V K I T S G V I |
| 12036 | gatatgctatttgcgcatttgaaaaactttagcaaatcaccacct |
| 1186 | D M L F A H L K N F S K S P P |
| 12081 | agtggcacgatggtaaagcccggtgatgttgttggtttaactggt |
| 1201 | S G T M V K P G D V V G L T G |
| 12126 | aataccggatttagtacaggaccacatttacattttgaaatgagg |
| 1216 | N T G F S T G P H L H F E M R |
| 12171 | agaaatggacgacattttgaccctgaaccatatttaaggaatgct |
| 1231 | R N G R H F D P E P Y L R N A |
| 12216 | aagaaaaaaggaagattatcaataggtggtggcggtgctacttct |
| 1246 | K K K G R L S I G G G G A T S |
| 12261 | ggaagtggcgcaacttatgccagtcgagtaatccgacaagcgcaa |
| 1261 | G S G A T Y A S R V I R Q A Q |
| 12306 | agtattttaggtggtcgttataaaggtaaatggattcatgaccaa |
| 1276 | S I L G G R Y K G K W I H D Q |
| 12351 | atgatgcgcgttgcaaaacgtgaaagtaactaccagtcaaatgca |
| 1291 | M M R V A K R E S N Y Q S N A |
| 12396 | gtgaataactgggatataaatgctcaaagaggagacccatcaaga |
| 1306 | V N N W D I N A Q R G D P S R |
| 12441 | ggattattccaaatcatcggctcaacttttagagcaaacgctaaa |
| 1321 | G L F Q I I G S T F R A N A K |
| 12486 | cgtggatatactaactttaataatccagtacatcaaggtatctca |
| 1336 | R G Y T N F N N P V H Q G I S |
| 12531 | gcaatgcagtacattgttagacgatatggttggggtggttttaaa |
| 1351 | A M Q Y I V R R Y G W G G F K |
| 12576 | cgtgctggtgattacgcatatgctacaggtggaaaagtttttgat |
| 1366 | R A G D Y A Y A T G G K V F D |

TABLE 3-continued

| | |
|---|---|
| 12621 | ggttggtataacttaggtgaagacggtcatccagaatggattatt |
| 1381 | G W Y N L G E D G H P E W I I |
| 12666 | ccaacagatccagctcgtagaaatgatgcaatgaagattttgcat |
| 1396 | P T D P A R R N D A M K I L H |
| 12711 | tatgcagcagcagaagtaagagggaaaaaagcgagtaaaaataag |
| 1411 | Y A A A E V R G K K A S K N K |
| 12756 | cgtcctagccaattatcagacttaaacgggtttgatgatcctagc |
| 1426 | R P S Q L S D L N G F D D P S |
| 12801 | ttattattgaaaatgattgaacaacagcaacaacaaatagcttta |
| 1441 | L L L K M I E Q Q Q Q Q I A L |
| 12846 | ttactgaaaatagcacaatctaacgatgtgattgcagataaagat |
| 1456 | L L K I A Q S N D V I A D K D |
| 12891 | tatcagccgattattgacgaatacgcttttgataaaaaggtgaac |
| 1471 | Y Q P I I D E Y A F D K K V N |
| 12936 | gcgtctatagaaaagcgagaaaggcaagaatcaacaaaagtaaag |
| 1486 | A S I E K R E R Q E S T K V K |
| 12981 | tttagaaaaggaggaattgctattcaatga 13010 |
| 1501 | F R K G G I A I Q * |

96ORF048, Nucleotides and amino acids sequences (SEQ ID NO. 28)

| | |
|---|---|
| 4952 | atgtattacaaaattggtgagataaaaaacaaaattataagcttt |
| 1 | M Y Y K I G E I K N K I I S F |
| 4997 | aacgggtttgaatttaaagtgtctgtgatgaagagacatgacggt |
| 16 | N G F E F K V S V M K R H D G |
| 5042 | atcagtatacaaatcaaggatatgaataatgttccacttaaatcg |
| 31 | I S I Q I K D M N N V P L K S |
| 5087 | tttcatgtcatagatttaagcgaactatatattgcgacggatgca |
| 46 | F H V I D L S E L Y I A T D A |
| 5132 | atgcgtgacgttataaacgaatggattgaaaataacacagatgaa |
| 61 | M R D V I N E W I E N N T D E |
| 5177 | caggacaaactaattaacttagtcatgaaatggtag 5212 |
| 76 | Q D K L I N L V M K W * |

96ORF078, Nucleotides and amino acids sequences (SEQ ID NO. 30)

| | |
|---|---|
| 10148 | atgaatataatgcaattcaaaagcttattgaaatcgatgtatgaa |
| 1 | M N I M Q F K S L L K S M Y E |
| 10193 | gagacaaagcaaagcgacccgattgtagcaaatgtatatatcgag |
| 16 | E T K Q S D P I V A N V Y I E |
| 10238 | actggttgggcggtcaatagattgttggacaataacgagttatcg |
| 31 | T G W A V N R L L D N N E L S |
| 10283 | cctttcgatgattacgacagagttgaaaagaaaatcatgaatgaa |
| 46 | P F D D Y D R V E K K I M N E |
| 10328 | atcaactggaagaaaacacacattaaggagtgttaa 10363 |
| 61 | I N W K K T H I K E C * |

96ORF100, Nucleotides and amino acids sequences (SEQ ID NO. 32)

| | |
|---|---|
| 11008 | atgcaacaacaagcatatataaacgcaacaattgatataagaata |
| 1 | M Q Q Q A Y I N A T I D I R I |
| 11053 | cctacagaagttgaatatcagcattacgatgatgtggataaagaa |
| 16 | P T E V E Y Q H Y D D V D K E |
| 11098 | aaagatacgctggcaaagcgcttagatgacaatccggacgaatta |
| 31 | K D T L A K R L D D N P D E L |
| 11143 | ctaaagtatgacaacataacaataagacatgcatatatagaggtg |
| 46 | L K Y D N I T I R H A Y I E V |
| 11188 | gaataa 11193 |
| 61 | E * |

TABLE 4

Similarities with public sequences

Query = pt|100214 3AORF033 3A_NT|30089-30451|2 1
(120 letters)
Database: nr
445,337 sequences; 137,034,979 total letters

| Sequences producing significant alignments: | Score (bits) | E Value |
|---|---|---|
| gi\|246049\|bbs\|83873 neurofilament protein M [rats, Peptide Part . . . | 35 | 0.16 |
| gi\|56752\|emb\|CAA78136\|(Z12152) Neurofilament protein middle (N . . . | 35 | 0.16 |
| gi\|128150\|sp\|P12839\|NFM_RAT NEUROFILAMENT TRIPLET M PROTEIN (16 . . . | 35 | 0.16 |
| gi\|482393\|pir\|\|A45669 neurofilament triplet M protein - rat > gi . . . | 35 | 0.16 |
| gi\|6587836\|gb\|AAF18525.1\|AC006551_11 (AC006551) Unknown protein . . . | 35 | 0.16 |
| gi\|2459888 (AF005844) anon1A3 [*Drosophila yakuba*] | 35 | 0.21 |
| gi\|1621107 (U62026) cardiac muscle factor 1 CMF1 [*Gallus gallus*] | 34 | 0.27 |
| gi\|160409 (M69183) mature-parasite-infected erythrocyte surface . . . | 34 | 0.36 |

TABLE 4-continued

| Similarities with public sequences | | |
|---|---|---|
| gi\|3044185 (AF056936) mature parasite-infected erythrocyte surf . . . | 34 | 0.36 |
| gi\|323126\|pir\|\|A45605 mature-parasite-infected erythrocyte surf . . . | 34 | 0.36 |
| gi\|482391\|pir\|\|A45555 glutamate rich protein - Plasmodium falci . . . | 34 | 0.47 |
| gi\|3413892\|dbj\|BAA32310\| (AB007934) KIAA0465 protein [Homo sapi . . . | 33 | 0.61 |
| gi\|6273778\|gb\|AAF06360.1\|AF141968_1 (AF141968) trabeculin-alpha . . . | 33 | 0.61 |
| gi\|5821434\|dbj\|BAA83821.1\| (AB029290) actin binding protein ABP . . . | 33 | 0.61 |
| Query = pt\|100214 3AORF033 3A_NT\|30089-30451\|2 1<br>(120 letters)<br>Database: swissprot<br>83,367 sequences; 30,300,539 total letters | | |
| Sequences producing significant alignments: | Score (bits) | E Value |
| sp\|P12839 NFN_RAT NEUROFILAMENT TRIPLET M PROTEIN (160 KD NEUR . . . | 35 | 0.040 |
| sp\|Q02555 RNT1_YEAST RIBONUCLEASE III (EC 3.1.26.3) (RNASE III) . | 32 | 0.34 |
| sp\|P32841 R114_YEAST MEIOTIC RECOMBINATION PROTEIN REC114. | 32 | 0.34 |
| sp\|P29681 IMP2_DROME 20-HYDROXYECDYSONE PROTEIN PRECURSOR (20- . . . | 32 | 0.45 |
| sp\|O00294 TUL1_HUMAN TUBBY RELATED PROTEIN 1 (TUBBY-LIKE PROTE . . . | 32 | 0.45 |
| sp\|P28608 DNAK_BORBU DNAK PROTEIN (HEAT SHOCK PROTEIN 70) (HSP . . . | 31 | 0.77 |
| sp\|Q57639 Y175_METJA HYPOTHETICAL PROTEIN MJ0175. | 31 | 0.77 |
| Query = pt\|100222 3AORF041 3A_NT\|21497-21796\|2 1<br>(99 letters)<br>Database: nr<br>445,337 sequences; 137,034,979 total letters | | |
| Sequences producing significant alignments: | Score (bits) | E Value |
| gi\|6382413\|gb\|AAF07723.1\|AE001584_20 (AE001584) conserved hypot . . . | 30 | 6.6 |
| gi\|130509\|sp\|P29152\|POLG_PSBMV GENOME POLYPROTEIN (CONTAINS: N- . . . | 29 | 8.7 |
| gi\|5104896\|dbj\|BAA80210.1\| (AP000061) 356aa long hypothetical t . . . | 29 | 8.7 |
| Query = pt\|100222 3AORF041 3A_NT\|21497-21796\|2 1<br>(99 letters)<br>Database: swissprot<br>83,367 sequences; 30,300,539 total letters | | |
| Sequences producing significant alignments: | Score (bits) | E Value |
| sp\|P29152 POLG_PSBMV GENOME POLYPROTEIN [CONTAINS: N-TERMINAL . . . | 29 | 2.1 |
| sp\|P54470 YQFL_BACSU HYPOTHETICAL 30.3 KD PROTEIN IN GLYS-DNAG . . . | 29 | 2.8 |
| Query = pt\|100260 3AORF079 3A_NT\|34231-34416\|1 1<br>(61 letters)<br>Database: nr<br>445,337 sequences; 137,034,979 total letters | | |
| Sequences producing significant alignments: | Score (bits) | E Value |
| gi\|2496354\|sp\|P75400\|Y264_MYCPN HYPOTHETICAL PROTEIN MG264 HOMO . . . | 29 | 3.7 |
| gi\|6175671\|gb\|AAF05141.1\|AF162221_27 (AF162221) ORF27 [Xestia c . . . | 29 | 4.8 |
| gi\|6136641\|sp\|O78467\|YCF4_GUITH HYPOTHETICAL 20.9 KD PROTEIN YC . . . | 29 | 6.3 |
| gi\|2621735 (AE000845) conserved protein [Methanobacterium therm . . . | 28 | 8.3 |
| gi\|3845294 (AE001421) rRNA methylase (SpoU family) (OO, TP) [Pl . . . | 28 | 8.3 |
| Query = pt\|100260 3AORF079 3A_NT\|34231-34416\|1 1<br>(61 letters)<br>Database: swissprot<br>83,367 sequences; 30,300,539 total letters | | |
| Sequences producing significant alignments: | Score (bits) | E Value |
| sp\|P75400 Y264_MYCPN HYPOTHETICAL PROTEIN MG264 HOMOLOG. | 29 | 0.83 |
| sp\|078467 YCF4_GUITH HYPOTHETICAL 20.9 KD PROTEIN YCF4. | 29 | 1.4 |
| sp\|P30619 SEC1_YEAST PROTEIN TRANSPORT PROTEIN SEC1. | 27 | 3.2 |
| sp\|P43055 YLI1_MYCHO HYPOTHETICAL 59.8 KD PROTEIN IN LICA 3'RE . . . | 27 | 4.2 |
| sp\|O62757 CSF2_FELCA GRANULOCYTE-MACROPHAGE COLONY-STIMULATING . . . | 27 | 5.5 |
| sp\|P35725 YKG3_YEAST HYPOTHETICAL 19.0 KD PROTEIN IN MNR2-MSN4 . . . | 26 | 7.2 |
| sp\|P10942 YHA2_CRYPA HYPOTHETICAL PROTEIN 2 IN HYPOVIRULENCE-A . . . | 26 | 9.5 |
| sp\|P48749 CSF2_CANFA GRANULOCYTE-MACROPHAGE COLONY-STIMULATING . . . | 26 | 9.5 |
| sp\|P54679 PMA1_DICDI PROBABLE PLASMA MEMBRANE ATPASE (EC 3.6.1 . . . | 26 | 9.5 |

TABLE 4-continued

Similarities with public sequences

Query = pt|100001 77ORF001 77_NT|8481-13010|3 1
(1509 letters)
Database: nr
445,337 sequences; 137,034,979 total letters
Searching...............................................done

| Sequences producing significant alignments: | Score (bits) | E Value |
|---|---|---|
| gi|3341923|dbj|BAA31889.1)|(AB009866) orf 16 [bacteriophage phi . . . | 797 | 0.0 |
| gi|3341922|dbj|BAA31888.1)|(AB009866) orf 15 [bacteriophage phi . . . | 268 | 3e-70 |
| gi|3341924|dbj|BAA31890.1)|(AB009866) orf 17 [bacteriophage phi . . . | 234 | 4e-60 |
| gi|2392838 (AF011378) unknown [Bacteriophage sk1] | 150 | 8e-35 |
| gi|3282276 (AF009630) 116 [bacteriophage bIL170] | 131 | 6e-29 |
| gi|4530151|gb|AAD21891.1|(AF085222) putative tail component pr . . . | 126 | 1e-27 |
| gi|2935689|gb|AAC39295.1|(AF115102) orf1626 gp [Streptococcus . . . | 116 | 1e-24 |
| gi|1926360|emb|CAA66745|(X98106) minor capsid protein [Bacteri . . . | 106 | 2e-21 |
| gi|2935674|gb|AAC39281.1|(AF115103) orf1560 gp [Streptococcus . . . | 98 | 5e-19 |
| gi|4530152|gb|AAD21892.1|(AF085222) putative tail component pr . . . | 96 | 2e-18 |
| gi|1722872|sp|P54334|XKDO_BACSU PHAGE-LIKE ELEMENT PBSX PROTEIN . . . | 83 | 2e-14 |
| gi|2764873|emb|CAA66557|(X97918) gene 18.1 [Bacteriophage SPP1] | 78 | 7e-13 |
| gi|1353559 (U38906) ORF42 [Bacteriophage rlt] | 78 | 7e-13 |
| gi|1176754|sp|P45931|YQBO_BACSU HYPOTHETICAL 171.0 KD PROTEIN I . . . | 77 | 9e-13 |
| gi|2313617|gb|AAD07571.1|(AE000565) conserved hypothetical sec . . . | 77 | 1e-12 |
| gi|4154996 (AE001480) putative Outer membrane protein [Helicoba . . . | 75 | 3e-12 |
| gi|2688140 (AE001134) *B. burgdorferi* predicted coding region BB . . . | 71 | 5e-11 |
| gi|6599346|emb|CAB63691.1| (AJ251790) hypothetical protein [Lac . . . | 70 | 1e-10 |
| gi|1073751|pir||JC2569 tagE protein - Vibrio cholerae (strain 0 . . . | 70 | 2e-10 |
| gi|2688203 (AE001137) conserved hypothetical protein [Borrelia . . . | 70 | 2e-10 |
| gi|3860964|emb|CAA14864|](AJ235271) unknown [Rickettsia prowaze . . . | 70 | 2e-10 |
| gi|623073 (L02496) unknown protein [Bacteriophage LL-H] | 69 | 3e-10 |
| gi|4980914|gb|AAD35494.1|AE001720_8 (AE001720) conserved hypoth . . . | 69 | 3e-10 |
| gi|1175836|sp|P44693|YEBA_HAEIN HYPOTHETICAL PPOTEIN HI0409 > gi . . . | 68 | 8e-10 |
| gi|1944592|emb|CAB08078|(Z94121) hypothetical protein Rv3896c . . . | 65 | 4e-09 |
| gi|6136204|sp|O64220|VG26_BPMD2 MINOR TAIL PROTEIN GP26 > gi|317 . . . | 65 | 4e-09 |
| gi|1369948|emb|CAA59194| (X84706) host interacting protein [Bac . . . | 63 | 1e-08 |
| gi|3947462|emb|CAA07113.1| (AJ006589) gp43 [Bacteriophage phi-C31] | 63 | 1e-08 |
| gi|2444119 (U88974) ORF40 [*Streptococcus thermophilus* temperate . . . | 62 | 3e-08 |
| gi|4336054|gb|AAD17585|(AF068845) gp17 [Mycobacteriophage TM4] | 61 | 1e-07 |
| gi|6460534|gb|AAF12240.1|AE001862_66 (AE001862) minor tail prot . . . | 61 | 1e-07 |
| gi|3287732|sp|O05156|ALE1_STACP GLYCYL-GLYCINE ENDOPEPTIDASE AL . . . | 59 | 4e-07 |
| gi|6137045|emb|CAB59600.1|(AL132662) possible peptidase [Strep . . . | 58 | 5e-07 |
| gi|79926|pir||A25881 lysostaphin precursor - Staphylococcus sim . . . | 58 | 7e-07 |
| gi|126496|sp|P10548|LSTP_STAST LYSOSTAPHIN PRECURSOR (GLYCYL-GL . . . | 58 | 7e-07 |
| gi|3287967|sp|P10547|LSTP_STASI LYSOSTAPHIN PRECURSOR (GLYCYL-G . . . | 58 | 7e-07 |
| qi|5042257|emb|CAB44511.1| (AL078618) hypothetical protein [Str . . . | 57 | 1e-06 |

Query = pt|100001 77ORF001 77_NT|8481-13010|3 1
(1509 letters)
Database: swissprot
83,367 sequences; 30,300,539 total letters

| Sequences producing significant alignments: | Score (bits) | E Value |
|---|---|---|
| sp|P54334 XKDO_BACSU PHAGE-LIKE ELEMENT PBSX PROTEIN XKDO. | 83 | 5e-15 |
| sp|P45931 YQBO_BACSU HYPOTHETICAL 171.0 KD PROTEIN IN SPOIIIC- . . . | 77 | 2e-13 |
| sp|P44693 YEBA_HAEIN HYPOTHETICAL PROTEIN HI0409. | 68 | 2e-10 |
| sp|O64220 VG26_BPMD2 MINOR TAIL PROTEIN GP26. | 65 | 9e-10 |
| sp|O05156 ALE1_STACP GLYCYL-GLYCINE ENDOPEPTIDASE ALE-1 PRECUR . . . | 59 | 9e-08 |
| sp|P10547 LSTP_STASI LYSOSTAPHIN PRECURSOR (EC 3.4.24.75) (GLY . . . | 58 | 2e-07 |
| sp|P10548 LSTP_STAST LYSOSTAPHIN PRECURSOR (EC 3.4.24.75) (GLY . . . | 58 | 2e-07 |
| sp|P24204 YEBA_ECOLI HYPOTHETICAL 46.7 KD PROTEIN IN MSBB-RUVB . . . | 55 | 1e-06 |
| sp|P51731 YO27_BPHP1 HYPOTHETICAL 72.8 KD PROTEIN IN LYS 3'REG . . . | 55 | 1e-06 |
| sp|Q09857 YAF3_SCHPO HYPOTHETICAL 118.6 KD PROTEIN C29E6.03C I . . . | 51 | 2e-05 |
| sp|QC5233 VG26_BPML5 MINOR TAIL PROTEIN GP26. | 47 | 2e-04 |
| sp|P39922 MYS3_HYDAT MYOSIN HEAVY CHAIN, CLONE 203 (FRAGMENT) . . . | 47 | 3e-04 |
| sp|P12844 MYSA_CAEEL MYCSIN HEAVY CHAIN A (MHC A) . . . | 47 | 3e-04 |
| sp|P12845 MYSC_CAEEL MYCSIN HEAVY CHAIN C (MHC C) . . . | 46 | 5e-04 |
| sp|P37690 YIBP_ECOLI HYPOTHETICAL 46.6 KD PROTEIN IN SECB-TDH . . . | 46 | 5e-04 |
| sp|P24733 MYS_AEQIR MYOSIN HEAVY CHAIN, STRIATED MUSCLE. | 45 | 9e-04 |

Query = pt|100405 96ORF048 96_NT|4952-5212|1 1
(86 letters)
Database: nr
445,337 sequences; 137,034,979 total letters

| Sequences producing significant alignments: | Score (bits) | E Value |
|---|---|---|

TABLE 4-continued

| Similarities with public sequences | | |
|---|---|---|
| gi\|3341947\|dbj\|BAA31913.1\| (AB009866) orf 39 [bacteriophage phi . . . | 116 | 4e-26 |
| gi\|3183240\|sp\|Q58352\|Y942_METJA PROBABLE ATP-DEPENDENT HELICASE . . . | 31 | 2.7 |
| gi\|4033401\|sp\|P94281\|GYRB_BARBA DNA GYRASE SUBUNIT B > gi\|176606 . . . | 30 | 4.6 |
| gi\|3258109\|dbj\|BAA30792\|(AP000006) 320aa long hypothetical pro . . . | 29 | 6.1 |
| gi\|5457925\|emb\|CAB49415.1\| (AJ248284) hypothetical protein [Pyr . . . | 29 | 6.1 |
| gi\|4678268\|emb\|CAB41176.1\| (AL049660) putative protein [Arabido . . . | 29 | 8.0 |

Query = pt|100405 96ORF048 96_NT|4952-5212|1 1
(86 letters)
Database: swissprot
83,367 sequences; 30,300,539 total letters

| Sequences producing significant alignments: | Score (bits) | E Value |
|---|---|---|
| sp\|Q58352 Y942_METJA PROBABLE ATP-DEPENDENT HELICASE MJ0942. | 31 | 0.69 |
| sp\|P94281 GYRB_BARBA DNA GYRASE SUBUNIT B (EC 5.99.1.3). | 30 | 1.2 |
| sp\|Q60384 Y077_METJA HYPOTHETICAL PROTEIN MJ0077. | 29 | 2.7 |
| sp\|Q03164 HRX_HUMAN ZINC FINGER PROTEIN HRX (ALL-1) (TRITHORAX . . . | 28 | 3.5 |
| sp\|P55200 HRX_MOUSE ZINC FINGER PROTEIN HRX (ALL-1) (FRAGMENT). | 28 | 3.5 |
| sp\|Q01926 MRS2_YEAST MITOCHONDRIAL RNA SPLICING PROTEIN MRS2 P . . . | 27 | 6.0 |
| sp\|P47508 SYL_MYCGE LEUCYL-TRNA SYNTHETASE (EC 6.1.1.4) (LEUCI . . . | 27 | 6.0 |
| sp\|P14933 YP60_METTM HYPOTHETICAL 60.5 KD PROTEIN. | 27 | 7.9 |

Query = pt|100435 96ORF078 96_NT|10148-10363|1 1
(71 letters)
Database: nr
445,337 sequences; 137,034,979 total letters

| Sequences producing significant alignments: | Score (bits) | E Value |
|---|---|---|
| gi\|167324 (M92051) 5' start site is putative; putative [Gossypi . . . | 30 | 2.1 |
| gi\|3875068\|emb\|CAB03979.1\| (Z81485) cDNA EST EMBL:T02038 comes . . . | 30 | 2.1 |
| gi\|232024\|sp\|Q01197\|E6_GOSHI PROTEIN E6 > gi\|421806\|pir\|\|A46130 . . . | 30 | 2.1 |
| gi\|2129495\|pir\|\|S65063 fiber protein E6 (clone SIE6-2A) - sea-i . . . | 30 | 2.1 |
| gi\|2982648\|emb\|CAA05305\| (AJ002294) penicillin-binding protein . . . | 30 | 2.7 |
| gi\|4033461\|sp\|O51889\|REP_BUCAP ATP-DEPENDENT DNA HELICASE REP > . . . | 29 | 3.5 |

Query = pt|100435 96ORF078 96_NT|10148-10363|1 1
(71 letters)
Database: swissprot
83,367 sequences; 30,300,539 total letters

| Sequences producing significant alignments: | Score (bits) | E Value |
|---|---|---|
| sp\|Q01197 E6_GOSHI PROTEIN E6. | 30 | 0.57 |
| sp\|O51889 REP_BUCAP ATP-DEPENDENT DNA HELICASE REP (EC 3.6.1.-). | 29 | 0.97 |
| sp\|P53125 YGN3_YEAST HYPOTHETICAL 145.6 KD PROTEIN IN RPL1B-CE . . . | 28 | 2.9 |
| sp\|P03459 HEMA_IAFPR HEMAGGLUTININ PRECURSOR [CONTAINS: HEMAGG . . . | 28 | 2.9 |

Query = pt|100457 96ORF100 96_NT|11008-11193|3 1
(61 letters)
Database: nr
445,337 sequences; 137,034,979 total letters

| Sequences producing significant alignments: | Score (bits) | E Value |
|---|---|---|
| gi\|6687541\|emb\|CAB65007.1\| (Y17316) transmembrane protein [Erys . . . | 29 | 3.7 |
| gi\|6175777\|gb\|AAF05247.1\|AF162221_133 (AF162221) ORF133 [Xestia . . . | 29 | 6.3 |
| gi\|4508013\|ref\|NP_003445.1\|\|zinc finger protein 200 > gi\|622650 . . . | 28 | 8.3 |

Query = pt|100457 96ORF100 96_NT|11008-11193|3 1
(61 letters)
Database: swissprot
83,367 sequences; 30,300,539 total letters

| Sequences producing significant alignments: | Score (bits) | E Value |
|---|---|---|
| sp\|P98182 Z200_HUMAN ZINC FINGER PROTEIN ZNF200. | 28 | 1.9 |
| sp\|Q08014 MEDB_GIALA MEDIAN BODY PROTEIN. | 28 | 2.5 |
| sp\|P18247 POLG_PVYN GENOME POLYPROTEIN [CONTAINS: N-TERMINAL P . . . | 27 | 4.2 |
| sp\|P75211 P200_MYCPN PROTEIN P200. | 27 | 4.2 |
| sp\|Q02963 POLG_PVYHU GENOME POLYPROTEIN [CONTAINS: N-TERMINAL . . . | 27 | 4.2 |
| sp\|P43864 LON_HAEIN ATP-DEPENDENT PROTEASE LA (EC 3.4.21.53). | 26 | 7.2 |
| sp\|P54784 ORC1_YEAST ORIGIN RECOGNITION COMPLEX SUBUNIT 1 (ORI . . . | 26 | 7.2 |

TABLE 5

Optimal global alignment

```
Sequence 1: 3AORF079
Sequence 2: 96ORF100
Substitution matrix: blosum62
Gap penalty: - (11 + 1 * (gap length))
Identical: 37/61 (0.61)
Similar:   47/61 (0.77)
Score:     181

seq1   1 MQHQAYINASVDIRIPTEVESVNYNQIDKEKENLADYLFNNPGELLKYNVINIKVLDLEV 60
         || ||||||::|||||||||  :|:  ||||: ||  | :|| |||||: | |:   :||
seq2   1 MQQQAYINATIDIRIPTEVEYQHYDDVDKEKDTLAKRLDDNPDELLKYDNITIRHAYIEV 60

seq1  61 E 61
         |
seq2  61 E 61

Sequence 1: 96ORF048
Sequence 2: 77ORF043
Substitution matrix: blosum62
Gap penalty: - (11 + 1 * (gap length))
Identical: 53/86 (0.62)
Similar:   68/86 (0.79)
Score:     287

seq1   1 MYYKIGEIKNKIISFNGFEFKVSVMKRHDGISIQIKDMNNVPLKSFHVIDLSELYIATDA 60
         || ||||||::|||||||||  :|:  ||||: ||  | :|| |||||: | |:   :||
seq2   1 MYYEIGEIIRKNIHVNGFDFKLFILKGHMGISIQVKDMNNVPIKHAYVVDENDLDMASDL 60

seq1  61 MRDVINEWIENNTDEQDKLINLVMKW 86
             |:|||| ||||||:||||||||
seq2  61 FNQAIDEWIEENTDEQDRLINLVMKW 86

Sequence 1: 96ORF048
Sequence 2: 77ORF182
Substitution matrix: blosum62
Gap penalty: - (11 + 1 * (gap length))
Identical: 53/98 (0.54)
Similar:   68/98 (0.69)
Score:     264

seq1   0 ------------MYYKIGEIKNKIISFNGFEFKVSVMKRHDGISIQIKDMNNVPLKSFHV 48
                     |||:||||  | |  |||:||: ::| | |||||:|||||||:|  :|
seq2   1 MFNIKRKTEEVKMYYEIGEIIRKNIHVNGFDFKLFILKGHMGISIQVKDMNNVPIKHAYV 60

seq1  49 IDLSELYIATDAMRDVINEWIENNTDEQDKLINLVMKW 86
         :| ::| :|:|     |:|||| ||||||:||||||||
seq2  61 VDENDLDMASDLFNQAIDEWIEENTDEQDRLINLVMKW 98
```

Table 1

Bacteriophage 3A, complete genome sequence (SEQ ID NO. 17).

| | | | | | | |
|---|---|---|---|---|---|---|
| 1 | tttaaataaa | attttatgcc | cccctgccca | tcggcttaaa | atgtttttc | gccgggtacc |
| 61 | ggagaggccc | aaacgctagc | aacgcggata | aatttttcat | gaaagggggt | ctttatatga |
| 121 | agttaacaaa | aaaacagcta | aaagaatata | tagaagatta | caaaaaatct | gatgacatat |
| 181 | taattaattt | gtatatagaa | acatatgaat | tttattgtcg | gttaagagat | gaacttaaaa |
| 241 | atagtgattt | aatgatagag | catacaaaca | aggctggtgc | gagcaatatt | attaagaatc |
| 301 | cattaagcat | agaactgaca | aaaacagttc | aaacactaaa | taacttactc | aagtctatgg |
| 361 | gtttaactgc | agcacaaaga | aaaaagatag | ttcaagaaga | aggtggattc | ggtgactatt |
| 421 | aaagttttaa | atgaaccttc | accaaaacta | ttaacaacat | ggtatgcaga | gcaagtcact |
| 481 | caagggaaaa | taaaaacaag | caaatatgtt | agaaaagaat | gtgagagaca | tcttagatat |
| 541 | ctagaaaatg | gaggtaaatg | ggtatttgat | gaagaattag | cgcatcgtcc | tattcgattt |
| 601 | atagaaaagt | tttgtaaacc | ttccaaagga | tctaaacgtc | aacttgtatt | acagccatgg |
| 661 | caacatttta | ttatcggcag | tttgtttggt | tgggttcata | aagaaacaaa | actgcgcagg |
| 721 | tttaaagaag | ctttgatatt | tatggggcga | aaaaatggta | aaacaaccac | tatttctggg |
| 781 | gttgctaact | atgctgtatc | acaagatgga | gaaaatggtg | cagaaattca | tttgttagca |
| 841 | aacgtaatga | aacaagctag | gattctattt | gatgaatcta | aggcgatgat | taaagctagc |
| 901 | ccaaagcttg | ataaaaattt | cagaacattt | agagatgaaa | tccattatga | cgcaacgata |
| 961 | tcaaaaatta | tgccccaagc | atcagatagc | gataagttag | atggattgaa | tacacacatg |
| 1021 | gggatttttg | atgaaattca | tgaatttaaa | gactataaat | tgatttcagt | tataaaaaac |
| 1081 | tcaagagctg | caaggttaca | acctcttctc | atctacatta | cgacagcagg | gtatcaatta |
| 1141 | gatggtccac | ttgttgatat | ggtagaagcg | ggaagagaca | ccttagatca | aatcatagaa |
| 1201 | gacgaaagaa | ctttttatta | tttagcatct | ttggatgatg | acgatgatat | taatgattcg |
| 1261 | tcgaactgga | taaaagcaaa | tcccaactta | ggtgtctcta | taaatttaga | tgagatgaaa |
| 1321 | gaagagtggg | aaaaagctaa | gagaacacca | gctgaacgtg | gagattttat | aaccaaaagg |
| 1381 | tttaatatct | ttgctaataa | tgacgagatg | agttttattg | attacccaac | actccaaaaa |
| 1441 | aataatgaaa | ttgtttcttt | agaagagctg | gaaggcagac | cgtgcacgat | tggttatgat |
| 1501 | ttatcagaaa | cagaggactt | tacagccgcg | tgtgctactt | ttgcgttaga | taatggtaaa |
| 1561 | gttgcagttt | tatcgcattc | atggattcct | aagcacaaag | ttgaatattc | taacgaaaaa |
| 1621 | ataccctata | gagaatggga | agaagatggc | ttattaacag | tgcaagataa | gccttatatt |
| 1681 | gactaccaag | atgttttaaa | ttggataatt | aagatgaatg | agcattatgt | agtagaaaaa |
| 1741 | attacttatg | atagagcgaa | cgcattcaaa | ctaaatcaag | agttaaaaaa | ttacgggttt |
| 1801 | gaaacggaag | aaacaagaca | aggagctttg | accttgagcc | ctgcattgaa | ggatttaaaa |
| 1861 | gaaatgtttt | tagatgggaa | aataatattt | aataataatc | ctttaatgaa | atggtatatc |
| 1921 | aataatgttc | agttgaaact | agacagaaac | ggaaactggt | tgccgtctaa | gcaaagcaga |
| 1981 | tatcgtaaaa | tagatggctt | tgcagcattt | ttaaacacat | atacagatat | tatgaataaa |
| 2041 | gttgtttctg | atagtggtga | aggaaacata | gagtttatta | gtattaaaga | cataatgcgt |
| 2101 | taaggaggtg | aatgttatcg | caaaagagaa | tattgtcaca | cgcataaaga | aaaaattgat |
| 2161 | agacaattgg | attgatcagt | caacttctaa | gctttatgac | tttagcccat | ggaaaaatag |
| 2221 | atctttttgg | ggtgtaatta | ataatacgct | tgaaactaat | gaaacgatat | tttcagctat |
| 2281 | tacaaagtta | tctaattcga | tggctagttt | gcccttgaaa | atgtatgaag | attataaagt |
| 2341 | agttaataca | gaagtatctg | atttacttac | agtgtcaccg | aataattctc | tgagcagttt |
| 2401 | tgattttatt | aatcaaattg | aaacaatcag | aaatgaaaaa | ggtaatgcat | atgtgctaat |
| 2461 | tgaacgagac | atctatcatc | aaccatcaaa | gcttttctta | ttaaatccag | atgttgttga |
| 2521 | aatgttaatt | gaaaaccaat | cacgtgaact | ttattattcc | attcatgctg | caactggaaa |
| 2581 | taaattgatt | gttcataata | tggacatgtt | gcattttaaa | cacatcgtgg | catctaatat |
| 2641 | ggtgcaaggc | attagtccga | ttgatgtgtt | gaagaataca | actgattttg | ataatgcagt |
| 2701 | aagaaccttt | aatcttacag | aaatgcaaaa | acctgattct | ttcatgctta | aatatggttc |
| 2761 | caatgtaggt | aaagaaaaaa | ggcagcaagt | gttagaagat | ttcaaacagt | actatgaaga |
| 2821 | aaacggtgga | atattattcc | aagagcctgg | tgttgaaatc | gaaccgttac | ctaaaaaata |
| 2881 | tgtctctgaa | gatatagtgg | caagcgagaa | tttaacaaga | gaaagagtag | ctaacgtttt |
| 2941 | tcaattgccc | tcagtattct | taaatgcaag | atcaaataca | aatttcgcga | aaaatgaaga |
| 3001 | gttaaacaga | ttttacttgc | agcatacctt | attgccaatc | gtcaaacagt | atgaagaaga |
| 3061 | atttaatcgg | aaactactta | ctaaaacaga | cagagaaaaa | aataggtatt | ttaaatttaa |
| 3121 | cgttaaatct | tatttaaggg | ctgatagtgc | aacacaagca | gaagtgtact | ttaaagcagt |
| 3181 | tcgtagtggt | tactacacta | taaatgacat | tagagagtgg | gaagatttac | caccagttga |
| 3241 | aggtggagat | aagccgctaa | taagcggtga | tttataccca | attgacacgc | cacttgaatt |

```
3301  aagaaaatct ttgaaaggtg gtgataaaaa tgtcaatgaa agctaagtat tttcaaatga
3361  aaagaaaatc aaaaagtaaa ggtgaaatat ttatttatgg tgatattgta agtgataaat
3421  ggtttgaaag tgatgtaact gctacagatt tcaaaaataa actagatgaa ctaggagaca
3481  tcagtgaaat agatgttcat ataaattcat ctggaggcag tgtatttgaa gggcatgcaa
3541  tatacaatat gctaaaaatg catcctgcaa aaattaatat ctatgtcgat gccttagcgg
3601  catcaattgc tagtgttatc gctatgagtg gtgacactat ttttatgcac aaaaatagtt
3661  ttttaatgat tcataattca tgggttatga ctgtaggtaa tgcagaagag ttaagaaaga
3721  cagcggattt acttgaaaaa acagatgctg ttagtaattc agcttattta gataaagcaa
3781  aagatttaga tcaagaacac ttaaaacaga tgttagatgc agaaacttgg cttactgcag
3841  aagaagcctt gtctttcggc ttgatagatg aaattttagg agctaatgaa ataactgcta
3901  gtatctctaa agagcaatat aagcgtttcg agaacgtccc agaagattta aagaaagatg
3961  tagacaaaat cactaaaatc gatgatgtag atacgtttga attggttgaa acacctaaag
4021  aaagtatgtc actagaagaa aaagaaaaaa gagaaaaaat taaacgcgaa tgcgaaattt
4081  taaaaatgac aatgagttat taggaggaaa tgaaatgccg acattatatg aattaaaaca
4141  atccttaggt atgattggac aacaattaaa aaataaaaat gatgaattga gtcagaaagc
4201  aacagaccca aatattgata tggaagacat caaacaacta gaaacagaaa aagcaggctt
4261  acaacaaaga tttaacattg ttgaaagaca agtaaaagac attgaagaaa aagaaaaagc
4321  gaaagttaaa gacacaggag aagcttatca atctttaaat gatcatgaga agatggttaa
4381  agctaaggca gagttttatc gtcacgcgat tttaccaaat gaatttgaaa aaccttcaat
4441  ggaggcacaa cgtttattac acgctttacc aacaggtaat gattcaggtg gtgataagct
4501  cttaccaaaa acactttcta aagaaattgt ttcagaacca tttgctaaaa accaattacg
4561  tgaaaaagct cgtctaacta acattaaagg tttagagatt ccaagagttt catatacttt
4621  agacgatgat gacttcatta cagatgtaga aacagcaaaa gaattaaaat taaaaggtga
4681  tacagttaaa ttcactacta ataaattcaa agtatttgct gcaatttcag atactgtaat
4741  tcatggatca gatgtagatt tagtaaactg ggttgaaaac gcactacaat caggtctagc
4801  agctaaagaa cgtaaagatg ccttagcagt aagtcctaaa tctggattag atcacatgtc
4861  attttacaat ggatctgtta aagaagttga gggagcagac atgtatgatg ctattattaa
4921  cgctttagca gatttacatg aagattaccg tgataacgca acaatttata tgcgatatgc
4981  ggattatgtc aaaattatta gtgttctttc aaatggaaca acaaatttct ttgacacacc
5041  agcagaaaaa gtatttggca aaccagtagt atttacagat gcagcagtta aacctattgt
5101  gggagatttc aattattttg gaattaacta tgatggaaca acttatgaca ctgataaaga
5161  tgttaaaaaa ggcgaatatt tgtttgtatt aactgcatgg tatgatcagc aacgtacatt
5221  agacagtgca ttcagaattg caaaagcaaa agaaaataca ggttcattac ccagctaagc
5281  cccaaaaggt taatgtaaca gctaaggcta aatcagctgt aatatcagcc gaataggggt
5341  gatgaaatga gtttagaaga aattaaattg tggttgagaa ttgactataa tttcgaaaat
5401  gatttaattg aaggtctcat tcaatcggct aagtctgaat tactattaag tggggttcca
5461  gattatgaca aagatgactt ggaatacccg ctttttgta cagcgattag atatatcatt
5521  gcaagagatt atgaaagtcg tgggtactca aatgaccaat ctagaagcaa ggtttttaat
5581  gaaaagggat tgcaaaaaat gattctgaaa ttaaaaaagt ggtaggtgat ttttaaatgg
5641  aatttaatga atttaaagat cgcgcatatt tttttcaata tgtaaataaa gggccgtatc
5701  cagatgaaga ggaaaaaatg aagttgtata gttgcttttg taaaatatat aatccttcta
5761  tgaaagatag agaaatttta aaagcgactg aatcaaagtc aggactaacc ataattatga
5821  ggtcttctaa aattgaatat ctaccacaaa caaatcactt agttaaaatt gacagaggct
5881  tatattccga taaattattc aacattaaag aaataagaat tgatacacca gatattggct
5941  ataatacagt ggttttatca gaaaaatgag tgtagaaatt aaagggatac ctgaagtgtt
6001  gaagaaatta gaatcggtat acggtaaaca atcaatgcaa gctaagagtg atagagcttt
6061  aaatgaagca tctgaatttt ttataaaggc tttaaagaaa gaattcgaga gttttaaaga
6121  tacgggtgct agcatagaag aaatgactaa atctaagcct tatacaaaag taggaagtca
6181  agaaagagct gttttaattg aatgggtagg ccctatgaat cgcaaaaaca ttattcactt
6241  gaatgaacat ggttatacaa gagatggaaa aaaatataca ccaagaggtt ttggagttat
6301  tgcaaaaaca ttagctgcta atgaacggaa gtatagagaa attataaaaa aggagttggc
6361  cagataaatg aatatattaa acaccataaa agaaatttta ttatctgatg cagagctcca
6421  aacatatata aattctagaa tatactatta taaagtcact gaaaatgctg aaacttccaa
6481  acctttgtt gttattacac ctatttatga tttaccttca gacttcatgt ctgataaata
6541  tcttagtgaa gaatacttaa ttcaaataga tgtagaatct tcaaataatc agaaaacaat
6601  tgatataaca aaacgaataa gatatctgtt atatcaacaa aatttaattc aagcatctag
6661  tcagttagat gcttattttg aagaaactaa acgttatgtg atgtcgagac gttatcaagg
```

6721 cataccaaaa aatatatatt ataaaaatca gcgcatcgaa taggtgtgct ttttaatttt
6781 taaggaggaa ataagcaatg gcagaaggac aaggttctta taaagtaggt tttaaaagat
6841 tatacgttgg agtttttaac ccagaagcaa caaaagtagt taaacgcatg acatgggaag
6901 atgaaaaagg tggtacagtt gatctaaata tcacaggttt agcaccagat ttagtagata
6961 tgtttgcatc taacaaacgt gtttggatga aaaaacaagg tactaatgaa gttaagtctg
7021 acatgagtat ttttaatatt ccaagtgaag atctaaatac agttattggt cgttctaaag
7081 ataaaaatgg tacatcttgg gtaggagaga atacaagagc accatacgta acagttattg
7141 gagaatctga agatggttta acaggtcaac cagtgtacgt tgcgctactt aaaggtactt
7201 ttagcttgga ttcaattgaa tttaaaacac gaggagaaaa agcagaagca ccagagccaa
7261 caaaattaac tggtgactgg atgaacagaa aagttgatgt tgatggtact ccacaaggta
7321 ttgtatacgg gtatcatgaa ggtaaagaag gagaagcaga attcttcaaa aaagtattcg
7381 ttggatacac ggacagtgaa gatcattcag aggattctgc aagttcgtta cccagctaac
7441 ccccaaaatg ttgaagtagc agttaattca aaatctgcaa cagtttcagc agaatagggg
7501 ctttcaaaat aaatcaaagg agaataattt atgactaaaa ctttaaaggt ttataaagga
7561 gacgacgtcg tagcttctga acaaggtgaa ggcaaagtgt cagtaacttt atctaattta
7621 gaagcggata caacttatcc aaaaggtact taccaagtgg catgggaaga aaatggtaaa
7681 gaatctagta aagttgatgt acctcaattc aaaaccaatc caattctagt ctcaggcgta
7741 tcatttacac ccgaaactaa atcaatcacg gtaaatgctg atgacaatgt tgaaccaaac
7801 attgcaccaa gtacagcaac gaataaaacg ttgaaatata caagtgaaca tccagagttt
7861 gttactgttg atgagagaac aggagcaatt cacggtgtag ctgagggaac ttcagttatc
7921 actgctacgt ctactgacgg aagtgacaag tctggacaaa ttacagtaac agtaacaaat
7981 ggataattat ttgagacgca gaatatctgc gtctttttta tttgaataaa aggagctaat
8041 acaatgatta aatttgaaat taaagaccgt aaaacaggaa aaacagagag ctatacaaaa
8101 gaagatgtga caatgggcga agcagaaaaa tgctatgagt atttagaatt agtaaatcaa
8161 gagaataaaa aagaagtacc taacgcaaca aaaatgagac aaaaagagcg acagttatta
8221 gtagatttat ttaaagatga aggattgact gaagaagatg ttttgaacaa gatgagcact
8281 aaaacttata caaaagcctt gaaagatata tttcgagaaa tcaatggtga agatgaagaa
8341 gattcagaaa ctgaaccaga agagatggga aagacagaag aacaatctca ataaaagata
8401 ttttatcgaa cattaagaaa atacaacgtt tctgtatgga gcagtatggg tggacattaa
8461 ctgaagtcag aaaacagccg tatgtaaaac ttttagaaat acttaatgaa gagaataaag
8521 aagagactga agaaaaacaa agtgaacaaa aagtcattac aggtacggat ttaagaaaac
8581 tttttggaag ctagaaagga ggttaatatg aatgaaaaag tagaaggcat gaccttggag
8641 ctgaaattag accatttagg tgtccaagaa ggcatgaagg gtttaaagcg acaattaggt
8701 gttgttaata gtgaaatgaa agctaatctg tcatcatttg ataagtctga aaaatcaatg
8761 gaaaagtatc aggcgagaat taagggggtta aatgataagc ttaaagttca aaaaaagatg
8821 tattctcaag tagaagatga gcttaaacaa gttaacgcta attatcaaaa agctaaatct
8881 agtgtaaaag atgttgagaa agcatattta aagctagtag aagctaataa aaaagaaaaa
8941 ttagctcttg ataaatctaa agaagcctta aaatcttcga atacagaact taaaaaagct
9001 gaaaatcaat ataaacgtac aaatcaacgt aaacaagatg catatcaaaa acttaaacag
9061 ttgagagatg cagaacaaaa gcttaagaat agtaaccaag ctactactgc acaactaaaa
9121 agagcaagtg acgcagtaca gaagcagtcc gctaagcata aagcacttgt tgaacaatat
9181 aaacaagaag gcaatcaagt tcaaaaacta aaagtacaaa atgataatct ttcaaaatca
9241 aacgaaaaaa tagaaaattc ttacgctaaa actaatacta aattaaagca aacagaaaaa
9301 gaatttaatg atttaaataa tactattaag aatcatagcg ctaatgtcgc aaaagctgaa
9361 acagctgtta acaaagaaaa agctgcttta aataatttag agcgttcaat agataaagct
9421 tcatccgaaa tgaagacttt taacaaagaa caaatgatag ctcaaagtca tttcggcaaa
9481 cttgctagtc aagcggatgt catgtcaaag aaatttagtt ctattggaga taaaatgact
9541 tccctaggac gtacgatgac gatgggcgta tctacaccga ttactttagg gttaggtgca
9601 gcattaaaaa caagtgcaga cttcgaaggg caaatgtctc gagttggagc gattgcacaa
9661 gcaagcagta aagacttaaa aagcatgtct aatcaagcgg ttgacttagg cgctaaaaca
9721 agtaaaagtg ctaacgaagt tgctaaaggt atggaagaat tggcagcttt aggctttaat
9781 gccaaacaaa caatggaggc tatgccgggt gttatcagtg cagcagaagc aagcggtgca
9841 gaaatggcta caactgcaac tgtaatggca tcagcaatta attctttcgg tttaaaagca
9901 tctgatgcaa accatgttgc tgatttactt gcgagatcag ctaatgatag tgctgcagat
9961 attcaataca tgggagatgc attaaaatat gcaggtactc cagcaaaagc attaggagtt
10021 tcaatagagg acacttctgc agcaattgaa gttttatcta actcagggtt agagggtct
10081 caagcaggta ctgcattaag agcttcgttt attaggctag ctaatccaag taaaagtaca

```
10141 gctaaggaaa tgaaaaaatt aggtattcat ttgtctgatg ctaaaggtca atttgttggc
10201 atgggtgaat tgattagaca gttccaagac aacatgaaag gcatgacgag agaacaaaaa
10261 ctagcaacag tggctacaat agttggcact gaagcagcaa gtggattttt agccttgatt
10321 gaagcgggtc cagataaaat taatagctat agcaaatcat tgaagaactc taatggtgaa
10381 agtaaaaaag cagctgattt gatgaaagac aacctcaaag gtgctctgga acaattaggt
10441 ggcgcttttg aatcgttagc aattgaagtt ggtaaagatt taacgcctat gattagagca
10501 ggtgcggaag gattaacaaa attagttgat ggatttacac atcttcctgg ttggtttaga
10561 aaggcttcgg taggtttagc gatttttggt gcatctattg gccctgctgt tcttgctggt
10621 ggcttattaa tacgtgcagt tggaagcgcg gctaaaggct atgcatcatt aaatagacgc
10681 attgctgaaa atacaatact gtctaatacc aattcaaaag caatgaaatc tttaggtctt
10741 caaaccttat ttcttggttc tacaacagga aaaacgtcaa aaggctttaa aggattagcc
10801 ggagctatgt tgtttaattt aaaacctata aatgttttga aaaattctgc aaagctagca
10861 attttaccgt tcaaactttt gaaaaacggt ttaggattag ccgcaaaatc cttatttgca
10921 gtaagtggag gcgcaagatt tgctggtgta gccttaaagt ttttaacagg acctataggt
10981 gctacaataa ctgctattac aattgcatat aaagttttta aaaccgcata tgatcgtgtg
11041 gaatggttca gaaacggtat taacggttta ggagaaacta taaagttttt tggtggcaaa
11101 attattggcg gtgctgttag gaagctagga gagtttaaaa attatcttgg aagtataggc
11161 aaaagcttca aagaaaagtt ttcaaaggat atgaaagatg gttataaatc tttgagtgac
11221 gatgaccttc tgaaagtagg agtcaacaag tttaaaggat ttatgcaaac catgggcaca
11281 gcttctaaaa aagcatctga tactgtaaaa gtgttgggga aaggtgtttc aaaagaaaca
11341 gaaaaagctt tagaaaaata cgtacactat tctgaagaga acaacagaat catggaaaaa
11401 gtacgtttaa actcgggtca aataacagaa gacaaagcaa aaaaactttt gaaaattgaa
11461 gcggatttat ctaataacct tatagctgaa atagaaaaaa gaaataaaaa ggaactcgaa
11521 aaaactcaag aacttattga taagtatagt gcgttcgatg aacaagaaaa gcaaaacatt
11581 ttaactagaa ctaaagaaaa aaatgacttg cgaattaaaa aagagcaaga actcaatcag
11641 aaaatcaaag aattgaaaga aaaagcttta agtgatggtc agatttcaga aaatgaaaga
11701 aaagaaattg aaaagcttga aaatcaaaga cgtgacatca ctgttaaaga attgagtaag
11761 actgaaaaag agcaagagcg tattttagta agaatgcaaa gaaacagaaa tgcttattca
11821 atagacgaag cgagcaaagc aattaaagaa gcagaaaaag caagaaaagc aagaaaaaaa
11881 gaagtggaca agcaatatga agatgatgtc attgctataa aaaataacgt caacctttct
11941 aagtctgaaa aagataaatt attagctatt gctgatcaaa gacataagga tgaagtaaga
12001 aaggcaaaat ctaaaaaaga tgctgtagta gacgttgtta aaaagcaaaa taaagatatt
12061 gataaagaga tggatttatc cagtggtcgt gtatataaaa atactgaaaa gtggtggaat
12121 ggccttaaaa gttggtggtc taacttcaga gaagaccaaa agaagaaaag tgataagtac
12181 gctaaagaac aagaagaaac agctcgtaga aacagagaaa atataaagaa atggtttgga
12241 aatgcttggg acggcgtaaa aactaaaact ggcgaagctt ttagtaaaat gggcagaaat
12301 gctaatcatt ttggcggcga aatgaaaaaa atgtggagtg gaatcaaagg aattccaagc
12361 aaattaagtt caggttggag ctcagccaaa agttctgtag gatatcacac taaggctata
12421 gctaatagta ctggtaaatg gtttggaaaa gcttggcaat ctgttaaatc gactacagga
12481 agtatttaca atcaaactaa gcaaaagtat tcagatgcct cagataaagc ttgggcgcat
12541 tcaaaatcta tttggaaagg gacatcaaaa tggtttagca atgcatataa aagtgcaaag
12601 ggctggctaa cggatatggc taataaatcg cgctcgaaat gggataatat ttctagtaca
12661 gcatggtcga atgcaaaatc cgtttggaaa ggaacatcga aatggtttag taactcatac
12721 aaatctttaa aaggttggac tggagatatg tattcaagag cccacgatcg ttttgatgca
12781 atttcaagtt cggcatggtc taacgctaaa tcagtattta atggttttag aaaatggcta
12841 tcaagaacat atgaatggat tagagatatt ggtaaagaca tgggaagagc tgcggctgat
12901 ttaggtaaaa atgttgctaa taaagctatt ggcggtttaa atagcatgat tggcggtatt
12961 aataaaatat ctaaagccat tactgataaa aatctcatca agccaatacc tacattgtct
13021 actggtactt tagcaggaaa gggtgtagct accgataatt cgggagcatt aacgcaaccg
13081 acatttgctg tattaaatga tagaggttct ggaaacgccc caggtggtgg agttcaagaa
13141 gtaattcaca gggctgacgg aacattccat gcaccccaag gacgagatgt ggttgttcca
13201 ctaggagttg gagatagtgt aataaatgcc aatgacactc tgaagttaca gcggatgggt
13261 gttttgccaa aattccatgg tggtacgaaa aagaaagatt ggctagacca acttaaaggt
13321 aatataggta aaaaagcagg agaatttgga gctacagcta aaaacacagc gcataatatc
13381 aaaaaaggtg cagaagaaat ggttgaagca gcaggcgata aaatcaaaga tggtgcatct
13441 tggttaggcg ataaaatcgg cgatgtgtgg gattacgtac aacatccagg gaaactagta
13501 aataaagtaa tgtcaggttt aaatattaat tttggaggcg gactaacgct acagtaaaaa
```

```
13561 ttgctaaagg cgcgtactca ttgctcaaaa agaaattaat agacaaagta aaatcgtggt
13621 ttgaagattt tggtggtgga ggcgatggaa gctatctatt tgaatatcca atctggcaaa
13681 gatttggacg ctacacaggt ggacttaact ttaatgacgg tcgtcactat ggtatagact
13741 ttggtatgcc tactggaaca aacgtttatg ccgttaaagg tggtatagca gataaggtat
13801 ggactgatta cggtggcggt aattctatac aaattaagac cggtgctaac gaatggaact
13861 ggtatatgca tttatctaag caattagcaa gacaaggcca acgtattaaa gctggtcaac
13921 tgatagggaa atcaggtgct acaggtaatt tcgttagagg agcacactta catttccaat
13981 tgatgcaagg gtcacatcca gggaatgata cagctaaaga tccagaaaaa tggttgaagt
14041 cacttaaagg tagtggcgtt cgaagtggtt caggtgttaa taaggctgca tctgcttggg
14101 caggcgatat acgtcgtgca gcaaaacgaa tgggtgttaa tgttacttcg ggtgatgtag
14161 gaaatatcat tagcttgatt caacacgaat caggaggaaa tgcaggtata actcaatcta
14221 gttcgcttag agacatcaac gttttacagg gcaatccagc aaaaggattg cttcaatata
14281 tcccacaaac atttagacat tatgctgtta gaggtcacaa caatatatat agtggttacg
14341 atcagttatt agcgttcttt aacaacagat attggcgctc acagtttaac ccaagaggtg
14401 gttggtctcc aagtggtcca agaagatatg cgaatggtgg tttgattaca aagcatcaac
14461 ttgctgaagt gggtgaagga gataaacagg agatggttat ccctttaact agacgtaaac
14521 gagcaattca attaactgaa caggttatgc gcatcatcgg tatggatggc aagccaaata
14581 acatcactgt aaataatgat acttctacag ttgaaaaatt gttgaaacaa attgttatgt
14641 taagtgataa aggaaataaa ttaacagatg cattgattca aactgtttct tctcaggata
14701 ataacttagg ttctaatgat gcaattagag gtttagaaaa aatattgtca aaacaaagtg
14761 ggcatagagc aaatgcaaat aattatatgg gaggtttgac taattaatgc aatcttttgt
14821 aaaaatcata gatggttaca aggaagaagt aataacagat tttaatcagc ttatattttt
14881 agatgcaagg gctgaaagtc caaacaccaa tgataacagt gtaactatta acggagtaga
14941 tggtatttta ccgggcgcaa ttagttttgc gcctttttca ttagtattaa ggtttggcta
15001 tgatggtata gatgttatag atttaaattt atttgagcat tggtttagat ctgtgtttaa
15061 tcgcagacat ccttattatg ttattacttc tcaaatgcct ggtgttaaat atgcagtgaa
15121 tacagctaat gttacatcta atttaaaaga tggttcttca actgaaattg aagtaagttt
15181 aaatgtttat aaagggtatt ctgaatcagt taattggacc gatagcgagt tcttattcga
15241 ctctaattgg atgtttgaaa atggaattcc tcttgatttc acacctaaat atactcatac
15301 atcaaatcaa tttactattt ggaacggttc tactgatacg ataaatccac gattcaagca
15361 cgatttgaaa atattaatta atttaaatgc gagtggagga tttgaactgg ttaactatac
15421 aacaggtgat atttttaagt acaacaaaag tatagataaa aacactgatt ttgttttaga
15481 tggtgtgtat gcatatcgag atataaatag agtgggaatt gatacaaata gaggcattat
15541 aacattagcg ccaggtaaaa atgaatttaa gattaaagga gacatcagtg atattaaaac
15601 tacatttaag tttcctttta tttataggta ggtgatttaa tggattatca tgatcattta
15661 tcagtaatgg attttaatga attgatttgt gaaaatttac tagatgtaga ttatggttct
15721 tttaaagaat attatgaact gaatgaagct aggtacatca cttttacagt ttatagaact
15781 actcataata gttttgtttt cgatttacta atttgtgaaa acttcataat ttatcatggt
15841 gaaaaataca caattaagca gacagcgcca aaggttgaag gtgataaagt tttattgaa
15901 gttacggcat atcacataat gtatgaattt caaaatcact cagtggaatc aaataagctt
15961 gatgacgaca gtagcgaaac tggtaaaacg ccagaatact ctttagatga gtacttaaga
16021 tatggatttg caaatcaaaa aacttcggtc aaaatgacct ataaaataat tggaaatttt
16081 aagcgaaaag taccgattga cgaattaggt aacaaaaacg gcttagaata ctgtaaagaa
16141 gcggtagacc tatttggctg tataatttac ccaaatgata cggagatatg tttttattct
16201 cctgaaacat tttatcaaag aagcgagaaa gtgattcgat atcaatataa tactgatact
16261 gtatctgcaa ctgtcagtac attggaatta agaacagcta taaaagtttt tggaaaaaag
16321 tatacagctg aggaaaagaa aaattataat cctattagaa caactgacat taaatattca
16381 aatggtttta taaaagaagg tacttatcgt accgcaacaa ttgggtctaa agctactatt
16441 aactttgatt gcaagtatgg taatgaaaca gttagattta caataaaaaa gggctctcaa
16501 ggtggaatat ataagttgat tttagacggc aagcaaatta agcaaatttc ttgttttgct
16561 aagtcggttc agtctgaaac aatagattta ataaaaaata ttgataaagg caagcacgtt
16621 ttagaaatga tatttttagg agaagacccc aaaaatagaa ttgatatatc ttcaaataaa
16681 aaagctaagc cttgtatgta tgttggaact gaaaaatcaa cagtcttaaa tttaattgct
16741 gacaactcag gtcgcaatca atacaaagca attgttgact acgtcgcaga tagtgcaaag
16801 cagtttggga ttcgatatgc taatacgcaa acaaatgaag atatcgaaac acaggataag
16861 ctgttagaat ttgcaaaaaa gcaaataaat gatactccta agactgaatt agatgttaat
16921 tatataggtt atgaaaaaat agagccaaga gatagcgtat tctttgttca tgaattaatg
```

16981 ggatataaca ctgaattaaa ggttgttaaa cttgataggt cacatccatt tgtaaacgca
17041 atagatgaag tgtctttcag caatgaaata aaggatatgg tacaaattca acaagcgctt
17101 aacagacgag ttattgcaca agataataga tataactatc aagcaaatcg tataaatcat
17161 ttatacacta gtactttgaa ttctcctttc gagacaatgg atatagggag tgtattaata
17221 taatggcaac agaagaagtt aaaatcaaag cgctacttga aaacgataaa cagtactttc
17281 cagctacaca ttggaaagct ataaatggga taccttatgc aggcagtagt gatattgatg
17341 gattgcctca agacggtatc atttcggtag atgataaaaa taaattagat aatttaaaaa
17401 taggcgaagc aggaattatt caaaatagca ttgtacagaa atccccaaac ggtaaattgt
17461 ggaaaataac agttgacgat agtgggaaac ttggtacagt gctattttat tagaaaggaa
17521 ggtgcattat ggaaaatttg tatttaataa aggatttggg agctttagca ggtcgagatt
17581 atagagctaa ggaaatacaa aacttacaaa gaatagagca atttgcgctt ggcttgacaa
17641 cagagtttaa gttgcatcag aaagctaaaa caattcaaca cttcgctgag caaatttatt
17701 ataatggtag atcgcaagca gcagtaaaca aatctttaca aagtcaaatt aacgcacttg
17761 ttgtggcacc acgtaataac agtgctaatg agattgttca agctcgagtt aatgtaaacg
17821 gcgaaacctt tgacacatta aaagaacatt tagacgattg ggaaacccaa actcaaatta
17881 ataaagagga aactataaga gaattaaata agaccaaaca agaaattctt gatatcgagt
17941 atcgttttga acctgataag caagaatttt tatttgtgac agaacttgca cctcttacaa
18001 atgcagtaat gcaatccttc tggtttgata atagaacagg catagtatac atgacacaag
18061 ctagaaataa tggctatatg ctaagtcgtc taagacctaa tggtcaattt atagacagct
18121 cattgattgt aggtgggggt catggtacac ataacggtta tagatatatt gatgatgagt
18181 tatggattta tagttttatc ttaaatggta ataatgagaa tacattagtt cgtttcaagt
18241 atacgcctaa tgtggaaatt agctatggca agtatggtat gcaagatgta tttacaggac
18301 acccagaaaa accctacatc accccctgtca taaatgaaaa agaaaataaa attctataca
18361 gaattgagag acctagaagt cactgggaac ttgaaaactc aatgaattat atagagataa
18421 gaagtttaga cgatgttgat aaaaatattg ataaagtttt gcataaaatc agtatcccta
18481 tgagactaac aaacgaaacc caaccaatgc agggtgtgac ttttgatgaa aaatacttgt
18541 attggtatac aggagacagt aatccaaata atagaaacta tttaacggct ttcgatttag
18601 aaacaggaga agaagcgtat caggttaatg ctgactatgg tggaacacta gattcatttc
18661 ctggcgaatt tgcggaagca gaaggtttgc aaatatacta tgacaaagat agtggtaaaa
18721 aagctttgat gctaggtgtt actgtcggtg gtgatggaaa tagaacacat cgtattttca
18781 tgattgggca aagaggtatt ttagaaatac ttcactcaag aggcgttcct tttatcatga
18841 gtgacacagg tggtagagtt aaacctttac caatgaggcc tgataaactt aagaatcttg
18901 ggatgttaac agagccaggt ctttactatt tatacactga tcatacagtt caaatcgatg
18961 atttcccatt accaagagaa tggcgtgatg caggttggtt cttggaagtt aagccaccac
19021 aaactggcgg tgatgtaatt cagatattga cgcgtaatag ttatgcaagg aatatgatga
19081 cttttgaaag ggtgctttct ggaagaactg gagacatttc ggactggaat tatgtgccta
19141 aaaatagtgg taaatgggag agagtacctt cattcatcac aaaaatgtca gatattaaca
19201 tagtaggcat gtcgttttat ttaactacgg atgatacaaa acgttttaca gattttccaa
19261 ctgaacgtaa aggggtagct ggttggaact tatatgtaga agcttcaaac acaggtggct
19321 ttgttcatag gctagttcgt aatagtgtta cagcatctgc tgagatacta ttgaaaaatt
19381 atgatagtaa aacaagttca gggccatgga ctttacacga agggagaatt ataagttaat
19441 gagtaattta gagaaatctg tagctataaa tttagaaaac acagcgcatt atgaaaatat
19501 ttcaaatcta gatataactt ttagaacagg agagagtgat tcttctgttc ttcttttttaa
19561 tatcactaaa aataatcaac cgttattatt gagtgaagaa aatatcaaag cacgaatagc
19621 gattcgaggt aaaggagtca tggtagttgc tccactagaa atattagatc catttaaagg
19681 tattttaaaa tttcaattac ctaatgatgt aattaaacga gatggaagtt atcaagctca
19741 agtttcggtt gcagaattag gtaattcaga cgtggtagtt gtcgagagaa ctatcacatt
19801 taacgttgaa aaaagtttgt ttagcatgat tccatctgaa acaaaattac actatattgt
19861 tgaatttcag gaattagaaa aaactattat ggatcgtgcg aaagcaatgg acgaggctat
19921 aaaaaatggt gaagattatg cgagtctgat tgaaaaagct aaagaaaaag gtctatcaga
19981 tattcaaata gcaaaatctt caagtataga tgaattaaag caacttgcta atagccatat
20041 atctgatttg gaaaataaag cgcaagcata ttcaagaaca ttcgatgagc aaaagcgata
20101 tatggatgag aaacatgaag ccttcaagca gtcagtgaat agtggtggtt tagtcacaag
20161 tggttctact tcaaattggc aaaaagctaa gattactaaa gatgatggta agataatgca
20221 gattactgga tttgatttta ataatccaga acaaagaata ggtgattcaa cccaatttat
20281 ttatgtttcg caagctataa attatccaag aggtgttagt actaacggta ctgtcgaata
20341 tttagtagta acttcagatt acaagcgtat gacttatcga ccgaacggta caaataaagt 20401 gtttgttaaa agaaaagaag cgggttcatg gtctgagtgg tcagaattag ctattaatga
20461 ttacaataca ccttttgaaa ctgttcaaag tgcccaatca aaagctaata tggccgaaag
20521 taacgctaaa ttatacgcag atgacaagtt taataaaagg tattcggtta tttttgatgg
20581 aacagcaaat ggtgtgggct ctacattgta cttaaatgag agtttagacc aatttatttt
20641 attaattttt tatgggactt ttccaggtgg tgactttaca gagtttggca gtccttttgg
20701 aggaggaaag atttcattga atccctcaaa tcttccagat ggtgatggaa atggtggagg
20761 tgtttatgag tttggattaa ctaaatctag tcgtacatct ttaactatat caaacgatgt
20821 ctatttcgac ttaggaagtc aaagaggctc tggtgcgaac gcaaatagag ggacaattaa
20881 caaaattata ggagtgagaa aataatgcaa atattagtta acaagcgtaa tgagataatt
20941 tcatacgcta tcattggtgg ctttgaagaa ggtattgata ttgaaaattt accagaaaat
21001 ttctctcaag tttttagacc taaagccttt aaatattcaa atggggaaat agtttttaac
21061 gaagattatt cagaagaaaa agatgacttg catcaacaga ttgacagtga agaacaaaac
21121 acagtcgctt ctgatgacat cttacgaaaa atggttgcta gtatgcagaa acaagttgtt
21181 caaagtacaa agttatcgat gcaagttaat aagcaaaatg cactaatggc aaaacaactt
21241 gtgacactta ataaaaaatt agaagaggtt aaaggagaga ctgaaaatgc ttaaattaat
21301 ttcaccaaca ttcgaagata ttaaaacatg gtatcaattg aaagaatata gtaaagaaga
21361 tatagcgtgg tatgtagata tggaagttat agataaagag gaatatgcaa ttattacagg
21421 agaaaagtat ccagaaaatc tagagtcata ggttataatc ttatggcttt ttaatttgaa
21481 taaagtgggt ggtgtaatgt ttggatttac caaacgacac gaacaagatt ggcgtttaac
21541 gcgattagaa gaaaatgata agactatgtt tgaaaaattc gacagaatag aagacagtct
21601 gagaacgcaa gaaaaaattt atgacaagtt agatagaaat ttcgaagaac taaggcgtga
21661 caaagaagaa gatgaaaaaa ataaagagaa aaatgctaaa aatattagag acatcaagat
21721 gtggattcta ggattaatag ggacgattct aagtacattt gttatagcct tgttaaaaac
21781 tatttttggc atttaaagga ggtgattacc atgcttaagg gaattttagg atatagcttt
21841 tggtcgtgtt tctggtttag taagtgtaag taatagttaa gagtcagtgc ttcggcactg
21901 gctttttatt ttggaaaaaa ggagcaaaca aatggatgca aaagtaataa caagatacat
21961 cgtattgatc ttagcattag taaatcaatt cttagcgaac aaaggtatta gcccgattcc
22021 agtagacgat gagaatatat catcaataat acttactgtt gttgctttat atactacgta
22081 taaagacaat ccaacatctc aagaaggtaa atgggcaaat caaaagctaa agaaatataa
22141 agctgaaaac aagtatagaa aagcaacagg gcaagcgcca attaaagaag taatgacacc
22201 tacgaatatg aacgacacaa atgatttagg gtaggtgttg accaatgttg ataacaaaaa
22261 accaagcaga aaaatggttt gataattcat tagggaagca gttcaatcct gatttgtttt
22321 atggatttca gtgttacgat tacgcaaata tgttttttat gatagcaaca ggcgaaaggt
22381 tacaaggttt atacgcttat aatattccat ttgataataa agcaaggatt gaaaaatacg
22441 ggcaaataat taaaaactat gatagctttt taccgcaaaa gttggacatt gtcgttttcc
22501 cgtcaaagta tggtggcgga gctggacatg ttgaaattgt tgagagcgct aatctaaaca
22561 ctttcacatc gtttggccaa aattggaatg gtaaaggttg gacaaatggc gttgcgcaac
22621 ctggttgggg tcccgaaacc gttacaagac atgttcatta ttacgatgac ccaatgtatt
22681 ttattagatt aaatttccca gataaagtaa gtgttggaga taaagctaaa agcgttatta
22741 agcaagcaac tgccaaaaag caagcagtaa ttaaacctaa aaaaattatg cttgtagccg
22801 gtcatggtta taacgatcct ggagcagtag gaaacggaac aaacgaacgc gattttatac
22861 gtaaatatat aacgccaaat atcgctaagt atttaagaca tgccggtcat gaagtcgcat
22921 tatatggtgg ctcaagtcaa tcacaagaca tgtatcaaga tacagcatac ggtgttaatg
22981 taggtaataa aaaagattat ggcttatatt gggttaaatc acaggggtat gacattgttc
23041 tagaaataca tttagacgca gcaggagaaa gcgcaagtgg tgggcatgtt attatctcaa
23101 gtcaattcaa tgcagatact attgataaaa gtatacaaga tgttattaaa aataacttag
23161 gacaaataag aggtgtaaca cctcgtaacg atttactaaa tgttaacgta tcagcagaaa
23221 taaatataaa ttatcgctta tctgaattag gttttatcac taataaaaat gatatggatt
23281 ggattaagaa aaactatgac ttgtattcta aattaatagc cggtgcgatt catggtaagc
23341 ctatcggtgg tgtgatatct agtgaggtta aaacaccagt taaaaacgaa aagaatccgc
23401 cagtgccagc aggttataca cccgataaaa ataatgtacc gtataaaaaa gaaactggtt
23461 attacacagt tgccaatgtt aaaggtaata acgtaaggga cggctattca actaattcaa
23521 gaattactgg tgtattacct aataacgcaa caatcaaata tgacggcgca tattgtatca
23581 atggctatag atggattact tatattgcta atagtggaca acgtcgttat attgctacag
23641 gagaggtaga caaggcaggt aatagaataa gcagttttgg taagtttagt gcagtttgat
23701 aattgtatat gatgaatctt aggcaggtac ttcggtactt gcctattatt taaaattaat
23761 aaacagttaa tttttacatg aatatattaa attttaaaaa aacaaacgtt tttagtatat

```
23821 aaattatttt gtgttcgtat tgtgtgctat gattaaaaag ttgttatggt caactatatc
23881 gtggttttat gtttattatc aatcaaaata taaattattt ataatttgtt tggtaatgaa
23941 cgggtttttt tcgaaataat agtaaaaaaa cacatttgta gatattttaa actcggtaaa
24001 tcttttaata aatatttaat tttattaaaa gttaaaaagg tttaatataa aaatgtaata
24061 aaatttataa agaaaggaaa tgatttttat ggtcaaaaaa agactattag ctgcaacatt
24121 gtcgttagga ataatcactc ctattgctac ttcgtttcat gaatctaaag ctgataacaa
24181 tattgagaat attggtgatg gcgctgaggt agtcaaaaga acagaagata caagtagcga
24241 taagtggggg gtcacacaaa atattcagtt tgattttgtt aaagataaaa agtataacaa
24301 agacgctttg attttaaaaa tgcaaggttt tatcaattca aagactactt attacaatta
24361 caaaaacaca gatcatataa aagcaatgag gtggcctttc caatacaata ttggtctcaa
24421 aacaaatgac cccaatgtag atttaataaa ttatctacct aaaaataaaa tagattcagt
24481 aaatgttagt caaacattag gttataacat aggtggtaat tttaatagtg gtccatcaac
24541 aggaggtaat ggttcattta attattcaaa aacaattagt tataataaaa taaaaagtag
24601 gtgataagat gactcaattt ctaggggcgc ttcttcttac aggagtttta ggttacatac
24661 catataaata tctaacaatg ataggtttag ttagtgaaaa aaacaaggtt atcaatactc
24721 ctgtattatt gatttttctt attgaaacat gtttgatatg gttttatagt tttataattt
24781 ttaataatgt tgatttaaaa aatttgaatt taattcagtt gcttacaggt ctaaaagcaa
24841 atattttgtt tctatttatt tttgttttaa cagtgtttgt atttaatcct ttaattgtta
24901 aatttattat ctggttaatt aatataacca gaaagtttat gaaattggat tgtataagct
24961 tattagacaa aagagacaag ttgtttaata acaacggtaa accagtattt atagttataa
25021 aagactttga aaacagaatc attgaagagg gtgaacttaa aacctataat tcagctggta
25081 gcgatttcga tttactagaa gttgagcgac aagatttcaa agtatctgat ttaccgtcaa
25141 acgatgaatt gtatattaaa catacacttg tagaccttaa acaacaaatt aaattggatt
25201 tatatttaat gaatgaatac taatcttttt tcttagcttt ttctgataaa gtgcttttta
25261 atttttcgct ggcgcccggc ttttcaaaac ttttgtttat tgggttacta cgagtagctt
25321 cttgtttttt gtttttatcc gccataaaat tctcaccacc attcaacgtc tacacttgta
25381 ggcgtttttt tatttagtaa agtcataatg aatcttcttt ggttaactta tctccatcta
25441 tttttgtga aataaattcc aagtatttac gcgcattatg tgacgataaa tctttaggta
25501 actcataagt gaatggttga ttaccactag ttaaaacttc atatactata gtttcttttt
25561 ttattttgca attagttatt ttcattataa acttcctttc aaacactgct gaaatagacg
25621 tcttttatat taaagcgcca cacaggcgct gttaatcaca atacaacttt gcccattact
25681 ttaatattac taaacgaagc gactttgata tcatcatact tcggatttag agataccaaa
25741 ttaatatagt cttcgcatat atctacacgc ttgataagac ttactccatc taatacaacg
25801 agtgcaattg taccatcttt aatagaatct tctttcttaa taaaagcgta tgttccttgt
25861 tttaacatag gttccattga atcaccatta actaaaatac aaaaatcagc atttgatggc
25921 gtttcgtctt ctttaaaaaa tacttcttca tgcaatatgt catcatataa ttcttctcct
25981 atgccagcac cagttgcacc acatgcaata tacgatacta gtttagactc tttatatcca
26041 tctatagaag tgactttatt ctgttcttcc aattgttcat ttgcatagtt aagtacgttt
26101 tcttggcggg gaggtgtgag tttgttgtat atggaagtga tgtcgttatc gtctttgtat
26161 gtagtatttg attcactata caaatcatta atcttcacat tgaagtactc agccaaaatt
26221 ttggcagttg ataatcgagg ttcttccttt tcattttccc attttgatat cttgcctttc
26281 gttaatttca ttaagtcggg atatttatta ttaagatcag ttgctaattg ttccatagtc
26341 atatttttat tttttctta gcttctttaa accttcacca atacccatac gaaaccctcc
26401 ttatataaga taatttcatt ataaaagttt cgaaaacgaa acgcaaggaa aatattattg
26461 caaaagttgt tgacatcgaa acttttatga tgtattctta aatcaagttg ttacaaacga
26521 aacaaaagga gggggttcaa tgacaactag tgtagcagat aaaccatact taaaaataaa
26581 aagcttgatt gcacttaaag gaactaacca aaaagaagtt gctaaagcaa tcggaatgag
26641 tagaagttta ttgagtataa agataaatcg aattaatggc agagatttta caacttcaga
26701 agctaaaaaa ttagcagatc atttaaatgt taaagttgat gatttttttt aaactttaag
26761 tttcgaaagt gacaactaaa taaaaataag gaggacacta tggaacaaat aacgttaacc
26821 aaagaagagt tgaaagaaat tatagcgaaa gaagttagaa atgctataaa aggcgagaaa
26881 ccaatcagct caggtgcaat tttcagtaaa gtaagaatca ataatgacga tttagaagaa
26941 atcaataaaa aactcaattt cgcaaaagat ttgtcgctag gaagattgag gaagctcaat
27001 catccgattc cgctaaaaaa gtatcagcat ggcttcgaat caattcatca aaaagcttat
27061 gtacaagatg ttcatgacca tattagaaaa ttaacattat caatttttgg agtgacactt
27121 aattcagact tgagtgaaag tgaatacaac ctagcagcaa aaatttatag agatatcaaa
27181 aactattatt tatatatcta tgaaaagaga gtttcagaat taactatcga tgatttcgaa
```

27241 tgaaggagga actacaaatg aaactactaa gaaggctatt caataaaaaa cacgaaaact
27301 taattgacgt gtggcatgga aatcaatggt taaaagtgaa agaaagcaaa ttaaaaaaat
27361 ataaagtggt ctcggataga gaaggtaaga aatatctaat taaataagcg cacttaatta
27421 gtgcaagtaa tcaagtgcgc tattgcctta caatcctaaa tcttttctgc tttttcttc
27481 ttcttgtaat cccaataaca cagaagagta aatgctgaaa tagtcacgag caacgctatc
27541 tttagcgaat gcaattacgt catcaccgac ttcttgccat tcgttatgaa tcttatgtct
27601 atctagagct ctaggtaata gcgagattgt aatatcgtga gcaattttct ctaaatccat
27661 aaatttcacc tccttccact gggagataac taaattatat aacaaaacaa cttaaaggag
27721 gaacgacaaa tgcaagctca aaacaaaaaa gtcatctatt actactatga cgaagaaggt
27781 aataggcgac cattagatat tcaaattaat gacggatatg aactgatggt ccgatctcat
27841 ttcatcaaca acaccattga agaaatacca tacgtaaata ataacttata tgccttggtt
27901 gatggttatg aatttaagtt agattgaatt tttgagaaag atattgaaaa gctaatttcc
27961 ccataagatt aagagacata ctggatgttt tgttaacgac tcttttaact tcgttccaag
28021 ttttattgtc tctaatatta tcgagaaatt catggccaga ccaagtgatg tcatcaataa
28081 tccaagaaac gaccctgcct tcgatgaatt tcagatcgca acaaataaat ttagcttctt
28141 ctaattttaa aagtgagtac attactgttt caaaatcata tttatcaaaa ataatattat
28201 cgttgaaatt atgtcgagta agtggttcac ctattttctt attagattct atttctaaga
28261 gcaagagtct aacgcaatcg tgattaagtt tcatcctatc acctccataa caggagtata
28321 gcagaaagga tcataaacat cttaaaagga ggaataacaa atgaacattc aagaagcaac
28381 taagatagct acaaaaaatc ttgtctctat gacacggaaa gattggaaag aaagtcatcg
28441 aactaagata ttaccaacaa atgatagttt tttacaatgc atcatttcaa atagcgatgg
28501 gacaaacctt atcagatatt ggcaaccttc agccgatgac ctcatggcaa atgattggga
28561 agttataaac ccaactagag accaggaatt attgaagcaa ttttagaaat gctatcaatg
28621 atacttttta aattgttttt aaactcattt tcaaagtaaa caacagtctt gtctgaaatt
28681 gttacatgat aaatagtgtt actagcatac acgccgttta ggaacccaga gtttttaagt
28741 ttatttaaat cgtattttac atcttcgaaa tgtagttttt gaaaatactt tgtatgtata
28801 tctttagcac ttccaaaatt attgcaggtt aatttaaccg aacctaactt tacacattct
28861 aaataatctt tgtagagtac ggacaagata tattgttggt ctttagtaag tgtatcaaat
28921 tcatcagata tcaagggcat gttatcacct ccttaggttg ataacaacat tatacacgaa
28981 aggagcataa acaaatgaac acaagatcag aaggattgcg tataggcgtc ccacaagttt
29041 ctagcaaagc tgatgcttct tcatcctatt taacggaaaa ggaacgtaac ttaggagcgg
29101 aaatattaga gcttattaaa aaaagtgatt acagctactt agaaataaac aaagttttct
29161 atgcattaga tagagaactt caatacaggg cgaataataa caaactttaa catttatcta
29221 aaggagtgat agagatgcca aaaatcataa taccaccaac accagaaaac acatatcgag
29281 gcgaagaaaa atttgtgaaa aagttatacg caacacctac acaaatccat caattgtttg
29341 gagtatgtag aagtacagta tacaactggt tgaaatatta ccgtgaagat aatttaggtg
29401 tagaaaattt atacattgat tattcagcaa cgggaacatt gattaatatt tctaaattag
29461 aagagtattt gatcagaaag cataaaaaat ggtattagga ggattatcaa atgagcgaca
29521 catataaaag ctacctatta gcagtgttgt gcttcacggt cttagcgatt gtactcatgc
29581 cgtttctata cttcactaca gcatggtcaa ttgcgggatt cgcaagtatc gcaacattca
29641 tattttataa ggaatacttt tatgaagaat aaagaaactg ctacttgttg gagcaagtaa
29701 cagtgcaaga tgagcaattg tcttaaataa ttatataagg agttattaat atgaccttac
29761 aacaaaaaat actatcacat tttgcaacat atgacaattt caattctgat gatgttgttg
29821 aagtttttgg gatatctaaa acacatgcaa aatccacact ttcaagactt aagaaaaaag
29881 gaaagattga attggaaagt tggggtatct ggcgtgttgt tgaaccgcag ttacatttaa
29941 ctgttgtaga acgtaagaaa gagatattag aagaacaatt cgagttattg gcaagattaa
30001 acgaacaaag tgatgaccct agagaaatag aagaacgcat caagttaatg attcgtttag
30061 ccaaccaatt ttaaggagga gttaatcaat ggcaatatta gaaggtattt ttgaagaatt
30121 aaaactatta aataagaatt tacgtgtgct aaatactgaa ctatcaactg tagattcatc
30181 aattgtacaa gagaaagtta aagaagcacc aatgccaaaa gatgaaacag ctcaactgga
30241 atcagttgaa gaagttaagg aaacttctgc tgatttaact aaagattatg ttttatcagt
30301 aggaaaagag ttccttaaaa aagcagatac ttctgataag aaagaattta gaaataaact
30361 taacgaactt ggtgcggata agctatctac tatcaaagaa gagcattatg aaaaaattgt
30421 tgattttatg aatgcgagaa taaatgcatg aagctagatc actcaaatag agctcatgca
30481 aagcttagtg caagtggagc aaaacaatgg ctaaactgtc caccgagtat taaggcaagt
30541 gaaggtattg cagataaaag ttcagttttt gctgaagaag gtacattcgc tcatgagtta
30601 agtgagttat atttcagtct taaatatgaa ggcctaacac agtttgagtt taataaagct 30661 tttcaaaatt ataagcgaaa tcaatattac agtgaagagt tgcgcgaata tgttgaagag
30721 tacgtagcta atgtagaaga aaaatataac gaagctttga gtagagatga cgatgtaata
30781 gctttatttg aaacaaaatt ggatttaggt aaatacgtcc ctgaatcttt tggtactggt
30841 gatgtcatta tattttcagg tggtgtactt gaaattattg accttaaata cggtaaaggc
30901 attgaagttt cagctataga taatcctcaa cttagattat atggcttggg cgcatatgaa
30961 ctgcttagtt taatgtatga cattcataca gttcgcatga ctatcataca accacgaata
31021 gataactttt ctactgaaga gttaccaata tcaagattac ttcaatgggg aaccgatttt
31081 gttaaaccat tagccagact tgcttataac ggtgaaggtg agtttaaagc aggtagtcat
31141 tgtagattct gtaagataaa gcattcatgt agaacacgtg cagaatacat gcaaaatgtg
31201 cctcaaaagc caccacattt gttgagtgat gaagagattg cagaactttt atataaactg
31261 cctgacatca aaaaatgggc tgatgaagta gaaaaatatg cactagatca agcgaaagaa
31321 aatgataaaa actattctgg ttggaagctt gtagaaggtc gctcgcgaag aatgataact
31381 gatacaaatg caacgcttga aaagttagtt gaagcaggtt ataaacctga agatattaca
31441 gaaaccaagt tacttagcat tacgaattta gaaaaattaa tcggcaaaaa agcattttct
31501 aaaattgcag aaggctttat agaaaagcca caaggtaaat taacacttgc taccgagtct
31561 gataaacgac cagctataaa gcaatctgct gaagatgatt ttgacaaact ataaaaatta
31621 aaaaggacgg tatataaaca tgaaagcaaa agtattaaat aaaactaaag tgattacagg
31681 aaaagtaaga gcatcatatg cacatatttt tgaacctcac agtatgcaag aagggcaaga
31741 agcaaagtat tcaatcagtt taatcattcc taaatcagat acaagtacga taaaagccat
31801 tgaacaagct atagaagctg ctaaagaaga aggaaaagtt agtaagtttg gaggcaaagt
31861 tcctgcaaat ctgaaacttc cattacgtga tggagatact gaaagagaag atgatgtgaa
31921 ttatcaagac gcttatttta ttaacgcatc aagcaaacaa gcacctggta ttattgacca
31981 aaacaaaatt agattaacgg attctggaac tattgtaagt ggtgactata ttagagcttc
32041 aatcaattta tttccattca acacaaatgg taataagggt atcgcagttg gattgaacaa
32101 cattcaactt gtagaaaaag gcgaacctct tggcggtgca agtgcagcag aagatgattt
32161 cgatgaatta gacactgatg atgaggattt cttataagtc aataggtggg gtttttagcc
32221 ccactttaat tttaaagaaa ttgaggtgtc aagaatttga aatttatgaa tatagatatt
32281 gaaacatata gcagtaacga tatttcgaaa tgtggtgtct ataaatacac agaagctgaa
32341 gatttcgaaa tcttaattat agcttattca atagatggtg gaccgattag tgcgattgac
32401 atgactaaag tagataatga gcctttccac gctgattatg agacgtttaa aattgctcta
32461 tttgaccctg ctgtaaaaaa gtatgcattc aatgctaatt tcgaaagaac ttgtcttgct
32521 aaacatttta ataaacagat gccacctgaa gaatggattt gcacaatggt taattcaatg
32581 cgtattggct tacctgcttc gcttgataaa gttggagaag ttttaagact acaaaaccaa
32641 aaagataaag caggtaaaaa tttaattcgt tatttctcta taccttgtaa gccaacaaaa
32701 gttaatggag gaagaacaag aaatttgcct gaacatgatc ttgaaaaatg gcaacaattt
32761 atagattact gtattcgaga tgtagaagta gaaatgacaa ttgctaataa aattaaagac
32821 tttccagtaa ctgtaattga acaagcatat tgggtttttg accaacatat aaacgacaga
32881 ggtattaagc tttctaaatc attgatgtta ggagctaatg tgctcgataa gcagagtaaa
32941 gaagaattgc ttaaacaagc taaacatata acaggtttag aaaatcctaa tagtcctaca
33001 cagttattgg cttggttaaa ggatgaacaa ggattagata tacctaattt acaaaagaaa
33061 acggttcagg attacttaaa agtagcaaca ggaaaagcta aaaaaatgct agaaattaga
33121 ttgcaaatgt ctaaaaccag tgtgaaaaaa tacaacaaaa tgcatgacat gatgtgcagt
33181 gatgaacggg taagaggtct gtttcaattc tacggtgccg gtactggaag atgggcaggt
33241 agaggtgtac aacttcagaa tttaacaaag cattatattt cagatactga attagaaata
33301 gcaagagatc ttattaaaga acaacgtttt gacgatttag atttattact caatgttcat
33361 cctcaagact tattaagtca attagttagg acgacattta ctgctgaaga aggtaatgaa
33421 ctagcagtaa gtgattttc tgcaatagag gcaagagtca tagcatggta tgcaaaagaa
33481 caatggcgtt tagatgtgtt caacacacac ggaaagatat atgaagcatc ggcttctcaa
33541 atgtttaatg taccggtaga aagcataact aaaggcgacc ctctcagaca aaaaggaaaa
33601 gtgtccgaat tagctttagg ctatcaaggt ggcgctggag ctttaaaagc aatgggtgca
33661 ttggaaatgg gcattgaaga aaacgagtta caaggtttag ttgatagttg gcgtaacgca
33721 aatcctaaca tagttaattt ttggaaggct tgccaagagg ctgcaattaa tactgtaaaa
33781 tcccgaaaga cgcatcatac acatggactt agattttata tgaaaaaagg ttttctaatg
33841 attgaactgc ctagtggaag agctttagct tatccaaaag ctttagttgg tgaaaatagt
33901 tggggtagtc aagttgttga atttatgggg ttagatctta accgtaaatg gtcaaagtta
33961 aaaacgtatg gtgggaagtt agtcgagaat attgttcaag caactgcaag ggatttactt
34021 gcgatttcta tagcaaggct tgaagcatta ggttttaaaa tagttggcca tgtccatgat

```
34081 gaagtaattg tagaaatacc tagaggttca aatggactta aggaaatcga aactatcatg
34141 aataagcctg ttgattgggc aaaaggattg aatttgaata gtgacgggtt tacttctccg
34201 ttttatatga aggattagga gtgtgattgc atgcaacatc aagcttatat caatgcttct
34261 gttgacatta gaattcctac agaagtcgaa agtgttaatt acaatcagat tgataaagaa
34321 aaagaaaatt tggcggacta tttatttaat aatccaggtg aactattaaa atataacgtt
34381 ataaatatta aggttttaga tttagaggtg gaatgatggc tagaagaaaa gttataagag
34441 tgcgtatcaa aggaaaacta atgacattga gagaagtttc agaaaaatat cacatatctc
34501 cagaacttct tagatataga tacaaacata aaatgcgcgg cgatgaatta ttgtgtggaa
34561 gaaaagactc aaaatctaaa gatgaagttg aatatatgca gagtcaaata aaagatgaag
34621 aaaaagagag agaaaaaatc agaaaaaaag cgattttgaa cctataccaa cgaaatgtga
34681 gagcggaata tgaagaagaa agaaagagaa gattgagacc atggctttat gatggaacgc
34741 cacaaaaaca ttcacgtgat ccgtactggt tcgatgtcac ttataaccaa atgttcaaga
34801 aatggagtga agcataatga gcgtaatcag taacagaaaa gtagatatga acgaagcgca
34861 agacaatgtt aagcaaccag cgcactacac atacggcgac attgaaatta tagattttat
34921 cgaacaggtt acggcacagt atccacctca actagcattc gcaataggta atgcaataaa
34981 atacttgtct agagcacctt taaagaatgg tcatgaggat ttagcaaagg cgaagtttta
35041 cgtccaaaga gcttttgact tgtgggagtg atgaccatga cagatagcgc atgtaaagaa
35101 tacttaaacc aatttttcgg atctaagaga tatctgtatc aggataacga acgagtggca
35161 catatccatg tagtgaatgg cacttattac tttcacgggc atatcgtacc aggctggcaa
35221 ggcgtgaaaa agacatttga tacagcggaa gagctcgaaa catatataaa gcaacatggt
35281 ttggaatacg aggaacagaa gcaactaact ttattttaag gagatagaaa tgatgaaaat
35341 caaagttgaa aaaataatga aaatagacga attaattaag tgggcgcgag aaaatccgga
35401 gctatcattt ggcagaaaat attatacaac agacaaaaat gatgaaaact ttatttactt
35461 cggtgttttt aaaaattgtt ttaaaataag cgattttata ttagttaatg ctacttttag
35521 tgtcaaagtt gaagaagaag taaccgaaga aactaagttt gataggttgt ttgaagtgta
35581 cgagattcaa gaaggagtct ataaatctgc atcatatgag aatgctagta taaacgaacg
35641 tttaaaaaat gacagaattt ttcttgctaa agcattctac atcttaaacg acgacctaac
35701 tatgacgtta atttggaaag aaggagagtt gattaaataa tggaacacgg ttcaaaagaa
35761 tattacgaaa agcaaagtga atactggttt gatgaagcaa gcaagttttt gaagcaacgt
35821 gatgagctta ttggagatat agctaagtta agagagtgca acaaagagct ggagaagaaa
35881 gcaagtgcat gggataggta ttgcaagagc gttgaaaaag atttaataaa cgaatttggc
35941 aaagatggtg aaagagttaa atttggaatg gaattaaaca ataaaatttt tatggaggaa
36001 gacgcaaatg aataaccgcg aacaaatcga acaatcagtt attagtgcta gcgcgtataa
36061 cggcaatgac acagagggat tattaaaaga gattgaggac gtgtataaga aagcgcaagc
36121 gtttgatgaa atacttgagg gtttacctaa tgctatgcaa gatgcaatca aagaagatat
36181 tggtcttgat gaagcagtag gaattatgac gggtcaagtt gtctataaat atgaggagga
36241 gcaggaaaat gactaacata ttacaagtga aactattatc aaaagacgct agaatgccag
36301 aacgaaatca taagacggat gcaggttatg acatatttc agctaaaact gtcgtacttg
36361 agccacaaga aaaggcagtg atcaaaacag atgtagctgt aagcattcca gagggctatg
36421 tcggtttatt aactagccgt agtggtgtaa gtagtaaaac gcatttagtg attgaaacag
36481 gcaagataga cgcgggatat catggtaatt tagggattaa tatcaagaat gataatgaaa
36541 cgttagagag tgaggatatg agtaactttg gtcggagtcc ttctggtata gatggaaaat
36601 acaccctact acctgtaaca gataaatttt tatgtatgaa tggtagttat gtcataaata
36661 aaggcgacaa actagctcaa ttggttatcg tgcctatatg gacacctgaa ctaaagcaag
36721 tggaggaatt cgagagtgtt tcagaacgtg gagcaaaagg cttcggaagt agcggagtgt
36781 aaagacatat tagatcgagt caaggaggtt ttggggaagt gagtgacatg ttagaaatat
36841 ttttcatagg gtttggtgtt tatctatttt gtcgcatagg tattattttt ctcaagagta
36901 aaaagactat acacacaaac ctatatgaaa tgttgttgat tgctactatc tttgtgacat
36961 ctacatttgc tgataaacat caaaagacgc atatcttaat agcattttta gtaatgtttt
37021 ttatgagtaa gctcaaacaa gttcaaggga gctatgagga atgacacaat acctagtcac
37081 aacatttaaa gattcaacag gacgtaagca tacacacata actaaagcta agagcaatca
37141 aaggtttaca gttgttgatg cggagagtaa agaagaagcg aaagagaagt acgaggcaca
37201 agttaaaaga aatgcagtta ttaaattagg gcagttgttt gaaaatataa gggagtgtgg
37261 gaaatgacta aacaaatact aagattatta ttcttactag cgatgtatga gctaggcaag
37321 tatgtaactg agcaagtata tattatgatg acggctaatg atgatgcaga ggcgccgagt
37381 gactttgaaa aaatcagagc tgaagtttca tggtaatagc tattatcatt tttgaattaa
37441 ttatattaat gtgtttagca atagcactgg aggtgttgta aatatgtgga ttgtcatttc
```

37501 aattgtttta tctatatttt tattgatctt gttaagtagc atttctcata agatgaaaac
37561 catagaagca ttggagtata tgaatgctta tcttttcaag cagttagtaa aaaataatgg
37621 tgttgaaggt atagaagatt atgaaaatga agttgaacga attagaaaaa gatttaaaag
37681 ctaaagagag gcgttggctt ctctgttcta tttaaaataa tgaaaggagc cgaacatgtt
37741 agacaaagtc actcaaatag aaacaattaa atatgatcgt gatgtttcat attcttatgc
37801 tgctagtcgt ttatctacac attggactaa tcacaatatg gcttggtctg actttatgca
37861 gaagctagca caaacagtta gaactaaaga agatttaact gagtacaata aaatgtctaa
37921 gtctgaacaa gccgatataa aagatgttgg cggatttgtc ggtggttatt taaaagaagg
37981 caaacgacgt gctggtcaag tcatgaatcg ttcaatgtta acacttgata tcgattatgc
38041 tgctcaagat atgactgaca tattatctat gttttatgat tttgcatatt gtttatattc
38101 aacacataag catagagaga taagtccaag actgcgttta gtgattcctt taaaacgaaa
38161 tgtaaatgca gatgagtatg aagctattgg gcgtaaagtc gcagatatcg ttggcatgga
38221 ttacttcgat gatacaactt atcaaccaca taggttaatg tattggcctt caactagtaa
38281 cgatgcggaa tttttcttta cctatgaaga tttacctttg ttagacccag ataaaatatt
38341 aaatgaatat gttgattgga ctgacacatt agaatggcca acgtcttcaa gggaagagag
38401 taagactaaa agattagcag ataagcaagg cgacccagaa gaaaagccgg gaattgttgg
38461 tgcattttgt agagcctata cgatagaaga agctatagaa acttttattc ctgatttata
38521 cgaaaaacat tctactaacc gttataccta tcatgaaggt tcaactgcag gtggattggt
38581 gttatacgaa aataacaagt ttgcctattc tcatcataat acggatcccg taagcggtat
38641 gcttgtgaac agttttgatt tagtacgcat acacttatat ggtgctcaag atgaagacgc
38701 taaaacagat actccggtta atcgactacc tagttataaa gcaatgcagc aaagagcgca
38761 aaatgatgaa gttgttaaaa agcaattaat taacgacaaa atgtctgatg caatgcagga
38821 tttcgatgaa atagtaaata gcgatgatgc atggtctgag acgttagaaa ttacttcgaa
38881 aggtactttc aaagctagta tcccaaatat agaaattata ttgcgtaatg atccaaattt
38941 aaaaggaaaa atagcattta atgaatttac aaaacaaatt gaatgcttag ggaaaatgcc
39001 atggaataat aattttaaaa tacgtcaatg gcaagacggt gatgatagca gtttaagaag
39061 ttatatcgaa aagatttatg acatacacca ttcaggcaaa acaaaagatg ccattataag
39121 cgtagcaatg caaaatgcct atcatccagt aagagattat ctaaataaaa tatcgtggga
39181 tggacataaa cgtcttgaaa agttatttat caaatactta ggtgttgaag acactgaagt
39241 gaatagaaca actaccaaaa aggcattgac tgctggaatc gctcgagtaa tggagccagg
39301 atgtaaattt gactatatgc ttacacttta tggtcctcaa ggtgtaggta aatctgcttt
39361 gctaaaaaaa ataggtggtg catggttttc tgacagttta gtttctgtta ctggtaagga
39421 agcatatgag gcattacaag gcgtttggtt aatggaaatg gcagaacttg cagctacaag
39481 aaaagctgaa gttgaagcta ttaagcattt catatctaaa caagttgacc ggtttcgtgt
39541 tgcttatgga cattatattg aagattttcc aaggcaatgt attttcattg gtacaactaa
39601 taaagttgat ttcttaagag atgaaactgg tggaagacgt ttttggccaa tgactgtaaa
39661 tccagagaga gttgaagtga actggtctaa actaaccaaa gaagagatcg accaaatctg
39721 ggcagaagct aaatactatt atgaacaagg agaagagttg ttccttaacc ctgaactaga
39781 agaagaaatg cgttcaatcc aaagtaaaca tactgaggaa tctccatata caggtattat
39841 tgatgaatat cttaacacgc caatcccaag caattgggaa gacttaacta tctttgaaag
39901 aagacgattt tatcaaggtg atgttgatat gttaccaaca ggaaatgtag attacattga
39961 aagagacaag gtctgtgcgc ttgaagtgtt tgttgaatgt tttggtaaag ataagggaga
40021 tagtagagga tctatggaaa ttagaaagat ttctaacgtc ttaagacaat tagacaattg
40081 gtctgtatat gaaggcaata aaagtgggaa aattcgattt ggaaaagatt atggtgtaca
40141 gatagcgtat gtaagagatg aaagtttaga ggatttaata taagaaatat tgaataaata
40201 tacattttta gatgttgtat caaatgttgc atcatttttt gagtgatgca acacggtggt
40261 gtaaaaagta atcgtaggtg ttgtatcatt tttggtgatg caacattgat gcaacaaatg
40321 atacaacacc tctttccctt ctcgctgtaa ggttcaaccc tgtttgtttc caatgttgca
40381 tcaaattcac tataaagttt aaaaagtagt gttagggagt aaaggggtat aggggtaacc
40441 ctctaacagc tatttttaaa agtttggcaa gaattgatgc aacatcggaa cacaaatata
40501 aattttgtat acaaggtgaa taaatgaaag aatcgacatt agaaaaatat ttagtgaaag
40561 agataacaaa gttaaatgga ttatgtttaa aatgggtcgc acctggaaca agaggtgtac
40621 cagatagaat tattattatg ccagaaggaa aaacatattt tgtagaaatg aagcaagaaa
40681 agggaaagtt acatccttta caaaaatatg tgcatcggca atttgaaaac agagatcata
40741 cagtgtatgt gttatggaat aaagaacaag taaatacttt tataagaatg gtaggtggaa
40801 catttggcga ttgatttcaa accacatagc tatcaaaagt atgcaataga taaagtgatt
40861 gataatgaga aatacggttt gtttttagat atggggctag ggaaaacagt atcaacactt

```
40921 acagcattta gtgaattgca gttgttagac actaaaaaa tgttagtcat agcacctaaa
40981 caagttgcta aagatacatg ggttgatgaa gttgataagt ggaaccattt aaatcatctg
41041 aaagtgtctt tagtcttagg aacacctaaa gaaagaaatg atgcattaaa cacagaggct
41101 gatatctatg taaccaataa agaaaatact aaatggttat gtgatcaata taaaaaagaa
41161 tggccatttg acatggttgt aattgatgaa ctgtctacat ttaaaagtcc taagagtcaa
41221 aggtttaaat ctattaaaaa gaaattacca ctcattaata gatttatagg attaacagga
41281 acacctagtc caaatagttt acaggattta tgggctcaag tttatttgat agacagaggc
41341 gaaagacttg agtcttcatt cagtcgttat cgagaaaggt actttaaacc aacacatcaa
41401 gttagcgaac atgtttttaa ctgggagcta agagacggat ctgaagaaaa gatatatgaa
41461 cgaatagaag atatatgttt aagcatgaaa gcgaaagatt atctggatat gcctgacaga
41521 gttgatacta aacaaacagt agtcttatct gaaaaagaaa gaaaagtata tgaagaatta
41581 gaaaaaaact atattttaga atcggaagaa gaaggaacag ttgtagctca gaatggggca
41641 tcattaagtc aaaaactact tcaactatct aacggtgcag tttatacaga tgatgaagat
41701 gtaagactta tacatgataa gaagttagat aagttagagg aaattataga ggagtctcaa
41761 ggccaaccaa tattattgtt ttataacttc aaacatgata aagaaagaat acttcaaagg
41821 tttaaggaag caaccacatt agaggattca aactataaag aacgttggaa tagtggagac
41881 attaagctgc ttatagcaca tccagcaagt gcagggcatg gattaaactt acaacaaggt
41941 gggcacatta ttgtttggtt tggacttaca tggtcattgg aattatacca acaagcaaat
42001 gcaagattat atagacaagg acaaaatcat acgactatta ttcatcacat catgaccgat
42061 aacacaatag atcaaagagt atataaagct ttacaaaata aagaactaac gcaagaagaa
42121 ttgatgaaag ctattaaagc aagaatagct aagcataagt aatggaggta taagatggga
42181 aaggcgtcat atgatattaa gccaggaaca tttaaatata ttgaatcaga aatatataat
42241 ttaaatgaga acaagaaaga gataaataga ttgagaatgg agatacttaa cccaacgaaa
42301 gaactagaca ccaacattgt gtatggaccg ttacaaaaag gagagccagt tagaacaact
42361 gagttaatgg cgacaaggtt attgactaat aagatgttac gtaacttaga agagatggtt
42421 gaagcagttg aaagtgagta cttaaagtta cctgaagatc ataagaaagt aataaggtta
42481 aagtattgga ataaagataa gaagctaaag atagaacaaa taggggatgc ttgtcacatg
42541 catcgcaata cagttactac aatacgaaag aactttgtta aagcgatagc gtatcatgca
42601 ggtatcaaat aacattgtgc aaagattgtg caaaaggcct acaaatctgt agtaatatga
42661 tagtatcgga aagatgtata aagttatctg aaagttatac gacataaata catgaggcac
42721 atcgctaagc ggtgtgtctt ttgttatgca atcaaagagg tgtaagagat gaccaagcat
42781 aataacattt ataagcatgg tcgtaagtca tatcaatacg attggttcta tcattcaaaa
42841 gcatggaaga agttaagaga gatagcatta gatagagata attatctttg tcaaatgtgt
42901 ttacgcgaag atattataac agatgcaaag attgtgcatc acattattta tgttgatgaa
42961 gattttaaca aagctttaga cttagataat ctaatgtcag tttgttatag ctgtcataac
43021 aaaattcatg caaatgataa tgacaaaagt aatcttaaga aaattagagt tctaaaaatt
43081 taaataaaaa aatta
```

Bacteriophage 77, complete genome Sequence (SEQ ID NO. 18).

```
1     gatcaaaata cttggggaac ggttagggag taaacttcgc gataatttta aaaattcatg
61    tataaccccc ctcttataac cattttaagg caggtgatga aatggagatt atagtcgatg
121   aaaatttagt gcttaaagaa aaagaaaggc tacaagtatt atataaagac atacctagca
181   ataaattaaa agtagttgat ggtttaatta ttcaagcagc aaggctacgt gtaatgcttg
241   attacatgtg ggaagacata aaagaaaaag gtgattatga tttatttact caatctgaaa
301   aggcgccacc atatgaaagg gaaagaccag tagccaaact atttaatgct agagatgctg
361   catatcaaaa aataatcaaa caattatcgg atttattgcc cgaagagaaa gaagacacag
421   aaacgccatc tgatgattac ctatgattag taataaatac gttgatgaat atataaattt
481   gtggaaacaa ggaaagataa ttttaaataa agaaagaatt gatctcttta attatctaca
541   aaaacatata tattcacgag atgatgtata ttttgatgaa cagaaaatcg aggattgtat
601   caaatttatt gaaaaatggt attttccaac attaccattt caaaggttta tcatagctaa
661   tatatttctt atagataaaa atacagatga agctttcttt acagaatttg ctattttcat
721   gggacgtgga ggcgggaaaa acggtctaat aagtgctatt agtgattttc tttctacgcc
781   cttacacgga gttaaagaat atcacatctc cattgttgct aatagtgaag atcaagcaaa
841   aacatcgttt gatgaaatca gaaccgtttt aatggataac aaacgaaata agacgggtaa
901   aacgccaaaa gctccttatg aagttagtaa agcaaaaata ataaaccgtg caactaaatc
961   ggttattcga tataacacat caaacacaaa aaccaaagac ggtggacgtg aggggtgtgt
1021  tatttttgat gaaattcatt atttctttgg tcctgaaatg gtaaacgtca aacgtggtgg
1081  attaggtaaa aagaaaaata gaagaacgtt ttatataagt actgatggtt ttgttagaga
1141  gggttatatc gatgcaatga agcacaaaat tgcaagtgta ttaagtggca aggttaaaaa
1201  tagtagattg tttgcttttt attgtaagtt agacgatcca aaagaagttg atgacagaca
1261  gacgtgggaa aaggcgaacc caatgttaca taaaccgtta tcagaatacg ctaaaacact
1321  gctaagcacg attgaagaag aatataacga tttaccattc aaccgttcaa ataagcccga
1381  attcatgact aagcgaatga atttgcctga agttgacctt gaaaaagtaa tagcaccatg
1441  gaaagaaata ctagcgacta atagagagat accaaattta gataatcaaa tgtgtattgg
1501  tggtttagac tttgcaaaca ttcgagattt tgcaagtgta gggctattat tccgaaaaaa
1561  cgatgattac atttggttag gacattcgtt tgtaagacaa gggtttttgg atgatgtcaa
1621  attagaacct cctattaaag aatgggaaaa aatgggatta ttgaccattg tcgatgatga
1681  tgtcattgaa attgaatata tagttgattg gtttttaaag gctagagaaa aatatgggct
1741  tgaaaaagtc atagctgata attatagaac tgatattgta agacgtgcgt ttgaggatgc
1801  tggcataaaa cttgaagtac ttagaaatcc aaaagcaata catggattac ttgcaccacg
1861  tatcgataca atgtttgcga aacataacgt aatatatgga gacaatcctt tgatgcgttg
1921  gtttactaat aatgttgctg taaaaatcaa gccggatgga aataaagagt atatcaaaaa
1981  agatgaagtc agacgtaaaa cggatggatt catggctttt gttcacgcat tatatagagc
2041  agacgatata gtagacaaag acatgtctaa agcgcttgat gcattaatga gtatagattt
2101  ctaatagagg aggtgagaca tgagtattct agaaaagata tttaaaacta ggaaagatat
2161  aacatatatg cttgatttag atatgataga agatctatca caacaagcgt atgtgaaacg
2221  tttagcgatt gatagttgta ttgaatttgt tgcgcgagct gtcgctcaaa gtcattttaa
2281  agtattggaa ggtaatagaa ttcaaaagaa tgatgtttac tacaagttaa atataaaacc
2341  aaatactgac ttatcaagcg atagtttttg gcaacaagtt atatataaac taatttatga
2401  taacgaggtt ttaatcgtag taagtgacag caaagaatta cttatcgcag atagctttta
2461  cagagaagag tacgctttgt atgatgatat attcaaagat gtaacggtta aagattatac
2521  ttatcaacgt actttcacaa tgcaagaggt catatattta aagtacaaca acaataaagt
2581  gacacacttt gtagaaagtc tattcgaaga ttacgggaaa atattcggaa gaatgatagg
2641  tgcacaatta aaaaactatc aaataagagg gattttgaaa tctgcctcta gcgcatatga
2701  cgaaaagaat atagaaaaat tacaagcgtt cacaaataaa ttattcaata cttttaataa
2761  aaatcaacta gcaatcgcgc ctttgataga aggttttgat tatgaggaat tatctaatgg
2821  tggtaagaat agtaacatgc ctttttctga attgagtgag ctaatgagag atgcaataaa
2881  aaatgttgcg ttgatgattg gtatacctcc aggtttgatt tacggagaaa cagctgattt
2941  ggaaaaaaac acgcttgtat ttgagaagtt ctgtttaaca cctttattaa aaaagattca
3001  gaacgaatta aacgcgaaac tcataacaca aagcatgtat ttgaaagata caagaataga
3061  aattgtcggt gtgaataaaa aagacccact tcaatatgct gaagcaattg acaaacttgt
3121  aagttctggt tcatttacaa ggaatgaggt gcggattatg ttaggtgaag aaccatcaga
3181  caatcctgaa ttagacgaat acctgattac taaaaactac gaaaaagcta acagtggtga
```

3241 aaatgatgaa aaagaaaaag atgaaaacac tttgaaaggt ggtgatgaag atgaaagcgg
3301 agattaaagg cgtcatcgtt tccaacgaag ataaatgggt ttacgaaatg cttggtatgg
3361 attcgacttg tcctaaagat gttttaacac aactagaatt tagtgatgaa gatgttgata
3421 ttataattaa ctcaaatggt ggtaacctag tagctggtag tgaaatatat acacatttaa
3481 gagctcataa aggcaaagtg aatgttcgta tcacagcaat agcagcaagt gcggcatcgc
3541 ttatcgcaat ggctggtgac cacatcgaaa tgagtccggt tgctagaatg atgattcaca
3601 atccttcaag tattgcgcaa ggagaagtga aagatctaaa tcatgctgca gaaacattag
3661 aacatgttgg tcaaataatg gctgaggcat atgcggttag agctggtaaa aacaaacaag
3721 aacttataga aatgatggct aaggaaacgt ggctaaatgc tgatgaagcc attgaacaag
3781 gttttgcgga tagtaaaatg tttgaaaacg acaatatgca aattgtagca agcgatacac
3841 aagtgttatc gaaagatgta ttaaatcgtg taacagcttt ggtaagtaaa acgccagagg
3901 ttaacattga tattgacgca atagcaaata aagtaattga aaaaataaat atgaaagaaa
3961 aggaatcaga aatcgatgtt gcagatagta aattatcagc aaatggattt tcaagattcc
4021 tttttaata caaaaatagg aggtcataaa atgactataa atttatcgga aacattcgca
4081 aatgcgaaaa acgaatttat taatgcagta aacaacggtg aaccgcaaga aagacaaaat
4141 gaattgtacg gtgacatgat taaccaacta tttgaagaaa ctaaattaca agcaaaagca
4201 gaagctgaaa gagtttctag tttacctaaa tcagcacaaa ctttgagtgc aaaccaaaga
4261 aatttcttta tggatatcaa taagagtgtt ggatataaag aagaaaaact tttaccagaa
4321 gaaacaattg atagaatctt cgaagattta acaacgaatc atccattatt agctgactta
4381 ggtattaaaa atgctggttt gcgtttgaag ttcttaaaat ccgaaacttc tggcgtggct
4441 gtttggggta aaatctatgg tgaaattaaa ggtcaattag atgctgcgtt cagtgaagaa
4501 acagcaattc aaaataaatt gacagcgttt gttgttttac caaaagattt aaatgatttt
4561 ggtcctgcgt ggattgaaag atttgttcgt gttcaaatcg aagaagcatt tgcagtggcg
4621 cttgaaactg cgttcttaaa aggtactggt aaagaccaac cgattggctt aaaccgtcaa
4681 gtacaaaaag gtgtatcggt aactgatggt gcttatccag agaaagaaga acaaggtacg
4741 cttacatttg ctaatccgcg cgctacggtt aatgaattga cgcaagtgtt taaataccac
4801 tcaactaacg agaaaggtaa atcagtagcg gttaaaggta atgtaacaat ggttgttaat
4861 ccgtccgatg cttttgaggt tcaagcacag tatacacatt taaatgcaaa tggcgtatat
4921 gttactgctt taccatttaa tttgaatgtt attgagtcta cagttcaaga agcaggtaag
4981 gttttaacgt acgttaaagg tctatatgat ggttatttag ctggtggtat taatgttcag
5041 aaatttaaag aaacacttgc gttagatgat atggatttat acactgcaaa acaatttgct
5101 tacggcaaag cgaaagataa taaagttgct gctgtttgga aattagattt aaaaggacat
5161 aaaccagctt tagaagatac cgaagaaaca ctataaaatt ttatgaggtg ataaaatggt
5221 gaaatttaaa gttgttagag aatttaaaga catagagcac aatcaacaca agtacaaagt
5281 aggggagttg tatccagctg aagggtataa caatcctcgt gttgaattgt tgacaaatca
5341 aatcaaaaat aagtacgaca aagtttatat cgtaccttta gataagctga caaaacaaga
5401 attattagaa ctatgcgaat cattacaaaa aaaagcgtct agttcaatgg ttaaaagtga
5461 aatcatcgac ttattgaatg gtgaagacaa tgacgattga tgatttgctt gtcaaattta
5521 aatcacttga aaagattgac cataattcag aggatgagta cttaaagcag ttgttaaaaa
5581 tgtcgtacga gcgtataaaa aatcagtgcg gagtttttga attagagaat ttaataggtc
5641 aagaattgat acttatacgc gctagatatg cttatcaaga tttattagaa cacttcaacg
5701 acaattacag acctgaaata atagattttt cgttatctct aatggaggta tcagaagatg
5761 aagaaagtgt ttaagaaacc tagaattaca actaaacgtt taaatacgcg tgttcatttt
5821 tataagtata ctgaaaataa tggtccagaa gctggagaaa aagaagaaaa attattatat
5881 agctgttggg cgagtattga tggtgtctgg ttacgtgaat tagaacaagc tatctcaaac
5941 ggaacgcaaa atgacattaa attgtatatt cgtgatccgc aaggtgatta tttacccagt
6001 gaagaacatt atcttgaaat tgaatcaaga tatttcaaaa atcgtttgaa tataaagcaa
6061 gtatcaccag atttggataa taaagacttt attatgattc gcggaggata tagttcatga
6121 gtgtgaaagt gacaggtgat aaagcattag aaagagaatt agaaaaacat tttggcataa
6181 aagagatggt aaaagttcaa gataaggcgt taatagctgg tgctaaggta attgttgaag
6241 aaataaaaaa acaactcaaa ccttcagaag actcaggagc actgattagt gagattggtc
6301 gtactgaacc tgaatggata aaggggaaac gtactgttac aattaggtgg cgtgggcctt
6361 ttgaacgatt tagaatagta catttaattg aaaatggtca tgttgagaaa aagtcaggaa
6421 aatttgtaaa acctaaagct atgggtggga ttaatagagc aataagacaa gggcaaaata
6481 agtattttga gacgctaaaa agggagttga aaaaattgtg attgatattt tgtacaaagt
6541 tcatgaagtg attagtcaag acagaattat tagagagcac gtaaatatca ataatattaa
6601 gttcaataaa taccctaatg taaaagatac tgatgtacct tttattgtta ttgacgatat 6661 cgacgaccca atacctacaa cttatactga cggagatgag tgtgcatata gttatattgt
6721 ccaaatagat gtttttgtta agtacaatga tgaatataat gcgagaatca taagaaataa
6781 gatatctaat cgcattcaaa agttattatg gtctgaacta aaaatgggaa atgtttcaaa
6841 tggaaaaccg gaatatatag aagaatttaa aacatataga agctctcgcg tttacgaggg
6901 catttttat aaggaggaaa attaaatggc agtaaaacat gcaagtgcgc caaaggcgta
6961 tattaacatt actggtttag gtttcgctaa attaacgaaa gaaggcgcgg aattaaaata
7021 tagtgatatt acaaaaacaa gaggattaca aaaaattggt gttgaaactg gtggagaact
7081 aaaaacagct tatgctgatg gcggtccaat tgaatcaggg aatacagacg gagaaggtaa
7141 aatctcatta caaatgcatg cgttccctaa agagattcgc aaaattgttt ttaatgaaga
7201 ttatgatgaa gatggcgttt acgaagagaa acaaggtaaa caaaacaatt acgtagctgt
7261 atggttcaga caagagcgta aagacggtac atttagaaca gttttattac ctaaagttat
7321 gtttacaaat cctaaaatcg atggagaaac ggctgagaaa gattgggatt tctcaagtga
7381 agaggttgaa ggtgaggcac ttttcccttt agttgataat aaaaagtcag tacgtaagta
7441 tatctttgat tcagctaaca tgacaaatca tgatggagac ggtgaaaaag gcgaagaggc
7501 tttcttaaag aaaattttag gcgaagaata tactggaaac gtgacagagg gtaacgaaga
7561 aactttgtaa caaaaccggc ttcatcggaa actgcggtaa agtcggttaa tataccagat
7621 agcattaaaa cacttaaagt tggcgacaca tacgatttaa atgttgtagt agagccatct
7681 aatcaaagta agttattgaa atacacaaca gatcaaacga atattgtatc aatcaatagt
7741 gatggtcaag ttactgcgga agcacaaggc attgctacgg ttaaagcaac agttggtaat
7801 atgagtgaca ctataacaat aaatgtagaa gcataagagg gggcaacccc tctattttat
7861 ttgaaaataa ggagagtatt ataaaatggc aaaattaaaa cgtaacatta ttcaattagt
7921 agaagatcca aaagcaaatg aaattaaatt acaaacgtac ttaacaccac acttcatttc
7981 atttgaaatt gtatacgaag caatggattt aatcgatgat attgaggacg aaaatagcac
8041 gatgaagcca agagaaatcg ctgacagatt gatggatatg gttgtaaaaa tttacgataa
8101 ccaattcaca gttaaagacc taaaagaacg tatgcatgca cctgatggaa tgaatgcact
8161 tcgtgaacaa gtgattttca ttactcaagg tcaacaaact gaggaaacta gaaattttat
8221 ccagaacatg aaataaagcc tgaagattta acatataaag caatgttgaa aaatatggat
8281 actctcatga tggacttaat tgaaaatggt aaagacgcta acgaagtttt aaaaatgcca
8341 tttcattatg tgctttccat atatcaaaat aaaaataatg acatttctga agaaaaagca
8401 gaggctttaa ttgatgcatt ttaaccttaa ccgtttggtt agggttattt ttttgaactt
8461 ttttagaaag gaggtaaaaa atgggagaaa gaataaaagg tttatctata ggtttggatt
8521 tagatgcagc aaatttaaat agatcatttg cagaaatcaa acgaaacttt aaaactttaa
8581 attctgactt aaaattaaca ggcaacaact tcaaatatac cgaaaaatca actgatagtt
8641 acaaacaaag gattaaagaa cttgatggaa ctatcacagg ttataagaaa aacgttgatg
8701 atttagccaa gcaatatgac aaggtatctc aagaacaggg cgaaaacagt gcagaagctc
8761 aaaagttacg acaagaatat aacaaacaag caaatgagct gaattattta gaaagagaat
8821 tacaaaaaac atcagccgaa tttgaagagt tcaaaaaagc tcaagttgaa gctcaaagaa
8881 tggcagaaag tggctgggga aaaaccagta aagtttttga aagtatggga cctaaattaa
8941 caaaaatggg tgatggttta aaatccattg gtaaaggttt gatgattggt gtaactgcac
9001 ctgttttagg tattgcagca gcatcaggaa aagcttttgc agaagttgat aaaggtttag
9061 atactgttac tcaagcaaca ggcgcaacag gcagtgaatt aaaaaaattg cagaactcat
9121 ttaaagatgt ttatggcaat tttccagcag atgctgaaac tgttggtgga gttttaggag
9181 aagttaatac aaggttaggt tttacaggta aagaacttga aaatgccaca gagtcattct
9241 tgaaattcag tcatataaca ggttctgacg gtgtgcaagc cgtacagtta attacccgtg
9301 caatgggcga tgcaggtatc gaagcaagtg aatatcaaag tgttttggat atggtagcaa
9361 aagcggcgca agctagtggg ataagtgttg atacattagc tgatagtatt actaaatacg
9421 gcgctccaat gagagctatg ggctttgaga tgaaagaatc aattgcttta ttctctcaat
9481 gggaaaagtc aggcgttaat actgaaatag cattcagtgg tttgaaaaaa gctatatcaa
9541 attggggtaa agctggtaaa aacccaagag aagaatttaa gaagacatta gcagaaattg
9601 aaaagacgcc ggatatagct agcgcaacaa gtttagcgat tgaagcattt ggtgcaaagg
9661 caggtcctga tttagcagac gctattaaag gtggtcgctt tagttatcaa gaatttttaa
9721 aaactattga agattcccaa ggcacagtaa accaaacatt taaagattct gaaagtggct
9781 ccgaaagatt taaagtagca atgaataaat taaaattagt aggtgctgat gtatgggctt
9841 ctattgaaag tgcgtttgct cccgtaatgg aagaattaat caaaaagcta tctatagcgg
9901 ttgattggtt ttccaattta agtgatggtt ctaaaagatc aattgttatt ttcagtggta
9961 ttgctgctgc aattggtcct gtagtttttg ggttaggtgc atttataagt acaattggca
10021 atgcagtaac tgtattagct ccattgttag ctagtattgc aaaggctggt ggattgatta 10081 gtttttatc gactaaagta cctatattag gaactgtctt cacagcttta actggtccaa
10141 ttggcattgt attaggtgta ttggctggtt tagcagtcgc atttacaatt gcttataaga
10201 aatctgaaac atttagaaat tttgttaatg gtgcaattga aagtgttaaa caaacattta
10261 gtaattttat tcaatttatt caacctttcg ttgattctgt taaaaacatc tttaaacaag
10321 cgatatcagc aatagttgat ttcgcaaaag atatttggag tcaaatcaat ggattcttta
10381 atgaaaacgg aatttccatt gttcaagcac ttcaaaatat atgcaacttt attaaagcga
10441 tatttgaatt tattttaaat tttgtaatta aaccaattat gttcgcgatt tggcaagtga
10501 tgcaatttat ttggccggcg gttaaagcct tgattgtcag tacttgggag aacataaaag
10561 gtgtaataca aggtgcttta aatatcatac ttggcttgat taagttcttc tcaagtttat
10621 tcgttggtga ttggcgagga gtttgggacg ccgttgtgat gattcttaaa ggagcagttc
10681 aattaatttg gaatttagtt caattatggt ttgtaggtaa aatacttggt gttgttaggt
10741 actttggcgg gttgctaaaa ggattgatag caggaatttg ggacgtaata agaagtatat
10801 tcagtaaatc tttatcagca atttggaatg caacaaaaag tatttttgga tttttattta
10861 atagcgtaaa atcaattttc acaaatatga aaaattggtt atctaatact tggagcagta
10921 tccgtacgaa tacaatagga aaagcgcagt cattatttag tggcgtcaaa tcaaaattta
10981 ctaatttatg gaatgcgacg aaagaaattt ttagtaattt aagaaattgg atgtcaaata
11041 tttggaattc cattaaagat aatacggtag gaattgcaag ccgtttatgg agtaaggtac
11101 gtggaatttt cacaaatatg cgcgatggct tgagttccat tatagataag attaaaagtc
11161 atatcggcgg tatggtaagc gctattaaaa aaggacttaa taaattaatc gacggtttaa
11221 actgggtcgg tggtaagttg ggaatggata aaatacctaa gttacacact ggtacagagc
11281 acacacatac tactacaaga ttagttaaga acggtaagat tgcacgtgac acattcgcta
11341 cagttgggga taagggacgc ggaaatggtc caaatggttt tagaaatgaa atgattgaat
11401 tccctaacgg taaacgtgta atcacaccta atacagatac taccgcttat ttacctaaag
11461 gctcaaaagt atacaacggt gcacaaactt attcaatgtt aaacggaacg cttccaagat
11521 ttagtttagg tactatgtgg aaagatatta aatctggtgc atcatcggca tttaactgga
11581 caaaagataa aataggtaaa ggtaccaaat ggcttggcga taaagttggc gatgttttag
11641 attttatgga aaatccaggc aaactttttaa attatatact tgaagctttt ggaattgatt
11701 tcaattcttt aactaaaggt atgggaattg caggcgacat aacaaaagct gcatggtcta
11761 agattaagaa aagtgctact gattggataa aagaaaattt agaagctatg ggcggtggcg
11821 atttagtcgg cggaatatta gaccctgaca aaattaatta tcattatgga cgtaccgcag
11881 cttataccgc tgcaactgga agaccatttc atgaaggtgt cgattttcca tttgtatatc
11941 aagaagttag aacgccgatg ggtggcagac ttacaagaat gccatttatg tctggtggtt
12001 atggtaatta tgtaaaaatt actagtggcg ttatcgatat gctatttgcg catttgaaaa
12061 actttagcaa atcaccacct agtggcacga tggtaaagcc cggtgatgtt gttggtttaa
12121 ctggtaatac cggatttagt acaggaccac atttacattt tgaaatgagg agaaatggac
12181 gacattttga ccctgaacca tatttaagga atgctaagaa aaaaggaaga ttatcaatag
12241 gtggtggcgg tgctacttct ggaagtggcg caacttatgc cagtcgagta atccgacaag
12301 cgcaaagtat tttaggtggt cgttataaag gtaaatggat tcatgaccaa atgatgcgcg
12361 ttgcaaaacg tgaaagtaac taccagtcaa atgcagtgaa taactgggat ataaatgctc
12421 aaagaggaga cccatcaaga ggattattcc aaatcatcgg ctcaactttt agagcaaacg
12481 ctaaacgtgg atatactaac tttaataatc cagtacatca aggtatctca gcaatgcagt
12541 acattgttag acgatatggt tggggtggtt ttaaacgtgc tggtgattac gcatatgcta
12601 caggtggaaa agtttttgat ggttggtata acttaggtga agacggtcat ccagaatgga
12661 ttattccaac agatccagct cgtagaaatg atgcaatgaa gattttgcat tatgcagcag
12721 cagaagtaag agggaaaaaa gcgagtaaaa ataagcgtcc tagccaatta tcagacttaa
12781 acgggtttga tgatcctagc ttattattga aaatgattga acaacagcaa caacaaatag
12841 ctttattact gaaaatagca caatctaacg atgtgattgc agataaagat tatcagccga
12901 ttattgacga atacgctttt gataaaaagg tgaacgcgtc tatagaaaag cgagaaaggc
12961 aagaatcaac aaaagtaaag tttagaaaag gaggaattgc tattcaatga tagacactat
13021 taaagtgaac aacaaaacaa ttccttggtt gtatgtcgaa agagggtttg aaataccctc
13081 ttttaattat gttttaaaaa cagaaaatgt agatggacgt tcggggtcta tatataaagg
13141 gcgtaggctt gaatcttata gttttgatat acctttggtg gtacgtaatg actatttatc
13201 tcacaacggc attaaaacac atgatgacgt cttgaatgaa ttagtaaagt tttttaacta
13261 cgaggaacaa gttaaattac aattcaaatc taaagattgg tactggaacg cttatttcga
13321 aggaccaata aagctgcaca aagaatttac aatacctgtt aagttcacta tcaaagtagt
13381 actaacagac ccttacaaat attcagtaac aggaaataaa aatactgcga tttcagacca
13441 agtttcagtt gtaaatagtg ggactgctga cactccttta attgttgaag cccgagcaat

```
13501 taaaccatct agttacttta tgattactaa aaatgatgaa gattatttta tggttggtga
13561 tgatgaggta accaaagaag ttaaggatta catgcctcct gtttatcata gtgagtttcg
13621 tgatttcaaa ggttggacta agatgattac tgaagatatt ccaagtaatg acttaggtgg
13681 taaggtcggc ggtgactttg tgatatccaa tcttggcgaa ggatataaag caactaattt
13741 tcctgatgca aaaggttggg ttggtgctgg cacgaaacga gggctcccta aagcgatgac
13801 agattttcaa attacctata aatgtattgt tgaacaaaaa ggtaaaggtg ccggaagaac
13861 agcacaacat atttatgata gtgatggtaa gttacttgct tctattggtt atgaaaataa
13921 atatcatgat agaaaaatag gacatattgt tgttacgttg tataaccaaa aaggagaccc
13981 caaaaagata tacgactatc agaataaacc gataatgtat aacttggaca gaatcgttgt
14041 ttatatgcgg ctcagaagag taggtaataa attttctatt aaaacttgga aatttgatca
14101 cattaaagac ccagatagac gtaaacctat tgatatggat gagaaagagt ggatagatgg
14161 cggtaagttt tatcagcgtc cagcttctat catagctgtc tatagtgcga agtataacgg
14221 ttataagtgg atggagatga atgggttagg ttcattcaat acggagattc taccgaaacc
14281 gaaaggcgca agggatgtca ttatacaaaa aggtgattta gtaaaaatag atatgcaagc
14341 aaaaagtgtt gtcatcaatg aggaaccaat gttgagcgag aaatcgtttg gaagtaatta
14401 tttcaatgtt gattctgggt acagtgaatt aatcatacaa cctgaaaacg tctttgatac
14461 gacggttaaa tggcaagata gatatttata gaaaggagat gagagtgtga tacatgtttt
14521 agattttaac gacaagatta tagatttcct ttctactgat gacccttcct tagttagagc
14581 gattcataaa cgtaatgtta atgacaattc agaaatgctt gaactgctca tatcatcaga
14641 aagagctgaa aagttccgtg aacgacatcg tgttattata agggattcaa acaaacaatg
14701 gcgtgaattt attattaact gggttcaaga tacgatggac ggctacacag agatagaatg
14761 tatagcgtct tatcttgctg atataacaac agctaaaccg tatgcaccag gcaaatttga
14821 gaaaaagaca acttcagaag cattgaaaga tgtgttgagc gatacaggtt gggaagtttc
14881 tgaacaaacc gaatacgatg gcttacgtac tacgtcatgg acttcttatc aaactagata
14941 tgaagtttta aagcaattat gtacaaccta taaaatggtt ttagattttt atattgagct
15001 tagctctaat accgtcaaag gtagatatgt agtactcaaa aagaaaaaca gcttattcaa
15061 aggtaaagaa attgaatatg gtaaagattt agtcgggtta actaggaaga ttgatatgtc
15121 agaaatcaaa acagcattaa ttgctgtggg acctgaaaat gacaaaggga agcgtttaga
15181 gctagttgtg acagatgacg aagcgcaaag tcaattcaac ctacctatgc gctatatttg
15241 ggggatatat gaaccacaat cagatgatca aaatatgaat gaaacacgat taagttcttt
15301 agccaaaaca gagttaaata aacgtaagtc ggcagttatg tcatatgaga ttacttctac
15361 tgatttggaa gttacgtatc cgcacgagat tatatcaatt ggcgatacag tcagagtaaa
15421 acatagagat tttaacccgc cattgtatgt agaggcagaa gttattgctg aagaatataa
15481 cataatttca gaaaatagca catatacatt cggtcaacct aaagagttca aagaatcaga
15541 attacgagaa gagtttaaca agcgattgaa cataatacat caaaagttaa acgataatat
15601 tagcaatatc aacactatag ttaaagatgt tgtagatggt gaattagaat actttgaacg
15661 caaaatacac aaaagtgata caccgccaga aaatccagtc aatgatatgc tttggtatga
15721 tacaagtaac cctgatgttg ctgtcttgcg tagatattgg aatggtcgat ggattgaagc
15781 aacaccaaat gatgttgaaa aattaggtgg tataacaaga gagaaagcgc tattcagtga
15841 attaaacaat atttttatta atttatctat acaacacgct agtcttttgt cagaagctac
15901 agaattactg aatagcgagt acttagtaga taatgatttg aaagcggact tacaagcaag
15961 tttagacgct gtgattgatg tttataatca aattaaaaat aatttagaat ctatgacacc
16021 cgaaactgca acgattggtc ggttggtaga tacacaagct ttatttcttg agtatagaaa
16081 gaaattacaa gatgtttata cagatgtaga agatgtcaaa atcgccattt cagatagatt
16141 taaattatta cagtcacaat acactgatga aaaatataaa gaagcgttgg aaataatagc
16201 aacaaaattt ggtttaacgg tgaatgaaga tttgcagtta gtcggagaac ctaatgttgt
16261 taaatcagct attgaagcag ctagagaatc cacaaaagaa caattacgtg actatgtaaa
16321 aacatcggac tataaaacag acaaagacgg tattgttgaa cgtttagata ctgctgaagc
16381 tgagagaacg actttaaaag gtgaaatcaa agataaagtt acgttaaacg aatatcgaaa
16441 cggattggaa gaacaaaaac aatatactga tgaccagtta agtgatttgt ccaataatcc
16501 tgagattaaa gcaagtattg aacaagcaaa tcaagaagcg caagaagctt taaaatcata
16561 cattgatgct caagatgatc ttaaagagaa ggaatcgcaa gcgtatgctg atggtaaaat
16621 ttcggaagaa gagcaacgcg ctatacaaga tgctcaagct aaacttgaag aggcaaaaca
16681 aaacgcagaa ctaaaggcta gaaacgctga aaagaaagct aatgcttata cagacaacaa
16741 ggtcaaagaa agcacagatg cacagaggaa aacattgact cgctatggtt ctcaaattat
16801 acaaaatggt aaggaaatca aattaagaac tactaaagaa gagtttaatg caaccaatcg
16861 tacactttca aatatattaa acgagattgt tcaaaatgtt acagatggaa caacaatcag
```

```
16921 atatgatgat aacggagtgg ctcaagcttt gaatgtgggg ccacgtggta ttagattaaa
16981 tgctgataaa attgatatta acggtaatag agaaataaac cttcttatcc aaaatatgcg
17041 agataaagta gataaaaccg atattgtcaa cagtcttaat ttatcaagag agggtcttga
17101 tatcaatgtt aatagaattg gaattaaagg cggtgacaat aacagatatg ttcaaataca
17161 gaatgattct attgaactag gtggtattgt gcaacgtact tggagaggga aacgttcaac
17221 agacgatatt tttacgcgac tgaaagacgg tcacctaaga tttagaaata acaccgctgg
17281 cggttcactt tatatgtcac attttggtat ttcgacttat attgatggtg aaggtgaaga
17341 cggtggttca tctggtacga ttcaatggtg ggataaaact tacagtgata gtggcatgaa
17401 tggtataaca atcaattcct atggtggtgt cgttgcacta acgtcagata ataatcgggt
17461 tgttctggag tcttacgctt catcgaatat caaaagcaaa caggcaccgg tgtatttata
17521 tccaaacaca gacaaagtgc ctggattaaa ccgatttgca ttcacgctgt ctaatgcaga
17581 taatgcttat tcgagtgacg gttatattat gtttggttct gatgagaact atgattacgg
17641 tgcgggtatc aggttttcta aagaaagaaa taaaggtctt gttcaaattg ttaatggacg
17701 atatgcaaca ggtggagata caacaatcga agcagggtat ggcaaattta atatgctgaa
17761 acgacgtgat ggtaataggt atattcatat acagagtaca gacctactgt ctgtaggttc
17821 agatgatgca ggagatagga tagcttctaa ctcaatttat agacgtactt attcggccgc
17881 agctaatttg catattactt ctgctggcac aattgggcgt tcgacatcag cgcgtaaata
17941 caagttatct atcgaaaatc aatataacga tagagatgaa caactggaac attcaaaagc
18001 tattcttaac ttacctatta gaacgtggtt tgataaagct gagtctgaaa ttttagctag
18061 agagctgaga gaagatagaa aattatcgga agacacctat aaacttgata gatacgtagg
18121 tttgattgct gaagaggtgg agaatttagg attaaaagag tttgtcacgt atgatgacaa
18181 aggagaaatt gaaggtatag cgtatgatcg tctatggatt catcttatcc ctgttatcaa
18241 agaacaacaa ctaagaatca agaaattgga ggagtcaaag aatgcaggat aacaaacaag
18301 gattacaagc taatcctgaa tatacaattc attatttatc acaggaaatt atgaggttaa
18361 cacaagaaaa cgcgatgtta aaagcgtata tacaagaaaa taaagaaaat caacaatgtg
18421 ctgaggaaga gtaatcctta gcactatttt tatacaaaaa tttaaggagg tcatttaatt
18481 atggcaaaag aaattatcaa caatacagaa aggtttattt tagtacaaat cgacaaagaa
18541 ggtacagaac gtgtagtata tcaagatttc acaggaagtt ttacaacttc tgaaatggtt
18601 aaccatgctc aagattttaa atctgaagaa aacgctaaga aaattgcgga gacgttaaat
18661 ttgttatatc aattaactaa caaaaaacaa cgtgtgaaag tagttaaaga agtagttgaa
18721 agatcagatt tatctccaga ggtaacagtt aacactgaaa cagtatgaaa agctatgagt
18781 tagatactca tagtctttat tcttttagaa agcgggtgta ctgaattggg gtggttcaaa
18841 aaacacgaac atgaatggcg catcagaagg ttagaagaga atgataaaac aatgctcagc
18901 acactcaacg aaattaaatt aggtcaaaaa acccaagagc aagttaacat taaattagat
18961 aaaaccttag atgctattca aaaagaaaga gaaatagatg aaaagaataa gaaagaaaat
19021 gataagaaca tacgtgatat gaaaatgtgg gtgcttggtt tagttgggac aatatttggg
19081 tcgctaatta tagcattatt gcgtatgctt atgggcatat aagagaggtg attaccatgt
19141 tcggattaaa ttttggagct tcgctgtgga cgtgtttctg gtttggtaag tgtaagtaat
19201 agttaagagt cagtgcttcg gcactggctt tttattttgg ataaaaggag caaacaaatg
19261 gatgcaaaag taataacaag atacatcgta ttgatcttag cattagtaaa tcaattctta
19321 gcgaacaaag gtattagccc aattccagta gacgatgaaa ctatatcatc aataatactt
19381 actgtagtcg ctttatatac aacgtataaa gacaatccaa catctcaaga aggtaaatgg
19441 gcaaatcaaa aattaaagaa atataaagct gaaaataagt atagaaaagc aacagggcaa
19501 gcgccaatta aagaagtaat gacacctacg aatatgaacg acacaaatga tttagggtag
19561 gtggttgata tatgttaatg acaaaaaatc aagcagaaaa atggtttgac aattcattag
19621 ggaaacaatt caacccagat ggttggtatg gatttcagtg ttatgattac gccaatatgt
19681 tctttatgtt agcgacaggc gaaaggctgc aaggtttata tgcttataat atcccgtttg
19741 ataataaagc aaagattgaa aaatatggtc aaataattaa aaactatgac agctttttac
19801 cgcaaaagtt ggatattgtc gttttcccgt caaagtatgg tggcggagct ggacacgttg
19861 aaattgttga gagcgcaaat ttaaatactt tcacatcatt tggtcaaaac tggaacggta
19921 aaggttggac taatggcgtt gcgcaacctg gttggggtcc tgaaactgtg acaagacatg
19981 ttcattatta tgacaatcca atgtatttta ttaggttaaa cttccctaac aacttaagcg
20041 ttggcaataa agctaaaggt attattaagc aagcgactac aaaaaaagag gcagtaatta
20101 aacctaaaaa aattatgctt gtagccggtc atggttataa cgatcctgga gcagtaggaa
20161 acggaacaaa cgaacgcgat tttatacgta aatatataac gcctaatatc gctaagtatt
20221 taagacatgc aggacatgaa gttgcattat acggtggctc aagtcaatca caagatatgt
20281 atcaagatac tgcatacggt gttaatgtag gcaataaaaa agattatggc ttatattggg
```

20341 ttaaatcaca ggggtatgac attgttctag aaatacattt agacgcagca ggagaaagcg
20401 caagtggtgg gcatgttatt atctcaagtc aattcaatgc agatactatt gataaaagta
20461 tacaagatgt tattaaaaat aacttaggac aaataagagg tgtgacacct cgtaatgatt
20521 tactaaatgt taatgtatca gcagaaataa atataaatta tcgtttatct gaattaggtt
20581 ttattactaa taaaaatgat atggattgga ttaagaaaaa ctatgacttg tattctaaat
20641 taatagccgg tgcgattcat ggtaagccta taggtggttt ggtagctggt aatgttaaaa
20701 catcagctaa aaacaaaaaa aatccaccag tgccagcagg ttatacactc gataagaata
20761 atgtccctta taaaaaagaa caaggcaatt acacagtagc taatgttaaa ggtaataatg
20821 taagagacgg ttattcaact aattcaagaa ttacaggggt attacccaac aacacaacaa
20881 ttacgtatga cggtgcatat tgtattaatg gttatagatg gattacttat attgctaata
20941 gtggacaacg tcgttatata gcgacaggag aggtagacaa ggcaggtaat agaataagta
21001 gttttggtaa gtttagcacg atttagtatt tacttagaat aaaaattttg ctacattaat
21061 tatagggaat cttacagtta ttaaataact atttggatgg atgttaatat tcctatacac
21121 tttttaacat ttctctcaag atttaaatgt agataacagg caggtacttc ggtacttgcc
21181 tatttttta tgttatagct agccttcggg ctagtttttt gttatgatgt gttacacatg
21241 catcaactat ttacatctat ccttgttcac ccaagcatgt cactggatgt tttttcttgc
21301 gatagagagc atagttttca tactactccc cgtagtatat atgactttag cattcccgta
21361 taacagttta cggggtgctt ttatgttata attgctttta tatagtagga gtgaactata
21421 tagccgggca gaggccatgt atctgactgt tggtcccaca ggagacatct tccttgtcat
21481 cactcgatac atatatctta acaacataga aatgttacat tcgctataac cgtatcttaa
21541 tcgatacggt tatatttatt cccctacaac caacaaaacc acagatccta ttaatttagg
21601 attgtggtta ttttttgcgt tttttggggg caaaaaaagg gcagattatt tgaaaaaggg
21661 caaacgcttg tggaaaagct aaaaggttaa aaatgacaaa aaccttgata caacagtgtt
21721 tttggacgct cgtgtacgtt agagaatgac cggtttacca tcatacaagg gtgggattaa
21781 cttgtgttaa aaagccttta atatcagttg ttacaaagga tttgtagcgt ctttaaaaat
21841 aaaaaagggc agaaaaaggg cagatacctt ttagtacaca agtttttcta atttttgctc
21901 taactctctg tccattttct ctgttacatg tgtatacacc tttatagtcg tttttttcatc
21961 tgtatgtcct actcttttca taattgcttt taacgatata ttcatttccg ccaataaact
22021 tatgtgtgta tgccttagtg tgtgagtagt aactttttta tttatattta atgattctgc
22081 agctgaggac aatcgtttgt ttatcctact gccttgcata ggatttcctt ggcaagttgt
22141 gaatataaac cctctatcaa catagcttgg ttcccattgt tgcatctttt tattttctaa
22201 cattattttt ttcaatacat ttgctatcct tgaattgatg gcgatttttc ttcttgaacc
22261 tgcggtctta gtagtatctt tgtgaccaaa tccagcatta catttgattc tgtgaatagt
22321 gccattaata gcgatcgttt tatttttgag gtcaacatct ttaacttgga gagctaataa
22381 ctcacctatg cgcatacctg ttaaagcttg aacttctaca gccccagcaa ctaaaatacg
22441 agctctatac tgcatgttat tatcgttcag tataaaatcg cgtatctgta ttacctgttc
22501 catctctaaa tagttataca ttttcgcttc ttctttttct atatcttcta tcgtcttact
22561 cttctttggt agtgtgacgc tatttaatat gtgttcgttt ggataattgt aaaatttaac
22621 ggcgtattta atagcttctt tcatatgtcc aagttgacgc tttacctgat ttgcagaata
22681 tacgtttgat aatttgttaa taaatgtttg catgtacttt gtatcaattt tgtttaaaag
22741 taaattttga gaactgttct ttttgatgtt tttgattctt gttttcaaat tatcaagcgt
22801 cgttacttta aagccagatg tttttatatg atattcaagc cattcatcta ataacgcgtg
22861 aaaagtcaaa gtttttaatt cgcttgacga cttgttgttt agtttttctt ttattttttc
22921 ttctaaacga aacattgcct ctttttgcga ttgctttgta ttcttattca agacaacact
22981 tacacgtttc catttatctg tatacggatc tttgtatttc tcgtagtatc tatacttcgt
23041 ttcattgttc ttatttttaa atttttcaaa ccacatttta catccctcct caaaattggc
23101 aaaaaataat aagggtaggc gggctaccca tgaaaattgt ataaaaaaag acgcctgtat
23161 aaaatacaga cgccacttat aattataaga ttacatggtt aattaccaaa aatggtaacg
23221 aatatatacg tgttttaaag gataaacctt taatatatta aaattatatc atcttatatc
23281 agggatctgc aatatattat tattaattct atttatcagt aacataatat ccgaagaatc
23341 tattactgga tttttaattt tttggggtaa aactttttctt atgcgaaact tactaatcgg
23401 ctggaaagaa tttatgcaag cgtaactatt acctttttaat ttttttacct tatcaattgc
23461 tgatactatg ttattaatgt ttctgtcaat tttatttaat ttattttcaa tttctaaact
23521 atcagatata aattcaataa aataatcttt agtgatgaat tctgtgttgt ttttttggta
23581 tttttttatcg aaaacttctt ttaatatagc tgaattattt tgcgcgctaa ttaaatttaa
23641 aaacaatctt aaataatact cccatttcaa atcaaaattc atctttaaat actttttgtt
23701 ttctttagag gataagggaa taacatttac tatatcctcc gtattagaat cattttttatt

```
23761 catcactatt gcaaagtgtg aattagaaaa ttctttatta acgtttatac cgaaatctac
23821 aaaaactatt tctccttgtt taaactttgg ataaaaacct ttatggtttt tttcaccttc
23881 aaatctcttg agtaaatagt gaatatctga atctaacttt ttaaattttg gatttccaga
23941 agtttttaat ttattaatgc gtttttctat attatgcgtc atcatttctc ctttattctc
24001 gctcacactc tcaccaccat tcaacgtcta cacttgtagg cgtttttga ttagtaaaat
24061 cataatgaat cttctttggt taacttatcg ccatctattt tttgtgaaat aaattccaag
24121 tatttacgcg cattatgtga cgataaatct ttaggtaact cataagtgaa tggttgatta
24181 ccactagtta aaacttcata tactatagtt tcttttttta ttttgcaatt agttattttc
24241 attataaact ccttttaaac actgctgaaa tagacgtctt tttcaaataa gcatgattaa
24301 tactttaatt ctttaatcca catatattta aaagtgaggt agtaggtaat aaatataaga
24361 cttaaagtta agattgcttt tttcatgtca atttctcctt tgtttatatt tatattaaag
24421 cgctaaatat acgttattaa tcacaataca actttgccca ttactttaat atcactaaac
24481 gaagcgactt tgatatcatc atacttcgga tttagagata ccaaattaat atagtcttcg
24541 catatatcta cacgcttgat aagacttact ccatctaata caacgagtgc aattgtacca
24601 tctttaatag aatcttcttt cttaataaaa gcgtatgttc cttgttttaa cataggttcc
24661 attgaatcac cattaactaa aatacaaaaa tcagcatttg atggcgtttc gtcttcttta
24721 aaaaatactt cttcatgcaa tatgtcatca tataattctt ctcctatgcc agcaccagtt
24781 gcaccacatg caatatacga tactagttta gactctttat attcatctat agaagtgact
24841 ttattctgtt catctaattg ctcatttgca tagttaagta cgttttcttg gcggggaggt
24901 gtgagttgag aaaatatgtt attgattttt gacattatcg tttcatcttg acgttcttcg
24961 tcaggaactc gataagaatc tacatcatac cccataagcc acgcttcacc gacatttaaa
25021 gttttagata ataagaataa tttatgttgg tctggagaag accttccatt aacatactgg
25081 gataagtgac tttttgacat tttaatattc aattcttttt gaaagggttt cgacttttct
25141 agaatatcta cttgacgcaa gttcctatct ttcataattt gttttaatct ttcagaagtg
25201 ttttgcattg gtaatgcctc cttgaaattc attatatagg aagggaaata aaaatcaata
25261 caaaagttca actttttaa cttttttgtgt tgacattgtt caaaattggg gttatagtta
25321 ttatagttca aatgtttgaa cttaggaggt gattatttga atactaatac aacttttgat
25381 ttttcgttat tgaacggtaa gatagtcgaa gtgtactcga cacaatttaa ctttgctata
25441 gctttaggtg tatcagaaag aactttgtct ttgaagttga acaacaaagt accatggaaa
25501 acaacagaca ttattaaagc ttgtaagtta ttgggaatac ctataaaaga tgttcacaaa
25561 tattttttta aacagaaagt tcaaatgttt gaacttaata agtaaaggag gcataacaca
25621 tgcaagaacg agaaaaggtt aataaaagta acacatcttc aaatgaagca tcaaaacctt
25681 ttaggacaaa ttgaagctta cgacaaaacg cttaaagaaa taaagtacac tcgagacctt
25741 tacaacaaac acctaagcat gaacaacgaa gacgcattcg ctggtttgga aatggtagag
25801 gatgaaatta ctaaaaagct acgaagtgct atcaaagagt tccaaaaagt agtgaaagcg
25861 ttagacaagc ttaacggtgt tgaaagcgat aacaaagtta ctgatttaac agagtggcgg
25921 aaagtgaatc agtaacattc acttcttaat ataaccacgc ttatcaacat ccacattgag
25981 cagatgtgag cgagagctgg cgatgatatg agccgcgttt aaatacattc gatagtcatt
26041 gcgataaccg tctgctgaat gtgggtgttg aggaaaaagg aggatactca aatgcaagca
26101 ttacaaacat ttaattttaa agagctacca gtaagaacag tagaaattga aaacgaacct
26161 tattttgtag gaaaagatat tgctgagatt ttaggatatg caagatcaaa caatgccatt
26221 agaaatcatg ttgatagcga ggacaagctg acgcaccaat ttagtgcatc aggtcaaaac
26281 agaaatatga tcattatcaa cgaatcagga ttatacagtc taatcttcga tgcttctaaa
26341 caaagcaaaa acgaaaaaat tagagaaacc gctagaaaat tcaaacgctg ggtaacatca
26401 gatgtcctac cagctattcg caaacacggt atatacgcaa cagacaatgt aattgaacaa
26461 acattaaaag atccagacta catcattaca gtgttgactg agtataagaa agaaaaagag
26521 caaaacttac ttttacaaca gcaagtagaa gttaacaaac caaaagtatt attcgctgac
26581 tcggtagctg gtagtgataa ttcaatactt gttggagaac tagcgaaaat acttaaacaa
26641 aacggtgttg atataggaca aaacagattg ttcaaatggt taagaaataa tggatatctc
26701 attaaaaaga gtggagaaag ttataactta ccaactcaaa agagtatgga tctaaaaatc
26761 ttggatatca aaaaacgaat aattaataat ccagatggtt caagtaaagt atcacgtaca
26821 ccaaaagtaa caggcaaagg acaacaatac tttgttaata agtttttagg agaaaaacaa
26881 acatcttaaa aggaggaaca caatggaaca aatcacatta accaaagaag agttgaaaga
26941 aattatagca aaagaagtta gagaggctat aaatggcaag aaaccaatca gttcaggttc
27001 aattttcagt aaagtaagaa tcaataatga cgatttagaa gaaatcaata aaaaactcaa
27061 tttcgcaaaa gatttgtcgc taggaagatt gaggaagctc aatcatccga ttccgctaaa
27121 aaagtatcag catggcttcg aatcaattca tcaaaaagct tatgtacaag atgttcatga
```

```
27181 ccatattaga aaattaacat tatcaatttt tggagtgaca cttaattcag acttgagtga
27241 aagtgaatac aacctagcag caaaagttta tcgagaaatc aaaaactatt atttatacat
27301 ctatgaaaag agagtttcag aattaactat cgatgatttc gaataaagga ggaacaacaa
27361 atgttacaaa aatttagaat tgcgaaagaa aaaaataaat taaaactcaa attactcaag
27421 catgctagtt actgtttaga aagaaacaac aaccctgaac tgttgcgagc agttgcagag
27481 ttgttgaaaa aggttagcta aattcaacgg taaggatttg ccctgcctcc acacttagag
27541 tttgagatcc aacaaacaca taagttttag tagggtctag aaaaaatgtt tcgatttcct
27601 cttttgtaac agtttcaatt ccttcatatc ctggaaaaac aattttcttt aaatccgaaa
27661 catgtttttt tgaaccatcc tttaaagtaa ctagaagttt catacttatc acctccttag
27721 gttgataaca acattataca cgaaaggagc ataaacaata tgcaagcatt acaaacaaat
27781 tcgaacatcg gagaaatgtt caatattcaa gaaaaagaaa atggagaaat cgcaatcagc
27841 ggtcgagaac ttcatcaagc attagaagtt aagacagcat ataaagattg gtttccaaga
27901 atgcttaaat acggatttga agaaaataca gattacacag ctatcgctca aaaaagagca
27961 acagctcaag gcaatatgac tcactatatt gaccacgcac tcacactaga cactgcaaaa
28021 gaaatcgcaa tgattcaacg tagtgaacct ggcaaacgtg caagacaata tttcatccaa
28081 gttgaaaaag catggaacag cccagaaatg attatgcaac gtgctttaaa aattgctaac
28141 aacacaatca atcaattaga aacaaagatt gcacgtgaca aaccaaaaat tgtatttgca
28201 gatgcagtag ctactactaa gacatcaatt ttagttggag agttagcaaa gatcattaaa
28261 caaaacggta taaacatcgg gcaacgcaga ttgtttgagt ggttacgtca aaacggattc
28321 cttattaaac gcaagggtgt ggattataac atgcctacac agtattcaat ggaacgtgag
28381 ttattcgaaa ttaaagaaac atcaatcaca cattcggacg gtcacacatc aattagtaag
28441 acgccaaaag taacaggtaa aggacaacaa tactttgtta acaagttttt aggagaaaaa
28501 caaacaactt aataggagga attacaaatg aacgcactat acaaaacaac cctcctcatc
28561 acaatggcag ttgtgacgtg gaaggtttgg aagattgaga agcacactag aaaacctgtg
28621 attagtagca gggcgttgag tgactatcta aacaacaaat ctttaaccat accgaaagat
28681 gctgaaaatt ctactgaatc tgctcgtcgc cttttgaagt tcgccgaaca aactattagc
28741 aaataacaac attatacacg aaaggaaaga tagaaatgcc aaaaatcata gtaccaccaa
28801 caccagaaaa cacatataga ggcgaagaaa aatttgtgaa aaagttatac gcaacaccta
28861 cacaaatcca tcaattgttt ggagtatgta gaagtacagt atacaactgg ttgaaatatt
28921 accgcaaaga taatttaggt gtagaaaatt tatacattga ttattcacca acaggcactc
28981 tgattaatat ttctaaattg gaagagtatt tgatcagaaa gcataaaaaa tggtattagg
29041 aggatattaa atgagcaaca tttataaaag ctacctagta gcagtattat gcttcacagt
29101 cttagcgatt gtacttatgc cgtttctata cttcactaca gcatggtcaa ttgcgggatt
29161 cgcaagtatc gcaacattca tgtactacaa agaatgcttt ttcaaagaat aaaaaaactg
29221 ctacttgttg gagcaagtaa cagtatcaaa cacttaagaa aaaattcatg ttcaatataa
29281 aacgaaaaac ggaggaagtc aagatgtatt acgaaatagg cgaaatcata cgcaaaaata
29341 ttcatgttaa cggattcgat tttaagctat tcattttaaa aggtcatatg ggcatatcaa
29401 tacaagttaa agatatgaac aacgtaccaa ttaaacatgc ttatgtcgta gatgagaatg
29461 acttagatat ggcatcagac ttatttaacc aagcaataga tgaatggatt gaagagaaca
29521 cagacgaaca ggacagacta attaacttag tcatgaaatg gtaggaggtc gctatgaagc
29581 agactgtaac ttatatcatt cgtcataggg atatgccaat ttatataact aacaaaccaa
29641 ctgataacaa ttcagatatt agttactcca caaatagaaa tagagctagg gagtttaacg
29701 gtatggaaga agcgagtatc aatatggatt atcacaaagc aatcaagaaa acagtgacag
29761 aaactattga gtacgaggag gtagaacatg actgaggaaa aacaagaacc acaagaaaaa
29821 gtaagcatac tcaaaaaact aaagataaat aatatcgctg agaaaaataa aaggaaattc
29881 tataaatttg cagtatacgg aaaaattggc tcaggaaaaa ccacgtttgc tacaagagat
29941 aaagacgctt tcgtcattga cattaacgaa ggtggaacaa cggttactga cgaaggatca
30001 gacgtagaaa tcgagaacta tcaacacttt gtttatgttg taaatttttt acctcaaatt
30061 ttacaggaga tgagagaaaa cggacaagaa atcaatgttg tagttattga aactattcaa
30121 aaacttagag atatgacatt gaatgatgtg atgaaaaata agtctaaaaa accaacgttt
30181 aatgattggg gagaagttgc tgaacgaatt gtcagtatgt acagattaat aggaaaactt
30241 caagaagaat acaaattcca ctttgttatt acaggtcatg aaggtatcaa caaagataaa
30301 gatgatgaag gtagcactat caaccctact atcactattg aagcgcaaga acaaattaaa
30361 aaagctatta cttctcaaag tgatgtgtta gctagggcaa tgattgaaga atttgatgat
30421 aacggagaaa agaaagctag atatattcta aacgctgaac cttctaatac gtttgaaaca
30481 aagattagac attcaccttc aataacaatt aacaataaga aatttgcaaa tcctagcatt
30541 acggacgtag tagaagcaat tagaaatgga aactaaaaat taattaaaag gacggtattt
```

```
30601 aattatgaaa atcacaggac aagcgcaatt tactaaagaa acaaatcaag aaaagtttta
30661 taacggctca gcagggtttc aagctggaga attcacagtg aaagttaaaa atattgaatt
30721 caatgataga gaaaatagat atttcacaat cgtatttgaa aatgatgaag gcaaacaata
30781 taaacataat caatttgtac cgccgtataa atatgatttc caagaaaaac aattgattga
30841 attagttact cgattaggta ttaagttaaa tcttcctagc ttagattttg ataccaatga
30901 tcttattggt aagttttgtc acttggtatt gaaatggaaa ttcaatgaag atgaaggtaa
30961 gtattttacg gatttttcat ttattaaacc ttacaaaaag ggcgatgatg ttgttaacaa
31021 acctattccg aagacagata agcaaaaagc tgaagaaaat aacggggcac aacaacaaac
31081 atcaatgtct caacaaagca atccatttga aagcagtggc caatttggat atgacgacca
31141 agatttagcg ttttaaggtg tggtttaaat gcaatacatt acaagatacc agaaagataa
31201 cgacggtact tattccgtcg ttgctactgg tgttgaactt gaacaaagtc acattgactt
31261 actagaaaac ggatatccac taaaagcaga agtagaggtt ccggacaata aaaaactatc
31321 tatagaacaa cgcaaaaaaa tattcgcaat gtgtagagat atagaacttc actggggcga
31381 accagtagaa tcaactagaa aattattaca aacagaattg gaaattatga aaggttatga
31441 agaaatcagt ctgcgcgact gttctatgaa agttgcaagg gagttaatag aactgattat
31501 agcgtttatg tttcatcatc aaatacctat gagtgtagaa acgagtaagt tgttaagcga
31561 agataaagcg ttattatatt gggctacaat caaccgcaac tgtgtaatat gcggaaagcc
31621 tcacgcagac ctggcacatt atgaagcagt cggcagaggc atgaacagaa acaaaatgaa
31681 ccactatgac aaacatgtat tagcgttatg tcgcgaacat cacaacgagc aacatgcgat
31741 tggcgttaag tcgtttgatg ataaatacca cttgcatgac tcgtggataa aagttgatga
31801 gaggctcaat aaaatgttga aaggagagaa aaaggaatga atagactaag aataataaaa
31861 atagcactcc taatcgtcat cttggcggaa gagattagaa atgctatgca tgctgtaaaa
31921 gtggagaaaa ttttaaaatc tccgtttagt taatacaggt ttttacaaaa gctttaccat
31981 aggcggacaa actaattgag cctttttttga tgtctattac ccaggggctg taatgtaact
32041 ttaatacttc aaattcaatg ccagaaagtt tacttattgt ttctaggttg tgtcctgact
32101 ttaacattct tttaacaaat tctaatcccg aaacaaatct ttgtttttct ataatcttat
32161 taaagtgatt taaaaactga ggagcataaa acttattata aattcctttt tttgttaagt
32221 aagacatgtc aaaagtttca tttaaaaccc ctaaccttac taggttatta attgaaattt
32281 cggttgattc tatatctaac ggagagtctt ttattaacgt gtccgatata ttcataccgt
32341 cattctttgg gtttaaaacc gctctatatt taacggcagg atgtacttcg tgattcttta
32401 aatgttttaa aagaatagca tcatttgggg ataattgttt aattatttca acaaatgaat
32461 ggtgggttaa tgagtttttt ctgtcatcca tagatgatgc tattagtttt gcgaacatat
32521 tacttaaagt tttttcacta atgtaaaact ttgaagcttc tagagcagga cctagaagag
32581 aaaattgtgg ttcttgtaaa ttatttttag gtacagaaga tatttctttt ttaaattgtt
32641 ctttgaattt ttcaaattct acttctcttt gataaataac tttatccaca taaaggtgga
32701 atttcccaaa gacaagttcc caagttttag agaatgtttc tacaggccct tttgatgcgc
32761 cttcaataat tttatcaata cctttaccta aaataggatc cataattatt cacccccaat
32821 ctaacgcaat agcgataata aaattatacc agaaaggaga atcaacatga ctgaccaacc
32881 aagttactac tcaataatta cagcaaatgt cagatacgat aaccgactta ctgacagcga
32941 aaagttactt tttgcagaaa taacatcttt aagtaacaaa tacggatact gcacagcaag
33001 taatggttac tttgcaactt tatacaacgt tgttaaggaa actatatctc gtagaatttc
33061 gaaccttacc aactttggtt atctaaaaat cgaaattatc aaagaaggta atgaagttaa
33121 acaaaggaag atgtacccct tgacgcaaac gtcaatacct attgacgcaa aaatcaatac
33181 ccctattgat aattctgtca atacccctat tgacgcaaat gtcaaagaga atattacaag
33241 tattaataat acaagtaata acaatataaa tagaatagat atattgtcgg gcaacccgac
33301 agcatcttct ataccctata aagaaattat cgattactta aacaaaaaag cgggcaagca
33361 ttttaaacac aatacagcta aaacaaaaga ttttattaaa gcaagatgga atcaagattt
33421 taggttggag gattttaaaa aggtgattga tatcaaaaca gctgagtggc taaacacgga
33481 tagcgataaa taccttagac cagaaacact tttggcagt aaatttgagg ggtacctcaa
33541 tcaaaaaata caaccaactg gcacggatca attggaacgc atgaagtacg acgaaagtta
33601 ttgggattag gggatatta tgaaaccact attcagcgaa aagataaacg aaagcttgaa
33661 aaaatatcaa cctactcatg tcgaaaaagg attgaaatgt gagagatgtg gaagtgaata
33721 cgacttatat aagtttgctc ctactaaaaa acacccgaat ggttacgagt ataaagacgg
33781 ttgcaaatgt gaaatctatg aggaatataa gcgaaacaag caacggaaga taaacaacat
33841 attcaatcaa tcaaacgtta atccgtcttt aagagatgca acagtcaaaa actacaagcc
33901 acaaaatgaa aaacaagtac acgctaaaca aacagcaata gagtacgtac aaggcttctc
33961 tacaaaagaa ccaaaatcat taatattgca aggttcatac ggaactggta aaagccacct
```

34021 agcatacgct atcgcaaaag cagtcaaagc taaagggcat acggttgctt ttatgcacat
34081 accaatgttg atggatcgta tcaaagcgac atacaacaaa aatgcagtag agactacaga
34141 cgagctagtc agattgctaa gtgatattga tttacttgta ctagatgata tgggtgtaga
34201 aaacacagag cacactttaa ataaactttt cagcattgtt gataacagag taggtaaaaa
34261 caacatcttt acaactaact ttagtgataa agaactaaat caaaatatga actggcaacg
34321 tataaattcg agaatgaaaa aaagagcaag aaaagtaaga gtaatcggag acgatttcag
34381 ggagcgagat gcatggtaac caaagaattt ttaaaaacta aacttgagtg ttcagatatg
34441 tacgctcaga aactcataga tgaggcacag ggcgatgaaa ataggttgta cgacctattt
34501 atccaaaaac ttgcagaacg tcatacacgc cccgctatcg tcgaatatta aggagtgtta
34561 aaaatgccga aagaaaaata ttacttatac cgagaagatg gcacagaaga tattaaggtc
34621 atcaagtata aagacaacgt aaatgaggtt tattcgctca caggagccca tttcagcgac
34681 gaaaagaaaa ttatgactga tagtgaccta aaacgattca aggcgctca cgggcttcta
34741 tatgagcaag aattaggttt acaagcaacg atatttgata tttagaggtg gacgatgagt
34801 aaatacaacg ctaagaaagt tgagtacaaa ggaattgtat ttgatagcaa agtagagtgt
34861 gaatattacc aatatttaga aagtaatatg aatggcacta attatgatca tatcgaaata
34921 caaccgaaat tcgaattatt accaaaacta gataaacaac gaaagattga atatattgca
34981 gacttcgcgt tatatctcga tggcaaactg attgaagtta tcgacattaa aggtatgcca
35041 accgaagtag caaaacttaa agctaagatt ttcagacata aatacagaaa cataaaactc
35101 aattggatat gtaaagcgcc taagtataca ggtaaaacat ggattacgta cgaggaatta
35161 attaaagcaa gacgagaacg caaaagagaa atgaagtgat ctaatgcaac aacaagcata
35221 tataaatgca acgattgata taaggatacc tacagaagtt gaatatcagc attttgatga
35281 tgtggataaa gaaaaagaag cgctggcaga ttacttatat aacaatcctg acgaaatact
35341 agagtatgac aatttaaaaa ttagaaacgt aaatgtagag gtggaataaa tgggcagtgt
35401 tgtaatcatt aataataaac catataaatt taacaatttt gaaaaaagaa ataatggcaa
35461 agcgtgggat aaatgctgga attgtttcta aacgtgttag aggttgttgg gagttttcag
35521 aagctttaga cgcgccttat ggcatgcacc taaaagaata tagagaaatg aaacaaatgg
35581 aaaagattaa acaagcgaga ctcgaacgtg aattggaaag agagcgaaag aaagaggctg
35641 agctacgtaa gaagaagcca catttgttta atgtacctca aaaacattca cgtgatccgt
35701 actggttcga tgtcacttat aaccaaatgt tcaagaaatg gagtgaagca taatgagcat
35761 aatcagtaac agaaaagtag atatgaacaa aacgcaagac aacgttaagc aacctgcgca
35821 ttacacatac ggcgacattg aaattataga ttttattgaa caagttacgg cacagtaccc
35881 accacaatta gcattcgcaa taggtaatgc aattaaatac ttgtctagag caccgttaaa
35941 gaatggtcat gaggatttag caaaggcgaa gttttacgtc gatagagtat ttgacttgtg
36001 ggagtgatga ccatgacaga tagcggacgt aaagaatact taaaacattt tttcggctct
36061 aagagatatc tgtatcagga taacgaacga gtggcacata tccatgtagt aaatggcact
36121 tattactttc acggtcatat cgtgccaggt tggcaaggtg tgaaaaagac atttgataca
36181 gcggaagagc ttgaaacata tataaagcaa agtgatttgg aatatgagga acagaagcaa
36241 ctaactttat tttaaaaggg cggaaacaat gaaaatcaaa attgaaaaag aaatgaattt
36301 acctgaactt atccaatggg cttgggataa ccccaagtta tcaggtaata aaagattcta
36361 ttcaaatgat gttgagcgca actgttttgt gacttttcat gttgatagca tcttatgtaa
36421 tgtgactgga tatgtatcaa ttaacgataa atttactgtt caagaggaga tataacaatg
36481 aaaatcaaag ttaaaaaaga aatgagatta gatgaattaa ttaaatgggc gcgagaaaat
36541 ccggatctat cacaaggaaa aatatttttt tcaacaggat ttagtgatgg attcgttcgt
36601 tttcatccaa atacaaataa gtgttcgacg tcaagtttta ttccaattga tatccccttc
36661 atagttgata ttgaaaaaga agtaacggaa gagactaagg ttgataggtt gattgaatta
36721 ttcgagattc aagaaggaga ctataactct acactatatg agaacactag tataaaagaa
36781 tgtttatatg gcagatgtgt gcctaccaaa gcattctaca tcttaaacga tgacctaact
36841 atgacgttaa tctggaaaga tggggagttg ctagtatgat gttgaaattt aaagcttggg
36901 ataaagataa aaaagttatg agtattattg acgaaatcga ttttaatagt gggtacattt
36961 tgatttcaac aggttataaa agtttcaatg aagtaaaact attacaatac acaggattta
37021 aagatgtgca cggtgtggag atttatgaag ggatattgt tcaagattgt tattcgagag
37081 aagtaagttt tatcgagttt aaagaaggag ccttttatat aacttttagc aatgtaactg
37141 aattactaag tgaaaatgac gatattattg aaattgttgg aaatattttt gaaaatgaga
37201 tgctattgga ggttatgaga tgacgttcac cttatcagat gaacaatata aaaatctttg
37261 tactaactct aacaagttat tagataaact tcacaaagca ttaaaagatc gtgaagagta
37321 caagaagcaa cgagatgagc ttattgggga tatagcgaag ttacgagatt gtaacaaaga
37381 tctagagaag aaagcaagcg catgggatag gtattgcaag agcgttgaaa aagatttaat 37441 aaacgaattc ggtaacgatg atgaaagagt taaattcgga atggaattaa acaataaaat
37501 ttttatggag gatgacacaa atgaataatc gcgaaaaaat cgaacagtcc gttattagtg
37561 ctagtgcgta taacggtaat gacacagagg ggttgctaaa agagattgag gacgtgtata
37621 agaaagcgca agcgtttgat gaaatacttg agggaatgac aaatgctatt caacattcag
37681 ttaaagaagg tattgaactt gatgaagcag tagggattat ggcaggtcaa gttgtctata
37741 aatatgagga ggaataggaa aatgactaac acattacaag taaaactatt atcaaaaaat
37801 gctagaatgc ccgaacgaaa tcataagacg gatgcaggtt atgacatatt ctcagctgaa
37861 actgtcgtac tcgaaccaca agaaaaagca gtgatcaaaa cagatgtagc tgtgagtata
37921 ccagagggct atgtcggact attaactagt cgtagtggtg taagtagtaa aacgtattta
37981 gtgattgaaa caggcaagat agacgcggga tatcatggca atttagggat taatatcaag
38041 aatgatgaag aacgtgatgg aatacccttt ttatatgatg atatagacgc tgaattagaa
38101 gatggattaa taagcatttt agatataaaa ggtaactatg tacaagatgg aagaggcata
38161 agaagagttt accaaatcaa caaaggcgat aaactagctc aattggttat cgtgcctata
38221 tggacaccgg aactaaagca agtggaggaa ttcgaaagtg tttcagaacg tggagcaaaa
38281 ggcttcggaa gtagcggagt gtaaagacat cttagatcga gttaaggagg ttttggggaa
38341 gtgacgcaat acttagtcac aacattcaaa gattcaacag gacgaccaca tgaacatatt
38401 actgtggcta gagataatca gacgtttaca gttattgagg cagagagtaa agaagaagcg
38461 aaagagaagt acgaggcaca agttaaaaga gatgcagtta ttaaagtggg tcagttgtat
38521 gaaaatataa gggagtgtgg gaaatgacgg atgttaaaat taaaactatt tcaggtggag
38581 tttattttgt aaaaacagct gaacctttg aaaaatatgt tgaaagaatg acgagtttta
38641 atggttatat ttacgcaagt actataatca agaaaccaac gtatattaaa acagatacga
38701 ttgaatcaat cacacttatt gaggagcatg ggaaatgaat cagctgagaa ttttattaca
38761 tgacggtagt agtttgatat tacatgaaga tgaattattt aacgaaatag tatttgtttt
38821 ggacaatttt agaaatgatg atgactattt aacgatagaa aaagattatg gcagagaact
38881 tgtattgaac aaaggttata tagttgggat caatgttgag gaggcagatg atgattaaca
38941 tacctaaaat gaaattcccg aaaaagtaca ctgaaataat caaaaaatat aaaaataaag
39001 cacctgaaga aaaggctaag attgaagatg attttattaa agaaattaaa gataaagaca
39061 gtgaatttta cagtcctacg atggctaata tgaatgaata tgaattaagg gctatgttaa
39121 gaatgatgcc tagtttaatt gatactggag atgacaatga tgattaaaaa acttaaaaat
39181 atggatgggt tcgacatctt tattgttgga atactgtcat tattcggtat attcgcattg
39241 ctacttgtta tcacattgcc tatctataca gtggctagtt accaacacaa agaattacat
39301 caaggaacta ttacagataa atataacaag agacaagata aagaagacaa gttctatatt
39361 gtattagaca acaaacaagt cattgaaaat tccgacttat tattcaaaaa gaaatttgat
39421 agcgcagata tacaagctag gttaaaagta ggcgataagg tagaagttaa aacaatcggt
39481 tatagaatac actttttaaa tttatatccg gtcttatacg aagtaaagaa ggtagataaa
39541 caatgattaa acaaatacta agactattat tcttactagc aatgtatgag ttaggtaagt
39601 atgtaactga gcaagtgtat attatgatga cggctaatga tgatgtagag gcgccgagtg
39661 attacgtctt tcgagcggag gtgagtgaat aatgagaata tttatttatg atttgatcgt
39721 tttgctgttt gctttcttaa tatccatata tattattgat gatggagtga taataaatgc
39781 attaggaatt tttggtatgt ataaaattat agattccttt tcagaaaata ttataaagag
39841 gtagataaaa atgaacgagc aaataatagg aagcatatat actttagcag gaggtgttgt
39901 gctttattca gttaaagaga tttttaggta ttttacagat tctaacttac aacgtaaaaa
39961 aatcaattta gaacaaatat atccgatata tttagattgt tttaaaaagg ctaaaaagat
40021 gattggagct tatattattc caacagaaca gcatgaattt ttagattttt ttgatattga
40081 agtctttaat aatttagata agcaaagtaa aaaagcgtat gaaaatgtta ttggatttag
40141 acaaatgatt aatttatcaa atagagttaa ggcaatggaa gattttaaga tgagtttcaa
40201 caatgaattt agtacaaatc agattttttt taatccttct tttgttatgg aaacaattgc
40261 tattataaat gaatatcaaa aagatatatc ttatttaaaa aatataatta ataaaatgaa
40321 tgaaaataga gcttataatc atattgatag ttttatcact tcagagtacc gacgaaaaat
40381 aaacgattat aatctttatc ttgataaatt tgaagaacag tttagtcaaa agtttaaaat
40441 aaacagaact tcgataaaag aaagaattat tattaattta aacaagagga gatttaaatg
40501 atgtggatta ctatgactat tgtatttgct atattgctat tagtttgtat cagtattaat
40561 agtgatcgtg caagagagat acaagcactt agatatatga atgattatct acttgatgaa
40621 gtagttaaaa ctaaagggta caacgggtta gaagaataca ggattgaatt gaagcgaatg
40681 aataacgata ttaaaaagta atttatatta tcggaggtat tgcattgaat gataaagatt
40741 gagaaacacg atatcaaaaa gcttgaagaa tacattcagc acatcgataa ctatcgaaga
40801 gagttgaaga tgcgagaata tgaattactt gaaagtcatg aaccagataa tgcgggagct

```
40861 ggcaaaagta atttgccggg taacccgatt gaacgatgtg caataaagaa gtttagtgat
40921 aacaggtaca atacattaag aaatatagtt aacggtgtag atagattgat aggtgaaagt
40981 gatgaggata cgcttgagtt attaaggttt agatattggg attgtcctat tggttgttat
41041 gaatgggaag atatagcaca ttactttggt acaagtaaga caagtatatt acgtagaagg
41101 aatgcactga tcgataagtt agcaaagtat attggttatg tgtagcggac ttttacccta
41161 tgtaagtccg cattaaaaca gtttattatg ttagtatcag attaatattt aaagttatta
41221 aatgctaata cgacgcatga acaagaggcg catcactatg tgatgtgtct ttttatttat
41281 gaggtatgaa catgttcaaa ctaattgtaa atacattact acacatcaag tatagatgag
41341 tcttgatact acttaagtta tataaggtga aacattatga tgactaaaga cgaacgtata
41401 cgattctata agtctaaaga atggcaaata acaagaaaaa gagtgctaga aagagataat
41461 tatgaatgtc aacaatgtaa gagagacggc aagttaacga catatgacaa aagcaagcgt
41521 aagtcgttgg atgtagatca tatattatcg ctagaacatc atccggagtt tgctcatgac
41581 ttaaacaatt tagaaacact gtgtattaaa tgtcacaaca aaaaagaaaa gagatttata
41641 aaaaaagaaa ataaatggaa agacgaaaaa tggtaaatac ccccgggtca aaaaaatcaa
41701 aagcgatc
```

Bacteriophage 96, complete genome sequence (SEQ ID No. 19).

1 tctccataaa aatatgcttg gaaaccttga tttaatgggg ttttaatcta gcaagtgtca
61 aatatgtgtc aagaaaataa ttttctgaca cgttgacctt gctctttttt atgttcatca
121 agtaagtgag agtaggtgtc taaagttata gatatattat aatggcctaa tcttttgcta
181 atatattcaa taggtatacc tttagaaagt aggaaagatg tatgcgtgtg tcttaatgaa
241 taaggtgtta ttgtagtatc atttagtcct atttgactct tagcatggtt aaatgacttt
301 ttaacggcat tatgactcaa tttaaacaac ttattatctg tacgttttgg taattttgat
361 aatttagctt taatatgttg tatatccttt tttggtacct ccacaagtct gtccgcgtta
421 actgtttttg ttccacgaag atgtattgta ccctcttttt cgtttagatc gataggcaac
481 atattaatta catcgctgta tcttgcacca gtgatagcta ggatgaataa aaaaatataa
541 ctcgattcgt ctctagattt aaagtattct atcaattgca agtattgttc tatggtgatg
601 aatttagagt gttcgtcttt tgattttttt gtaccacgaa tatctatttg atagctaggg
661 tctttcttta aatagccctc atatactgca tctctgaagc attgtgataa acaactgttt
721 aatttacgaa ccgtttcatt agtacgacct cgaccgaatt cgttcaaaaa cttttgatac
781 tccgaacgtt tgatgttttt tattaaaaaa tcactcccga aatattcgtt aaataatttt
841 aatgaacgtt gataccaata gaattgttgt gaagcgacat gtttcttatt ttttgaatct
901 aaccaatcat tgtaatattc ttcaaacttt ttattttcat ctaaattgtt tccatcatcc
961 aaatctctaa gcagttgttg agcagcgttg gttgcctcag ctttagtttt gaatcctgac
1021 tttcttttct ttcctgattt gaaagacgga tgttttacgt cgtactgcca agatgctgtt
1081 gctttattct tccttttgt aattgtaaat gacgccattt tacttttcct cctcaaaatt
1141 ggcaaaaaat aataagggta ggcgagctac ccgaaatttt attgttgaac aactattgct
1201 tcacttcttg cttttcctac ttcttttcta aaactatcat atgattgatt agggtgtgtt
1261 aacgacattc ctggaccacc tccagcatgt tggtttttgt ccggattatt ttccatttct
1321 tcagtggctc ttttagcatt taaatattct tcgtaactag gttcgtttgg gtcgcgtggt
1381 tgtgcttgtt gtccattatt ggtagctgga agattcttct gtacctgttg cttagatgtg
1441 ttattggttt gttgattgtt gttaatgttt gtgttgttct cgttgtttac ttgattattg
1501 ttatcgtttt gattactatt ttcttttttc gcttctgctt tatctttagt ttctttcttt
1561 ttgtctttgt tctctttctt tgtttcggtt ttcttgcttt cctctttctt atcgccgtcg
1621 ttgctaccgc atgcacctaa cactaacgca ctagctaata ataaaactaa taatcttttc
1681 atgttttaca ctcctttatt tgctatttgt tttaataaat ctatgatttc attgttttgt
1741 tctatgattt tgttttcatt tttaagatgt tcgtctaaca tctctattaa gacgaaattt
1801 tgatttatca tttcgtaagt aaacatttga cctgtgttgt taggattaga aaacgaacta
1861 ctgaaacgcg ttgaaaagct atctataaat tgaccaactt tattttttaa taacatatct
1921 ttaccgctct cagacattgt atttagttcg cgcttattta aagtttttc tataattttg
1981 tattttgttt cctgatttct ttcgatttct tctacttcaa aagggatatt gttattaaat
2041 ttttcgataa tatcacgttt ttcagaaact gacatacgat caaatacttg tttttgacct
2101 ttatttaact tccctcgaat ttttccggca gtccaagact ctttaactgt taacttatca
2161 ttaggaactt gattcatctt ttatatgact ccttttctca tatttcttta tatttaaaaa
2221 ctctcaacgg ctcaaatgta atcgaatact cgccatagtg agttccaata ccgtatatct
2281 tcttatattg ttctattgcc tccaatatgt attcttcgct taattgtaga tactcagaca
2341 actcatacaa gttacgtacg ccataattgt aagcttctac aatttcgcgt aacgggactg
2401 ctgagataaa gccgtgtcgt cttgcgtaat tttcgaactt gcgattgttg aatttcgatt
2461 gatctaaaat gttgccatac gtcaacttgt ggtgggcaag ttcttcatat aatacttcta
2521 atttgttcct ttcggataag gaaggtctaa taaaaatttc tccttcttga taccaaccat
2581 cgaatcctcg aggtactctt tgtgtttctt tcacttcaac ttcacatttc ataagcaatt
2641 cttcgtattt tcccatgcgc caaacccctt tggtgtctta tttctttcta tctctaaccc
2701 attgcataaa attttcgatt tcttcccatt cttcgggagt aaattcatct ttatttgcat
2761 gaccggctat agtttcttga tgaatacttc tttcttctgt aattctcgat ttaggtacat
2821 taaagtaatc tgctaattgt tggacttttg atattctagg atatttaagt tctttaagcc
2881 agttagagat tgttgattga cttaccccga ttgcttcaga caattctact tgagtaatgt
2941 tgttctcttt cataagttgt tctaagttct ctgataaaat ttttctagca ctcttatatt
3001 ccataatttt ctcctttagt attacttaat gtaatactaa tttaccataa gtaatatcac
3061 ttttcaatac aaaatattac tttttgaaa taaatatcac tttaggtgtt gacatattac
3121 tttaagtgat agtatagttg taaatgtcaa cgggaggtga tacgaaatgc cagaaaattt
3181 taaagagttc tctgtaaagg tctggagaac taattcgaat atgacacaac aagatgtcgc
3241 tgataaatta ggcgttacta aacaatctgt aataagatgg gaaaaagatg acgcagaatt

```
3301 aaaaggctta caattgtatg ctttagccaa attattcaac acagaagttg attatataaa
3361 ggctaaaaaa atttaacatt aatatcactt taagtgataa aggaggaaac tgaaatgcaa
3421 gaattacaaa catttaattt tgaagaatta ccagtaagga aaattgaagt ggaaggagaa
3481 cccttctttt taggtaagga tgttgctgaa attttagggt atgcacgagc agataacgcc
3541 atacgcaatc atgttgatag tgaagatagg ctgatgcacc aaattagtgc gtcaggtcaa
3601 aacagaaata tgatcatcat caacgaatct ggattataca gtttaatctt tgacgcttct
3661 aaacaaagta aaaacgaaaa cattagagaa accgctagga aattcaaacg ctgggtaact
3721 tcggaagttt taccgacgtt aagaaaaact ggtgcttacc aagtacctag tgacccaatg
3781 caagcattga gattaatgtt tgaagctaca gaagaaacaa aacaagaaat taaaaacgtg
3841 aaagatgatg ttattgattt gaaagaaaat caaaaactgg atgcgggaga ctacaatttc
3901 ttaactagaa caatcaatca aagagtagct catatacaaa gactacatgc gataacaaac
3961 caaaaacaac gtagcgaatt attcagggat attaattcag aagtgaaaaa gatgactggt
4021 gcgagttcaa gaacgaacgt aagacaaaaa catttcgacg atgtaattga aatgattgct
4081 aattggttcc cgtcacaagc tactttatac agaatcaagc aaattgaaat gaaattttaa
4141 aacgaaatat aggagaggct gaatatggaa tacatcggat atgcagacgc aaatgcgttt
4201 gtaaaaataa gtggcatttc aaaagatgat ctagagaaaa aagtctactc gaacaaagag
4261 tttcaaaaag aatgcatgta cagatttggt cgaggacaaa agcgttatat aaaaattgac
4321 aaagctattc aatttatcgg taccaattta atgattaatg aatacgaatt ataggaggag
4381 ttatcaaatg agtaaaactt ataaaagcta cctagtagca gtactatgct tcacagtctt
4441 agcgattgta cttatgccgt ttctatactt cactacagcg tggtcaattg caggattcgc
4501 aagtatcgca acattcatat actacaaaga atacttttat gaagaataaa aaaactgcta
4561 cttgcgtcaa caagtaacag tgacaaacat ttatcaaaat atacaactta attaaatcaa
4621 aatatacgga ggtagtcaac tatggctgaa aatattaaaa ctgaacaaca ttattacact
4681 aaagatttct caggatacag aaatgaagaa gataactttg tagcaaatca agaattgaca
4741 gtaacaatca cattgaacga gtacagaaaa cttattgaaa taaaggctgt taaagataaa
4801 gaagaagata cttacagagg taagtatttt gcggaagaaa gaaaaaacga aaaattggaa
4861 aaagaaaata taaaactaaa aaacaaaatt tatgaattac aaaacgaaga agataacgag
4921 gaggacgaag aagacaagga ggacgagaac gatgtattac aaaattggtg agataaaaaa
4981 caaaattata agctttaacg ggtttgaatt taaagtgtct gtgatgaaga gacatgacgg
5041 tatcagtata caaatcaagg atatgaataa tgttccactt aaatcgtttc atgtcataga
5101 tttaagcgaa ctatatattg cgacggatgc aatgcgtgac gttataaacg aatggattga
5161 aaataacaca gatgaacagg acaaactaat taacttagtc atgaaatggt aggaggtatg
5221 aaaagtgaat gatttacaag agagagaatt agaaacattc gaacaagacg accgattcaa
5281 agtaactgat ctagacagtg ctaactgggt ttttaagaaa ctggatgcaa tcacaactaa
5341 agagaatgaa atcaacgatt tagcaaataa agaaattgaa cgcataaacg aatggaaaga
5401 taaagaagta gaaaaattac agagtggcaa agaatattta caaagccttg taattgaata
5461 ttacagaata caaaaagaac aagatagcaa attcaagttg aatacacctt acggaaaagt
5521 gacagccaga aaaggttcaa aagtcattca agttagcaat gagcaagaag tcattaaaca
5581 acttgagcaa cgaggttttg acaactatgt aaaagtaact aaaaaactta gccaatcaga
5641 cattaagaaa gatttcaatg taactgaaaa cggcacattg attgacgcaa acggcgaagt
5701 tttagagggt gctagcattg tggagaaacc aacgtcatac acggtaaagg tgggagaata
5761 gatgactgaa aaaactaatc aagatgtcga tattttaacg caactaggtg taaaagacat
5821 cagcaaacaa aatgcaaaca agttttataa atttgcgata tacggcaagt tcggtactgg
5881 taaaactacg tttttaacaa aagataacaa taccttagta ctagatataa atgaggacgg
5941 aacaacggta acagaagatg ggcagttgt gcagattaag aattataagc attttagtgc
6001 agtgattaaa atgctgccta aaattattga acaactaaga gaaaacggaa aacaaattga
6061 tgttgtagtg attgaaacaa tccaaaagtt acgtgatatc actatggacg acatcatgga
6121 cggtaaatca aagaaaccga catttaatga ttggggcgag tgtgctacac gcattgtaag
6181 tatttatcgt tatatttcta aattacaaga acattatcaa tttcatcttg ctataagcgg
6241 acacgagggc attaacaaag acaaagatga tgagggaagt actatcaatc caacaatcac
6301 gatagaggca caagaccaaa taaaaaaagc agtcatcagt caatctgacg tgttagcaag
6361 aatgacaata gaagaacatg agcaagacgg cgaaaaaact tatcaatatg tacttaacgc
6421 tgaaccatca aatttattcg agacaaagat aagacactca agcaacatca aaattaacaa
6481 caaacgtttc attaatccaa gtattaacga tgttgtacaa gcaattagaa atggtaatta
6541 aaaattaatt aaaaggacgg tataaaaatt atgaaaatca ctggtagaac acaatacatt
6601 caagaaacta atcaagaggc attcatgaaa ggtggggact tttaggagc tggagaattt
6661 acagtaaaag ttgcaaatgt cgagtttaac gacagagaaa acagatactt cacgattgtt
```

6721 tttgaaaaca acgaaggtaa acaatacaaa cacaaccaat tcgtcccacc attccaacaa
6781 gattatcaag aaaaacaata tatcgagtta cttagtagat taggaattaa attgaactta
6841 ccagatttaa cttttgacac agatcaatta attaacaaaa tcggaactat tgtacttaaa
6901 aataaattta acgaggaaca aggcaagtat tttgtaagac tctcatatgt aaaagtttgg
6961 aataaagacg atgaagtagt taataaacca gaacctaaaa ctgatgagat gaaacaaaaa
7021 gaacagcaag caaatggtaa acagacacct atgagtcaac aatcaaaccc attcgctaat
7081 gctaatggtc caatagaaat caatgatgat gatttaccgt tctaggacgt ggtttaaatg
7141 caatacatta caagatacca gaaagacaat gacggtactt attccgtcgt tgctactggt
7201 gttgaacttg aacaaagtca cattgattta ctagaaaacg gatatccgct aaaagcagaa
7261 gtagaggttc cggacaataa aaaactatct atagaacaac gcaaaaaaat attcgcaatg
7321 tgtagagata tagaacttca ctggggcgaa ccagtagaat caactagaaa attattacaa
7381 acagaattgg aaattatgaa aggttatgaa gaaatcagtc tgcgtgactg ttcaatgaaa
7441 gttgcgagag agttaataga actgattata tcgtttatgt ttcatcatca aatacctatg
7501 agtgtagaaa cgagtaagtt gttaagcgaa gataaagcgt tattatattg ggctacaatc
7561 aaccgcaact gtgtaatatg cggaaagcct cacgcagacc tggcacatta tgaagcagtc
7621 ggcagaggta tgaacagaaa caagatgaat cactacgaca aacatgtgtt agcactgtgt
7681 agacaacatc ataatgaaca gcacgcaatt ggtgttaagt cgtttgatga taaatatcaa
7741 ttgcatgact cgtggataaa agttgatgag aggctcaata aaatgttgaa aggagagaaa
7801 aatgaataag ttactaatag atgactatcc gatacaagta ttaccgaaat tagctgaatt
7861 aatagggtta aacgaagcaa tagtattgca acaaattcat tattggctaa acaactcaaa
7921 acataaatac gatggcaaaa cttggatttt taattcttat ccagaatggc aaaaacaatt
7981 tccattttgg agcgagagaa ctataaaaag gacatttggg agtttagaaa aacaaaattt
8041 attgcatgta ggtaactaca acaaggctgg atttgaccgt acaaaatggt attcaatcaa
8101 ttatgaaaca ttaaacaaac tagtggcacg accatcggga caaaatggcc cgacgatgag
8161 gacaaattgg cacgatgcaa gaggacaaaa tgacccgacc aataccatag actacacaga
8221 gactaacaaa catagagaga cagacgacgt ctcaaagtca tttaagtata ttagtaccaa
8281 tttagaaatt atacaaaacc ctttaaaagc agaacagtta gaacacgaaa ttaaatcatt
8341 taagcaagat cagttcgaaa tagtaaaagt cgctaccgat tactgcaaag aaaacaacaa
8401 aggtctgaat tacttactaa ctgtattaaa gaactggaat aaagaaggcg tttcagataa
8461 agaaagtgct gaaaacaaat tgaaacctcg taactctaaa aaagaaacta ctgatgatgt
8521 catagcacaa atggaaaaag aattgagtga tgactaatgc cgatgagcaa aacacaagca
8581 ttagaaatta ttaaaaaagt taggtacgta tacaacatcg attttgataa accaaagtta
8641 gaaatgtgga ttgatgtatt aagtcaaaac ggggattatc aaccaactgt aaaagctgta
8701 gatggatata tcaacagtaa caacccgtac ccgcctaacc taccagcaat catgcgtaag
8761 gcacctaaaa aagtatctat tgagccggta gacaacgaaa ccgctacaca ccaatggaaa
8821 atgcagaatg accccgaata tgtcagacaa agaaaaatag cgctagataa cttcatgaat
8881 aagttggcag aatttggggg cgataacgaa tgaattacgg tcaatttgaa attgaaagca
8941 caataatcgc tacgctactt aaacaaccgg acgtactaga aaagataaga gttaaagatt
9001 acatgtttac gaacgaaaag tttaaaacct tttcaatta tgtaatggac gtcggaaaga
9061 tagatcatca agaaatctat ttaaaagcaa ctaaagataa agagttttta gatgcagata
9121 ctataactaa actttacaac tccgatttca ttggatacgg attctttgaa cgttatcaac
9181 aagaattatt ggaaagttat caaatcaaca aagcgaaaga attggtaact gagttcaaac
9241 aacaacctac gaaccaaaat tttaataact tgattgatga actcaaggat ttaaaaacaa
9301 ttactaacag aaaagaagac ggaaccaaga agtttgttga ggagtttgtc gatgagttat
9361 acagcgatag ccctaagaag caaattaaga cgggttataa gctcatggat tacaaaatag
9421 ggggattgga gccgtcgcaa ttaatcgtca tcgcagcgcg tccctcagtg ggtaagacag
9481 gttttgcatt aaacatgatg ctgaacatag cacaaaatgg atacaaaaca tctttcttta
9541 gtctcgaaac aactggcaca tcagtattga aacgtatgtt atcaacaatt actggtattg
9601 agttaacaaa gataaaagaa atcaggaact taacgccgga tgacttaaca aagttaacga
9661 atgcgatgga taaaatcatg aaattaggca tcgatatttc tgataaaagt aatatcacac
9721 cgcaagatgt gcgagcgcaa gcaatgaggc attcagacag gcaacaagtt atttttatag
9781 attatcttca actgatggat actgatgcga aagttgatag acgtgtagca gtagaaaaga
9841 tatcacgtga cttaaagata atcgctaacg agacaggcgc aatcatcgta ctactttcac
9901 aactgaatcg tggtgtcgag tctagacagg ataaaagacc aatgctatcg gacatgaaag
9961 aatcaggcgg aatagaagca gatgcgagtt tagcgatgct actttaccgt gatgattatt
10021 ataaccgtga cgaagatgac agtatcactg gcaaatctat tgttgaatgt aacatagcca
10081 aaaacaaaga cggcgaaacc ggaataattg aatttgagta ttacaagaag actcagaggt 10141 ttttcacatg aatataatgc aattcaaaag cttattgaaa tcgatgtatg aagagacaaa
10201 gcaaagcgac ccgattgtag caaatgtata tatcgagact ggttgggcgg tcaatagatt
10261 gttggacaat aacgagttat cgcctttcga tgattacgac agagttgaaa agaaaatcat
10321 gaatgaaatc aactggaaga aaacacacat taaggagtgt taaaaaatgc cgaaagaaaa
10381 atattactta taccgagaag atggcacgga agatattaag gtcatcaagt ataaagacaa
10441 cgtaaatgaa gtttattcgc tcacaggagc ccatttcagc gacgaaaaga aaattatgac
10501 tgatagtgac ctaaaacgat ttaaaggcgc tcacgggctt ctatatgagc aagagctagg
10561 attgcaagca acgatatttg atatttagag gtggcacaat gagtaaatac aatgctaaga
10621 aagttgagta caaaggaatt gtatttgata gcaaagtaga gtgcgaatat taccaatatt
10681 tagaaagtaa tatgaatggc actaactatg atcgtatcga aatacaaccg aaatttgaat
10741 tacaacctaa attcgggaaa caaagaccga ttacgtatat agccgatttc tctttgtgga
10801 aggaagggaa actggttgaa gttatagacg ttaaaggtaa ggcgactgaa gttgccaaca
10861 tcaaagcgaa gatattcaga tatcagtata gagatgtgaa tttaacgtgg atatgtaaag
10921 cgcctaaata cacaggtcaa gaatggatgg tatatgagga cttagtgaaa gtcagacgta
10981 aaagaaaaag agaaatgaag tgatctaatg caacaacaag catatataaa cgcaacaatt
11041 gatataagaa tacctacaga agttgaatat cagcattacg atgatgtgga taaagaaaaa
11101 gatacgctgg caaagcgctt agatgacaat ccggacgaat tactaaagta tgacaacata
11161 acaataagac atgcatatat agaggtggaa taaatgaagt tgaacgaagt attcgcaact
11221 aatttaaggg taatcatggc tagagataac gtaagtgtcc aagatttgca caatgaaact
11281 ggcgtatcaa gatcaactat tagtggatat aaaaacggaa aagctgagat ggttaactta
11341 aatgtattag ataaattggc agatgctcta ggtgttaatg taagtgaact atttactaga
11401 aatcacaaca cgcacaaatt agaggattgg attaaaaaag taaatgtata gaggtggaat
11461 aaatgagtat cgtaaagatt aacggtaaac catataaatt taccgaacat gaaaatgaat
11521 tgataaaaaa gaacggttta actccaggaa tggttgcaaa aagagtacga ggtggctggg
11581 cgttgttaga agccttacat gcaccttatg gtatgcgctt agctgagtat aaagaaattg
11641 tgttatccaa aatcatggag cgagagagca aagagcgtga aatggttagg caacgacgta
11701 aagaggctga actacgtaag aagaagccac atttgtttaa tgtgcctcaa aaacattctc
11761 gtgatccgta ctggttcgat gtcacttata accaaatgtt caagaaatgg agtgaagcat
11821 aatgagcata atcagtaaca gaaaagtaga tatgaacaaa acgcaagaca atgttaaaca
11881 accggcgcat tacacatacg gcaacattga aattatagat tttatcgaac aggttacggc
11941 acagtatcca cctcaactag cattcgcaat aggtaatgca atcaaatact tgtctagagc
12001 accgttaaag aatggtcatg aggatttagc aaaggcgaag ttttacgtcc aaagagcttt
12061 tgacttgtgg gagggttaac gatggcaacg caaaaacaag ttgattacgt aatgtcatta
12121 caggaacaat tgggattaga agactgtgaa aaatatacag acgaacaagt taaagctatg
12181 agtcataaag aagttagcaa tgtgattgaa aactataaga caagcatatg ggatgaagag
12241 ctatataacg aatgcatgtc gtttggtctg cctaattgtt aaaaggagtg atgaccatga
12301 acgatagcgc acgcaaagaa tacttaaacc aatttttcag ctctaagaga tatctgtatc
12361 aagacaacga gcgagtggca catatccatg tagtaaatgg cacttattac tttcacggac
12421 attataaaac gatgtttaaa ggcgtgaaaa agacatttga tactgctgaa gagctcgaaa
12481 tatatataaa gcaacatgat ttggaatatg aggaacagaa gcaaccaact ttattttaga
12541 ggagatggaa ataatggcaa agattaaaag aaaaaagaag atgacgctac tcgaactggt
12601 ggaatgggca tggaacaatc ctgaacaagt tgaaagtaaa gtgtttcaat cagatagaat
12661 gggcacgctt ggagaatgta gcgaagtaca tttttcaact gatgggcatg ggttttatac
12721 aaaagtagta acagataaag atatttttac tgtagaaatc acagaggaag tcactgaaga
12781 tactgagttt gattgtctag tagaactaaa cgatattgaa ggttttgaaa tatatgaaaa
12841 tgattcaatc agagagttga tagacggtac ttccagagcg ttttatatac taaacgaaga
12901 taaaactatg acattaattt ggaaagatgg ggagttggta gtatgatgca aacctataaa
12961 gtatgtcttt gtatcaagtt ctttgcatct aaatgtgatt ataaattaaa gaaacattat
13021 ttcgtgaaaa gtacgaatga ggaaaaagcc acgaacatgg tattaaaact gattcgtaaa
13081 aagctcccgt tcgaaactgc aagcatagaa gtcgaaaaag tggaggcaat ataatgatac
13141 aaccaacaag agaagaatta attaatttca tgaaaaaaca tggagctgaa aatgttgact
13201 ctatcactga tgagcaaagt gcaataagac actttagagc tcaatcaaaa gtttttaaag
13261 acgaacgtga tgagtacaag aagcaacgag atgagcttat cgaggatata gctaagttaa
13321 gaaaacgtaa cgaagagctg gagaacatgt ggcgcacagt caaaaatgaa ttgcttggaa
13381 gatacgaaca ttactgtttt aaaattagag aactacaccc tgagagcaaa gcgaacagga
13441 taggagctct ctatatagga ggtaaaagca ctgcagatat tatactgtcg cgaatggaag
13501 aactagacgg aacaaatgag ttctacgaat ttttagggca aatggaggca gacacaaatg

```
13561 aataaccgtg aacaaataga acaatcagtg atcagtacta gtgcgtataa cggtaatgac
13621 acagaggggt tactaaaaga gattgaggac gtgtataaga aagcgcaagc gtttgatgaa
13681 atacttgagg gaatgacaaa tgctattcaa cattcagtta aagaaggtat tgaacttgat
13741 gaagcagtag gggttatggc aggtcaagtt gtctataaat atgaggagga gcaggaaaat
13801 gagtattagt gtaggagata aagtatataa ccatgaaaca aacgaaagtc tagagattgt
13861 gcaattggtc ggagatatta gagatacaca ttataaactg tctgatgatt cagttattag
13921 cattatagat tttattacta aaccaattta tctaattaag gggacgagt gagtggaatg
13981 gaaacgatta aaaaatgtgg tgccgcaccc agttatcaaa aataaaaatt taaagtcggt
14041 atacgtaaca aaagataatg tgaaagaggt tcaaaaagaa ttaggtttct ttgaaatttt
14101 taatgaagaa gtgttattaa ctggattttt atcatttcaa aggataccta tttacattat
14161 ttggattaat cctaaatctc ataagacgcc tagatattac tttgctaacg agcatgagat
14221 tgaaagatat tttgaatttt tggaggacga gtaaatgctt gaaatcatcg accaacgtga
14281 tgcattgcta gaagaaaagt atttaaacga cgactggtgg tacgagctag attattggtt
14341 gaataaacgc aagtcagaaa atgaacagat tgatattgat agagtgctta aatttattga
14401 ggaattaaaa cgataggaga taacgaataa atgaataatt taacagtaga tcaattaaaa
14461 gaacttttac aaatacaaaa ggagttcgac gatagaatac cgactagaaa tttaaatgac
14521 acagtagcta gtatgattat tgaatttgcg gagtgggtta acacacttga gtttttttaaa
14581 aattggaaga aacaaccagg taagccatta gatacacaat tagatgagat tgctgattac
14641 ttagctttca gtttgcaatt aactctgact attgttgatg aagaagattt ggaagagact
14701 actgaggtta tggttgattt gattgaaaat gaagttactt tacctaaact acattcagtt
14761 tattttgttc atgtaatgca tacactaaca gaacaatttg taaaaggtat tgataatagt
14821 attgtacaag ttttaataat gcctttttttg tacgccaata cttactatac aatcgaccaa
14881 ctcattgacg catacaaaaa gaaaatgaaa aggaaccacg aaagacaaga tggaacagca
14941 gacgcaggaa aaggatacgt gtaaagacat cttagatcga gtcaaggagg ttttggggaa
15001 gtgacgcaat acttagtcac aacattcaaa gattcaacag gacaaccaca tgaacatttt
15061 actgctgcta gagataatca gacgtttaca gttgttgagg cggagagtaa agaaggagcg
15121 aaagagaagt acgagaaaca agttaagata aggagagatg gagatgccaa agaaaacggt
15181 aacgattgat gtagatgaaa acttattagt agtagctagt aatgaaatat cagaactatt
15241 atatgaatat gacagtgagt taatgtcagc tgatgaagat ggcgataata gagatatcga
15301 aaaaaaaaga gacgcattaa aacaagctat acaaattatc gataaattaa catgtcgagg
15361 aggcagacga tgattaacat acctaaaatg aaattcccga aaaagtacac tgaaataatc
15421 aagaaatata aaaataaaac acctgaagaa aaagctaaga ttgaagatga tttcattaaa
15481 gaaattaatg ataaagacag tgaattttac agtcctatga tggctaatat gaatgaacat
15541 gaattaaggg ctatgttaag aatgatgcct agtttaattg atactggaga tggcaatgat
15601 gattaaaaaa cttaaaaata tggattggtt cgatatcttt attgctggaa tactgcgatt
15661 attcggcgta atcgcactga tgcttgttgt catatcgcct atctatacag tggctagtta
15721 ccaaaacaaa gaagtatatc aagggacaat tacagataaa tataacaaga gacaagataa
15781 agaagacaag ttctatattg tgttagacaa caagcaagtc atcgaaaact ctgacttact
15841 attcaaaaag aaatttgata gcgcagacat acaagctagg ttaaaagtag gcgacaaagt
15901 agaagttaaa acgattggtt atagaataca ctttttaaat ttatatccgg tcttatacga
15961 agtaaagaag gtagataaat aatgattaaa caaatattaa gactattatt cttactagcg
16021 atgtatgagc taggtaagta tgtaactgag aaagtatata ttatgacgac ggctaatgat
16081 gatgtagagg cgccgagtga cttcgcaaag ttgagcgatc agtctgattt gatgagggcg
16141 gaggtgtcag agtagatgta tagcaaagag tcaattgtta atatgatagg cacacataaa
16201 atgaagtgta atgtattagc tgatgtaata ccggaatatg atagcaattc aattgcacag
16261 tatggcatac aagcaacgtt gccgaaacca caaggggaaa actcaagtaa agttgaagat
16321 gttgttgtga ggcttgagag agcaaataaa aggtatgctc agatgttaaa agaggttgag
16381 tttataaatc aatcgcaaca gagattggga cacgttgact tttgcttctt agagttattg
16441 aagaaaggtt ataacaggga tgcgattatc aagaagatgc ctaactctaa attaaataga
16501 aacaacttct tagcgcgccg tgatgagtta gcagaaaaga tttatctact acagtgacga
16561 aaatgacaaa aatgacagaa atgacgaaaa tgacactatt tttaaactgt gaattaattt
16621 tatataattg atttgtaaga attatcttaa gacgtggggt aatagccaca ttagatgttc
16681 tcatcgatgt gattgagaag tgacaaacat ataaaagatg atatgttacg ctattaatca
16741 cctactacct gcctatatgg tgggtagttt aattcttgca ttttgagtca taactatttt
16801 cctcctttca catttattga acgtagctcc tgcacaagat gtaggggcat tttttatatt
16861 taaataacta gagtaattaa cgtaaaggcg tgtgatacag tgaaaacaat tgattaaatt
16921 aacaccgaag caagaaaagt ttgtgctagg actcatagag ggcaagagcc aacggaaagc
```

```
16981 atatattgac gcagggtatt cgactaaagg taagagtggg gaatatctag ataaagaagc
17041 gagtacactt tttaaaaatc ggaaggtttc cggaaggtac gaaaaattgc gtcaagaagt
17101 agctgaacaa tcaaaatgga cacgccaaaa ggcctttgaa gaatatgagt ggctaaagaa
17161 tgtagctaag aatgacattg aaatagaggg agtgaagaaa gcgacagctg atgcattcct
17221 cgctagttta gatggtatga atagaatgac gttaggtaac gaagttttag ctaaaaagaa
17281 aatagaaact gaaattaaga tgcttgagaa gaagattgaa caaatagata aaggtgacag
17341 tggaacagaa gataaaatca aacaacttca cgacgcaata acggaagtga tcgtcaatga
17401 ataaacttaa atctttatat acggacaaac aaattgaaat attgaagcaa acgcaaaaac
17461 aagattggtt tatgttaatt aatcacggag caaagcgtac aggtaaaaca atattaaaca
17521 atgacttatt tttacgtgag ttaatgcgtg tgcgaaagat agcagacgaa gaaggaattg
17581 agacacctca atatatactt gctggtgcaa cattaggtac gattcaaaaa aacgtactaa
17641 tagagttaac taacaaatat ggcattgagt ttaattttga taaatataat tcattcatgt
17701 tatttggcgt tcaagtggtt cagacaggtc acagtaaagt aagtggtata ggagctatac
17761 gtggtatgac atcgtttggt gcatatatca atgaagcgtc gttagcgcat gaagaggtgt
17821 ttgacgagat taagtcacgt tgtagtggaa ctggtgcaag aatattggta gataccaacc
17881 ctgaccatcc cgagcattgg ttgttgaaag attatattga aaatacagat cctaaagcag
17941 gtatactgag tcaccaattt aagctcgatg acaataactt tcttaatgat agatataaag
18001 agtctattaa ggcttcaaca ccatcaggta tgttctatga acgtaatatc aacggtatgt
18061 gggtgtctgg tgacggtgta gtatatgccg actttgattt gaatgagaat acgattaaag
18121 cagatgaact ggacgacata cctatcaaag aatactttgc tggtgtcgac tggggttacg
18181 agcactatgg atctattgtg ttaataggac gaggtataga tggtaacttt tattttattg
18241 aggagcacgc acaccaattt aagtttattg atgattgggt ggttattgca aaagatattg
18301 taagtagata tggcaatatt aatttttact gcgatactgc acgacctgaa tacatcactg
18361 aatttagaag acatagatta cgtgcaatta acgctgataa aagtaaacta tcgggtgtgg
18421 aggaagttgc taagttgttc aaacaaaaca agttacttgt tctttatgat aatatggata
18481 ggtttaagca agaggtattt aaatatgttt ggcaccctac aaacggagag cctataaaag
18541 aatttgatga cgtgttggac tcgttaagat atgccatata cacacatact aaacctgaac
18601 gattaaggag ggggaaatga cattgtataa gttaatagat gatattgaag cacaaggaat
18661 attgcctaag catattgagg ctctaataga gtcacataaa gacgatagag agagaatggt
18721 taatctctat aatagataca agacacatat tgactatgta ccaatattca aacgtcgacc
18781 aattgaagaa aaagaagatt ttgaaactgg tggaaatgta aggcgattag acgtgtctgt
18841 taataacaaa cttaacaact cttttgacag cgaaattgtt gatacacgtg ttggttattt
18901 acatggtgtt cctgttactt atgatttaga tgaaaacgca gaaaaaaacg aaaagttgaa
18961 aaagtttata accaactttg ccattagaaa tagtgttgat gatgaggatt ctgaaatagg
19021 taaaatggca gcaatttgcg gatatggtgc taggttagca tatattgata cgaatggtga
19081 tattaggatt aagaatatag atccctataa tgttattttt gttggcgaca atattttaga
19141 acctacatac tcattgcgct acttttatga aaaagatgat gataatggca ctgattatgt
19201 gtacgcagag ttttacgata atgcttatta ttatgtattt cgaggagaag gtattgacgc
19261 tttgcaagaa gttggacgat atgaacattt atttgattac aatccattgt ttggtgtacc
19321 taacaacaaa gagatgatag gagatgctga aaaggttatt cacttaattg acgcatatga
19381 tttaacaatg agcgatgcat caagtgagat tagtcagaca cgtttagcat accttgtgtt
19441 acgcggtatg ggtatgagtg aagaaatgat tcaagaaaca caaaagagtg gcgcatttga
19501 gttgttcgac aaagatatgg acgttaaata cttaacaaaa gatgtaaatg acacaatgat
19561 tgagaaccat ttagatcgaa tcgaaaagaa tatcatgcgt tttgcaaagt cagtaaactt
19621 taattctgac gagtttaacg gaaatgtacc tatcattgga atgaaactta aacttatggc
19681 tttagagaac aagtgtatga cgtttgagcg taagatgaca gctatgttga ggtatcaatt
19741 caaagttatt ttatctgcat taaagcgtaa agggtacaac ttggatgatg atagttattt
19801 aaacctgata tttaagttca ctcgtaacat tccagttaat aagttagaag aatcacaagt
19861 gctaattaac ctgaagggac aagtttcaga acgaacaagg ttaggacaat cacaactagt
19921 tgatgatgtt gattacgaat tagacgaaat ggaaaaagaa agtcttgaat ttaatgacaa
19981 attacctgac atagatgaag gtgacgcaaa tgacaaatcc caaaataacc aatcagaatg
20041 atattgatga gtatatcgag ggtttaatct ctaaagcaga aaaaccaata gaacaactat
20101 ttgctaatcg acttaaagag ataaaacaaa tcatcgcaga tatgtttgag aaatatcaaa
20161 atgatgatgt gtatgttaca tggactgaat tcaataaata caacaggctc aataaggagt
20221 taactcgtat aggtacaatg ttgacttatg actataggca agtagctaag atgattcaga
20281 agtcacaaga agatgcttat atagaaaaat tccttatgag cctttattta tatgaaatgg
20341 cgagtcaaac atctatgcag tttgatgttc cgagtaaaga ggtaatcaaa tcagctattg
```

```
20401 aacaacctat tgagttcatt cgtttaatgc caacactaca aaaacatcgt gatgaagtat
20461 tgaaaaagat acgtatgcac attacacaag gtattatgag tggagagggt tactctaaga
20521 tagctaaagc aatacgtgat gatgtcggca tgtctaaagc tcaatcattg cgtgtggctc
20581 gtacagaagc aggcagagca atgtcacaag ctggacttga tagcgcaatg gttgctaaag
20641 ataacggttt gaatatgaag aaacgttggc atgctactaa agatacacga acacgtgata
20701 ctcatcgtca tttagatggg gaatcagtgg aaatagatca gaattttaaa tcaagtgggt
20761 gtgttgggca ggcgcccaag ctatttattg gtgtaaacag tgcgaaagag aatattaatt
20821 gtcgttgcaa attactttat tatattgatg aaaatgaatt gccaactgta atgagagcac
20881 gtaaagacga tggtaaaaat gaagttatcc cattcatgac ttatcgtgag tgggagaaat
20941 ataagcgaaa aggtggtaat tgatatggat tttaaaataa aagtaaatgt tgatactggc
21001 gaagctatag aaaagttaga acgcattaaa tccttgtacg aagagataat agagttacaa
21061 aacgaaaaag ttgttgtaaa cgtaacagtt aaaaatgaag ctgatttaga tatggttaaa
21121 acatctatta gcgaagaaaa tgctaaaaat aatgatttca cacttttta gttgtctctt
21181 tgctactcga ccttagcatg tcgttaaact gctttttatt atgcactttt cggactgtta
21241 gggtacgcga agggcaaaaa ggagttttga tatatgaata tcgaagaagt taagtctttt
21301 tttgaagaac acaaagacga taaagaagta aaagattatc taaagggact taagacggtg
21361 tctgttgatg acgttaaagg ctttttagat acagaagaag gtaaacgatt cattcaacct
21421 gaattagatc gttatcattc gaaaggatta gaatcatgga aagagaaaaa tcttgaggat
21481 ctaatcgaac aagaagtacg gaagcgtaat cctgagcaat cagaagaaca aaaacgtatt
21541 agtgctcttg aacaagagtt agaaaaacgc gacgcagagg caaaacgtga gaagttaaga
21601 agtaacgcgc taggtaaagc gcaggaacta aatttaccaa catccttagt tgatagattt
21661 ttaggcgatt ctgatgaaga tactgagcaa aacttaaaag ctttaaaaga aacctttgac
21721 aagtatgttc aaaaaggcgt tgagtctaaa tttaaatcga gtggaagaga tgttaaagaa
21781 tcacgaaatc aagatttaga cccttcaaat gtaaagtcca ttgaagaaat ggcgaaagaa
21841 atcaatatta gaaaataaag tgaggtaata aaatatggca actccaacat acacgccagg
21901 caatgttatt ttatcggatt ttaaaaacgg cgttattcca gcagaacaag gtactttaat
21961 catgaaagac attatggcta attcagcaat tatgaaatta gctaaaaatg agccaatgac
22021 agcacaaaag aaaaaattta cttacttagc aaaaggtgta ggcgcctact gggtatcaga
22081 aacggaacgt attcaaactt ctaagcctga atatgcgcaa gcagaaatgg aagctaagaa
22141 aattggtgta attattccgt tatcaaaaga gtttcttaaa tggactgcaa aagatttctt
22201 taatgaggtt aaacctctaa ttgcagaggc attttacaaa gcgtttgacc aagctgttat
22261 ctttggtact aaatcacctt acaacacttc aactagtggt aaaccgcttg ttgaaggcgc
22321 agaagagaaa ggtaacgttg ttacagatac taataattta tacgtagacc tttcggcatt
22381 aatggctact attgaagatg aagagttaga tccaaacgga gtattaacta cacgttcatt
22441 cagaagtaaa atgcgtaatg ctttagatgc taatgacaga ccattatttg atgctaacgg
22501 gaacgagatt atgggattac cactatctta tactggagcg gatgtatacg acaaaaagaa
22561 atcgttagca ctaatgggtg attgggatta cgcacgttac ggtatcttac aaggtattga
22621 gtatgcaatt tctgaagatg ccacgttaac gacgttacaa gcatcagatg cttctggcca
22681 accagtatca ttatttgaac gtgatatgtt cgctttacgt gcgacgatgc atattgcata
22741 catgaacgtt aaaccagaag cgttcgcaac gcttaaacca actgaatagg aggagatatg
22801 atggctaatc ctgcagaaga gattaaggta aaaaaagaca atatgactat tactgttaca
22861 aagaaggcat ttgactctta ttacagtctt gtcggttaca aagaggttaa atcacgtcgt
22921 actacgtctg ataagagcga gtgataaaaa tgactcttta tgaagatgtt aaacttttac
22981 tcaagaaaaa tggagtggaa gttaaaagtg atgaagaaga aatatttaag atggaagttg
23041 acggaatact agaagatgtt agggatataa caaacaatga ttttatgaaa gatggtcaag
23101 tcatttatcc ttactcaatc aaaaagtatg tcgcagatgt cctagagtat tatcaacgac
23161 ctgaagttaa aaagaattta aagtcaagaa gtatggggac agtgtcgtac acttataacg
23221 atggtgtccc tgattacatt agtggagtat taaacaggta taaacgagca aagtttcatc
23281 cgtttaaacc aataaggtag aggtgttgtt tgtgtttaac ccatacgacg aattccctca
23341 cactatttct attggaagta tcaaaaaagt aggagagtat ccaattatac aagagcgctt
23401 tgtaagcgat aaaacaatta aaggatttat ggatacgcct actacatctg aacaactaaa
23461 atttcatcaa atgtcacaag aatatgacag aaacctatat gtaccttatg acttgccaat
23521 atctaaaaac aatttatttg agtatgaggg tagaatcttt agtattgaag gtgattctgt
23581 agatcagggc ggacaacatg aaattaagtt actacgactt aagcaggtgc catatggcaa
23641 aagttaagta cggtgctgat agcatggttg ttgaattgga taagttcgat aagaaaatag
23701 aagagtgggt taaaaaaggt attgctaaaa caacgacgaa gatttacaac actgctgtag
23761 cattagctcc tgttgactta ggttttttag aagaaagtat tgactttaaa tatttcgatg
```

```
23821 gtgggttatc cagtgttata agtgtcggcg cagattatgc aatatacgtt gaatacggta
23881 ctggtatata tgctactggt cctggtggta gtcgtgctac aaagattccg tggagtttta
23941 aaggtgatga cggcgaatgg tacaccacat atggtcaagc gccacagcca ttttggaacc
24001 ctgcaattga cgcaggacgc aagacattcg agcagtattt ttcatagagg tggttaaata
24061 tgtgggtatc agttgagcct gaacttacaa atcaaatata taaaagatta atctcagacc
24121 ctaacattaa caaactagtt gatgataggg tttttgacgt tgttcaagat gacgctgttt
24181 acccatatat tgttgtgggt gaatcaaacg tcactaacaa cgaatctagc gcaacaatga
24241 gagaaacagt cggtattgtc atacatgtgt attcacagtt cgctacacaa tacgaggcta
24301 agctcatttt aagcgcgata ggttatgtgc ttaacagacc tatagaaata gataattacg
24361 agtttcaatt tagccgtatc gatagtcaag cagtattccc tgatatagac aggtttacta
24421 agcatggcac gatacggctt ttatttaagt acagacataa aaagaaaaac gaaggagtgt
24481 attaaatggc gcaaaaaaac tatttagcag ttgtacgtcc agctgaaact gacttagatc
24541 cagtagaatc tttattatta gctgacttac aagaaggtgg acatacgatt gaaaatgatt
24601 tagctgaaat agtacgaggc ggtaaaacgg actattctcc caatgcaatg tcagaatcat
24661 ttaaattaac aattggtaat gtgcctggag ataaaggaat tgaagcagtg aaacacgctg
24721 tacaaacagg tggacagttg cgtatatggc tttatgagcg taataaacgt gcagacggta
24781 aacatcacgg aatgtttggt tatgttgttc cagaatcatt tgaaatgtca tttgatgatg
24841 aaagtgacaa aatcgaacta tcattaaaag ttaaatggaa tacagcagaa ggtgctgaag
24901 ataacttgcc gaaagagtgg tttgaagctg caggtgcgcc tacagttgaa tacgaaaaat
24961 tcggcgaaaa agtcggaaca ttcgagaatc aaaagaaagc tagtgttgta tctgattcac
25021 acacggaaga ccattctatg taaactaata gatcaagggg gcgtaagctc cctatttttt
25081 tataaaaaaa ttgaaaagag gtatatattt tgactgaatt taatccaatt acaacattaa
25141 aaattaatga cggagaaaaa gattacgaag tagaagcaaa agtaacattt gcatttgacc
25201 gaaaagctga aaaattctca gaagatagcg aagatgggag aaaaggagca atgccaggat
25261 tcaatgttat ctttaacggt ttgctagaat ctagaaacaa agcgatttta caattttggg
25321 aatgtgctac tgcttattta aaaaacccac caactcgaga acaattagaa aaagcaattg
25381 atgatttcat cactgaaaac gaggatactt tgccgttatt acaaggggct ttggacaaac
25441 ttaacaatag tggtttttttc aagagggaga gtcgctcgta ctggatgaca ttgaacaaag
25501 caccgaatat ggccaaaagc gaggacaaag aaatgacgaa agcaggcata gaaatgatga
25561 aagagaatta caaggaaatc atgggcgcag aaccttacac gattactcaa aaataaggca
25621 actgacagct agatatttag gatatatccc tgaacatgaa ttgttagcac taacacctgc
25681 tgaatggcgt gattggctta ttggtggtca ggataggtac ctagatcaaa gacaattatt
25741 aattgaacaa gcgcaagcta acggcttagt acaagcttct aagaggctaa ctagtatgat
25801 tcgtgacatt gagaaacaac gttacgaaat aagagaacct ggtagctatg ctcgtgtaca
25861 aaaagctaga ttagaagaag aaaaaagaag acgtgaactc ttcaaagaag gtacaagaaa
25921 attccttgaa tcgaaaggag gttagccttt ggatactcat tttatggcaa agattatggc
25981 caatattaga gatttccaaa gcaacgtaag gaaagctcaa cgattagcaa agacgtctgt
26041 accaaacgaa attgaaacag atgtaaaagc agatatttca agattccaaa gagctttaca
26101 acgcgctaaa tcaatggctc aacgatggcg agagcattct gttaaattat tcatgaaaac
26161 agatgagtat aaagcgaatt tagaacgcgc taaagctcaa gtagagcgat ttaaacaaca
26221 taaagtagat ttgaaactaa gtaacactga attaatggcc aaatataatg caactaaagc
26281 tactgtcgaa gcttggagaa aacatgttgt taagttggat ttagatgcaa accccgctaa
26341 aatggcggtt aaagggttta aagaagattt aatagatctt agcaggcata gttttgatat
26401 tgattccagc agatggaaat taggaaataa attcacaaaa gaattcaatg aagtcgaagg
26461 agcagttaaa cgttctttcg gaagaattgg tcagattatg agaaaagaag taaatggaac
26521 aagtgatatt tggggtaaac ttaacaactc attgaaagat tacggcgaga aaatggacgc
26581 cttagctact aaaatccgaa ctttcggtac tatcttcgcg caacaggtca aaggcttaat
26641 gattgctagt atacaagcat tgataccagt gattgccgga ttagtacctg caataatggc
26701 agtacttaat gcggttggtg tattaggtgg tggcgtttta ggtttagttg gcgcattctc
26761 tgtcgcaggt cttggagttg ttggctttgg tgcaatggct attagcgctc ttaaaatggt
26821 tgaagatgga acattggcag taacaaaaga agttcaaaac tttagagatg cgagcgatca
26881 gttaaaaact acatggcgtg atattgttaa agagaatcaa gcaagtatct ttaatgcgat
26941 gtcagcaggt atcagaggcg ttacaagtgc gatgtctcaa ttaaaaccat tcttatccga
27001 agtatctatg ctagttgaag caaacgcacg cgagtttgag aattgggtta aacattccga
27061 aacagctaag aaagcgtttg aagcattgaa tagcataggt ggcgcaatct tcggagattt
27121 attgaacgct gcaggacgat ttggcgacgg attagttaac attttcactc aattaatgcc
27181 gttgttcaaa tttgtgtctc aaggactaca gaacatgtct atagctttcc aaaattgggc
```

```
27241 taatagtgta gctggtcaga atgctattaa agcgtttatt gactacacta ccactaactt
27301 acctaagatt ggtcagatat ttggtaatgt gttcgctggt attggtaatt taatgattgc
27361 ttttgcacaa aacagttcca acatttttga ttggttggtt aaattaactt ctcaatttag
27421 agcatggtca gaacaagtag gacaatcaca agggtttaaa gactttatca gttatgttca
27481 agagaatggt cctactatta tgcagttaat cggtaatatc gtaaaagcat tagttgcttt
27541 tggtactgca atggctccta tagctagtaa attgttagac tttatcacta atctagctgg
27601 atttatcgct aaactattcg aaacacaccc agctatagca caagttgctg gcgttatggg
27661 tattttaggc ggtgtatttt gggctttaat ggctccgatt gttgctataa gtagtgtact
27721 tacaaatgtg tttggtttga gcttattcag cgtcactgaa aagattttag acttcgttag
27781 aacatcaagt ttagttactg gagctacgga agcattaata ggtgcattcg gttcgatttc
27841 agcacctatt ttagcagttg ttgcagtaat tggtgcattc attggtgtcc tcgtttattt
27901 atggaaaaca aacgagaact ttagaaatac tattactgaa gcgtggaacg gtgttaaaac
27961 ggcagtttct ggtgcgattc aaggtgtagt cggctggtta actgaattgt ggggcaaaat
28021 ccaatctacc ttacaaccga taatgcctat attgcaagta ttaggacaaa tattcatgca
28081 agttttaggt gttttggtaa taggcatcat tacaaacgtt atgaatatca tacaaggttt
28141 gtggacttta attacaattg cgttccaagc cataggaaca gtgatatccg tagcagtcca
28201 aatcatagta ggtttgttca ctgctttaat tcagttgctt actggcgact tctcaggtgc
28261 ttgggagact attaaaacta cggttaccaa tgtgcttgat acgatttggc aatacatgca
28321 atcagtttgg gagtcaatta tcggcttttt aactggcgta atgaatcgaa cactttctat
28381 gtttggtaca agttggtcac agatatggag tacaatcact aattttgtta gcagtatttg
28441 gaacactgtt acaagttggt tcagtcgagt ggcttcgagt gtagctgaaa aaatggggca
28501 agcactaaac tttattatca caaaaggttc tgaatgggtt tctaacattt ggaatacagt
28561 tacaagtttc gcgagtaaag tagctgatgg gtttaaaaga gttgtctcaa atgtaggtga
28621 cggtatgagt gatgcacttg gtaagattaa aagtttcttc agtgatttct taaatgccgg
28681 agcggaatta atcggcaaag tagctgaggg tgtagccaat gctgcgcaca aagtagtcag
28741 cgcggtaggc gatgcgattt catcagcttg ggactctgta acttcattcg taagtggaca
28801 cggtggaggt agtagcttag gtaaaggttt agcggtatca caagcaaaag taattgctac
28861 agactttggc agtgccttta ataaagagct atcctctact ttgacagata gtatagtaaa
28921 tcctgtaagt acttctatag acagacacat gactagcgat gttcaacata gcttaaaaga
28981 aaataataga cctattgtga atgtaacgat tagaaatgag ggcgaccttg atttaattaa
29041 atcacgcatt gatgacatga acgctataga cggaagtttc aacttattat aagggaggtt
29101 tgttagttga tagcgcacga tatagaagta ataaggaatg gttcacagta tcgcgtcagt
29161 gacaatcctt tcacttataa tcacttggaa gtagttgaat ataacgttac aggcgcagga
29221 tatcatcgta actattctga tatagagggt attgatggta gatttcataa ttacgctaaa
29281 gaagaactta aaaaagtaga gcttaagata aggtataaag tacctaaaat tgcttatgct
29341 tcacatttaa agtcagacgt ccaagcacta tttgctggac gtttttattt aagggaatta
29401 gctacaccag acaattcaat taagtatgag catatattag atataccaaa agacaaacaa
29461 gcatttgagc ttgattatgt tgatggacga caactttttg taggactagt aagtgaagtt
29521 tcttttgaca caacacaaac atcaggggaa ttttctttgt cgtttgaaac aaccgaacta
29581 ccatactttg aaagtgtcgg ttatagtact gatcttgaaa gtaataacga ccctgaaaaa
29641 tggtcggtac ctgatagatt gcctacaaac gaaggtgata agaggcgtca aatgacattt
29701 tacaacacta actcaggaga agtttattat aacggtgatg ttcctttaac acagtttaat
29761 cagtttaatg ttgttgaaat agagttagct gaagatgtta aagctaatga taaggatgga
29821 ttcactttct atacagataa aggaaatatc tcagttatta aggaagttga tttaaaagcc
29881 ggagataaaa taatcttcga cggtaaacat acctatagag gttatttaaa tatagattct
29941 tttaataaaa ctttagaaca accggtttta tatccaggct ggaatcgatt caagtctaat
30001 aaagtaatga aacaaattac atttagacac aaattatatt ttagataagg agtagcctat
30061 gccaatttta ttaaaaagtc tacagggtgt agggcacgct attaatgtta gtacaaaggt
30121 aagtaaaaag ctaaatgaag atagttcttt ggatctaact attatcgaga acgcgagtac
30181 gtttgacgca ataggtgcta taactaaaat gtggacgatc actcatgttg aaggtgaaga
30241 tgatttcaac gaatatgtaa ttgtcatact tgataagtct actattggcg aaaaaataag
30301 gcttgatatc aaagctaggc aaaaagaact tgatgacctt aacaattcta ggatttacca
30361 agagtataac gaaagtttta caggcgttga gttcttcaat actgtcttta aaggaacggg
30421 ttataagtat gtattacatc caaaagtaga tgcatctaaa ttcgagggat taggcaaagg
30481 agatacacga ttagaaatct ttaaaaaagg acttgagcgt tatcatctcg aatatgaata
30541 cgatgcaaag actaaaacgt ttcatttgta tgatgaatta tctaagtttg ccaattatta
30601 cattaaagct ggtgtgaatg ctgataacgt caaaatacaa gaagatgcat ctaaatgtta
```

30661 tacctttatt aaaggttatg gtgattttga tggacaacag acttttgcag aagcgggact
30721 acaaattgaa ttcactcatc cattagcaca attgataggt aaaagagaag cgccaccgct
30781 tgttgatgga cgtattaaaa aagaagatag tttaaaaaaa gcaatggagt tattgataaa
30841 gaaaagtgtc actgcttcta tttccttaga ctttgtagcg ttacgtgaac atttcccaga
30901 agctaaccct aaaataggtg atgttgttag agtggtggat tctgccatag gatataacga
30961 cttagtgaga atagtcgaaa tcactacaca tagagatgcg tacaataata tcactaagca
31021 agatgtagta ttaggagact ttacaaggcg taatcgttat aacaaagcag ttcatgatgc
31081 tgcaaattat gttaaaagcg taaaatctac aaaatccgac ccatctaaag aactaaaagc
31141 attaaacgca aaagttaacg caagtttatc tataaataat gaattggtta agcagaatga
31201 aaaaataaac gctaaagtcg ataagatgaa tactaaaaca gttacaactg ctaatggtac
31261 gatcatgtac gactttacta gtcaatcaag tataagaaac atcaaatcaa ttggaacgat
31321 tggcgactct gtagctagag ggtcgcacgc aaaaactaat ttcacagaaa tgttaggcaa
31381 gaaattgaaa gctaaaacga ctaatcttgc aagaggtggc gcaacaatgg caacagttcc
31441 aataggtaaa gaagcggtag aaaacagcat ttatagacaa gcagagcaaa taagaggaga
31501 cctaatcata ttacaaggca ctgatgatga ctggttacac ggttattggg caggcgtacc
31561 gataggcact gataaaacgg atacaaaaac gttttacggt gccttttgtt ctgcaattga
31621 agttattaga aagaataatc cagattcaaa aatactagtg atgacagcta caagacaatg
31681 ccctatgagt ggtacaacaa tacgccgtaa agacacggac aaaaacaaac tagggttaac
31741 acttgaggac tatgtaaacg ctcaaatatt agcttgtagt gagttagatg taccagtgtt
31801 tgacgcatat cacacagatt actttaagcc atacaatcca gcttttagga aagcgagcat
31861 ggaggacggc ttacacccta acgaaaaagg tcacgaggtt attatgtacg agttaatcaa
31921 ggattattac agtttttacg actaaaggag gcaaccaatg gcttacggat taattacaag
31981 tttacattca atgacaggtc ggaaaatagt tgctcaacat gagtataact atcgcttgtt
32041 agatgaaggt atgagcaaac ttgagaaaat gtttatatac catcaaaaag aagaaatata
32101 cgcacactca gcgaaacaaa ttaaatactt gaatgacagt gttgaagatt atttaacgta
32161 tttaaatagc cgttttagca atatgattct aggccataac ggcgacggta tcaatgaagt
32221 aaaagacgcg cgtattgata atacaggtta tggtcataag acattgcaag atcgtttgta
32281 tcatgattat tcaacactag atgctttcac taaaaaggtt gagaaagctg tagatgaaca
32341 ctataaagaa tatcgagcga cagaataccg attcgaacca aaagagcaag aaccggaatt
32401 tatcactgat ttatcgccat atacaaatgc agtaatgcaa tcattttggg tagaccctag
32461 aacgaaaatt atttatatga cgcaagctcg tccaggtaat cattacatgt tatctagatt
32521 gaagcccaac ggacaattta ttgatagatt gcttgttaaa aacggcggtc acggtacaca
32581 caatgcgtat agatacattg atggagaatt atggatttat tcagctgtat tggacagtaa
32641 caaaaacaac aagtttgtac gtttccaata tagaactgga gaaataactt atggtaatga
32701 aatgcaagat gtcatgccga atatatttaa cgacagatat acgtcagcga tttataatcc
32761 tatagaaaat ttaatgattt tcagacgtga atataaagct tctgaaagac aagctaagaa
32821 ttcattgaat ttcattgaag taagaagtgc tgacgatatt gataaaggta tagacaaagt
32881 attgtatcaa atggatatac ctatggaata cacttcagat acacaaccta tgcaaggtat
32941 cacttatgat gcaggtatct tatattggta tacaggtgat tcgaatacag ccaaccctaa
33001 ctacttacaa ggtttcgata taaaaacaaa agaattgtta tttaaacgac gtatcgatat
33061 tggcggtgtg aataataact ttaaaggaga cttccaagaa gctgagggtc tagatatgta
33121 ttacgatcta gaaacaggac gtaaagcact tttaataggg gtaactattg gacctggtaa
33181 taacagacat cactcaattt attctatcgg ccaaagaggt gttaaccaat tcttaaaaaa
33241 cattgcacct caagtatcga tgactgattc aggtggacgt gttaaaccgt taccaataca
33301 gaacccagca tatctaagtg atattacgga agttggtcat tactatatct atacgcaaga
33361 cacacaaaat gcattagatt tcccgttacc gaaagcgttt agagatgcag ggtggttctt
33421 ggatgtactg cctggacact ataatggtgc tctaagacaa gtacttacca gaaacagcac
33481 aggtagaaat atgcttaaat tcgaacgtgt cattgacatt ttcaataaga aaaacaacgg
33541 agcatggaat ttctgtccgc aaaacgccgg ttattgggaa catatcccta agagtattac
33601 aaaattatca gatttaaaaa tcgttggttt agatttctat atcactactg aagaatcaaa
33661 acgatttact gattttccta aagactttaa aggtattgca ggttggatat tagaagtaaa
33721 atcgaataca ccaggtaaca caacacaagt attaagacgt aataacttcc cgtctgcaca
33781 tcaattttta gttagaaact ttggtactgg tggcgttggt aaatggagtt tattcgaagg
33841 aaaggtggtt gaataatgat agtagataat ttttcgaaag acgataactt aatcgagtta
33901 caaacaacat cacaatataa tccaattatt gacacaaaca tcagtttcta tgaatcagat
33961 agaggaactg gtgttttaaa ttttgcagta actaagaata acagaccgtt atctataagt
34021 tctgaacatg ttaaaacatc tatcgtgtta aaaaccgatg attataacgt agatagaggc 34081 gcttatattt cagacgaatt aacgatagta gacgcaatta atgggcgttt gcagtatgtg
34141 ataccgaatg aatttttaaa acattcaggc aaggtgcatg ctcaggcatt ctttacacaa
34201 aacgggagta ataatgttgt tgttgaacgt caatttagct tcaatattga aaatgattta
34261 gttagtgggt ttgatggtat aacaaagctt gtttatatca aatctattca agatactatc
34321 gaagcagtcg gtaaagactt taaccaatta aagcaagata tggatgatac acaaacgtta
34381 atagcaaaag tgaatgatag tgcgacaaaa ggcattcaac aaatcgaaat caagcaaaac
34441 gaagctatac aagctattac tgcgacgcaa actagtgcaa cacaagctgt tacagctgaa
34501 gtcgataaaa tagttgaaaa agagcaagcg atttttgaac gtgttaacga agttgaacaa
34561 caaatcaatg gcgctgacct tgttaaaggt aattcaacaa caaattggca aaagtctaaa
34621 cttacagatg attacggtaa agcaattgaa tcgtatgagc agtccataga tagcgtttta
34681 agcgcagtta acacatctag gattattcat attactaatg caacagatgc gccagaaaag
34741 acggatatag gcacgttaga gaagcctgga caagatggtg ttgatgacgg ttcttcgttc
34801 gatgaatcaa cttatacatc aagcaaatct ggtgtgttag ttgtttatgt tgttgataat
34861 aatactgctc gtgcaacatg gtacccagac gattcaaacg atgagtacac aaaatacaaa
34921 atctacggca catggtaccc gttttataaa aagaatgatg gaaacttaac taagcaattt
34981 gttgaagaaa cgtctaacaa cgctttaaat caagctaagc agtatgtaga tgataaattc
35041 ggaacaacga gctggcaaca acataagatg acagaggcga atggtcaatc aattcaagtt
35101 aacttaaata atgcgcaagg cgatttggga tatttaactg ctggtaatta ctatgcaaca
35161 agagtgccgg atttaccagg tagtgttgaa agttatgagg gttatttatc ggtattcgtt
35221 aaagacgata caaacaagct atttaacttc acgccttata actctaaaaa gatttacaca
35281 cgatcaatca caaacggcag acttgagcaa cagtggacag ttcctaatga acataagtca
35341 acggtattgt tcgacggtgg agcaaatggt gtaggtacaa caatcaatct aaccgaacca
35401 tacacaaact attctatttt attagtaagt ggaacttatc caggtggcgt tattgaggga
35461 ttcggactaa ccacattacc taatgcaatt caattaagta aagcgaatgt agttgactca
35521 gacggtaacg gtggcggtat ttatgagtgt ttactatcca aaacaagtag cactacttta
35581 agaatcgata acgatgtgta ctttgattta ggtaaaacat caggttctgg agcgaatgcc
35641 aacaaagtta ctataactaa aattatgggg tggaaataat gaaaatcaca gtaaatgata
35701 aaaatgaagt tatcggatac gttaatactg gcggtttacg caatagttta gatgtagacg
35761 ataacaatgt gtctatcaaa ttcaaagaag agttcgaacc tagaaagttc gttttcacta
35821 acggcgaaat taaatacaat agcaatttcg aaaaagaaga cgtaccgaat gcatcaaacc
35881 aacaaagtgc gtcagattta agtgatgagg aacttcgcgg aatggttgca agtatgcaaa
35941 tgcagatgac gcaagtgaac atgttgacaa tgcaattgac gcaacaaaac gctatgttaa
36001 cacaacagtt gaccgaactg aaaactaaca aaacaaatac tgaggggac gtttaaatga
36061 tgaagatgat ttatccaact tttaaagaca ttaaaacttt ttatgtgtgg ggttgctata
36121 aaaatgagca aattaagtgg tacgtagaca tgggtgtaat cgacaaagaa gaatatgcat
36181 tgatcactgg tgaaaaatat ccagaggcaa aagatgaaaa gtcacaggtg taatgcttga
36241 ggctttttaa tttaacacaa agtaggtggc gtaatgtttg gatttaccaa acggcacgaa
36301 catgaatggc gaattagaag attagaagag aatgataaaa caatgcttag cactctcaat
36361 gagattaaat taggtcaaaa aactcaagag caagttaaca ttaaattaga taaaacttta
36421 gatgctatcc agagggaaag acagatagac gaaaaaaata agaaagaaaa cgacaaaaat
36481 atacgcgata tgaaaatgtg gattctcggt ttgataggga ctatcttcag tacgattgtc
36541 atagctttac taagaactat ttttggtatt taaaggaggt gattaccatg cttaaaggga
36601 ttttaggata tagcttctgg gcgtgcttct ggtttggtaa atgtaaataa cagttaagag
36661 tcagtgcttc ggcactggct ttttattttg attgaaatga ggtgcataca tgggattacc
36721 taacccaaag actagaaagc ctacagctag tgaagtggtg gagtgggcaa agtcgaatat
36781 tggtaagagg attaatatag ataattatcg gggcagtcaa tgttgggata cacctaactt
36841 tatttttaaa agatattggg gttttgtaac atggggcaat gctaaggata tggctaatta
36901 cagatatcct aagggtttcc gattctatcg ttattcatct ggatttgtac cggaacctgg
36961 agacatcgca gtttggcacc ctggcaacgg aataggttcg gacggacaca ccgcaatagt
37021 agtaggacca tctaataaaa gttattttta tagcgttgac caaaactggg ttaattctaa
37081 tagttggaca ggttctccag gaagattagt aagacaccct tatgtaagtg ttacaggctt
37141 tgttaggcct ccatactcaa aagatactag caaacctagt agtactgata caagttcagc
37201 atcaaaagcc aatgactcaa caattactgg cgaagcgaag aaaccgcaat ttaaagaagt
37261 taaaacagta aaatacactg cttacagcaa tgttttagat aaagaagagc acttcattga
37321 tcatatagtt gtaatgggtg atgaacgctc agatattcaa ggattatata taaaagaatc
37381 aatgcatatg cgttctgtag acgaactgta tacgcaaaga aataagttta taagcgatta
37441 tgaaataccg catttatatg tcgatagaga ggctacatgg cttgctagac caaccaattt 37501 tgatgacccg cgtcacccta attggctagt tattgaagta tgtggtggtc aaacagatag
37561 caaacgacaa ttcttattga atcaaataca agcgttaata cgtggtgttt ggttattgtc
37621 agggattgat aaaaacttat ctgaaacgac gttaaaggta gaccctaata tttggcgtag
37681 tatgaaagat ttaattaatt acgacttgat taagcaaggt ataccggata acgcaaagta
37741 tgagcaagtt aaaaagaaaa tgcttgagac atacattaaa cgagatatat tgacacgaga
37801 aaatataaaa gaagtaacga caaaaacaac aataagaatt agtgataaaa catcagttga
37861 cagtgcgtcc acacgaggcc ctactccatc agacgaaaaa ccaagcatcg ttactgaaac
37921 aagtccattc acattccagc aagcactgga tagacaaatg tctaggggta acccgaaaaa
37981 atctcataca tggggctggg ctaatgcaac acgagcacaa acgagctcgg caatgaatgt
38041 taagcgaata tgggaaagta acacgcaatg ctatcaaatg cttaatttag gcaagtatca
38101 aggcatttca gttagtgcgc ttaacaaaat acttaaagga aaaggaacgc tcgacggaca
38161 aggcaaagca ttcgcggaag cttgtaagaa aaacaacatt aacgaaattt atttgatcgc
38221 gcacgctttc ttagaaagtg gatacggaac aagtaacttc gctagtggta gatacggtgc
38281 atataattac ttcggtattg gtgcattcga caacgaccct gattatgcaa tgacgtttgc
38341 taaaaataaa ggttggacat ctccagcaaa agcaatcatg ggcggtgcta gcttcgtaag
38401 aaaggattac atcaataaag gtcaaaacac attgtaccga attagatgga atcctaagaa
38461 tccagctacc caccaatacg ctactgctat agagtggtgc caacatcaag caagtacaat
38521 cgctaagtta tataaacaaa tcggcttaaa aggtatctac ttcacaaggg ataaatataa
38581 ataaagaggt gtgtaaatgt acaaaataaa agatgttgaa acgagaataa aaaatgatgg
38641 tgttgactta ggtgacattg gctgtcgatt ttacactgaa gatgaaaata cagcatctat
38701 aagaataggt atcaatgaca aacaaggtcg tatcgatcta aaagcacatg gcttaacacc
38761 tagattacat ttgtttatgg aagatggctc tatattcaaa aatgagcccc ttattatcga
38821 cgatgttgta aaagggttcc ttacctacaa aatacctaaa aaggttatca aacacgctgg
38881 ttatgttcgc tgtaagctgt ttttagagaa agaagaagaa aaaatacatg tcgcaaactt
38941 ttctttcaat atcgttgata gtggtattga atctgctgta gcaaaagaaa tcgatgttaa
39001 attggtagat gatgctatta cgagaatttt aaaagataac gcgacagatt tattgagcaa
39061 agactttaaa gagaaaatag ataaagatgt catttcttac atcgaaaaga atgaaagtag
39121 atttaaaggt gcgaaaggtg ataaaggcga accgggacaa cctggtgcga aaggtgatac
39181 aggtaaaaaa ggagaacaag gcgcacccgg taaaaacggt actgtagtat caatcaatcc
39241 tgacactaaa atgtggcaaa ttgatggtaa agatacagat atcaaagcag aacctgagtt
39301 attggacaaa atcaatatcg caaatgttga agggttagaa gataaattgc aagaagttaa
39361 aaaaatcaaa gatacaactc tcaacgactc taaaacgtat acggattcaa aaattgctga
39421 actagttgat agcgcgcctg aatctatgaa tacattaaga gaattagcag aagcaataca
39481 aaacaactct atttcagaaa gtgtattgca acagattggc tcaaaagtta gtacagaaga
39541 ttttgaggaa ttcaaacaaa cactaaacga tttatatgct ccaaaaaatc ataatcatga
39601 tgagcggtat gttttgtcat ctcaagcttt tactaaacaa caagcggata atttatatca
39661 actaaaaagc gcatctcaac cgacggttaa aatttggaca ggaacagaaa atgaatataa
39721 ctatatatat caaaaagacc ctaatacact ttacttaatt aaggggtgat ttttatggaa
39781 ggtaatttta aaaatgtaaa gaagtttatt tacgaaggtg aagaatatac aaaagtatat
39841 gctggaaata tccaagtatg gaaaaagcct tcatcttttg taataaaacc cttacctaaa
39901 aataaatatc cggatagcat agaagaatca acagcaaaat ggacaataaa tggagttgaa
39961 cctaataaaa gttatcaggt gacaatagaa aatgtacgta gcggtataat gagggtttcg
40021 caaactaatt taggttcaag tgatttagga atatcaggag tcaatagcgg agttgcaagt
40081 aaaaatatca actttagtaa tccttcaggg atgttgtatg tcactataag tgatgtttat
40141 tcaggatctc caacattgac cattgaataa ttttaaacga ctaatttttt agtcgttttt
40201 tattttggat aaaaggagca aacaaatgga tgcaaaagta ataacaagat acatcgtatt
40261 gatcttagca ttagtaaatc aattcttagc gaacaaaggt attagcccga ttccagtaga
40321 cgatgagact atatcatcaa taatacttac tgttgttgct ttatatacta cgtataaaga
40381 caatccaaca tctcaagaag gtaaatgggc aaatcaaaag ctaaagaaat ataaagctga
40441 aaacaagtat agaaaagcaa cagggcaagc gccaattaaa gaagtaatga cacctacgaa
40501 tatgaacgac acaaatgatt tagggtaggt gttgaccaat gttgataaca aaaaaccaag
40561 cagaaaaatg gtttgataat tcattaggga agcagttcaa tcctgatttg ttttatggat
40621 ttcagtgtta cgattacgca aatatgtttt ttatgatagc aacaggcgaa aggttacaag
40681 gtttatacgc ttataatatt ccatttgata ataaagcaag gattgaaaaa tacgggcaaa
40741 taattaaaaa ctatgatagc tttttaccgc aaaagttgga tattgtcgtt ttcccgtcaa
40801 agtatggtgg cggagctgga catgttgaaa ttgttgagag cgcaaattta aacactttca
40861 catcatatgg gcaaaattgg aatggtaaag gttggacaaa tggcgttgcg caacctggtt

```
40921 ggggtcctga aactgttaca agacatgttc attattacga tgacccaatg tattttatta
40981 gattaaattt cccagataaa gtaagtgttg gagataaagc taaaagcgtt attaagcaag
41041 caactgccaa aaagcaagca gtaattaaac ctaaaaaaat tatgcttgta gccggtcatg
41101 gttataacga tcctggagca gtaggaaacg gaacaaacga acgcgatttt atccgtaaat
41161 atataacgcc aaatatcgct aagtatttaa gacatgcagg tcatgaagtt gcattatatg
41221 gtggctcaag tcaatcacaa gacatgtatc aagatactgc atacggtgtt aatgtaggaa
41281 ataataaaga ttatggatta tattgggtta aatcacaggg gtatgacatt gttctagaga
41341 ttcatttaga cgcagcagga gaaaatgcaa gtggtgggca tgttattatc tcaagtcaat
41401 tcaatgcgga tactattgat aaaagtatac aagatgttat taaaaataac ttaggacaaa
41461 taagaggtgt aacacctcgt aatgatttac tgaacgttaa tgtatcagca gaaataaata
41521 tcaattatcg tttatctgaa ttaggtttta ttactaataa aaaagatatg gattggatta
41581 agaagaatta tgacttgtat tctaaattaa tagctggtgc gattcatggt aagcctatag
41641 gtggtttggt agctggtaat gttaaaacat cagctaaaaa ccaaaaaaat ccaccagtgc
41701 cagcaggtta tacacttgat aagaataatg tgccttataa aaaagagact ggtaattaca
41761 cagttgccaa tgttaaaggt aataacgtaa gggacggcta ttcaactaat tcaagaatta
41821 caggtgtatt acctaataac gcaacaatca aatatgacgg cgcatattgc atcaatgggt
41881 atagatggat tacttatatt gctaatagtg gacaacgtcg ctatattgcg acaggagagg
41941 tagataaagc aggtaatagg ataagtagtt ttggtaagtt tagcacgatt tagtatttac
42001 ttagaataaa aattttgcta cattaattat agggaatctt acagttatta aataactatt
42061 tggatggatg ttaatattcc tatacacttt ttaacattac tctcaagatt taaatgtaga
42121 taacaggcag gtactacggt acttgcctat tttttgtta taatgtaatt acattaccag
42181 taaccaatct ggcttaaaac cacatttccg gtagccaatc cggctatgca gaggacttac
42241 ttgcgtaaag tagtaagaag ctgactgcat atttaaacca cccatactag ttgctgggtg
42301 gttgtttttt atgttatatt ataaatgatc aaaccacacc acctattaat ttaggagtgt
42361 ggttattttt tatgcaaaaa aaacgaaaaa aagttcataa aaagtattgc atatcacgtt
42421 taaccgtgtt ataataaggt ataccagttg agaggaggat aaaaagtgtt agaaaatttt
42481 aaaactatag cagaaatcgc cttttataca atgtcagcaa ttgccatagc gaaaacattg
42541 aaaaaagacg ataagtaagt agacaagccc gaaagggctg tctatatata aattctaaca
42601 ctaaaatact atgaaaacaa tttacattat tttaatcatt cttatttgga taaacgtgtt
42661 tttaggcaac gatataagta aaagtgttgt tgcactgctt actactttac tgcttatcaa
42721 tttatggaag agggataaaa atgacagcaa taaaagaaat aattgaatca atagaaaagt
42781 tattcgaaaa agaaacggga tataaaattg ctaaaaattc cggattacca tatcaaactg
42841 tgcaagattt aagaaatgga aaaacatctt tatcagatgc cagatttaga acgataataa
42901 agttatacga gtatcaaaga tcgcttgaaa acgaagaaga taaataaaag gagccaaaaa
42961 tatgtttgtt acaaaagaag aatttaaaac tttgaatgta aaagaagtat ttgaatcagg
43021 taaaaacttt ataaaaatta cagatggaag acatgcaata tattgggtaa atgatagata
43081 cgtagtactt gaccataaaa aaggcgattt gtacccgcaa aaagcatacc caaaatatat
43141 caaaagaaaa ttagtaagtt aaataattag aaaaccacgt cttaattgac gtggttattt
43201 tttaggtttg cgcgtgtcaa atacgtgtca atttagttct atttctttag ttttctttct
43261 aaacttaatt gcttgtaaac cgcatagtta taggcttttc agctatatac caagataaga
43321 tttatcccgc cgtctccata aaaatatgct tggaaacctt gatttaatgg ggttttaatc
43381 tagcaagtgt caaatatgtg tcaagaaaat aattttctga cacgttgacc ttgctctttt
43441 ttatgttcat caagtaagtg agagtaggtg tctaaagtta tagatatatt ataatggcct
43501 aatcttttgc taatatattc aataggcata gttataggct tttcagctat ataccaagat
43561 aagatttatc ccgccg
```

Table 6

Physico-chemical parameters for 3AORF033

```
1       MAILEGIFEE LKLLNKNLRV LNTELSTVDS SIVQEKVKEA PMPKDETAQL ESVEEVKETS
61      ADLTKDYVLS VGKEFLKKAD TSDKKEFRNK LNELGADKLS TIKEEHYEKI VDFMNARINA
```

| | |
|---|---|
| **Number of amino acids:** | 120 |
| **Average molecular weight (Daltons):** | 13647.60 |
| **Mean amino acid weight (Daltons):** | 113.73 |
| **Monoisotopic molecular weight (Daltons):** | 13639.11 |
| **Mean amino acid monoisotopic weight (Daltons):** | 113.66 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 8 | 6.67% | 7.58% | Cys | C | 0 | 0.00% | 1.66% |
| Asp | D | 8 | 6.67% | 5.28% | Glu | E | 17 | 14.17% | 6.37% |
| Phe | F | 4 | 3.33% | 4.09% | Gly | G | 3 | 2.50% | 6.84% |
| His | H | 1 | 0.83% | 2.24% | Ile | I | 6 | 5.00% | 5.81% |
| Lys | K | 16 | 13.33% | 5.95% | Leu | L | 14 | 11.67% | 9.42% |
| Met | M | 3 | 2.50% | 2.37% | Asn | N | 7 | 5.83% | 4.45% |
| Pro | P | 2 | 1.67% | 4.9% | Gln | Q | 2 | 1.67% | 3.97% |
| Arg | R | 3 | 2.50% | 5.16% | Ser | S | 8 | 6.67% | 7.12% |
| Thr | T | 7 | 5.83% | 5.67% | Val | V | 9 | 7.50% | 6.58% |
| Trp | W | 0 | 0.00% | 1.23% | Tyr | Y | 2 | 1.67% | 3.18% |

| | | |
|---|---|---|
| **Number of acidic (negative) amino acids (ED):** | 25 | 20.83% |
| **Number of basic (positive) amino acids (KR):** | 19 | 15.83% |
| **Total charge (KRED):** | 44 | 36.67% |
| **Net charge (KR - ED):** | -6 | -5.00% |
| **Theoritical pI:** | 4.74 | |
| **Total linear charge density:** | 0.38 | |

| | |
|---|---|
| **Average hydrophobicity:** | -5.59 |
| **Ratio of hydrophilicity to hydrophobicity:** | 1.45 |
| **Percentage of hydrophilic amino acid:** | 59.17% |
| **Percentage of hydrophobic amino acid:** | 40.83% |
| **Ratio of %hydrophilic to %hydrophobic:** | 1.45 |

Hydrophobicity plot

Kyte-Doolittle scale

```
Ala:   1.800  Arg:  -4.500  Asn:  -3.500
Asp:  -3.500  Cys:   2.500  Gly:  -0.400
Gln:  -3.500  Glu:  -3.500  His:  -3.200
Ile:   4.500  Leu:   3.800  Lys:  -3.900
Met:   1.900  Phe:   2.800  Pro:  -1.600
Ser:  -0.800  Thr:  -0.700  Trp:  -0.900
Tyr:  -1.300  Val:   4.200
```

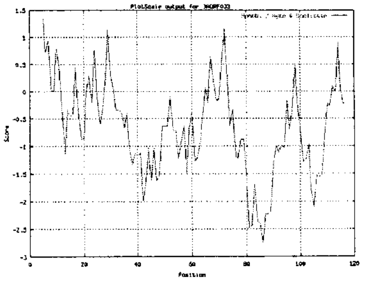

Physico-chemical parameters for 3AORF041

```
1       MFGFTKRHEQ DWRLTRLEEN DKTMFEKFDR IEDSLRTQEK IYDKLDRNFE ELRRDKEEDE
61      KNKEKNAKNI RDIKMWILGL IGTILSTFVI ALLKTIFGI
```

| | |
|---|---|
| **Number of amino acids:** | 99 |
| **Average molecular weight (Daltons):** | 12084.92 |
| **Mean amino acid weight (Daltons):** | 122.07 |
| **Monoisotopic molecular weight (Daltons):** | 12077.32 |
| **Mean amino acid monoisotopic weight (Daltons):** | 121.99 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 2 | 2.02% | 7.58% | Cys | C | 0 | 0.00% | 1.66% |
| Asp | D | 9 | 9.09% | 5.28% | Glu | E | 12 | 12.12% | 6.37% |
| Phe | F | 7 | 7.07% | 4.09% | Gly | G | 4 | 4.04% | 6.84% |
| His | H | 1 | 1.01% | 2.24% | Ile | I | 10 | 10.10% | 5.81% |
| Lys | K | 12 | 12.12% | 5.95% | Leu | L | 10 | 10.10% | 9.42% |
| Met | M | 3 | 3.03% | 2.37% | Asn | N | 5 | 5.05% | 4.45% |
| Pro | P | 0 | 0.00% | 4.9% | Gln | Q | 2 | 2.02% | 3.97% |
| Arg | R | 9 | 9.09% | 5.16% | Ser | S | 2 | 2.02% | 7.12% |
| Thr | T | 7 | 7.07% | 5.67% | Val | V | 1 | 1.01% | 6.58% |
| Trp | W | 2 | 2.02% | 1.23% | Tyr | Y | 1 | 1.01% | 3.18% |

| | | |
|---|---|---|
| **Number of acidic (negative) amino acids (ED):** | 21 | 21.21% |
| **Number of basic (positive) amino acids (KR):** | 21 | 21.21% |
| **Total charge (KRED):** | 42 | 42.42% |
| **Net charge (KR - ED):** | 0 | 0.00% |
| **Theoritical pI:** | 7.53 | |
| **Total linear charge density:** | 0.44 | |

| | |
|---|---|
| **Average hydrophobicity:** | -8.44 |
| **Ratio of hydrophilicity to hydrophobicity:** | 1.72 |
| **Percentage of hydrophilic amino acid:** | 59.60% |
| **Percentage of hydrophobic amino acid:** | 40.40% |
| **Ratio of %hydrophilic to %hydrophobic:** | 1.48 |

Hydrophobicity plot

Kyte-Doolittle scale

```
Ala:   1.800  Arg:  -4.500  Asn:  -3.500
Asp:  -3.500  Cys:   2.500  Gly:  -0.400
Gln:  -3.500  Glu:  -3.500  His:  -3.200
Ile:   4.500  Leu:   3.800  Lys:  -3.900
Met:   1.900  Phe:   2.800  Pro:  -1.600
Ser:  -0.800  Thr:  -0.700  Trp:  -0.900
Tyr:  -1.300  Val:   4.200
```

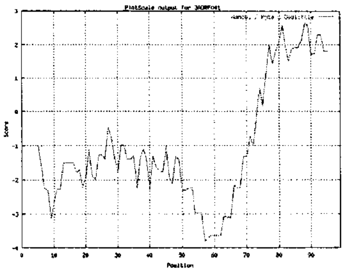

Physico-chemical parameters for 3AORF079

```
1       MQHQAYINAS VDIRIPTEVE SVNYNQIDKE KENLADYLFN NPGELLKYNV INIKVLDLEV
61      E
```

| | |
|---|---|
| Number of amino acids: | 61 |
| Average molecular weight (Daltons): | 7109.00 |
| Mean amino acid weight (Daltons): | 116.54 |
| Monoisotopic molecular weight (Daltons): | 7104.59 |
| Mean amino acid monoisotopic weight (Daltons): | 116.47 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 3 | 4.92% | 7.58% | Cys | C | 0 | 0.00% | 1.66% |
| Asp | D | 4 | 6.56% | 5.28% | Glu | E | 7 | 11.48% | 6.37% |
| Phe | F | 1 | 1.64% | 4.09% | Gly | G | 1 | 1.64% | 6.84% |
| His | H | 1 | 1.64% | 2.24% | Ile | I | 6 | 9.84% | 5.81% |
| Lys | K | 4 | 6.56% | 5.95% | Leu | L | 6 | 9.84% | 9.42% |
| Met | M | 1 | 1.64% | 2.37% | Asn | N | 8 | 13.11% | 4.45% |
| Pro | P | 2 | 3.28% | 4.9% | Gln | Q | 3 | 4.92% | 3.97% |
| Arg | R | 1 | 1.64% | 5.16% | Ser | S | 2 | 3.28% | 7.12% |
| Thr | T | 1 | 1.64% | 5.67% | Val | V | 6 | 9.84% | 6.58% |
| Trp | W | 0 | 0.00% | 1.23% | Tyr | Y | 4 | 6.56% | 3.18% |

| | | |
|---|---|---|
| Number of acidic (negative) amino acids (ED): | 11 | 18.03% |
| Number of basic (positive) amino acids (KR): | 5 | 8.20% |
| Total charge (KRED): | 16 | 26.23% |
| Net charge (KR - ED): | -6 | -9.84% |
| Theoritical pI: | 4.19 | |
| Total linear charge density: | 0.30 | |

| | |
|---|---|
| Average hydrophobicity: | -4.31 |
| Ratio of hydrophilicity to hydrophobicity: | 1.31 |
| Percentage of hydrophilic amino acid: | 54.10% |
| Percentage of hydrophobic amino acid: | 45.90% |
| Ratio of %hydrophilic to %hydrophobic: | 1.18 |

Hydrophobicity plot

Kyte-Doolittle scale

```
Ala:   1.800  Arg:  -4.500  Asn:  -3.500
Asp:  -3.500  Cys:   2.500  Gly:  -0.400
Gln:  -3.500  Glu:  -3.500  His:  -3.200
Ile:   4.500  Leu:   3.800  Lys:  -3.900
Met:   1.900  Phe:   2.800  Pro:  -1.600
Ser:  -0.800  Thr:  -0.700  Trp:  -0.900
Tyr:  -1.300  Val:   4.200
```

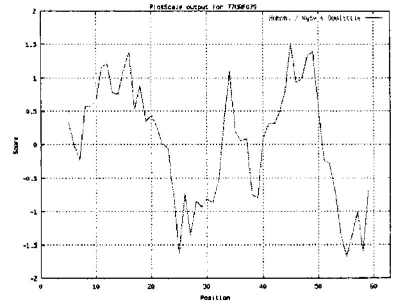

Physico-chemical parameters for 77ORF001

```
1       MGERIKGLSI GLDLDAANLN RSFAEIKRNF KTLNSDLKLT GNNFKYTEKS TDSYKQRIKE
61      LDGTITGYKK NVDDLAKQYD KVSQEQGENS AEAQKLRQEY NKQANELNYL ERELQKTSAE
121     FEEFKKAQVE AQRMAESGWG KTSKVFESMG PKLTKMGDGL KSIGKGLMIG VTAPVLGIAA
181     ASGKAFAEVD KGLDTVTQAT GATGSELKKL QNSFKDVYGN FPADAETVGG VLGEVNTRLG
241     FTGKELENAT ESFLKFSHIT GSDGVQAVQL ITRAMGDAGI EASEYQSVLD MVAKAAQASG
301     ISVDTLADSI TKYGAPMRAM GFEMKESIAL FSQWEKSGVN TEIAFSGLKK AISNWGKAGK
361     NPREEFKKTL AEIEKTPDIA SATSLAIEAF GAKAGPDLAD AIKGGRFSYQ EFLKTIEDSQ
421     GTVNQTFKDS ESGSERFKVA MNKLKLVGAD VWASIESAFA PVMEELIKKL SIAVDWFSNL
481     SDGSKRSIVI FSGIAAAIGP VVFGLGAFIS TIGNAVTVLA PLLASIAKAG GLISFLSTKV
541     PILGTVFTAL TGPIGIVLGV LAGLAVAFTI AYKKSETFRN FVNGAIESVK QTFSNFIQFI
601     QPFVDSVKNI FKQAISAIVD FAKDIWSQIN GFFNENGISI VQALQNICNF IKAIFEFILN
661     FVIKPIMFAI WQVMQFIWPA VKALIVSTWE NIKGVIQGAL NIILGLIKFF SSLFVGDWRG
721     VWDAVVMILK GAVQLIWNLV QLWFVGKILG VVRYFGGLLK GLIAGIWDVI RSIFSKSLSA
781     IWNATKSIFG FLFNSVKSIF TNMKNWLSNT WSSIRTNTIG KAQSLFSGVK SKFTNLWNAT
841     KEIFSNLRNW MSNIWNSIKD NTVGIASRLW SKVRGIFTNM RDGLSSIIDK IKSHIGGMVS
901     AIKKGLNKLI DGLNWVGGKL GMDKIPKLHT GTEHTHTTTR LVKNGKIARD TFATVGDKGR
961     GNGPNGFRNE MIEFPNGKRV ITPNTDTTAY LPKGSKVYNG AQTYSMLNGT LPRFSLGTMW
1021    KDIKSGASSA FNWTKDKIGK GTKWLGDKVG DVLDFMENPG KLLNYILEAF GIDFNSLTKG
1081    MGIAGDITKA AWSKIKKSAT DWIKENLEAM GGGDLVGGIL DPDKINYHYG RTAAYTAATG
1141    RPFHEGVDFP FVYQEVRTPM GGRLTRMPFM SGGYGNYVKI TSGVIDMLFA HLKNFSKSPP
1201    SGTMVKPGDV VGLTGNTGFS TGPHLHFEMR RNGRHFDPEP YLRNAKKKGR LSIGGGGATS
1261    GSGATYASRV IRQAQSILGG RYKGKWIHDQ MMRVAKRESN YQSNAVNNWD INAQRGDPSR
1321    GLFQIIGSTF RANAKRGYTN FNNPVHQGIS AMQYIVRRYG WGGFKRAGDY AYATGGKVFD
1381    GWYNLGEDGH PEWIIPTDPA RRNDAMKILH YAAAEVRGKK ASKNKRPSQL SDLNGFDDPS
1441    LLLKMIEQQQ QQIALLLKIA QSNDVIADKD YQPIIDEYAF DKKVNASIEK RERQESTKVK
1501    FRKGGIAIQ
```

| | |
|---|---|
| **Number of amino acids:** | 1509 |
| **Average molecular weight (Daltons):** | 165404.34 |
| **Mean amino acid weight (Daltons):** | 109.61 |
| **Monoisotopic molecular weight (Daltons):** | 165299.76 |
| **Mean amino acid monoisotopic weight (Daltons):** | 109.54 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 128 | 8.48% | 7.58% | Cys | C | 1 | 0.07% | 1.66% |
| Asp | D | 71 | 4.71% | 5.28% | Glu | E | 68 | 4.51% | 6.37% |
| Phe | F | 84 | 5.57% | 4.09% | Gly | G | 156 | 10.34% | 6.84% |
| His | H | 15 | 0.99% | 2.24% | Ile | I | 120 | 7.95% | 5.81% |
| Lys | K | 133 | 8.81% | 5.95% | Leu | L | 110 | 7.29% | 9.42% |
| Met | M | 37 | 2.45% | 2.37% | Asn | N | 85 | 5.63% | 4.45% |
| Pro | P | 41 | 2.72% | 4.9% | Gln | Q | 53 | 3.51% | 3.97% |
| Arg | R | 58 | 3.84% | 5.16% | Ser | S | 111 | 7.36% | 7.12% |
| Thr | T | 85 | 5.63% | 5.67% | Val | V | 86 | 5.70% | 6.58% |
| Trp | W | 32 | 2.12% | 1.23% | Tyr | Y | 35 | 2.32% | 3.18% |

| | | |
|---|---|---|
| **Number of acidic (negative) amino acids (ED):** | 139 | 9.21% |
| **Number of basic (positive) amino acids (KR):** | 191 | 12.66% |
| **Total charge (KRED):** | 330 | 21.87% |
| **Net charge (KR - ED):** | 52 | 3.45% |
| **Theoritical pI:** | 10.01 | |
| **Total linear charge density:** | 0.22 | |

| | |
|---|---|
| **Average hydrophobicity:** | -1.92 |
| **Ratio of hydrophilicity to hydrophobicity:** | 1.16 |
| **Percentage of hydrophilic amino acid:** | 47.71% |
| **Percentage of hydrophobic amino acid:** | 52.29% |
| **Ratio of %hydrophilic to %hydrophobic:** | 0.91 |
Hydrophobicity plot
Kyte-Doolittle scale
| | | | | | |
|---|---|---|---|---|---|
| Ala: | 1.800 | Arg: | -4.500 | Asn: | -3.500 |
| Asp: | -3.500 | Cys: | 2.500 | Gly: | -0.400 |
| Gln: | -3.500 | Glu: | -3.500 | His: | -3.200 |
| Ile: | 4.500 | Leu: | 3.800 | Lys: | -3.900 |
| Met: | 1.900 | Phe: | 2.800 | Pro: | -1.600 |
| Ser: | -0.800 | Thr: | -0.700 | Trp: | -0.900 |
| Tyr: | -1.300 | Val: | 4.200 | | |
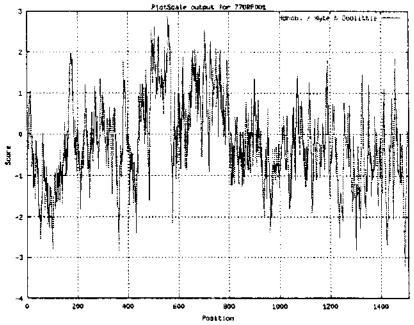

Physico-chemical parameters for 96ORF048

```
1       MYYKIGEIKN KIISFNGFEF KVSVMKRHDG ISIQIKDMNN VPLKSFHVID LSELYIATDA
61      MRDVINEWIE NNTDEQDKLI NLVMKW
```

| | |
|---|---|
| Number of amino acids: | 86 |
| Average molecular weight (Daltons): | 10180.84 |
| Mean amino acid weight (Daltons): | 118.38 |
| Monoisotopic molecular weight (Daltons): | 10174.18 |
| Mean amino acid monoisotopic weight (Daltons): | 118.30 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 2 | 2.33% | 7.58% | Cys | C | 0 | 0.00% | 1.66% |
| Asp | D | 7 | 8.14% | 5.28% | Glu | E | 6 | 6.98% | 6.37% |
| Phe | F | 4 | 4.65% | 4.09% | Gly | G | 3 | 3.49% | 6.84% |
| His | H | 2 | 2.33% | 2.24% | Ile | I | 12 | 13.95% | 5.81% |
| Lys | K | 9 | 10.47% | 5.95% | Leu | L | 5 | 5.81% | 9.42% |
| Met | M | 5 | 5.81% | 2.37% | Asn | N | 8 | 9.30% | 4.45% |
| Pro | P | 1 | 1.16% | 4.9% | Gln | Q | 2 | 2.33% | 3.97% |
| Arg | R | 2 | 2.33% | 5.16% | Ser | S | 5 | 5.81% | 7.12% |
| Thr | T | 2 | 2.33% | 5.67% | Val | V | 6 | 6.98% | 6.58% |
| Trp | W | 2 | 2.33% | 1.23% | Tyr | Y | 3 | 3.49% | 3.18% |

| | | |
|---|---|---|
| Number of acidic (negative) amino acids (ED): | 13 | 15.12% |
| Number of basic (positive) amino acids (KR): | 11 | 12.79% |
| Total charge (KRED): | 24 | 27.91% |
| Net charge (KR - ED): | -2 | -2.33% |
| Theoritical pI: | 5.50 | |
| Total linear charge density: | 0.30 | |

| | |
|---|---|
| Average hydrophobicity: | -2.60 |
| Ratio of hydrophilicity to hydrophobicity: | 1.18 |
| Percentage of hydrophilic amino acid: | 51.16% |
| Percentage of hydrophobic amino acid: | 48.84% |
| Ratio of %hydrophilic to %hydrophobic: | 1.05 |

Hydrophobicity plot

Kyte-Doolittle scale

```
Ala:   1.800  Arg:  -4.500  Asn:  -3.500
Asp:  -3.500  Cys:   2.500  Gly:  -0.400
Gln:  -3.500  Glu:  -3.500  His:  -3.200
Ile:   4.500  Leu:   3.800  Lys:  -3.900
Met:   1.900  Phe:   2.800  Pro:  -1.600
Ser:  -0.800  Thr:  -0.700  Trp:  -0.900
Tyr:  -1.300  Val:   4.200
```

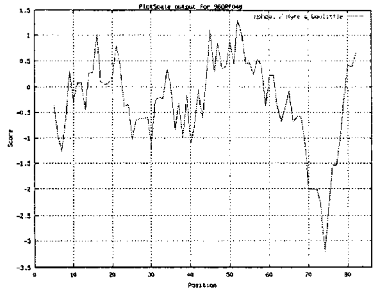

Physico-chemical parameters for 96ORF078

```
1        MNIMQFKSLL KSMYEETKQS DPIVANVYIE TGWAVNRLLD NNELSPFDDY DRVEKKIMNE
61       INWKKTHIKE C
```

| | |
|---|---|
| **Number of amino acids:** | 71 |
| **Average molecular weight (Daltons):** | 8497.77 |
| **Mean amino acid weight (Daltons):** | 119.69 |
| **Monoisotopic molecular weight (Daltons):** | 8492.19 |
| **Mean amino acid monoisotopic weight (Daltons):** | 119.61 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 2 | 2.82% | 7.58% | Cys | C | 1 | 1.41% | 1.66% |
| Asp | D | 5 | 7.04% | 5.28% | Glu | E | 7 | 9.86% | 6.37% |
| Phe | F | 2 | 2.82% | 4.09% | Gly | G | 1 | 1.41% | 6.84% |
| His | H | 1 | 1.41% | 2.24% | Ile | I | 6 | 8.45% | 5.81% |
| Lys | K | 8 | 11.27% | 5.95% | Leu | L | 5 | 7.04% | 9.42% |
| Met | M | 4 | 5.63% | 2.37% | Asn | N | 7 | 9.86% | 4.45% |
| Pro | P | 2 | 2.82% | 4.9% | Gln | Q | 2 | 2.82% | 3.97% |
| Arg | R | 2 | 2.82% | 5.16% | Ser | S | 4 | 5.63% | 7.12% |
| Thr | T | 3 | 4.23% | 5.67% | Val | V | 4 | 5.63% | 6.58% |
| Trp | W | 2 | 2.82% | 1.23% | Tyr | Y | 3 | 4.23% | 3.18% |

| | | |
|---|---|---|
| **Number of acidic (negative) amino acids (ED):** | 12 | 16.90% |
| **Number of basic (positive) amino acids (KR):** | 10 | 14.08% |
| **Total charge (KRED):** | 22 | 30.99% |
| **Net charge (KR - ED):** | -2 | -2.82% |
| **Theoritical pI:** | 5.11 | |
| **Total linear charge density:** | 0.34 | |

| | |
|---|---|
| **Average hydrophobicity:** | -6.96 |
| **Ratio of hydrophilicity to hydrophobicity:** | 1.60 |
| **Percentage of hydrophilic amino acid:** | 57.75% |
| **Percentage of hydrophobic amino acid:** | 42.25% |
| **Ratio of %hydrophilic to %hydrophobic:** | 1.37 |

Hydrophobicity plot

Kyte-Doolittle scale

```
Ala:   1.800  Arg:  -4.500  Asn:  -3.500
Asp:  -3.500  Cys:   2.500  Gly:  -0.400
Gln:  -3.500  Glu:  -3.500  His:  -3.200
Ile:   4.500  Leu:   3.800  Lys:  -3.900
Met:   1.900  Phe:   2.800  Pro:  -1.600
Ser:  -0.800  Thr:  -0.700  Trp:  -0.900
Tyr:  -1.300  Val:   4.200
```

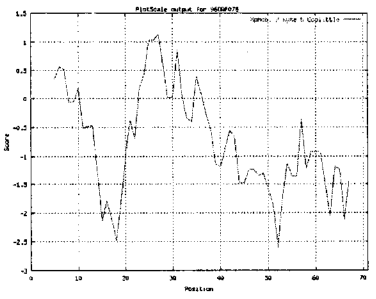

Physico-chemical parameters for 96ORF100

```
1       MQQQAYINAT IDIRIPTEVE YQHYDDVDKE KDTLAKRLDD NPDELLKYDN ITIRHAYIEV
61      E
```

| | |
|---|---|
| **Number of amino acids:** | 61 |
| **Average molecular weight (Daltons):** | 7311.08 |
| **Mean amino acid weight (Daltons):** | 119.85 |
| **Monoisotopic molecular weight (Daltons):** | 7306.58 |
| **Mean amino acid monoisotopic weight (Daltons):** | 119.78 |

Amino acid composition

| Acid | Symbol | Number | % | Average % in Swissprot | Acid | Symbol | Number | % | Average % in Swissprot |
|---|---|---|---|---|---|---|---|---|---|
| Ala | A | 4 | 6.56% | 7.58% | Cys | C | 0 | 0.00% | 1.66% |
| Asp | D | 9 | 14.75% | 5.28% | Glu | E | 6 | 9.84% | 6.37% |
| Phe | F | 0 | 0.00% | 4.09% | Gly | G | 0 | 0.00% | 6.84% |
| His | H | 2 | 3.28% | 2.24% | Ile | I | 7 | 11.48% | 5.81% |
| Lys | K | 4 | 6.56% | 5.95% | Leu | L | 4 | 6.56% | 9.42% |
| Met | M | 1 | 1.64% | 2.37% | Asn | N | 3 | 4.92% | 4.45% |
| Pro | P | 2 | 3.28% | 4.9% | Gln | Q | 4 | 6.56% | 3.97% |
| Arg | R | 3 | 4.92% | 5.16% | Ser | S | 0 | 0.00% | 7.12% |
| Thr | T | 4 | 6.56% | 5.67% | Val | V | 3 | 4.92% | 6.58% |
| Trp | W | 0 | 0.00% | 1.23% | Tyr | Y | 5 | 8.20% | 3.18% |

| | | |
|---|---|---|
| **Number of acidic (negative) amino acids (ED):** | 15 | 24.59% |
| **Number of basic (positive) amino acids (KR):** | 7 | 11.48% |
| **Total charge (KRED):** | 22 | 36.07% |
| **Net charge (KR - ED):** | -8 | -13.11% |
| **Theoritical pI:** | 4.20 | |
| **Total linear charge density:** | 0.39 | |

| | |
|---|---|
| **Average hydrophobicity:** | -9.28 |
| **Ratio of hydrophilicity to hydrophobicity:** | 1.83 |
| **Percentage of hydrophilic amino acid:** | 60.66% |
| **Percentage of hydrophobic amino acid:** | 39.34% |
| **Ratio of %hydrophilic to %hydrophobic:** | 1.54 |

Hydrophobicity plot

Kyte-Doolittle scale

```
Ala:   1.800  Arg:  -4.500  Asn:  -3.500
Asp:  -3.500  Cys:   2.500  Gly:  -0.400
Gln:  -3.500  Glu:  -3.500  His:  -3.200
Ile:   4.500  Leu:   3.800  Lys:  -3.900
Met:   1.900  Phe:   2.800  Pro:  -1.600
Ser:  -0.800  Thr:  -0.700  Trp:  -0.900
Tyr:  -1.300  Val:   4.200
```

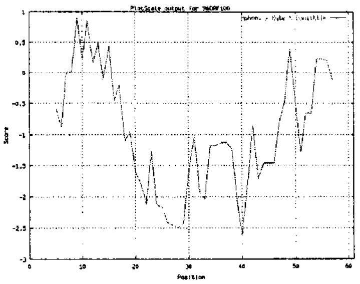

Table 7

1: AF228662
Staphylococcus aureus putative undecaprenol kinase (bacA) gene, complete cds
gi|8895762|gb|AF228662.1|AF228662[8895762]

2: AC027138
Staphylococcus aureus clone sabac-9, complete sequence
gi|8671928|gb|AC027138.9|AC027138[8671928]

3: AC025591
Staphylococcus aureus clone sabac-134, complete sequence
gi|8570488|gb|AC025591.7|AC025591[8570488]

4: AJ005352
Staphylococcus aureus, Sst putative iron transport operon
gi|3724154|emb|AJ005352.1|SAA005352[3724154]

5: AF156894
Staphylococcus aureus enterotoxin I (sei) gene, partial cds, and enterotoxin I-enterotoxin G intergenic spacer region
gi|8885989|gb|AF156894.1|AF156894[8885989]

6: AC025948
Staphylococcus aureus clone sabac-101, WORKING DRAFT SEQUENCE, 2 ordered pieces
gi|8671927|gb|AC025948.8|AC025948[8671927]

7: AJ243541
Cloning vector pAMY-em1 cat, amyL and ermAM genes
gi|5459335|emb|AJ243541.1|CVE243541[5459335]

8: AJ290973
Staphylococcus aureus map-ND2C gene
gi|8648964|emb|AJ290973.1|SAU290973[8648964]

9: AC025592
Staphylococcus aureus clone sabac-43, WORKING DRAFT SEQUENCE, 2 unordered pieces
gi|8573065|gb|AC025592.7|AC025592[8573065]

10: AC069081
Staphylococcus aureus clone sabac-47, WORKING DRAFT SEQUENCE, 1 ordered pieces
gi|8570490|gb|AC069081.4|AC069081[8570490]

11: AC025950
Staphylococcus aureus clone sabac-130, WORKING DRAFT SEQUENCE, 2 ordered pieces
gi|8570487|gb|AC025950.7|AC025950[8570487]

12: AC027137
Staphylococcus aureus clone sabac-123, WORKING DRAFT SEQUENCE, 1 ordered pieces
gi|8567823|gb|AC027137.6|AC027137[8567823]

13: AC027136
Staphylococcus aureus clone sabac-106, WORKING DRAFT SEQUENCE, 1 ordered pieces
gi|8567822|gb|AC027136.5|AC027136[8567822]

14: AC069311
Staphylococcus aureus clone sabac-4, WORKING DRAFT SEQUENCE, 2 ordered pieces
gi|8314320|gb|AC069311.3|AC069311[8314320]

15: AC025951
Staphylococcus aureus clone sabac-32, WORKING DRAFT SEQUENCE, 4 ordered pieces
gi|8225130|gb|AC025951.3|AC025951[8225130]

16: AC025949
Staphylococcus aureus clone sabac-114, complete sequence gi|8225127|gb|AC025949.4|AC025949[8225127]

17: AC061959
Staphylococcus aureus clone sabac-10, WORKING DRAFT SEQUENCE, 1 ordered pieces
gi|8225109|gb|AC061959.4|AC061959[8225109]

18: AF189239
Staphylococcus aureus repressor of toxins Rot (rot) gene, complete cds
gi|8121120|gb|AF189239.2|AF189239[8121120]

19: AF259960
Staphylococcus aureus major cold shock protein CspA (cspA) gene, complete cds
gi|8101859|gb|AF259960.1|AF259960[8101859]

20: AF255950
Staphylococcus aureus AgrD signal peptide precursor (agrD) gene, complete cds
gi|8099633|gb|AF255950.1|AF255950[8099633]

21: AF223920
Staphylococcus aureus isolate SMI46 genomic sequence
gi|6980066|gb|AF223920.1|AF223920[6980066]

22: AF223919
Staphylococcus aureus isolate SMI44 genomic sequence
gi|6980065|gb|AF223919.1|AF223919[6980065]

23: AF223918
Staphylococcus aureus isolate SMI43 genomic sequence
gi|6980064|gb|AF223918.1|AF223918[6980064]

24: AF223917
Staphylococcus aureus isolate SMI40 genomic sequence
gi|6980063|gb|AF223917.1|AF223917[6980063]

25: AF223916
Staphylococcus aureus isolate SMI35 genomic sequence
gi|6980062|gb|AF223916.1|AF223916[6980062]

26: AF223915
Staphylococcus aureus isolate SMI33 genomic sequence
gi|6980061|gb|AF223915.1|AF223915[6980061]

27: AF223914
Staphylococcus aureus isolate SMI32 genomic sequence
gi|6980060|gb|AF223914.1|AF223914[6980060]

28: AF223913
Staphylococcus aureus isolate SMI29 genomic sequence
gi|6980059|gb|AF223913.1|AF223913[6980059]

29: AF223912
Staphylococcus aureus isolate SMI27 genomic sequence
gi|6980058|gb|AF223912.1|AF223912[6980058]

30: AF223911
Staphylococcus aureus isolate SMI26 genomic sequence
gi|6980057|gb|AF223911.1|AF223911[6980057]

31: AF223910
Staphylococcus aureus isolate SMI25 genomic sequence
gi|6980056|gb|AF223910.1|AF223910[6980056]

32: AF223909
Staphylococcus aureus isolate SMI24 genomic sequence gi|6980055|gb|AF223909.1|AF223909[6980055]

33: AF223908
Staphylococcus aureus isolate SMI20 genomic sequence
gi|6980054|gb|AF223908.1|AF223908[6980054]

34: AF223907
Staphylococcus aureus isolate SMI19 genomic sequence
gi|6980053|gb|AF223907.1|AF223907[6980053]

35: AF223906
Staphylococcus aureus isolate SMI18 genomic sequence
gi|6980052|gb|AF223906.1|AF223906[6980052]

36: AF223905
Staphylococcus aureus isolate SMI17 genomic sequence
gi|6980051|gb|AF223905.1|AF223905[6980051]

37: AF223904
Staphylococcus aureus isolate SMI16 genomic sequence
gi|6980050|gb|AF223904.1|AF223904[6980050]

38: AF223903
Staphylococcus aureus isolate SMI15 genomic sequence
gi|6980049|gb|AF223903.1|AF223903[6980049]

39: AF223902
Staphylococcus aureus isolate SMI13 genomic sequence
gi|6980048|gb|AF223902.1|AF223902[6980048]

40: AF223901
Staphylococcus aureus isolate SMI12 genomic sequence
gi|6980047|gb|AF223901.1|AF223901[6980047]

41: AF223900
Staphylococcus aureus isolate SMI09 genomic sequence
gi|6980046|gb|AF223900.1|AF223900[6980046]

42: AF223899
Staphylococcus aureus isolate SMI08 genomic sequence
gi|6980045|gb|AF223899.1|AF223899[6980045]

43: AF223898
Staphylococcus aureus isolate SMI07 genomic sequence
gi|6980044|gb|AF223898.1|AF223898[6980044]

44: AF223897
Staphylococcus aureus isolate SMI06 genomic sequence
gi|6980043|gb|AF223897.1|AF223897[6980043]

45: AF223896
Staphylococcus aureus isolate SMI05 genomic sequence
gi|6980042|gb|AF223896.1|AF223896[6980042]

46: AF223895
Staphylococcus aureus isolate SMI04 genomic sequence
gi|6980041|gb|AF223895.1|AF223895[6980041]

47: AF223894
Staphylococcus aureus isolate SMI02 genomic sequence
gi|6980040|gb|AF223894.1|AF223894[6980040]

48: AF223893
Staphylococcus aureus isolate SMI01 genomic sequence gi|6980039|gb|AF223893.1|AF223893[6980039]

49: AB042839
Staphylococcus aureus sai-2 gene for secretory protein SAI-B, complete cds
gi|7959130|dbj|AB042839.1|AB042839[7959130]

50: AB033232
Staphylococcus aureus genes for KdpA homolog, KdpB homolog, KdpC homolog, hypothetical protein, staphylokinase, TagA homolog, TagH homolog, TagG homolog, complete cds
gi|7670319|dbj|AB033232.1|AB033232[7670319]

51: AF260326
Staphylococcus aureus SrrA (srrA) and SrrB (srrB) genes, complete cds
gi|7839532|gb|AF260326.1|AF260326[7839532]

52: L43098
Transposon Tn5404 and insertion sequences IS1181 and IS1182 (from Staphylococcus aureus) DNA
gi|1280355|gb|L43098.1|INSTN5405R[1280355]

53: L43082
Transposon Tn5405 and insertion sequence IS1182 (from Staphylococcus aureus) ORFA and transposase gene, complete cds
gi|1280353|gb|L43082.1|INSTN5405L[1280353]

54: AF144682
Staphylococcus aureus immunodominant antigen B (isaB) gene, complete cds
gi|7672994|gb|AF144682.1|AF144682[7672994]

55: AF144681
Staphylococcus aureus immunodominant antigen A (isaA) gene, complete cds
gi|7672992|gb|AF144681.1|AF144681[7672992]

56: AF142103
Staphylococcus aureus strain HU106 hypervariable region sequence
gi|7672714|gb|AF142103.1|AF142103[7672714]

57: AF142102
Staphylococcus aureus strain HU41 hypervariable region sequence
gi|7672713|gb|AF142102.1|AF142102[7672713]

58: AF142101
Staphylococcus aureus strain HU101 hypervariable region sequence
gi|7672712|gb|AF142101.1|AF142101[7672712]

59: AF142100
Staphylococcus aureus methicillin-resistance MecR1 protein (mecR1) gene, partial sequence
gi|7672711|gb|AF142100.1|AF142100[7672711]

60: AB033763
Staphylococcus aureus DNA, SRImec-I and SCCmec-I region, strain:NCTC10442
gi|7592605|dbj|AB033763.2|AB033763[7592605]

61: D86934
Staphylococcus aureus genes, mec region, partial and complete cds
gi|5360799|dbj|D86934.1|D86934[5360799]

62: AH003057
Staphylococcus aureus dihydrolipoamide acetyltransferase E2 subunit (E25), dihydrolipoamide dehydrogenase E2 subunit (E25), and dihydrolipoamide acetyltransferase E3 subunit (E3) genes, partial cds
gi|152993|gb|AH003057.1|SEG_STADLDE[152993]

63: M73535
Staphylococcus aureus dihydrolipoamide acetyltransferase E2 subunit (E25) and dihydrolipoamide acetyltransferase E3 subunit (E3) genes, partial cds
gi|152992|gb|M73535.1|STADLDE2[152992]

64: M73536
Staphylococcus aureus dihydrolipoamide dehydrogenase E2 subunit (E25) gene, partial cds
gi|152991|gb|M73536.1|STADLDE1[152991]

65: D42143
Staphylococcus aureus hlg2 gene for gamma-hemolysin, complete cds
gi|577646|dbj|D42143.1|STAHLG2[577646]

66: AF121672
Staphylococcus aureus probable endonuclease IV (yqfS) gene, partial cds; and ABC transporter MreA (mreA), ABC transporter MreB (mreB), zinc uptake regulation protein homolog Zur (zur), and superoxide dismutase SodA (sodA) genes, complete cds
gi|7548683|gb|AF121672.3|AF121672[7548683]

67: AF203377
Staphylococcus aureus plasmid pI9789::Tn552 replication-associated protein (orf256) and replication initiation protein (rep) genes, complete cds
gi|7532835|gb|AF203377.1|AF203377[7532835]

68: AF203376
Staphylococcus aureus plasmid pSK1 replication-associated protein (orf245) and replication initiation protein (rep) genes, complete cds
gi|7532832|gb|AF203376.1|AF203376[7532832]

69: Y13639
Staphylococcus aureus pknB gene
gi|7328256|emb|Y13639.1|SAPKNB[7328256]

70: U11702
Staphylococcus aureus D4508 enterotoxin H (seh) gene, complete cds
gi|510691|gb|U11702.1|SAU11702[510691]

71: AB025716
Staphylococcus aureus gene for FmtB, complete cds
gi|7415523|dbj|AB025716.1|AB025716[7415523]

72: AB015223
Staphylococcus aureus gene for FmtB, complete cds
gi|7415417|dbj|AB015223.1|AB015223[7415417]

73: AF135268
Staphylococcus aureus ribonuclease P protein component (rnpA) gene, complete cds
gi|7381166|gb|AF135268.1|AF135268[7381166]

74: AF118839
Staphylococcus aureus iron uptake regulatory protein (fur) gene, complete cds; and site-specific recombinase (XerD) gene, partial cds
gi|6648969|gb|AF118839.1|AF118839[6648969]

75: AF132117
Staphylococcus aureus ferrichrome uptake operon, complete sequence and unknown genes
gi|6470342|gb|AF132117.2|AF132117[6470342]

76: AF195967
Staphylococcus aureus strain ATCC 35556 IcaC (icaC) and Geh (geh) genes, partial cds
gi|7330781|gb|AF195967.1|AF195967[7330781]

77: AF195966
Staphylococcus aureus strain ATCC 12601 IcaC (icaC) and Geh (geh) genes, partial cds
gi|7330778|gb|AF195966.1|AF195966[7330778]

78: AF195965
Staphylococcus aureus strain ATCC 49834 IcaC (icaC) and Geh (geh) genes, partial cds
gi|7330775|gb|AF195965.1|AF195965[7330775]

79: AF195964
Staphylococcus aureus strain 601055 IcaC (icaC) and Geh (geh) genes, partial cds
gi|7330772|gb|AF195964.1|AF195964[7330772]

80: AF195963
Staphylococcus aureus strain ATCC 10832 IcaC (icaC) and Geh (geh) genes, partial cds
gi|7330769|gb|AF195963.1|AF195963[7330769]

81: AF195962
Staphylococcus aureus strain ATCC 12600 UvrA and HprK genes, partial cds
gi|7330766|gb|AF195962.1|AF195962[7330766]

82: AF195961
Staphylococcus aureus strain ATCC 49834 UvrA and HprK genes, partial cds
gi|7330763|gb|AF195961.1|AF195961[7330763]

83: AF195960
Staphylococcus aureus strain DSM 20232 UvrA and HprK genes, partial cds
gi|7330760|gb|AF195960.1|AF195960[7330760]

84: AF195959
Staphylococcus aureus strain ATCC 10832 UvrA and HprK genes, partial cds
gi|7330757|gb|AF195959.1|AF195959[7330757]

85: AF195958
Staphylococcus aureus strain 8325-4 UvrA and HprK genes, partial cds
gi|7330754|gb|AF195958.1|AF195958[7330754]

86: AF195957
Staphylococcus aureus strain 601055 UvrA and HprK genes, partial cds
gi|7330751|gb|AF195957.1|AF195957[7330751]

87: AF210055
Staphylococcus aureus strain CMRSA-1 accessory gene regulator locus, partial sequence
gi|6671348|gb|AF210055.1|AF210055[6671348]

88: AJ132348
Staphylococcus aureus ORF1 and partial ORF2, mutant RUSA164
gi|7328296|emb|AJ132348.1|SAU132348[7328296]

89: AJ131755
Staphylococcus aureus mutL (partial) and mutS (partial) genes
gi|7328293|emb|AJ131755.1|SAU131755[7328293]

90: AJ131754
Staphylococcus aureus ORF1 (partial), ORF2, ORF3, ORF4 and ORF5 (partial)
gi|7328287|emb|AJ131754.1|SAU131754[7328287]

91: Y18632

Staphylococcus aureus lysA gene, partial
gi|7328285|emb|Y18632.1|SAU18632[7328285]

92: Y18631
Staphylococcus aureus mutS gene, partial
gi|7328283|emb|Y18631.1|SAU18631[7328283]

93: Y18630
Staphylococcus aureus ccpA gene, partial
gi|7328281|emb|Y18630.1|SAU18630[7328281]

94: Y14816
Staphylococcus aureus DNA for ORF231, ORF141, ORF470, ORF283, ORF242, ORF215, ORF259
gi|7328273|emb|Y14816.1|SAY14816[7328273]

95: Y14324
Staphylococcus aureus partial ORF292 and ORF271, ORF331 and ORF314
gi|7328268|emb|Y14324.1|SAY14324[7328268]

96: AJ272085
Staphylococcus aureus otc gene for ornithine carbamoyltransferase, strain Newman
gi|7106005|emb|AJ272085.1|SAU272085[7106005]

97: M62650
Staphylococcus aureus blaZ (blaZ) gene, partial cds; blaR1 (blaR1) and blaI (blaI) genes, complete cds; and binR (binR) gene, partial cds
gi|152964|gb|M62650.1|STABLA[152964]

98: AF230358
Staphylococcus aureus delta-haemolysin precurser (hld), accessory gene regulator protein B (agrB), and accessory gene regulator protein D (agrD) genes, complete cds
gi|7239367|gb|AF230358.1|AF230358[7239367]

99: S72488
hemB=porphobilinogen synthase [Staphylococcus aureus, SA1959, Genomic, 1087 nt]
gi|632815|gb|S72488.1|S72488[632815]

100: L11998
Staphylococcus aureus conjugative transfer gene complex (trs)
gi|310606|gb|L11998.1|STATRSC[310606]

101: AB016487
Staphylococcus aureus gene for enterotoxin type Gv, complete cds
gi|4126682|dbj|AB016487.1|AB016487[4126682]

102: AJ271510
Staphylococcus aureus partial pta gene for phosphate actyltransferase allele 15
gi|7162102|emb|AJ271510.1|SAU271510[7162102]

103: AJ271509
Staphylococcus aureus partial pta gene for phosphate actyltransferase allele 14
gi|7162100|emb|AJ271509.1|SAU271509[7162100]

104: AJ271508
Staphylococcus aureus partial pta gene for phosphate actyltransferase allele 13
gi|7162098|emb|AJ271508.1|SAU271508[7162098]

105: AJ271507
Staphylococcus aureus partial pta gene for phosphate actyltransferase allele 12
gi|7162096|emb|AJ271507.1|SAU271507[7162096]

106: AJ271506

Staphylococcus aureus partial pta gene for phosphate actyltransferase allele 11
gi|7162094|emb|AJ271506.1|SAU271506[7162094]

107: AJ271505
Staphylococcus aureus partial pta gene for phosphate actyltransferase allele 10
gi|7162092|emb|AJ271505.1|SAU271505[7162092]

108: AJ271504
Staphylococcus aureus partial pta gene for phosphate actyltransferase allele 9
gi|7162090|emb|AJ271504.1|SAU271504[7162090]

109: AJ271503
Staphylococcus aureus partial pta gene for phosphate actyltransferase allele 8
gi|7162088|emb|AJ271503.1|SAU271503[7162088]

110: AJ271502
Staphylococcus aureus partial pta gene for phosphate actyltransferase allele 7
gi|7162086|emb|AJ271502.1|SAU271502[7162086]

111: AJ271501
Staphylococcus aureus partial pta gene for phosphate actyltransferase allele 6
gi|7162084|emb|AJ271501.1|SAU271501[7162084]

112: AJ271500
Staphylococcus aureus partial pta gene for phosphate actyltransferase allele 5
gi|7162082|emb|AJ271500.1|SAU271500[7162082]

113: AJ271499
Staphylococcus aureus partial pta gene for phosphate actyltransferase allele 4
gi|7162080|emb|AJ271499.1|SAU271499[7162080]

114: AJ271498
Staphylococcus aureus partial pta gene for phosphate actyltransferase allele 3
gi|7162078|emb|AJ271498.1|SAU271498[7162078]

115: AJ271497
Staphylococcus aureus partial pta gene for phosphate actyltransferase allele 2
gi|7162076|emb|AJ271497.1|SAU271497[7162076]

116: AJ271496
Staphylococcus aureus partial pta gene for phosphate actyltransferase allele 1
gi|7162074|emb|AJ271496.1|SAU271496[7162074]

117: AJ271495
Staphylococcus aureus partial tpi gene for triosephosphate isomerase, allele 14
gi|7162072|emb|AJ271495.1|SAU271495[7162072]

118: AJ271494
Staphylococcus aureus partial tpi gene for triosephosphate isomerase, allele 13
gi|7162070|emb|AJ271494.1|SAU271494[7162070]

119: AJ271493
Staphylococcus aureus partial tpi gene for triosephosphate isomerase, allele 12
gi|7162068|emb|AJ271493.1|SAU271493[7162068]

120: AJ271492
Staphylococcus aureus partial tpi gene for triosephosphate isomerase, allele 11
gi|7162066|emb|AJ271492.1|SAU271492[7162066]

121: AJ271491
Staphylococcus aureus partial tpi gene for triosephosphate isomerase, allele 10
gi|7162064|emb|AJ271491.1|SAU271491[7162064]

122: AJ271490

Staphylococcus aureus partial tpi gene for triosephosphate isomerase, allele 9
gi|7162062|emb|AJ271490.1|SAU271490[7162062]

123: AJ271489
Staphylococcus aureus partial tpi gene for triosephosphate isomerase, allele 8
gi|7162060|emb|AJ271489.1|SAU271489[7162060]

124: AJ271488
Staphylococcus aureus partial tpi gene for triosephosphate isomerase, allele 7
gi|7162058|emb|AJ271488.1|SAU271488[7162058]

125: AJ271487
Staphylococcus aureus partial tpi gene for triosephosphate isomerase, allele 6
gi|7162056|emb|AJ271487.1|SAU271487[7162056]

126: AJ271486
Staphylococcus aureus partial tpi gene for triosephosphate isomerase, allele 5
gi|7162054|emb|AJ271486.1|SAU271486[7162054]

127: AJ271485
Staphylococcus aureus partial tpi gene for triosephosphate isomerase, allele 4
gi|7162052|emb|AJ271485.1|SAU271485[7162052]

128: AJ271484
Staphylococcus aureus partial tpi gene for triosephosphate isomerase, allele 3
gi|7162050|emb|AJ271484.1|SAU271484[7162050]

129: AJ271483
Staphylococcus aureus partial tpi gene for triosephosphate isomerase, allele 2
gi|7162048|emb|AJ271483.1|SAU271483[7162048]

130: AJ271482
Staphylococcus aureus partial tpi gene for triosephosphate isomerase, allele 1
gi|7162046|emb|AJ271482.1|SAU271482[7162046]

131: AJ271403
Staphylococcus aureus partial arcC gene for carbamate kinase, allele 17
gi|7162044|emb|AJ271403.1|SAU271403[7162044]

132: AJ271402
Staphylococcus aureus partial arcC gene for carbamate kinase, allele 16
gi|7162042|emb|AJ271402.1|SAU271402[7162042]

133: AJ271401
Staphylococcus aureus partial arcC gene for carbamate kinase, allele 15
gi|7162040|emb|AJ271401.1|SAU271401[7162040]

134: AJ271400
Staphylococcus aureus partial arcC gene for carbamate kinase, allele 14
gi|7162038|emb|AJ271400.1|SAU271400[7162038]

135: AJ271399
Staphylococcus aureus partial arcC gene for carbamate kinase, allele 13
gi|7162036|emb|AJ271399.1|SAU271399[7162036]

136: AJ271398
Staphylococcus aureus partial arcC gene for carbamate kinase, allele 12
gi|7162034|emb|AJ271398.1|SAU271398[7162034]

137: AJ271397
Staphylococcus aureus partial arcC gene for carbamate kinase, allele 11
gi|7162032|emb|AJ271397.1|SAU271397[7162032]

138: AJ271396

Staphylococcus aureus partial arcC gene for carbamate kinase, allele 10
gi|7162030|emb|AJ271396.1|SAU271396[7162030]

139: AJ271395
Staphylococcus aureus partial arcC gene for carbamate kinase, allele 9
gi|7162028|emb|AJ271395.1|SAU271395[7162028]

140: AJ271394
Staphylococcus aureus partial arcC gene for carbamate kinase, allele 8
gi|7162026|emb|AJ271394.1|SAU271394[7162026]

141: AJ271393
Staphylococcus aureus partial arcC gene for carbamate kinase, allele 7
gi|7162024|emb|AJ271393.1|SAU271393[7162024]

142: AJ271392
Staphylococcus aureus partial arcC gene for carbamate kinase, allele 6
gi|7162022|emb|AJ271392.1|SAU271392[7162022]

143: AJ271391
Staphylococcus aureus partial arcC gene for carbamate kinase, allele 5
gi|7162020|emb|AJ271391.1|SAU271391[7162020]

144: AJ271390
Staphylococcus aureus partial arcC gene for carbamate kinase, allele 4
gi|7162018|emb|AJ271390.1|SAU271390[7162018]

145: AJ271389
Staphylococcus aureus partial arcC gene for carbamate kinase, allele 3
gi|7162016|emb|AJ271389.1|SAU271389[7162016]

146: AJ271388
Staphylococcus aureus partial arcC gene for carbamate kinase, allele 2
gi|7162014|emb|AJ271388.1|SAU271388[7162014]

147: AJ271387
Staphylococcus aureus partial arcC gene for carbamate kinase, allele 1
gi|7162012|emb|AJ271387.1|SAU271387[7162012]

148: AJ271289
Staphylococcus aureus partial aroE gene for shikimate dehydrogenase, allele 17
gi|7162010|emb|AJ271289.1|SAU271289[7162010]

149: AJ271288
Staphylococcus aureus partial aroE gene for shikimate dehydrogenase, allele 16
gi|7162008|emb|AJ271288.1|SAU271288[7162008]

150: AJ271287
Staphylococcus aureus partial aroE gene for shikimate dehydrogenase, allele 15
gi|7162006|emb|AJ271287.1|SAU271287[7162006]

151: AJ271286
Staphylococcus aureus partial aroE gene for shikimate dehydrogenase, allele 14
gi|7162004|emb|AJ271286.1|SAU271286[7162004]

152: AJ271285
Staphylococcus aureus partial aroE gene for shikimate dehydrogenase, allele 13
gi|7162002|emb|AJ271285.1|SAU271285[7162002]

153: AJ271284
Staphylococcus aureus partial aroE gene for shikimate dehydrogenase, allele 12
gi|7162000|emb|AJ271284.1|SAU271284[7162000]

154: AJ271283

Staphylococcus aureus partial aroE gene for shikimate dehydrogenase, allele 11
gi|7161998|emb|AJ271283.1|SAU271283[7161998]

155: AJ271281
Staphylococcus aureus partial aroE gene for shikimate dehydrogenase, allele 9
gi|7161996|emb|AJ271281.1|SAU271281[7161996]

156: AJ271280
Staphylococcus aureus partial aroE gene for shikimate dehydrogenase, allele 8
gi|7161994|emb|AJ271280.1|SAU271280[7161994]

157: AJ271279
Staphylococcus aureus partial aroE gene for shikimate dehydrogenase, allele 7
gi|7161992|emb|AJ271279.1|SAU271279[7161992]

158: AJ271278
Staphylococcus aureus partial aroE gene for shikimate dehydrogenase, allele 6
gi|7161990|emb|AJ271278.1|SAU271278[7161990]

159: AJ271277
Staphylococcus aureus partial aroE gene for shikimate dehydrogenase, allele 5
gi|7161988|emb|AJ271277.1|SAU271277[7161988]

160: AJ271276
Staphylococcus aureus partial aroE gene for shikimate dehydrogenase, allele 3
gi|7161986|emb|AJ271276.1|SAU271276[7161986]

161: AJ271275
Staphylococcus aureus partial aroE gene for shikimate dehydrogenase, allele 3
gi|7161984|emb|AJ271275.1|SAU271275[7161984]

162: AJ271274
Staphylococcus aureus partial aroE gene for shikimate dehydrogenase, allele 2
gi|7161982|emb|AJ271274.1|SAU271274[7161982]

163: AJ271273
Staphylococcus aureus partial aroE gene for shikimate dehydrogenase, allele 1
gi|7161980|emb|AJ271273.1|SAU271273[7161980]

164: AJ271272
Staphylococcus aureus partial glpF gene for glycerol kinase, allele 11
gi|7161978|emb|AJ271272.1|SAU271272[7161978]

165: AJ271271
Staphylococcus aureus partial glpF gene for glycerol kinase, allele 10
gi|7161976|emb|AJ271271.1|SAU271271[7161976]

166: AJ271270
Staphylococcus aureus partial glpF gene for glycerol kinase, allele 9
gi|7161974|emb|AJ271270.1|SAU271270[7161974]

167: AJ271269
Staphylococcus aureus partial glpF gene for glycerol kinase, allele 8
gi|7161972|emb|AJ271269.1|SAU271269[7161972]

168: AJ271268
Staphylococcus aureus partial glpF gene for glycerol kinase, allele 7
gi|7161970|emb|AJ271268.1|SAU271268[7161970]

169: AJ271267
Staphylococcus aureus partial glpF gene for glycerol kinase, allele 6
gi|7161968|emb|AJ271267.1|SAU271267[7161968]

170: AJ271266

Staphylococcus aureus partial glpF gene for glycerol kinase, allele 5
gi|7161966|emb|AJ271266.1|SAU271266[7161966]

171: AJ271265
Staphylococcus aureus partial glpF gene for glycerol kinase, allele 4
gi|7161964|emb|AJ271265.1|SAU271265[7161964]

172: AJ271264
Staphylococcus aureus partial glpF gene for glycerol kinase, allele 3
gi|7161962|emb|AJ271264.1|SAU271264[7161962]

173: AJ271263
Staphylococcus aureus partial glpF gene for glycerol kinase, allele 2
gi|7161960|emb|AJ271263.1|SAU271263[7161960]

174: AJ271262
Staphylococcus aureus partial glpF gene for glycerol kinase, allele 1
gi|7161958|emb|AJ271262.1|SAU271262[7161958]

175: AJ271261
Staphylococcus aureus partial gmk gene for guanylate kinase, allele 11
gi|7161956|emb|AJ271261.1|SAU271261[7161956]

176: AJ271260
Staphylococcus aureus partial gmk gene for guanylate kinase, allele 10
gi|7161954|emb|AJ271260.1|SAU271260[7161954]

177: AJ271259
Staphylococcus aureus partial gmk gene for guanylate kinase, allele 9
gi|7161952|emb|AJ271259.1|SAU271259[7161952]

178: AJ271258
Staphylococcus aureus partial gmk gene for guanylate kinase, allele 8
gi|7161950|emb|AJ271258.1|SAU271258[7161950]

179: AJ271257
Staphylococcus aureus partial gmk gene for guanylate kinase, allele 7
gi|7161948|emb|AJ271257.1|SAU271257[7161948]

180: AJ271256
Staphylococcus aureus partial gmk gene for guanylate kinase, allele 6
gi|7161946|emb|AJ271256.1|SAU271256[7161946]

181: AJ271255
Staphylococcus aureus partial gmk gene for guanylate kinase, allele 5
gi|7161944|emb|AJ271255.1|SAU271255[7161944]

182: AJ271254
Staphylococcus aureus partial gmk gene for guanylate kinase, allele 4
gi|7161942|emb|AJ271254.1|SAU271254[7161942]

183: AJ271253
Staphylococcus aureus partial gmk gene for guanylate kinase, allele 3
gi|7161940|emb|AJ271253.1|SAU271253[7161940]

184: AJ271252
Staphylococcus aureus partial gmk gene for guanylate kinase, allele 2
gi|7161938|emb|AJ271252.1|SAU271252[7161938]

185: AJ271251
Staphylococcus aureus partial gmk gene for guanylate kinase, allele 1
gi|7161936|emb|AJ271251.1|SAU271251[7161936]

186: AJ252310

Staphylococcus aureus partial yqiL gene for acetyl coenzyme A acetyltransferase, allele 16
gi|7161926|emb|AJ252310.1|SAU252310[7161926]

187: AJ252309
Staphylococcus aureus partial yqiL gene for acetyl coenzyme A acetyltransferase, allele 15
gi|7161924|emb|AJ252309.1|SAU252309[7161924]

188: AJ252308
Staphylococcus aureus partial yqiL gene for acetyl coenzyme A acetyltransferase, allele 14
gi|7161922|emb|AJ252308.1|SAU252308[7161922]

189: AJ252307
Staphylococcus aureus partial yqiL gene for acetyl coenzyme A acetyltransferase, allele 13
gi|7161920|emb|AJ252307.1|SAU252307[7161920]

190: AJ252306
Staphylococcus aureus partial yqiL gene for acetyl coenzyme A acetyltransferase, allele 12
gi|7161918|emb|AJ252306.1|SAU252306[7161918]

191: AJ252305
Staphylococcus aureus partial yqiL gene for acetyl coenzyme A acetyltransferase, allele 11
gi|7161916|emb|AJ252305.1|SAU252305[7161916]

192: AJ252304
Staphylococcus aureus partial yqiL gene for acetyl coenzyme A acetyltransferase, allele 10
gi|7161914|emb|AJ252304.1|SAU252304[7161914]

193: AJ252303
Staphylococcus aureus partial yqiL gene for acetyl coenzyme A acetyltransferase, allele 9
gi|7161912|emb|AJ252303.1|SAU252303[7161912]

194: AJ252302
Staphylococcus aureus partial yqiL gene for acetyl coenzyme A acetyltransferase, allele 8
gi|7161910|emb|AJ252302.1|SAU252302[7161910]

195: AJ252301
Staphylococcus aureus partial yqiL gene for acetyl coenzyme A acetyltransferase, allele 7
gi|7161908|emb|AJ252301.1|SAU252301[7161908]

196: AJ252300
Staphylococcus aureus partial yqiL gene for acetyl coenzyme A acetyltransferase, allele 6
gi|7161906|emb|AJ252300.1|SAU252300[7161906]

197: AJ252299
Staphylococcus aureus partial yqiL gene for acetyl coenzyme A acetyltransferase, allele 5
gi|7161904|emb|AJ252299.1|SAU252299[7161904]

198: AJ252298
Staphylococcus aureus partial yqiL gene for acetyl coenzyme A acetyltransferase, allele 4
gi|7161902|emb|AJ252298.1|SAU252298[7161902]

199: AJ252297
Staphylococcus aureus partial yqiL gene for acetyl coenzyme A acetyltransferase, allele 3
gi|7161900|emb|AJ252297.1|SAU252297[7161900]

200: AJ252296
Staphylococcus aureus partial yqiL gene for acetyl coenzyme A acetyltransferase, allele 2
gi|7161898|emb|AJ252296.1|SAU252296[7161898]

201: AJ252295
Staphylococcus aureus partial yqiL gene for acetyl coenzyme A acetyltransferase, allele 1
gi|7161896|emb|AJ252295.1|SAU252295[7161896]

202: AJ000472
Staphylococcus aureus catalase gene, strain ATCC12600
gi|7161886|emb|AJ000472.1|SAATCCATA[7161886]

203: AJ000471
Staphylococcus aureus catalase gene, strain MVF213
gi|7161884|emb|AJ000471.1|SAMVFCATA[7161884]

204: AF235026
Staphylococcus aureus pyruvate dehydrogenase beta subunit PdhB (pdhB) gene, complete cds
gi|7107451|gb|AF235026.1|AF235026[7107451]

205: AJ272086
Staphylococcus aureus otc6850 gene for ornithine carbamoyltransferase strain 6850
gi|7106007|emb|AJ272086.1|SAU272086[7106007]

206: AJ272084
Staphylococcus aureus empbp gene for extracellular matrix and plasma binding protein, strain 6850
gi|7106003|emb|AJ272084.1|SAU272084[7106003]

207: AJ272083
Staphylococcus aureus empbp gene for extracellular matrix and plasma binding protein, strain SA 113
gi|7106001|emb|AJ272083.1|SAU272083[7106001]

208: Y18653
Staphylococcus aureus bbp gene, strain 024
gi|7019228|emb|Y18653.1|SAU18653[7019228]

209: AF197058
Staphylococcus aureus trans-2-enoyl-ACP reductase (fabI) gene, complete cds
gi|6180190|gb|AF197058.1|AF197058[6180190]

210: AJ271971
Staphylococcus aureus transposon Tn552 insertion site, right junction, strain NCTC9789
gi|6967302|emb|AJ271971.1|SAU271971[6967302]

211: AJ271970
Staphylococcus aureus transposon Tn552 insertion site, left junction, strain NCTC9789
gi|6967299|emb|AJ271970.1|SAU271970[6967299]

212: AJ243120
Staphylococcus aureus pbp3 gene for penicillin-binding protein 3
gi|6912038|emb|AJ243120.1|SAU243120[6912038]

213: D42078
Staphylococcus aureus DNA for N-acetyl-glucosaminidase, partial cds
gi|2506026|dbj|D42078.1|D42078[2506026]

214: D42144
Staphylococcus aureus gene for LUKM, complete cds
gi|577648|dbj|D42144.1|STAPLUKM[577648]

215: D00730
S. aureus glutamic acid specific protease (EC 3.4.21.19) gene
gi|216970|dbj|D00730.1|STAGASP[216970]

216: AJ249169
Staphylococcus aureus aur gene, strain 017
gi|6119706|emb|AJ249169.1|SAU249169[6119706]

217: AJ249168
Staphylococcus aureus aur gene, strain 01
gi|6119704|emb|AJ249168.1|SAU249168[6119704]

218: AJ249167
Staphylococcus aureus aur gene, strain 022
gi|6119702|emb|AJ249167.1|SAU249167[6119702]

219: AJ249166
Staphylococcus aureus aur gene, strain V8-BC10
gi|6119700|emb|AJ249166.1|SAU249166[6119700]

220: AJ271347
Staphylococcus aureus ssp gene for secretory protein
gi|6729656|emb|AJ271347.1|SAU271347[6729656]

221: AF193842
Staphylococcus aureus DNA polymerase I (polA) gene, complete cds
gi|6110604|gb|AF193842.1|AF193842[6110604]

222: AF117259
Staphylococcus aureus plasmid pIP680 replication protein (repX) and ATP binding protein VgA genes, complete cds; and unknown gene
gi|6690332|gb|AF117259.1|AF117259[6690332]

223: AF117258
Staphylococcus aureus plasmid pIP680 replication protein RepE (repE) gene, partial cds; resolvase (res), acetyltransferase Vat (vat), and hydrolase VgB (vgb) genes, complete cds; and unknown gene
gi|6690326|gb|AF117258.1|AF117258[6690326]

224: AJ012052
Staphylococcus aureus vic operon and flanking genes
gi|6689204|emb|AJ012052.1|SAU012052[6689204]

225: AB014438
Staphylococcus aureus gene for cassette chromosome recombinase A, cassette chromosome recombinase B, complete cds, strain 85/3907
gi|6681573|dbj|AB014438.1|AB014438[6681573]

226: AB014437
Staphylococcus aureus gene for cassette chromosome recombinase A, cassette chromosome recombinase B, complete cds, strain 85/1340
gi|6681570|dbj|AB014437.1|AB014437[6681570]

227: AB014436
Staphylococcus aureus gene for cassette chromosome recombinase A, cassette chromosome recombinase B, complete cds, strain 85/2082
gi|6681567|dbj|AB014436.1|AB014436[6681567]

228: AB014435
Staphylococcus aureus DNA, 3' flanking region of mecDNA, strain 64/3846
gi|6681566|dbj|AB014435.1|AB014435[6681566]

229: AB014434
Staphylococcus aureus DNA, 3' flanking region of mecDNA, strain 64/4176
gi|6681565|dbj|AB014434.1|AB014434[6681565]

230: AB014433
Staphylococcus aureus DNA, 3' flanking region of mecDNA, strain 61/6219
gi|6681564|dbj|AB014433.1|AB014433[6681564]

231: AB014432
Staphylococcus aureus DNA, 3' flanking region of mecDNA, strain 85/1940
gi|6681563|dbj|AB014432.1|AB014432[6681563]

232: AB014431
Staphylococcus aureus DNA, 3' flanking region of mecDNA, strain 84/9580
gi|6681562|dbj|AB014431.1|AB014431[6681562]

233: AB014430
Staphylococcus aureus DNA, 3' flanking region of mecDNA, strain 85/9302
gi|6681561|dbj|AB014430.1|AB014430[6681561]

234: AB014428
Staphylococcus aureus DNA, 5' flanking region of mecDNA, strain 85/4231
gi|6681560|dbj|AB014428.1|AB014428[6681560]

235: AB014427
Staphylococcus aureus DNA, 5' flanking region of mecDNA, strain 85/2235
gi|6681559|dbj|AB014427.1|AB014427[6681559]

236: AB014426
Staphylococcus aureus DNA, 5' flanking region of mecDNA, strain 64/4176
gi|6681558|dbj|AB014426.1|AB014426[6681558]

237: AB014425
Staphylococcus aureus DNA, 5' flanking region of mecDNA, strain 64/3846
gi|6681557|dbj|AB014425.1|AB014425[6681557]

238: AB014424
Staphylococcus aureus DNA, 5' flanking region of mecDNA, strain 61/6219
gi|6681556|dbj|AB014424.1|AB014424[6681556]

239: AB014423
Staphylococcus aureus DNA, 5' flanking region of mecDNA, strain 85/1940
gi|6681555|dbj|AB014423.1|AB014423[6681555]

240: AB014422
Staphylococcus aureus DNA, 5' flanking region of mecDNA, strain 85/1774
gi|6681554|dbj|AB014422.1|AB014422[6681554]

241: AB014421
Staphylococcus aureus DNA, 5' flanking region of mecDNA, strain 84/9580
gi|6681553|dbj|AB014421.1|AB014421[6681553]

242: AB014420
Staphylococcus aureus DNA, 5' flanking region of mecDNA, strain 85/9302
gi|6681552|dbj|AB014420.1|AB014420[6681552]

243: AB014418

Staphylococcus aureus DNA, 5' flanking region of mecDNA, strain 85/3566
gi|6681551|dbj|AB014418.1|AB014418[6681551]

244: AB014417
Staphylococcus aureus DNA, 5' flanking region of mecDNA, strain 86/2652
gi|6681550|dbj|AB014417.1|AB014417[6681550]

245: AB014416
Staphylococcus aureus DNA, 5' flanking region of mecDNA, strain 86/961
gi|6681549|dbj|AB014416.1|AB014416[6681549]

246: AB014415
Staphylococcus aureus DNA, 5' flanking region of mecDNA, strain 86/560
gi|6681548|dbj|AB014415.1|AB014415[6681548]

247: AB014414
Staphylococcus aureus DNA, 5' flanking region of mecDNA, strain 85/5328
gi|6681547|dbj|AB014414.1|AB014414[6681547]

248: AB014413
Staphylococcus aureus DNA, 5' flanking region of mecDNA, strain 85/3907
gi|6681546|dbj|AB014413.1|AB014413[6681546]

249: AB014412
Staphylococcus aureus DNA, 5' flanking region of mecDNA, strain 85/3619
gi|6681545|dbj|AB014412.1|AB014412[6681545]

250: AB014411
Staphylococcus aureus DNA, 5' flanking region of mecDNA, strain 85/2147
gi|6681544|dbj|AB014411.1|AB014411[6681544]

251: AB014410
Staphylococcus aureus DNA, 5' flanking region of mecDNA, strain 85/1836
gi|6681543|dbj|AB014410.1|AB014410[6681543]

252: AB014409
Staphylococcus aureus DNA, 5' flanking region of mecDNA, strain 85/5495
gi|6681542|dbj|AB014409.1|AB014409[6681542]

253: AB014408
Staphylococcus aureus DNA, 5' flanking region of mecDNA, strain 85/1340
gi|6681541|dbj|AB014408.1|AB014408[6681541]

254: AB014407
Staphylococcus aureus DNA, 5' flanking region of mecDNA, strain 85/2082
gi|6681540|dbj|AB014407.1|AB014407[6681540]

255: AB014406
Staphylococcus aureus DNA, 5' flanking region of mecDNA, strain 85/1762
gi|6681539|dbj|AB014406.1|AB014406[6681539]

256: AB014405
Staphylococcus aureus DNA, 5' flanking region of mecDNA, strain 85/2111
gi|6681538|dbj|AB014405.1|AB014405[6681538]

257: AB014404
Staphylococcus aureus DNA, 3' flanking region of mecDNA, strain MR108
gi|6681537|dbj|AB014404.1|AB014404[6681537]

258: AB014403
Staphylococcus aureus DNA, 3' flanking region of mecDNA, strain 85/2235
gi|6681536|dbj|AB014403.1|AB014403[6681536]

259: AB014402

Staphylococcus aureus DNA, 3' flanking region of mecDNA, strain 85/2232
gi|6681535|dbj|AB014402.1|AB014402[6681535]

260: AB013483
Staphylococcus aureus DNA, adjacent region to right extremity of type III mec DNA, strain:85/3566
gi|6681452|dbj|AB013483.1|AB013483[6681452]

261: AB013482
Staphylococcus aureus DNA, adjacent region to right extremity of type III mec DNA, strain:85/3619
gi|6681451|dbj|AB013482.1|AB013482[6681451]

262: AB013481
Staphylococcus aureus DNA, adjacent region to right extremity of type III mec DNA, strain:85/2147
gi|6681450|dbj|AB013481.1|AB013481[6681450]

263: AB013480
Staphylococcus aureus DNA, adjacent region to right extremity of type III mec DNA, strain:85/1836
gi|6681449|dbj|AB013480.1|AB013480[6681449]

264: AB013479
Staphylococcus aureus DNA, adjacent region to right extremity of type III mec DNA, strain:85/5495
gi|6681448|dbj|AB013479.1|AB013479[6681448]

265: AB013478
Staphylococcus aureus DNA, adjacent region to right extremity of type III mec DNA, strain:85/2111
gi|6681447|dbj|AB013478.1|AB013478[6681447]

266: AB013477
Staphylococcus aureus DNA, adjacent region to right extremity of type III mec DNA, strain:85/2082
gi|6681446|dbj|AB013477.1|AB013477[6681446]

267: AB013476
Staphylococcus aureus DNA, adjacent region to right extremity of type III mec DNA, strain:85/1762
gi|6681445|dbj|AB013476.1|AB013476[6681445]

268: AB013475
Staphylococcus aureus DNA, adjacent region to right extremity of type III mec DNA, strain:85/1340
gi|6681444|dbj|AB013475.1|AB013475[6681444]

269: AB013474
Staphylococcus aureus DNA, adjacent region to right extremity of type III mec DNA, strain:86/2652
gi|6681443|dbj|AB013474.1|AB013474[6681443]

270: AB013473
Staphylococcus aureus DNA, adjacent region to right extremity of type III mec DNA, strain:85/3907
gi|6681442|dbj|AB013473.1|AB013473[6681442]

271: AB013472
Staphylococcus aureus DNA, adjacent region to right extremity of type III mec DNA, strain:86/961
gi|6681441|dbj|AB013472.1|AB013472[6681441]

272: AB013471

Staphylococcus aureus DNA, adjacent region to right extremity of type III mec DNA, strain:86/560
gi|6681440|dbj|AB013471.1|AB013471[6681440]

273: AF209197
Staphylococcus aureus UDP-GlcNAc 2-epimerase (mnaA) gene, complete cds
gi|6644367|gb|AF209197.1|AF209197[6644367]

274: AB016615
Staphylococcus aureus plasmid pSP6 smpA and stpA genes and msrSA pseudogene, complete cds
gi|6594282|dbj|AB016615.1|AB016615[6594282]

275: AB016614
Staphylococcus aureus plasmid pMC38 smpA, atpA and msrSA genes, complete cds
gi|6594278|dbj|AB016614.1|AB016614[6594278]

276: AB016613
Staphylococcus aureus plasmid pEP2104 smpA, stpA and msrSA genes, complete cds
gi|6594274|dbj|AB016613.1|AB016613[6594274]

277: AF115379
Staphylococcus aureus surface protein Pls (pls) gene, complete cds
gi|6579184|gb|AF115379.2|AF115379[6579184]

278: AF205033
Staphylococcus aureus glutamyl-tRNAGln amidotransferase subunit C (gatC), glutamyl-tRNAGln amidotransferase subunit A (gatA), and glutamyl-tRNAGln amidotransferase subunit B (gatB) genes, complete cds
gi|6578922|gb|AF205033.1|AF205033[6578922]

279: AF105976
Staphylococcus aureus FemX (femX) gene, complete cds; and putative transmembrane protein gene, partial cds
gi|6492110|gb|AF105976.1|AF105976[6492110]

280: AB030228
Staphylococcus aureus gene for Drp35, complete cds
gi|6441049|dbj|AB030228.1|AB030228[6441049]

281: Y18641
Staphylococcus aureus genes coding for ATP-binding protein and permease, and ORF1, strain RUSA221
gi|6434051|emb|Y18641.1|SAU18641[6434051]

282: Y18640
Staphylococcus aureus trpF gene and genes encoding indole-3-glycerol phosphate synthase, anthranilate phosphoribosyltransferase and anthranilate synthase component II
gi|6434046|emb|Y18640.1|SAU18640[6434046]

283: Y18639
Staphylococcus aureus ORF1 and ORF2 (partial), strain SA1
gi|6434043|emb|Y18639.1|SAU18639[6434043]

284: Y18638
Staphylococcus aureus ORF1, ORF2 and ORF3, strain RUSA162
gi|6434039|emb|Y18638.1|SAU18638[6434039]

285: Y18637
Staphylococcus aureus phoX gene and gene encoding hypothetical protein
gi|6434036|emb|Y18637.1|SAU18637[6434036]

286: Y18636

Staphylococcus aureus gene encoding thioredoxine reductase and ORF2, ORF3, ORF4
gi|6434032|emb|Y18636.1|SAU18636[6434032]

287: Y18635
Staphylococcus aureus tag, yhjN, gsa-at and pbg (partial) genes
gi|6434027|emb|Y18635.1|SAU18635[6434027]

288: Y13600
Staphylococcus aureus transposon Tn551 DNA (complete)
gi|6273677|emb|Y13600.1|SATN551[6273677]

289: AF188837
Staphylococcus aureus exotoxin 1 (set1) gene, set1-C allele, complete cds
gi|6176431|gb|AF188837.1|AF188837[6176431]

290: AF188836
Staphylococcus aureus exotoxin 1 (set1) gene, set1-B allele, complete cds
gi|6176430|gb|AF188836.1|AF188836[6176430]

291: AF188835
Staphylococcus aureus exotoxin 1 (set1) gene, set1-A allele, complete cds
gi|6176429|gb|AF188835.1|AF188835[6176429]

292: 1QU3T
Chain T, Insights Into Editing From An Ile-Trna Synthetase Structure With Trna(Ile) And Mupirocin
gi|6137711|pdb|1QU3|T[6137711]

293: 1QU2T
Chain T, Insights Into Editing From An Ile-Trna Synthetase Structure With Trna(Ile) And Mupirocin
gi|6137709|pdb|1QU2|T[6137709]

294: AF003593
Staphylococcus aureus CspC (cspC) gene, complete cds
gi|2226348|gb|AF003593.1|AF003593[2226348]

295: AF003592
Staphylococcus aureus CspB (cspB) gene, complete cds
gi|2226346|gb|AF003592.1|AF003592[2226346]

296: AF086783
Staphylococcus aureus intercellular adhesion locus, partial sequence
gi|5813898|gb|AF086783.1|AF086783[5813898]

297: AF095597
Staphylococcus aureus strain ISP3 ferric uptake regulator homolog (furC) gene, complete cds
gi|6002651|gb|AF095597.1|AF095597[6002651]

298: AF095596
Staphylococcus aureus strain ISP3 ferric uptake regulator homolog (furB) gene, complete cds
gi|6002649|gb|AF095596.1|AF095596[6002649]

299: AF095595
Staphylococcus aureus strain ISP3 ferric uptake regulator homolog (furA) gene, complete cds
gi|6002647|gb|AF095595.1|AF095595[6002647]

300: Y09929
S.aureus rsbU, rsbV, rsbW & sigB genes
gi|1729791|emb|Y09929.1|SAUSIGB[1729791]

301: Y09927
Staphylococcus aureus glmM gene cluster
gi|5834644|emb|Y09927.2|SAURED[5834644]

302: Y09928
S.aureus CTORF1365, partial
gi|4775550|emb|Y09928.1|SACTORF13[4775550]

303: Y09594
S.aureus arg gene
gi|4775541|emb|Y09594.1|SAARG[4775541]

304: X00342
Staphylococcus aureus 3' end of the gene for protein A
gi|46694|emb|X00342.1|SASPAY[46694]

305: AF077865
Staphylococcus aureus beta-lactamase (ear) gene, complete cds
gi|5739083|gb|AF077865.1|AF077865[5739083]

306: AF162687
Staphylococcus aureus sortase (srtA) gene, complete cds
gi|5726435|gb|AF162687.1|AF162687[5726435]

307: AF129010
Staphylococcus aureus response regulator SaeR (saeR), histidine protein kinase SaeS (saeS), and CsbB homolog genes, complete cds
gi|5726299|gb|AF129010.1|AF129010[5726299]

308: AF147744
Staphylococcus aureus strain C55 lantibiotic structural protein alpha, lantibiotic structural protein beta, lantibiotic modifying enzyme, and transporter genes, complete cds
gi|5690273|gb|AF147744.1|AF147744[5690273]

309: D86240
Staphylococcus aureus gene for unkown function and dlt operon dltA, dltB, dltC and dltD genes,complete cds
gi|5672688|dbj|D86240.2|D86240[5672688]

310: AJ245439
Staphylococcus aureus map-w gene for cell surface protein map-w, strain wood 46
gi|5679713|emb|AJ245439.1|SAU245439[5679713]

311: AJ243790
Staphylococcus aureus map-7 gene
gi|5531419|emb|AJ243790.1|SAU243790[5531419]

312: AF060191
Staphylococcus aureus strain ATCC27664 heat shock protein 60 kDa (hsp60) gene, partial cds
gi|4558749|gb|AF060191.1|AF060191[4558749]

313: AF060190
Staphylococcus aureus strain ATCC19095 heat shock protein 60 kDa (hsp60) gene, partial cds
gi|4558747|gb|AF060190.1|AF060190[4558747]

314: AF060189
Staphylococcus aureus strain ATCC14458 heat shock protein 60 kDa (hsp60) gene, partial cds
gi|4558745|gb|AF060189.1|AF060189[4558745]

315: AF060188

Staphylococcus aureus strain ATCC13565 heat shock protein 60 kDa (hsp60) gene, partial cds
gi|4558743|gb|AF060188.1|AF060188[4558743]

316: AF060187
Staphylococcus aureus strain ATCC10832 heat shock protein 60 kDa (hsp60) gene, partial cds
gi|4558741|gb|AF060187.1|AF060187[4558741]

317: AF060186
Staphylococcus aureus strain ATCC12598 heat shock protein 60 kDa (hsp60) gene, partial cds
gi|4558739|gb|AF060186.1|AF060186[4558739]

318: AF060185
Staphylococcus aureus strain ATCC25178 heat shock protein 60 kDa (hsp60) gene, partial cds
gi|4558737|gb|AF060185.1|AF060185[4558737]

319: AF060184
Staphylococcus aureus strain ATCC27217 heat shock protein 60 kDa (hsp60) gene, partial cds
gi|4558735|gb|AF060184.1|AF060184[4558735]

320: AF036324
Staphylococcus aureus subsp. aureus heat shock protein 60 (GroEL) gene, partial cds
gi|4558705|gb|AF036324.1|[4558705]

321: AF036323
Staphylococcus aureus subsp. anaerobius heat shock protein 60 (GroEL) gene, partial cds
gi|4558703|gb|AF036323.1|AF036323[4558703]

322: AF053568
Staphylococcus aureus ATCC 25923 heat shock protein 60 gene, partial cds
gi|4205742|gb|AF053568.1|AF053568[4205742]

323: AF034076
Staphylococcus aureus UDP-N-acetylmuramoyl-L-alanine synthetase (murC) gene, complete cds
gi|2642658|gb|AF034076.1|AF034076[2642658]

324: AF134905
Staphylococcus aureus plasmid pRW001 CadD (cadD) gene, complete cds
gi|4680369|gb|AF134905.1|AF134905[4680369]

325: AF098801
Staphylococcus aureus penicillin-binding protein Pbp2b (pbpF) gene, complete cds
gi|5441302|gb|AF098801.1|AF098801[5441302]

326: X63598
S.aureus mecR1 and mecI genes
gi|46612|emb|X63598.1|SAMECR1I[46612]

327: AB014440
Staphylococcus aureus genes for orf1, orfX, orf2, orf3, partial and complete cds
gi|5391436|dbj|AB014440.1|AB014440[5391436]

328: Y17294
Staphylococcus aureus plasmid pSES31 DNA for ermC gene region
gi|5327229|emb|Y17294.1|SAU17294[5327229]

329: AF098688

Staphylococcus aureus strain 8325-4, genomic survey sequence
gi|5230722|gb|AF098688.1|AF098688[5230722]

330: AF098687
Staphylococcus aureus strain 8325-4, genomic survey sequence
gi|5230721|gb|AF098687.1|AF098687[5230721]

331: AF098686
Staphylococcus aureus strain 8325-4, genomic survey sequence
gi|5230720|gb|AF098686.1|AF098686[5230720]

332: AF098685
Staphylococcus aureus strain 8325-4, genomic survey sequence
gi|5230719|gb|AF098685.1|AF098685[5230719]

333: AF136709
Staphylococcus aureus response regulator YycF (yycF) and histidine kinase YycG (yycG) genes, complete cds
gi|5114229|gb|AF136709.1|AF136709[5114229]

334: AB015195
Staphylococcus aureus gene for LytN and Eprh, complete cds
gi|3767591|dbj|AB015195.1|AB015195[3767591]

335: AF146368
Staphylococcus aureus 16S ribosomal RNA gene, partial sequence
gi|4929362|gb|AF146368.1|AF146368[4929362]

336: U77328
Staphylococcus aureus staphylokinase gene, partial cds
gi|2605637|gb|U77328.1|SAU77328[2605637]

337: AF151117
Staphylococcus aureus plasmid pKH3, complete sequence
gi|5031412|gb|AF151117.1|AF151117[5031412]

338: AF151218
Staphylococcus aureus ribonuclease P RNA gene, complete sequence
gi|4929536|gb|AF151218.1|AF151218[4929536]

339: AF144661
Staphylococcus aureus subsp. anaerobius factor essential for methicillin resistance (femA) gene, complete cds
gi|4929298|gb|AF144661.1|AF144661[4929298]

340: Y15477
Staphylococcus aureus argI, glmM genes and ORF1 and ORF2
gi|3892891|emb|Y15477.1|SAARGFEMD[3892891]

341: AB019536
Staphylococcus aureus norA23 gene for NorA, complete cds
gi|4115706|dbj|AB019536.1|AB019536[4115706]

342: AJ237696
Staphylococcus aureus fus gene
gi|4582215|emb|AJ237696.1|SAU237696[4582215]

343: AF106851
Staphylococcus aureus LytN (lytN) and FmhC (fmhC) genes, complete cds
gi|4574236|gb|AF106851.1|AF106851[4574236]

344: AF106850
Staphylococcus aureus FmhB (fmhB) gene, complete cds
gi|4574234|gb|AF106850.1|AF106850[4574234]

345: AF106849
Staphylococcus aureus FmhA (fmhA) gene, complete cds
gi|4574232|gb|AF106849.1|AF106849[4574232]

346: M26321
Staphylococcus aureus plasmid pT181 repC gene, partial cds
gi|151689|gb|M26321.1|PT1REPC[151689]

347: AJ132841
Staphylococcus aureus mapN gene
gi|4454323|emb|AJ132841.1|SAU132841[4454323]

348: Y13766
Staphylococcus aureus pnpA gene
gi|3970796|emb|Y13766.1|SAPNPA[3970796]

349: AF101234
Staphylococcus aureus dltABCD operon, complete sequence; and unknown gene
gi|4530239|gb|AF101234.1|AF101234[4530239]

350: AJ133520
Staphylococcus aureus gap operon (gapR, gap, pgk and tpi genes)
gi|4490611|emb|AJ133520.1|SAU133520[4490611]

351: AJ133495
Staphylococcus aureus ribonucleotide reductase operon
gi|4490607|emb|AJ133495.1|SAU133495[4490607]

352: AJ132803
Staphylococcus aureus ORF1 and ORF2 (partial)
gi|4454320|emb|AJ132803.1|SAU132803[4454320]

353: AB016431
Staphylococcus aureus, zinc responsible operon czr genes, complete and partial cds
gi|4126670|dbj|AB016431.1|AB016431[4126670]

354: AB015981
Staphylococcus aureus genes for OrfA, MnhA, MnhB, MnhC, MnhD, MnhE, MnhF and MnhG, complete cds
gi|4001723|dbj|AB015981.1|AB015981[4001723]

355: AF107307
Staphylococcus aureus subsp. anaerobius 16S ribosomal RNA gene, partial sequence
gi|4406286|gb|AF107307.1|AF107307[4406286]

356: AF079518
Staphylococcus aureus lipoprotein SirA (sirA), SirB (sirB), and SirC (sirC) genes, complete cds
gi|3694941|gb|AF079518.1|AF079518[3694941]

357: AJ223806
Staphylococcus aureus map gene, partial
gi|4138455|emb|AJ223806.1|SAU223806[4138455]

358: Y18018
Staphylococcus aureus plasmid pSES30 including ermC gene, partial
gi|4138444|emb|Y18018.1|SAU18018[4138444]

359: Y17795
Staphylococcus aureus prfA, pbp2 genes
gi|3955029|emb|Y17795.1|SAU17795[3955029]

360: AJ005647
Staphylococcus aureus sdrE gene
gi|3550595|emb|AJ005647.1|SAU5647[3550595]

361: AJ005646
Staphylococcus aureus sdrD gene
gi|3550593|emb|AJ005646.1|SAU5646[3550593]

362: AJ005645
Staphylococcus aureus sdrC gene
gi|3550591|emb|AJ005645.1|SAU5645[3550591]

363: V01282
Staphylococcus aureus plasmid pSN2 Includes an unknown gene
gi|46653|emb|V01282.1|SAPSN2[46653]

364: AF072726
Staphylococcus aureus putative heme A synthase (ctaA) gene, complete cds
gi|3320605|gb|AF072726.1|AF072726[3320605]

365: AF034153
Staphylococcus aureus phospho-N-acetylmuramoyl-pentapeptide translocase (mraY) gene, complete cds
gi|4104229|gb|AF034153.1|AF034153[4104229]

366: AF029244
Staphylococcus aureus 60 kDa heat shock protein (hsp60) gene, partial cds
gi|4103899|gb|AF029244.1|AF029244[4103899]

367: U67965
Staphylococcus aureus lytic regulatory protein gene, complete cds
gi|4097756|gb|U67965.1|SAU67965[4097756]

368: U96610
Staphylococcus aureus plasmid pSK6, complete genome
gi|4090653|gb|U96610.1|SAU96610[4090653]

369: U96609
Staphylococcus aureus plasmid pSK3, complete genome
gi|4090650|gb|U96609.1|SAU96609[4090650]

370: U73027
Staphylococcus aureus transposon Tn5405 unknown gene, complete cds
gi|2811117|gb|U73027.1|SAU73027[2811117]

371: U73026
Staphylococcus aureus transposon Tn5405 streptothricine-acetyl-transferase (sat4) pseudogene, complete sequence
gi|2811116|gb|U73026.1|SAU73026[2811116]

372: U73025
Staphylococcus aureus transposon Tn5405 unknown gene, complete cds
gi|2811114|gb|U73025.1|SAU73025[2811114]

373: AF068904
Staphylococcus aureus cell division protein FtsZ (ftsZ) gene, partial cds; YlmD (ylmD), YlmE (ylmE), YlmF (ylmF), YlmG (ylmG), and YlmH (ylmH) genes, complete cds; and cell division protein DivIVA (divIVA) gene, partial cds
gi|4009490|gb|AF068904.1|AF068904[4009490]

374: U60050
Staphylococcus aureus major cold-shock protein (cspA) gene, partial cds
gi|1402770|gb|U60050.1|SAU60050[1402770]

375: D10907
Staphylococcus aureus insertion element IS431, partial sequence, clone:MR108-4
gi|216973|dbj|D10907.1|STAIS431B[216973]

376: D10906
Staphylococcus aureus insertion element IS431, partial sequence, clone:MR108-3
gi|216972|dbj|D10906.1|STAIS431A[216972]

377: AF053140
Staphylococcus aureus plasmid pIB485 enterotoxin D (sed) gene, partial cds; and enterotoxin J (sej) gene, complete cds
gi|3372540|gb|AF053140.1|AF053140[3372540]

378: AB013298
Staphylococcus aureus genes for leader peptide, MsrSA and MphBM, complete cds
gi|3892641|dbj|AB013298.1|AB013298[3892641]

379: Y16431
Staphylococcus aureus dpj, alr genes, partial kdpC gene and 4 ORF's
gi|3850845|emb|Y16431.1|SAU16431[3850845]

380: AF076684
Staphylococcus aureus oligopeptide transporter putative membrane permease domain (opp-2B), oligopeptide transporter putative membrane permease domain (opp-2C), oligopeptide transporter putative ATPase domain (opp-2D), and oligopeptide transporter putative ATPase domain (opp-2F) genes, complete cds
gi|3800824|gb|AF076684.1|AF076684[3800824]

381: AF076683
Staphylococcus aureus oligopeptide transporter putative substrate binding domain (opp-1A), oligopeptide transporter putative membrane permease domain (opp-1B), oligopeptide transporter putative membrane permease domain (opp-1C), oligopeptide transporter putative ATPase domain (opp-1D), and oligopeptide transporter putative ATPase domain (opp-1F) genes, complete cds; and unknown gene
gi|3800817|gb|AF076683.1|AF076683[3800817]

382: Y13225
Staphylococcus aureus lukE, lukD genes
gi|2765302|emb|Y13225.1|SALUKED[2765302]

383: AF094826
Staphylococcus aureus novel exotoxins gene cluster, complete sequence; and HsdM-like protein gene, partial cds
gi|3806103|gb|AF094826.1|AF094826[3806103]

384: AJ223480
Staphylococcus aureus trxA and uvrC genes and partial mutS and dhsC genes
gi|3776109|emb|AJ223480.1|SATRXA[3776109]

385: AF093548
Staphylococcus aureus tyrosine recombinase XerD (xerD) gene, complete cds
gi|3747041|gb|AF093548.1|AF093548[3747041]

386: AF051916
Staphylococcus aureus plasmid pJE1 remnant of replication protein Rep (rep), trimethoprim resistance protein DfrA (dfrA), thymidylate synthetase ThyE (thyE), and putative transposase Tnp (tnp) genes, complete cds; and unknown gene
gi|3676404|gb|AF051916.1|AF051916[3676404]

387: AF051917
Staphylococcus aureus plasmid pSK41, complete sequence
gi|3676412|gb|AF051917.1|AF051917[3676412]

388: S77058
bler=bleomycin-resistance gene [Staphylococcus aureus, MRSA, B-26, Genomic, 297 nt]
gi|913952|gb|S77058.1|S77058[913952]

389: S65052
hlg2=gamma-hemolysin II...lukF=leukocidin F component [Staphylococcus aureus, MRSA No. 4, Genomic, 3 genes, 4353 nt]
gi|410004|gb|S65052.1|S65052[410004]

390: AF009671
Staphylococcus aureus UDP-N-acetylmuramoyl-L-alanine : D-glutamate ligase (murD) gene, complete cds
gi|2305091|gb|AF009671.1|AF009671[2305091]

391: U81973
Staphylococcus aureus capsule gene cluster Cap5A through Cap5P genes, complete cds
gi|1773339|gb|U81973.1|SAU81973[1773339]

392: U77308
Staphylococcus aureus O-acetyl transferase (cap5H) gene, complete cds
gi|1673628|gb|U77308.1|SAU77308[1673628]

393: U20869
Staphylococcus aureus ribosomal protein S12 (rpsL) gene, complete cds, ribosomal protein S7 (rpsG) and ORF 1 genes, partial cds
gi|706919|gb|U20869.1|SAU20869[706919]

394: U89396
Staphylococcus aureus hemCDBL gene cluster: porphobilinogen deaminase (hemC), uroporphyrinogen III synthase (hemD), d-aminolevulinic acid dehydratase (hemB) and GSA-1-aminotransferase (hemL) genes, complete cds
gi|2589180|gb|U89396.1|SAU89396[2589180]

395: U94706
Staphylococcus aureus strain ATCC 8325-4 cell wall/cell division gene cluster, yllB, yllC, yllD, pbpA, mraY, murD, divlB, ftsA and ftsZ genes, complete cds
gi|2149889|gb|U94706.1|SAU94706[2149889]

396: U41072
Staphylococcus aureus isoleucyl-tRNA synthetase (ileS) gene, partial cds
gi|1314300|gb|U41072.1|SAU41072[1314300]

397: U52961
Staphylococcus aureus holin-like protein LrgA (lrgA) and LrgB (lrgB) genes, complete cds
gi|1841516|gb|U52961.1|SAU52961[1841516]

398: U21636
Staphylococcus aureus cmp-binding-factor 1 (cbf1) and ORF X genes, complete cds
gi|710420|gb|U21636.1|SAU21636[710420]

399: U65000
Staphylococcus aureus type-I signal peptidase SpsA (spsA) gene, and type-I signal peptidase SpsB (spsB) gene, complete cds
gi|1595808|gb|U65000.1|SAU65000[1595808]

400: U48826
Staphylococcus aureus elastin binding protein (ebpS) gene, complete cds
gi|1397238|gb|U48826.1|SAU48826[1397238]

401: U20503
Staphylococcus aureus MHC class II analog gene, complete cds gi|1001960|gb|U20503.1|SAU20503[1001960]

402: U11789
Staphylococcus aureus methicillin-resistant isolate H11 clone RRNV8 16S-23S rRNA spacer region
gi|644560|gb|U11789.1|SAU11789[644560]

403: U11788
Staphylococcus aureus methicillin-resistant isolate H11 clone RRNV7 16S-23S rRNA spacer region
gi|644559|gb|U11788.1|SAU11788[644559]

404: U11787
Staphylococcus aureus methicillin-resistant ATCC 33952 clone RRNV43 16S-23S rRNA spacer region
gi|644558|gb|U11787.1|SAU11787[644558]

405: U11786
Staphylococcus aureus methicillin-resistant ATCC 33952 clone RRNV42 16S-23S rRNA spacer region
gi|644557|gb|U11786.1|SAU11786[644557]

406: U11785
Staphylococcus aureus methicillin-resistant ATCC 33952 clone RRNV41 16S-23S rRNA spacer region
gi|644556|gb|U11785.1|SAU11785[644556]

407: U11784
Staphylococcus aureus methicillin-resistant ATCC 33952 clone RRNV40 16S-23S rRNA spacer region
gi|644555|gb|U11784.1|SAU11784[644555]

408: U11783
Staphylococcus aureus methicillin-resistant isolate H11 clone RRNV4 16S-23S rRNA spacer region
gi|644554|gb|U11783.1|SAU11783[644554]

409: U11782
Staphylococcus aureus methicillin-resistant ATCC 33952 clone RRNV38 16S-23S rRNA spacer region
gi|644553|gb|U11782.1|SAU11782[644553]

410: U11781
Staphylococcus aureus methicillin-resistant ATCC 33952 clone RRNV34 16S-23S rRNA spacer region
gi|644552|gb|U11781.1|SAU11781[644552]

411: U11780
Staphylococcus aureus methicillin-resistant ATCC 33952 clone RRNV32 16S-23S rRNA spacer region
gi|644551|gb|U11780.1|SAU11780[644551]

412: U11779
Staphylococcus aureus methicillin-resistant ATCC 33952 clone RRNV30 16S-23S rRNA spacer region
gi|644550|gb|U11779.1|SAU11779[644550]

413: U11778
Staphylococcus aureus methicillin-resistant ATCC 33952 clone RRNV27 16S-23S rRNA spacer region
gi|644549|gb|U11778.1|SAU11778[644549]

414: U11777
Staphylococcus aureus methicillin-resistant isolate H11 clone RRNV2 16S-23S rRNA spacer region
gi|644548|gb|U11777.1|SAU11777[644548]

415: U11776
Staphylococcus aureus methicillin-resistant isolate H11 clone RRNV17 16S-23S rRNA spacer region
gi|644547|gb|U11776.1|SAU11776[644547]

416: U11775
Staphylococcus aureus methicillin-resistant isolate H11 clone RRNV13 16S-23S rRNA spacer region
gi|644546|gb|U11775.1|SAU11775[644546]

417: U11774
Staphylococcus aureus methicillin-resistant isolate H11 clone RRNV12 16S-23S rRNA spacer region
gi|644545|gb|U11774.1|SAU11774[644545]

418: U11773
Staphylococcus aureus methicillin-resistant isolate D46 clone RRN4 16S-23S rRNA spacer region
gi|644544|gb|U11773.1|SAU11773[644544]

419: AF053772
Staphylococcus aureus plasmid pSK23 putative recombinase Sin (sin) gene, partial cds; and transcriptional regulator QacR (qacR) and multidrug efflux protein QacB (qacB) genes, complete cds
gi|3327946|gb|AF053772.1|AF053772[3327946]

420: AF053771
Staphylococcus aureus plasmid pSK156 transcriptional regulator QacR (qacR), multidrug efflux protein QacB, delta-orf186, and putative transposase TnpA (tnpA) genes, complete cds
gi|3327941|gb|AF053771.1|AF053771[3327941]

421: AF029731
Staphylococcus aureus large conductance mechanosensitive channel (mscL) gene, complete cds
gi|3135291|gb|AF029731.1|AF029731[3135291]

422: AF027155
Staphylococcus aureus IgG-binding protein SBI (sbi) gene, complete cds
gi|2827911|gb|AF027155.1|AF027155[2827911]

423: AF024571
Staphylococcus aureus high affinity proline permease (putP) gene, complete cds
gi|2565310|gb|AF024571.1|AF024571[2565310]

424: U87144
Staphylococcus aureus branched-chain amino acid carrier protein gene, complete cds
gi|2315994|gb|U87144.1|SAU87144[2315994]

425: AF086644
Staphylococcus aureus type b beta-lactamase (blaZ) gene, partial cds
gi|3603440|gb|AF086644.1|AF086644[3603440]

426: AJ223781
Staphylococcus aureus trxB gene
gi|4379427|emb|AJ223781.1|SAAJ3781[4379427]

427: AF076030
Staphylococcus aureus 16S ribosomal RNA gene, partial sequence
gi|3551854|gb|AF076030.1|AF076030[3551854]

428: AF044951
Staphylococcus aureus repressor protein (rzcA) and transport protein (rzcB) genes, complete cds
gi|3445565|gb|AF044951.1|AF044951[3445565]

429: AF044906
Staphylococcus aureus isolate SA92 DNA topoisomerase IV subunit A (grlA) gene, partial cds
gi|3411113|gb|AF044906.1|AF044906[3411113]

430: AF044905
Staphylococcus aureus isolate SA32 DNA topoisomerase IV subunit A (grlA) gene, partial cds
gi|3411111|gb|AF044905.1|AF044905[3411111]

431: AF044904
Staphylococcus aureus isolate SA22 DNA topoisomerase IV subunit A (grlA) gene, partial cds
gi|3411109|gb|AF044904.1|AF044904[3411109]

432: AF044903
Staphylococcus aureus isolate SA198 DNA topoisomerase IV subunit A (grlA) gene, partial cds
gi|3411107|gb|AF044903.1|AF044903[3411107]

433: AF044902
Staphylococcus aureus isolate SA85 DNA topoisomerase IV subunit A (grlA) gene, partial cds
gi|3411105|gb|AF044902.1|AF044902[3411105]

434: AF044901
Staphylococcus aureus isolate SA76 DNA topoisomerase IV subunit A (grlA) gene, partial cds
gi|3411103|gb|AF044901.1|AF044901[3411103]

435: AF044900
Staphylococcus aureus isolate SA75 DNA topoisomerase IV subunit A (grlA) gene, partial cds
gi|3411101|gb|AF044900.1|AF044900[3411101]

436: AF044899
Staphylococcus aureus isolate R155 DNA topoisomerase IV subunit A (grlA) gene, partial cds
gi|3411099|gb|AF044899.1|AF044899[3411099]

437: AF044898
Staphylococcus aureus isolate SAM1 DNA topoisomerase IV subunit A (grlA) gene, partial cds
gi|3411097|gb|AF044898.1|AF044898[3411097]

438: AF044897
Staphylococcus aureus isolate SA74 DNA topoisomerase IV subunit A (grlA) gene, partial cds
gi|3411095|gb|AF044897.1|AF044897[3411095]

439: AF044075
Staphylococcus aureus isolate sa92 DNA gyrase subunit A (gyrA) gene, partial cds
gi|3411091|gb|AF044075.1|AF044075[3411091]

440: AF044074
Staphylococcus aureus isolate sa32 DNA gyrase subunit A (gyrA) gene, partial cds
gi|3411089|gb|AF044074.1|AF044074[3411089]

441: AF044073
Staphylococcus aureus isolate sa22 DNA gyrase subunit A (gyrA) gene, partial cds
gi|3411087|gb|AF044073.1|AF044073[3411087]

442: AF044072
Staphylococcus aureus isolate sa198 DNA gyrase subunit A (gyrA) gene, partial cds
gi|3411085|gb|AF044072.1|AF044072[3411085]

443: AF044071
Staphylococcus aureus isolate sa85 DNA gyrase subunit A (gyrA) gene, partial cds
gi|3411083|gb|AF044071.1|AF044071[3411083]

444: AF044070
Staphylococcus aureus isolate sa76 DNA gyrase subunit A (gyrA) gene, partial cds
gi|3411081|gb|AF044070.1|AF044070[3411081]

445: AF044069
Staphylococcus aureus isolate sa75 DNA gyrase subunit A (gyrA) gene, partial cds
gi|3411079|gb|AF044069.1|AF044069[3411079]

446: AF044068
Staphylococcus aureus isolate R155 DNA gyrase subunit A (gyrA) gene, partial cds
gi|3411077|gb|AF044068.1|AF044068[3411077]

447: AF044067
Staphylococcus aureus isolate SAM1 DNA gyrase subunit A (gyrA) gene, partial cds
gi|3411075|gb|AF044067.1|AF044067[3411075]

448: AF044066
Staphylococcus aureus isolate sa74 DNA gyrase subunit A (gyrA) gene, partial cds
gi|3411073|gb|AF044066.1|AF044066[3411073]

449: U93688
Staphylococcus aureus toxic shock syndrome toxin-1 (tst), enterotoxin (ent), and integrase (int) genes, complete cds
gi|2689547|gb|U93688.1|U93688[2689547]

450: U93687
Staphylococcus aureus attachment site for Tn557
gi|2689546|gb|U93687.1|U93687[2689546]

451: AJ224764
Staphylococcus aureus strain Newman clumping factor B (clfB) gene
gi|3393010|emb|AJ224764.1|SAA224764[3393010]

452: AF064774
Staphylococcus aureus extracellular enterotoxin type I precursor (SEI) gene, complete cds
gi|3323612|gb|AF064774.1|AF064774[3323612]

453: AF064773
Staphylococcus aureus extracellular enterotoxin type G precursor (SEG) gene, complete cds
gi|3323610|gb|AF064773.1|AF064773[3323610]

454: Y14370
Staphylococcus aureus RF3, murE, ypfP genes
gi|3256221|emb|Y14370.1|SAY14370[3256221]

455: AF065394
Staphylococcus aureus enolase (eno) gene, complete cds
gi|3152724|gb|AF065394.1|AF065394[3152724]

456: AF062376
Staphylococcus aureus strain E3452, unidentified sequence 2
gi|3142435|gb|AF062376.1|AF062376[3142435]

457: AF062375
Staphylococcus aureus strain E3452, unidentified sequence 1
gi|3142434|gb|AF062375.1|AF062375[3142434]

458: AF062374
Staphylococcus aureus strain W6652, unidentified sequence 2
gi|3142433|gb|AF062374.1|AF062374[3142433]

459: AF062373
Staphylococcus aureus strain W6652, unidentified sequence 1
gi|3142432|gb|AF062373.1|AF062373[3142432]

460: AB007500
Staphylococcus aureus genes for penicillin-binding protein 1, MraY, MurD, partial and complete cds
gi|2463558|dbj|AB007500.1|AB007500[2463558]

461: Y09924
S.aureus serS gene
gi|1835217|emb|Y09924.1|SASERS[1835217]

462: U63529
Staphylococcus aureus novel antigen gene, complete cds
gi|1488694|gb|U63529.1|SAU63529[1488694]

463: AF033191
Staphylococcus aureus strain ATCC25923 clone pSa-442 Sau3AI fragment
gi|2988485|gb|AF033191.1|AF033191[2988485]

464: Y15856
Staphylococcus aureus 16S rRNA gene
gi|2950318|emb|Y15856.1|SAY15856[2950318]

465: AB000439
Staphylococcus aureus recG gene, complete cds
gi|2826895|dbj|AB000439.1|AB000439[2826895]

466: AF041467
Staphylococcus aureus coenzyme A disulfide reductase gene, complete cds
gi|2792489|gb|AF041467.1|AF041467[2792489]

467: Y14051
Staphylococcus aureus mecA, mecR1, mecI genes and ORF168, ORF142, ORF44, ORF145 and ORF224
gi|2791983|emb|Y14051.1|SAMECAR1I[2791983]

468: U82085
Staphylococcus aureus plasmid pIP1633 pristinamycin resistance protein VgaB (vgaB) gene, complete cds
gi|2769707|gb|U82085.1|SAU82085[2769707]

469: AF026122
Staphylococcus aureus plasmid pIM51 signal transduction protein (agrB) gene, partial cds; pre-pheromone (agrD) and mutant sensor protein (agrC) genes, complete cds; and transducer protein (agrA) gene, partial cds
gi|2736224|gb|AF026122.1|AF026122[2736224]

470: AF026121
Staphylococcus aureus plasmid pIM50 signal transduction protein (agrB) gene, partial cds; pre-pheromone (agrD) and mutant sensor protein (agrC) genes, complete cds; and transducer protein (agrA) gene, partial cds
gi|2736219|gb|AF026121.1|AF026121[2736219]

471: AF026120
Staphylococcus aureus plasmid pIM49 signal transduction protein (agrB) gene, partial cds; pre-pheromone (agrD) and mutant sensor protein (agrC) genes, complete cds; and transducer protein (agrA) gene, partial cds
gi|2736214|gb|AF026120.1|AF026120[2736214]

472: AB009635
Staphylococcus aureus DNA for Fmt, complete cds
gi|2696795|dbj|AB009635.1|AB009635[2696795]

473: AB006796
Staphylococcus aureus genes for LukS-PV, LukF-PV and integrase, complete cds
gi|2696710|dbj|AB006796.1|AB006796[2696710]

474: U39769
Staphylococcus aureus 16S-23S ribosomal RNA spacer region
gi|2668542|gb|U39769.1|SAU39769[2668542]

475: D00184
Staphylococcus aureus gene for staphylocoagulase, complete cds
gi|216976|dbj|D00184.1|STASCAG[216976]

476: X56628
Staphylococcus aureus qacA gene for antiseptic resistance protein
gi|773395|emb|X56628.1|SAQACA[773395]

477: AF033018
Staphylococcus aureus ribosome recycling factor (frr) gene, complete cds
gi|2645712|gb|AF033018.1|AF033018[2645712]

478: D82063
Staphylococcus aureus gene for lipophilic protein, partial cds
gi|2641997|dbj|D82063.1|D82063[2641997]

479: D76414
Staphylococcus aureus gene for histidyl-tRNA synthetase, ppGpp hydrolase, lytic enzyme, complete cds
gi|2580431|dbj|D76414.1|D76414[2580431]

480: U57060
Staphylococcus aureus scdA gene, complete cds
gi|1575060|gb|U57060.1|SAU57060[1575060]

481: D89066
Staphylococcus aureus DNA for DnaA, complete cds
gi|1854450|dbj|D89066.1|D89066[1854450]

482: U85095
Staphylococcus aureus strain KSI9051 agr signal transduction pathway genes: AgrB (agrB) gene, partial cds; pre-pheromone AgrD (agrD) and truncated sensor protein AgrC-31 (agrC) genes, complete cds; and transducer protein AgrA (agrA) gene, partial cds
gi|1916237|gb|U85095.1|SAU85095[1916237]

483: U85097
Staphylococcus aureus strain RN4282 agr signal transduction pathway genes: AgrB (agrB) gene, partial cds,pre-pheromone AgrD (agrD) and sensor protein AgrC (agrC) genes, complete cds, and transducer protein AgrA (agrA) gene, partial cds
gi|1916245|gb|U85097.1|SAU85097[1916245]

484: U85096

Staphylococcus aureus strain KSI54 agr signal transduction pathway genes: AgrB (agrB) gene, partial cds, pre-pheromone AgrD (agrD) and sensor protein AgrC (agrC) genes, complete cds, and transducer protein AgrA (agrA) gene, partial cds
gi|1916241|gb|U85096.1|SAU85096[1916241]

485: AF015929
Staphylococcus aureus 16S ribosomal RNA gene, partial sequence
gi|2353761|gb|AF015929.1|AF015929[2353761]

486: D10369
Staphylococcus aureus gene for glutamic acid-specific protease, partial cds
gi|2344764|dbj|D10369.1|D10369[2344764]

487: A48955
Sequence 2 from Patent WO9604380
gi|2302593|emb|A48955.1|A48955[2302593]

488: A48501
Sequence 3 from Patent WO9603516
gi|2302280|emb|A48501.1|A48501[2302280]

489: A48500
Sequence 2 from Patent WO9603516
gi|2302278|emb|A48500.1|A48500[2302278]

490: A48499
Sequence 1 from Patent WO9603516
gi|2302277|emb|A48499.1|A48499[2302277]

491: A47600
Sequence 13 from Patent EP0688873
gi|2301548|emb|A47600.1|A47600[2301548]

492: A47599
Sequence 12 from Patent EP0688873
gi|2301547|emb|A47599.1|A47599[2301547]

493: A47598
Sequence 11 from Patent EP0688873
gi|2301546|emb|A47598.1|A47598[2301546]

494: A47597
Sequence 10 from Patent EP0688873
gi|2301545|emb|A47597.1|A47597[2301545]

495: A47596
Sequence 9 from Patent EP0688873
gi|2301544|emb|A47596.1|A47596[2301544]

496: A47595
Sequence 8 from Patent EP0688873
gi|2301543|emb|A47595.1|A47595[2301543]

497: A47594
Sequence 7 from Patent EP0688873
gi|2301542|emb|A47594.1|A47594[2301542]

498: A44534
Sequence 10 from Patent WO9513395
gi|2299352|emb|A44534.1|A44534[2299352]

499: A44533
Sequence 9 from Patent WO9513395
gi|2299351|emb|A44533.1|A44533[2299351]

500: A44529
Sequence 5 from Patent WO9513395
gi|2299347|emb|A44529.1|A44529[2299347]

501: A44528
Sequence 4 from Patent WO9513395
gi|2299346|emb|A44528.1|A44528[2299346]

502: A44527
Sequence 3 from Patent WO9513395
gi|2299345|emb|A44527.1|A44527[2299345]

503: A44526
Sequence 2 from Patent WO9513395
gi|2299344|emb|A44526.1|A44526[2299344]

504: A44525
Sequence 1 from Patent WO9513395
gi|2299343|emb|A44525.1|A44525[2299343]

505: A39696
Sequence 9 from Patent WO9418327
gi|2295954|emb|A39696.1|A39696[2295954]

506: AF001783
Staphylococcus aureus strain RN8462 AgrB (agrB), AgrD (agrD) and AgrC (agrC) genes, complete cds
gi|2258297|gb|AF001783.1|AF001783[2258297]

507: AF001782
Staphylococcus aureus strain SA502A AgrB (agrB), AgrD (agrD) and AgrC (agrC) genes, complete cds
gi|2258293|gb|AF001782.1|AF001782[2258293]

508: L77194
Staphylococcus aureus peptidoglycan hydrolase (lytM) gene, complete cds
gi|2239273|gb|L77194.1|STALYTM[2239273]

509: X73889
S.aureus genes crtM and crtN
gi|2224840|emb|X73889.1|SAP1P2[2224840]

510: X74219
S.aureus gene for isoleucyl-tRNA synthetase
gi|437915|emb|X74219.1|SAILES[437915]

511: Y10419
S.aureus gene encoding outer surface binding 70kD protein, partial
gi|2190506|emb|Y10419.1|SAOSB70KD[2190506]

512: M63177
S.aureus sigma factor (plaC) gene, complete cds
gi|153068|gb|M63177.1|STAPLAC[153068]

513: E08773
DNA encoding Protein A
gi|2176885|dbj|E08773.1|E08773[2176885]

514: E07163
Partial sequence of Staphylococcus aureus
gi|2175310|dbj|E07163.1|E07163[2175310]

515: E07162

Partial sequence of Staphylococcus aureus
gi|2175309|dbj|E07162.1|E07162[2175309]

516: E07161
Partial sequence of Staphylococcus aureus
gi|2175308|dbj|E07161.1|E07161[2175308]

517: E07160
Partial sequence of Staphylococcus aureus
gi|2175307|dbj|E07160.1|E07160[2175307]

518: E07159
Partial sequence of Staphylococcus aureus
gi|2175306|dbj|E07159.1|E07159[2175306]

519: E07158
Partial sequence of Staphylococcus aureus
gi|2175305|dbj|E07158.1|E07158[2175305]

520: E07157
Partial sequence of Staphylococcus aureus
gi|2175304|dbj|E07157.1|E07157[2175304]

521: E07156
Partial sequence of Staphylococcus aureus
gi|2175303|dbj|E07156.1|E07156[2175303]

522: E07155
Partial sequence of Staphylococcus aureus
gi|2175302|dbj|E07155.1|E07155[2175302]

523: E03836
DNA encoding V8 protease
gi|2172050|dbj|E03836.1|E03836[2172050]

524: E03835
DNA encoding V8-like protease
gi|2172049|dbj|E03835.1|E03835[2172049]

525: E03526
gDNA encoding protein A
gi|2171742|dbj|E03526.1|E03526[2171742]

526: E02873
DNA encoding staphylokinase(SAK)
gi|2171098|dbj|E02873.1|E02873[2171098]

527: E01690
Genomic DNA of protein A of staphylococcus aureus
gi|2169943|dbj|E01690.1|E01690[2169943]

528: E00876
DNA fragment comprising a promoter of sak gene and the region coding the signal peptide
gi|2169137|dbj|E00876.1|E00876[2169137]

529: E00203
DNA sequence of protein A-like molecule
gi|2168499|dbj|E00203.1|E00203[2168499]

530: D83951
Staphylococcus aureus DNA for LukM component, LukF-PV like component, complete cds
gi|1230553|dbj|D83951.1|STALUK[1230553]

531: D17366
Staphylococcus aureus atl gene for autolysin, complete cds and other ORFs
gi|643603|dbj|D17366.1|STAATLA[643603]

532: D10489
Staphylococcus aureus genes for DNA gyrase A and B, complete cds
gi|540540|dbj|D10489.1|STAGYRABA[540540]

533: D21131
Staphylococcus aureus gene for a participant in homogeneous expression of high-level methicillin resistance, complete cds
gi|531264|dbj|D21131.1|STASRM551A[531264]

534: D30690
Staphylococcus aureus genes for ORF37; HSP20; HSP70; HSP40; ORF35, complete cds
gi|487326|dbj|D30690.1|STANHS[487326]

535: D14711
Staphylococcus aureus HSP10 and HSP60 genes
gi|441206|dbj|D14711.1|STAHSP[441206]

536: D90119
S. aureus norA gene
gi|216974|dbj|D90119.1|STANORA[216974]

537: D83357
Staphylococcus aureus (strain ATCC12600T) gene for 16S rRNA, partial sequence
gi|1199939|dbj|D83357.1|STA16SRR05[1199939]

538: D83356
Staphylococcus aureus (strain OA1) gene for 16S rRNA, partial sequence
gi|1199938|dbj|D83356.1|STA16SRR04[1199938]

539: D83355
Staphylococcus aureus (strain ATCC35844T) gene for 16S rRNA, partial sequence
gi|1199937|dbj|D83355.1|STA16SRR03[1199937]

540: D83354
Staphylococcus aureus (strain Kitami) gene for 16S rRNA, partial sequence
gi|1199936|dbj|D83354.1|STA16SRR02[1199936]

541: D83353
Staphylococcus aureus (strain FU16A2) gene for 16S rRNA, partial sequence
gi|1199935|dbj|D83353.1|STA16SRR01[1199935]

542: D12572
Staphylococcus aureus rrnA gene for 23S ribosomal RNA
gi|216969|dbj|D12572.1|STA23SRNA[216969]

543: D86727
Staphylococcus aureus DNA for DNA polymerase III, complete cds
gi|1483181|dbj|D86727.1|D86727[1483181]

544: D67075
Staphylococcus aureus DNA for DNA topoisomerase IV GrlB subunit, DNA topoisomerase IV GrlA subunit, complete cds
gi|1777319|dbj|D67075.1|D67075[1777319]

545: D67074
Staphylococcus aureus DNA for DNA topoisomerase IV GrlB subunit, DNA topoisomerase IV GrlA subunit, complete cds
gi|1777316|dbj|D67074.1|D67074[1777316]

546: U97062
Staphylococcus aureus NCTC 8325 SecA (secA) gene, complete cds
gi|2078389|gb|U97062.1|SAU97062[2078389]

547: U96620
Staphylococcus aureus NCTC 8325 ribosomal protein L30 (L30), ribosomal protein L15 (L15) and SecY (secY) genes, complete cds
gi|2078379|gb|U96620.1|SAU96620[2078379]

548: U96619
Staphylococcus aureus NCTC 8325 SecE (secE), NusG (nusG) and RplK (rplK) genes, complete cds
gi|2078375|gb|U96619.1|SAU96619[2078375]

549: Z84573
S.aureus dihydropteroate synthase gene
gi|2058355|emb|Z84573.1|SADHPS01[2058355]

550: AB001896
Staphylococcus aureus DNA for sigma70 operon, complete cds
gi|1943991|dbj|AB001896.1|AB001896[1943991]

551: Y07645
S.aureus sigB gene
gi|1934986|emb|Y07645.1|SASIGFACB[1934986]

552: U92441
Staphylococcus aureus alkyl hydroperoxide reductase subunit C (aphC) and subunit F (aphF) genes, complete cds
gi|1916315|gb|U92441.1|SAU92441[1916315]

553: U91741
Staphylococcus aureus teichoic acid biosynthesis TagB gene, partial cds and TagX and TagD genes, complete cds
gi|1913904|gb|U91741.1|SAU91741[1913904]

554: U29454
Staphylococcus aureus penicillin binding protein 4 (pbpD) gene, complete cds
gi|1905928|gb|U29454.1|SAU29454[1905928]

555: U29478
Staphylococcus aureus ABC transporter-like protein AbcA (abcA) gene, complete cds
gi|1841513|gb|U29478.1|SAU29478[1841513]

556: U73374
Staphylococcus aureus type 8 capsule genes, cap8A, cap8B, cap8C, cap8D, cap8E, cap8F, cap8G, cap8H, cap8I, cap8J, cap8K, cap8L, cap8M, cap8N, cap8O, cap8P, complete cds
gi|1657639|gb|U73374.1|SAU73374[1657639]

557: L42945
Staphylococcus aureus lytS and lytR genes, complete cds
gi|1854576|gb|L42945.1|STALYTS[1854576]

558: U38429
Staphylococcus aureus chloramphenicol resistance plasmid pKH7, complete sequence
gi|1731451|gb|U38429.1|SAU38429[1731451]

559: U81980
Staphylococcus aureus plasmid pKH4 replication protein Rep (rep) and quaternary ammonium compounds resistance protein Qac genes, complete cds
gi|1848267|gb|U81980.1|SAU81980[1848267]

560: X55185
S. aureus hla gene for truncated alpha-toxin
gi|46745|emb|X55185.1|SATAT[46745]

561: V01278
S.aureus plasmid pE194 ORF's A,B,C,D,E, and F
gi|46555|emb|V01278.1|SAE194[46555]

562: U31979
Staphylococcus aureus chorismate synthase (aroC) and nucleoside diphosphate kinase (ndk) genes, complete cds, dehydroauinate synthase (aroB) and geranylgeranyl pyrophosphate synthetase homolog (gerCC) genes, partial cds
gi|987495|gb|U31979.1|SAU31979[987495]

563: X91786
S.aureus abcA, pbp4, and tagD genes
gi|1262135|emb|X91786.1|SAPBP4GEN[1262135]

564: U36912
Staphylococcus aureus plasmid J3356::POX7;3, complete sequence
gi|1045528|gb|U36912.1|SAU36912[1045528]

565: U36911
Staphylococcus aureus plasmid J3356::POX7;1, complete sequence
gi|1045526|gb|U36911.1|SAU36911[1045526]

566: U36910
Staphylococcus aureus plasmid J3358, complete sequence
gi|1045523|gb|U36910.1|SAU36910[1045523]

567: U64885
Staphylococcus aureus ribonuclease P RNA (rnpB) gene, partial sequence
gi|1498078|gb|U64885.1|SAU64885[1498078]

568: U76872
Staphylococcus aureus isolate EMRSA-9 coagulase gene, VNTR sequence, sequence tagged site
gi|1753154|gb|U76872.1|SAU76872[1753154]

569: U76871
Staphylococcus aureus isolate EMRSA-9 coagulase gene, VNTR sequence, sequence tagged site
gi|1753153|gb|U76871.1|SAU76871[1753153]

570: U76870
Staphylococcus aureus isolate EMRSA-2 coagulase gene, VNTR sequence, sequence tagged site
gi|1753152|gb|U76870.1|SAU76870[1753152]

571: U76869
Staphylococcus aureus isolate EMRSA-2 coagulase gene, VNTR sequence, sequence tagged site
gi|1753151|gb|U76869.1|SAU76869[1753151]

572: U76868
Staphylococcus aureus isolate EMRSA-16 coagulase gene, VNTR sequence, sequence tagged site
gi|1753150|gb|U76868.1|SAU76868[1753150]

573: U76867
Staphylococcus aureus isolate EMRSA-16 coagulase gene, VNTR sequence, sequence tagged site
gi|1753149|gb|U76867.1|SAU76867[1753149]

574: U76866
Staphylococcus aureus isolate EMRSA-15 coagulase gene, VNTR sequence, sequence tagged site
gi|1753148|gb|U76866.1|SAU76866[1753148]

575: U76865
Staphylococcus aureus isolate EMRSA-5 coagulase gene, VNTR sequence, sequence tagged site
gi|1753147|gb|U76865.1|SAU76865[1753147]

576: U76864
Staphylococcus aureus isolate EMRSA-12 coagulase gene, VNTR sequence, sequence tagged site
gi|1753146|gb|U76864.1|SAU76864[1753146]

577: U76863
Staphylococcus aureus isolate EMRSA-6 coagulase gene, VNTR sequence, sequence tagged site
gi|1753145|gb|U76863.1|SAU76863[1753145]

578: U76862
Staphylococcus aureus isolate EMRSA-10 coagulase gene, VNTR sequence, sequence tagged site
gi|1753144|gb|U76862.1|SAU76862[1753144]

579: U76861
Staphylococcus aureus isolate Jevons coagulase gene, VNTR sequence, sequence tagged site
gi|1753143|gb|U76861.1|SAU76861[1753143]

580: U76860
Staphylococcus aureus isolate EMRSA-3 coagulase gene, VNTR sequence, sequence tagged site
gi|1753142|gb|U76860.1|SAU76860[1753142]

581: U76859
Staphylococcus aureus isolate EMRSA-14 coagulase gene, VNTR sequence, sequence tagged site
gi|1753141|gb|U76859.1|SAU76859[1753141]

582: U76858
Staphylococcus aureus German coagulase gene, VNTR sequence, sequence tagged site
gi|1753140|gb|U76858.1|SAU76858[1753140]

583: U76857
Staphylococcus aureus isolate ps42e coagulase gene, VNTR sequence, sequence tagged site
gi|1753139|gb|U76857.1|SAU76857[1753139]

584: U76856
Staphylococcus aureus isolate EMRSA-7 coagulase gene, VNTR sequence, sequence tagged site
gi|1753138|gb|U76856.1|SAU76856[1753138]

585: U76855
Staphylococcus aureus isolate EMRSA-1 coagulase gene, VNTR sequence, sequence tagged site
gi|1753137|gb|U76855.1|SAU76855[1753137]

586: U76854
Staphylococcus aureus isolate EMRSA-4 coagulase gene, VNTR sequence, sequence tagged site
gi|1753136|gb|U76854.1|SAU76854[1753136]

587: U76853
Staphylococcus aureus isolate EMRSA-1 coagulase gene, VNTR sequence, sequence tagged site
gi|1753135|gb|U76853.1|SAU76853[1753135]

588: U76852
Staphylococcus aureus isolate EMRSA-11 coagulase gene, VNTR sequence, sequence tagged site
gi|1753134|gb|U76852.1|SAU76852[1753134]

589: U76851
Staphylococcus aureus isolate EMRSA-15 coagulase gene, VNTR sequence, sequence tagged site
gi|1753133|gb|U76851.1|SAU76851[1753133]

590: U76850
Staphylococcus aureus isolate ps 71 coagulase gene, VNTR sequence, sequence tagged site
gi|1753132|gb|U76850.1|SAU76850[1753132]

591: U76849
Staphylococcus aureus isolate EMRSA-13 coagulase gene, VNTR sequence, sequence tagged site
gi|1753131|gb|U76849.1|SAU76849[1753131]

592: U76848
Staphylococcus aureus isolate EMRSA-15 coagulase gene, VNTR sequence, sequence tagged site
gi|1753130|gb|U76848.1|SAU76848[1753130]

593: U76847
Staphylococcus aureus isolate EMRSA-15 coagulase gene, VNTR sequence, sequence tagged site
gi|1753129|gb|U76847.1|SAU76847[1753129]

594: Y09570
S.aureus femD gene
gi|1684748|emb|Y09570.1|SAFEMD[1684748]

595: X95848
S.aureus fnbA gene
gi|1204145|emb|X95848.1|SAFNBA[1204145]

596: Y09428
S.aureus rpoC gene
gi|1684750|emb|Y09428.1|SARPOCGE1[1684750]

597: S76611
{dru element, hypervariable region, methicillin resistance determinant} [Staphylococcus aureus, MRSA, HVR genotype B, Genomic, 411 nt]
gi|913625|gb|S76611.1|S76611[913625]

598: S76213
asp23=alkaline shock protein 23 {methicillin resistant} [Staphylococcus aureus, 912, Genomic, 1360 nt]
gi|894288|gb|S76213.1|S76213[894288]

599: S75707
mec A {5' region, mutation IV} [Staphylococcus aureus, methicillin-resistant MR108, Genomic Mutant, 67 nt]
gi|913672|gb|S75707.1|S75707[913672]

600: S75706
mec A {5' region, mutation III} [Staphylococcus aureus, methicillin-resistant MR108, Genomic Mutant, 67 nt]
gi|913671|gb|S75706.1|S75706[913671]

601: S75705
mec A {5' region, mutation II} [Staphylococcus aureus, methicillin-resistant MR108, Genomic Mutant, 67 nt]
gi|913670|gb|S75705.1|S75705[913670]

602: S76270
16S rRNA {16S-23S ribosomal RNA intergenic region} [Staphylococcus aureus, clinical isolate, Genomic, 94 nt]
gi|894286|gb|S76270.1|S76270[894286]

603: S72497
plc=beta-hemolysin [Staphylococcus aureus, 126/89, Genomic, 1308 nt]
gi|619316|gb|S72497.1|S72497[619316]

604: S74031
norA=NorA {ISP794} [Staphylococcus aureus, NCTC 8325, Insertion, 1820 nt]
gi|693734|gb|S74031.1|S74031[693734]

605: S67449
tet(K)=tetracycline efflux protein [Staphylococcus aureus, pT181, Plasmid, 1380 nt]
gi|456769|gb|S67449.1|S67449[456769]

606: U75367
Staphylococcus aureus transposon Tn551 transposase gene, partial cds
gi|1673526|gb|U75367.1|SATN551S2[1673526]

607: U75368
Staphylococcus aureus transposon Tn551 transposase gene, partial cds
gi|1673524|gb|U75368.1|SATN551S1[1673524]

608: U31175
Staphylococcus aureus D-specific D-2-hydroxyacid dehydrogenase (ddh) gene, complete cds
gi|1644432|gb|U31175.1|SAU31175[1644432]

609: X53096
S.aureus genes encoding Sau96I DNA methyltransferase and Sau96I restriction endonuclease
gi|46616|emb|X53096.1|SAMTRE[46616]

610: X53951
S.aureus plasmid pSH6 DNA for insertion sequences IS257-2, IS257-3 and IS256
gi|46598|emb|X53951.1|SAIS2572[46598]

611: X53952
S.aureus plasmid pSH6 DNA for insertion sequences IS257-1 and IS256
gi|46596|emb|X53952.1|SAIS2571[46596]

612: X03408
Staphylococcus aureus plasmid pUB110dB sequence
gi|46495|emb|X03408.1|SA110KAR[46495]

613: U50629
Staphylococcus aureus nicking enzyme (nes) gene, complete cds
gi|1245473|gb|U50629.1|SAU50629[1245473]

614: U38656
Staphylococcus aureus tetracycline resistance plasmid pKH1, tet gene, complete cds
gi|1580803|gb|U38656.1|SAU38656[1580803]

615: U58139
Staphylococcus aureus beta-lactamase (blaz) gene, complete cds
gi|1575124|gb|U58139.1|SAU58139[1575124]

616: A31894
S.aureus pUB110 Ble gene
gi|1567207|emb|A31894.1|A31894[1567207]

617: L42943
Staphylococcus aureus (clone KIN50) phosphoenolpyruvate carboxykinase (pckA) gene, complete cds
gi|860731|gb|L42943.1|STAPEPCK[860731]

618: U51474
Staphylococcus aureus truncated streptothricin acetyl transferase (sat) and 3'5'-aminoglycoside phosphotransferase (aphA-3) genes, complete cds
gi|1272325|gb|U51474.1|SAU51474[1272325]

619: U50077
Staphylococcus aureus multidrug resistance plasmid pKH8 replication protein (rep) gene, qacC' gene, and multidrug resistance protein (qacC) gene, complete cds
gi|1236637|gb|U50077.1|SAU50077[1236637]

620: U38428
Staphylococcus aureus tetracycline resistance plasmid pKH6, complete sequence
gi|1052997|gb|U38428.1|SAU38428[1052997]

621: U66665
Staphylococcus aureus DNA fragment with class II promoter activity
gi|1519432|gb|U66665.1|SAU66665[1519432]

622: U66664
Staphylococcus aureus DNA fragment with class II promoter activity
gi|1519431|gb|U66664.1|SAU66664[1519431]

623: U66663
Staphylococcus aureus DNA fragment with class II promoter activity
gi|1519430|gb|U66663.1|SAU66663[1519430]

624: X87104
S.aureus mdr, pbp4 and taqD genes (SG511-55 isolate)
gi|1125684|emb|X87104.1|SADNAS55[1125684]

625: X87105
S.aureus mdr, pbp4 and taqD genes (PVI-25 isolate)
gi|1125680|emb|X87105.1|SADNAS25[1125680]

626: X89233
S.aureus DNA for rpoC gene
gi|1495790|emb|X89233.1|SARPOCGEN[1495790]

627: M28521
Staphylococcus aureus enterotoxin D (entD) gene, complete cds
gi|1492109|gb|M28521.1|STAENTD[1492109]

628: U54636
Staphylococcus aureus protein A, complete cds
gi|1480566|gb|U54636.1|SAU54636[1480566]

629: U46541
Staphylococcus aureus sarA gene, complete cds
gi|1477531|gb|U46541.1|SAU46541[1477531]

630: L14017
Staphylococcus aureus methicillin-resistance protein (mecR) gene and unknown ORF, complete cds
gi|1408062|gb|L14017.1|STAMECRA[1408062]

631: U60589
Staphylococcus aureus novel antigen gene, complete cds
gi|1407783|gb|U60589.1|SAU60589[1407783]

632: Z48003
S.aureus gene for DNA polymerase III
gi|642269|emb|Z48003.1|SADNAPOL3[642269]

633: M37889
Staphylococcus aureus replication (rep), control of replication (cop), and resistance protein (QacC) genes, complete cds
gi|153091|gb|M37889.1|STAREPQAC[153091]

634: V01281
S.aureus mRNA for nuclease
gi|46623|emb|V01281.1|SANUCX[46623]

635: X97985
S.aureus orfs 1,2,3 & 4
gi|1340127|emb|X97985.1|SA1234[1340127]

636: X00127
Staphylococcus aureus S-phi-C gene for staphylokinase
gi|47425|emb|X00127.1|SPSAK1[47425]

637: X03286
Staphylococcus aureus mutant strain V1 spa gene for protein A
gi|46774|emb|X03286.1|SAV1SPA[46774]

638: X62282
S.aureus target site DNA for IS431 insertion
gi|46769|emb|X62282.1|SATSIS431[46769]

639: X01645
Staphylococcus aureus (Wood 46) gene for alpha-toxin
gi|46763|emb|X01645.1|SATOXA[46763]

640: X16471
Staphylococcus aureus transposon Tn4002 blaZ gene for beta-lactamase
gi|46761|emb|X16471.1|SATNBLAZ[46761]

641: X52734
S.aureus Tn552 transposable element
gi|46754|emb|X52734.1|SATN552[46754]

642: X13290
Staphylococcus aureus multi-resistance plasmid pSK1 DNA containing transposon Tn4003
gi|46747|emb|X13290.1|SATN4003[46747]

643: X66088
S.aureus tRNA-Asp gene
gi|46744|emb|X66088.1|SATASP[46744]

644: Z30588
S.aureus (RN4220) genes for potential ABC transporter and potential membrane spanning protein
gi|459255|emb|Z30588.1|SASTPSMP[459255]

645: X16457
Staphylococcus aureus gene for staphylocoagulase
gi|46736|emb|X16457.1|SASTPHLC[46736]

646: V01287
Staphylococcus aureus gene (spa) fragment encoding protein A
gi|46692|emb|V01287.1|SASPAX[46692]

647: X61307
Staphylococcus aureus spa gene for protein A
gi|46690|emb|X61307.1|SASPAPA[46690]

648: Y00356
Staphylococcus aureus V8 serine protease gene
gi|46686|emb|Y00356.1|SASP[46686]

649: X06603
Staphylococcus aureus phage 42D for staphylokinase
gi|46676|emb|X06603.1|SASAK42D[46676]

650: X93205
S.aureus ptsH and ptsI genes
gi|1070384|emb|X93205.1|SAPTSHI[1070384]

651: X64172
S.aureus rplL, orf202, rpoB(rif) and rpoC genes for ribosomal protein L7/L12, hypothetical protein ORF202, DNA-directed RNA polymerase beta & beta' chains
gi|677848|emb|X64172.1|SARPLRPO[677848]

652: X72700
S.aureus genes for S and F components of Panton-Valentine leucocidins
gi|551668|emb|X72700.1|SAPVLSF[551668]

653: X60827
S.aureus (plasmid pSCS6) cat gene for chloramphenicol acetyltransferase
gi|46651|emb|X60827.1|SAPSCS6[46651]

654: X64389
S.aureus leuF-P83 gene for F component of leucocidin R
gi|488528|emb|X64389.1|SALEUF[488528]

655: X62288
S.aureus DNA for penicillin-binding protein 2
gi|483533|emb|X62288.1|SAPENBP2[483533]

656: X55798
S.aureus plasmid pOX2000
gi|295833|emb|X55798.1|SAPOX2000[295833]

657: X58434
S.aureus pdhB, pdhC and pdhD genes for pyruvate decarboxylase, dihydrolipoamide acetyltransferase and dihydrolipoamide dehydrogenase
gi|48871|emb|X58434.1|SAPDHDNA[48871]

658: X06627
Staphylococcus aureus plasmid pS194 sequence
gi|46643|emb|X06627.1|SAPS194[46643]

659: X12831
Staphylococcus aureus chloramphenicol resistance plasmid pC223 DNA (nt 1250 - 3072)
gi|46637|emb|X12831.1|SAPC223A[46637]

660: X07371
Staphylococcus aureus plasmid pC223 basic replicon DNA
gi|46635|emb|X07371.1|SAPC223[46635]

661: X02529
Staphylococcus aureus plasmid pC221 complete DNA sequence
gi|46630|emb|X02529.1|SAPC221[46630]

662: Y00688
Staphylococcus aureus (MRSA) PBP gene for beta-lactam-inducible penicillin-binding protein
gi|46628|emb|Y00688.1|SAPBP[46628]

663: X04121
S. aureus PC1 beta-lactamase gene blaZ from plasmid pI258
gi|46626|emb|X04121.1|SAPBLAZ[46626]

664: X59477
S.aureus plasmid DNA for part of mupirocin resistance gene (XhoI site)
gi|46621|emb|X59477.1|SAMUPIRES[46621]

665: X59478
S.aureus plasmid DNA for mupirocin resistance gene (NcoI-NcoI fragment)
gi|46619|emb|X59478.1|SAMUPIREI[46619]

666: X52593
S. aureus mecA gene for PBP2' (penicillin binding protein 2')
gi|46610|emb|X52593.1|SAMECAPB[46610]

667: X76490
S.aureus (bb270) glnA and glnR genes
gi|1134885|emb|X76490.1|SAGLNAR[1134885]

668: X81586
S.aureus hlgA, hlgB and hlgC genes
gi|550421|emb|X81586.1|SAHLGABC[550421]

669: X72014
S.aureus fib gene for fibrinogen-binding protein
gi|311975|emb|X72014.1|SAFIBB[311975]

670: X72013
S.aureus fib gene for fibrinogen-binding protein
gi|311973|emb|X72013.1|SAFIBA[311973]

671: X71437
S.aureus genes gyrB, gyrA and recF (partial)
gi|296393|emb|X71437.1|SAGYRREC[296393]

672: X62992
S.aureus fnbB gene for fibronectin binding protein B
gi|49040|emb|X62992.1|SAFNBB[49040]

673: X52594
S. aureus hypervariable region, 3' to mecA gene
gi|48712|emb|X52594.1|SAHVR[48712]

674: X14827
Staphylococcus aureus lacC and lacD genes
gi|46604|emb|X14827.1|SALACCD[46604]

675: X13404
Staphylococcus aureus hlb gene for beta-hemolysin
gi|46586|emb|X13404.1|SAHLB[46586]

676: X17301
S.aureus DNA for hld gene and for part of agr gene
gi|46585|emb|X17301.1|SAHDLAGR[46585]

677: X17688
S.aureus factor essential for expression of methicillin resistance (femA) gene, complete cds, and trpA gene, 3' end
gi|46579|emb|X17688.1|SAFEMA[46579]

678: X03097
Staphylococcus aureus plasmid pE194 mRNA for ermC leader region
gi|46574|emb|X03097.1|SAERMCTR[46574]

679: Z16422
S.aureus dfrB gene for dihydrofolate reductase
gi|671631|emb|Z16422.1|SADIRED[671631]

680: Z33409
S.aureus (C6-coa-EM) coagulase gene repeat region
gi|495298|emb|Z33409.1|SACOAGR6[495298]

681: Z33408
S.aureus (C50-coa-E) coagulase gene repeat region
gi|495297|emb|Z33408.1|SACOAGR5[495297]

682: Z33407
S.aureus (C35-coa-E) coagulase gene repeat region
gi|495296|emb|Z33407.1|SACOAGR4[495296]

683: Z33406
S.aureus (C26-coa-E) coagulase gene repeat region
gi|495295|emb|Z33406.1|SACOAGR3[495295]

684: Z33405
S.aureus (C20-coa-E) coagulase gene repeat region
gi|495294|emb|Z33405.1|SACOAGR2[495294]

685: Z33404
S.aureus (C14-coa-E) coagulase gene repeat region
gi|495293|emb|Z33404.1|SACOAGR1[495293]

686: X75439
S.aureus plasmid encoded DNA, mup R gene
gi|438226|emb|X75439.1|SADNAMUPR[438226]

687: X62587
S.aureus ebr gene for ethidium bromide resistance protein
gi|49016|emb|X62587.1|SAEBRN20[49016]

688: X54338
S.aureus plasmid pA22 ermC gene (5' region)
gi|46572|emb|X54338.1|SAERMC[46572]

689: X51661
S.aureus enterotoxin C3 gene (entC3)
gi|46570|emb|X51661.1|SAENTC3A[46570]

690: X05815
Staphylococcus enterotoxin C1 gene (entC1)
gi|46566|emb|X05815.1|SAENTC1[46566]

691: X15574
Staphylococcus aureus plasmid gene for ethidium bromide resistance (ebr)

gi|46560|emb|X15574.1|SAEBR[46560]

692: Y07536
S. aureus genes for thymidylate synthetase and diydrofolate reductase type S1 in plamid pABU 1
gi|46551|emb|Y07536.1|SADHFR[46551]

693: X02166
Staphylococcus plasmid pC221
gi|46545|emb|X02166.1|SACP221[46545]

694: Z49245
S.aureus partial sod gene for superoxide dismutase
gi|806584|emb|Z49245.1|SA4220SOD[806584]

695: X16298
Staphylococcus aureus plasmid pI9789 DNA with binR and bin3 genes, derived from transposon TN552
gi|398181|emb|X16298.1|SABINR3[398181]

696: Z18852
S.aureus gene for clumping factor
gi|397525|emb|Z18852.1|SACFG[397525]

697: X68417
S.aureus gene for 16S rRNA
gi|312111|emb|X68417.1|SA16SRRN[312111]

698: X68425
S.aureus gene for 23S rRNA
gi|288516|emb|X68425.1|SA23SRRN[288516]

699: X17679
Staphylococcus aureus coa gene for coagulase
gi|46539|emb|X17679.1|SACOA[46539]

700: X63072
S.aureus DNA for cat transcription terminator region
gi|46538|emb|X63072.1|SACATTERM[46538]

701: X02872
Staphylococcus aureus plasmid pUB112 CAT-gene for chloramphenicol acetyltransferase
gi|46536|emb|X02872.1|SACATG[46536]

702: V01277
Staphylococcus aureus plasmid pC194. Includes gene for chloramphenicol acetyl transferase and three further genes (one of which is necessary for replication)
gi|46531|emb|V01277.1|SAC194[46531]

703: X52543
S.aureus agrA, agrB and hld genes
gi|46505|emb|X52543.1|SAAGRAB[46505]

704: A19943
SEQ ID NO: 8, strain 1335 nucleotide probe
gi|580681|emb|A19943.1|A19943[580681]

705: A19942
SEQ ID NO: 7, strain 06231 nucleotide probe
gi|580680|emb|A19942.1|A19942[580680]

706: A19941
SEQ ID NO: 6, strain 215C nucleotide probe gi|580679|emb|A19941.1|A19941[580679]

707: A19940
SEQ ID NO: 5, strain 214 nucleotide probe
gi|580678|emb|A19940.1|A19940[580678]

708: A19939
SEQ ID NO: 4, strain 02599 nucleotide probe
gi|580677|emb|A19939.1|A19939[580677]

709: A19938
SEQ ID NO: 3, strain A216 nucleotide probe
gi|580676|emb|A19938.1|A19938[580676]

710: A19937
SEQ ID NO: 2, strain 00646 nucleotide probe
gi|580675|emb|A19937.1|A19937[580675]

711: A19936
SEQ ID NO: 1, strain 05723 nucleotide probe
gi|580674|emb|A19936.1|A19936[580674]

712: A17958
sau3AI R and sau3AI M coding region
gi|512529|emb|A17958.1|A17958[512529]

713: A12915
S.aureus DNA (pSDF203) for fibronectin binding protein (partial)
gi|512507|emb|A12915.1|A12915[512507]

714: A12913
S.aureus DNA (pSDF102) for fibronectin binding protein (partial)
gi|512506|emb|A12913.1|A12913[512506]

715: A12906
S.aureus DNA for fibronectin binding protein (partial)
gi|512505|emb|A12906.1|A12906[512505]

716: A12905
S.aureus DNA for fibronectin binding protein (partial)
gi|512503|emb|A12905.1|A12905[512503]

717: A12904
S.aureus DNA for fibronectin binding protein (partial)
gi|512501|emb|A12904.1|A12904[512501]

718: A12903
S.aureus DNA for fibronectin binding protein (partial)
gi|512499|emb|A12903.1|A12903[512499]

719: A12902
S.aureus DNA for fibronectin binding protein (partial)
gi|512497|emb|A12902.1|A12902[512497]

720: A12901
S.aureus DNA for fibronectin binding protein (partial)
gi|512495|emb|A12901.1|A12901[512495]

721: A12900
S.aureus DNA for fibronectin binding protein (partial)
gi|512494|emb|A12900.1|A12900[512494]

722: A12899
S.aureus DNA for fibronectin binding protein (partial)

gi|512492|emb|A12899.1|A12899[512492]

723: A12898
S.aureus DNA for fibronectin binding protein (partial)
gi|512490|emb|A12898.1|A12898[512490]

724: A12897
S.aureus DNA for fibronectin binding protein (partial)
gi|512488|emb|A12897.1|A12897[512488]

725: A12896
S.aureus DNA for fibronectin binding protein (partial)
gi|512486|emb|A12896.1|A12896[512486]

726: A09523
S.aureus Arp 4 gene
gi|412258|emb|A09523.1|A09523[412258]

727: A04518
S.aureus gene for structural protein A, duplicate
gi|412213|emb|A04518.1|A04518[412213]

728: A04517
S.aureus gene for structural protein A
gi|412212|emb|A04517.1|A04517[412212]

729: A04512
S.aureus gene for structural protein A
gi|412210|emb|A04512.1|A04512[412210]

730: L41499
Staphylococcus aureus ORF1, partial cds, ORF2, ORF3, autolysin (atl) genes, complete cds
gi|765069|gb|L41499.1|STAATL[765069]

731: U19770
Staphylococcus aureus pyrrolidone carboxyl peptidase (pcp) gene, complete cds
gi|790572|gb|U19770.1|SAU19770[790572]

732: X53818
S. aureus IS431mec gene associated with methicillin resistance
gi|46601|emb|X53818.1|SAIS431M[46601]

733: M20129
Staphylococcus aureus vgh gene, complete cds
gi|153076|gb|M20129.1|STAPVGHG[153076]

734: X03216
Staphylococcus aureus transposon Tn554
gi|43726|emb|X03216.1|ISTN554[43726]

735: X70648
S.aureus 16S rRNA (partial)
gi|46498|emb|X70648.1|SA16S[46498]

736: U51133
Staphylococcus aureus phosphoenolpyruvate carboxykinase (pcka) gene, complete cds
gi|1255261|gb|U51133.1|SAU51133[1255261]

737: U51132
Staphylococcus aureus o-succinylbenzoic acid CoA ligase (mene), and o-succinylbenzoic acid synthetase (menc) genes, complete cds
gi|1255258|gb|U51132.1|SAU51132[1255258]

738: X02588
S. aureus Tn554 spc gene for sp adenyltransferase AAD(9) (sp = spectinomycin)
gi|46696|emb|X02588.1|SASPCG[46696]

739: X61716
S.aureus hlb gene encoding sphingomyelinase
gi|46590|emb|X61716.1|SAHLBG[46590]

740: X61719
S.aureus phi-13 lysogen right chromosome/bacteriophage DNA junction
gi|46625|emb|X61719.1|SAP13RJNC[46625]

741: X61718
S.aureus phi-13 lysogen left chromosomal/bacteriophage DNA junction
gi|46624|emb|X61718.1|SAP13LJNC[46624]

742: X67743
S.aureus (strain 42CR3-L) right junction DNA
gi|46518|emb|X67743.1|SAATTSB2[46518]

743: X67742
S.aureus (strain 42CR3-L) left junction DNA
gi|46517|emb|X67742.1|SAATTSB1[46517]

744: X67741
S.aureus (strain A3CR3-L) left junction DNA
gi|46516|emb|X67741.1|SAATTSA2[46516]

745: X67740
S.aureus (strain A3CR3-L) right junction DNA
gi|46515|emb|X67740.1|SAATTSA1[46515]

746: X67738
S.aureus (strain 80CR3) attB gene
gi|46514|emb|X67738.1|SAATTBA[46514]

747: U02910
Staphylococcus aureus ATCC 25923 16S rRNA gene, partial sequence
gi|455053|gb|U02910.1|SAU02910[455053]

748: AH003349
Transposon IS431 (from S.aureus penicillinase plasmid pI524), 5' copy
gi|154887|gb|AH003349.1|SEG_TRN431[154887]

749: M11118
S.aureus enterotoxin B gene, complete cds
gi|152999|gb|M11118.1|STAENTB[152999]

750: M18086
S.aureus transposon 4001 aacA-aphD aminoglycoside resistance gene, complete cds, and right and left IS256 transposase genes
gi|152946|gb|M18086.1|STAAGLSRA[152946]

751: U19459
Staphylococcus aureus acetyltransferase VAT B (vat B) gene, complete cds
gi|1181626|gb|U19459.1|SAU19459[1181626]

752: U35773
Staphylococcus aureus prolipoprotein diacylglyceryl transferase (lgt) gene, complete cds
gi|1016769|gb|U35773.1|SAU35773[1016769]

753: U26702

Staphylococcus aureus recombination site for plasmid pS1
gi|849134|gb|U26702.1|SAU26702[849134]

754: U21221
Staphylococcus aureus hyaluronate lyase (hysA) gene, complete cds
gi|705405|gb|U21221.1|SAU21221[705405]

755: U36379
Staphylococcus aureus S-adenosylmethionine synthetase gene, complete cds
gi|1020316|gb|U36379.1|SAU36379[1020316]

756: U06451
Staphylococcus aureus proline permease homolog (putP) gene, complete cds
gi|458419|gb|U06451.1|SAU06451[458419]

757: U35036
Staphylococcus aureus R-plasmid pSBK203 replication initiation protein gene, chloramphenicol acetyltransferase gene, and Pre protein gene, complete cds
gi|1015405|gb|U35036.1|SAU35036[1015405]

758: U20794
Staphylococcus aureus fibrinogen binding protein (fbpA) gene, complete cds
gi|915307|gb|U20794.1|SAU20794[915307]

759: L25426
Staphylococcus aureus penicillin-binding protein 2 (pbp2) gene, complete cds
gi|409240|gb|L25426.1|STAPBP2X[409240]

760: M86227
Staphylococcus aureus DNA gyrase B subunit (gyrB) RecF homologue (recF) and DNA gyrase A subunit (gyrA) gene, complete cds
gi|153083|gb|M86227.1|STARECF[153083]

761: M63176
Staphylococcus aureus helicase required for T181 replication (pcrA) gene, complete cds
gi|153060|gb|M63176.1|STAPCRA[153060]

762: L05004
Staphylococcus aureus dehydroquinate synthase (aroB) gene, 3' end cds; 3-phosphoshikimate-1-carboxyvinyltransferase (aroA) gene, complete cds; ORF3, complete cds
gi|152954|gb|L05004.1|STAAROA[152954]

763: L42764
Staphylococcus aureus (clone pS120+) DNA fragment
gi|852065|gb|L42764.1|STAFRA[852065]

764: M32103
Staphylococcus aureus lac repressor (lacR) gene, complete cds and lacA repressor (lacA), partial cds
gi|845685|gb|M32103.1|STALACR[845685]

765: U10927
Staphylococcus aureus M type 1 capsular polysaccharide biosynthesis (capA, capB, capC, capD, capE, capF, capG, capH, capI, capJ, capK, capL, capM) genes, complete cds
gi|567035|gb|U10927.1|SAU10927[567035]

766: U20782
Staphylococcus aureus staphylococcal accessory regulator A (sarA) gene, complete cds
gi|684949|gb|U20782.1|SAU20782[684949]

767: L37598
Staphylococcus auricularis 16S ribosomal RNA (16S rRNA) gene
gi|576604|gb|L37598.1|STARGDC[576604]

768: L37597
Staphylococcus aureus 16S ribosomal RNA (16S rRNA) gene
gi|576603|gb|L37597.1|STARGDB[576603]

769: L36472
Staphylococcus aureus lysyl-tRNA sythetase gene, complete cds, transfer RNA (tRNA) genes, 5S ribosomal RNA (5S rRNA) gene, 16S ribosomal RNA (16S rRNA) gene, 23S ribosomal RNA (23S rRNA) gene
gi|567883|gb|L36472.1|STA5SRR[567883]

770: L25288
Staphylococcus aureus gyrase-like protein alpha and beta subunit (grlA and grlB) genes, complete cds
gi|561878|gb|L25288.1|STAGYRASL[561878]

771: L25893
Staphylococcus aureus recA gene, complete cds
gi|463284|gb|L25893.1|STARECAA[463284]

772: K02687
S.aureus 5S ribosomal RNA
gi|176018|gb|K02687.1|STARRASA[176018]

773: L23109
Staphylococcus aureus recombinase (sin) gene, complete cds
gi|495088|gb|L23109.1|STASINA[495088]

774: L07778
Staphylococcus aureus acetyltransferase (vat) gene, complete cds
gi|398084|gb|L07778.1|STAVAT[398084]

775: M90056
Staphylococcus aureus plasmid ATP-binding protein (vga) gene, complete cds
gi|153124|gb|M90056.1|STAVGA[153124]

776: J02615
S.aureus toxic shock syndrome toxin-1 gene, complete cds
gi|153122|gb|J02615.1|STATSST1[153122]

777: M18970
S.aureus enterotoxin A (entA) gene, complete cds
gi|153120|gb|M18970.1|STATOXAA[153120]

778: K02985
S.aureus (strain RN450) transposon Tn554 insertion site
gi|153118|gb|K02985.1|STATNIS5[153118]

779: M21136
S.aureus tetracycline resistance (tetM) gene, complete cds
gi|153114|gb|M21136.1|STATETM[153114]

780: M10501
S.aureus/transposon Tn551 left junction C
gi|153113|gb|M10501.1|STAT551C[153113]

781: AH000935
S.aureus/transposon Tn551 left junction B
gi|153112|gb|AH000935.1|SEG_STAT551B[153112]

782: M10500

S.aureus/transposon Tn551 right junction B
gi|153111|gb|M10500.1|STAT551B2[153111]

783: M10499
S.aureus/transposon Tn551 left junction B
gi|153110|gb|M10499.1|STAT551B1[153110]

784: AH000934
S.aureus/transposon Tn551 left junction A
gi|153109|gb|AH000934.1|SEG_STAT551A[153109]

785: M10498
S.aureus/transposon Tn551 right junction A
gi|153108|gb|M10498.1|STAT551A2[153108]

786: M10497
S.aureus/transposon Tn551 left junction A
gi|153107|gb|M10497.1|STAT551A1[153107]

787: M18264
S.aureus staphylococcal protein A (SPA) gene, complete cds
gi|153105|gb|M18264.1|STASPAA[153105]

788: J01786
S.aureus spa gene coding for protein A, complete csd
gi|153103|gb|J01786.1|STASPA[153103]

789: M33833
S.aureus enterotoxin B (seb) gene, 5' flank
gi|153101|gb|M33833.1|STASEB[153101]

790: M32470
S.aureus Sau3AI-restriction-enzyme and Sau3AI-modification-enzyme genes, complete cds
gi|153098|gb|M32470.1|STASAU3AIM[153098]

791: M20270
S.aureus neomycin resistance gene, partial cds, and bleomycin resistance gene, complete cds
gi|153095|gb|M20270.1|STARESA[153095]

792: J03323
S.aureus plasmid pCW7 REP N protein (rep N) gene, complete cds
gi|153089|gb|J03323.1|STAREPNA[153089]

793: M33479
S.aureus ethidium resistance (ebr) and replication protein (repA) genes, complete cds
gi|153087|gb|M33479.1|STAREPEBR[153087]

794: M94061
Staphylococcus aureus recombination enzyme (recA) gene, partial cds
gi|153081|gb|M94061.1|STARECA[153081]

795: M37888
Staphylococcus aureus resistance protein (qacD) gene, complete cds
gi|153078|gb|M37888.1|STAQACD[153078]

796: M76714
Staphylococcus aureus peptidoglycan hydrolase gene, complete cds
gi|153066|gb|M76714.1|STAPEPHYD[153066]

797: M17123
S.aureus nuclease gene, partial cds gi|153056|gb|M17123.1|STANUC[153056]

798: M97169
Staphylococcus aureus fluoroquinolone resistance protein (norA) gene, complete cds
gi|153054|gb|M97169.1|STANORAX[153054]

799: M81346
Staphylococcus aureus (methicillin resistant) leucocidin S-component (lukS) gene, complete cds
gi|475838|gb|M81346.1|STALUKS[475838]

800: M90693
Staphylococcus aureus glycerol ester hydrolase (lip) gene, complete cds
gi|393265|gb|M90693.1|STAGEHLIP[393265]

801: M25257
Staphylococcus aureus (clone pUB10) beta-lactamase gene, complete cds
gi|341312|gb|M25257.1|STALACBAF[341312]

802: M25256
Staphylococcus aureus (clone pII3804) beta-lactamase gene, 5' end
gi|341311|gb|M25256.1|STALACBAE[341311]

803: M25255
Staphylococcus aureus (clone pI3796) beta-lactamase gene, 5' end
gi|341310|gb|M25255.1|STALACBAD[341310]

804: M25254
Staphylococcus aureus (clone pI1071) beta-lactamase gene, complete cds
gi|341309|gb|M25254.1|STALACBAC[341309]

805: M25253
Staphylococcus aureus (clone pS1) beta-lactamase gene, complete cds
gi|341308|gb|M25253.1|STALACBAB[341308]

806: M25252
Staphylococcus aureus (clone pPC1) beta-lactamase gene, complete cds
gi|341307|gb|M25252.1|STALACBAA[341307]

807: L01055
Staphylococcus aureus gamma-hemolysin components A, B and C (hlgA, hlgB, hglC) genes, complete cds
gi|295153|gb|L01055.1|STAHLGA[295153]

808: M83994
Staphylococcus aureus prolipoprotein signal peptidase (lsp) gene, complete cds
gi|153044|gb|M83994.1|STALSP[153044]

809: J03947
S.aureus lincosaminide nucleotidyltransferase (linA) gene, complete cds
gi|153040|gb|J03947.1|STALINA[153040]

810: J03479
S.aureus enzyme III-lac (lacF), enzyme II-lac (lacE), and phospho-beta-galactosidase (lacG) genes, complete cds
gi|153036|gb|J03479.1|STALACS[153036]

811: M64724
S.aureus tagatose 6-phosphate isomerase gene, complete cds
gi|153032|gb|M64724.1|STALACAA[153032]

812: M14372
S.aureus phage L54 attP site gi|153031|gb|M14372.1|STAL54POP[153031]

813: M14371
S.aureus phage L54
gi|153030|gb|M14371.1|STAL54POB[153030]

814: M14374
S.aureus phage L54 attL site
gi|153029|gb|M14374.1|STAL54BOP[153029]

815: M15215
S.aureus phage L54 attB site
gi|153028|gb|M15215.1|STAL54BOB[153028]

816: M36694
B.amyloliquefaciens neutral protease gene, complete cds
gi|153026|gb|M36694.1|STAINVSA[153026]

817: M37915
S.aureus gyrase (gyrB and gryA) genes, 3' and 5' ends, respectively
gi|153023|gb|M37915.1|STAGYRAB[153023]

818: M12715
S.aureus geh gene encoding lipase (glycerol ester hydrolase)
gi|153019|gb|M12715.1|STAGEH[153019]

819: J04151
S.aureus fibronectin-binding protein (fnbA) mRNA, complete cds
gi|153017|gb|J04151.1|STAFNBP[153017]

820: L22566
Staphylococcus aureus enterotoxin A gene
gi|349129|gb|L22566.1|STAENTAB[349129]

821: L13379
Staphylococcus aureus enterotoxin gene, 3' end
gi|295150|gb|L13379.1|STAENTEROF[295150]

822: L13378
Staphylococcus aureus enterotoxin gene, 3' end
gi|295148|gb|L13378.1|STAENTEROE[295148]

823: L13377
Staphylococcus aureus enterotoxin gene, 3' end
gi|295146|gb|L13377.1|STAENTEROD[295146]

824: L13376
Staphylococcus aureus enterotoxin gene, 3' end
gi|295144|gb|L13376.1|STAENTEROC[295144]

825: L13375
Staphylococcus aureus enterotoxin gene, 3' end
gi|295142|gb|L13375.1|STAENTEROB[295142]

826: L13374
Staphylococcus aureus enterotoxin gene, 3' end
gi|295140|gb|L13374.1|STAENTEROA[295140]

827: M17348
S.aureus exfoliative toxin B (ETB), complete cds
gi|153011|gb|M17348.1|STAETB[153011]

828: M17357
S.aureus eta gene encoding epidermolytic toxin A, complete cds gi|153007|gb|M17357.1|STAETAA[153007]

829: M17347
S.aureus exfoliative toxin A (ETA), complete cds
gi|153005|gb|M17347.1|STAETA[153005]

830: M28364
Staphylococcus aureus enterotoxin C3 gene, complete cds
gi|153003|gb|M28364.1|STAENTTXC[153003]

831: M21319
S.aureus entertoxin type E (entE) gene, complete cds
gi|153001|gb|M21319.1|STAENTE[153001]

832: M63917
S.aureus epidermal cell differentiation inhibitor (EDIN) gene, complete cds
gi|152997|gb|M63917.1|STAEDIN[152997]

833: M58515
Staphylococcus aureus precursor protein and chloramphenicol acetyltransferase (CAT) genes, complete cds
gi|152980|gb|M58515.1|STACATA[152980]

834: L10909
Staphylococcus aureus tnpA gene, tnpB gene, tnpC gene, DS RF gene, complete cds's; cadmium resistance (cadA) gene, complete cds; E1-E2 cadmium efflux adenosine triphosphatase (cadC) gene, complete cds
gi|152973|gb|L10909.1|STACADRES[152973]

835: M15067
S.aureus beta-lactamase (blaZ) gene, 5' end
gi|152971|gb|M15067.1|STABLAZA[152971]

836: M92376
Staphylococcus aureus beta-lactamase repressor (BlaI) gene, complete cds
gi|152969|gb|M92376.1|STABLAIA[152969]

837: M32312
S.aureus right arm of secondary Tn554 attachment site
gi|152959|gb|M32312.1|STAATTX[152959]

838: M20393
S.aureus bacteriophage phi-11 attachment site (attB)
gi|152958|gb|M20393.1|STAATTB[152958]

839: M90536
Staphylococcus aureus alpha-hemolysin gene, 3' end
gi|152952|gb|M90536.1|STAALPHYM[152952]

840: M21854
S.aureus agr gene encoding an accessory gene regulator protein, complete cds
gi|152950|gb|M21854.1|STAAGR[152950]

841: M36771
S.aureus aminocyclitol-3'-phosphotransferase gene, complete cds
gi|152944|gb|M36771.1|STAAAC[152944]

842: L14020
Staphylococcus aureus methicillin-resistance (mecR and mecI) genes, complete cds
gi|295157|gb|L14020.1|STAMECR[295157]

843: M81736
Staphylococcus aureus collagen adhesin (cna) gene, complete cds gi|387879|gb|M81736.1|STACNA[387879]

844: L19300
Staphylococcus aureus DNA sequence encoding three ORFs, complete cds; prophage phi-11 sequence homology, 5' flank
gi|310601|gb|L19300.1|STAORFPHI[310601]

845: L25372
Staphylococcus aureus exfoliative toxin A (eta) gene, complete cds
gi|409062|gb|L25372.1|STASETA[409062]

846: L22565
Staphylococcus aureus FRI100 enterotoxin A (sea) gene
gi|349128|gb|L22565.1|STAENTAA[349128]

847: M58516
Staphylococcus aureus precursor protein and chloramphenicol acetyltransferase (CAT) genes, complete cds
gi|152983|gb|M58516.1|STACATB[152983]

848: U06462
Staphylococcus aureus SA4 FtsZ (ftsZ) gene, complete cds
gi|458427|gb|U06462.1|SAU06462[458427]

849: L19298
Staphylococcus aures phosphatidylinositol-specific phospholipase C (plc) gene, complete cds
gi|425477|gb|L19298.1|STAPIPLC[425477]

850: M80252
Staphylococcus aureus norA1199 gene (which mediates active efflux of fluoroquinolones), complete cds
gi|295163|gb|M80252.1|STANORA11[295163]

851: L11530
Staphylococcus aureus transfer RNA sequence with two rRNAs
gi|310605|gb|L11530.1|STATRNAA[310605]

What is claimed is:

1. An isolated, purified, or enriched polypeptide comprising at least a fragment of a protein encoded by *Staphylococcus aureus* bacteriophage 3A open reading frame 33, 41 or 79, a bacteriophage 77 open reading frame 1, or a bacteriophage 96 open reading frame 48, 78 or 100, wherein said fragment is at least 15, contiguous amino acid residues in length.

2. The polypeptide of claim 1, wherein said polypeptide comprises a fragment at least 30 amino acid residues in length of a said polypeptide normally encoded by said bacteriophage.

3. A novel protein which is encoded by a nucleic acid molecule which corresponds to a nucleic acid molecule from *Staphylococcus aureus* bacteriophages 3A, 77 or 96, as shown in SEQ ID Nos.: 17, 18 and 19, respectively.

4. The novel protein of claim 3, wherein said protein is isolated from a bacteriophage.

5. The polypeptide of claim 2, wherein said polypeptide comprises a fragment at least 50 amino acid residues in length of a said polypeptide normally encoded by said bacteriophage.

6. The polypeptide of claim 1, wherein said fragment binds to a bacterial polypeptide bound by a full-length protein encoded by said *Staphylococcus aureus* bacteriophage open reading frame.

7. The polypeptide of claim 1, wherein said polypeptide has the amino acid sequence of SEQ ID NO: 31 (96ORF78).

8. The novel protein of claim 3, wherein said protein is encoded by a nucleic acid molecule having at least 50% identity with nucleic acids 10148 to 10363 of SEQ ID NO: 19.

9. An isolated, purified, or enriched polypeptide having at least 50% identity with the amino acid sequence of SEQ ID NO: 31 (96ORF78).

10. The polypeptide of claim 9, wherein said identity is at least 75%.

11. The polypeptide of claim 10, wherein said identity is at least 95%.

* * * * *

UNITED STATES PATENT AND TRADEMARK OFFICE

CERTIFICATE OF CORRECTION

PATENT NO. : 6,737,508 B1 
DATED : May 18, 2004
INVENTOR(S) : Jerry Pelletier, Gros Phillippe and Michael Dubow It is certified that error appears in the above-identified patent and that said Letters Patent is hereby corrected as shown below:

Title page,
Item [54], Title, should read as follows: -- [54] DNA SEQUENCES FROM STAPHYLOCOCCUS AUREUS BACTERIOPHAGES 3A, 77, AND 96 THAT ENCODE ANTI-MICROBIAL POLYPEPTIDES --
Item [73], Assignee, should read as follows: -- [73] Assignee: PhageTech, Inc., Montreal, Quebec (CA) --

Signed and Sealed this

Twelfth Day of October, 2004

JON W. DUDAS
*Director of the United States Patent and Trademark Office*

SEQUENCE LISTING

<160> NUMBER OF SEQ ID NOS: 36

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
aattctcgag taaaataaca t 21

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
cgggatccgc ctccttttct caacagtcac ctgattt 37

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
cgggatccat gaggggttcc gaagacg 27

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
cccaagctta caatttggac tttc 24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
tgagaaaagg aggcggatcc atg 23

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6

-continued

```
agctgtcgac gcgt                                                    14


<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

agctacgcgt cgac                                                    14


<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

taagctgtcg acgcgta                                                 17


<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

gatcccggtc gaccaagctt tacccatacg acgtcccaga ctacgccagc tga         53


<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

agcttcagct ggcgtagtct gggacgtcgt atgggtaaag cttggtcgac cgg         53


<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

ccgctcgagc tccaaattcc aaaacag                                      27


<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
```

-continued

```
cgggatccaa taagactcct ttttac                                          26


<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

aggagtctta ttggatccat g                                               21


<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14

tattatccaa aacttgaaca                                                 20


<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15

cggtggtata tccagtgatt                                                 20


<210> SEQ ID NO 16
<211> LENGTH: 100
<212> TYPE: PRT
<213> ORGANISM: Staphylococcus aureus

<400> SEQUENCE: 16

Met Val Asn Val Asp Asn Ala Pro Glu Glu Lys Gly Gln Ala Tyr Thr
  1               5                  10                  15

Glu Met Leu Gln Leu Phe Asn Lys Leu Ile Gln Trp Asn Pro Ala Tyr
             20                  25                  30

Thr Phe Asp Asn Ala Ile Asn Leu Leu Ser Ala Cys Gln Gln Leu Leu
         35                  40                  45

Leu Asn Tyr Asn Ser Ser Val Val Gln Phe Leu Asn Asp Glu Leu Asn
     50                  55                  60

Asn Glu Thr Lys Pro Glu Ser Ile Leu Ser Tyr Ile Ala Gly Asp Asp
 65                  70                  75                  80

Pro Ile Glu Gln Trp Asn Met His Lys Gly Phe Tyr Glu Thr Tyr Asn
                 85                  90                  95

Val Tyr Val Phe
            100


<210> SEQ ID NO 17
<211> LENGTH: 43095
<212> TYPE: DNA
<213> ORGANISM: Staphylococcus bacteriophage

<400> SEQUENCE: 17

tttaaataaa attttatgcc cccctgccca tcggcttaaa atgttttttc gccgggtacc     60

ggagaggccc aaacgctagc aacgcggata aatttttcat gaaaggggggt ctttatatga    120
```

-continued

```
agttaacaaa aaaacagcta aaagaatata tagaagatta caaaaaatct gatgacatat    180
taattaattt gtatatagaa acatatgaat tttattgtcg gttaagagat gaacttaaaa    240
atagtgattt aatgatagag catacaaaca aggctggtgc gagcaatatt attaagaatc    300
cattaagcat agaactgaca aaaacagttc aaacactaaa taacttactc aagtctatgg    360
gtttaactgc agcacaaaga aaaaagatag ttcaagaaga aggtggattc ggtgactatt    420
aaagttttaa atgaaccttc accaaaacta ttaacaacat ggtatgcaga gcaagtcact    480
caagggaaaa taaaaacaag caaatatgtt agaaaagaat gtgagagaca tcttagatat    540
ctagaaaatg gaggtaaatg ggtatttgat gaagaattag cgcatcgtcc tattcgattt    600
atagaaaagt tttgtaaacc ttccaaagga tctaaacgtc aacttgtatt acagccatgg    660
caacatttta ttatcggcag tttgtttggt tgggttcata aagaaacaaa actgcgcagg    720
tttaaagaag ctttgatatt tatggggcga aaaaatggta aaacaaccac tatttctggg    780
gttgctaact atgctgtatc acaagatgga gaaaatggtg cagaaattca tttgttagca    840
aacgtaatga aacaagctag gattctattt gatgaatcta aggcgatgat taaagctagc    900
ccaaagcttg ataaaaattt cagaacatta agagatgaaa tccattatga cgcaacgata    960
tcaaaaatta tgccccaagc atcagatagc gataagttag atggattgaa tacacacatg   1020
gggatttttg atgaaattca tgaatttaaa gactataaat tgatttcagt tataaaaaac   1080
tcaagagctg caaggttaca acctcttctc atctacatta cgacagcagg gtatcaatta   1140
gatggtccac ttgttgatat ggtagaagcg ggaagagaca ccttagatca aatcatagaa   1200
gacgaaagaa ctttttatta tttagcatct ttggatgatg acgatgatat taatgattcg   1260
tcgaactgga taaaagcaaa tcccaactta ggtgtctcta taaatttaga tgagatgaaa   1320
gaagagtggg aaaaagctaa gagaacacca gctgaacgtg gagattttat aaccaaaagg   1380
tttaatatct ttgctaataa tgacgagatg agttttattg attacccaac actccaaaaa   1440
aataatgaaa ttgtttcttt agaagagctg gaaggcagac cgtgcacgat tggttatgat   1500
ttatcagaaa cagaggactt tacagccgcg tgtgctactt ttgcgttaga taatggtaaa   1560
gttgcagttt tatcgcattc atggattcct aagcacaaag ttgaatattc taacgaaaaa   1620
ataccctata gagaatggga agaagatggc ttattaacag tgcaagataa gccttatatt   1680
gactaccaag atgttttaaa ttggataatt aagatgaatg agcattatgt agtagaaaaa   1740
attacttatg atagagcgaa cgcattcaaa ctaaatcaag agttaaaaaa ttacgggttt   1800
gaaacggaag aaacaagaca aggagctttg accttgagcc ctgcattgaa ggatttaaaa   1860
gaaatgtttt tagatgggaa aataatattt aataataatc ctttaatgaa atggtatatc   1920
aataatgttc agttgaaact agacagaaac ggaaactggt tgccgtctaa gcaaagcaga   1980
tatcgtaaaa tagatggctt tgcagcattt ttaaacacat atacagatat tatgaataaa   2040
gttgtttctg atagtggtga aggaaacata gagtttatta gtattaaaga cataatgcgt   2100
taaggaggtg aatgttatcg caaaagagaa tattgtcaca cgcataaaga aaaaattgat   2160
agacaattgg attgatcagt caacttctaa gctttatgac tttagcccat ggaaaaatag   2220
atctttttgg ggtgtaatta ataatacgct tgaaactaat gaaacgatat tttcagctat   2280
tacaaagtta tctaattcga tggctagttt gcccttgaaa atgtatgaag attataaagt   2340
agttaataca gaagtatctg atttacttac agtgtcaccg aataattctc tgagcagttt   2400
tgattttatt aatcaaattg aaacaatcag aaatgaaaaa ggtaatgcat atgtgctaat   2460
```

-continued

```
tgaacgagac atctatcatc aaccatcaaa gcttttctta ttaaatccag atgttgttga   2520
aatgttaatt gaaaaccaat cacgtgaact ttattattcc attcatgctg caactggaaa   2580
taaattgatt gttcataata tggacatgtt gcattttaaa cacatcgtgg catctaatat   2640
ggtgcaaggc attagtccga ttgatgtgtt gaagaataca actgattttg ataatgcagt   2700
aagaaccttt aatcttacag aaatgcaaaa acctgattct ttcatgctta aatatggttc   2760
caatgtaggt aaagaaaaaa ggcagcaagt gttagaagat ttcaaacagt actatgaaga   2820
aaacggtgga atattattcc aagagcctgg tgttgaaatc gaaccgttac ctaaaaaata   2880
tgtctctgaa gatatagtgg caagcgagaa tttaacaaga gaaagagtag ctaacgtttt   2940
tcaattgccc tcagtattct taaatgcaag atcaaataca aatttcgcga aaaatgaaga   3000
gttaaacaga ttttacttgc agcatacctt attgccaatc gtcaaacagt atgaagaaga   3060
atttaatcgg aaactactta ctaaaacaga cagagaaaaa aataggtatt ttaaatttaa   3120
cgttaaatct tatttaaggg ctgatagtgc aacacaagca gaagtgtact ttaaagcagt   3180
tcgtagtggt tactacacta taaatgacat tagagagtgg gaagatttac caccagttga   3240
aggtggagat aagccgctaa taagcggtga tttataccca attgacacgc cacttgaatt   3300
aagaaaatct ttgaaaggtg gtgataaaaa tgtcaatgaa agctaagtat tttcaaatga   3360
aaagaaaatc aaaaagtaaa ggtgaaatat ttatttatgg tgatattgta agtgataaat   3420
ggtttgaaag tgatgtaact gctacagatt tcaaaaataa actagatgaa ctaggagaca   3480
tcagtgaaat agatgttcat ataaattcat ctggaggcag tgtatttgaa gggcatgcaa   3540
tatacaatat gctaaaaatg catcctgcaa aaattaatat ctatgtcgat gccttagcgg   3600
catcaattgc tagtgttatc gctatgagtg gtgacactat ttttatgcac aaaaatagtt   3660
ttttaatgat tcataattca tgggttatga ctgtaggtaa tgcagaagag ttaagaaaga   3720
cagcggattt acttgaaaaa acagatgctg ttagtaattc agcttattta gataaagcaa   3780
aagatttaga tcaagaacac ttaaaacaga tgttagatgc agaaacttgg cttactgcag   3840
aagaagcctt gtctttcggc ttgatagatg aaattttagg agctaatgaa ataactgcta   3900
gtatctctaa agagcaatat aagcgtttcg agaacgtccc agaagattta aagaaagatg   3960
tagacaaaat cactaaaatc gatgatgtag atacgtttga attggttgaa acacctaaag   4020
aaagtatgtc actagaagaa aaagaaaaaa gagaaaaaat taaacgcgaa tgcgaaattt   4080
taaaaatgac aatgagttat taggaggaaa tgaaatgccg acattatatg aattaaaaca   4140
atccttaggt atgattggac aacaattaaa aaataaaaat gatgaattga gtcagaaagc   4200
aacagaccca aatattgata tggaagacat caaacaacta gaaacagaaa aagcaggctt   4260
acaacaaaga tttaacattg ttgaaagaca agtaaaagac attgaagaaa aagaaaaagc   4320
gaaagttaaa gacacaggag aagcttatca atctttaaat gatcatgaga agatggttaa   4380
agctaaggca gagttttatc gtcacgcgat tttaccaaat gaatttgaaa aaccttcaat   4440
ggaggcacaa cgtttattac acgctttacc aacaggtaat gattcaggtg gtgataagct   4500
cttaccaaaa acactttcta aagaaattgt ttcagaacca tttgctaaaa accaattacg   4560
tgaaaaagct cgtctaacta acattaaagg tttagagatt ccaagagttt catatacttt   4620
agacgatgat gacttcatta cagatgtaga aacagcaaaa gaattaaaat taaaaggtga   4680
tacagttaaa ttcactacta ataaattcaa agtatttgct gcaatttcag atactgtaat   4740
tcatggatca gatgtagatt tagtaaactg ggttgaaaac gcactacaat caggtctagc   4800
agctaaagaa cgtaaagatg ccttagcagt aagtcctaaa tctggattag atcacatgtc   4860
```

-continued

```
attttacaat ggatctgtta aagaagttga gggagcagac atgtatgatg ctattattaa   4920
cgctttagca gatttacatg aagattaccg tgataacgca acaatttata tgcgatatgc   4980
ggattatgtc aaaattatta gtgttctttc aaatggaaca acaaatttct ttgacacacc   5040
agcagaaaaa gtatttggca aaccagtagt atttacagat gcagcagtta aacctattgt   5100
gggagatttc aattattttg gaattaacta tgatggaaca acttatgaca ctgataaaga   5160
tgttaaaaaa ggcgaatatt tgtttgtatt aactgcatgg tatgatcagc aacgtacatt   5220
agacagtgca ttcagaattg caaaagcaaa agaaaataca ggttcattac ccagctaagc   5280
cccaaaaggt taatgtaaca gctaaggcta aatcagctgt aatatcagcc gaataggggt   5340
gatgaaatga gtttagaaga aattaaattg tggttgagaa ttgactataa tttcgaaaat   5400
gatttaattg aaggtctcat tcaatcggct aagtctgaat tactattaag tggggttcca   5460
gattatgaca aagatgactt ggaatacccg ctttttttgta cagcgattag atatatcatt   5520
gcaagagatt atgaaagtcg tgggtactca aatgaccaat ctagaagcaa ggtttttaat   5580
gaaaagggat tgcaaaaaat gattctgaaa ttaaaaaagt ggtaggtgat ttttaaatgg   5640
aatttaatga atttaaagat cgcgcatatt tttttcaata tgtaaataaa gggccgtatc   5700
cagatgaaga ggaaaaaatg aagttgtata gttgcttttg taaaatatat aatccttcta   5760
tgaaagatag agaaatttta aaagcgactg aatcaaagtc aggactaacc ataattatga   5820
ggtcttctaa aattgaatat ctaccacaaa caaatcactt agttaaaatt gacagaggct   5880
tatattccga taaattattc aacattaaag aaataagaat tgatacacca gatattggct   5940
ataatacagt ggttttatca gaaaaatgag tgtagaaatt aaagggatac ctgaagtgtt   6000
gaagaaatta gaatcggtat acggtaaaca atcaatgcaa gctaagagtg atagagcttt   6060
aaatgaagca tctgaatttt ttataaaggc tttaaagaaa gaattcgaga gttttaaaga   6120
tacgggtgct agcatagaag aaatgactaa atctaagcct tatacaaaag taggaagtca   6180
agaaagagct gttttaattg aatgggtagg ccctatgaat cgcaaaaaca ttattcactt   6240
gaatgaacat ggttatacaa gagatggaaa aaaatataca ccaagaggtt ttggagttat   6300
tgcaaaaaca ttagctgcta atgaacggaa gtatagagaa attataaaaa aggagttggc   6360
cagataaatg aatatattaa acaccataaa agaaatttta ttatctgatg cagagctcca   6420
aacatatata aattctagaa tatactatta taaagtcact gaaaatgctg aaacttccaa   6480
accttttgtt gttattacac ctatttatga tttaccttca gacttcatgt ctgataaata   6540
tcttagtgaa gaatacttaa ttcaaataga tgtagaatct tcaaataatc agaaaacaat   6600
tgatataaca aaacgaataa gatatctgtt atatcaacaa aatttaattc aagcatctag   6660
tcagttagat gcttattttg aagaaactaa acgttatgtg atgtcgagac gttatcaagg   6720
cataccaaaa aatatatatt ataaaaatca gcgcatcgaa taggtgtgct ttttaatttt   6780
taaggaggaa ataagcaatg gcagaaggac aaggttctta taaagtaggt tttaaaagat   6840
tatacgttgg agtttttaac ccagaagcaa caaaagtagt taaacgcatg acatgggaag   6900
atgaaaaagg tggtacagtt gatctaaata tcacaggttt agcaccagat ttagtagata   6960
tgtttgcatc taacaaacgt gtttggatga aaaaacaagg tactaatgaa gttaagtctg   7020
acatgagtat ttttaatatt ccaagtgaag atctaaatac agttattggt cgttctaaag   7080
ataaaaatgg tacatcttgg gtaggagaga atacaagagc accatacgta acagttattg   7140
gagaatctga agatggttta acaggtcaac cagtgtacgt tgcgctactt aaaggtactt   7200
```

-continued

```
ttagcttgga ttcaattgaa tttaaaacac gaggagaaaa agcagaagca ccagagccaa   7260
caaaattaac tggtgactgg atgaacagaa aagttgatgt tgatggtact ccacaaggta   7320
ttgtatacgg gtatcatgaa ggtaaagaag gagaagcaga attcttcaaa aaagtattcg   7380
ttggatacac ggacagtgaa gatcattcag aggattctgc aagttcgtta cccagctaac   7440
ccccaaaatg ttgaagtagc agttaattca aaatctgcaa cagtttcagc agaataggggg   7500
ctttcaaaat aaatcaaagg agaataattt atgactaaaa ctttaaaggt ttataaagga   7560
gacgacgtcg tagcttctga acaaggtgaa ggcaaagtgt cagtaacttt atctaattta   7620
gaagcggata caacttatcc aaaaggtact taccaagtgg catgggaaga aaatggtaaa   7680
gaatctagta aagttgatgt acctcaattc aaaaccaatc caattctagt ctcaggcgta   7740
tcatttacac ccgaaactaa atcaatcacg gtaaatgctg atgacaatgt tgaaccaaac   7800
attgcaccaa gtacagcaac gaataaaacg ttgaaatata caagtgaaca tccagagttt   7860
gttactgttg atgagagaac aggagcaatt cacggtgtag ctgagggaac ttcagttatc   7920
actgctacgt ctactgacgg aagtgacaag tctggacaaa ttacagtaac agtaacaaat   7980
ggataattat ttgagacgca gaatatctgc gtcttttta tttgaataaa aggagctaat   8040
acaatgatta aatttgaaat taaagaccgt aaaacaggaa aaacagagag ctatacaaaa   8100
gaagatgtga caatgggcga agcagaaaaa tgctatgagt atttagaatt agtaaatcaa   8160
gagaataaaa aagaagtacc taacgcaaca aaaatgagac aaaaagagcg acagttatta   8220
gtagatttat ttaaagatga aggattgact gaagaagatg ttttgaacaa gatgagcact   8280
aaaacttata caaaagcctt gaaagatata tttcgagaaa tcaatggtga agatgaagaa   8340
gattcagaaa ctgaaccaga agagatggga aagacagaag aacaatctca ataaaagata   8400
ttttatcgaa cattaagaaa atacaacgtt tctgtatgga gcagtatggg tggacattaa   8460
ctgaagtcag aaaacagccg tatgtaaaac ttttagaaat acttaatgaa gagaataaag   8520
aagagactga agaaaaacaa agtgaacaaa aagtcattac aggtacggat ttaagaaaac   8580
tttttggaag ctagaaagga ggttaatatg aatgaaaaag tagaaggcat gaccttggag   8640
ctgaaattag accatttagg tgtccaagaa ggcatgaagg gtttaaagcg acaattaggt   8700
gttgttaata gtgaaatgaa agctaatctg tcatcatttg ataagtctga aaaatcaatg   8760
gaaaagtatc aggcgagaat taaggggtta aatgataagc ttaaagttca aaaaaagatg   8820
tattctcaag tagaagatga gcttaaacaa gttaacgcta attatcaaaa agctaaatct   8880
agtgtaaaag atgttgagaa agcatattta aagctagtag aagctaataa aaaagaaaaa   8940
ttagctcttg ataaatctaa agaagcctta aaatcttcga atacagaact taaaaaagct   9000
gaaaatcaat ataaacgtac aaatcaacgt aaacaagatg catatcaaaa acttaaacag   9060
ttgagagatg cagaacaaaa gcttaagaat agtaaccaag ctactactgc acaactaaaa   9120
agagcaagtg acgcagtaca gaagcagtcc gctaagcata aagcacttgt tgaacaatat   9180
aaacaagaag gcaatcaagt tcaaaaacta aaagtacaaa atgataatct ttcaaaatca   9240
aacgaaaaaa tagaaaattc ttacgctaaa actaatacta aattaaagca aacagaaaaa   9300
gaatttaatg atttaaataa tactattaag aatcatagcg ctaatgtcgc aaaagctgaa   9360
acagctgtta acaaagaaaa agctgcttta aataatttag agcgttcaat agataaagct   9420
tcatccgaaa tgaagacttt taacaaagaa caaatgatag ctcaaagtca tttcggcaaa   9480
cttgctagtc aagcggatgt catgtcaaag aaatttagtt ctattggaga taaaatgact   9540
tccctaggac gtacgatgac gatgggcgta tctacaccga ttactttagg gttaggtgca   9600
```

-continued

```
gcattaaaaa caagtgcaga cttcgaaggg caaatgtctc gagttggagc gattgcacaa   9660
gcaagcagta aagacttaaa aagcatgtct aatcaagcgg ttgacttagg cgctaaaaca   9720
agtaaaagtg ctaacgaagt tgctaaaggt atggaagaat tggcagcttt aggctttaat   9780
gccaaacaaa caatggaggc tatgccgggt gttatcagtg cagcagaagc aagcggtgca   9840
gaaatggcta caactgcaac tgtaatggca tcagcaatta attctttcgg tttaaaagca   9900
tctgatgcaa accatgttgc tgatttactt gcgagatcag ctaatgatag tgctgcagat   9960
attcaataca tgggagatgc attaaaatat gcaggtactc cagcaaaagc attaggagtt  10020
tcaatagagg acacttctgc agcaattgaa gttttatcta actcagggtt agaggggtct  10080
caagcaggta ctgcattaag agcttcgttt attaggctag ctaatccaag taaaagtaca  10140
gctaaggaaa tgaaaaaatt aggtattcat ttgtctgatg ctaaaggtca atttgttggc  10200
atgggtgaat tgattagaca gttccaagac aacatgaaag gcatgacgag agaacaaaaa  10260
ctagcaacag tggctacaat agttggcact gaagcagcaa gtggattttt agccttgatt  10320
gaagcgggtc cagataaaat taatagctat agcaaatcat tgaagaactc taatggtgaa  10380
agtaaaaaag cagctgattt gatgaaagac aacctcaaag gtgctctgga acaattaggt  10440
ggcgcttttg aatcgttagc aattgaagtt ggtaaagatt taacgcctat gattagagca  10500
ggtgcggaag gattaacaaa attagttgat ggatttacac atcttcctgg ttggtttaga  10560
aaggcttcgg taggtttagc gatttttggt gcatctattg gccctgctgt tcttgctggt  10620
ggcttattaa tacgtgcagt tggaagcgcg gctaaaggct atgcatcatt aaatagacgc  10680
attgctgaaa atacaatact gtctaatacc aattcaaaag caatgaaatc tttaggtctt  10740
caaaccttat ttcttggttc tacaacagga aaaacgtcaa aaggctttaa aggattagcc  10800
ggagctatgt tgtttaattt aaaacctata aatgttttga aaaattctgc aaagctagca  10860
attttaccgt tcaaactttt gaaaaacggt ttaggattag ccgcaaaatc cttatttgca  10920
gtaagtggag gcgcaagatt tgctggtgta gccttaaagt tttaacagg acctataggt  10980
gctacaataa ctgctattac aattgcatat aaagttttta aaaccgcata tgatcgtgtg  11040
gaatggttca gaaacggtat taacggttta ggagaaacta taaagttttt tggtggcaaa  11100
attattggcg gtgctgttag gaagctagga gagtttaaaa attatcttgg aagtataggc  11160
aaaagcttca aagaaaagtt ttcaaaggat atgaaagatg gttataaatc tttgagtgac  11220
gatgaccttc tgaaagtagg agtcaacaag tttaaaggat ttatgcaaac catgggcaca  11280
gcttctaaaa aagcatctga tactgtaaaa gtgttgggga aaggtgtttc aaaagaaaca  11340
gaaaaagctt tagaaaaata cgtacactat tctgaagaga acaacagaat catggaaaaa  11400
gtacgtttaa actcgggtca aataacagaa gacaaagcaa aaaaactttt gaaaattgaa  11460
gcggatttat ctaataacct tatagctgaa atagaaaaaa gaaataaaaa ggaactcgaa  11520
aaaactcaag aacttattga taagtatagt gcgttcgatg aacaagaaaa gcaaaacatt  11580
ttaactagaa ctaaagaaaa aaatgacttg cgaattaaaa aagagcaaga actcaatcag  11640
aaaatcaaag aattgaaaga aaaagcttta agtgatggtc agatttcaga aaatgaaaga  11700
aaagaaattg aaaagcttga aaatcaaaga cgtgacatca ctgttaaaga attgagtaag  11760
actgaaaaag agcaagagcg tattttagta agaatgcaaa gaaacagaaa tgcttattca  11820
atagacgaag cgagcaaagc aattaaagaa gcagaaaaag caagaaaagc aagaaaaaaa  11880
gaagtggaca agcaatatga agatgatgtc attgctataa aaaataacgt caacctttct  11940
```

-continued aagtctgaaa aagataaatt attagctatt gctgatcaaa gacataagga tgaagtaaga 12000
aaggcaaaat ctaaaaaaga tgctgtagta gacgttgtta aaaagcaaaa taaagatatt 12060
gataaagaga tggatttatc cagtggtcgt gtatataaaa atactgaaaa gtggtggaat 12120
ggccttaaaa gttggtggtc taacttcaga gaagaccaaa agaagaaaag tgataagtac 12180
gctaaagaac aagaagaaac agctcgtaga aacagagaaa atataaagaa atggtttgga 12240
aatgcttggg acggcgtaaa aactaaaact ggcgaagctt ttagtaaaat gggcagaaat 12300
gctaatcatt ttggcggcga aatgaaaaaa atgtggagtg gaatcaaagg aattccaagc 12360
aaattaagtt caggttggag ctcagccaaa agttctgtag gatatcacac taaggctata 12420
gctaatagta ctggtaaatg gtttggaaaa gcttggcaat ctgttaaatc gactacagga 12480
agtatttaca atcaaactaa gcaaaagtat tcagatgcct cagataaagc ttgggcgcat 12540
tcaaaatcta tttggaaagg gacatcaaaa tggtttagca atgcatataa aagtgcaaag 12600
ggctggctaa cggatatggc taataaatcg cgctcgaaat gggataatat ttctagtaca 12660
gcatggtcga atgcaaaatc cgtttggaaa ggaacatcga aatggtttag taactcatac 12720
aaatctttaa aaggttggac tggagatatg tattcaagag cccacgatcg ttttgatgca 12780
atttcaagtt cggcatggtc taacgctaaa tcagtattta atggttttag aaaatggcta 12840
tcaagaacat atgaatggat tagagatatt ggtaaagaca tgggaagagc tgcggctgat 12900
ttaggtaaaa atgttgctaa taaagctatt ggcggtttaa atagcatgat tggcggtatt 12960
aataaaatat ctaaagccat tactgataaa aatctcatca agccaatacc tacattgtct 13020
actggtactt tagcaggaaa gggtgtagct accgataatt cgggagcatt aacgcaaccg 13080
acatttgctg tattaaatga tagaggttct ggaaacgccc caggtggtgg agttcaagaa 13140
gtaattcaca gggctgacgg aacattccat gcaccccaag gacgagatgt ggttgttcca 13200
ctaggagttg gagatagtgt aataaatgcc aatgacactc tgaagttaca gcggatgggt 13260
gttttgccaa aattccatgg tggtacgaaa aagaaagatt ggctagacca acttaaaggt 13320
aatataggta aaaaagcagg agaatttgga gctacagcta aaaacacagc gcataatatc 13380
aaaaaaggtg cagaagaaat ggttgaagca gcaggcgata aaatcaaaga tggtgcatct 13440
tggttaggcg ataaaatcgg cgatgtgtgg gattacgtac aacatccagg gaaactagta 13500
aataaagtaa tgtcaggttt aaatattaat tttggaggcg gactaacgct acagtaaaaa 13560
ttgctaaagg cgcgtactca ttgctcaaaa agaaattaat agacaaagta aaatcgtggt 13620
ttgaagattt tggtggtgga ggcgatggaa gctatctatt tgaatatcca atctggcaaa 13680
gatttggacg ctacacaggt ggacttaact ttaatgacgg tcgtcactat ggtatagact 13740
ttggtatgcc tactggaaca aacgtttatg ccgttaaagg tggtatagca gataaggtat 13800
ggactgatta cggtggcggt aattctatac aaattaagac cggtgctaac gaatggaact 13860
ggtatatgca tttatctaag caattagcaa gacaaggcca acgtattaaa gctggtcaac 13920
tgatagggaa atcaggtgct acaggtaatt tcgttagagg agcacactta catttccaat 13980
tgatgcaagg gtcacatcca gggaatgata cagctaaaga tccagaaaaa tggttgaagt 14040
cacttaaagg tagtggcgtt cgaagtggtt caggtgttaa taaggctgca tctgcttggg 14100
caggcgatat acgtcgtgca gcaaaacgaa tgggtgttaa tgttacttcg ggtgatgtag 14160
gaaatatcat tagcttgatt caacacgaat caggaggaaa tgcaggtata actcaatcta 14220
gttcgcttag agacatcaac gttttacagg gcaatccagc aaaaggattg cttcaatata 14280
tcccacaaac atttagacat tatgctgtta gaggtcacaa caatatatat agtggttacg 14340

-continued

```
atcagttatt agcgttcttt aacaacagat attggcgctc acagtttaac ccaagaggtg  14400
gttggtctcc aagtggtcca agaagatatg cgaatggtgg tttgattaca aagcatcaac  14460
ttgctgaagt gggtgaagga gataaacagg agatggttat ccctttaact agacgtaaac  14520
gagcaattca attaactgaa caggttatgc gcatcatcgg tatggatggc aagccaaata  14580
acatcactgt aaataatgat acttctacag ttgaaaaatt gttgaaacaa attgttatgt  14640
taagtgataa aggaaataaa ttaacagatg cattgattca aactgtttct tctcaggata  14700
ataacttagg ttctaatgat gcaattagag gtttagaaaa aatattgtca aaacaaagtg  14760
ggcatagagc aaatgcaaat aattatatgg gaggtttgac taattaatgc aatcttttgt  14820
aaaaatcata gatggttaca aggaagaagt aataacagat tttaatcagc ttatattttt  14880
agatgcaagg gctgaaagtc caaacaccaa tgataacagt gtaactatta acggagtaga  14940
tggtatttta ccgggcgcaa ttagttttgc gcctttttca ttagtattaa ggtttggcta  15000
tgatggtata gatgttatag atttaaattt atttgagcat tggtttagat ctgtgtttaa  15060
tcgcagacat ccttattatg ttattacttc tcaaatgcct ggtgttaaat atgcagtgaa  15120
tacagctaat gttacatcta atttaaaaga tggttcttca actgaaattg aagtaagttt  15180
aaatgtttat aaagggtatt ctgaatcagt taattggacc gatagcgagt tcttattcga  15240
ctctaattgg atgtttgaaa atggaattcc tcttgatttc acacctaaat atactcatac  15300
atcaaatcaa tttactattt ggaacggttc tactgatacg ataaatccac gattcaagca  15360
cgatttgaaa atattaatta atttaaatgc gagtggagga tttgaactgg ttaactatac  15420
aacaggtgat atttttaagt acaacaaaag tatagataaa aacactgatt ttgttttaga  15480
tggtgtgtat gcatatcgag atataaatag agtgggaatt gatacaaata gaggcattat  15540
aacattagcg ccaggtaaaa atgaatttaa gattaaagga gacatcagtg atattaaaac  15600
tacatttaag tttcctttta tttataggta ggtgatttaa tggattatca tgatcattta  15660
tcagtaatgg attttaatga attgatttgt gaaaatttac tagatgtaga ttatggttct  15720
tttaaagaat attatgaact gaatgaagct aggtacatca cttttacagt ttatagaact  15780
actcataata gttttgtttt cgatttacta atttgtgaaa acttcataat ttatcatggt  15840
gaaaaataca caattaagca gacagcgcca aaggttgaag gtgataaagt ttttattgaa  15900
gttacggcat atcacataat gtatgaattt caaaatcact cagtggaatc aaataagctt  15960
gatgacgaca gtagcgaaac tggtaaaacg ccagaatact ctttagatga gtacttaaga  16020
tatggatttg caaatcaaaa aacttcggtc aaaatgacct ataaaaataat tggaaatttt  16080
aagcgaaaag taccgattga cgaattaggt aacaaaaacg gcttagaata ctgtaaagaa  16140
gcggtagacc tatttggctg tataatttac ccaaatgata cggagatatg tttttattct  16200
cctgaaacat tttatcaaag aagcgagaaa gtgattcgat atcaatataa tactgatact  16260
gtatctgcaa ctgtcagtac attggaatta agaacagcta taaaagtttt tggaaaaaag  16320
tatacagctg aggaaaagaa aaattataat cctattagaa caactgacat taaatattca  16380
aatggtttta taaaagaagg tacttatcgt accgcaacaa ttgggtctaa agctactatt  16440
aactttgatt gcaagtatgg taatgaaaca gttagattta caataaaaaa gggctctcaa  16500
ggtggaatat ataagttgat tttagacggc aagcaaatta agcaaatttc ttgttttgct  16560
aagtcggttc agtctgaaac aatagattta ataaaaaata ttgataaagg caagcacgtt  16620
ttagaaatga tatttttagg agaagacccc aaaaatagaa ttgatatatc ttcaaataaa  16680
```

-continued

```
aaagctaagc cttgtatgta tgttggaact gaaaaatcaa cagtcttaaa tttaattgct  16740
gacaactcag gtcgcaatca atacaaagca attgttgact acgtcgcaga tagtgcaaag  16800
cagtttggga ttcgatatgc taatacgcaa acaaatgaag atatcgaaac acaggataag  16860
ctgttagaat ttgcaaaaaa gcaaataaat gatactccta agactgaatt agatgttaat  16920
tatataggtt atgaaaaaat agagccaaga gatagcgtat tctttgttca tgaattaatg  16980
ggatataaca ctgaattaaa ggttgttaaa cttgataggt cacatccatt tgtaaacgca  17040
atagatgaag tgtctttcag caatgaaata aaggatatgg tacaaattca acaagcgctt  17100
aacagacgag ttattgcaca agataataga tataactatc aagcaaatcg tataaatcat  17160
ttatacacta gtactttgaa ttctcctttc gagacaatgg atatagggag tgtattaata  17220
taatggcaac agaagaagtt aaaatcaaag cgctacttga aaacgataaa cagtactttc  17280
cagctacaca ttggaaagct ataaatggga taccttatgc aggcagtagt gatattgatg  17340
gattgcctca agacggtatc atttcggtag atgataaaaa taaattagat aatttaaaaa  17400
taggcgaagc aggaattatt caaaatagca ttgtacagaa atccccaaac ggtaaattgt  17460
ggaaaataac agttgacgat agtgggaaac ttggtacagt gctattttat tagaaaggaa  17520
ggtgcattat ggaaaatttg tatttaataa aggatttggg agctttagca ggtcgagatt  17580
atagagctaa ggaaatacaa aacttacaaa gaatagagca atttgcgctt ggcttgacaa  17640
cagagtttaa gttgcatcag aaagctaaaa caattcaaca cttcgctgag caaatttatt  17700
ataatggtag atcgcaagca gcagtaaaca aatctttaca aagtcaaatt aacgcacttg  17760
ttgtggcacc acgtaataac agtgctaatg agattgttca agctcgagtt aatgtaaacg  17820
gcgaaacctt tgacacatta aaagaacatt tagacgattg ggaaacccaa actcaaatta  17880
ataaagagga aactataaga gaattaaata agaccaaaca agaaattctt gatatcgagt  17940
atcgttttga acctgataag caagaatttt tatttgtgac agaacttgca cctcttacaa  18000
atgcagtaat gcaatccttc tggtttgata atagaacagg catagtatac atgacacaag  18060
ctagaaataa tggctatatg ctaagtcgtc taagacctaa tggtcaattt atagacagct  18120
cattgattgt aggtgggggt catggtacac ataacggtta tagatatatt gatgatgagt  18180
tatggattta tagttttatc ttaaatggta ataatgagaa tacattagtt cgtttcaagt  18240
atacgcctaa tgtggaaatt agctatggca agtatggtat gcaagatgta tttacaggac  18300
acccagaaaa accctacatc acccctgtca taaatgaaaa agaaaataaa attctataca  18360
gaattgagag acctagaagt cactgggaac ttgaaaactc aatgaattat atagagataa  18420
gaagtttaga cgatgttgat aaaaatattg ataaagtttt gcataaaatc agtatcccta  18480
tgagactaac aaacgaaacc caaccaatgc agggtgtgac ttttgatgaa aaatacttgt  18540
attggtatac aggagacagt aatccaaata atagaaacta tttaacggct ttcgatttag  18600
aaacaggaga agaagcgtat caggttaatg ctgactatgg tggaacacta gattcatttc  18660
ctggcgaatt tgcggaagca gaaggtttgc aaatatacta tgacaaagat agtggtaaaa  18720
aagctttgat gctaggtgtt actgtcggtg gtgatggaaa tagaacacat cgtattttca  18780
tgattgggca aagaggtatt ttagaaatac ttcactcaag aggcgttcct tttatcatga  18840
gtgacacagg tggtagagtt aaacctttac caatgaggcc tgataaactt aagaatcttg  18900
ggatgttaac agagccaggt ctttactatt tatacactga tcatacagtt caaatcgatg  18960
atttcccatt accaagagaa tggcgtgatg caggttggtt cttggaagtt aagccaccac  19020
aaactggcgg tgatgtaatt cagatattga cgcgtaatag ttatgcaagg aatatgatga  19080
```

-continued cttttgaaag ggtgctttct ggaagaactg gagacatttc ggactggaat tatgtgccta 19140
aaaatagtgg taaatgggag agagtacctt cattcatcac aaaaatgtca gatattaaca 19200
tagtaggcat gtcgttttat ttaactacgg atgatacaaa acgttttaca gattttccaa 19260
ctgaacgtaa aggggtagct ggttggaact tatatgtaga agcttcaaac acaggtggct 19320
ttgttcatag gctagttcgt aatagtgtta cagcatctgc tgagatacta ttgaaaaatt 19380
atgatagtaa aacaagttca gggccatgga ctttacacga agggagaatt ataagttaat 19440
gagtaattta gagaaatctg tagctataaa tttagaaaac acagcgcatt atgaaaatat 19500
ttcaaatcta gatataactt ttagaacagg agagagtgat tcttctgttc ttctttttaa 19560
tatcactaaa aataatcaac cgttattatt gagtgaagaa aatatcaaag cacgaatagc 19620
gattcgaggt aaaggagtca tggtagttgc tccactagaa atattagatc catttaaagg 19680
tattttaaaa tttcaattac ctaatgatgt aattaaacga gatggaagtt atcaagctca 19740
agtttcggtt gcagaattag gtaattcaga cgtggtagtt gtcgagagaa ctatcacatt 19800
taacgttgaa aaaagtttgt ttagcatgat tccatctgaa acaaaattac actatattgt 19860
tgaatttcag gaattagaaa aaactattat ggatcgtgcg aaagcaatgg acgaggctat 19920
aaaaaatggt gaagattatg cgagtctgat tgaaaaagct aaagaaaaag gtctatcaga 19980
tattcaaata gcaaaatctt caagtataga tgaattaaag caacttgcta atagccatat 20040
atctgatttg gaaaataaag cgcaagcata ttcaagaaca ttcgatgagc aaaagcgata 20100
tatggatgag aaacatgaag ccttcaagca gtcagtgaat agtggtggtt tagtcacaag 20160
tggttctact tcaaattggc aaaaagctaa gattactaaa gatgatggta agataatgca 20220
gattactgga tttgatttta ataatccaga acaaagaata ggtgattcaa cccaatttat 20280
ttatgtttcg caagctataa attatccaag aggtgttagt actaacggta ctgtcgaata 20340
tttagtagta acttcagatt acaagcgtat gacttatcga ccgaacggta caaataaagt 20400
gtttgttaaa agaaaagaag cgggttcatg gtctgagtgg tcagaattag ctattaatga 20460
ttacaataca ccttttgaaa ctgttcaaag tgcccaatca aaagctaata tggccgaaag 20520
taacgctaaa ttatacgcag atgacaagtt taataaaagg tattcggtta tttttgatgg 20580
aacagcaaat ggtgtgggct ctacattgta cttaaatgag agtttagacc aatttatttt 20640
attaattttt tatgggactt ttccaggtgg tgactttaca gagtttggca gtccttttgg 20700
aggaggaaag atttcattga atccctcaaa tcttccagat ggtgatggaa atggtggagg 20760
tgtttatgag tttggattaa ctaaatctag tcgtacatct ttaactatat caaacgatgt 20820
ctatttcgac ttaggaagtc aaagaggctc tggtgcgaac gcaaatagag ggacaattaa 20880
caaaattata ggagtgagaa aataatgcaa atattagtta acaagcgtaa tgagataatt 20940
tcatacgcta tcattggtgg ctttgaagaa ggtattgata ttgaaaattt accagaaaat 21000
ttctctcaag tttttagacc taaagccttt aaatattcaa atggggaaat agtttttaac 21060
gaagattatt cagaagaaaa agatgacttg catcaacaga ttgacagtga agaacaaaac 21120
acagtcgctt ctgatgacat cttacgaaaa atggttgcta gtatgcagaa acaagttgtt 21180
caaagtacaa agttatcgat gcaagttaat aagcaaaatg cactaatggc aaaacaactt 21240
gtgacactta ataaaaaatt agaagaggtt aaaggagaga ctgaaaatgc ttaaattaat 21300
ttcaccaaca ttcgaagata ttaaaacatg gtatcaattg aaagaatata gtaaagaaga 21360
tatagcgtgg tatgtagata tggaagttat agataaagag gaatatgcaa ttattacagg 21420

-continued agaaaagtat ccagaaaatc tagagtcata ggttataatc ttatggcttt ttaatttgaa 21480
taaagtgggt ggtgtaatgt ttggatttac caaacgacac gaacaagatt ggcgtttaac 21540
gcgattagaa gaaaatgata agactatgtt tgaaaaattc gacagaatag aagacagtct 21600
gagaacgcaa gaaaaaattt atgacaagtt agatagaaat ttcgaagaac taaggcgtga 21660
caaagaagaa gatgaaaaaa ataaagagaa aaatgctaaa aatattagag acatcaagat 21720
gtggattcta ggattaatag ggacgattct aagtacattt gttatagcct tgttaaaaac 21780
tatttttggc atttaaagga ggtgattacc atgcttaagg gaattttagg atatagcttt 21840
tggtcgtgtt tctggtttag taagtgtaag taatagttaa gagtcagtgc ttcggcactg 21900
gctttttatt ttggaaaaaa ggagcaaaca aatggatgca aaagtaataa caagatacat 21960
cgtattgatc ttagcattag taaatcaatt cttagcgaac aaaggtatta gcccgattcc 22020
agtagacgat gagaatatat catcaataat acttactgtt gttgctttat atactacgta 22080
taaagacaat ccaacatctc aagaaggtaa atgggcaaat caaaagctaa agaaatataa 22140
agctgaaaac aagtatagaa aagcaacagg gcaagcgcca attaaagaag taatgacacc 22200
tacgaatatg aacgacacaa atgatttagg gtaggtgttg accaatgttg ataacaaaaa 22260
accaagcaga aaaatggttt gataattcat tagggaagca gttcaatcct gatttgtttt 22320
atggatttca gtgttacgat tacgcaaata tgttttttat gatagcaaca ggcgaaaggt 22380
tacaaggttt atacgcttat aatattccat ttgataataa agcaaggatt gaaaaatacg 22440
ggcaaataat taaaaactat gatagctttt taccgcaaaa gttggacatt gtcgttttcc 22500
cgtcaaagta tggtggcgga gctggacatg ttgaaattgt tgagagcgct aatctaaaca 22560
ctttcacatc gtttggccaa aattggaatg gtaaaggttg gacaaatggc gttgcgcaac 22620
ctggttgggg tcccgaaacc gttacaagac atgttcatta ttacgatgac ccaatgtatt 22680
ttattagatt aaatttccca gataaagtaa gtgttggaga taaagctaaa agcgttatta 22740
agcaagcaac tgccaaaaag caagcagtaa ttaaacctaa aaaaattatg cttgtagccg 22800
gtcatggtta taacgatcct ggagcagtag gaaacggaac aaacgaacgc gattttatac 22860
gtaaatatat aacgccaaat atcgctaagt atttaagaca tgccggtcat gaagtcgcat 22920
tatatggtgg ctcaagtcaa tcacaagaca tgtatcaaga tacagcatac ggtgttaatg 22980
taggtaataa aaaagattat ggcttatatt gggttaaatc acaggggtat gacattgttc 23040
tagaaataca tttagacgca gcaggagaaa gcgcaagtgg tgggcatgtt attatctcaa 23100
gtcaattcaa tgcagatact attgataaaa gtatacaaga tgttattaaa aataacttag 23160
gacaaataag aggtgtaaca cctcgtaacg atttactaaa tgttaacgta tcagcagaaa 23220
taaatataaa ttatcgctta tctgaattag gttttatcac taataaaaat gatatggatt 23280
ggattaagaa aaactatgac ttgtattcta aattaatagc cggtgcgatt catggtaagc 23340
ctatcggtgg tgtgatatct agtgaggtta aaacaccagt taaaaacgaa aagaatccgc 23400
cagtgccagc aggttataca cccgataaaa ataatgtacc gtataaaaaa gaaactggtt 23460
attacacagt tgccaatgtt aaaggtaata acgtaaggga cggctattca actaattcaa 23520
gaattactgg tgtattacct aataacgcaa caatcaaata tgacggcgca tattgtatca 23580
atggctatag atggattact tatattgcta atagtggaca acgtcgttat attgctacag 23640
gagaggtaga caaggcaggt aatagaataa gcagttttgg taagtttagt gcagtttgat 23700
aattgtatat gatgaatctt aggcaggtac ttcggtactt gcctattatt taaaattaat 23760
aaacagttaa tttttacatg aatatattaa attttaaaaa aacaaacgtt tttagtatat 23820

-continued

```
aaattatttt gtgttcgtat tgtgtgctat gattaaaaag ttgttatggt caactatatc  23880
gtggttttat gtttattatc aatcaaaata taaattattt ataatttgtt tggtaatgaa  23940
cgggtttttt tcgaaataat agtaaaaaaa cacatttgta gatattttaa actcggtaaa  24000
tcttttaata aatatttaat tttattaaaa gttaaaaagg tttaatataa aaatgtaata  24060
aaatttataa agaaaggaaa tgatttttat ggtcaaaaaa agactattag ctgcaacatt  24120
gtcgttagga ataatcactc ctattgctac ttcgtttcat gaatctaaag ctgataacaa  24180
tattgagaat attggtgatg gcgctgaggt agtcaaaaga acagaagata caagtagcga  24240
taagtggggg gtcacacaaa atattcagtt tgattttgtt aaagataaaa agtataacaa  24300
agacgctttg attttaaaaa tgcaaggttt tatcaattca aagactactt attacaatta  24360
caaaaacaca gatcatataa aagcaatgag gtggcctttc caatacaata ttggtctcaa  24420
aacaaatgac cccaatgtag atttaataaa ttatctacct aaaaataaaa tagattcagt  24480
aaatgttagt caaacattag gttataacat aggtggtaat tttaatagtg gtccatcaac  24540
aggaggtaat ggttcattta attattcaaa aacaattagt tataataaaa taaaaagtag  24600
gtgataagat gactcaattt ctaggggcgc ttcttcttac aggagtttta ggttacatac  24660
catataaata tctaacaatg ataggtttag ttagtgaaaa aaacaaggtt atcaatactc  24720
ctgtattatt gatttttct attgaaacat gtttgatatg gttttatagt tttataattt  24780
ttaataatgt tgatttaaaa aatttgaatt taattcagtt gcttacaggt ctaaaagcaa  24840
atattttgtt tctatttatt tttgttttaa cagtgtttgt atttaatcct ttaattgtta  24900
aatttattat ctggttaatt aatataacca gaaagtttat gaaattggat tgtataagct  24960
tattagacaa aagagacaag ttgtttaata acaacggtaa accagtattt atagttataa  25020
aagactttga aaacagaatc attgaagagg gtgaacttaa aacctataat tcagctggta  25080
gcgatttcga tttactagaa gttgagcgac aagatttcaa agtatctgat ttaccgtcaa  25140
acgatgaatt gtatattaaa catacacttg tagaccttaa acaacaaatt aaattggatt  25200
tatatttaat gaatgaatac taatcttttt tcttagcttt ttctgataaa gtgcttttta  25260
atttttcgct ggcgcccggc ttttcaaaac ttttgtttat tgggttacta cgagtagctt  25320
cttgtttttt gtttttatcc gccataaaat tctcaccacc attcaacgtc tacacttgta  25380
ggcgtttttt tatttagtaa agtcataatg aatcttcttt ggttaactta tctccatcta  25440
ttttttgtga aataaattcc aagtatttac gcgcattatg tgacgataaa tctttaggta  25500
actcataagt gaatggttga ttaccactag ttaaaacttc atatactata gtttcttttt  25560
ttattttgca attagttatt ttcattataa acttcctttc aaacactgct gaaatagacg  25620
tcttttatat taaagcgcca cacaggcgct gttaatcaca atacaacttt gcccattact  25680
ttaatattac taaacgaagc gactttgata tcatcatact tcggatttag agataccaaa  25740
ttaatatagt cttcgcatat atctacacgc ttgataagac ttactccatc taatacaacg  25800
agtgcaattg taccatcttt aatagaatct tctttcttaa taaaagcgta tgttccttgt  25860
tttaacatag gttccattga atcaccatta actaaaatac aaaaatcagc atttgatggc  25920
gtttcgtctt ctttaaaaaa tacttcttca tgcaatatgt catcatataa ttcttctcct  25980
atgccagcac cagttgcacc acatgcaata tacgatacta gtttagactc tttatatcca  26040
tctatagaag tgactttatt ctgttcttcc aattgttcat ttgcatagtt aagtacgttt  26100
tcttggcggg gaggtgtgag tttgttgtat atggaagtga tgtcgttatc gtctttgtat  26160
```

-continued

```
gtagtatttg attcactata caaatcatta atcttcacat tgaagtactc agccaaaatt  26220
ttggcagttg ataatcgagg ttcttccttt tcattttccc attttgatat cttgcctttc  26280
gttaatttca ttaagtcggg atatttatta ttaagatcag ttgctaattg ttccatagtc  26340
atatttttat ttttttctta gcttctttaa accttcacca atacccatac gaaaccctcc  26400
ttatataaga taatttcatt ataaaagttt cgaaaacgaa acgcaaggaa aatattattg  26460
caaaagttgt tgacatcgaa acttttatga tgtattctta aatcaagttg ttacaaacga  26520
aacaaaagga gggggttcaa tgacaactag tgtagcagat aaaccatact taaaaataaa  26580
aagcttgatt gcacttaaag gaactaacca aaaagaagtt gctaaagcaa tcggaatgag  26640
tagaagttta ttgagtataa agataaatcg aattaatggc agagatttta caacttcaga  26700
agctaaaaaa ttagcagatc atttaaatgt taaagttgat gatttttttt aaactttaag  26760
tttcgaaagt gacaactaaa taaaaataag gaggacacta tggaacaaat aacgttaacc  26820
aaagaagagt tgaaagaaat tatagcgaaa gaagttagaa atgctataaa aggcgagaaa  26880
ccaatcagct caggtgcaat tttcagtaaa gtaagaatca ataatgacga tttagaagaa  26940
atcaataaaa aactcaattt cgcaaaagat ttgtcgctag gaagattgag gaagctcaat  27000
catccgattc cgctaaaaaa gtatcagcat ggcttcgaat caattcatca aaaagcttat  27060
gtacaagatg ttcatgacca tattagaaaa ttaacattat caatttttgg agtgacactt  27120
aattcagact tgagtgaaag tgaatacaac ctagcagcaa aaatttatag agatatcaaa  27180
aactattatt tatatatcta tgaaaagaga gtttcagaat taactatcga tgatttcgaa  27240
tgaaggagga actacaaatg aaactactaa gaaggctatt caataaaaaa cacgaaaact  27300
taattgacgt gtggcatgga aatcaatggt taaaagtgaa agaaagcaaa ttaaaaaaat  27360
ataaagtggt ctcggataga gaaggtaaga aatatctaat taaataagcg cacttaatta  27420
gtgcaagtaa tcaagtgcgc tattgcctta caatcctaaa tcttttctgc tttttttcttc  27480
ttcttgtaat cccaataaca cagaagagta aatgctgaaa tagtcacgag caacgctatc  27540
tttagcgaat gcaattacgt catcaccgac ttcttgccat tcgttatgaa tcttatgtct  27600
atctagagct ctaggtaata gcgagattgt aatatcgtga gcaattttct ctaaatccat  27660
aaatttcacc tccttccact gggagataac taaattatat aacaaaacaa cttaaaggag  27720
gaacgacaaa tgcaagctca aaacaaaaaa gtcatctatt actactatga cgaagaaggt  27780
aataggcgac cattagatat tcaaattaat gacggatatg aactgatggt ccgatctcat  27840
ttcatcaaca acaccattga agaaatacca tacgtaaata ataacttata tgccttggtt  27900
gatggttatg aatttaagtt agattgaatt tttgagaaag atattgaaaa gctaatttcc  27960
ccataagatt aagagacata ctggatgttt tgttaacgac tcttttaact tcgttccaag  28020
ttttattgtc tctaatatta tcgagaaatt catggccaga ccaagtgatg tcatcaataa  28080
tccaagaaac gaccctgcct tcgatgaatt tcagatcgca acaaataaat ttagcttctt  28140
ctaattttaa aagtgagtac attactgttt caaaatcata tttatcaaaa ataatattat  28200
cgttgaaatt atgtcgagta agtggttcac ctattttctt attagattct atttctaaga  28260
gcaagagtct aacgcaatcg tgattaagtt tcatcctatc acctccataa caggagtata  28320
gcagaaagga tcataaacat cttaaaagga ggaataacaa atgaacattc aagaagcaac  28380
taagatagct acaaaaaatc ttgtctctat gacacggaaa gattggaaag aaagtcatcg  28440
aactaagata ttaccaacaa atgatagttt tttacaatgc atcatttcaa atagcgatgg  28500
gacaaacctt atcagatatt ggcaaccttc agccgatgac ctcatggcaa atgattggga  28560
```

-continued

```
agttataaac ccaactagag accaggaatt attgaagcaa ttttagaaat gctatcaatg  28620
atacttttta aattgttttt aaactcattt tcaaagtaaa caacagtctt gtctgaaatt  28680
gttacatgat aaatagtgtt actagcatac acgccgttta ggaacccaga gtttttaagt  28740
ttatttaaat cgtattttac atcttcgaaa tgtagttttt gaaaatactt tgtatgtata  28800
tctttagcac ttccaaaatt attgcaggtt aatttaaccg aacctaactt tacacattct  28860
aaataatctt tgtagagtac ggacaagata tattgttggt ctttagtaag tgtatcaaat  28920
tcatcagata tcaagggcat gttatcacct ccttaggttg ataacaacat tatacacgaa  28980
aggagcataa acaaatgaac acaagatcag aaggattgcg tataggcgtc ccacaagttt  29040
ctagcaaagc tgatgcttct tcatcctatt taacggaaaa ggaacgtaac ttaggagcgg  29100
aaatattaga gcttattaaa aaaagtgatt acagctactt agaaataaac aaagttttct  29160
atgcattaga tagagaactt caatacaggg cgaataataa caaactttaa catttatcta  29220
aaggagtgat agagatgcca aaaatcataa taccaccaac accagaaaac acatatcgag  29280
gcgaagaaaa atttgtgaaa aagttatacg caacacctac acaaatccat caattgtttg  29340
gagtatgtag aagtacagta tacaactggt tgaaatatta ccgtgaagat aatttaggtg  29400
tagaaaattt atacattgat tattcagcaa cgggaacatt gattaatatt tctaaattag  29460
aagagtattt gatcagaaag cataaaaaat ggtattagga ggattatcaa atgagcgaca  29520
catataaaag ctacctatta gcagtgttgt gcttcacggt cttagcgatt gtactcatgc  29580
cgtttctata cttcactaca gcatggtcaa ttgcgggatt cgcaagtatc gcaacattca  29640
tattttataa ggaatacttt tatgaagaat aaagaaactg ctacttgttg gagcaagtaa  29700
cagtgcaaga tgagcaattg tcttaaataa ttatataagg agttattaat atgaccttac  29760
aacaaaaaat actatcacat tttgcaacat atgacaattt caattctgat gatgttgttg  29820
aagtttttgg gatatctaaa acacatgcaa aatccacact ttcaagactt aagaaaaaag  29880
gaaagattga attggaaagt tggggtatct ggcgtgttgt tgaaccgcag ttacatttaa  29940
ctgttgtaga acgtaagaaa gagatattag aagaacaatt cgagttattg gcaagattaa  30000
acgaacaaag tgatgaccct agagaaatag aagaacgcat caagttaatg attcgtttag  30060
ccaaccaatt ttaaggagga gttaatcaat ggcaatatta gaaggtattt ttgaagaatt  30120
aaaactatta aataagaatt tacgtgtgct aaatactgaa ctatcaactg tagattcatc  30180
aattgtacaa gagaaagtta aagaagcacc aatgccaaaa gatgaaacag ctcaactgga  30240
atcagttgaa gaagttaagg aaacttctgc tgatttaact aaagattatg ttttatcagt  30300
aggaaaagag ttccttaaaa aagcagatac ttctgataag aaagaattta gaaataaact  30360
taacgaactt ggtgcggata agctatctac tatcaaagaa gagcattatg aaaaaattgt  30420
tgattttatg aatgcgagaa taaatgcatg aagctagatc actcaaatag agctcatgca  30480
aagcttagtg caagtggagc aaaacaatgg ctaaactgtc caccgagtat taaggcaagt  30540
gaaggtattg cagataaaag ttcagttttt gctgaagaag gtacattcgc tcatgagtta  30600
agtgagttat atttcagtct taaatatgaa ggcctaacac agtttgagtt taataaagct  30660
tttcaaaatt ataagcgaaa tcaatattac agtgaagagt tgcgcgaata tgttgaagag  30720
tacgtagcta atgtagaaga aaaatataac gaagctttga gtagagatga cgatgtaata  30780
gctttatttg aaacaaaatt ggatttaggt aaatacgtcc ctgaatcttt tggtactggt  30840
gatgtcatta tattttcagg tggtgtactt gaaattattg accttaaata cggtaaaggc  30900
```

-continued

```
attgaagttt cagctataga taatcctcaa cttagattat atggcttggg cgcatatgaa  30960
ctgcttagtt taatgtatga cattcataca gttcgcatga ctatcataca accacgaata  31020
gataactttt ctactgaaga gttaccaata tcaagattac ttcaatgggg aaccgatttt  31080
gttaaaccat tagccagact tgcttataac ggtgaaggtg agtttaaagc aggtagtcat  31140
tgtagattct gtaagataaa gcattcatgt agaacacgtg cagaatacat gcaaaatgtg  31200
cctcaaaagc caccacattt gttgagtgat gaagagattg cagaactttt atataaactg  31260
cctgacatca aaaaatgggc tgatgaagta gaaaaatatg cactagatca agcgaaagaa  31320
aatgataaaa actattctgg ttggaagctt gtagaaggtc gctcgcgaag aatgataact  31380
gatacaaatg caacgcttga aaagttagtt gaagcaggtt ataaacctga agatattaca  31440
gaaaccaagt tacttagcat tacgaattta gaaaaattaa tcggcaaaaa agcatttct  31500
aaaattgcag aaggctttat agaaaagcca caaggtaaat taacacttgc taccgagtct  31560
gataaacgac cagctataaa gcaatctgct gaagatgatt ttgacaaact ataaaaatta  31620
aaaaggacgg tatataaaca tgaaagcaaa agtattaaat aaaactaaag tgattacagg  31680
aaaagtaaga gcatcatatg cacatatttt tgaacctcac agtatgcaag aagggcaaga  31740
agcaaagtat tcaatcagtt taatcattcc taaatcagat acaagtacga taaaagccat  31800
tgaacaagct atagaagctg ctaaagaaga aggaaaagtt agtaagtttg gaggcaaagt  31860
tcctgcaaat ctgaaacttc cattacgtga tggagatact gaaagagaag atgatgtgaa  31920
ttatcaagac gcttatttta ttaacgcatc aagcaaacaa gcacctggta ttattgacca  31980
aaacaaaatt agattaacgg attctggaac tattgtaagt ggtgactata ttagagcttc  32040
aatcaattta tttccattca acacaaatgg taataagggt atcgcagttg gattgaacaa  32100
cattcaactt gtagaaaaag gcgaacctct tggcggtgca agtgcagcag aagatgattt  32160
cgatgaatta gacactgatg atgaggattt cttataagtc aataggtggg gtttttagcc  32220
ccactttaat tttaaagaaa ttgaggtgtc aagaatttga aatttatgaa tatagatatt  32280
gaaacatata gcagtaacga tatttcgaaa tgtggtgtct ataaatacac agaagctgaa  32340
gatttcgaaa tcttaattat agcttattca atagatggtg gaccgattag tgcgattgac  32400
atgactaaag tagataatga gcctttccac gctgattatg agacgtttaa aattgctcta  32460
tttgaccctg ctgtaaaaaa gtatgcattc aatgctaatt tcgaaagaac ttgtcttgct  32520
aaacatttta ataaacagat gccacctgaa gaatggattt gcacaatggt taattcaatg  32580
cgtattggct tacctgcttc gcttgataaa gttggagaag ttttaagact acaaaaccaa  32640
aaagataaag caggtaaaaa tttaattcgt tatttctcta taccttgtaa gccaacaaaa  32700
gttaatggag gaagaacaag aaatttgcct gaacatgatc ttgaaaaatg gcaacaattt  32760
atagattact gtattcgaga tgtagaagta gaaatgacaa ttgctaataa aattaaagac  32820
tttccagtaa ctgtaattga acaagcatat tgggtttttg accaacatat aaacgacaga  32880
ggtattaagc tttctaaatc attgatgtta ggagctaatg tgctcgataa gcagagtaaa  32940
gaagaattgc ttaaacaagc taaacatata acaggtttag aaaatcctaa tagtcctaca  33000
cagttattgg cttggttaaa ggatgaacaa ggattagata tacctaattt acaaaagaaa  33060
acggttcagg attacttaaa agtagcaaca ggaaaagcta aaaaaatgct agaaattaga  33120
ttgcaaatgt ctaaaaccag tgtgaaaaaa tacaacaaaa tgcatgacat gatgtgcagt  33180
gatgaacggg taagaggtct gtttcaattc tacggtgccg gtactggaag atgggcaggt  33240
agaggtgtac aacttcagaa tttaacaaag cattatattt cagatactga attagaaata  33300
```

-continued

```
gcaagagatc ttattaaaga acaacgtttt gacgatttag atttattact caatgttcat  33360
cctcaagact tattaagtca attagttagg acgacattta ctgctgaaga aggtaatgaa  33420
ctagcagtaa gtgatttttc tgcaatagag gcaagagtca tagcatggta tgcaaaagaa  33480
caatggcgtt tagatgtgtt caacacacac ggaaagatat atgaagcatc ggcttctcaa  33540
atgtttaatg taccggtaga aagcataact aaaggcgacc ctctcagaca aaaaggaaaa  33600
gtgtccgaat tagctttagg ctatcaaggt ggcgctggag ctttaaaagc aatgggtgca  33660
ttggaaatgg gcattgaaga aaacgagtta caaggtttag ttgatagttg gcgtaacgca  33720
aatcctaaca tagttaattt ttggaaggct tgccaagagg ctgcaattaa tactgtaaaa  33780
tcccgaaaga cgcatcatac acatggactt agattttata tgaaaaaagg ttttctaatg  33840
attgaactgc ctagtggaag agctttagct tatccaaaag ctttagttgg tgaaaatagt  33900
tggggtagtc aagttgttga atttatgggg ttagatctta accgtaaatg gtcaaagtta  33960
aaaacgtatg gtgggaagtt agtcgagaat attgttcaag caactgcaag ggatttactt  34020
gcgatttcta tagcaaggct tgaagcatta ggttttaaaa tagttggcca tgtccatgat  34080
gaagtaattg tagaaatacc tagaggttca aatggactta aggaaatcga aactatcatg  34140
aataagcctg ttgattgggc aaaaggattg aatttgaata gtgacgggtt tacttctccg  34200
ttttatatga aggattagga gtgtgattgc atgcaacatc aagcttatat caatgcttct  34260
gttgacatta gaattcctac agaagtcgaa agtgttaatt acaatcagat tgataaagaa  34320
aaagaaaatt tggcggacta tttatttaat aatccaggtg aactattaaa atataacgtt  34380
ataaatatta aggttttaga tttagaggtg gaatgatggc tagaagaaaa gttataagag  34440
tgcgtatcaa aggaaaacta atgacattga gagaagtttc agaaaaatat cacatatctc  34500
cagaacttct tagatataga tacaaacata aaatgcgcgg cgatgaatta ttgtgtggaa  34560
gaaaagactc aaaatctaaa gatgaagttg aatatatgca gagtcaaata aaagatgaag  34620
aaaaagagag agaaaaaatc agaaaaaaag cgattttgaa cctataccaa cgaaatgtga  34680
gagcggaata tgaagaagaa agaaagagaa gattgagacc atggctttat gatggaacgc  34740
cacaaaaaca ttcacgtgat ccgtactggt tcgatgtcac ttataaccaa atgttcaaga  34800
aatggagtga agcataatga gcgtaatcag taacagaaaa gtagatatga acgaagcgca  34860
agacaatgtt aagcaaccag cgcactacac atacggcgac attgaaatta tagattttat  34920
cgaacaggtt acggcacagt atccacctca actagcattc gcaataggta atgcaataaa  34980
atacttgtct agagcacctt taaagaatgg tcatgaggat ttagcaaagg cgaagtttta  35040
cgtccaaaga gcttttgact tgtgggagtg atgaccatga cagatagcgc atgtaaagaa  35100
tacttaaacc aatttttcgg atctaagaga tatctgtatc aggataacga acgagtggca  35160
catatccatg tagtgaatgg cacttattac tttcacgggc atatcgtacc aggctggcaa  35220
ggcgtgaaaa agacatttga tacagcggaa gagctcgaaa catatataaa gcaacatggt  35280
ttggaatacg aggaacagaa gcaactaact ttattttaag gagatagaaa tgatgaaaat  35340
caaagttgaa aaaataatga aaatagacga attaattaag tgggcgcgag aaaatccgga  35400
gctatcattt ggcagaaaat attatacaac agacaaaaat gatgaaaact ttatttactt  35460
cggtgttttt aaaaattgtt ttaaaataag cgattttata ttagttaatg ctacttttag  35520
tgtcaaagtt gaagaagaag taaccgaaga aactaagttt gataggttgt ttgaagtgta  35580
cgagattcaa gaaggagtct ataaatctgc atcatatgag aatgctagta taaacgaacg  35640
```

-continued

```
tttaaaaaat gacagaattt ttcttgctaa agcattctac atcttaaacg acgacctaac  35700
tatgacgtta atttggaaag aaggagagtt gattaaataa tggaacacgg ttcaaaagaa  35760
tattacgaaa agcaaagtga atactggttt gatgaagcaa gcaagttttt gaagcaacgt  35820
gatgagctta ttggagatat agctaagtta agagagtgca acaaagagct ggagaagaaa  35880
gcaagtgcat gggataggta ttgcaagagc gttgaaaaag atttaataaa cgaatttggc  35940
aaagatggtg aaagagttaa atttggaatg gaattaaaca ataaaatttt tatggaggaa  36000
gacgcaaatg aataaccgcg aacaaatcga acaatcagtt attagtgcta gcgcgtataa  36060
cggcaatgac acagagggat tattaaaaga gattgaggac gtgtataaga aagcgcaagc  36120
gtttgatgaa atacttgagg gtttacctaa tgctatgcaa gatgcaatca aagaagatat  36180
tggtcttgat gaagcagtag gaattatgac gggtcaagtt gtctataaat atgaggagga  36240
gcaggaaaat gactaacata ttacaagtga aactattatc aaaagacgct agaatgccag  36300
aacgaaatca taagacggat gcaggttatg acatattttc agctaaaact gtcgtacttg  36360
agccacaaga aaaggcagtg atcaaaacag atgtagctgt aagcattcca gagggctatg  36420
tcggtttatt aactagccgt agtggtgtaa gtagtaaaac gcatttagtg attgaaacag  36480
gcaagataga cgcgggatat catggtaatt tagggattaa tatcaagaat gataatgaaa  36540
cgttagagag tgaggatatg agtaactttg gtcggagtcc ttctggtata gatggaaaat  36600
acaccctact acctgtaaca gataaatttt tatgtatgaa tggtagttat gtcataaata  36660
aaggcgacaa actagctcaa ttggttatcg tgcctatatg gacacctgaa ctaaagcaag  36720
tggaggaatt cgagagtgtt tcagaacgtg gagcaaaagg cttcggaagt agcggagtgt  36780
aaagacatat tagatcgagt caaggaggtt ttggggaagt gagtgacatg ttagaaatat  36840
ttttcatagg gtttggtgtt tatctatttt gtcgcatagg tattattttt ctcaagagta  36900
aaaagactat acacacaaac ctatatgaaa tgttgttgat tgctactatc tttgtgacat  36960
ctacatttgc tgataaacat caaaagacgc atatcttaat agcattttta gtaatgtttt  37020
ttatgagtaa gctcaaacaa gttcaaggga gctatgagga atgacacaat acctagtcac  37080
aacatttaaa gattcaacag gacgtaagca tacacacata actaaagcta agagcaatca  37140
aaggtttaca gttgttgatg cggagagtaa agaagaagcg aaagagaagt acgaggcaca  37200
agttaaaaga aatgcagtta ttaaattagg gcagttgttt gaaaatataa gggagtgtgg  37260
gaaatgacta aacaaatact aagattatta ttcttactag cgatgtatga gctaggcaag  37320
tatgtaactg agcaagtata tattatgatg acggctaatg atgatgcaga ggcgccgagt  37380
gactttgaaa aaatcagagc tgaagtttca tggtaatagc tattatcatt tttgaattaa  37440
ttatattaat gtgtttagca atagcactgg aggtgttgta aatatgtgga ttgtcatttc  37500
aattgtttta tctatatttt tattgatctt gttaagtagc atttctcata agatgaaaac  37560
catagaagca ttggagtata tgaatgctta tcttttcaag cagttagtaa aaaataatgg  37620
tgttgaaggt atagaagatt atgaaaatga agttgaacga attagaaaaa gatttaaaag  37680
ctaaagagag gcgttggctt ctctgttcta tttaaaataa tgaaaggagc cgaacatgtt  37740
agacaaagtc actcaaatag aaacaattaa atatgatcgt gatgtttcat attcttatgc  37800
tgctagtcgt ttatctacac attggactaa tcacaatatg gcttggtctg actttatgca  37860
gaagctagca caaacagtta gaactaaaga agatttaact gagtacaata aaatgtctaa  37920
gtctgaacaa gccgatataa aagatgttgg cggatttgtc ggtggttatt taaaagaagg  37980
caaacgacgt gctggtcaag tcatgaatcg ttcaatgtta acacttgata tcgattatgc  38040
```

-continued

```
tgctcaagat atgactgaca tattatctat gttttatgat tttgcatatt gtttatattc  38100
aacacataag catagagaga taagtccaag actgcgttta gtgattcctt taaaacgaaa  38160
tgtaaatgca gatgagtatg aagctattgg gcgtaaagtc gcagatatcg ttggcatgga  38220
ttacttcgat gatacaactt atcaaccaca taggttaatg tattggcctt caactagtaa  38280
cgatgcggaa tttttcttta cctatgaaga tttacctttg ttagacccag ataaaatatt  38340
aaatgaatat gttgattgga ctgacacatt agaatggcca acgtcttcaa gggaagagag  38400
taagactaaa agattagcag ataagcaagg cgacccagaa gaaaagccgg gaattgttgg  38460
tgcattttgt agagcctata cgatagaaga agctatagaa acttttattc ctgatttata  38520
cgaaaaacat tctactaacc gttataccta tcatgaaggt tcaactgcag gtggattggt  38580
gttatacgaa aataacaagt ttgcctattc tcatcataat acggatcccg taagcggtat  38640
gcttgtgaac agttttgatt tagtacgcat acacttatat ggtgctcaag atgaagacgc  38700
taaaacagat actccggtta atcgactacc tagttataaa gcaatgcagc aaagagcgca  38760
aaatgatgaa gttgttaaaa agcaattaat taacgacaaa atgtctgatg caatgcagga  38820
tttcgatgaa atagtaaata gcgatgatgc atggtctgag acgttagaaa ttacttcgaa  38880
aggtactttc aaagctagta tcccaaatat agaaattata ttgcgtaatg atccaaattt  38940
aaaaggaaaa atagcattta atgaatttac aaaacaaatt gaatgcttag ggaaaatgcc  39000
atggaataat aattttaaaa tacgtcaatg gcaagacggt gatgatagca gtttaagaag  39060
ttatatcgaa aagatttatg acatacacca ttcaggcaaa acaaaagatg ccattataag  39120
cgtagcaatg caaaatgcct atcatccagt aagagattat ctaaataaaa tatcgtggga  39180
tggacataaa cgtcttgaaa agttatttat caaatactta ggtgttgaag acactgaagt  39240
gaatagaaca actaccaaaa aggcattgac tgctggaatc gctcgagtaa tggagccagg  39300
atgtaaattt gactatatgc ttacacttta tggtcctcaa ggtgtaggta aatctgcttt  39360
gctaaaaaaa ataggtggtg catggttttc tgacagttta gtttctgtta ctggtaagga  39420
agcatatgag gcattacaag gcgtttggtt aatggaaatg gcagaacttg cagctacaag  39480
aaaagctgaa gttgaagcta ttaagcattt catatctaaa caagttgacc ggtttcgtgt  39540
tgcttatgga cattatattg aagattttcc aaggcaatgt attttcattg gtacaactaa  39600
taaagttgat ttcttaagag atgaaactgg tggaagacgt ttttggccaa tgactgtaaa  39660
tccagagaga gttgaagtga actggtctaa actaaccaaa gaagagatcg accaaatctg  39720
ggcagaagct aaatactatt atgaacaagg agaagagttg ttccttaacc ctgaactaga  39780
agaagaaatg cgttcaatcc aaagtaaaca tactgaggaa tctccatata caggtattat  39840
tgatgaatat cttaacacgc caatcccaag caattgggaa gacttaacta tctttgaaag  39900
aagacgattt tatcaaggtg atgttgatat gttaccaaca ggaaatgtag attacattga  39960
aagagacaag gtctgtgcgc ttgaagtgtt tgttgaatgt tttggtaaag ataagggaga  40020
tagtagagga tctatggaaa ttagaaagat ttctaacgtc ttaagacaat tagacaattg  40080
gtctgtatat gaaggcaata aaagtgggaa aattcgattt ggaaaagatt atggtgtaca  40140
gatagcgtat gtaagagatg aaagtttaga ggatttaata taagaaatat tgaataaata  40200
tacattttta gatgttgtat caaatgttgc atcatttttt gagtgatgca acacggtggt  40260
gtaaaaagta atcgtaggtg ttgtatcatt tttggtgatg caacattgat gcaacaaatg  40320
atacaacacc tctttccctt ctcgctgtaa ggttcaaccc tgtttgtttc caatgttgca  40380
```

-continued

```
tcaaattcac tataaagttt aaaaagtagt gttagggagt aaaggggtat aggggtaacc  40440
ctctaacagc tatttttaaa agtttggcaa gaattgatgc aacatcggaa cacaaatata  40500
aattttgtat acaaggtgaa taaatgaaag aatcgacatt agaaaaatat ttagtgaaag  40560
agataacaaa gttaaatgga ttatgtttaa aatgggtcgc acctggaaca agaggtgtac  40620
cagatagaat tattattatg ccagaaggaa aaacatattt tgtagaaatg aagcaagaaa  40680
agggaaagtt acatccttta caaaaatatg tgcatcggca atttgaaaac agagatcata  40740
cagtgtatgt gttatggaat aaagaacaag taaatacttt tataagaatg gtaggtggaa  40800
catttggcga ttgatttcaa accacatagc tatcaaaagt atgcaataga taaagtgatt  40860
gataatgaga aatacggttt gtttttagat atggggctag ggaaaacagt atcaacactt  40920
acagcattta gtgaattgca gttgttagac actaaaaaaa tgttagtcat agcacctaaa  40980
caagttgcta aagatacatg ggttgatgaa gttgataagt ggaaccattt aaatcatctg  41040
aaagtgtctt tagtcttagg aacacctaaa gaaagaaatg atgcattaaa cacagaggct  41100
gatatctatg taaccaataa agaaaatact aaatggttat gtgatcaata taaaaaagaa  41160
tggccatttg acatggttgt aattgatgaa ctgtctacat ttaaaagtcc taagagtcaa  41220
aggtttaaat ctattaaaaa gaaattacca ctcattaata gatttatagg attaacagga  41280
acacctagtc caaatagttt acaggattta tgggctcaag tttatttgat agacagaggc  41340
gaaagacttg agtcttcatt cagtcgttat cgagaaaggt actttaaacc aacacatcaa  41400
gttagcgaac atgtttttaa ctgggagcta agagacggat ctgaagaaaa gatatatgaa  41460
cgaatagaag atatatgttt aagcatgaaa gcgaaagatt atctggatat gcctgacaga  41520
gttgatacta aacaaacagt agtcttatct gaaaaagaaa gaaaagtata tgaagaatta  41580
gaaaaaaact atattttaga atcggaagaa gaaggaacag ttgtagctca gaatggggca  41640
tcattaagtc aaaaactact tcaactatct aacggtgcag tttatacaga tgatgaagat  41700
gtaagactta tacatgataa gaagttagat aagttagagg aaattataga ggagtctcaa  41760
ggccaaccaa tattattgtt ttataacttc aaacatgata aagaaagaat acttcaaagg  41820
tttaaggaag caaccacatt agaggattca aactataaag aacgttggaa tagtggagac  41880
attaagctgc ttatagcaca tccagcaagt gcagggcatg gattaaactt acaacaaggt  41940
gggcacatta ttgtttggtt tggacttaca tggtcattgg aattatacca acaagcaaat  42000
gcaagattat atagacaagg acaaaatcat acgactatta ttcatcacat catgaccgat  42060
aacacaatag atcaaagagt atataaagct ttacaaaata aagaactaac gcaagaagaa  42120
ttgatgaaag ctattaaagc aagaatagct aagcataagt aatggaggta taagatggga  42180
aaggcgtcat atgatattaa gccaggaaca tttaaatata ttgaatcaga aatatataat  42240
ttaaatgaga acaagaaaga gataaataga ttgagaatgg agatacttaa cccaacgaaa  42300
gaactagaca ccaacattgt gtatggaccg ttacaaaaag gagagccagt tagaacaact  42360
gagttaatgg cgacaaggtt attgactaat aagatgttac gtaacttaga agagatggtt  42420
gaagcagttg aaagtgagta cttaaagtta cctgaagatc ataagaaagt aataaggtta  42480
aagtattgga ataaagataa gaagctaaag atagaacaaa taggggatgc ttgtcacatg  42540
catcgcaata cagttactac aatacgaaag aactttgtta aagcgatagc gtatcatgca  42600
ggtatcaaat aacattgtgc aaagattgtg caaaaggcct acaaatctgt agtaatatga  42660
tagtatcgga aagatgtata aagttatctg aaagttatac gacataaata catgaggcac  42720
atcgctaagc ggtgtgtctt ttgttatgca atcaaagagg tgtaagagat gaccaagcat  42780
```

-continued

```
aataacattt ataagcatgg tcgtaagtca tatcaatacg attggttcta tcattcaaaa  42840

gcatggaaga agttaagaga gatagcatta gatagagata attatctttg tcaaatgtgt  42900

ttacgcgaag atattataac agatgcaaag attgtgcatc acattattta tgttgatgaa  42960

gattttaaca aagctttaga cttagataat ctaatgtcag tttgttatag ctgtcataac  43020

aaaattcatg caaatgataa tgacaaaagt aatcttaaga aaattagagt tctaaaaatt  43080

taaataaaaa aatta                                                   43095
```

<210> SEQ ID NO 18
<211> LENGTH: 41708
<212> TYPE: DNA
<213> ORGANISM: Staphylococcus bacteriophage

<400> SEQUENCE: 18

```
gatcaaaata cttggggaac ggttagggag taaacttcgc gataatttta aaaattcatg     60

tataaccccc ctcttataac cattttaagg caggtgatga aatggagatt atagtcgatg    120

aaaatttagt gcttaaagaa aaagaaaggc tacaagtatt atataaagac atacctagca    180

ataaattaaa agtagttgat ggtttaatta ttcaagcagc aaggctacgt gtaatgcttg    240

attacatgtg ggaagacata aaagaaaaag gtgattatga tttatttact caatctgaaa    300

aggcgccacc atatgaaagg gaaagaccag tagccaaact atttaatgct agagatgctg    360

catatcaaaa aataatcaaa caattatcgg atttattgcc cgaagagaaa gaagacacag    420

aaacgccatc tgatgattac ctatgattag taataaatac gttgatgaat atataaattt    480

gtggaaacaa ggaaagataa ttttaaataa agaaagaatt gatctcttta attatctaca    540

aaaacatata tattcacgag atgatgtata ttttgatgaa cagaaaatcg aggattgtat    600

caaatttatt gaaaaatggt attttccaac attaccattt caaaggttta tcatagctaa    660

tatatttctt atagataaaa atacagatga agctttcttt acagaatttg ctattttcat    720

gggacgtgga ggcgggaaaa acggtctaat aagtgctatt agtgattttc tttctacgcc    780

cttacacgga gttaaagaat atcacatctc cattgttgct aatagtgaag atcaagcaaa    840

aacatcgttt gatgaaatca gaaccgtttt aatggataac aaacgaaata agacgggtaa    900

aacgccaaaa gctccttatg aagttagtaa agcaaaaata ataaaccgtg caactaaatc    960

ggttattcga tataacacat caaacacaaa aaccaaagac ggtggacgtg aggggtgtgt   1020

tatttttgat gaaattcatt atttctttgg tcctgaaatg gtaaacgtca aacgtggtgg   1080

attaggtaaa aagaaaaata gaagaacgtt ttatataagt actgatggtt ttgttagaga   1140

gggttatatc gatgcaatga agcacaaaat tgcaagtgta ttaagtggca aggttaaaaa   1200

tagtagattg tttgcttttt attgtaagtt agacgatcca aaagaagttg atgacagaca   1260

gacgtgggaa aaggcgaacc caatgttaca taaaccgtta tcagaatacg ctaaaacact   1320

gctaagcacg attgaagaag aatataacga tttaccattc aaccgttcaa ataagcccga   1380

attcatgact aagcgaatga atttgcctga agttgacctt gaaaaagtaa tagcaccatg   1440

gaaagaaata ctagcgacta atagagagat accaaattta gataatcaaa tgtgtattgg   1500

tggtttagac tttgcaaaca ttcgagattt tgcaagtgta gggctattat tccgaaaaaa   1560

cgatgattac atttggttag gacattcgtt tgtaagacaa gggtttttgg atgatgtcaa   1620

attagaacct cctattaaag aatgggaaaa aatgggatta ttgaccattg tcgatgatga   1680

tgtcattgaa attgaatata tagttgattg gtttttaaag gctagagaaa aatatgggct   1740
```

-continued

```
tgaaaaagtc atagctgata attatagaac tgatattgta agacgtgcgt ttgaggatgc   1800
tggcataaaa cttgaagtac ttagaaatcc aaaagcaata catggattac ttgcaccacg   1860
tatcgataca atgtttgcga aacataacgt aatatatgga gacaatcctt tgatgcgttg   1920
gtttactaat aatgttgctg taaaaatcaa gccggatgga aataaagagt atatcaaaaa   1980
agatgaagtc agacgtaaaa cggatggatt catggctttt gttcacgcat tatatagagc   2040
agacgatata gtagacaaag acatgtctaa agcgcttgat gcattaatga gtatagattt   2100
ctaatagagg aggtgagaca tgagtattct agaaaagata tttaaaacta ggaaagatat   2160
aacatatatg cttgatttag atatgataga agatctatca caacaagcgt atgtgaaacg   2220
tttagcgatt gatagttgta ttgaatttgt tgcgcgagct gtcgctcaaa gtcattttaa   2280
agtattggaa ggtaatagaa ttcaaaagaa tgatgtttac tacaagttaa atataaaacc   2340
aaatactgac ttatcaagcg atagtttttg gcaacaagtt atatataaac taatttatga   2400
taacgaggtt ttaatcgtag taagtgacag caaagaatta cttatcgcag atagctttta   2460
cagagaagag tacgctttgt atgatgatat attcaaagat gtaacggtta aagattatac   2520
ttatcaacgt actttcacaa tgcaagaggt catatattta aagtacaaca acaataaagt   2580
gacacacttt gtagaaagtc tattcgaaga ttacgggaaa atattcggaa gaatgatagg   2640
tgcacaatta aaaaactatc aaataagagg gattttgaaa tctgcctcta gcgcatatga   2700
cgaaaagaat atagaaaaat tacaagcgtt cacaaataaa ttattcaata cttttaataa   2760
aaatcaacta gcaatcgcgc ctttgataga aggttttgat tatgaggaat tatctaatgg   2820
tggtaagaat agtaacatgc ctttttctga attgagtgag ctaatgagag atgcaataaa   2880
aaatgttgcg ttgatgattg gtatacctcc aggtttgatt tacggagaaa cagctgattt   2940
ggaaaaaaac acgcttgtat ttgagaagtt ctgtttaaca cctttattaa aaaagattca   3000
gaacgaatta aacgcgaaac tcataacaca aagcatgtat ttgaaagata caagaataga   3060
aattgtcggt gtgaataaaa aagacccact tcaatatgct gaagcaattg acaaacttgt   3120
aagttctggt tcatttacaa ggaatgaggt gcggattatg ttaggtgaag aaccatcaga   3180
caatcctgaa ttagacgaat acctgattac taaaaactac gaaaaagcta acagtggtga   3240
aaatgatgaa aaagaaaaag atgaaaacac tttgaaaggt ggtgatgaag atgaaagcgg   3300
agattaaagg cgtcatcgtt tccaacgaag ataaatgggt ttacgaaatg cttggtatgg   3360
attcgacttg tcctaaagat gttttaacac aactagaatt tagtgatgaa gatgttgata   3420
ttataattaa ctcaaatggt ggtaacctag tagctggtag tgaaatatat acacatttaa   3480
gagctcataa aggcaaagtg aatgttcgta tcacagcaat agcagcaagt gcggcatcgc   3540
ttatcgcaat ggctggtgac cacatcgaaa tgagtccggt tgctagaatg atgattcaca   3600
atccttcaag tattgcgcaa ggagaagtga aagatctaaa tcatgctgca gaaacattag   3660
aacatgttgg tcaaataatg gctgaggcat atgcggttag agctggtaaa aacaaacaag   3720
aacttataga aatgatggct aaggaaacgt ggctaaatgc tgatgaagcc attgaacaag   3780
gttttgcgga tagtaaaatg tttgaaaacg acaatatgca aattgtagca agcgatacac   3840
aagtgttatc gaaagatgta ttaaatcgtg taacagcttt ggtaagtaaa acgccagagg   3900
ttaacattga tattgacgca atagcaaata aagtaattga aaaaataaat atgaaagaaa   3960
aggaatcaga aatcgatgtt gcagatagta aattatcagc aaatggattt tcaagattcc   4020
ttttttaata caaaaatagg aggtcataaa atgactataa atttatcgga aacattcgca   4080
aatgcgaaaa acgaatttat taatgcagta aacaacggtg aaccgcaaga aagacaaaat   4140
```

-continued

```
gaattgtacg gtgacatgat taaccaacta tttgaagaaa ctaaattaca agcaaaagca   4200
gaagctgaaa gagtttctag tttacctaaa tcagcacaaa ctttgagtgc aaaccaaaga   4260
aatttcttta tggatatcaa taagagtgtt ggatataaag aagaaaaact tttaccagaa   4320
gaaacaattg atagaatctt cgaagattta acaacgaatc atccattatt agctgactta   4380
ggtattaaaa atgctggttt gcgtttgaag ttcttaaaat ccgaaacttc tggcgtggct   4440
gtttggggta aaatctatgg tgaaattaaa ggtcaattag atgctgcgtt cagtgaagaa   4500
acagcaattc aaaataaatt gacagcgttt gttgttttac caaaagattt aaatgatttt   4560
ggtcctgcgt ggattgaaag atttgttcgt gttcaaatcg aagaagcatt tgcagtggcg   4620
cttgaaactg cgttcttaaa aggtactggt aaagaccaac cgattggctt aaaccgtcaa   4680
gtacaaaaag gtgtatcggt aactgatggt gcttatccag agaaagaaga acaaggtacg   4740
cttacatttg ctaatccgcg cgctacggtt aatgaattga cgcaagtgtt taaataccac   4800
tcaactaacg agaaaggtaa atcagtagcg gttaaaggta atgtaacaat ggttgttaat   4860
ccgtccgatg cttttgaggt tcaagcacag tatacacatt taaatgcaaa tggcgtatat   4920
gttactgctt taccatttaa tttgaatgtt attgagtcta cagttcaaga agcaggtaag   4980
gttttaacgt acgttaaagg tctatatgat ggttatttag ctggtggtat taatgttcag   5040
aaatttaaag aaacacttgc gttagatgat atggatttat acactgcaaa acaatttgct   5100
tacggcaaag cgaaagataa taaagttgct gctgtttgga aattagattt aaaaggacat   5160
aaaccagctt tagaagatac cgaagaaaca ctataaaatt ttatgaggtg ataaaatggt   5220
gaaatttaaa gttgttagag aatttaaaga catagagcac aatcaacaca agtacaaagt   5280
aggggagttg tatccagctg aagggtataa caatcctcgt gttgaattgt tgacaaatca   5340
aatcaaaaat aagtacgaca aagtttatat cgtaccttta gataagctga caaaacaaga   5400
attattagaa ctatgcgaat cattacaaaa aaaagcgtct agttcaatgg ttaaaagtga   5460
aatcatcgac ttattgaatg gtgaagacaa tgacgattga tgatttgctt gtcaaattta   5520
aatcacttga aaagattgac cataattcag aggatgagta cttaaagcag ttgttaaaaa   5580
tgtcgtacga gcgtataaaa aatcagtgcg gagtttttga attagagaat ttaataggtc   5640
aagaattgat acttatacgc gctagatatg cttatcaaga tttattagaa cacttcaacg   5700
acaattacag acctgaaata atagattttt cgttatctct aatggaggta tcagaagatg   5760
aagaaagtgt ttaagaaacc tagaattaca actaaacgtt taaatacgcg tgttcatttt   5820
tataagtata ctgaaaataa tggtccagaa gctggagaaa aagaagaaaa attattatat   5880
agctgttggg cgagtattga tggtgtctgg ttacgtgaat tagaacaagc tatctcaaac   5940
ggaacgcaaa atgacattaa attgtatatt cgtgatccgc aaggtgatta tttacccagt   6000
gaagaacatt atcttgaaat tgaatcaaga tatttcaaaa atcgtttgaa tataaagcaa   6060
gtatcaccag atttggataa taaagacttt attatgattc gcggaggata tagttcatga   6120
gtgtgaaagt gacaggtgat aaagcattag aaagagaatt agaaaaacat tttggcataa   6180
aagagatggt aaaagttcaa gataaggcgt taatagctgg tgctaaggta attgttgaag   6240
aaataaaaaa acaactcaaa ccttcagaag actcaggagc actgattagt gagattggtc   6300
gtactgaacc tgaatggata aaggggaaac gtactgttac aattaggtgg cgtgggcctt   6360
ttgaacgatt tagaatagta catttaattg aaaatggtca tgttgagaaa aagtcaggaa   6420
aatttgtaaa acctaaagct atgggtggga ttaatagagc aataagacaa gggcaaaata   6480
```

-continued

```
agtattttga gacgctaaaa agggagttga aaaaattgtg attgatattt tgtacaaagt   6540
tcatgaagtg attagtcaag acagaattat tagagagcac gtaaatatca ataatattaa   6600
gttcaataaa taccctaatg taaaagatac tgatgtacct tttattgtta ttgacgatat   6660
cgacgaccca atacctacaa cttatactga cggagatgag tgtgcatata gttatattgt   6720
ccaaatagat gtttttgtta agtacaatga tgaatataat gcgagaatca taagaaataa   6780
gatatctaat cgcattcaaa agttattatg gtctgaacta aaaatgggaa atgtttcaaa   6840
tggaaaaccg gaatatatag aagaatttaa aacatataga agctctcgcg tttacgaggg   6900
catttttat aaggaggaaa attaaatggc agtaaaacat gcaagtgcgc caaaggcgta    6960
tattaacatt actggtttag gtttcgctaa attaacgaaa gaaggcgcgg aattaaaata   7020
tagtgatatt acaaaaacaa gaggattaca aaaaattggt gttgaaactg gtggagaact   7080
aaaaacagct tatgctgatg gcggtccaat tgaatcaggg aatacagacg gagaaggtaa   7140
aatctcatta caaatgcatg cgttccctaa agagattcgc aaaattgttt ttaatgaaga   7200
ttatgatgaa gatggcgttt acgaagagaa acaaggtaaa caaaacaatt acgtagctgt   7260
atggttcaga caagagcgta aagacggtac atttagaaca gttttattac ctaaagttat   7320
gtttacaaat cctaaaatcg atggagaaac ggctgagaaa gattgggatt tctcaagtga   7380
agaggttgaa ggtgaggcac ttttcccttt agttgataat aaaaagtcag tacgtaagta   7440
tatctttgat tcagctaaca tgacaaatca tgatggagac ggtgaaaaag gcgaagaggc   7500
tttcttaaag aaaattttag gcgaagaata tactggaaac gtgacagagg gtaacgaaga   7560
aactttgtaa caaaaccggc ttcatcggaa actgcggtaa agtcggttaa tataccagat   7620
agcattaaaa cacttaaagt tggcgacaca tacgatttaa atgttgtagt agagccatct   7680
aatcaaagta agttattgaa atacacaaca gatcaaacga atattgtatc aatcaatagt   7740
gatggtcaag ttactgcgga agcacaaggc attgctacgg ttaaagcaac agttggtaat   7800
atgagtgaca ctataacaat aaatgtagaa gcataagagg gggcaacccc tctattttat   7860
ttgaaaataa ggagagtatt ataaaatggc aaaattaaaa cgtaacatta ttcaattagt   7920
agaagatcca aaagcaaatg aaattaaatt acaaacgtac ttaacaccac acttcatttc   7980
atttgaaatt gtatacgaag caatggattt aatcgatgat attgaggacg aaaatagcac   8040
gatgaagcca agagaaatcg ctgacagatt gatggatatg gttgtaaaaa tttacgataa   8100
ccaattcaca gttaaagacc taaaagaacg tatgcatgca cctgatggaa tgaatgcact   8160
tcgtgaacaa gtgattttca ttactcaagg tcaacaaact gaggaaacta gaaattttat   8220
ccagaacatg aaataaagcc tgaagattta acatataaag caatgttgaa aaatatggat   8280
actctcatga tggacttaat tgaaaatggt aaagacgcta acgaagtttt aaaaatgcca   8340
tttcattatg tgctttccat atatcaaaat aaaaataatg acatttctga agaaaaagca   8400
gaggctttaa ttgatgcatt ttaaccttaa ccgtttggtt agggttattt ttttgaactt   8460
ttttagaaag gaggtaaaaa atgggagaaa gaataaaagg tttatctata ggtttggatt   8520
tagatgcagc aaatttaaat agatcatttg cagaaatcaa acgaaacttt aaaactttaa   8580
attctgactt aaaattaaca ggcaacaact tcaaatatac cgaaaaatca actgatagtt   8640
acaaacaaag gattaaagaa cttgatggaa ctatcacagg ttataagaaa aacgttgatg   8700
atttagccaa gcaatatgac aaggtatctc aagaacaggg cgaaaacagt gcagaagctc   8760
aaaagttacg acaagaatat aacaaacaag caaatgagct gaattattta gaaagagaat   8820
tacaaaaaac atcagccgaa tttgaagagt tcaaaaaagc tcaagttgaa gctcaaagaa   8880
```

-continued

```
tggcagaaag tggctgggga aaaaccagta aagtttttga aagtatggga cctaaattaa   8940
caaaaatggg tgatggttta aaatccattg gtaaaggttt gatgattggt gtaactgcac   9000
ctgttttagg tattgcagca gcatcaggaa aagcttttgc agaagttgat aaaggtttag   9060
atactgttac tcaagcaaca ggcgcaacag gcagtgaatt aaaaaaattg cagaactcat   9120
ttaaagatgt ttatggcaat tttccagcag atgctgaaac tgttggtgga gttttaggag   9180
aagttaatac aaggttaggt tttacaggta aagaacttga aaatgccaca gagtcattct   9240
tgaaattcag tcatataaca ggttctgacg gtgtgcaagc cgtacagtta attacccgtg   9300
caatgggcga tgcaggtatc gaagcaagtg aatatcaaag tgttttggat atggtagcaa   9360
aagcggcgca agctagtggg ataagtgttg atacattagc tgatagtatt actaaatacg   9420
gcgctccaat gagagctatg ggctttgaga tgaaagaatc aattgcttta ttctctcaat   9480
gggaaaagtc aggcgttaat actgaaatag cattcagtgg tttgaaaaaa gctatatcaa   9540
attggggtaa agctggtaaa aacccaagag aagaatttaa gaagacatta gcagaaattg   9600
aaaagacgcc ggatatagct agcgcaacaa gtttagcgat tgaagcattt ggtgcaaagg   9660
caggtcctga tttagcagac gctattaaag gtggtcgctt tagttatcaa gaatttttaa   9720
aaactattga agattcccaa ggcacagtaa accaaacatt taaagattct gaaagtggct   9780
ccgaaagatt taaagtagca atgaataaat taaaattagt aggtgctgat gtatgggctt   9840
ctattgaaag tgcgtttgct cccgtaatgg aagaattaat caaaaagcta tctatagcgg   9900
ttgattggtt ttccaattta agtgatggtt ctaaaagatc aattgttatt ttcagtggta   9960
ttgctgctgc aattggtcct gtagtttttg ggttaggtgc atttataagt acaattggca  10020
atgcagtaac tgtattagct ccattgttag ctagtattgc aaaggctggt ggattgatta  10080
gtttttttatc gactaaagta cctatattag gaactgtctt cacagcttta actggtccaa  10140
ttggcattgt attaggtgta ttggctggtt tagcagtcgc atttacaatt gcttataaga  10200
aatctgaaac atttagaaat tttgttaatg gtgcaattga aagtgttaaa caaacattta  10260
gtaattttat tcaatttatt caacctttcg ttgattctgt taaaaacatc tttaaacaag  10320
cgatatcagc aatagttgat ttcgcaaaag atatttggag tcaaatcaat ggattcttta  10380
atgaaaacgg aatttccatt gttcaagcac ttcaaaatat atgcaacttt attaaagcga  10440
tatttgaatt tattttaaat tttgtaatta aaccaattat gttcgcgatt tggcaagtga  10500
tgcaatttat ttggccggcg gttaaagcct tgattgtcag tacttgggag aacataaaag  10560
gtgtaataca aggtgcttta aaatatcatac ttggcttgat taagttcttc tcaagtttat  10620
tcgttggtga ttggcgagga gtttgggacg ccgttgtgat gattcttaaa ggagcagttc  10680
aattaatttg gaatttagtt caattatggt ttgtaggtaa aatacttggt gttgttaggt  10740
actttggcgg gttgctaaaa ggattgatag caggaatttg ggacgtaata agaagtatat  10800
tcagtaaatc tttatcagca atttggaatg caacaaaaag tatttttgga tttttattta  10860
atagcgtaaa atcaattttc acaaatatga aaaattggtt atctaatact tggagcagta  10920
tccgtacgaa tacaatagga aaagcgcagt cattatttag tggcgtcaaa tcaaaattta  10980
ctaatttatg gaatgcgacg aaagaaattt ttagtaattt aagaaattgg atgtcaaata  11040
tttggaattc cattaaagat aatacggtag gaattgcaag ccgtttatgg agtaaggtac  11100
gtggaatttt cacaaatatg cgcgatggct tgagttccat tatagataag attaaaagtc  11160
atatcggcgg tatggtaagc gctattaaaa aaggacttaa taaattaatc gacggtttaa  11220
```

-continued actgggtcgg tggtaagttg ggaatggata aaatacctaa gttacacact ggtacagagc 11280
acacacatac tactacaaga ttagttaaga acggtaagat tgcacgtgac acattcgcta 11340
cagttgggga taagggacgc ggaaatggtc caaatggttt tagaaatgaa atgattgaat 11400
tccctaacgg taaacgtgta atcacaccta atacagatac taccgcttat ttacctaaag 11460
gctcaaaagt atacaacggt gcacaaactt attcaatgtt aaacggaacg cttccaagat 11520
ttagtttagg tactatgtgg aaagatatta aatctggtgc atcatcggca tttaactgga 11580
caaaagataa aataggtaaa ggtaccaaat ggcttggcga taaagttggc gatgttttag 11640
attttatgga aaatccaggc aaacttttaa attatatact tgaagctttt ggaattgatt 11700
tcaattcttt aactaaaggt atgggaattg caggcgacat aacaaaagct gcatggtcta 11760
agattaagaa aagtgctact gattggataa aagaaaattt agaagctatg ggcggtggcg 11820
atttagtcgg cggaatatta gaccctgaca aaattaatta tcattatgga cgtaccgcag 11880
cttataccgc tgcaactgga agaccatttc atgaaggtgt cgattttcca tttgtatatc 11940
aagaagttag aacgccgatg ggtggcagac ttacaagaat gccatttatg tctggtggtt 12000
atggtaatta tgtaaaaatt actagtggcg ttatcgatat gctatttgcg catttgaaaa 12060
actttagcaa atcaccacct agtggcacga tggtaaagcc cggtgatgtt gttggtttaa 12120
ctggtaatac cggatttagt acaggaccac atttacattt tgaaatgagg agaaatggac 12180
gacattttga ccctgaacca tatttaagga atgctaagaa aaaaggaaga ttatcaatag 12240
gtggtggcgg tgctacttct ggaagtggcg caacttatgc cagtcgagta atccgacaag 12300
cgcaaagtat tttaggtggt cgttataaag gtaaatggat tcatgaccaa atgatgcgcg 12360
ttgcaaaacg tgaaagtaac taccagtcaa atgcagtgaa taactgggat ataaatgctc 12420
aaagaggaga cccatcaaga ggattattcc aaatcatcgg ctcaactttt agagcaaacg 12480
ctaaacgtgg atatactaac tttaataatc cagtacatca aggtatctca gcaatgcagt 12540
acattgttag acgatatggt tggggtggtt ttaaacgtgc tggtgattac gcatatgcta 12600
caggtggaaa agtttttgat ggttggtata acttaggtga agacggtcat ccagaatgga 12660
ttattccaac agatccagct cgtagaaatg atgcaatgaa gattttgcat tatgcagcag 12720
cagaagtaag agggaaaaaa gcgagtaaaa ataagcgtcc tagccaatta tcagacttaa 12780
acgggtttga tgatcctagc ttattattga aaatgattga acaacagcaa caacaaatag 12840
ctttattact gaaaatagca caatctaacg atgtgattgc agataaagat tatcagccga 12900
ttattgacga atacgctttt gataaaaagg tgaacgcgtc tatagaaaag cgagaaaggc 12960
aagaatcaac aaaagtaaag tttagaaaag gaggaattgc tattcaatga tagacactat 13020
taaagtgaac aacaaaacaa ttccttggtt gtatgtcgaa agagggtttg aaataccctc 13080
ttttaattat gttttaaaaa cagaaaatgt agatggacgt tcggggtcta tatataaagg 13140
gcgtaggctt gaatcttata gttttgatat acctttggtg gtacgtaatg actatttatc 13200
tcacaacggc attaaaacac atgatgacgt cttgaatgaa ttagtaaagt tttttaacta 13260
cgaggaacaa gttaaattac aattcaaatc taaagattgg tactggaacg cttatttcga 13320
aggaccaata aagctgcaca aagaatttac aatacctgtt aagttcacta tcaaagtagt 13380
actaacagac ccttacaaat attcagtaac aggaaataaa aatactgcga tttcagacca 13440
agtttcagtt gtaaatagtg ggactgctga cactccttta attgttgaag cccgagcaat 13500
taaaccatct agttacttta tgattactaa aaatgatgaa gattatttta tggttggtga 13560
tgatgaggta accaaagaag ttaaggatta catgcctcct gtttatcata gtgagtttcg 13620

-continued

```
tgatttcaaa ggttggacta agatgattac tgaagatatt ccaagtaatg acttaggtgg  13680
taaggtcggc ggtgactttg tgatatccaa tcttggcgaa ggatataaag caactaattt  13740
tcctgatgca aaaggttggg ttggtgctgg cacgaaacga gggctcccta aagcgatgac  13800
agattttcaa attacctata aatgtattgt tgaacaaaaa ggtaaaggtg ccggaagaac  13860
agcacaacat atttatgata gtgatggtaa gttacttgct tctattggtt atgaaaataa  13920
atatcatgat agaaaaatag gacatattgt tgttacgttg tataaccaaa aaggagaccc  13980
caaaaagata tacgactatc agaataaacc gataatgtat aacttggaca gaatcgttgt  14040
ttatatgcgg ctcagaagag taggtaataa attttctatt aaaacttgga aatttgatca  14100
cattaaagac ccagatagac gtaaacctat tgatatggat gagaaagagt ggatagatgg  14160
cggtaagttt tatcagcgtc cagcttctat catagctgtc tatagtgcga agtataacgg  14220
ttataagtgg atggagatga atgggttagg ttcattcaat acggagattc taccgaaacc  14280
gaaaggcgca agggatgtca ttatacaaaa aggtgattta gtaaaaatag atatgcaagc  14340
aaaaagtgtt gtcatcaatg aggaaccaat gttgagcgag aaatcgtttg gaagtaatta  14400
tttcaatgtt gattctgggt acagtgaatt aatcatacaa cctgaaaacg tctttgatac  14460
gacggttaaa tggcaagata gatatttata gaaaggagat gagagtgtga tacatgtttt  14520
agattttaac gacaagatta tagatttcct ttctactgat gacccttcct tagttagagc  14580
gattcataaa cgtaatgtta atgacaattc agaaatgctt gaactgctca tatcatcaga  14640
aagagctgaa aagttccgtg aacgacatcg tgttattata agggattcaa acaaacaatg  14700
gcgtgaattt attattaact gggttcaaga tacgatggac ggctacacag agatagaatg  14760
tatagcgtct tatcttgctg atataacaac agctaaaccg tatgcaccag gcaaatttga  14820
gaaaaagaca acttcagaag cattgaaaga tgtgttgagc gatacaggtt gggaagtttc  14880
tgaacaaacc gaatacgatg gcttacgtac tacgtcatgg acttcttatc aaactagata  14940
tgaagtttta aagcaattat gtacaaccta taaaatggtt ttagattttt atattgagct  15000
tagctctaat accgtcaaag gtagatatgt agtactcaaa aagaaaaaca gcttattcaa  15060
aggtaaagaa attgaatatg gtaaagattt agtcgggtta actaggaaga ttgatatgtc  15120
agaaatcaaa acagcattaa ttgctgtggg acctgaaaat gacaaaggga agcgtttaga  15180
gctagttgtg acagatgacg aagcgcaaag tcaattcaac ctacctatgc gctatatttg  15240
ggggatatat gaaccacaat cagatgatca aaatatgaat gaaacacgat taagttcttt  15300
agccaaaaca gagttaaata aacgtaagtc ggcagttatg tcatatgaga ttacttctac  15360
tgatttggaa gttacgtatc cgcacgagat tatatcaatt ggcgatacag tcagagtaaa  15420
acatagagat tttaacccgc cattgtatgt agaggcagaa gttattgctg aagaatataa  15480
cataatttca gaaaatagca catatacatt cggtcaacct aaagagttca aagaatcaga  15540
attacgagaa gagtttaaca agcgattgaa cataatacat caaaagttaa acgataatat  15600
tagcaatatc aacactatag ttaaagatgt tgtagatggt gaattagaat actttgaacg  15660
caaaatacac aaaagtgata caccgccaga aaatccagtc aatgatatgc tttggtatga  15720
tacaagtaac cctgatgttg ctgtcttgcg tagatattgg aatggtcgat ggattgaagc  15780
aacaccaaat gatgttgaaa aattaggtgg tataacaaga gagaaagcgc tattcagtga  15840
attaaacaat atttttatta atttatctat acaacacgct agtcttttgt cagaagctac  15900
agaattactg aatagcgagt acttagtaga taatgatttg aaagcggact tacaagcaag  15960
```

-continued

```
tttagacgct gtgattgatg tttataatca aattaaaaat aatttagaat ctatgacacc  16020
cgaaactgca acgattggtc ggttggtaga tacacaagct ttatttcttg agtatagaaa  16080
gaaattacaa gatgtttata cagatgtaga agatgtcaaa atcgccattt cagatagatt  16140
taaattatta cagtcacaat acactgatga aaaatataaa gaagcgttgg aaataatagc  16200
aacaaaattt ggtttaacgg tgaatgaaga tttgcagtta gtcggagaac ctaatgttgt  16260
taaatcagct attgaagcag ctagagaatc cacaaaagaa caattacgtg actatgtaaa  16320
aacatcggac tataaaacag acaaagacgg tattgttgaa cgtttagata ctgctgaagc  16380
tgagagaacg actttaaaag gtgaaatcaa agataaagtt acgttaaacg aatatcgaaa  16440
cggattggaa gaacaaaaac aatatactga tgaccagtta agtgatttgt ccaataatcc  16500
tgagattaaa gcaagtattg aacaagcaaa tcaagaagcg caagaagctt taaaatcata  16560
cattgatgct caagatgatc ttaaagagaa ggaatcgcaa gcgtatgctg atggtaaaat  16620
ttcggaagaa gagcaacgcg ctatacaaga tgctcaagct aaacttgaag aggcaaaaca  16680
aaacgcagaa ctaaaggcta gaaacgctga aaagaaagct aatgcttata cagacaacaa  16740
ggtcaaagaa agcacagatg cacagaggaa aacattgact cgctatggtt ctcaaattat  16800
acaaaatggt aaggaaatca aattaagaac tactaaagaa gagtttaatg caaccaatcg  16860
tacactttca aatatattaa acgagattgt tcaaaatgtt acagatggaa caacaatcag  16920
atatgatgat aacggagtgg ctcaagcttt gaatgtgggg ccacgtggta ttagattaaa  16980
tgctgataaa attgatatta acggtaatag agaaataaac cttcttatcc aaaatatgcg  17040
agataaagta gataaaaccg atattgtcaa cagtcttaat ttatcaagag agggtcttga  17100
tatcaatgtt aatagaattg gaattaaagg cggtgacaat aacagatatg ttcaaataca  17160
gaatgattct attgaactag gtggtattgt gcaacgtact tggagaggga aacgttcaac  17220
agacgatatt tttacgcgac tgaaagacgg tcacctaaga tttagaaata acaccgctgg  17280
cggttcactt tatatgtcac attttggtat ttcgacttat attgatggtg aaggtgaaga  17340
cggtggttca tctggtacga ttcaatggtg ggataaaact tacagtgata gtggcatgaa  17400
tggtataaca atcaattcct atggtggtgt cgttgcacta acgtcagata ataatcgggt  17460
tgttctggag tcttacgctt catcgaatat caaaagcaaa caggcaccgg tgtatttata  17520
tccaaacaca gacaaagtgc ctggattaaa ccgatttgca ttcacgctgt ctaatgcaga  17580
taatgcttat tcgagtgacg gttatattat gtttggttct gatgagaact atgattacgg  17640
tgcgggtatc aggttttcta aagaaagaaa taaaggtctt gttcaaattg ttaatggacg  17700
atatgcaaca ggtggagata caacaatcga agcagggtat ggcaaattta atatgctgaa  17760
acgacgtgat ggtaataggt atattcatat acagagtaca gacctactgt ctgtaggttc  17820
agatgatgca ggagatagga tagcttctaa ctcaatttat agacgtactt attcggccgc  17880
agctaatttg catattactt ctgctggcac aattgggcgt tcgacatcag cgcgtaaata  17940
caagttatct atcgaaaatc aatataacga tagagatgaa caactggaac attcaaaagc  18000
tattcttaac ttacctatta gaacgtggtt tgataaagct gagtctgaaa ttttagctag  18060
agagctgaga gaagatagaa aattatcgga agacacctat aaacttgata gatacgtagg  18120
tttgattgct gaagaggtgg agaatttagg attaaaagag tttgtcacgt atgatgacaa  18180
aggagaaatt gaaggtatag cgtatgatcg tctatggatt catcttatcc ctgttatcaa  18240
agaacaacaa ctaagaatca agaaattgga ggagtcaaag aatgcaggat aacaaacaag  18300
gattacaagc taatcctgaa tatacaattc attatttatc acaggaaatt atgaggttaa  18360
```

-continued

```
cacaagaaaa cgcgatgtta aaagcgtata tacaagaaaa taaagaaaat caacaatgtg  18420
ctgaggaaga gtaatcctta gcactatttt tatacaaaaa tttaaggagg tcatttaatt  18480
atggcaaaag aaattatcaa caatacagaa aggtttattt tagtacaaat cgacaaagaa  18540
ggtacagaac gtgtagtata tcaagatttc acaggaagtt ttacaacttc tgaaatggtt  18600
aaccatgctc aagattttaa atctgaagaa aacgctaaga aaattgcgga gacgttaaat  18660
ttgttatatc aattaactaa caaaaaacaa cgtgtgaaag tagttaaaga agtagttgaa  18720
agatcagatt tatctccaga ggtaacagtt aacactgaaa cagtatgaaa agctatgagt  18780
tagatactca tagtctttat tcttttagaa agcgggtgta ctgaattggg gtggttcaaa  18840
aaacacgaac atgaatggcg catcagaagg ttagaagaga atgataaaac aatgctcagc  18900
acactcaacg aaattaaatt aggtcaaaaa acccaagagc aagttaacat taaattagat  18960
aaaaccttag atgctattca aaaagaaaga gaaatagatg aaaagaataa gaaagaaaat  19020
gataagaaca tacgtgatat gaaaatgtgg gtgcttggtt tagttgggac aatatttggg  19080
tcgctaatta tagcattatt gcgtatgctt atgggcatat aagagaggtg attaccatgt  19140
tcggattaaa ttttggagct tcgctgtgga cgtgtttctg gtttggtaag tgtaagtaat  19200
agttaagagt cagtgcttcg gcactggctt tttattttgg ataaaaggag caaacaaatg  19260
gatgcaaaag taataacaag atacatcgta ttgatcttag cattagtaaa tcaattctta  19320
gcgaacaaag gtattagccc aattccagta gacgatgaaa ctatatcatc aataatactt  19380
actgtagtcg ctttatatac aacgtataaa gacaatccaa catctcaaga aggtaaatgg  19440
gcaaatcaaa aattaaagaa atataaagct gaaaataagt atagaaaagc aacagggcaa  19500
gcgccaatta aagaagtaat gacacctacg aatatgaacg acacaaatga tttagggtag  19560
gtggttgata tatgttaatg acaaaaaatc aagcagaaaa atggtttgac aattcattag  19620
ggaaacaatt caacccagat ggttggtatg gatttcagtg ttatgattac gccaatatgt  19680
tctttatgtt agcgacaggc gaaaggctgc aaggtttata tgcttataat atcccgtttg  19740
ataataaagc aaagattgaa aaatatggtc aaataattaa aaactatgac agctttttac  19800
cgcaaaagtt ggatattgtc gttttcccgt caaagtatgg tggcggagct ggacacgttg  19860
aaattgttga gagcgcaaat ttaaatactt tcacatcatt tggtcaaaac tggaacggta  19920
aaggttggac taatggcgtt gcgcaacctg gttggggtcc tgaaactgtg acaagacatg  19980
ttcattatta tgacaatcca atgtatttta ttaggttaaa cttccctaac aacttaagcg  20040
ttggcaataa agctaaaggt attattaagc aagcgactac aaaaaaagag gcagtaatta  20100
aacctaaaaa aattatgctt gtagccggtc atggttataa cgatcctgga gcagtaggaa  20160
acggaacaaa cgaacgcgat tttatacgta aatatataac gcctaatatc gctaagtatt  20220
taagacatgc aggacatgaa gttgcattat acggtggctc aagtcaatca caagatatgt  20280
atcaagatac tgcatacggt gttaatgtag gcaataaaaa agattatggc ttatattggg  20340
ttaaatcaca ggggtatgac attgttctag aaatacattt agacgcagca ggagaaagcg  20400
caagtggtgg gcatgttatt atctcaagtc aattcaatgc agatactatt gataaaagta  20460
tacaagatgt tattaaaaat aacttaggac aaataagagg tgtgacacct cgtaatgatt  20520
tactaaatgt taatgtatca gcagaaataa atataaatta tcgtttatct gaattaggtt  20580
ttattactaa taaaaatgat atggattgga ttaagaaaaa ctatgacttg tattctaaat  20640
taatagccgg tgcgattcat ggtaagccta taggtggttt ggtagctggt aatgttaaaa  20700
```

-continued

```
catcagctaa aaacaaaaaa aatccaccag tgccagcagg ttatacactc gataagaata  20760
atgtccctta taaaaaagaa caaggcaatt acacagtagc taatgttaaa ggtaataatg  20820
taagagacgg ttattcaact aattcaagaa ttacaggggt attacccaac aacacaacaa  20880
ttacgtatga cggtgcatat tgtattaatg gttatagatg gattacttat attgctaata  20940
gtggacaacg tcgttatata gcgacaggag aggtagacaa ggcaggtaat agaataagta  21000
gttttggtaa gtttagcacg atttagtatt tacttagaat aaaaattttg ctacattaat  21060
tatagggaat cttacagtta ttaaataact atttggatgg atgttaatat tcctatacac  21120
tttttaacat ttctctcaag atttaaatgt agataacagg caggtacttc ggtacttgcc  21180
tattttttta tgttatagct agccttcggg ctagtttttt gttatgatgt gttacacatg  21240
catcaactat ttacatctat ccttgttcac ccaagcatgt cactggatgt tttttcttgc  21300
gatagagagc atagttttca tactactccc cgtagtatat atgactttag cattcccgta  21360
taacagttta cggggtgctt ttatgttata attgctttta tatagtagga gtgaactata  21420
tagccgggca gaggccatgt atctgactgt tggtcccaca ggagacatct tccttgtcat  21480
cactcgatac atatatctta acaacataga aatgttacat tcgctataac cgtatcttaa  21540
tcgatacggt tatatttatt cccctacaac caacaaaacc acagatccta ttaatttagg  21600
attgtggtta ttttttgcgt ttttttgggg caaaaaaagg gcagattatt tgaaaaaggg  21660
caaacgcttg tggaaaagct aaaaggttaa aaatgacaaa aaccttgata caacagtgtt  21720
tttggacgct cgtgtacgtt agagaatgac cggtttacca tcatacaagg gtgggattaa  21780
cttgtgttaa aaagccttta atatcagttg ttacaaagga tttgtagcgt ctttaaaaat  21840
aaaaaagggc agaaaaaggg cagatacctt ttagtacaca agtttttcta atttttgctc  21900
taactctctg tccatttttct ctgttacatg tgtatacacc tttatagtcg ttttttcatc  21960
tgtatgtcct actcttttca taattgcttt taacgatata ttcatttccg ccaataaact  22020
tatgtgtgta tgccttagtg tgtgagtagt aacttttttta tttatattta atgattctgc  22080
agctgaggac aatcgtttgt ttatcctact gccttgcata ggatttcctt ggcaagttgt  22140
gaatataaac cctctatcaa catagcttgg ttcccattgt tgcatctttt tattttctaa  22200
cattattttt ttcaatacat ttgctatcct tgaattgatg gcgatttttc ttcttgaacc  22260
tgcggtctta gtagtatctt tgtgaccaaa tccagcatta catttgattc tgtgaatagt  22320
gccattaata gcgatcgttt tatttttgag gtcaacatct ttaacttgga gagctaataa  22380
ctcacctatg cgcatacctg ttaaagcttg aacttctaca gccccagcaa ctaaaatacg  22440
agctctatac tgcatgttat tatcgttcag tataaaatcg cgtatctgta ttacctgttc  22500
catctctaaa tagttataca ttttcgcttc ttctttttct atatcttcta tcgtcttact  22560
cttctttggt agtgtgacgc tatttaatat gtgttcgttt ggataattgt aaaatttaac  22620
ggcgtattta atagcttctt tcatatgtcc aagttgacgc tttacctgat ttgcagaata  22680
tacgtttgat aatttgttaa taaatgtttg catgtacttt gtatcaattt tgtttaaaag  22740
taaattttga gaactgttct ttttgatgtt tttgattctt gttttcaaat tatcaagcgt  22800
cgttacttta aagccagatg tttttatatg atattcaagc cattcatcta ataacgcgtg  22860
aaaagtcaaa gtttttaatt cgcttgacga cttgttgttt agtttttctt ttattttttc  22920
ttctaaacga aacattgcct ctttttgcga ttgctttgta ttcttattca agacaacact  22980
tacacgtttc catttatctg tatacggatc tttgtatttc tcgtagtatc tatacttcgt  23040
ttcattgttc ttatttttaa atttttcaaa ccacatttta catccctcct caaaattggc  23100
```

-continued

```
aaaaaataat aagggtaggc gggctaccca tgaaaattgt ataaaaaaag acgcctgtat  23160
aaaatacaga cgccacttat aattataaga ttacatggtt aattaccaaa aatggtaacg  23220
aatatatacg tgttttaaag gataaacctt taatatatta aaattatatc atcttatatc  23280
agggatctgc aatatattat tattaattct atttatcagt aacataatat ccgaagaatc  23340
tattactgga tttttaattt tttggggtaa aacttttctt atgcgaaact tactaatcgg  23400
ctggaaagaa tttatgcaag cgtaactatt accttttaat ttttttacct tatcaattgc  23460
tgatactatg ttattaatgt ttctgtcaat tttatttaat ttattttcaa tttctaaact  23520
atcagatata aattcaataa aataatcttt agtgatgaat tctgtgttgt ttttttggta  23580
ttttttatcg aaaacttctt ttaatatagc tgaattattt tgcgcgctaa ttaaatttaa  23640
aaacaatctt aaataatact cccatttcaa atcaaaattc atctttaaat actttttgtt  23700
ttctttagag gataagggaa taacatttac tatatcctcc gtattagaat catttttatt  23760
catcactatt gcaaagtgtg aattagaaaa ttctttatta acgtttatac cgaaatctac  23820
aaaaactatt tctccttgtt taaactttgg ataaaaacct ttatggtttt tttcaccttc  23880
aaatctcttg agtaaatagt gaatatctga atctaacttt ttaaattttg gatttccaga  23940
agtttttaat ttattaatgc gtttttctat attatgcgtc atcatttctc ctttattctc  24000
gctcacactc tcaccaccat tcaacgtcta cacttgtagg cgttttttga ttagtaaaat  24060
cataatgaat cttctttggt taacttatcg ccatctattt tttgtgaaat aaattccaag  24120
tatttacgcg cattatgtga cgataaatct ttaggtaact cataagtgaa tggttgatta  24180
ccactagtta aaacttcata tactatagtt tcttttttta ttttgcaatt agttattttc  24240
attataaact ccttttaaac actgctgaaa tagacgtctt tttcaaataa gcatgattaa  24300
tactttaatt ctttaatcca catatattta aaagtgaggt agtaggtaat aaatataaga  24360
cttaaagtta agattgcttt tttcatgtca atttctcctt tgtttatatt tatattaaag  24420
cgctaaatat acgttattaa tcacaataca actttgccca ttactttaat atcactaaac  24480
gaagcgactt tgatatcatc atacttcgga tttagagata ccaaattaat atagtcttcg  24540
catatatcta cacgcttgat aagacttact ccatctaata caacgagtgc aattgtacca  24600
tctttaatag aatcttcttt cttaataaaa gcgtatgttc cttgttttaa cataggttcc  24660
attgaatcac cattaactaa aatacaaaaa tcagcatttg atggcgtttc gtcttcttta  24720
aaaaatactt cttcatgcaa tatgtcatca tataattctt ctcctatgcc agcaccagtt  24780
gcaccacatg caatatacga tactagttta gactctttat attcatctat agaagtgact  24840
ttattctgtt catctaattg ctcatttgca tagttaagta cgttttcttg gcggggaggt  24900
gtgagttgag aaaatatgtt attgattttt gacattatcg tttcatcttg acgttcttcg  24960
tcaggaactc gataagaatc tacatcatac cccataagcc acgcttcacc gacatttaaa  25020
gttttagata ataagaataa tttatgttgg tctggagaag accttccatt aacatactgg  25080
gataagtgac tttttgacat tttaatattc aattcttttt gaaagggttt cgacttttct  25140
agaatatcta cttgacgcaa gttcctatct ttcataattt gttttaatct ttcagaagtg  25200
ttttgcattg gtaatgcctc cttgaaattc attatatagg aagggaaata aaaatcaata  25260
caaaagttca actttttaa ctttttgtgt tgacattgtt caaaattggg gttatagtta  25320
ttatagttca aatgtttgaa cttaggaggt gattatttga atactaatac aacttttgat  25380
ttttcgttat tgaacggtaa gatagtcgaa gtgtactcga cacaatttaa ctttgctata  25440
```

-continued

```
gctttaggtg tatcagaaag aactttgtct ttgaagttga acaacaaagt accatggaaa  25500
acaacagaca ttattaaagc ttgtaagtta ttgggaatac ctataaaaga tgttcacaaa  25560
tattttttta aacagaaagt tcaaatgttt gaacttaata agtaaaggag gcataacaca  25620
tgcaagaacg agaaaaggtt aataaaagta acacatcttc aaatgaagca tcaaaacctt  25680
ttaggacaaa ttgaagctta cgacaaaacg cttaaagaaa taaagtacac tcgagacctt  25740
tacaacaaac acctaagcat gaacaacgaa gacgcattcg ctggtttgga aatggtagag  25800
gatgaaatta ctaaaaagct acgaagtgct atcaaagagt tccaaaaagt agtgaaagcg  25860
ttagacaagc ttaacggtgt tgaaagcgat aacaaagtta ctgatttaac agagtggcgg  25920
aaagtgaatc agtaacattc acttcttaat ataaccacgc ttatcaacat ccacattgag  25980
cagatgtgag cgagagctgg cgatgatatg agccgcgttt aaatacattc gatagtcatt  26040
gcgataaccg tctgctgaat gtgggtgttg aggaaaaagg aggatactca aatgcaagca  26100
ttacaaacat ttaattttaa agagctacca gtaagaacag tagaaattga aaacgaacct  26160
tattttgtag gaaaagatat tgctgagatt ttaggatatg caagatcaaa caatgccatt  26220
agaaatcatg ttgatagcga ggacaagctg acgcaccaat ttagtgcatc aggtcaaaac  26280
agaaatatga tcattatcaa cgaatcagga ttatacagtc taatcttcga tgcttctaaa  26340
caaagcaaaa acgaaaaaat tagagaaacc gctagaaaat tcaaacgctg ggtaacatca  26400
gatgtcctac cagctattcg caaacacggt atatacgcaa cagacaatgt aattgaacaa  26460
acattaaaag atccagacta catcattaca gtgttgactg agtataagaa agaaaaagag  26520
caaaacttac ttttacaaca gcaagtagaa gttaacaaac caaaagtatt attcgctgac  26580
tcggtagctg gtagtgataa ttcaatactt gttggagaac tagcgaaaat acttaaacaa  26640
aacggtgttg atataggaca aaacagattg ttcaaatggt taagaaataa tggatatctc  26700
attaaaaaga gtggagaaag ttataactta ccaactcaaa agagtatgga tctaaaaatc  26760
ttggatatca aaaaacgaat aattaataat ccagatggtt caagtaaagt atcacgtaca  26820
ccaaaagtaa caggcaaagg acaacaatac tttgttaata agtttttagg agaaaaacaa  26880
acatcttaaa aggaggaaca caatggaaca aatcacatta accaaagaag agttgaaaga  26940
aattatagca aaagaagtta gagaggctat aaatggcaag aaaccaatca gttcaggttc  27000
aattttcagt aaagtaagaa tcaataatga cgatttagaa gaaatcaata aaaaactcaa  27060
tttcgcaaaa gatttgtcgc taggaagatt gaggaagctc aatcatccga ttccgctaaa  27120
aaagtatcag catggcttcg aatcaattca tcaaaaagct tatgtacaag atgttcatga  27180
ccatattaga aaattaacat tatcaatttt tggagtgaca cttaattcag acttgagtga  27240
aagtgaatac aacctagcag caaaagttta tcgagaaatc aaaaactatt atttatacat  27300
ctatgaaaag agagtttcag aattaactat cgatgatttc gaataaagga ggaacaacaa  27360
atgttacaaa aatttagaat tgcgaaagaa aaaaataaat taaaactcaa attactcaag  27420
catgctagtt actgtttaga aagaaacaac aaccctgaac tgttgcgagc agttgcagag  27480
ttgttgaaaa aggttagcta aattcaacgg taaggatttg ccctgcctcc acacttagag  27540
tttgagatcc aacaaacaca taagttttag tagggtctag aaaaaatgtt tcgatttcct  27600
cttttgtaac agtttcaatt ccttcatatc ctggaaaaac aattttcttt aaatccgaaa  27660
catgtttttt tgaaccatcc tttaaagtaa ctagaagttt catacttatc acctccttag  27720
gttgataaca acattataca cgaaaggagc ataaacaata tgcaagcatt acaaacaaat  27780
tcgaacatcg gagaaatgtt caatattcaa gaaaaagaaa atggagaaat cgcaatcagc  27840
```

-continued

```
ggtcgagaac ttcatcaagc attagaagtt aagacagcat ataaagattg gtttccaaga  27900
atgcttaaat acggatttga agaaaataca gattacacag ctatcgctca aaaaagagca  27960
acagctcaag gcaatatgac tcactatatt gaccacgcac tcacactaga cactgcaaaa  28020
gaaatcgcaa tgattcaacg tagtgaacct ggcaaacgtg caagacaata tttcatccaa  28080
gttgaaaaag catggaacag cccagaaatg attatgcaac gtgctttaaa aattgctaac  28140
aacacaatca atcaattaga aacaaagatt gcacgtgaca aaccaaaaat tgtatttgca  28200
gatgcagtag ctactactaa gacatcaatt ttagttggag agttagcaaa gatcattaaa  28260
caaaacggta taaacatcgg gcaacgcaga ttgtttgagt ggttacgtca aaacggattc  28320
cttattaaac gcaagggtgt ggattataac atgcctacac agtattcaat ggaacgtgag  28380
ttattcgaaa ttaaagaaac atcaatcaca cattcggacg gtcacacatc aattagtaag  28440
acgccaaaag taacaggtaa aggacaacaa tactttgtta acaagttttt aggagaaaaa  28500
caaacaactt aataggagga attacaaatg aacgcactat acaaaacaac cctcctcatc  28560
acaatggcag ttgtgacgtg gaaggtttgg aagattgaga agcacactag aaaacctgtg  28620
attagtagca gggcgttgag tgactatcta aacaacaaat ctttaaccat accgaaagat  28680
gctgaaaatt ctactgaatc tgctcgtcgc cttttgaagt tcgccgaaca aactattagc  28740
aaataacaac attatacacg aaaggaaaga tagaaatgcc aaaaatcata gtaccaccaa  28800
caccagaaaa cacatataga ggcgaagaaa aatttgtgaa aaagttatac gcaacaccta  28860
cacaaatcca tcaattgttt ggagtatgta gaagtacagt atacaactgg ttgaaatatt  28920
accgcaaaga taatttaggt gtagaaaatt tatacattga ttattcacca acaggcactc  28980
tgattaatat ttctaaattg gaagagtatt tgatcagaaa gcataaaaaa tggtattagg  29040
aggatattaa atgagcaaca tttataaaag ctacctagta gcagtattat gcttcacagt  29100
cttagcgatt gtacttatgc cgtttctata cttcactaca gcatggtcaa ttgcgggatt  29160
cgcaagtatc gcaacattca tgtactacaa agaatgcttt ttcaaagaat aaaaaaactg  29220
ctacttgttg gagcaagtaa cagtatcaaa cacttaagaa aaaattcatg ttcaatataa  29280
aacgaaaaac ggaggaagtc aagatgtatt acgaaatagg cgaaatcata cgcaaaaata  29340
ttcatgttaa cggattcgat tttaagctat tcattttaaa aggtcatatg ggcatatcaa  29400
tacaagttaa agatatgaac aacgtaccaa ttaaacatgc ttatgtcgta gatgagaatg  29460
acttagatat ggcatcagac ttatttaacc aagcaataga tgaatggatt gaagagaaca  29520
cagacgaaca ggacagacta attaacttag tcatgaaatg gtaggaggtc gctatgaagc  29580
agactgtaac ttatatcatt cgtcataggg atatgccaat ttatataact aacaaaccaa  29640
ctgataacaa ttcagatatt agttactcca caaatagaaa tagagctagg gagtttaacg  29700
gtatggaaga agcgagtatc aatatggatt atcacaaagc aatcaagaaa acagtgacag  29760
aaactattga gtacgaggag gtagaacatg actgaggaaa aacaagaacc acaagaaaaa  29820
gtaagcatac tcaaaaaact aaagataaat aatatcgctg agaaaaataa aaggaaattc  29880
tataaatttg cagtatacgg aaaaattggc tcaggaaaaa ccacgtttgc tacaagagat  29940
aaagacgctt tcgtcattga cattaacgaa ggtggaacaa cggttactga cgaaggatca  30000
gacgtagaaa tcgagaacta tcaacacttt gtttatgttg taaatttttt acctcaaatt  30060
ttacaggaga tgagagaaaa cggacaagaa atcaatgttg tagttattga aactattcaa  30120
aaacttagag atatgacatt gaatgatgtg atgaaaaata agtctaaaaa accaacgttt  30180
```

-continued

```
aatgattggg gagaagttgc tgaacgaatt gtcagtatgt acagattaat aggaaaactt  30240
caagaagaat acaaattcca ctttgttatt acaggtcatg aaggtatcaa caaagataaa  30300
gatgatgaag gtagcactat caaccctact atcactattg aagcgcaaga acaaattaaa  30360
aaagctatta cttctcaaag tgatgtgtta gctagggcaa tgattgaaga atttgatgat  30420
aacggagaaa agaaagctag atatattcta aacgctgaac cttctaatac gtttgaaaca  30480
aagattagac attcaccttc aataacaatt aacaataaga aatttgcaaa tcctagcatt  30540
acggacgtag tagaagcaat tagaaatgga aactaaaaat taattaaaag gacggtattt  30600
aattatgaaa atcacaggac aagcgcaatt tactaaagaa acaaatcaag aaaagtttta  30660
taacggctca gcagggtttc aagctggaga attcacagtg aaagttaaaa atattgaatt  30720
caatgataga gaaaatagat atttcacaat cgtatttgaa aatgatgaag gcaaacaata  30780
taaacataat caatttgtac cgccgtataa atatgatttc caagaaaaac aattgattga  30840
attagttact cgattaggta ttaagttaaa tcttcctagc ttagattttg ataccaatga  30900
tcttattggt aagttttgtc acttggtatt gaaatggaaa ttcaatgaag atgaaggtaa  30960
gtattttacg gatttttcat ttattaaacc ttacaaaaag ggcgatgatg ttgttaacaa  31020
acctattccg aagacagata agcaaaaagc tgaagaaaat aacggggcac aacaacaaac  31080
atcaatgtct caacaaagca atccatttga aagcagtggc caatttggat atgacgacca  31140
agatttagcg ttttaaggtg tggtttaaat gcaatacatt acaagatacc agaaagataa  31200
cgacggtact tattccgtcg ttgctactgg tgttgaactt gaacaaagtc acattgactt  31260
actagaaaac ggatatccac taaaagcaga agtagaggtt ccggacaata aaaaactatc  31320
tatagaacaa cgcaaaaaaa tattcgcaat gtgtagagat atagaacttc actggggcga  31380
accagtagaa tcaactagaa aattattaca aacagaattg gaaattatga aaggttatga  31440
agaaatcagt ctgcgcgact gttctatgaa agttgcaagg gagttaatag aactgattat  31500
agcgtttatg tttcatcatc aaatacctat gagtgtagaa acgagtaagt tgttaagcga  31560
agataaagcg ttattatatt gggctacaat caaccgcaac tgtgtaatat gcggaaagcc  31620
tcacgcagac ctggcacatt atgaagcagt cggcagaggc atgaacagaa acaaaatgaa  31680
ccactatgac aaacatgtat tagcgttatg tcgcgaacat cacaacgagc aacatgcgat  31740
tggcgttaag tcgtttgatg ataaatacca cttgcatgac tcgtggataa aagttgatga  31800
gaggctcaat aaaatgttga aaggagagaa aaaggaatga atagactaag aataataaaa  31860
atagcactcc taatcgtcat cttggcggaa gagattagaa atgctatgca tgctgtaaaa  31920
gtggagaaaa ttttaaaatc tccgtttagt taatacaggt ttttacaaaa gctttaccat  31980
aggcggacaa actaattgag ccttttttga tgtctattac ccaggggctg taatgtaact  32040
ttaatacttc aaattcaatg ccagaaagtt tacttattgt ttctaggttg tgtcctgact  32100
ttaacattct tttaacaaat tctaatcccg aaacaaatct ttgtttttct ataatcttat  32160
taaagtgatt taaaaactga ggagcataaa acttattata aattcctttt tttgttaagt  32220
aagacatgtc aaaagtttca tttaaaaccc ctaaccttac taggttatta attgaaattt  32280
cggttgattc tatatctaac ggagagtctt ttattaacgt gtccgatata ttcataccgt  32340
cattctttgg gtttaaaacc gctctatatt taacggcagg atgtacttcg tgattcttta  32400
aatgttttaa aagaatagca tcatttgggg ataattgttt aattatttca acaaatgaat  32460
ggtgggttaa tgagtttttt ctgtcatcca tagatgatgc tattagtttt gcgaacatat  32520
tacttaaagt tttttcacta atgtaaaact ttgaagcttc tagagcagga cctagaagag  32580
```

-continued aaaattgtgg ttcttgtaaa ttatttttag gtacagaaga tatttctttt ttaaattgtt 32640
ctttgaattt ttcaaattct acttctcttt gataaataac tttatccaca taaaggtgga 32700
atttcccaaa gacaagttcc caagttttag agaatgtttc tacaggccct tttgatgcgc 32760
cttcaataat tttatcaata cctttaccta aaataggatc cataattatt cacccccaat 32820
ctaacgcaat agcgataata aaattatacc agaaaggaga atcaacatga ctgaccaacc 32880
aagttactac tcaataatta cagcaaatgt cagatacgat aaccgactta ctgacagcga 32940
aaagttactt tttgcagaaa taacatcttt aagtaacaaa tacggatact gcacagcaag 33000
taatggttac tttgcaactt tatacaacgt tgttaaggaa actatatctc gtagaatttc 33060
gaaccttacc aactttggtt atctaaaaat cgaaattatc aaagaaggta atgaagttaa 33120
acaaaggaag atgtacccct tgacgcaaac gtcaatacct attgacgcaa aaatcaatac 33180
ccctattgat aattctgtca atacccctat tgacgcaaat gtcaaagaga atattacaag 33240
tattaataat acaagtaata acaatataaa tagaatagat atattgtcgg gcaacccgac 33300
agcatcttct ataccctata aagaaattat cgattactta aacaaaaaag cgggcaagca 33360
ttttaaacac aatacagcta aacaaaaaga ttttattaaa gcaagatgga atcaagattt 33420
taggttggag gattttaaaa aggtgattga tatcaaaaca gctgagtggc taaacacgga 33480
tagcgataaa taccttagac cagaaacact ttttggcagt aaatttgagg ggtacctcaa 33540
tcaaaaaata caaccaactg gcacggatca attggaacgc atgaagtacg acgaaagtta 33600
ttgggattag gggatattta tgaaaccact attcagcgaa aagataaacg aaagcttgaa 33660
aaaatatcaa cctactcatg tcgaaaaagg attgaaatgt gagagatgtg gaagtgaata 33720
cgacttatat aagtttgctc ctactaaaaa acacccgaat ggttacgagt ataaagacgg 33780
ttgcaaatgt gaaatctatg aggaatataa gcgaaacaag caacggaaga taaacaacat 33840
attcaatcaa tcaaacgtta atccgtcttt aagagatgca acagtcaaaa actacaagcc 33900
acaaaatgaa aaacaagtac acgctaaaca aacagcaata gagtacgtac aaggcttctc 33960
tacaaaagaa ccaaaatcat taatattgca aggttcatac ggaactggta aaagccacct 34020
agcatacgct atcgcaaaag cagtcaaagc taaagggcat acggttgctt ttatgcacat 34080
accaatgttg atggatcgta tcaaagcgac atacaacaaa aatgcagtag agactacaga 34140
cgagctagtc agattgctaa gtgatattga tttacttgta ctagatgata tgggtgtaga 34200
aaacacagag cacactttaa ataaactttt cagcattgtt gataacagag taggtaaaaa 34260
caacatcttt acaactaact ttagtgataa agaactaaat caaaatatga actggcaacg 34320
tataaattcg agaatgaaaa aaagagcaag aaaagtaaga gtaatcggag acgatttcag 34380
ggagcgagat gcatggtaac caaagaattt ttaaaaacta aacttgagtg ttcagatatg 34440
tacgctcaga aactcataga tgaggcacag ggcgatgaaa ataggttgta cgacctattt 34500
atccaaaaac ttgcagaacg tcatacacgc cccgctatcg tcgaatatta aggagtgtta 34560
aaaatgccga aagaaaaata ttacttatac cgagaagatg gcacagaaga tattaaggtc 34620
atcaagtata aagacaacgt aaatgaggtt tattcgctca caggagccca tttcagcgac 34680
gaaaagaaaa ttatgactga tagtgaccta aaacgattca aaggcgctca cgggcttcta 34740
tatgagcaag aattaggttt acaagcaacg atatttgata tttagaggtg gacgatgagt 34800
aaatacaacg ctaagaaagt tgagtacaaa ggaattgtat ttgatagcaa agtagagtgt 34860
gaatattacc aatatttaga aagtaatatg aatggcacta attatgatca tatcgaaata 34920

-continued

```
caaccgaaat tcgaattatt accaaaacta gataaacaac gaaagattga atatattgca  34980
gacttcgcgt tatatctcga tggcaaactg attgaagtta tcgacattaa aggtatgcca  35040
accgaagtag caaaacttaa agctaagatt ttcagacata aatacagaaa cataaaactc  35100
aattggatat gtaaagcgcc taagtataca ggtaaaacat ggattacgta cgaggaatta  35160
attaaagcaa gacgagaacg caaaagagaa atgaagtgat ctaatgcaac aacaagcata  35220
tataaatgca acgattgata taaggatacc tacagaagtt gaatatcagc attttgatga  35280
tgtggataaa gaaaaagaag cgctggcaga ttacttatat aacaatcctg acgaaatact  35340
agagtatgac aatttaaaaa ttagaaacgt aaatgtagag gtggaataaa tgggcagtgt  35400
tgtaatcatt aataataaac catataaatt taacaatttt gaaaaaagaa ataatggcaa  35460
agcgtgggat aaatgctgga attgtttcta aacgtgttag aggttgttgg gagttttcag  35520
aagctttaga cgcgccttat ggcatgcacc taaaagaata tagagaaatg aaacaaatgg  35580
aaaagattaa acaagcgaga ctcgaacgtg aattggaaag agagcgaaag aaagaggctg  35640
agctacgtaa gaagaagcca catttgttta atgtacctca aaaacattca cgtgatccgt  35700
actggttcga tgtcacttat aaccaaatgt tcaagaaatg gagtgaagca taatgagcat  35760
aatcagtaac agaaaagtag atatgaacaa aacgcaagac aacgttaagc aacctgcgca  35820
ttacacatac ggcgacattg aaattataga ttttattgaa caagttacgg cacagtaccc  35880
accacaatta gcattcgcaa taggtaatgc aattaaatac ttgtctagag caccgttaaa  35940
gaatggtcat gaggatttag caaaggcgaa gttttacgtc gatagagtat ttgacttgtg  36000
ggagtgatga ccatgacaga tagcggacgt aaagaatact taaaacattt tttcggctct  36060
aagagatatc tgtatcagga taacgaacga gtggcacata tccatgtagt aaatggcact  36120
tattactttc acggtcatat cgtgccaggt tggcaaggtg tgaaaaagac atttgataca  36180
gcggaagagc ttgaaacata tataaagcaa agtgatttgg aatatgagga acagaagcaa  36240
ctaactttat tttaaaaggg cggaaacaat gaaaatcaaa attgaaaaag aaatgaattt  36300
acctgaactt atccaatggg cttgggataa ccccaagtta tcaggtaata aaagattcta  36360
ttcaaatgat gttgagcgca actgttttgt gacttttcat gttgatagca tcttatgtaa  36420
tgtgactgga tatgtatcaa ttaacgataa atttactgtt caagaggaga tataacaatg  36480
aaaatcaaag ttaaaaaaga aatgagatta gatgaattaa ttaaatgggc gcgagaaaat  36540
ccggatctat cacaaggaaa aatatttttt tcaacaggat ttagtgatgg attcgttcgt  36600
tttcatccaa atacaaataa gtgttcgacg tcaagtttta ttccaattga tatccccttc  36660
atagttgata ttgaaaaaga agtaacggaa gagactaagg ttgataggtt gattgaatta  36720
ttcgagattc aagaaggaga ctataactct acactatatg agaacactag tataaaagaa  36780
tgtttatatg gcagatgtgt gcctaccaaa gcattctaca tcttaaacga tgacctaact  36840
atgacgttaa tctggaaaga tggggagttg ctagtatgat gttgaaattt aaagcttggg  36900
ataaagataa aaaagttatg agtattattg acgaaatcga ttttaatagt gggtacattt  36960
tgatttcaac aggttataaa agtttcaatg aagtaaaact attacaatac acaggattta  37020
aagatgtgca cggtgtggag atttatgaag gggatattgt tcaagattgt tattcgagag  37080
aagtaagttt tatcgagttt aaagaaggag ccttttatat aacttttagc aatgtaactg  37140
aattactaag tgaaaatgac gatattattg aaattgttgg aaatattttt gaaaatgaga  37200
tgctattgga ggttatgaga tgacgttcac cttatcagat gaacaatata aaaatctttg  37260
tactaactct aacaagttat tagataaact tcacaaagca ttaaaagatc gtgaagagta  37320
```

-continued caagaagcaa cgagatgagc ttattgggga tatagcgaag ttacgagatt gtaacaaaga 37380
tctagagaag aaagcaagcg catgggatag gtattgcaag agcgttgaaa aagatttaat 37440
aaacgaattc ggtaacgatg atgaaagagt taaattcgga atggaattaa acaataaaat 37500
ttttatggag gatgacacaa atgaataatc gcgaaaaaat cgaacagtcc gttattagtg 37560
ctagtgcgta taacggtaat gacacagagg ggttgctaaa agagattgag gacgtgtata 37620
agaaagcgca agcgtttgat gaaatacttg agggaatgac aaatgctatt caacattcag 37680
ttaaagaagg tattgaactt gatgaagcag tagggattat ggcaggtcaa gttgtctata 37740
aatatgagga ggaataggaa aatgactaac acattacaag taaaactatt atcaaaaaat 37800
gctagaatgc ccgaacgaaa tcataagacg gatgcaggtt atgacatatt ctcagctgaa 37860
actgtcgtac tcgaaccaca agaaaaagca gtgatcaaaa cagatgtagc tgtgagtata 37920
ccagagggct atgtcggact attaactagt cgtagtggtg taagtagtaa aacgtattta 37980
gtgattgaaa caggcaagat agacgcggga tatcatggca atttagggat taatatcaag 38040
aatgatgaag aacgtgatgg aataccottt ttatatgatg atatagacgc tgaattagaa 38100
gatggattaa taagcatttt agatataaaa ggtaactatg tacaagatgg aagaggcata 38160
agaagagttt accaaatcaa caaaggcgat aaactagctc aattggttat cgtgcctata 38220
tggacaccgg aactaaagca agtggaggaa ttcgaaagtg tttcagaacg tggagcaaaa 38280
ggcttcggaa gtagcggagt gtaaagacat cttagatcga gttaaggagg ttttggggaa 38340
gtgacgcaat acttagtcac aacattcaaa gattcaacag gacgaccaca tgaacatatt 38400
actgtggcta gagataatca gacgtttaca gttattgagg cagagagtaa agaagaagcg 38460
aaagagaagt acgaggcaca agttaaaaga gatgcagtta ttaaagtggg tcagttgtat 38520
gaaaatataa gggagtgtgg gaaatgacgg atgttaaaat taaaactatt tcaggtggag 38580
tttattttgt aaaaacagct gaacctttttg aaaaatatgt tgaaagaatg acgagtttta 38640
atggttatat ttacgcaagt actataatca agaaaccaac gtatattaaa acagatacga 38700
ttgaatcaat cacacttatt gaggagcatg ggaaatgaat cagctgagaa ttttattaca 38760
tgacggtagt agtttgatat tacatgaaga tgaattattt aacgaaatag tatttgtttt 38820
ggacaatttt agaaatgatg atgactattt aacgatagaa aaagattatg gcagagaact 38880
tgtattgaac aaaggttata tagttgggat caatgttgag gaggcagatg atgattaaca 38940
tacctaaaat gaaattcccg aaaaagtaca ctgaaataat caaaaaatat aaaaataaag 39000
cacctgaaga aaaggctaag attgaagatg attttattaa agaaattaaa gataaagaca 39060
gtgaatttta cagtcctacg atggctaata tgaatgaata tgaattaagg gctatgttaa 39120
gaatgatgcc tagtttaatt gatactggag atgacaatga tgattaaaaa acttaaaaat 39180
atggatgggt tcgacatctt tattgttgga atactgtcat tattcggtat attcgcattg 39240
ctacttgtta tcacattgcc tatctataca gtggctagtt accaacacaa agaattacat 39300
caaggaacta ttacagataa atataacaag agacaagata aagaagacaa gttctatatt 39360
gtattagaca acaaacaagt cattgaaaat tccgacttat tattcaaaaa gaaatttgat 39420
agcgcagata tacaagctag gttaaaagta ggcgataagg tagaagttaa aacaatcggt 39480
tatagaatac actttttaaa tttatatccg gtcttatacg aagtaaagaa ggtagataaa 39540
caatgattaa acaaatacta agactattat tcttactagc aatgtatgag ttaggtaagt 39600
atgtaactga gcaagtgtat attatgatga cggctaatga tgatgtagag gcgccgagtg 39660

-continued

```
attacgtctt tcgagcggag gtgagtgaat aatgagaata tttatttatg atttgatcgt  39720
tttgctgttt gctttcttaa tatccatata tattattgat gatggagtga taataaatgc  39780
attaggaatt tttggtatgt ataaaattat agattccttt tcagaaaata ttataaagag  39840
gtagataaaa atgaacgagc aaataatagg aagcatatat actttagcag gaggtgttgt  39900
gctttattca gttaaagaga tttttaggta ttttacagat tctaacttac aacgtaaaaa  39960
aatcaattta gaacaaatat atccgatata tttagattgt tttaaaaagg ctaaaaagat  40020
gattggagct tatattattc caacagaaca gcatgaattt ttagattttt ttgatattga  40080
agtctttaat aatttagata agcaaagtaa aaaagcgtat gaaaatgtta ttggatttag  40140
acaaatgatt aatttatcaa atagagttaa ggcaatggaa gattttaaga tgagtttcaa  40200
caatgaattt agtacaaatc agattttttt taatccttct tttgttatgg aaacaattgc  40260
tattataaat gaatatcaaa aagatatatc ttatttaaaa aatataatta ataaaatgaa  40320
tgaaaataga gcttataatc atattgatag ttttatcact tcagagtacc gacgaaaaat  40380
aaacgattat aatctttatc ttgataaatt tgaagaacag tttagtcaaa agtttaaaat  40440
aaacagaact tcgataaaag aaagaattat tattaattta aacaagagga gatttaaatg  40500
atgtggatta ctatgactat tgtatttgct atattgctat tagtttgtat cagtattaat  40560
agtgatcgtg caagagagat acaagcactt agatatatga atgattatct acttgatgaa  40620
gtagttaaaa ctaaagggta caacgggtta gaagaataca ggattgaatt gaagcgaatg  40680
aataacgata ttaaaaagta atttatatta tcggaggtat tgcattgaat gataaagatt  40740
gagaaacacg atatcaaaaa gcttgaagaa tacattcagc acatcgataa ctatcgaaga  40800
gagttgaaga tgcgagaata tgaattactt gaaagtcatg aaccagataa tgcgggagct  40860
ggcaaaagta atttgccggg taacccgatt gaacgatgtg caataaagaa gtttagtgat  40920
aacaggtaca atacattaag aaatatagtt aacggtgtag atagattgat aggtgaaagt  40980
gatgaggata cgcttgagtt attaaggttt agatattggg attgtcctat tggttgttat  41040
gaatgggaag atatagcaca ttactttggt acaagtaaga caagtatatt acgtagaagg  41100
aatgcactga tcgataagtt agcaaagtat attggttatg tgtagcggac ttttacccta  41160
tgtaagtccg cattaaaaca gtttattatg ttagtatcag attaatattt aaagttatta  41220
aatgctaata cgacgcatga acaagaggcg catcactatg tgatgtgtct ttttatttat  41280
gaggtatgaa catgttcaaa ctaattgtaa atacattact acacatcaag tatagatgag  41340
tcttgatact acttaagtta tataaggtga aacattatga tgactaaaga cgaacgtata  41400
cgattctata agtctaaaga atggcaaata acaagaaaaa gagtgctaga aagagataat  41460
tatgaatgtc aacaatgtaa gagagacggc aagttaacga catatgacaa aagcaagcgt  41520
aagtcgttgg atgtagatca tatattatcg ctagaacatc atccggagtt tgctcatgac  41580
ttaaacaatt tagaaacact gtgtattaaa tgtcacaaca aaaaagaaaa gagatttata  41640
aaaaaagaaa ataaatggaa agacgaaaaa tggtaaatac ccccgggtca aaaaaatcaa  41700
aagcgatc                                                           41708
```

<210> SEQ ID NO 19
<211> LENGTH: 43576
<212> TYPE: DNA
<213> ORGANISM: Staphylococcus bacteriophage

<400> SEQUENCE: 19

```
tctccataaa aatatgcttg gaaaccttga tttaatgggg ttttaatcta gcaagtgtca     60
```

-continued

```
aatatgtgtc aagaaaataa ttttctgaca cgttgacctt gctctttttt atgttcatca    120
agtaagtgag agtaggtgtc taaagttata gatatattat aatggcctaa tcttttgcta    180
atatattcaa taggtatacc tttagaaagt aggaaagatg tatgcgtgtg tcttaatgaa    240
taaggtgtta ttgtagtatc atttagtcct atttgactct tagcatggtt aaatgacttt    300
ttaacggcat tatgactcaa tttaaacaac ttattatctg tacgttttgg taattttgat    360
aatttagctt taatatgttg tatatccttt tttggtacct ccacaagtct gtccgcgtta    420
actgtttttg ttccacgaag atgtattgta ccctcttttt cgtttagatc gataggcaac    480
atattaatta catcgctgta tcttgcacca gtgatagcta ggatgaataa aaaaatataa    540
ctcgattcgt ctctagattt aaagtattct atcaattgca agtattgttc tatggtgatg    600
aatttagagt gttcgtcttt tgattttttt gtaccacgaa tatctatttg atagctaggg    660
tctttcttta aatagccctc atatactgca tctctgaagc attgtgataa acaactgttt    720
aatttacgaa ccgtttcatt agtacgacct cgaccgaatt cgttcaaaaa cttttgatac    780
tccgaacgtt tgatgttttt tattaaaaaa tcactcccga aatattcgtt aaataatttt    840
aatgaacgtt gataccaata gaattgttgt gaagcgacat gtttcttatt ttttgaatct    900
aaccaatcat tgtaatattc ttcaaacttt ttattttcat ctaaattgtt tccatcatcc    960
aaatctctaa gcagttgttg agcagcgttg gttgcctcag ctttagtttt gaatcctgac   1020
tttcttttct ttcctgattt gaaagacgga tgttttacgt cgtactgcca agatgctgtt   1080
gctttattct tcctttttgt aattgtaaat gacgccattt tacttttcct cctcaaaatt   1140
ggcaaaaaat aataagggta ggcgagctac ccgaaatttt attgttgaac aactattgct   1200
tcacttcttg cttttcctac ttcttttcta aaactatcat atgattgatt agggtgtgtt   1260
aacgacattc ctggaccacc tccagcatgt tggtttttgt ccggattatt ttccatttct   1320
tcagtggctc ttttagcatt taaatattct tcgtaactag gttcgtttgg gtcgcgtggt   1380
tgtgcttgtt gtccattatt ggtagctgga agattcttct gtacctgttg cttagatgtg   1440
ttattggttt gttgattgtt gttaatgttt gtgttgttct cgttgtttac ttgattattg   1500
ttatcgtttt gattactatt ttcttttttc gcttctgctt tatctttagt ttctttcttt   1560
ttgtctttgt tctctttctt tgtttcggtt ttcttgcttt cctctttctt atcgccgtcg   1620
ttgctaccgc atgcacctaa cactaacgca ctagctaata ataaaactaa taatcttttc   1680
atgttttaca ctcctttatt tgctatttgt tttaataaat ctatgatttc attgttttgt   1740
tctatgattt tgttttcatt tttaagatgt tcgtctaaca tctctattaa gacgaaattt   1800
tgatttatca tttcgtaagt aaacatttga cctgtgttgt taggattaga aaacgaacta   1860
ctgaaacgcg ttgaaaagct atctataaat tgaccaactt tattttttaa taacatatct   1920
ttaccgctct cagacattgt atttagttcg cgcttattta aagttttttc tataattttg   1980
tattttgttt cctgatttct ttcgatttct tctacttcaa aagggatatt gttattaaat   2040
ttttcgataa tatcacgttt ttcagaaact gacatacgat caaatacttg tttttgacct   2100
ttatttaact tccctcgaat ttttccggca gtccaagact ctttaactgt taacttatca   2160
ttaggaactt gattcatctt ttatatgact ccttttctca tatttcttta tatttaaaaa   2220
ctctcaacgg ctcaaatgta atcgaatact cgccatagtg agttccaata ccgtatatct   2280
tcttatattg ttctattgcc tccaatatgt attcttcgct taattgtaga tactcagaca   2340
actcatacaa gttacgtacg ccataattgt aagcttctac aatttcgcgt aacgggactg   2400
```

-continued

```
ctgagataaa gccgtgtcgt cttgcgtaat tttcgaactt gcgattgttg aatttcgatt   2460
gatctaaaat gttgccatac gtcaacttgt ggtgggcaag ttcttcatat aatacttcta   2520
atttgttcct ttcggataag gaaggtctaa taaaaatttc tccttcttga taccaaccat   2580
cgaatcctcg aggtactctt tgtgtttctt tcacttcaac ttcacatttc ataagcaatt   2640
cttcgtattt tcccatgcgc caaacccctt tggtgtctta tttctttcta tctctaaccc   2700
attgcataaa attttcgatt tcttcccatt cttcgggagt aaattcatct ttatttgcat   2760
gaccggctat agtttcttga tgaatacttc tttcttctgt aattctcgat ttaggtacat   2820
taaagtaatc tgctaattgt tggacttttg atattctagg atatttaagt tctttaagcc   2880
agttagagat tgttgattga cttaccccga ttgcttcaga caattctact tgagtaatgt   2940
tgttctcttt cataagttgt tctaagttct ctgataaaat ttttctagca ctcttatatt   3000
ccataatttt ctcctttagt attacttaat gtaatactaa tttaccataa gtaatatcac   3060
ttttcaatac aaaatattac ttttttgaaa taaatatcac tttaggtgtt gacatattac   3120
tttaagtgat agtatagttg taaatgtcaa cgggaggtga tacgaaatgc cagaaaattt   3180
taaagagttc tctgtaaagg tctggagaac taattcgaat atgacacaac aagatgtcgc   3240
tgataaatta ggcgttacta aacaatctgt aataagatgg gaaaaagatg acgcagaatt   3300
aaaaggctta caattgtatg ctttagccaa attattcaac acagaagttg attatataaa   3360
ggctaaaaaa atttaacatt aatatcactt taagtgataa aggaggaaac tgaaatgcaa   3420
gaattacaaa catttaattt tgaagaatta ccagtaagga aaattgaagt ggaaggagaa   3480
cccttctttt taggtaagga tgttgctgaa attttagggt atgcacgagc agataacgcc   3540
atacgcaatc atgttgatag tgaagatagg ctgatgcacc aaattagtgc gtcaggtcaa   3600
aacagaaata tgatcatcat caacgaatct ggattataca gtttaatctt tgacgcttct   3660
aaacaaagta aaaacgaaaa cattagagaa accgctagga aattcaaacg ctgggtaact   3720
tcggaagttt taccgacgtt aagaaaaact ggtgcttacc aagtacctag tgacccaatg   3780
caagcattga gattaatgtt tgaagctaca gaagaaacaa aacaagaaat taaaaacgtg   3840
aaagatgatg ttattgattt gaaagaaaat caaaaactgg atgcgggaga ctacaatttc   3900
ttaactagaa caatcaatca aagagtagct catatacaaa gactacatgc gataacaaac   3960
caaaaacaac gtagcgaatt attcagggat attaattcag aagtgaaaaa gatgactggt   4020
gcgagttcaa gaacgaacgt aagacaaaaa catttcgacg atgtaattga aatgattgct   4080
aattggttcc cgtcacaagc tactttatac agaatcaagc aaattgaaat gaaattttaa   4140
aacgaaatat aggagaggct gaatatggaa tacatcggat atgcagacgc aaatgcgttt   4200
gtaaaaataa gtggcatttc aaaagatgat ctagagaaaa aagtctactc gaacaaagag   4260
tttcaaaaag aatgcatgta cagatttggt cgaggacaaa agcgttatat aaaaattgac   4320
aaagctattc aatttatcgg taccaattta atgattaatg aatacgaatt ataggaggag   4380
ttatcaaatg agtaaaactt ataaaagcta cctagtagca gtactatgct tcacagtctt   4440
agcgattgta cttatgccgt ttctatactt cactacagcg tggtcaattg caggattcgc   4500
aagtatcgca acattcatat actacaaaga atacttttat gaagaataaa aaaactgcta   4560
cttgcgtcaa caagtaacag tgacaaacat ttatcaaaat atacaactta attaaatcaa   4620
aatatacgga ggtagtcaac tatggctgaa aatattaaaa ctgaacaaca ttattacact   4680
aaagatttct caggatacag aaatgaagaa gataactttg tagcaaatca agaattgaca   4740
gtaacaatca cattgaacga gtacagaaaa cttattgaaa taaaggctgt taaagataaa   4800
```

-continued

```
gaagaagata cttacagagg taagtatttt gcggaagaaa gaaaaaacga aaaattggaa   4860
aaagaaaata taaaactaaa aaacaaaatt tatgaattac aaaacgaaga agataacgag   4920
gaggacgaag aagacaagga ggacgagaac gatgtattac aaaattggtg agataaaaaa   4980
caaaattata agctttaacg ggtttgaatt taaagtgtct gtgatgaaga gacatgacgg   5040
tatcagtata caaatcaagg atatgaataa tgttccactt aaatcgtttc atgtcataga   5100
tttaagcgaa ctatatattg cgacggatgc aatgcgtgac gttataaacg aatggattga   5160
aaataacaca gatgaacagg acaaactaat taacttagtc atgaaatggt aggaggtatg   5220
aaaagtgaat gatttacaag agagagaatt agaaacattc gaacaagacg accgattcaa   5280
agtaactgat ctagacagtg ctaactgggt ttttaagaaa ctggatgcaa tcacaactaa   5340
agagaatgaa atcaacgatt tagcaaataa agaaattgaa cgcataaacg aatggaaaga   5400
taaagaagta gaaaaattac agagtggcaa agaatattta caaagccttg taattgaata   5460
ttacagaata caaaaagaac aagatagcaa attcaagttg aatacacctt acggaaaagt   5520
gacagccaga aaaggttcaa aagtcattca agttagcaat gagcaagaag tcattaaaca   5580
acttgagcaa cgaggttttg acaactatgt aaaagtaact aaaaaactta gccaatcaga   5640
cattaagaaa gatttcaatg taactgaaaa cggcacattg attgacgcaa acggcgaagt   5700
tttagagggt gctagcattg tggagaaacc aacgtcatac acggtaaagg tgggagaata   5760
gatgactgaa aaaactaatc aagatgtcga tattttaacg caactaggtg taaaagacat   5820
cagcaaacaa aatgcaaaca agttttataa atttgcgata tacggcaagt tcggtactgg   5880
taaaactacg tttttaacaa aagataacaa taccttagta ctagatataa atgaggacgg   5940
aacaacggta acagaagatg ggcagttgt gcagattaag aattataagc attttagtgc    6000
agtgattaaa atgctgccta aaattattga acaactaaga gaaaacggaa aacaaattga   6060
tgttgtagtg attgaaacaa tccaaaagtt acgtgatatc actatggacg acatcatgga   6120
cggtaaatca aagaaaccga catttaatga ttggggcgag tgtgctacac gcattgtaag   6180
tatttatcgt tatatttcta aattacaaga acattatcaa tttcatcttg ctataagcgg   6240
acacgagggc attaacaaag acaaagatga tgagggaagt actatcaatc caacaatcac   6300
gatagaggca caagaccaaa taaaaaaagc agtcatcagt caatctgacg tgttagcaag   6360
aatgacaata gaagaacatg agcaagacgg cgaaaaaact tatcaatatg tacttaacgc   6420
tgaaccatca aatttattcg agacaaagat aagacactca agcaacatca aaattaacaa   6480
caaacgtttc attaatccaa gtattaacga tgttgtacaa gcaattagaa atggtaatta   6540
aaaattaatt aaaaggacgg tataaaaatt atgaaaatca ctggtagaac acaatacatt   6600
caagaaacta atcaagaggc attcatgaaa ggtggggact ttttaggagc tggagaattt   6660
acagtaaaag ttgcaaatgt cgagtttaac gacagagaaa acagatactt cacgattgtt   6720
tttgaaaaca acgaaggtaa acaatacaaa cacaaccaat tcgtcccacc attccaacaa   6780
gattatcaag aaaaacaata tatcgagtta cttagtagat taggaattaa attgaactta   6840
ccagatttaa cttttgacac agatcaatta attaacaaaa tcggaactat tgtacttaaa   6900
aataaattta acgaggaaca aggcaagtat tttgtaagac tctcatatgt aaaagtttgg   6960
aataaagacg atgaagtagt taataaacca gaacctaaaa ctgatgagat gaaacaaaaa   7020
gaacagcaag caaatggtaa acagacacct atgagtcaac aatcaaaccc attcgctaat   7080
gctaatggtc caatagaaat caatgatgat gatttaccgt tctaggacgt ggtttaaatg   7140
```

-continued

```
caatacatta caagatacca gaaagacaat gacggtactt attccgtcgt tgctactggt   7200
gttgaacttg aacaaagtca cattgattta ctagaaaacg gatatccgct aaaagcagaa   7260
gtagaggttc cggacaataa aaaactatct atagaacaac gcaaaaaaat attcgcaatg   7320
tgtagagata tagaacttca ctggggcgaa ccagtagaat caactagaaa attattacaa   7380
acagaattgg aaattatgaa aggttatgaa gaaatcagtc tgcgtgactg ttcaatgaaa   7440
gttgcgagag agttaataga actgattata tcgtttatgt ttcatcatca aatacctatg   7500
agtgtagaaa cgagtaagtt gttaagcgaa gataaagcgt tattatattg ggctacaatc   7560
aaccgcaact gtgtaatatg cggaaagcct cacgcagacc tggcacatta tgaagcagtc   7620
ggcagaggta tgaacagaaa caagatgaat cactacgaca aacatgtgtt agcactgtgt   7680
agacaacatc ataatgaaca gcacgcaatt ggtgttaagt cgtttgatga taaatatcaa   7740
ttgcatgact cgtggataaa agttgatgag aggctcaata aaatgttgaa aggagagaaa   7800
aatgaataag ttactaatag atgactatcc gatacaagta ttaccgaaat tagctgaatt   7860
aatagggtta aacgaagcaa tagtattgca acaaattcat tattggctaa acaactcaaa   7920
acataaatac gatggcaaaa cttggatttt taattcttat ccagaatggc aaaaacaatt   7980
tccattttgg agcgagagaa ctataaaaag gacatttggg agtttagaaa aacaaaattt   8040
attgcatgta ggtaactaca acaaggctgg atttgaccgt acaaaatggt attcaatcaa   8100
ttatgaaaca ttaaacaaac tagtggcacg accatcggga caaaatggcc cgacgatgag   8160
gacaaattgg cacgatgcaa gaggacaaaa tgacccgacc aataccatag actacacaga   8220
gactaacaaa catagagaga cagacgacgt ctcaaagtca tttaagtata ttagtaccaa   8280
tttagaaatt atacaaaacc ctttaaaagc agaacagtta gaacacgaaa ttaaatcatt   8340
taagcaagat cagttcgaaa tagtaaaagt cgctaccgat tactgcaaag aaaacaacaa   8400
aggtctgaat tacttactaa ctgtattaaa gaactggaat aaagaaggcg tttcagataa   8460
agaaagtgct gaaaacaaat tgaaacctcg taactctaaa aaagaaacta ctgatgatgt   8520
catagcacaa atggaaaaag aattgagtga tgactaatgc cgatgagcaa aacacaagca   8580
ttagaaatta ttaaaaaagt taggtacgta tacaacatcg attttgataa accaaagtta   8640
gaaatgtgga ttgatgtatt aagtcaaaac ggggattatc aaccaactgt aaaagctgta   8700
gatggatata tcaacagtaa caacccgtac ccgcctaacc taccagcaat catgcgtaag   8760
gcacctaaaa aagtatctat tgagccggta gacaacgaaa ccgctacaca ccaatggaaa   8820
atgcagaatg accccgaata tgtcagacaa agaaaaatag cgctagataa cttcatgaat   8880
aagttggcag aatttggggg cgataacgaa tgaattacgg tcaatttgaa attgaaagca   8940
caataatcgc tacgctactt aaacaaccgg acgtactaga aaagataaga gttaaagatt   9000
acatgtttac gaacgaaaag tttaaaacct ttttcaatta tgtaatggac gtcggaaaga   9060
tagatcatca agaaatctat ttaaaagcaa ctaaagataa agagtttttta gatgcagata   9120
ctataactaa actttacaac tccgatttca ttggatacgg attctttgaa cgttatcaac   9180
aagaattatt ggaaagttat caaatcaaca aagcgaaaga attggtaact gagttcaaac   9240
aacaacctac gaaccaaaat tttaataact tgattgatga actcaaggat ttaaaaacaa   9300
ttactaacag aaaagaagac ggaaccaaga agtttgttga ggagtttgtc gatgagttat   9360
acagcgatag ccctaagaag caaattaaga cgggttataa gctcatggat tacaaaatag   9420
ggggattgga gccgtcgcaa ttaatcgtca tcgcagcgcg tccctcagtg ggtaagacag   9480
gttttgcatt aaacatgatg ctgaacatag cacaaaatgg atacaaaaca tctttcttta   9540
```

-continued

```
gtctcgaaac aactggcaca tcagtattga aacgtatgtt atcaacaatt actggtattg   9600
agttaacaaa gataaaagaa atcaggaact taacgccgga tgacttaaca aagttaacga   9660
atgcgatgga taaaatcatg aaattaggca tcgatatttc tgataaaagt aatatcacac   9720
cgcaagatgt gcgagcgcaa gcaatgaggc attcagacag gcaacaagtt atttttatag   9780
attatcttca actgatggat actgatgcga aagttgatag acgtgtagca gtagaaaaga   9840
tatcacgtga cttaaagata atcgctaacg agacaggcgc aatcatcgta ctactttcac   9900
aactgaatcg tggtgtcgag tctagacagg ataaaagacc aatgctatcg gacatgaaag   9960
aatcaggcgg aatagaagca gatgcgagtt tagcgatgct actttaccgt gatgattatt  10020
ataaccgtga cgaagatgac agtatcactg gcaaatctat tgttgaatgt aacatagcca  10080
aaaacaaaga cggcgaaacc ggaataattg aatttgagta ttacaagaag actcagaggt  10140
ttttcacatg aatataatgc aattcaaaag cttattgaaa tcgatgtatg aagagacaaa  10200
gcaaagcgac ccgattgtag caaatgtata tatcgagact ggttgggcgg tcaatagatt  10260
gttggacaat aacgagttat cgcctttcga tgattacgac agagttgaaa agaaaatcat  10320
gaatgaaatc aactggaaga aaacacacat taaggagtgt taaaaaatgc cgaaagaaaa  10380
atattactta taccgagaag atggcacgga agatattaag gtcatcaagt ataaagacaa  10440
cgtaaatgaa gtttattcgc tcacaggagc ccatttcagc gacgaaaaga aaattatgac  10500
tgatagtgac ctaaaacgat ttaaaggcgc tcacgggctt ctatatgagc aagagctagg  10560
attgcaagca acgatatttg atatttagag gtggcacaat gagtaaatac aatgctaaga  10620
aagttgagta caaaggaatt gtatttgata gcaaagtaga gtgcgaatat taccaatatt  10680
tagaaagtaa tatgaatggc actaactatg atcgtatcga aatacaaccg aaatttgaat  10740
tacaacctaa attcgggaaa caaagaccga ttacgtatat agccgatttc tctttgtgga  10800
aggaagggaa actggttgaa gttatagacg ttaaaggtaa ggcgactgaa gttgccaaca  10860
tcaaagcgaa gatattcaga tatcagtata gagatgtgaa tttaacgtgg atatgtaaag  10920
cgcctaaata cacaggtcaa gaatggatgg tatatgagga cttagtgaaa gtcagacgta  10980
aaagaaaaag agaaatgaag tgatctaatg caacaacaag catatataaa cgcaacaatt  11040
gatataagaa tacctacaga agttgaatat cagcattacg atgatgtgga taaagaaaaa  11100
gatacgctgg caaagcgctt agatgacaat ccggacgaat tactaaagta tgacaacata  11160
acaataagac atgcatatat agaggtggaa taaatgaagt tgaacgaagt attcgcaact  11220
aatttaaggg taatcatggc tagagataac gtaagtgtcc aagatttgca caatgaaact  11280
ggcgtatcaa gatcaactat tagtggatat aaaaacggaa aagctgagat ggttaactta  11340
aatgtattag ataaattggc agatgctcta ggtgttaatg taagtgaact atttactaga  11400
aatcacaaca cgcacaaatt agaggattgg attaaaaaag taaatgtata gaggtggaat  11460
aaatgagtat cgtaaagatt aacggtaaac catataaatt taccgaacat gaaaatgaat  11520
tgataaaaaa gaacggttta actccaggaa tggttgcaaa aagagtacga ggtggctggg  11580
cgttgttaga agccttacat gcaccttatg gtatgcgctt agctgagtat aaagaaattg  11640
tgttatccaa aatcatggag cgagagagca aagagcgtga aatggttagg caacgacgta  11700
aagaggctga actacgtaag aagaagccac atttgtttaa tgtgcctcaa aaacattctc  11760
gtgatccgta ctggttcgat gtcacttata accaaatgtt caagaaatgg agtgaagcat  11820
aatgagcata atcagtaaca gaaaagtaga tatgaacaaa acgcaagaca atgttaaaca  11880
```

-continued

```
accggcgcat tacacatacg gcaacattga aattatagat tttatcgaac aggttacggc  11940
acagtatcca cctcaactag cattcgcaat aggtaatgca atcaaatact tgtctagagc  12000
accgttaaag aatggtcatg aggatttagc aaaggcgaag ttttacgtcc aaagagcttt  12060
tgacttgtgg gagggttaac gatggcaacg caaaaacaag ttgattacgt aatgtcatta  12120
caggaacaat tgggattaga agactgtgaa aaatatacag acgaacaagt taaagctatg  12180
agtcataaag aagttagcaa tgtgattgaa aactataaga caagcatatg ggatgaagag  12240
ctatataacg aatgcatgtc gtttggtctg cctaattgtt aaaaggagtg atgaccatga  12300
acgatagcgc acgcaaagaa tacttaaacc aatttttcag ctctaagaga tatctgtatc  12360
aagacaacga gcgagtggca catatccatg tagtaaatgg cacttattac tttcacggac  12420
attataaaac gatgtttaaa ggcgtgaaaa agacatttga tactgctgaa gagctcgaaa  12480
tatatataaa gcaacatgat ttggaatatg aggaacagaa gcaaccaact ttattttaga  12540
ggagatggaa ataatggcaa agattaaaag aaaaaagaag atgacgctac tcgaactggt  12600
ggaatgggca tggaacaatc ctgaacaagt tgaaagtaaa gtgtttcaat cagatagaat  12660
gggcacgctt ggagaatgta gcgaagtaca tttttcaact gatgggcatg ggttttatac  12720
aaaagtagta acagataaag atatttttac tgtagaaatc acagaggaag tcactgaaga  12780
tactgagttt gattgtctag tagaactaaa cgatattgaa ggttttgaaa tatatgaaaa  12840
tgattcaatc agagagttga tagacggtac ttccagagcg ttttatatac taaacgaaga  12900
taaaactatg acattaattt ggaaagatgg ggagttggta gtatgatgca aacctataaa  12960
gtatgtcttt gtatcaagtt ctttgcatct aaatgtgatt ataaattaaa gaaacattat  13020
ttcgtgaaaa gtacgaatga ggaaaaagcc acgaacatgg tattaaaact gattcgtaaa  13080
aagctcccgt tcgaaactgc aagcatagaa gtcgaaaaag tggaggcaat ataatgatac  13140
aaccaacaag agaagaatta attaatttca tgaaaaaaca tggagctgaa aatgttgact  13200
ctatcactga tgagcaaagt gcaataagac actttagagc tcaatcaaaa gtttttaaag  13260
acgaacgtga tgagtacaag aagcaacgag atgagcttat cgaggatata gctaagttaa  13320
gaaaacgtaa cgaagagctg gagaacatgt ggcgcacagt caaaaatgaa ttgcttggaa  13380
gatacgaaca ttactgtttt aaaattagag aactacaccc tgagagcaaa gcgaacagga  13440
taggagctct ctatatagga ggtaaaagca ctgcagatat tatactgtcg cgaatggaag  13500
aactagacgg aacaaatgag ttctacgaat ttttagggca aatggaggca gacacaaatg  13560
aataaccgtg aacaaataga acaatcagtg atcagtacta gtgcgtataa cggtaatgac  13620
acagaggggt tactaaaaga gattgaggac gtgtataaga aagcgcaagc gtttgatgaa  13680
atacttgagg gaatgacaaa tgctattcaa cattcagtta aagaaggtat tgaacttgat  13740
gaagcagtag gggttatggc aggtcaagtt gtctataaat atgaggagga gcaggaaaat  13800
gagtattagt gtaggagata aagtatataa ccatgaaaca aacgaaagtc tagagattgt  13860
gcaattggtc ggagatatta gagatacaca ttataaactg tctgatgatt cagttattag  13920
cattatagat tttattacta aaccaattta tctaattaag gggacgagt gagtggaatg  13980
gaaacgatta aaaaatgtgg tgccgcaccc agttatcaaa aataaaaatt taaagtcggt  14040
atacgtaaca aaagataatg tgaaagaggt tcaaaaagaa ttaggtttct ttgaaatttt  14100
taatgaagaa gtgttattaa ctggattttt atcatttcaa aggataccta tttacattat  14160
ttggattaat cctaaatctc ataagacgcc tagatattac tttgctaacg agcatgagat  14220
tgaaagatat tttgaatttt tggaggacga gtaaatgctt gaaatcatcg accaacgtga  14280
```

-continued

```
tgcattgcta gaagaaaagt atttaaacga cgactggtgg tacgagctag attattggtt  14340
gaataaacgc aagtcagaaa atgaacagat tgatattgat agagtgctta aatttattga  14400
ggaattaaaa cgataggaga taacgaataa atgaataatt taacagtaga tcaattaaaa  14460
gaacttttac aaatacaaaa ggagttcgac gatagaatac cgactagaaa tttaaatgac  14520
acagtagcta gtatgattat tgaatttgcg gagtgggtta acacacttga gtttttttaaa  14580
aattggaaga aacaaccagg taagccatta gatacacaat tagatgagat tgctgattac  14640
ttagctttca gtttgcaatt aactctgact attgttgatg aagaagattt ggaagagact  14700
actgaggtta tggttgattt gattgaaaat gaagttactt tacctaaact acattcagtt  14760
tattttgttc atgtaatgca tacactaaca gaacaatttg taaaaggtat tgataatagt  14820
attgtacaag ttttaataat gcctttttttg tacgccaata cttactatac aatcgaccaa  14880
ctcattgacg catacaaaaa gaaaatgaaa aggaaccacg aaagacaaga tggaacagca  14940
gacgcaggaa aaggatacgt gtaaagacat cttagatcga gtcaaggagg ttttggggaa  15000
gtgacgcaat acttagtcac aacattcaaa gattcaacag gacaaccaca tgaacatttt  15060
actgctgcta gagataatca gacgtttaca gttgttgagg cggagagtaa agaaggagcg  15120
aaagagaagt acgagaaaca agttaagata aggagagatg gagatgccaa agaaaacggt  15180
aacgattgat gtagatgaaa acttattagt agtagctagt aatgaaatat cagaactatt  15240
atatgaatat gacagtgagt taatgtcagc tgatgaagat ggcgataata gagatatcga  15300
aaaaaaaaga gacgcattaa aacaagctat acaaattatc gataaattaa catgtcgagg  15360
aggcagacga tgattaacat acctaaaatg aaattcccga aaaagtacac tgaaataatc  15420
aagaaatata aaaataaaac acctgaagaa aaagctaaga ttgaagatga tttcattaaa  15480
gaaattaatg ataaagacag tgaattttac agtcctatga tggctaatat gaatgaacat  15540
gaattaaggg ctatgttaag aatgatgcct agtttaattg atactggaga tggcaatgat  15600
gattaaaaaa cttaaaaata tggattggtt cgatatcttt attgctggaa tactgcgatt  15660
attcggcgta atcgcactga tgcttgttgt catatcgcct atctatacag tggctagtta  15720
ccaaaacaaa gaagtatatc aagggacaat tacagataaa tataacaaga gacaagataa  15780
agaagacaag ttctatattg tgttagacaa caagcaagtc atcgaaaact ctgacttact  15840
attcaaaaag aaatttgata gcgcagacat acaagctagg ttaaaagtag gcgacaaagt  15900
agaagttaaa acgattggtt atagaataca ctttttaaat ttatatccgg tcttatacga  15960
agtaaagaag gtagataaat aatgattaaa caaatattaa gactattatt cttactagcg  16020
atgtatgagc taggtaagta tgtaactgag aaagtatata ttatgacgac ggctaatgat  16080
gatgtagagg cgccgagtga cttcgcaaag ttgagcgatc agtctgattt gatgagggcg  16140
gaggtgtcag agtagatgta tagcaaagag tcaattgtta atatgatagg cacacataaa  16200
atgaagtgta atgtattagc tgatgtaata ccggaatatg atagcaattc aattgcacag  16260
tatggcatac aagcaacgtt gccgaaacca caaggggaaa actcaagtaa agttgaagat  16320
gttgttgtga ggcttgagag agcaaataaa aggtatgctc agatgttaaa agaggttgag  16380
tttataaatc aatcgcaaca gagattggga cacgttgact tttgcttctt agagttattg  16440
aagaaaggtt ataacaggga tgcgattatc aagaagatgc ctaactctaa attaaataga  16500
aacaacttct tagcgcgccg tgatgagtta gcagaaaaga tttatctact acagtgacga  16560
aaatgacaaa aatgacagaa atgacgaaaa tgacactatt tttaaactgt gaattaattt  16620
```

-continued tatataattg atttgtaaga attatcttaa gacgtggggt aatagccaca ttagatgttc 16680
tcatcgatgt gattgagaag tgacaaacat ataaaagatg atatgttacg ctattaatca 16740
cctactacct gcctatatgg tgggtagttt aattcttgca ttttgagtca taactatttt 16800
cctcctttca catttattga acgtagctcc tgcacaagat gtaggggcat tttttatatt 16860
taaataacta gagtaattaa cgtaaaggcg tgtgatacag tgaaaacaat tgattaaatt 16920
aacaccgaag caagaaaagt ttgtgctagg actcatagag ggcaagagcc aacggaaagc 16980
atatattgac gcagggtatt cgactaaagg taagagtggg gaatatctag ataaagaagc 17040
gagtacactt tttaaaaatc ggaaggtttc cggaaggtac gaaaaattgc gtcaagaagt 17100
agctgaacaa tcaaaatgga cacgccaaaa ggcctttgaa gaatatgagt ggctaaagaa 17160
tgtagctaag aatgacattg aaatagaggg agtgaagaaa gcgacagctg atgcattcct 17220
cgctagttta gatggtatga atagaatgac gttaggtaac gaagttttag ctaaaaagaa 17280
aatagaaact gaaattaaga tgcttgagaa gaagattgaa caaatagata aaggtgacag 17340
tggaacagaa gataaaatca aacaacttca cgacgcaata acggaagtga tcgtcaatga 17400
ataaacttaa atctttatat acggacaaac aaattgaaat attgaagcaa acgcaaaaac 17460
aagattggtt tatgttaatt aatcacggag caaagcgtac aggtaaaaca atattaaaca 17520
atgacttatt tttacgtgag ttaatgcgtg tgcgaaagat agcagacgaa gaaggaattg 17580
agacacctca atatatactt gctggtgcaa cattaggtac gattcaaaaa aacgtactaa 17640
tagagttaac taacaaatat ggcattgagt ttaattttga taaatataat tcattcatgt 17700
tatttggcgt tcaagtggtt cagacaggtc acagtaaagt aagtggtata ggagctatac 17760
gtggtatgac atcgtttggt gcatatatca atgaagcgtc gttagcgcat gaagaggtgt 17820
ttgacgagat taagtcacgt tgtagtggaa ctggtgcaag aatattggta gataccaacc 17880
ctgaccatcc cgagcattgg ttgttgaaag attatattga aaatacagat cctaaagcag 17940
gtatactgag tcaccaattt aagctcgatg acaataactt tcttaatgat agatataaag 18000
agtctattaa ggcttcaaca ccatcaggta tgttctatga acgtaatatc aacggtatgt 18060
gggtgtctgg tgacggtgta gtatatgccg actttgattt gaatgagaat acgattaaag 18120
cagatgaact ggacgacata cctatcaaag aatactttgc tggtgtcgac tggggttacg 18180
agcactatgg atctattgtg ttaataggac gaggtataga tggtaacttt tattttattg 18240
aggagcacgc acaccaattt aagtttattg atgattgggt ggttattgca aaagatattg 18300
taagtagata tggcaatatt aatttttact gcgatactgc acgacctgaa tacatcactg 18360
aatttagaag acatagatta cgtgcaatta acgctgataa aagtaaacta tcgggtgtgg 18420
aggaagttgc taagttgttc aaacaaaaca agttacttgt tctttatgat aatatggata 18480
ggtttaagca agaggtattt aaatatgttt ggcaccctac aaacggagag cctataaaag 18540
aatttgatga cgtgttggac tcgttaagat atgccatata cacacatact aaacctgaac 18600
gattaaggag ggggaaatga cattgtataa gttaatagat gatattgaag cacaaggaat 18660
attgcctaag catattgagg ctctaataga gtcacataaa gacgatagag agagaatggt 18720
taatctctat aatagataca agacacatat tgactatgta ccaatattca aacgtcgacc 18780
aattgaagaa aaagaagatt ttgaaactgg tggaaatgta aggcgattag acgtgtctgt 18840
taataacaaa cttaacaact cttttgacag cgaaattgtt gatacacgtg ttggttattt 18900
acatggtgtt cctgttactt atgatttaga tgaaaacgca gaaaaaaacg aaaagttgaa 18960
aaagtttata accaactttg ccattagaaa tagtgttgat gatgaggatt ctgaaatagg 19020

-continued taaaatggca gcaatttgcg gatatggtgc taggttagca tatattgata cgaatggtga 19080
tattaggatt aagaatatag atccctataa tgttattttt gttggcgaca atattttaga 19140
acctacatac tcattgcgct acttttatga aaaagatgat gataatggca ctgattatgt 19200
gtacgcagag ttttacgata atgcttatta ttatgtattt cgaggagaag gtattgacgc 19260
tttgcaagaa gttggacgat atgaacattt atttgattac aatccattgt ttggtgtacc 19320
taacaacaaa gagatgatag gagatgctga aaaggttatt cacttaattg acgcatatga 19380
tttaacaatg agcgatgcat caagtgagat tagtcagaca cgtttagcat accttgtgtt 19440
acgcggtatg ggtatgagtg aagaaatgat tcaagaaaca caaaagagtg gcgcatttga 19500
gttgttcgac aaagatatgg acgttaaata cttaacaaaa gatgtaaatg acacaatgat 19560
tgagaaccat ttagatcgaa tcgaaaagaa tatcatgcgt tttgcaaagt cagtaaactt 19620
taattctgac gagtttaacg gaaatgtacc tatcattgga atgaaactta aacttatggc 19680
tttagagaac aagtgtatga cgtttgagcg taagatgaca gctatgttga ggtatcaatt 19740
caaagttatt ttatctgcat taaagcgtaa agggtacaac ttggatgatg atagttattt 19800
aaacctgata tttaagttca ctcgtaacat tccagttaat aagttagaag aatcacaagt 19860
gctaattaac ctgaagggac aagtttcaga acgaacaagg ttaggacaat cacaactagt 19920
tgatgatgtt gattacgaat tagacgaaat ggaaaaagaa agtcttgaat ttaatgacaa 19980
attacctgac atagatgaag gtgacgcaaa tgacaaatcc caaaataacc aatcagaatg 20040
atattgatga gtatatcgag ggtttaatct ctaaagcaga aaaaccaata gaacaactat 20100
ttgctaatcg acttaaagag ataaaacaaa tcatcgcaga tatgtttgag aaatatcaaa 20160
atgatgatgt gtatgttaca tggactgaat tcaataaata caacaggctc aataaggagt 20220
taactcgtat aggtacaatg ttgacttatg actataggca agtagctaag atgattcaga 20280
agtcacaaga agatgcttat atagaaaaat tccttatgag cctttattta tatgaaatgg 20340
cgagtcaaac atctatgcag tttgatgttc cgagtaaaga ggtaatcaaa tcagctattg 20400
aacaacctat tgagttcatt cgtttaatgc caacactaca aaaacatcgt gatgaagtat 20460
tgaaaaagat acgtatgcac attacacaag gtattatgag tggagagggt tactctaaga 20520
tagctaaagc aatacgtgat gatgtcggca tgtctaaagc tcaatcattg cgtgtggctc 20580
gtacagaagc aggcagagca atgtcacaag ctggacttga tagcgcaatg gttgctaaag 20640
ataacggttt gaatatgaag aaacgttggc atgctactaa agatacacga acacgtgata 20700
ctcatcgtca tttagatggg gaatcagtgg aaatagatca gaattttaaa tcaagtgggt 20760
gtgttgggca ggcgcccaag ctatttattg gtgtaaacag tgcgaaagag aatattaatt 20820
gtcgttgcaa attactttat tatattgatg aaaatgaatt gccaactgta atgagagcac 20880
gtaaagacga tggtaaaaat gaagttatcc cattcatgac ttatcgtgag tgggagaaat 20940
ataagcgaaa aggtggtaat tgatatggat tttaaaataa aagtaaatgt tgatactggc 21000
gaagctatag aaaagttaga acgcattaaa tccttgtacg aagagataat agagttacaa 21060
aacgaaaaag ttgttgtaaa cgtaacagtt aaaaatgaag ctgatttaga tatggttaaa 21120
acatctatta gcgaagaaaa tgctaaaaat aatgatttca cactttttta gttgtctctt 21180
tgctactcga ccttagcatg tcgttaaact gctttttatt atgcactttt cggactgtta 21240
gggtacgcga agggcaaaaa ggagttttga tatatgaata tcgaagaagt taagtctttt 21300
tttgaagaac acaaagacga taaagaagta aaagattatc taaagggact taagacggtg 21360

-continued

```
tctgttgatg acgttaaagg ctttttagat acagaagaag gtaaacgatt cattcaacct  21420
gaattagatc gttatcattc gaaaggatta gaatcatgga aagagaaaaa tcttgaggat  21480
ctaatcgaac aagaagtacg gaagcgtaat cctgagcaat cagaagaaca aaaacgtatt  21540
agtgctcttg aacaagagtt agaaaaacgc gacgcagagg caaaacgtga gaagttaaga  21600
agtaacgcgc taggtaaagc gcaggaacta aatttaccaa catccttagt tgatagattt  21660
ttaggcgatt ctgatgaaga tactgagcaa aacttaaaag ctttaaaaga aacctttgac  21720
aagtatgttc aaaaaggcgt tgagtctaaa tttaaatcga gtggaagaga tgttaaagaa  21780
tcacgaaatc aagatttaga cccttcaaat gtaaagtcca ttgaagaaat ggcgaaagaa  21840
atcaatatta gaaaataaag tgaggtaata aaatatggca actccaacat acacgccagg  21900
caatgttatt ttatcggatt ttaaaaacgg cgttattcca gcagaacaag gtactttaat  21960
catgaaagac attatggcta attcagcaat tatgaaatta gctaaaaatg agccaatgac  22020
agcacaaaag aaaaaattta cttacttagc aaaaggtgta ggcgcctact gggtatcaga  22080
aacggaacgt attcaaactt ctaagcctga atatgcgcaa gcagaaatgg aagctaagaa  22140
aattggtgta attattccgt tatcaaaaga gtttcttaaa tggactgcaa aagatttctt  22200
taatgaggtt aaacctctaa ttgcagaggc attttacaaa gcgtttgacc aagctgttat  22260
ctttggtact aaatcacctt acaacacttc aactagtggt aaaccgcttg ttgaaggcgc  22320
agaagagaaa ggtaacgttg ttacagatac taataattta tacgtagacc tttcggcatt  22380
aatggctact attgaagatg aagagttaga tccaaacgga gtattaacta cacgttcatt  22440
cagaagtaaa atgcgtaatg ctttagatgc taatgacaga ccattatttg atgctaacgg  22500
gaacgagatt atgggattac cactatctta tactggagcg gatgtatacg acaaaaagaa  22560
atcgttagca ctaatgggtg attgggatta cgcacgttac ggtatcttac aaggtattga  22620
gtatgcaatt tctgaagatg ccacgttaac gacgttacaa gcatcagatg cttctggcca  22680
accagtatca ttatttgaac gtgatatgtt cgctttacgt gcgacgatgc atattgcata  22740
catgaacgtt aaaccagaag cgttcgcaac gcttaaacca actgaatagg aggagatatg  22800
atggctaatc ctgcagaaga gattaaggta aaaaaagaca atatgactat tactgttaca  22860
aagaaggcat ttgactctta ttacagtctt gtcggttaca aagaggttaa atcacgtcgt  22920
actacgtctg ataagagcga gtgataaaaa tgactcttta tgaagatgtt aaacttttac  22980
tcaagaaaaa tggagtggaa gttaaaagtg atgaagaaga aatatttaag atggaagttg  23040
acggaatact agaagatgtt agggatataa caaacaatga ttttatgaaa gatggtcaag  23100
tcatttatcc ttactcaatc aaaaagtatg tcgcagatgt cctagagtat tatcaacgac  23160
ctgaagttaa aaagaattta aagtcaagaa gtatggggac agtgtcgtac acttataacg  23220
atggtgtccc tgattacatt agtggagtat taaacaggta taaacgagca aagtttcatc  23280
cgtttaaacc aataaggtag aggtgttgtt tgtgtttaac ccatacgacg aattccctca  23340
cactatttct attggaagta tcaaaaaagt aggagagtat ccaattatac aagagcgctt  23400
tgtaagcgat aaaacaatta aaggatttat ggatacgcct actacatctg aacaactaaa  23460
atttcatcaa atgtcacaag aatatgacag aaacctatat gtaccttatg acttgccaat  23520
atctaaaaac aatttatttg agtatgaggg tagaatcttt agtattgaag gtgattctgt  23580
agatcagggc ggacaacatg aaattaagtt actacgactt aagcaggtgc catatggcaa  23640
aagttaagta cggtgctgat agcatggttg ttgaattgga taagttcgat aagaaaatag  23700
aagagtgggt taaaaaaggt attgctaaaa caacgacgaa gatttacaac actgctgtag  23760
```

-continued cattagctcc tgttgactta ggttttttag aagaaagtat tgactttaaa tatttcgatg 23820
gtgggttatc cagtgttata agtgtcggcg cagattatgc aatatacgtt gaatacggta 23880
ctggtatata tgctactggt cctggtggta gtcgtgctac aaagattccg tggagtttta 23940
aaggtgatga cggcgaatgg tacaccacat atggtcaagc gccacagcca ttttggaacc 24000
ctgcaattga cgcaggacgc aagacattcg agcagtattt ttcatagagg tggttaaata 24060
tgtgggtatc agttgagcct gaacttacaa atcaaatata taaaagatta atctcagacc 24120
ctaacattaa caaactagtt gatgataggg tttttgacgt tgttcaagat gacgctgttt 24180
acccatatat tgttgtgggt gaatcaaacg tcactaacaa cgaatctagc gcaacaatga 24240
gagaaacagt cggtattgtc atacatgtgt attcacagtt cgctacacaa tacgaggcta 24300
agctcatttt aagcgcgata ggttatgtgc ttaacagacc tatagaaata gataattacg 24360
agtttcaatt tagccgtatc gatagtcaag cagtattccc tgatatagac aggtttacta 24420
agcatggcac gatacggctt ttatttaagt acagacataa aaagaaaaac gaaggagtgt 24480
attaaatggc gcaaaaaaac tatttagcag ttgtacgtcc agctgaaact gacttagatc 24540
cagtagaatc tttattatta gctgacttac aagaaggtgg acatacgatt gaaaatgatt 24600
tagctgaaat agtacgaggc ggtaaaacgg actattctcc caatgcaatg tcagaatcat 24660
ttaaattaac aattggtaat gtgcctggag ataaaggaat tgaagcagtg aaacacgctg 24720
tacaaacagg tggacagttg cgtatatggc tttatgagcg taataaacgt gcagacggta 24780
aacatcacgg aatgtttggt tatgttgttc cagaatcatt tgaaatgtca tttgatgatg 24840
aaagtgacaa aatcgaacta tcattaaaag ttaaatggaa tacagcagaa ggtgctgaag 24900
ataacttgcc gaaagagtgg tttgaagctg caggtgcgcc tacagttgaa tacgaaaaat 24960
tcggcgaaaa agtcggaaca ttcgagaatc aaaagaaagc tagtgttgta tctgattcac 25020
acacggaaga ccattctatg taaactaata gatcaagggg gcgtaagctc cctatttttt 25080
tataaaaaaa ttgaaaagag gtatatattt tgactgaatt taatccaatt acaacattaa 25140
aaattaatga cggagaaaaa gattacgaag tagaagcaaa agtaacattt gcatttgacc 25200
gaaaagctga aaaattctca gaagatagcg aagatgggag aaaaggagca atgccaggat 25260
tcaatgttat ctttaacggt ttgctagaat ctagaaacaa agcgatttta caattttggg 25320
aatgtgctac tgcttattta aaaaacccac caactcgaga acaattagaa aaagcaattg 25380
atgatttcat cactgaaaac gaggatactt tgccgttatt acaaggggct ttggacaaac 25440
ttaacaatag tggtttttc aagagggaga gtcgctcgta ctggatgaca ttgaacaaag 25500
caccgaatat ggccaaaagc gaggacaaag aaatgacgaa agcaggcata gaaatgatga 25560
aagagaatta caaggaaatc atgggcgcag aaccttacac gattactcaa aaataaggca 25620
actgacagct agatatttag gatatatccc tgaacatgaa ttgttagcac taacacctgc 25680
tgaatggcgt gattggctta ttggtggtca ggataggtac ctagatcaaa gacaattatt 25740
aattgaacaa gcgcaagcta acggcttagt acaagcttct aagaggctaa ctagtatgat 25800
tcgtgacatt gagaaacaac gttacgaaat aagagaacct ggtagctatg ctcgtgtaca 25860
aaaagctaga ttagaagaag aaaaaagaag acgtgaactc ttcaaagaag gtacaagaaa 25920
attccttgaa tcgaaaggag gttagccttt ggatactcat tttatggcaa agattatggc 25980
caatattaga gatttccaaa gcaacgtaag gaaagctcaa cgattagcaa agacgtctgt 26040
accaaacgaa attgaaacag atgtaaaagc agatatttca agattccaaa gagctttaca 26100

-continued acgcgctaaa tcaatggctc aacgatggcg agagcattct gttaaattat tcatgaaaac 26160
agatgagtat aaagcgaatt tagaacgcgc taaagctcaa gtagagcgat ttaaacaaca 26220
taaagtagat ttgaaactaa gtaacactga attaatggcc aaatataatg caactaaagc 26280
tactgtcgaa gcttggagaa aacatgttgt taagttggat ttagatgcaa accccgctaa 26340
aatggcggtt aaagggttta aagaagattt aatagatctt agcaggcata gttttgatat 26400
tgattccagc agatggaaat taggaaataa attcacaaaa gaattcaatg aagtcgaagg 26460
agcagttaaa cgttctttcg gaagaattgg tcagattatg agaaaagaag taaatggaac 26520
aagtgatatt tggggtaaac ttaacaactc attgaaagat tacggcgaga aaatggacgc 26580
cttagctact aaaatccgaa ctttcggtac tatcttcgcg caacaggtca aaggcttaat 26640
gattgctagt atacaagcat tgataccagt gattgccgga ttagtacctg caataatggc 26700
agtacttaat gcggttggtg tattaggtgg tggcgtttta ggtttagttg gcgcattctc 26760
tgtcgcaggt cttggagttg ttggctttgg tgcaatggct attagcgctc ttaaaatggt 26820
tgaagatgga acattggcag taacaaaaga agttcaaaac tttagagatg cgagcgatca 26880
gttaaaaact acatggcgtg atattgttaa agagaatcaa gcaagtatct ttaatgcgat 26940
gtcagcaggt atcagaggcg ttacaagtgc gatgtctcaa ttaaaaccat tcttatccga 27000
agtatctatg ctagttgaag caaacgcacg cgagtttgag aattgggtta aacattccga 27060
aacagctaag aaagcgtttg aagcattgaa tagcataggt ggcgcaatct tcggagattt 27120
attgaacgct gcaggacgat ttggcgacgg attagttaac attttcactc aattaatgcc 27180
gttgttcaaa tttgtgtctc aaggactaca gaacatgtct atagctttcc aaaattgggc 27240
taatagtgta gctggtcaga atgctattaa agcgtttatt gactacacta ccactaactt 27300
acctaagatt ggtcagatat ttggtaatgt gttcgctggt attggtaatt taatgattgc 27360
ttttgcacaa aacagttcca acatttttga ttggttggtt aaattaactt ctcaatttag 27420
agcatggtca gaacaagtag gacaatcaca agggtttaaa gactttatca gttatgttca 27480
agagaatggt cctactatta tgcagttaat cggtaatatc gtaaaagcat tagttgcttt 27540
tggtactgca atggctccta tagctagtaa attgttagac tttatcacta atctagctgg 27600
atttatcgct aaactattcg aaacacaccc agctatagca caagttgctg gcgttatggg 27660
tattttaggc ggtgtatttt gggctttaat ggctccgatt gttgctataa gtagtgtact 27720
tacaaatgtg tttggtttga gcttattcag cgtcactgaa aagattttag acttcgttag 27780
aacatcaagt ttagttactg gagctacgga agcattaata ggtgcattcg gttcgatttc 27840
agcacctatt ttagcagttg ttgcagtaat tggtgcattc attggtgtcc tcgtttattt 27900
atggaaaaca aacgagaact ttagaaatac tattactgaa gcgtggaacg gtgttaaaac 27960
ggcagtttct ggtgcgattc aaggtgtagt cggctggtta actgaattgt ggggcaaaat 28020
ccaatctacc ttacaaccga taatgcctat attgcaagta ttaggacaaa tattcatgca 28080
agttttaggt gttttggtaa taggcatcat tacaaacgtt atgaatatca tacaaggttt 28140
gtggacttta attacaattg cgttccaagc cataggaaca gtgatatccg tagcagtcca 28200
aatcatagta ggtttgttca ctgctttaat tcagttgctt actggcgact tctcaggtgc 28260
ttgggagact attaaaacta cggttaccaa tgtgcttgat acgatttggc aatacatgca 28320
atcagtttgg gagtcaatta tcggcttttt aactggcgta atgaatcgaa cactttctat 28380
gtttggtaca agttggtcac agatatggag tacaatcact aattttgtta gcagtatttg 28440
gaacactgtt acaagttggt tcagtcgagt ggcttcgagt gtagctgaaa aaatggggca 28500

-continued

```
agcactaaac tttattatca caaaaggttc tgaatgggtt tctaacattt ggaatacagt  28560
tacaagtttc gcgagtaaag tagctgatgg gtttaaaaga gttgtctcaa atgtaggtga  28620
cggtatgagt gatgcacttg gtaagattaa aagtttcttc agtgatttct taaatgccgg  28680
agcggaatta atcggcaaag tagctgaggg tgtagccaat gctgcgcaca aagtagtcag  28740
cgcggtaggc gatgcgattt catcagcttg ggactctgta acttcattcg taagtggaca  28800
cggtggaggt agtagcttag gtaaaggttt agcggtatca caagcaaaag taattgctac  28860
agactttggc agtgccttta ataaagagct atcctctact ttgacagata gtatagtaaa  28920
tcctgtaagt acttctatag acagacacat gactagcgat gttcaacata gcttaaaaga  28980
aaataataga cctattgtga atgtaacgat tagaaatgag ggcgaccttg atttaattaa  29040
atcacgcatt gatgacatga acgctataga cggaagtttc aacttattat aagggaggtt  29100
tgttagttga tagcgcacga tatagaagta ataaggaatg gttcacagta tcgcgtcagt  29160
gacaatcctt tcacttataa tcacttggaa gtagttgaat ataacgttac aggcgcagga  29220
tatcatcgta actattctga tatagagggt attgatggta gatttcataa ttacgctaaa  29280
gaagaactta aaaaagtaga gcttaagata aggtataaag tacctaaaat tgcttatgct  29340
tcacatttaa agtcagacgt ccaagcacta tttgctggac gtttttattt aagggaatta  29400
gctacaccag acaattcaat taagtatgag catatattag atataccaaa agacaaacaa  29460
gcatttgagc ttgattatgt tgatggacga caactttttg taggactagt aagtgaagtt  29520
tcttttgaca caacacaaac atcaggggaa ttttctttgt cgtttgaaac aaccgaacta  29580
ccatactttg aaagtgtcgg ttatagtact gatcttgaaa gtaataacga ccctgaaaaa  29640
tggtcggtac ctgatagatt gcctacaaac gaaggtgata agaggcgtca aatgacattt  29700
tacaacacta actcaggaga agtttattat aacggtgatg ttcctttaac acagtttaat  29760
cagtttaatg ttgttgaaat agagttagct gaagatgtta aagctaatga taaggatgga  29820
ttcactttct atacagataa aggaaatatc tcagttatta aggaagttga tttaaaagcc  29880
ggagataaaa taatcttcga cggtaaacat acctatagag gttatttaaa tatagattct  29940
tttaataaaa ctttagaaca accggtttta tatccaggct ggaatcgatt caagtctaat  30000
aaagtaatga aacaaattac atttagacac aaattatatt ttagataagg agtagcctat  30060
gccaatttta ttaaaaagtc tacagggtgt agggcacgct attaatgtta gtacaaaggt  30120
aagtaaaaag ctaaatgaag atagttcttt ggatctaact attatcgaga acgcgagtac  30180
gtttgacgca ataggtgcta taactaaaat gtggacgatc actcatgttg aaggtgaaga  30240
tgatttcaac gaatatgtaa ttgtcatact tgataagtct actattggcg aaaaaataag  30300
gcttgatatc aaagctaggc aaaaagaact tgatgacctt aacaattcta ggatttacca  30360
agagtataac gaaagtttta caggcgttga gttcttcaat actgtcttta aaggaacggg  30420
ttataagtat gtattacatc caaaagtaga tgcatctaaa ttcgagggat taggcaaagg  30480
agatacacga ttagaaatct ttaaaaaagg acttgagcgt tatcatctcg aatatgaata  30540
cgatgcaaag actaaaacgt ttcatttgta tgatgaatta tctaagtttg ccaattatta  30600
cattaaagct ggtgtgaatg ctgataacgt caaaatacaa gaagatgcat ctaaatgtta  30660
tacctttatt aaaggttatg gtgattttga tggacaacag acttttgcag aagcgggact  30720
acaaattgaa ttcactcatc cattagcaca attgataggt aaaagagaag cgccaccgct  30780
tgttgatgga cgtattaaaa aagaagatag tttaaaaaaa gcaatggagt tattgataaa  30840
```

-continued

```
gaaaagtgtc actgcttcta tttccttaga ctttgtagcg ttacgtgaac atttcccaga  30900
agctaaccct aaaataggtg atgttgttag agtggtggat tctgccatag gatataacga  30960
cttagtgaga atagtcgaaa tcactacaca tagagatgcg tacaataata tcactaagca  31020
agatgtagta ttaggagact ttacaaggcg taatcgttat aacaaagcag ttcatgatgc  31080
tgcaaattat gttaaaagcg taaaatctac aaaatccgac ccatctaaag aactaaaagc  31140
attaaacgca aaagttaacg caagtttatc tataaataat gaattggtta agcagaatga  31200
aaaaataaac gctaaagtcg ataagatgaa tactaaaaca gttacaactg ctaatggtac  31260
gatcatgtac gactttacta gtcaatcaag tataagaaac atcaaatcaa ttggaacgat  31320
tggcgactct gtagctagag ggtcgcacgc aaaaactaat ttcacagaaa tgttaggcaa  31380
gaaattgaaa gctaaaacga ctaatcttgc aagaggtggc gcaacaatgg caacagttcc  31440
aataggtaaa gaagcggtag aaaacagcat ttatagacaa gcagagcaaa taagaggaga  31500
cctaatcata ttacaaggca ctgatgatga ctggttacac ggttattggg caggcgtacc  31560
gataggcact gataaaacgg atacaaaaac gttttacggt gccttttgtt ctgcaattga  31620
agttattaga aagaataatc cagattcaaa aatactagtg atgacagcta caagacaatg  31680
ccctatgagt ggtacaacaa tacgccgtaa agacacggac aaaaacaaac tagggttaac  31740
acttgaggac tatgtaaacg ctcaaatatt agcttgtagt gagttagatg taccagtgtt  31800
tgacgcatat cacacagatt actttaagcc atacaatcca gcttttagga aagcgagcat  31860
ggaggacggc ttacacccta acgaaaaagg tcacgaggtt attatgtacg agttaatcaa  31920
ggattattac agtttttacg actaaaggag gcaaccaatg gcttacggat taattacaag  31980
tttacattca atgacaggtc ggaaaatagt tgctcaacat gagtataact atcgcttgtt  32040
agatgaaggt atgagcaaac ttgagaaaat gtttatatac catcaaaaag aagaaatata  32100
cgcacactca gcgaaacaaa ttaaatactt gaatgacagt gttgaagatt atttaacgta  32160
tttaaatagc cgttttagca atatgattct aggccataac ggcgacggta tcaatgaagt  32220
aaaagacgcg cgtattgata atacaggtta tggtcataag acattgcaag atcgtttgta  32280
tcatgattat tcaacactag atgctttcac taaaaaggtt gagaaagctg tagatgaaca  32340
ctataaagaa tatcgagcga cagaataccg attcgaacca aaagagcaag aaccggaatt  32400
tatcactgat ttatcgccat atacaaatgc agtaatgcaa tcattttggg tagaccctag  32460
aacgaaaatt atttatatga cgcaagctcg tccaggtaat cattacatgt tatctagatt  32520
gaagcccaac ggacaattta ttgatagatt gcttgttaaa aacggcggtc acggtacaca  32580
caatgcgtat agatacattg atggagaatt atggatttat tcagctgtat tggacagtaa  32640
caaaaacaac aagtttgtac gtttccaata tagaactgga gaaataactt atggtaatga  32700
aatgcaagat gtcatgccga atatatttaa cgacagatat acgtcagcga tttataatcc  32760
tatagaaaat ttaatgattt tcagacgtga atataaagct tctgaaagac aagctaagaa  32820
ttcattgaat ttcattgaag taagaagtgc tgacgatatt gataaaggta tagacaaagt  32880
attgtatcaa atggatatac ctatggaata cacttcagat acacaaccta tgcaaggtat  32940
cacttatgat gcaggtatct tatattggta tacaggtgat tcgaatacag ccaaccctaa  33000
ctacttacaa ggtttcgata taaaaacaaa agaattgtta tttaaacgac gtatcgatat  33060
tggcggtgtg aataataact ttaaaggaga cttccaagaa gctgagggtc tagatatgta  33120
ttacgatcta gaaacaggac gtaaagcact tttaataggg gtaactattg gacctggtaa  33180
taacagacat cactcaattt attctatcgg ccaaagaggt gttaaccaat tcttaaaaaa  33240
```

-continued

```
cattgcacct caagtatcga tgactgattc aggtggacgt gttaaaccgt taccaataca  33300
gaacccagca tatctaagtg atattacgga agttggtcat tactatatct atacgcaaga  33360
cacacaaaat gcattagatt tcccgttacc gaaagcgttt agagatgcag ggtggttctt  33420
ggatgtactg cctggacact ataatggtgc tctaagacaa gtacttacca gaaacagcac  33480
aggtagaaat atgcttaaat tcgaacgtgt cattgacatt ttcaataaga aaaacaacgg  33540
agcatggaat ttctgtccgc aaaacgccgg ttattgggaa catatcccta agagtattac  33600
aaaattatca gatttaaaaa tcgttggttt agatttctat atcactactg aagaatcaaa  33660
acgatttact gattttccta aagactttaa aggtattgca ggttggatat tagaagtaaa  33720
atcgaataca ccaggtaaca caacacaagt attaagacgt aataacttcc cgtctgcaca  33780
tcaattttta gttagaaact ttggtactgg tggcgttggt aaatggagtt tattcgaagg  33840
aaaggtggtt gaataatgat agtagataat ttttcgaaag acgataactt aatcgagtta  33900
caaacaacat cacaatataa tccaattatt gacacaaaca tcagtttcta tgaatcagat  33960
agaggaactg gtgttttaaa ttttgcagta actaagaata acagaccgtt atctataagt  34020
tctgaacatg ttaaaacatc tatcgtgtta aaaaccgatg attataacgt agatagaggc  34080
gcttatattt cagacgaatt aacgatagta gacgcaatta atgggcgttt gcagtatgtg  34140
ataccgaatg aatttttaaa acattcaggc aaggtgcatg ctcaggcatt ctttacacaa  34200
aacgggagta ataatgttgt tgttgaacgt caatttagct tcaatattga aaatgattta  34260
gttagtgggt ttgatggtat aacaaagctt gtttatatca aatctattca agatactatc  34320
gaagcagtcg gtaaagactt taaccaatta aagcaagata tggatgatac acaaacgtta  34380
atagcaaaag tgaatgatag tgcgacaaaa ggcattcaac aaatcgaaat caagcaaaac  34440
gaagctatac aagctattac tgcgacgcaa actagtgcaa cacaagctgt tacagctgaa  34500
gtcgataaaa tagttgaaaa agagcaagcg atttttgaac gtgttaacga agttgaacaa  34560
caaatcaatg gcgctgacct tgttaaaggt aattcaacaa caaattggca aaagtctaaa  34620
cttacagatg attacggtaa agcaattgaa tcgtatgagc agtccataga tagcgtttta  34680
agcgcagtta acacatctag gattattcat attactaatg caacagatgc gccagaaaag  34740
acggatatag gcacgttaga gaagcctgga caagatggtg ttgatgacgg ttcttcgttc  34800
gatgaatcaa cttatacatc aagcaaatct ggtgtgttag ttgtttatgt tgttgataat  34860
aatactgctc gtgcaacatg gtacccagac gattcaaacg atgagtacac aaaatacaaa  34920
atctacggca catggtaccc gttttataaa aagaatgatg gaaacttaac taagcaattt  34980
gttgaagaaa cgtctaacaa cgctttaaat caagctaagc agtatgtaga tgataaattc  35040
ggaacaacga gctggcaaca acataagatg acagaggcga atggtcaatc aattcaagtt  35100
aacttaaata atgcgcaagg cgatttggga tatttaactg ctggtaatta ctatgcaaca  35160
agagtgccgg atttaccagg tagtgttgaa agttatgagg gttatttatc ggtattcgtt  35220
aaagacgata caaacaagct atttaacttc acgccttata actctaaaaa gatttacaca  35280
cgatcaatca caaacggcag acttgagcaa cagtggacag ttcctaatga acataagtca  35340
acggtattgt tcgacggtgg agcaaatggt gtaggtacaa caatcaatct aaccgaacca  35400
tacacaaact attctatttt attagtaagt ggaacttatc caggtggcgt tattgaggga  35460
ttcggactaa ccacattacc taatgcaatt caattaagta aagcgaatgt agttgactca  35520
gacggtaacg gtggcggtat ttatgagtgt ttactatcca aaacaagtag cactacttta  35580
```

-continued agaatcgata acgatgtgta ctttgattta ggtaaaacat caggttctgg agcgaatgcc 35640
aacaaagtta ctataactaa aattatgggg tggaaataat gaaaatcaca gtaaatgata 35700
aaaatgaagt tatcggatac gttaatactg gcggtttacg caatagttta gatgtagacg 35760
ataacaatgt gtctatcaaa ttcaaagaag agttcgaacc tagaaagttc gttttcacta 35820
acggcgaaat taaatacaat agcaatttcg aaaaagaaga cgtaccgaat gcatcaaacc 35880
aacaaagtgc gtcagattta agtgatgagg aacttcgcgg aatggttgca agtatgcaaa 35940
tgcagatgac gcaagtgaac atgttgacaa tgcaattgac gcaacaaaac gctatgttaa 36000
cacaacagtt gaccgaactg aaaactaaca aaacaaatac tgagggggac gtttaaatga 36060
tgaagatgat ttatccaact tttaaagaca ttaaaacttt ttatgtgtgg ggttgctata 36120
aaaatgagca aattaagtgg tacgtagaca tgggtgtaat cgacaaagaa gaatatgcat 36180
tgatcactgg tgaaaaatat ccagaggcaa aagatgaaaa gtcacaggtg taatgcttga 36240
ggctttttaa tttaacacaa agtaggtggc gtaatgtttg gatttaccaa acggcacgaa 36300
catgaatggc gaattagaag attagaagag aatgataaaa caatgcttag cactctcaat 36360
gagattaaat taggtcaaaa aactcaagag caagttaaca ttaaattaga taaaacttta 36420
gatgctatcc agagggaaag acagatagac gaaaaaaata agaaagaaaa cgacaaaaat 36480
atacgcgata tgaaaatgtg gattctcggt ttgataggga ctatcttcag tacgattgtc 36540
atagctttac taagaactat ttttggtatt taaaggaggt gattaccatg cttaaaggga 36600
ttttaggata tagcttctgg gcgtgcttct ggtttggtaa atgtaaataa cagttaagag 36660
tcagtgcttc ggcactggct ttttattttg attgaaatga ggtgcataca tgggattacc 36720
taacccaaag actagaaagc ctacagctag tgaagtggtg gagtgggcaa agtcgaatat 36780
tggtaagagg attaatatag ataattatcg gggcagtcaa tgttgggata cacctaactt 36840
tatttttaaa agatattggg gttttgtaac atggggcaat gctaaggata tggctaatta 36900
cagatatcct aagggtttcc gattctatcg ttattcatct ggatttgtac cggaacctgg 36960
agacatcgca gtttggcacc ctggcaacgg aataggttcg gacggacaca ccgcaatagt 37020
agtaggacca tctaataaaa gttattttta tagcgttgac caaaactggg ttaattctaa 37080
tagttggaca ggttctccag gaagattagt aagacaccct tatgtaagtg ttacaggctt 37140
tgttaggcct ccatactcaa aagatactag caaacctagt agtactgata caagttcagc 37200
atcaaaagcc aatgactcaa caattactgg cgaagcgaag aaaccgcaat ttaaagaagt 37260
taaaacagta aaatacactg cttacagcaa tgttttagat aaagaagagc acttcattga 37320
tcatatagtt gtaatgggtg atgaacgctc agatattcaa ggattatata taaaagaatc 37380
aatgcatatg cgttctgtag acgaactgta tacgcaaaga aataagttta taagcgatta 37440
tgaaataccg catttatatg tcgatagaga ggctacatgg cttgctagac caaccaattt 37500
tgatgacccg cgtcacccta attggctagt tattgaagta tgtggtggtc aaacagatag 37560
caaacgacaa ttcttattga atcaaataca agcgttaata cgtggtgttt ggttattgtc 37620
agggattgat aaaaacttat ctgaaacgac gttaaaggta gaccctaata tttggcgtag 37680
tatgaaagat ttaattaatt acgacttgat taagcaaggt ataccggata acgcaaagta 37740
tgagcaagtt aaaaagaaaa tgcttgagac atacattaaa cgagatatat tgacacgaga 37800
aaatataaaa gaagtaacga caaaaacaac aataagaatt agtgataaaa catcagttga 37860
cagtgcgtcc acacgaggcc ctactccatc agacgaaaaa ccaagcatcg ttactgaaac 37920
aagtccattc acattccagc aagcactgga tagacaaatg tctaggggta acccgaaaaa 37980

-continued atctcataca tggggctggg ctaatgcaac acgagcacaa acgagctcgg caatgaatgt 38040
taagcgaata tgggaaagta acacgcaatg ctatcaaatg cttaatttag gcaagtatca 38100
aggcatttca gttagtgcgc ttaacaaaat acttaaagga aaaggaacgc tcgacggaca 38160
aggcaaagca ttcgcggaag cttgtaagaa aaacaacatt aacgaaattt atttgatcgc 38220
gcacgctttc ttagaaagtg gatacggaac aagtaacttc gctagtggta gatacggtgc 38280
atataattac ttcggtattg gtgcattcga caacgaccct gattatgcaa tgacgtttgc 38340
taaaaataaa ggttggacat ctccagcaaa agcaatcatg ggcggtgcta gcttcgtaag 38400
aaaggattac atcaataaag gtcaaaacac attgtaccga attagatgga atcctaagaa 38460
tccagctacc caccaatacg ctactgctat agagtggtgc caacatcaag caagtacaat 38520
cgctaagtta tataaacaaa tcggcttaaa aggtatctac ttcacaaggg ataaatataa 38580
ataaagaggt gtgtaaatgt acaaaataaa agatgttgaa acgagaataa aaaatgatgg 38640
tgttgactta ggtgacattg gctgtcgatt ttacactgaa gatgaaaata cagcatctat 38700
aagaataggt atcaatgaca aacaaggtcg tatcgatcta aaagcacatg gcttaacacc 38760
tagattacat ttgtttatgg aagatggctc tatattcaaa aatgagcccc ttattatcga 38820
cgatgttgta aaagggttcc ttacctacaa aatacctaaa aaggttatca aacacgctgg 38880
ttatgttcgc tgtaagctgt ttttagagaa agaagaagaa aaaatacatg tcgcaaactt 38940
ttctttcaat atcgttgata gtggtattga atctgctgta gcaaaagaaa tcgatgttaa 39000
attggtagat gatgctatta cgagaatttt aaaagataac gcgacagatt tattgagcaa 39060
agactttaaa gagaaaatag ataaagatgt catttcttac atcgaaaaga atgaaagtag 39120
atttaaaggt gcgaaaggtg ataaaggcga accgggacaa cctggtgcga aaggtgatac 39180
aggtaaaaaa ggagaacaag gcgcacccgg taaaaacggt actgtagtat caatcaatcc 39240
tgacactaaa atgtggcaaa ttgatggtaa agatacagat atcaaagcag aacctgagtt 39300
attggacaaa atcaatatcg caaatgttga agggttagaa gataaattgc aagaagttaa 39360
aaaaatcaaa gatacaactc tcaacgactc taaaacgtat acggattcaa aaattgctga 39420
actagttgat agcgcgcctg aatctatgaa tacattaaga gaattagcag aagcaataca 39480
aaacaactct atttcagaaa gtgtattgca acagattggc tcaaaagtta gtacagaaga 39540
ttttgaggaa ttcaaacaaa cactaaacga tttatatgct ccaaaaaatc ataatcatga 39600
tgagcggtat gttttgtcat ctcaagcttt tactaaacaa caagcggata atttatatca 39660
actaaaaagc gcatctcaac cgacggttaa aatttggaca ggaacagaaa atgaatataa 39720
ctatatatat caaaaagacc ctaatacact ttacttaatt aaggggtgat ttttatggaa 39780
ggtaatttta aaaatgtaaa gaagtttatt tacgaaggtg aagaatatac aaaagtatat 39840
gctggaaata tccaagtatg gaaaaagcct tcatcttttg taataaaacc cttacctaaa 39900
aataaatatc cggatagcat agaagaatca acagcaaaat ggacaataaa tggagttgaa 39960
cctaataaaa gttatcaggt gacaatagaa aatgtacgta gcggtataat gagggtttcg 40020
caaactaatt taggttcaag tgatttagga atatcaggag tcaatagcgg agttgcaagt 40080
aaaaatatca actttagtaa tccttcaggg atgttgtatg tcactataag tgatgtttat 40140
tcaggatctc caacattgac cattgaataa ttttaaacga ctaatttttt agtcgttttt 40200
tattttggat aaaaggagca aacaaatgga tgcaaaagta ataacaagat acatcgtatt 40260
gatcttagca ttagtaaatc aattcttagc gaacaaaggt attagcccga ttccagtaga 40320

-continued

```
cgatgagact atatcatcaa taatacttac tgttgttgct ttatatacta cgtataaaga  40380
caatccaaca tctcaagaag gtaaatgggc aaatcaaaag ctaaagaaat ataaagctga  40440
aaacaagtat agaaaagcaa cagggcaagc gccaattaaa gaagtaatga cacctacgaa  40500
tatgaacgac acaaatgatt tagggtaggt gttgaccaat gttgataaca aaaaaccaag  40560
cagaaaaatg gtttgataat tcattaggga agcagttcaa tcctgatttg ttttatggat  40620
ttcagtgtta cgattacgca aatatgtttt ttatgatagc aacaggcgaa aggttacaag  40680
gtttatacgc ttataatatt ccatttgata ataaagcaag gattgaaaaa tacgggcaaa  40740
taattaaaaa ctatgatagc tttttaccgc aaaagttgga tattgtcgtt ttcccgtcaa  40800
agtatggtgg cggagctgga catgttgaaa ttgttgagag cgcaaattta aacactttca  40860
catcatatgg gcaaaattgg aatggtaaag gttggacaaa tggcgttgcg caacctggtt  40920
ggggtcctga aactgttaca agacatgttc attattacga tgacccaatg tattttatta  40980
gattaaattt cccagataaa gtaagtgttg gagataaagc taaaagcgtt attaagcaag  41040
caactgccaa aaagcaagca gtaattaaac ctaaaaaaat tatgcttgta gccggtcatg  41100
gttataacga tcctggagca gtaggaaacg gaacaaacga acgcgatttt atccgtaaat  41160
atataacgcc aaatatcgct aagtatttaa gacatgcagg tcatgaagtt gcattatatg  41220
gtggctcaag tcaatcacaa gacatgtatc aagatactgc atacggtgtt aatgtaggaa  41280
ataataaaga ttatggatta tattgggtta aatcacaggg gtatgacatt gttctagaga  41340
ttcatttaga cgcagcagga gaaaatgcaa gtggtgggca tgttattatc tcaagtcaat  41400
tcaatgcgga tactattgat aaaagtatac aagatgttat taaaaataac ttaggacaaa  41460
taagaggtgt aacacctcgt aatgatttac tgaacgttaa tgtatcagca gaaataaata  41520
tcaattatcg tttatctgaa ttaggtttta ttactaataa aaaagatatg gattggatta  41580
agaagaatta tgacttgtat tctaaattaa tagctggtgc gattcatggt aagcctatag  41640
gtggtttggt agctggtaat gttaaaacat cagctaaaaa ccaaaaaaat ccaccagtgc  41700
cagcaggtta tacacttgat aagaataatg tgccttataa aaaagagact ggtaattaca  41760
cagttgccaa tgttaaaggt aataacgtaa gggacggcta ttcaactaat tcaagaatta  41820
caggtgtatt acctaataac gcaacaatca aatatgacgg cgcatattgc atcaatgggt  41880
atagatggat tacttatatt gctaatagtg gacaacgtcg ctatattgcg acaggagagg  41940
tagataaagc aggtaatagg ataagtagtt ttggtaagtt tagcacgatt tagtatttac  42000
ttagaataaa aattttgcta cattaattat agggaatctt acagttatta aataactatt  42060
tggatggatg ttaatattcc tatacacttt ttaacattac tctcaagatt taaatgtaga  42120
taacaggcag gtactacggt acttgcctat ttttttgtta taatgtaatt acattaccag  42180
taaccaatct ggcttaaaac cacatttccg gtagccaatc cggctatgca gaggacttac  42240
ttgcgtaaag tagtaagaag ctgactgcat atttaaacca cccatactag ttgctgggtg  42300
gttgtttttt atgttatatt ataaatgatc aaaccacacc acctattaat ttaggagtgt  42360
ggttattttt tatgcaaaaa aaacgaaaaa aagttcataa aaagtattgc atatcacgtt  42420
taaccgtgtt ataataaggt ataccagttg agaggaggat aaaaagtgtt agaaaatttt  42480
aaaactatag cagaaatcgc cttttataca atgtcagcaa ttgccatagc gaaaacattg  42540
aaaaaagacg ataagtaagt agacaagccc gaaagggctg tctatatata aattctaaca  42600
ctaaaatact atgaaaacaa tttacattat tttaatcatt cttatttgga taaacgtgtt  42660
tttaggcaac gatataagta aaagtgttgt tgcactgctt actactttac tgcttatcaa  42720
```

-continued

```
tttatggaag agggataaaa atgacagcaa taaaagaaat aattgaatca atagaaaagt  42780

tattcgaaaa agaaacggga tataaaattg ctaaaaattc cggattacca tatcaaactg  42840

tgcaagattt aagaaatgga aaaacatctt tatcagatgc cagatttaga acgataataa  42900

agttatacga gtatcaaaga tcgcttgaaa acgaagaaga taaataaaag gagccaaaaa  42960

tatgtttgtt acaaaagaag aatttaaaac tttgaatgta aaagaagtat ttgaatcagg  43020

taaaaacttt ataaaaatta cagatggaag acatgcaata tattgggtaa atgatagata  43080

cgtagtactt gaccataaaa aaggcgattt gtacccgcaa aaagcatacc caaaatatat  43140

caaaagaaaa ttagtaagtt aaataattag aaaaccacgt cttaattgac gtggttattt  43200

tttaggtttg cgcgtgtcaa atacgtgtca atttagttct atttctttag ttttctttct  43260

aaacttaatt gcttgtaaac cgcatagtta taggcttttc agctatatac caagataaga  43320

tttatcccgc cgtctccata aaaatatgct tggaaacctt gatttaatgg ggttttaatc  43380

tagcaagtgt caaatatgtg tcaagaaaat aattttctga cacgttgacc ttgctctttt  43440

ttatgttcat caagtaagtg agagtaggtg tctaaagtta tagatatatt ataatggcct  43500

aatcttttgc taatatattc aataggcata gttataggct tttcagctat ataccaagat  43560

aagatttatc ccgccg                                                  43576
```

```
<210> SEQ ID NO 20
<211> LENGTH: 363
<212> TYPE: DNA
<213> ORGANISM: Staphylococcus bacteriophage
<220> FEATURE:
<221> NAME/KEY: CDS
<222> LOCATION: (1)..(360)

<400> SEQUENCE: 20

atg gca ata tta gaa ggt att ttt gaa gaa tta aaa cta tta aat aag       48
Met Ala Ile Leu Glu Gly Ile Phe Glu Glu Leu Lys Leu Leu Asn Lys
  1               5                  10                  15

aat tta cgt gtg cta aat act gaa cta tca act gta gat tca tca att       96
Asn Leu Arg Val Leu Asn Thr Glu Leu Ser Thr Val Asp Ser Ser Ile
             20                  25                  30

gta caa gag aaa gtt aaa gaa gca cca atg cca aaa gat gaa aca gct      144
Val Gln Glu Lys Val Lys Glu Ala Pro Met Pro Lys Asp Glu Thr Ala
         35                  40                  45

caa ctg gaa tca gtt gaa gaa gtt aag gaa act tct gct gat tta act      192
Gln Leu Glu Ser Val Glu Glu Val Lys Glu Thr Ser Ala Asp Leu Thr
     50                  55                  60

aaa gat tat gtt tta tca gta gga aaa gag ttc ctt aaa aaa gca gat      240
Lys Asp Tyr Val Leu Ser Val Gly Lys Glu Phe Leu Lys Lys Ala Asp
 65                  70                  75                  80

act tct gat aag aaa gaa ttt aga aat aaa ctt aac gaa ctt ggt gcg      288
Thr Ser Asp Lys Lys Glu Phe Arg Asn Lys Leu Asn Glu Leu Gly Ala
                 85                  90                  95

gat aag cta tct act atc aaa gaa gag cat tat gaa aaa att gtt gat      336
Asp Lys Leu Ser Thr Ile Lys Glu Glu His Tyr Glu Lys Ile Val Asp
            100                 105                 110

ttt atg aat gcg aga ata aat gca tga                                  363
Phe Met Asn Ala Arg Ile Asn Ala
        115                 120


<210> SEQ ID NO 21
<211> LENGTH: 120
<212> TYPE: PRT
<213> ORGANISM: Staphylococcus bacteriophage
```

-continued

<400> SEQUENCE: 21

```
Met Ala Ile Leu Glu Gly Ile Phe Glu Glu Leu Lys Leu Leu Asn Lys
  1               5                  10                  15

Asn Leu Arg Val Leu Asn Thr Glu Leu Ser Thr Val Asp Ser Ser Ile
             20                  25                  30

Val Gln Glu Lys Val Lys Glu Ala Pro Met Pro Lys Asp Glu Thr Ala
         35                  40                  45

Gln Leu Glu Ser Val Glu Glu Val Lys Glu Thr Ser Ala Asp Leu Thr
     50                  55                  60

Lys Asp Tyr Val Leu Ser Val Gly Lys Glu Phe Leu Lys Lys Ala Asp
 65                  70                  75                  80

Thr Ser Asp Lys Lys Glu Phe Arg Asn Lys Leu Asn Glu Leu Gly Ala
                 85                  90                  95

Asp Lys Leu Ser Thr Ile Lys Glu Glu His Tyr Glu Lys Ile Val Asp
            100                 105                 110

Phe Met Asn Ala Arg Ile Asn Ala
        115                 120
```

<210> SEQ ID NO 22
<211> LENGTH: 300
<212> TYPE: DNA
<213> ORGANISM: Staphylococcus bacteriophage
<220> FEATURE:
<221> NAME/KEY: CDS
<222> LOCATION: (1)..(297)

<400> SEQUENCE: 22

```
atg ttt gga ttt acc aaa cga cac gaa caa gat tgg cgt tta acg cga       48
Met Phe Gly Phe Thr Lys Arg His Glu Gln Asp Trp Arg Leu Thr Arg
  1               5                  10                  15

tta gaa gaa aat gat aag act atg ttt gaa aaa ttc gac aga ata gaa       96
Leu Glu Glu Asn Asp Lys Thr Met Phe Glu Lys Phe Asp Arg Ile Glu
             20                  25                  30

gac agt ctg aga acg caa gaa aaa att tat gac aag tta gat aga aat      144
Asp Ser Leu Arg Thr Gln Glu Lys Ile Tyr Asp Lys Leu Asp Arg Asn
         35                  40                  45

ttc gaa gaa cta agg cgt gac aaa gaa gaa gat gaa aaa aat aaa gag      192
Phe Glu Glu Leu Arg Arg Asp Lys Glu Glu Asp Glu Lys Asn Lys Glu
     50                  55                  60

aaa aat gct aaa aat att aga gac atc aag atg tgg att cta gga tta      240
Lys Asn Ala Lys Asn Ile Arg Asp Ile Lys Met Trp Ile Leu Gly Leu
 65                  70                  75                  80

ata ggg acg att cta agt aca ttt gtt ata gcc ttg tta aaa act att      288
Ile Gly Thr Ile Leu Ser Thr Phe Val Ile Ala Leu Leu Lys Thr Ile
                 85                  90                  95

ttt ggc att taa                                                      300
Phe Gly Ile
```

<210> SEQ ID NO 23
<211> LENGTH: 99
<212> TYPE: PRT
<213> ORGANISM: Staphylococcus bacteriophage

<400> SEQUENCE: 23

```
Met Phe Gly Phe Thr Lys Arg His Glu Gln Asp Trp Arg Leu Thr Arg
  1               5                  10                  15

Leu Glu Glu Asn Asp Lys Thr Met Phe Glu Lys Phe Asp Arg Ile Glu
             20                  25                  30
```

-continued

```
Asp Ser Leu Arg Thr Gln Glu Lys Ile Tyr Asp Lys Leu Asp Arg Asn
        35                  40                  45

Phe Glu Glu Leu Arg Arg Asp Lys Glu Glu Asp Glu Lys Asn Lys Glu
    50                  55                  60

Lys Asn Ala Lys Asn Ile Arg Asp Ile Lys Met Trp Ile Leu Gly Leu
65                  70                  75                  80

Ile Gly Thr Ile Leu Ser Thr Phe Val Ile Ala Leu Leu Lys Thr Ile
                85                  90                  95

Phe Gly Ile


<210> SEQ ID NO 24
<211> LENGTH: 186
<212> TYPE: DNA
<213> ORGANISM: Staphylococcus bacteriophage
<220> FEATURE:
<221> NAME/KEY: CDS
<222> LOCATION: (1)..(183)

<400> SEQUENCE: 24

atg caa cat caa gct tat atc aat gct tct gtt gac att aga att cct       48
Met Gln His Gln Ala Tyr Ile Asn Ala Ser Val Asp Ile Arg Ile Pro
  1               5                  10                  15

aca gaa gtc gaa agt gtt aat tac aat cag att gat aaa gaa aaa gaa       96
Thr Glu Val Glu Ser Val Asn Tyr Asn Gln Ile Asp Lys Glu Lys Glu
            20                  25                  30

aat ttg gcg gac tat tta ttt aat aat cca ggt gaa cta tta aaa tat      144
Asn Leu Ala Asp Tyr Leu Phe Asn Asn Pro Gly Glu Leu Leu Lys Tyr
        35                  40                  45

aac gtt ata aat att aag gtt tta gat tta gag gtg gaa tga              186
Asn Val Ile Asn Ile Lys Val Leu Asp Leu Glu Val Glu
    50                  55                  60


<210> SEQ ID NO 25
<211> LENGTH: 61
<212> TYPE: PRT
<213> ORGANISM: Staphylococcus bacteriophage

<400> SEQUENCE: 25

Met Gln His Gln Ala Tyr Ile Asn Ala Ser Val Asp Ile Arg Ile Pro
  1               5                  10                  15

Thr Glu Val Glu Ser Val Asn Tyr Asn Gln Ile Asp Lys Glu Lys Glu
            20                  25                  30

Asn Leu Ala Asp Tyr Leu Phe Asn Asn Pro Gly Glu Leu Leu Lys Tyr
        35                  40                  45

Asn Val Ile Asn Ile Lys Val Leu Asp Leu Glu Val Glu
    50                  55                  60


<210> SEQ ID NO 26
<211> LENGTH: 4530
<212> TYPE: DNA
<213> ORGANISM: Staphylococcus bacteriophage
<220> FEATURE:
<221> NAME/KEY: CDS
<222> LOCATION: (1)..(4527)

<400> SEQUENCE: 26

atg gga gaa aga ata aaa ggt tta tct ata ggt ttg gat tta gat gca       48
Met Gly Glu Arg Ile Lys Gly Leu Ser Ile Gly Leu Asp Leu Asp Ala
  1               5                  10                  15

gca aat tta aat aga tca ttt gca gaa atc aaa cga aac ttt aaa act       96
Ala Asn Leu Asn Arg Ser Phe Ala Glu Ile Lys Arg Asn Phe Lys Thr
            20                  25                  30
```

-continued

```
tta aat tct gac tta aaa tta aca ggc aac aac ttc aaa tat acc gaa      144
Leu Asn Ser Asp Leu Lys Leu Thr Gly Asn Asn Phe Lys Tyr Thr Glu
        35                  40                  45

aaa tca act gat agt tac aaa caa agg att aaa gaa ctt gat gga act      192
Lys Ser Thr Asp Ser Tyr Lys Gln Arg Ile Lys Glu Leu Asp Gly Thr
    50                  55                  60

atc aca ggt tat aag aaa aac gtt gat gat tta gcc aag caa tat gac      240
Ile Thr Gly Tyr Lys Lys Asn Val Asp Asp Leu Ala Lys Gln Tyr Asp
65                  70                  75                  80

aag gta tct caa gaa cag ggc gaa aac agt gca gaa gct caa aag tta      288
Lys Val Ser Gln Glu Gln Gly Glu Asn Ser Ala Glu Ala Gln Lys Leu
                85                  90                  95

cga caa gaa tat aac aaa caa gca aat gag ctg aat tat tta gaa aga      336
Arg Gln Glu Tyr Asn Lys Gln Ala Asn Glu Leu Asn Tyr Leu Glu Arg
            100                 105                 110

gaa tta caa aaa aca tca gcc gaa ttt gaa gag ttc aaa aaa gct caa      384
Glu Leu Gln Lys Thr Ser Ala Glu Phe Glu Glu Phe Lys Lys Ala Gln
        115                 120                 125

gtt gaa gct caa aga atg gca gaa agt ggc tgg gga aaa acc agt aaa      432
Val Glu Ala Gln Arg Met Ala Glu Ser Gly Trp Gly Lys Thr Ser Lys
    130                 135                 140

gtt ttt gaa agt atg gga cct aaa tta aca aaa atg ggt gat ggt tta      480
Val Phe Glu Ser Met Gly Pro Lys Leu Thr Lys Met Gly Asp Gly Leu
145                 150                 155                 160

aaa tcc att ggt aaa ggt ttg atg att ggt gta act gca cct gtt tta      528
Lys Ser Ile Gly Lys Gly Leu Met Ile Gly Val Thr Ala Pro Val Leu
                165                 170                 175

ggt att gca gca gca tca gga aaa gct ttt gca gaa gtt gat aaa ggt      576
Gly Ile Ala Ala Ala Ser Gly Lys Ala Phe Ala Glu Val Asp Lys Gly
            180                 185                 190

tta gat act gtt act caa gca aca ggc gca aca ggc agt gaa tta aaa      624
Leu Asp Thr Val Thr Gln Ala Thr Gly Ala Thr Gly Ser Glu Leu Lys
        195                 200                 205

aaa ttg cag aac tca ttt aaa gat gtt tat ggc aat ttt cca gca gat      672
Lys Leu Gln Asn Ser Phe Lys Asp Val Tyr Gly Asn Phe Pro Ala Asp
    210                 215                 220

gct gaa act gtt ggt gga gtt tta gga gaa gtt aat aca agg tta ggt      720
Ala Glu Thr Val Gly Gly Val Leu Gly Glu Val Asn Thr Arg Leu Gly
225                 230                 235                 240

ttt aca ggt aaa gaa ctt gaa aat gcc aca gag tca ttc ttg aaa ttc      768
Phe Thr Gly Lys Glu Leu Glu Asn Ala Thr Glu Ser Phe Leu Lys Phe
                245                 250                 255

agt cat ata aca ggt tct gac ggt gtg caa gcc gta cag tta att acc      816
Ser His Ile Thr Gly Ser Asp Gly Val Gln Ala Val Gln Leu Ile Thr
            260                 265                 270

cgt gca atg ggc gat gca ggt atc gaa gca agt gaa tat caa agt gtt      864
Arg Ala Met Gly Asp Ala Gly Ile Glu Ala Ser Glu Tyr Gln Ser Val
        275                 280                 285

ttg gat atg gta gca aaa gcg gcg caa gct agt ggg ata agt gtt gat      912
Leu Asp Met Val Ala Lys Ala Ala Gln Ala Ser Gly Ile Ser Val Asp
    290                 295                 300

aca tta gct gat agt att act aaa tac ggc gct cca atg aga gct atg      960
Thr Leu Ala Asp Ser Ile Thr Lys Tyr Gly Ala Pro Met Arg Ala Met
305                 310                 315                 320

ggc ttt gag atg aaa gaa tca att gct tta ttc tct caa tgg gaa aag     1008
Gly Phe Glu Met Lys Glu Ser Ile Ala Leu Phe Ser Gln Trp Glu Lys
                325                 330                 335

tca ggc gtt aat act gaa ata gca ttc agt ggt ttg aaa aaa gct ata     1056
Ser Gly Val Asn Thr Glu Ile Ala Phe Ser Gly Leu Lys Lys Ala Ile
```

-continued

```
            340                   345                   350

tca aat tgg ggt aaa gct ggt aaa aac cca aga gaa gaa ttt aag aag      1104
Ser Asn Trp Gly Lys Ala Gly Lys Asn Pro Arg Glu Glu Phe Lys Lys
        355                 360                 365

aca tta gca gaa att gaa aag acg ccg gat ata gct agc gca aca agt      1152
Thr Leu Ala Glu Ile Glu Lys Thr Pro Asp Ile Ala Ser Ala Thr Ser
    370                 375                 380

tta gcg att gaa gca ttt ggt gca aag gca ggt cct gat tta gca gac      1200
Leu Ala Ile Glu Ala Phe Gly Ala Lys Ala Gly Pro Asp Leu Ala Asp
385                 390                 395                 400

gct att aaa ggt ggt cgc ttt agt tat caa gaa ttt tta aaa act att      1248
Ala Ile Lys Gly Gly Arg Phe Ser Tyr Gln Glu Phe Leu Lys Thr Ile
                405                 410                 415

gaa gat tcc caa ggc aca gta aac caa aca ttt aaa gat tct gaa agt      1296
Glu Asp Ser Gln Gly Thr Val Asn Gln Thr Phe Lys Asp Ser Glu Ser
            420                 425                 430

ggc tcc gaa aga ttt aaa gta gca atg aat aaa tta aaa tta gta ggt      1344
Gly Ser Glu Arg Phe Lys Val Ala Met Asn Lys Leu Lys Leu Val Gly
        435                 440                 445

gct gat gta tgg gct tct att gaa agt gcg ttt gct ccc gta atg gaa      1392
Ala Asp Val Trp Ala Ser Ile Glu Ser Ala Phe Ala Pro Val Met Glu
    450                 455                 460

gaa tta atc aaa aag cta tct ata gcg gtt gat tgg ttt tcc aat tta      1440
Glu Leu Ile Lys Lys Leu Ser Ile Ala Val Asp Trp Phe Ser Asn Leu
465                 470                 475                 480

agt gat ggt tct aaa aga tca att gtt att ttc agt ggt att gct gct      1488
Ser Asp Gly Ser Lys Arg Ser Ile Val Ile Phe Ser Gly Ile Ala Ala
                485                 490                 495

gca att ggt cct gta gtt ttt ggg tta ggt gca ttt ata agt aca att      1536
Ala Ile Gly Pro Val Val Phe Gly Leu Gly Ala Phe Ile Ser Thr Ile
            500                 505                 510

ggc aat gca gta act gta tta gct cca ttg tta gct agt att gca aag      1584
Gly Asn Ala Val Thr Val Leu Ala Pro Leu Leu Ala Ser Ile Ala Lys
        515                 520                 525

gct ggt gga ttg att agt ttt tta tcg act aaa gta cct ata tta gga      1632
Ala Gly Gly Leu Ile Ser Phe Leu Ser Thr Lys Val Pro Ile Leu Gly
    530                 535                 540

act gtc ttc aca gct tta act ggt cca att ggc att gta tta ggt gta      1680
Thr Val Phe Thr Ala Leu Thr Gly Pro Ile Gly Ile Val Leu Gly Val
545                 550                 555                 560

ttg gct ggt tta gca gtc gca ttt aca att gct tat aag aaa tct gaa      1728
Leu Ala Gly Leu Ala Val Ala Phe Thr Ile Ala Tyr Lys Lys Ser Glu
                565                 570                 575

aca ttt aga aat ttt gtt aat ggt gca att gaa agt gtt aaa caa aca      1776
Thr Phe Arg Asn Phe Val Asn Gly Ala Ile Glu Ser Val Lys Gln Thr
            580                 585                 590

ttt agt aat ttt att caa ttt att caa cct ttc gtt gat tct gtt aaa      1824
Phe Ser Asn Phe Ile Gln Phe Ile Gln Pro Phe Val Asp Ser Val Lys
        595                 600                 605

aac atc ttt aaa caa gcg ata tca gca ata gtt gat ttc gca aaa gat      1872
Asn Ile Phe Lys Gln Ala Ile Ser Ala Ile Val Asp Phe Ala Lys Asp
    610                 615                 620

att tgg agt caa atc aat gga ttc ttt aat gaa aac gga att tcc att      1920
Ile Trp Ser Gln Ile Asn Gly Phe Phe Asn Glu Asn Gly Ile Ser Ile
625                 630                 635                 640

gtt caa gca ctt caa aat ata tgc aac ttt att aaa gcg ata ttt gaa      1968
Val Gln Ala Leu Gln Asn Ile Cys Asn Phe Ile Lys Ala Ile Phe Glu
                645                 650                 655

ttt att tta aat ttt gta att aaa cca att atg ttc gcg att tgg caa      2016
```

-continued

```
Phe Ile Leu Asn Phe Val Ile Lys Pro Ile Met Phe Ala Ile Trp Gln
            660                 665                 670

gtg atg caa ttt att tgg ccg gcg gtt aaa gcc ttg att gtc agt act      2064
Val Met Gln Phe Ile Trp Pro Ala Val Lys Ala Leu Ile Val Ser Thr
        675                 680                 685

tgg gag aac ata aaa ggt gta ata caa ggt gct tta aat atc ata ctt      2112
Trp Glu Asn Ile Lys Gly Val Ile Gln Gly Ala Leu Asn Ile Ile Leu
    690                 695                 700

ggc ttg att aag ttc ttc tca agt tta ttc gtt ggt gat tgg cga gga      2160
Gly Leu Ile Lys Phe Phe Ser Ser Leu Phe Val Gly Asp Trp Arg Gly
705                 710                 715                 720

gtt tgg gac gcc gtt gtg atg att ctt aaa gga gca gtt caa tta att      2208
Val Trp Asp Ala Val Val Met Ile Leu Lys Gly Ala Val Gln Leu Ile
                725                 730                 735

tgg aat tta gtt caa tta tgg ttt gta ggt aaa ata ctt ggt gtt gtt      2256
Trp Asn Leu Val Gln Leu Trp Phe Val Gly Lys Ile Leu Gly Val Val
            740                 745                 750

agg tac ttt ggc ggg ttg cta aaa gga ttg ata gca gga att tgg gac      2304
Arg Tyr Phe Gly Gly Leu Leu Lys Gly Leu Ile Ala Gly Ile Trp Asp
        755                 760                 765

gta ata aga agt ata ttc agt aaa tct tta tca gca att tgg aat gca      2352
Val Ile Arg Ser Ile Phe Ser Lys Ser Leu Ser Ala Ile Trp Asn Ala
    770                 775                 780

aca aaa agt att ttt gga ttt tta ttt aat agc gta aaa tca att ttc      2400
Thr Lys Ser Ile Phe Gly Phe Leu Phe Asn Ser Val Lys Ser Ile Phe
785                 790                 795                 800

aca aat atg aaa aat tgg tta tct aat act tgg agc agt atc cgt acg      2448
Thr Asn Met Lys Asn Trp Leu Ser Asn Thr Trp Ser Ser Ile Arg Thr
                805                 810                 815

aat aca ata gga aaa gcg cag tca tta ttt agt ggc gtc aaa tca aaa      2496
Asn Thr Ile Gly Lys Ala Gln Ser Leu Phe Ser Gly Val Lys Ser Lys
            820                 825                 830

ttt act aat tta tgg aat gcg acg aaa gaa att ttt agt aat tta aga      2544
Phe Thr Asn Leu Trp Asn Ala Thr Lys Glu Ile Phe Ser Asn Leu Arg
        835                 840                 845

aat tgg atg tca aat att tgg aat tcc att aaa gat aat acg gta gga      2592
Asn Trp Met Ser Asn Ile Trp Asn Ser Ile Lys Asp Asn Thr Val Gly
    850                 855                 860

att gca agc cgt tta tgg agt aag gta cgt gga att ttc aca aat atg      2640
Ile Ala Ser Arg Leu Trp Ser Lys Val Arg Gly Ile Phe Thr Asn Met
865                 870                 875                 880

cgc gat ggc ttg agt tcc att ata gat aag att aaa agt cat atc ggc      2688
Arg Asp Gly Leu Ser Ser Ile Ile Asp Lys Ile Lys Ser His Ile Gly
                885                 890                 895

ggt atg gta agc gct att aaa aaa gga ctt aat aaa tta atc gac ggt      2736
Gly Met Val Ser Ala Ile Lys Lys Gly Leu Asn Lys Leu Ile Asp Gly
            900                 905                 910

tta aac tgg gtc ggt ggt aag ttg gga atg gat aaa ata cct aag tta      2784
Leu Asn Trp Val Gly Gly Lys Leu Gly Met Asp Lys Ile Pro Lys Leu
        915                 920                 925

cac act ggt aca gag cac aca cat act act aca aga tta gtt aag aac      2832
His Thr Gly Thr Glu His Thr His Thr Thr Thr Arg Leu Val Lys Asn
    930                 935                 940

ggt aag att gca cgt gac aca ttc gct aca gtt ggg gat aag gga cgc      2880
Gly Lys Ile Ala Arg Asp Thr Phe Ala Thr Val Gly Asp Lys Gly Arg
945                 950                 955                 960

gga aat ggt cca aat ggt ttt aga aat gaa atg att gaa ttc cct aac      2928
Gly Asn Gly Pro Asn Gly Phe Arg Asn Glu Met Ile Glu Phe Pro Asn
                965                 970                 975
```

-continued

```
ggt aaa cgt gta atc aca cct aat aca gat act acc gct tat tta cct     2976
Gly Lys Arg Val Ile Thr Pro Asn Thr Asp Thr Thr Ala Tyr Leu Pro
            980                 985                 990

aaa ggc tca aaa gta tac aac ggt gca caa act tat tca atg tta aac     3024
Lys Gly Ser Lys Val Tyr Asn Gly Ala Gln Thr Tyr Ser Met Leu Asn
        995                1000                1005

gga acg ctt cca aga ttt agt tta ggt act atg tgg aaa gat att aaa     3072
Gly Thr Leu Pro Arg Phe Ser Leu Gly Thr Met Trp Lys Asp Ile Lys
   1010                1015                1020

tct ggt gca tca tcg gca ttt aac tgg aca aaa gat aaa ata ggt aaa     3120
Ser Gly Ala Ser Ser Ala Phe Asn Trp Thr Lys Asp Lys Ile Gly Lys
1025               1030                1035                1040

ggt acc aaa tgg ctt ggc gat aaa gtt ggc gat gtt tta gat ttt atg     3168
Gly Thr Lys Trp Leu Gly Asp Lys Val Gly Asp Val Leu Asp Phe Met
               1045                1050                1055

gaa aat cca ggc aaa ctt tta aat tat ata ctt gaa gct ttt gga att     3216
Glu Asn Pro Gly Lys Leu Leu Asn Tyr Ile Leu Glu Ala Phe Gly Ile
           1060                1065                1070

gat ttc aat tct tta act aaa ggt atg gga att gca ggc gac ata aca     3264
Asp Phe Asn Ser Leu Thr Lys Gly Met Gly Ile Ala Gly Asp Ile Thr
       1075                1080                1085

aaa gct gca tgg tct aag att aag aaa agt gct act gat tgg ata aaa     3312
Lys Ala Ala Trp Ser Lys Ile Lys Lys Ser Ala Thr Asp Trp Ile Lys
   1090                1095                1100

gaa aat tta gaa gct atg ggc ggt ggc gat tta gtc ggc gga ata tta     3360
Glu Asn Leu Glu Ala Met Gly Gly Gly Asp Leu Val Gly Gly Ile Leu
1105               1110                1115                1120

gac cct gac aaa att aat tat cat tat gga cgt acc gca gct tat acc     3408
Asp Pro Asp Lys Ile Asn Tyr His Tyr Gly Arg Thr Ala Ala Tyr Thr
               1125                1130                1135

gct gca act gga aga cca ttt cat gaa ggt gtc gat ttt cca ttt gta     3456
Ala Ala Thr Gly Arg Pro Phe His Glu Gly Val Asp Phe Pro Phe Val
           1140                1145                1150

tat caa gaa gtt aga acg ccg atg ggt ggc aga ctt aca aga atg cca     3504
Tyr Gln Glu Val Arg Thr Pro Met Gly Gly Arg Leu Thr Arg Met Pro
       1155                1160                1165

ttt atg tct ggt ggt tat ggt aat tat gta aaa att act agt ggc gtt     3552
Phe Met Ser Gly Gly Tyr Gly Asn Tyr Val Lys Ile Thr Ser Gly Val
   1170                1175                1180

atc gat atg cta ttt gcg cat ttg aaa aac ttt agc aaa tca cca cct     3600
Ile Asp Met Leu Phe Ala His Leu Lys Asn Phe Ser Lys Ser Pro Pro
1185               1190                1195                1200

agt ggc acg atg gta aag ccc ggt gat gtt gtt ggt tta act ggt aat     3648
Ser Gly Thr Met Val Lys Pro Gly Asp Val Val Gly Leu Thr Gly Asn
               1205                1210                1215

acc gga ttt agt aca gga cca cat tta cat ttt gaa atg agg aga aat     3696
Thr Gly Phe Ser Thr Gly Pro His Leu His Phe Glu Met Arg Arg Asn
           1220                1225                1230

gga cga cat ttt gac cct gaa cca tat tta agg aat gct aag aaa aaa     3744
Gly Arg His Phe Asp Pro Glu Pro Tyr Leu Arg Asn Ala Lys Lys Lys
       1235                1240                1245

gga aga tta tca ata ggt ggt ggc ggt gct act tct gga agt ggc gca     3792
Gly Arg Leu Ser Ile Gly Gly Gly Gly Ala Thr Ser Gly Ser Gly Ala
   1250                1255                1260

act tat gcc agt cga gta atc cga caa gcg caa agt att tta ggt ggt     3840
Thr Tyr Ala Ser Arg Val Ile Arg Gln Ala Gln Ser Ile Leu Gly Gly
1265               1270                1275                1280

cgt tat aaa ggt aaa tgg att cat gac caa atg atg cgc gtt gca aaa     3888
Arg Tyr Lys Gly Lys Trp Ile His Asp Gln Met Met Arg Val Ala Lys
               1285                1290                1295
```

-continued

```
cgt gaa agt aac tac cag tca aat gca gtg aat aac tgg gat ata aat     3936
Arg Glu Ser Asn Tyr Gln Ser Asn Ala Val Asn Asn Trp Asp Ile Asn
           1300                1305                1310

gct caa aga gga gac cca tca aga gga tta ttc caa atc atc ggc tca     3984
Ala Gln Arg Gly Asp Pro Ser Arg Gly Leu Phe Gln Ile Ile Gly Ser
       1315                1320                1325

act ttt aga gca aac gct aaa cgt gga tat act aac ttt aat aat cca     4032
Thr Phe Arg Ala Asn Ala Lys Arg Gly Tyr Thr Asn Phe Asn Asn Pro
   1330                1335                1340

gta cat caa ggt atc tca gca atg cag tac att gtt aga cga tat ggt     4080
Val His Gln Gly Ile Ser Ala Met Gln Tyr Ile Val Arg Arg Tyr Gly
1345                1350                1355                1360

tgg ggt ggt ttt aaa cgt gct ggt gat tac gca tat gct aca ggt gga     4128
Trp Gly Gly Phe Lys Arg Ala Gly Asp Tyr Ala Tyr Ala Thr Gly Gly
               1365                1370                1375

aaa gtt ttt gat ggt tgg tat aac tta ggt gaa gac ggt cat cca gaa     4176
Lys Val Phe Asp Gly Trp Tyr Asn Leu Gly Glu Asp Gly His Pro Glu
           1380                1385                1390

tgg att att cca aca gat cca gct cgt aga aat gat gca atg aag att     4224
Trp Ile Ile Pro Thr Asp Pro Ala Arg Arg Asn Asp Ala Met Lys Ile
       1395                1400                1405

ttg cat tat gca gca gca gaa gta aga ggg aaa aaa gcg agt aaa aat     4272
Leu His Tyr Ala Ala Ala Glu Val Arg Gly Lys Lys Ala Ser Lys Asn
   1410                1415                1420

aag cgt cct agc caa tta tca gac tta aac ggg ttt gat gat cct agc     4320
Lys Arg Pro Ser Gln Leu Ser Asp Leu Asn Gly Phe Asp Asp Pro Ser
1425                1430                1435                1440

tta tta ttg aaa atg att gaa caa cag caa caa caa ata gct tta tta     4368
Leu Leu Leu Lys Met Ile Glu Gln Gln Gln Gln Gln Ile Ala Leu Leu
               1445                1450                1455

ctg aaa ata gca caa tct aac gat gtg att gca gat aaa gat tat cag     4416
Leu Lys Ile Ala Gln Ser Asn Asp Val Ile Ala Asp Lys Asp Tyr Gln
           1460                1465                1470

ccg att att gac gaa tac gct ttt gat aaa aag gtg aac gcg tct ata     4464
Pro Ile Ile Asp Glu Tyr Ala Phe Asp Lys Lys Val Asn Ala Ser Ile
       1475                1480                1485

gaa aag cga gaa agg caa gaa tca aca aaa gta aag ttt aga aaa gga     4512
Glu Lys Arg Glu Arg Gln Glu Ser Thr Lys Val Lys Phe Arg Lys Gly
   1490                1495                1500

gga att gct att caa tga                                             4530
Gly Ile Ala Ile Gln
1505


<210> SEQ ID NO 27
<211> LENGTH: 1509
<212> TYPE: PRT
<213> ORGANISM: Staphylococcus bacteriophage

<400> SEQUENCE: 27

Met Gly Glu Arg Ile Lys Gly Leu Ser Ile Gly Leu Asp Leu Asp Ala
  1               5                  10                  15

Ala Asn Leu Asn Arg Ser Phe Ala Glu Ile Lys Arg Asn Phe Lys Thr
             20                  25                  30

Leu Asn Ser Asp Leu Lys Leu Thr Gly Asn Asn Phe Lys Tyr Thr Glu
         35                  40                  45

Lys Ser Thr Asp Ser Tyr Lys Gln Arg Ile Lys Glu Leu Asp Gly Thr
     50                  55                  60

Ile Thr Gly Tyr Lys Lys Asn Val Asp Asp Leu Ala Lys Gln Tyr Asp
 65                  70                  75                  80
```

-continued

```
Lys Val Ser Gln Glu Gln Gly Glu Asn Ser Ala Glu Ala Gln Lys Leu
                85                  90                  95

Arg Gln Glu Tyr Asn Lys Gln Ala Asn Glu Leu Asn Tyr Leu Glu Arg
            100                 105                 110

Glu Leu Gln Lys Thr Ser Ala Glu Phe Glu Glu Phe Lys Lys Ala Gln
        115                 120                 125

Val Glu Ala Gln Arg Met Ala Glu Ser Gly Trp Gly Lys Thr Ser Lys
    130                 135                 140

Val Phe Glu Ser Met Gly Pro Lys Leu Thr Lys Met Gly Asp Gly Leu
145                 150                 155                 160

Lys Ser Ile Gly Lys Gly Leu Met Ile Gly Val Thr Ala Pro Val Leu
                165                 170                 175

Gly Ile Ala Ala Ala Ser Gly Lys Ala Phe Ala Glu Val Asp Lys Gly
            180                 185                 190

Leu Asp Thr Val Thr Gln Ala Thr Gly Ala Thr Gly Ser Glu Leu Lys
        195                 200                 205

Lys Leu Gln Asn Ser Phe Lys Asp Val Tyr Gly Asn Phe Pro Ala Asp
    210                 215                 220

Ala Glu Thr Val Gly Gly Val Leu Gly Glu Val Asn Thr Arg Leu Gly
225                 230                 235                 240

Phe Thr Gly Lys Glu Leu Glu Asn Ala Thr Glu Ser Phe Leu Lys Phe
                245                 250                 255

Ser His Ile Thr Gly Ser Asp Gly Val Gln Ala Val Gln Leu Ile Thr
            260                 265                 270

Arg Ala Met Gly Asp Ala Gly Ile Glu Ala Ser Glu Tyr Gln Ser Val
        275                 280                 285

Leu Asp Met Val Ala Lys Ala Ala Gln Ala Ser Gly Ile Ser Val Asp
    290                 295                 300

Thr Leu Ala Asp Ser Ile Thr Lys Tyr Gly Ala Pro Met Arg Ala Met
305                 310                 315                 320

Gly Phe Glu Met Lys Glu Ser Ile Ala Leu Phe Ser Gln Trp Glu Lys
                325                 330                 335

Ser Gly Val Asn Thr Glu Ile Ala Phe Ser Gly Leu Lys Lys Ala Ile
            340                 345                 350

Ser Asn Trp Gly Lys Ala Gly Lys Asn Pro Arg Glu Glu Phe Lys Lys
        355                 360                 365

Thr Leu Ala Glu Ile Glu Lys Thr Pro Asp Ile Ala Ser Ala Thr Ser
    370                 375                 380

Leu Ala Ile Glu Ala Phe Gly Ala Lys Ala Gly Pro Asp Leu Ala Asp
385                 390                 395                 400

Ala Ile Lys Gly Gly Arg Phe Ser Tyr Gln Glu Phe Leu Lys Thr Ile
                405                 410                 415

Glu Asp Ser Gln Gly Thr Val Asn Gln Thr Phe Lys Asp Ser Glu Ser
            420                 425                 430

Gly Ser Glu Arg Phe Lys Val Ala Met Asn Lys Leu Lys Leu Val Gly
        435                 440                 445

Ala Asp Val Trp Ala Ser Ile Glu Ser Ala Phe Ala Pro Val Met Glu
    450                 455                 460

Glu Leu Ile Lys Lys Leu Ser Ile Ala Val Asp Trp Phe Ser Asn Leu
465                 470                 475                 480

Ser Asp Gly Ser Lys Arg Ser Ile Val Ile Phe Ser Gly Ile Ala Ala
                485                 490                 495
```

-continued

```
Ala Ile Gly Pro Val Val Phe Gly Leu Gly Ala Phe Ile Ser Thr Ile
            500                 505                 510

Gly Asn Ala Val Thr Val Leu Ala Pro Leu Leu Ala Ser Ile Ala Lys
        515                 520                 525

Ala Gly Gly Leu Ile Ser Phe Leu Ser Thr Lys Val Pro Ile Leu Gly
    530                 535                 540

Thr Val Phe Thr Ala Leu Thr Gly Pro Ile Gly Ile Val Leu Gly Val
545                 550                 555                 560

Leu Ala Gly Leu Ala Val Ala Phe Thr Ile Ala Tyr Lys Lys Ser Glu
                565                 570                 575

Thr Phe Arg Asn Phe Val Asn Gly Ala Ile Glu Ser Val Lys Gln Thr
            580                 585                 590

Phe Ser Asn Phe Ile Gln Phe Ile Gln Pro Phe Val Asp Ser Val Lys
        595                 600                 605

Asn Ile Phe Lys Gln Ala Ile Ser Ala Ile Val Asp Phe Ala Lys Asp
    610                 615                 620

Ile Trp Ser Gln Ile Asn Gly Phe Phe Asn Glu Asn Gly Ile Ser Ile
625                 630                 635                 640

Val Gln Ala Leu Gln Asn Ile Cys Asn Phe Ile Lys Ala Ile Phe Glu
                645                 650                 655

Phe Ile Leu Asn Phe Val Ile Lys Pro Ile Met Phe Ala Ile Trp Gln
            660                 665                 670

Val Met Gln Phe Ile Trp Pro Ala Val Lys Ala Leu Ile Val Ser Thr
        675                 680                 685

Trp Glu Asn Ile Lys Gly Val Ile Gln Gly Ala Leu Asn Ile Ile Leu
    690                 695                 700

Gly Leu Ile Lys Phe Phe Ser Ser Leu Phe Val Gly Asp Trp Arg Gly
705                 710                 715                 720

Val Trp Asp Ala Val Val Met Ile Leu Lys Gly Ala Val Gln Leu Ile
                725                 730                 735

Trp Asn Leu Val Gln Leu Trp Phe Val Gly Lys Ile Leu Gly Val Val
            740                 745                 750

Arg Tyr Phe Gly Gly Leu Leu Lys Gly Leu Ile Ala Gly Ile Trp Asp
        755                 760                 765

Val Ile Arg Ser Ile Phe Ser Lys Ser Leu Ser Ala Ile Trp Asn Ala
    770                 775                 780

Thr Lys Ser Ile Phe Gly Phe Leu Phe Asn Ser Val Lys Ser Ile Phe
785                 790                 795                 800

Thr Asn Met Lys Asn Trp Leu Ser Asn Thr Trp Ser Ser Ile Arg Thr
                805                 810                 815

Asn Thr Ile Gly Lys Ala Gln Ser Leu Phe Ser Gly Val Lys Ser Lys
            820                 825                 830

Phe Thr Asn Leu Trp Asn Ala Thr Lys Glu Ile Phe Ser Asn Leu Arg
        835                 840                 845

Asn Trp Met Ser Asn Ile Trp Asn Ser Ile Lys Asp Asn Thr Val Gly
    850                 855                 860

Ile Ala Ser Arg Leu Trp Ser Lys Val Arg Gly Ile Phe Thr Asn Met
865                 870                 875                 880

Arg Asp Gly Leu Ser Ser Ile Ile Asp Lys Ile Lys Ser His Ile Gly
                885                 890                 895

Gly Met Val Ser Ala Ile Lys Lys Gly Leu Asn Lys Leu Ile Asp Gly
            900                 905                 910

Leu Asn Trp Val Gly Gly Lys Leu Gly Met Asp Lys Ile Pro Lys Leu
```

-continued

```
        915                 920                 925

His Thr Gly Thr Glu His Thr His Thr Thr Thr Arg Leu Val Lys Asn
    930                 935                 940

Gly Lys Ile Ala Arg Asp Thr Phe Ala Thr Val Gly Asp Lys Gly Arg
945                 950                 955                 960

Gly Asn Gly Pro Asn Gly Phe Arg Asn Glu Met Ile Glu Phe Pro Asn
                965                 970                 975

Gly Lys Arg Val Ile Thr Pro Asn Thr Asp Thr Thr Ala Tyr Leu Pro
            980                 985                 990

Lys Gly Ser Lys Val Tyr Asn Gly Ala Gln Thr Tyr Ser Met Leu Asn
        995                1000                1005

Gly Thr Leu Pro Arg Phe Ser Leu Gly Thr Met Trp Lys Asp Ile Lys
   1010                1015                1020

Ser Gly Ala Ser Ser Ala Phe Asn Trp Thr Lys Asp Lys Ile Gly Lys
1025               1030                1035                1040

Gly Thr Lys Trp Leu Gly Asp Lys Val Gly Asp Val Leu Asp Phe Met
               1045                1050                1055

Glu Asn Pro Gly Lys Leu Leu Asn Tyr Ile Leu Glu Ala Phe Gly Ile
           1060                1065                1070

Asp Phe Asn Ser Leu Thr Lys Gly Met Gly Ile Ala Gly Asp Ile Thr
       1075                1080                1085

Lys Ala Ala Trp Ser Lys Ile Lys Lys Ser Ala Thr Asp Trp Ile Lys
   1090                1095                1100

Glu Asn Leu Glu Ala Met Gly Gly Gly Asp Leu Val Gly Gly Ile Leu
1105               1110                1115                1120

Asp Pro Asp Lys Ile Asn Tyr His Tyr Gly Arg Thr Ala Ala Tyr Thr
               1125                1130                1135

Ala Ala Thr Gly Arg Pro Phe His Glu Gly Val Asp Phe Pro Phe Val
           1140                1145                1150

Tyr Gln Glu Val Arg Thr Pro Met Gly Gly Arg Leu Thr Arg Met Pro
       1155                1160                1165

Phe Met Ser Gly Gly Tyr Gly Asn Tyr Val Lys Ile Thr Ser Gly Val
   1170                1175                1180

Ile Asp Met Leu Phe Ala His Leu Lys Asn Phe Ser Lys Ser Pro Pro
1185               1190                1195                1200

Ser Gly Thr Met Val Lys Pro Gly Asp Val Val Gly Leu Thr Gly Asn
               1205                1210                1215

Thr Gly Phe Ser Thr Gly Pro His Leu His Phe Glu Met Arg Arg Asn
           1220                1225                1230

Gly Arg His Phe Asp Pro Glu Pro Tyr Leu Arg Asn Ala Lys Lys Lys
       1235                1240                1245

Gly Arg Leu Ser Ile Gly Gly Gly Gly Ala Thr Ser Gly Ser Gly Ala
   1250                1255                1260

Thr Tyr Ala Ser Arg Val Ile Arg Gln Ala Gln Ser Ile Leu Gly Gly
1265               1270                1275                1280

Arg Tyr Lys Gly Lys Trp Ile His Asp Gln Met Met Arg Val Ala Lys
               1285                1290                1295

Arg Glu Ser Asn Tyr Gln Ser Asn Ala Val Asn Asn Trp Asp Ile Asn
           1300                1305                1310

Ala Gln Arg Gly Asp Pro Ser Arg Gly Leu Phe Gln Ile Ile Gly Ser
       1315                1320                1325

Thr Phe Arg Ala Asn Ala Lys Arg Gly Tyr Thr Asn Phe Asn Asn Pro
   1330                1335                1340
```

-continued

```
Val His Gln Gly Ile Ser Ala Met Gln Tyr Ile Val Arg Arg Tyr Gly
1345                1350                1355                1360

Trp Gly Gly Phe Lys Arg Ala Gly Asp Tyr Ala Tyr Ala Thr Gly Gly
                1365                1370                1375

Lys Val Phe Asp Gly Trp Tyr Asn Leu Gly Glu Asp Gly His Pro Glu
            1380                1385                1390

Trp Ile Ile Pro Thr Asp Pro Ala Arg Arg Asn Asp Ala Met Lys Ile
        1395                1400                1405

Leu His Tyr Ala Ala Ala Glu Val Arg Gly Lys Lys Ala Ser Lys Asn
    1410                1415                1420

Lys Arg Pro Ser Gln Leu Ser Asp Leu Asn Gly Phe Asp Asp Pro Ser
1425                1430                1435                1440

Leu Leu Leu Lys Met Ile Glu Gln Gln Gln Gln Gln Ile Ala Leu Leu
                1445                1450                1455

Leu Lys Ile Ala Gln Ser Asn Asp Val Ile Ala Asp Lys Asp Tyr Gln
            1460                1465                1470

Pro Ile Ile Asp Glu Tyr Ala Phe Asp Lys Lys Val Asn Ala Ser Ile
        1475                1480                1485

Glu Lys Arg Glu Arg Gln Glu Ser Thr Lys Val Lys Phe Arg Lys Gly
    1490                1495                1500

Gly Ile Ala Ile Gln
1505


<210> SEQ ID NO 28
<211> LENGTH: 261
<212> TYPE: DNA
<213> ORGANISM: Staphylococcus bacteriophage
<220> FEATURE:
<221> NAME/KEY: CDS
<222> LOCATION: (1)..(258)

<400> SEQUENCE: 28

atg tat tac aaa att ggt gag ata aaa aac aaa att ata agc ttt aac       48
Met Tyr Tyr Lys Ile Gly Glu Ile Lys Asn Lys Ile Ile Ser Phe Asn
  1               5                  10                  15

ggg ttt gaa ttt aaa gtg tct gtg atg aag aga cat gac ggt atc agt       96
Gly Phe Glu Phe Lys Val Ser Val Met Lys Arg His Asp Gly Ile Ser
             20                  25                  30

ata caa atc aag gat atg aat aat gtt cca ctt aaa tcg ttt cat gtc      144
Ile Gln Ile Lys Asp Met Asn Asn Val Pro Leu Lys Ser Phe His Val
         35                  40                  45

ata gat tta agc gaa cta tat att gcg acg gat gca atg cgt gac gtt      192
Ile Asp Leu Ser Glu Leu Tyr Ile Ala Thr Asp Ala Met Arg Asp Val
     50                  55                  60

ata aac gaa tgg att gaa aat aac aca gat gaa cag gac aaa cta att      240
Ile Asn Glu Trp Ile Glu Asn Asn Thr Asp Glu Gln Asp Lys Leu Ile
 65                  70                  75                  80

aac tta gtc atg aaa tgg tag                                          261
Asn Leu Val Met Lys Trp
                 85


<210> SEQ ID NO 29
<211> LENGTH: 86
<212> TYPE: PRT
<213> ORGANISM: Staphylococcus bacteriophage

<400> SEQUENCE: 29

Met Tyr Tyr Lys Ile Gly Glu Ile Lys Asn Lys Ile Ile Ser Phe Asn
  1               5                  10                  15
```

-continued

```
Gly Phe Glu Phe Lys Val Ser Val Met Lys Arg His Asp Gly Ile Ser
            20                  25                  30

Ile Gln Ile Lys Asp Met Asn Asn Val Pro Leu Lys Ser Phe His Val
        35                  40                  45

Ile Asp Leu Ser Glu Leu Tyr Ile Ala Thr Asp Ala Met Arg Asp Val
    50                  55                  60

Ile Asn Glu Trp Ile Glu Asn Asn Thr Asp Glu Gln Asp Lys Leu Ile
65                  70                  75                  80

Asn Leu Val Met Lys Trp
                85


<210> SEQ ID NO 30
<211> LENGTH: 216
<212> TYPE: DNA
<213> ORGANISM: Staphylococcus bacteriophage
<220> FEATURE:
<221> NAME/KEY: CDS
<222> LOCATION: (1)..(213)

<400> SEQUENCE: 30

atg aat ata atg caa ttc aaa agc tta ttg aaa tcg atg tat gaa gag       48
Met Asn Ile Met Gln Phe Lys Ser Leu Leu Lys Ser Met Tyr Glu Glu
  1               5                  10                  15

aca aag caa agc gac ccg att gta gca aat gta tat atc gag act ggt       96
Thr Lys Gln Ser Asp Pro Ile Val Ala Asn Val Tyr Ile Glu Thr Gly
            20                  25                  30

tgg gcg gtc aat aga ttg ttg gac aat aac gag tta tcg cct ttc gat      144
Trp Ala Val Asn Arg Leu Leu Asp Asn Asn Glu Leu Ser Pro Phe Asp
        35                  40                  45

gat tac gac aga gtt gaa aag aaa atc atg aat gaa atc aac tgg aag      192
Asp Tyr Asp Arg Val Glu Lys Lys Ile Met Asn Glu Ile Asn Trp Lys
    50                  55                  60

aaa aca cac att aag gag tgt taa                                      216
Lys Thr His Ile Lys Glu Cys
65                  70


<210> SEQ ID NO 31
<211> LENGTH: 71
<212> TYPE: PRT
<213> ORGANISM: Staphylococcus bacteriophage

<400> SEQUENCE: 31

Met Asn Ile Met Gln Phe Lys Ser Leu Leu Lys Ser Met Tyr Glu Glu
  1               5                  10                  15

Thr Lys Gln Ser Asp Pro Ile Val Ala Asn Val Tyr Ile Glu Thr Gly
            20                  25                  30

Trp Ala Val Asn Arg Leu Leu Asp Asn Asn Glu Leu Ser Pro Phe Asp
        35                  40                  45

Asp Tyr Asp Arg Val Glu Lys Lys Ile Met Asn Glu Ile Asn Trp Lys
    50                  55                  60

Lys Thr His Ile Lys Glu Cys
65                  70


<210> SEQ ID NO 32
<211> LENGTH: 186
<212> TYPE: DNA
<213> ORGANISM: Staphylococcus bacteriophage
<220> FEATURE:
<221> NAME/KEY: CDS
<222> LOCATION: (1)..(183)
```

-continued

<400> SEQUENCE: 32

```
atg caa caa caa gca tat ata aac gca aca att gat ata aga ata cct       48
Met Gln Gln Gln Ala Tyr Ile Asn Ala Thr Ile Asp Ile Arg Ile Pro
  1               5                  10                  15

aca gaa gtt gaa tat cag cat tac gat gat gtg gat aaa gaa aaa gat       96
Thr Glu Val Glu Tyr Gln His Tyr Asp Asp Val Asp Lys Glu Lys Asp
             20                  25                  30

acg ctg gca aag cgc tta gat gac aat ccg gac gaa tta cta aag tat      144
Thr Leu Ala Lys Arg Leu Asp Asp Asn Pro Asp Glu Leu Leu Lys Tyr
         35                  40                  45

gac aac ata aca ata aga cat gca tat ata gag gtg gaa taa              186
Asp Asn Ile Thr Ile Arg His Ala Tyr Ile Glu Val Glu
     50                  55                  60
```

<210> SEQ ID NO 33
<211> LENGTH: 61
<212> TYPE: PRT
<213> ORGANISM: Staphylococcus bacteriophage

<400> SEQUENCE: 33

```
Met Gln Gln Gln Ala Tyr Ile Asn Ala Thr Ile Asp Ile Arg Ile Pro
  1               5                  10                  15

Thr Glu Val Glu Tyr Gln His Tyr Asp Asp Val Asp Lys Glu Lys Asp
             20                  25                  30

Thr Leu Ala Lys Arg Leu Asp Asp Asn Pro Asp Glu Leu Leu Lys Tyr
         35                  40                  45

Asp Asn Ile Thr Ile Arg His Ala Tyr Ile Glu Val Glu
     50                  55                  60
```

<210> SEQ ID NO 34
<211> LENGTH: 86
<212> TYPE: PRT
<213> ORGANISM: Staphylococcus bacteriophage

<400> SEQUENCE: 34

```
Met Tyr Tyr Glu Ile Gly Glu Ile Ile Arg Lys Asn Ile His Val Asn
  1               5                  10                  15

Gly Phe Asp Phe Lys Leu Phe Ile Leu Lys Gly His Met Gly Ile Ser
             20                  25                  30

Ile Gln Val Lys Asp Met Asn Asn Val Pro Ile Lys His Ala Tyr Val
         35                  40                  45

Val Asp Glu Asn Asp Leu Asp Met Ala Ser Asp Leu Phe Asn Gln Ala
     50                  55                  60

Ile Asp Glu Trp Ile Glu Glu Asn Thr Asp Glu Gln Asp Arg Leu Ile
 65                  70                  75                  80

Asn Leu Val Met Lys Trp
                 85
```

<210> SEQ ID NO 35
<211> LENGTH: 98
<212> TYPE: PRT
<213> ORGANISM: Staphylococcus bacteriophage

<400> SEQUENCE: 35

```
Met Phe Asn Ile Lys Arg Lys Thr Glu Glu Val Lys Met Tyr Tyr Glu
  1               5                  10                  15

Ile Gly Glu Ile Ile Arg Lys Asn Ile His Val Asn Gly Phe Asp Phe
             20                  25                  30

Lys Leu Phe Ile Leu Lys Gly His Met Gly Ile Ser Ile Gln Val Lys
```

-continued

```
        35                  40                  45

Asp Met Asn Asn Val Pro Ile Lys His Ala Tyr Val Val Asp Glu Asn
     50                  55                  60

Asp Leu Asp Met Ala Ser Asp Leu Phe Asn Gln Ala Ile Asp Glu Trp
 65                  70                  75                  80

Ile Glu Glu Asn Thr Asp Glu Gln Asp Arg Leu Ile Asn Leu Val Met
                 85                  90                  95

Lys Trp


<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Synthetic
      Sal I restriction site

<400> SEQUENCE: 36

gcgtcgaccg                                                            10
```